(12) United States Patent
Hirose et al.

(10) Patent No.: US 8,344,135 B2
(45) Date of Patent: Jan. 1, 2013

(54) HETEROCYCLIC COMPOUND AND USE THEREOF

(75) Inventors: Masaaki Hirose, Tsukuba (JP);
Masanori Okaniwa, Tsukuba (JP);
Yoko Hayashi, Tsukuba (JP); Terufumi Takagi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 324 days.

(21) Appl. No.: 12/675,663

(22) PCT Filed: Aug. 28, 2008

(86) PCT No.: PCT/JP2008/065454
§ 371 (c)(1),
(2), (4) Date: Feb. 26, 2010

(87) PCT Pub. No.: WO2009/028629
PCT Pub. Date: Mar. 5, 2009

(65) Prior Publication Data
US 2010/0249119 A1    Sep. 30, 2010

(30) Foreign Application Priority Data

Aug. 29, 2007 (JP) .................. 2007-223284
Jul. 18, 2008 (JP) .................. 2008-187953

(51) Int. Cl.
*C07D 345/00* (2006.01)
(52) U.S. Cl. ......................................... 540/1
(58) Field of Classification Search ............ 540/1
See application file for complete search history.

(56) References Cited

U.S. PATENT DOCUMENTS

| 4,096,264 A | 6/1978 | Bochis et al. |
| 4,177,274 A | 12/1979 | Bochis et al. |
| 4,237,300 A | 12/1980 | Bochis et al. |
| 2008/0021048 A1 | 1/2008 | Bennett et al. |

FOREIGN PATENT DOCUMENTS

| JP | 52-73896 | 6/1977 |
| WO | 99/10325 | 3/1999 |
| WO | 99/16438 | 4/1999 |
| WO | 00/41698 | 7/2000 |
| WO | 00/42012 | 7/2000 |
| WO | 01/66539 | 9/2001 |
| WO | 01/66540 | 9/2001 |
| WO | 02/24680 | 3/2002 |
| WO | 02/44156 | 6/2002 |
| WO | 02/062763 | 8/2002 |
| WO | 02/094808 | 11/2002 |
| WO | 03/022833 | 3/2003 |
| WO | 03/022836 | 3/2003 |
| WO | 03/022837 | 3/2003 |
| WO | 03/022838 | 3/2003 |
| WO | 03/082272 | 10/2003 |
| WO | 2005/032548 | 4/2005 |
| WO | 2005/112932 | 12/2005 |
| WO | 2006/071035 | 7/2006 |
| WO | 2006/076376 | 7/2006 |
| WO | 2007/030377 | 3/2007 |
| WO | 2007/058482 | 5/2007 |
| WO | 2008/150015 | 12/2008 |
| WO | 2009/025358 | 2/2009 |

OTHER PUBLICATIONS

Waller et al 'Prodrugs' British Journal of Clinical Pharmacology, vol. 28, p. 497-507, 1989.*
International Search Report (Form PCT/ISA/210) issued in International Application No. PCT/JP2008/065454, mailed Sep. 22, 2008—4 pages.
Lowinger, et al., "Design and Discovery of Small Molecules Targeting Raf-1 Kinase", Current Pharmaceutical Design, vol. 8, 2002, pp. 2269-2278.
Das, et al., "Dithiocarbamate and CuO promoted one-pot synthesis of 2-(N-substituted)-aminobenzimidazoles and related heterocycles" Tetrahedron Letters, vol. 49, No. 6, 2008, pp. 992-995.

* cited by examiner

*Primary Examiner* — Brandon Fetterolf
*Assistant Examiner* — Christopher R Stone
(74) *Attorney, Agent, or Firm* — Hamre, Schumann, Mueller & Larson, P.C.

(57) ABSTRACT

The present invention provides a heterocyclic compound having a strong Raf inhibitory activity, which is represented by the following formula (III)

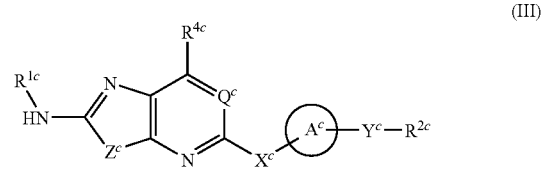

wherein each substituent is as defined in the present specification, or a salt thereof.

6 Claims, No Drawings

SEQUENCE LISTING

<160> NUMBER OF SEQ ID NOS: 4

<210> SEQ ID NO 1
<211> LENGTH: 64
<212> TYPE: DNA
<213> ORGANISM: Artificial
<220> FEATURE:
<223> OTHER INFORMATION: primer for cloning human BRAF gene

<400> SEQUENCE: 1
aaagaattca ccatggacta caaggacgac gatgacaaga ccccccctgc ctcattacct    60
ggct    64

<210> SEQ ID NO 2

```
<211> LENGTH: 35
<212> TYPE: DNA
<213> ORGANISM: Artificial
<220> FEATURE:
<223> OTHER INFORMATION: primer for cloning human BRAF gene

<400> SEQUENCE: 2
aaaagtcgac tcagtggaca ggaaacgcac catat                         35

<210> SEQ ID NO 3
<211> LENGTH: 29
<212> TYPE: DNA
<213> ORGANISM: Artificial
<220> FEATURE:
<223> OTHER INFORMATION: primer for cloning human BRAF gene

<400> SEQUENCE: 3
ggtctagcta cagagaaatc tcgatggag                                29

<210> SEQ ID NO 4
<211> LENGTH: 29
<212> TYPE: DNA
<213> ORGANISM: Artificial
<220> FEATURE:
<223> OTHER INFORMATION: primer for cloning human BRAF gene

<400> SEQUENCE: 4
ctccatcgag atttctctgt agctagacc                                29
```

HETEROCYCLIC COMPOUND AND USE THEREOF

TECHNICAL FIELD

The present invention relates to a heterocyclic compound and use thereof, and in detail, relates to a heterocyclic compound having strong Raf inhibitory activity and useful for the prophylaxis•treatment and the like of cancer, and use thereof.

BACKGROUND OF THE INVENTION

Many activities of cancer cells such as growth, metastasis, infiltration and the like are caused via intracellular signal transduction from RTK: receptor tyrosine kinases (EGFR, HER2 etc.), which is activated by stimulation by growth factors and mutation, and the activation signal thereof is transmitted downstream via RAS protein. As the intracellular signal transduction pathway via Ras, Ras/Raf/MEK/ERK pathway is best known, which is deeply involved in the control of various cell functions such as cell proliferation, cellular motility, transformation, apoptosis (cell death) resistance and the like.

To block the pathway, inhibitors of growth factor receptors, for example, epithelial growth factor receptor (EGFR) inhibitors gefinitib (trade name: Iressa), and erlotinib (trade name: Tarceva), and human epithelial growth factor receptor type 2 (HER2) inhibitory antibody trastuzumab (trade name: Herceptin) are placed on the market in recent years. They have been reported to be effective for the treatment of some cancer types in clinical practices, such as lung cancer, breast cancer and the like. In addition, it has been shown that inhibitory antibody bevacizumab (trade name: Avastin) against vascular endothelial growth factor (VEGF) inhibits activation of VEGFR in the intratumoral neovascular endothelial cells and shows an antitumor action. These pharmaceutical agents suppress signal transduction system at the downstream when showing a tumor growth inhibitory action in cancer to be the target cells and vascular endothelial cells, through inhibition of receptor enzyme activity and inhibition of receptor activation.

On the other hand, the Ras/Raf/MEK/ERK pathway is well known to cause highly frequent mutations in cancer. Ras gene is reported to undergo an activation type mutation at codon 12, 13 or 61 of various cancers, for example about 90% of the total of pancreatic cancer, about 35% of non-small cell lung cancer, about 30% of liver cancer and the like, and there are many reports on the correlation between Ras mutation and developing malignant tumor.

With regard to Raf gene, activation mutation in kinase domain of B-Raf in cancer has been reported. It is known that B-Raf mutation, particularly V600E, occurs in various cancers, for example, about 60% of the total of malignant melanoma, about 30% of thyroid cancer, about 15% of colon cancer and the like. Particularly, B-Raf (V600E) kinase has about 13-fold MEK phosphorylation activity as compared to wild-type B-Raf kinase, and the activity of B-Raf is deeply involved in the growth of cancer having a mutation in B-Raf.

In these cancers, inhibitions of the upstream growth factor receptor activity and Ras cannot suppress signal transduction system downstream of Raf kinase, which is constantly activated. In this case, since suppression of the downstream signal (Raf/MEK/ERK signal transduction system) cannot be expected, a tumor growth suppressive activity cannot be expected, either. For example, melanoma showing highly frequent B-Raf mutation is highly metastatic and the 5 year survival rate is about 6%, for which no promising therapeutic drug exists at present.

In the Ras/Raf/MEK/ERK pathway, Raf kinase is the most downstream molecule to be activated by mutation. A compound inhibiting Raf activity is considered to be effective as a therapeutic drug for any cancer caused by mutation of growth factor receptor or excessive activation by ligand stimulation, or cancer caused by activation type mutation of Ras.

Raf is a serine/threonine kinase, and is known to include three isoforms of A-Raf, B-Raf and c-Raf. Raf is activated by Ras and phosphorylates the downstream molecule MEK. The activated MEK further phosphorylates ERK to transmit the signal further downstream. Of three isoforms, B-Raf kinase shows an extreme strong activity of phosphorylating MEK in the basal state, which is about 15- to 20-fold that of A-Raf, c-Raf kinase activity. To undergo process of activation, moreover, c-Raf requires phosphorylation of the 338th serine in the activation loop to obtain the maximum activity (same for A-Raf). However, B-Raf is known to be easily activated as compared to A-Raf and c-Raf, since the corresponding sequence is always phosphorylated.

A compound that inhibits B-Raf kinase activity and mutant B-Raf kinase is considered to suppress cell proliferation particularly in cancer with poor prognosis. Accordingly, the compound becomes an effective therapeutic drug even for cancer for which a growth factor receptor enzyme activity inhibitor is ineffective.

As Raf inhibitors, sorafenib-related derivatives (patent references 1-3, non-patent reference 1), benzylidene derivatives (patent reference 4), imidazole derivatives (patent references 5-8), pyridylfuran derivatives (patent references 9-12), benzazole derivatives (patent references 13-15) and the like are known.

As a structural analog compound of the compound described in the present specification, a compound to be used as a prophylactic or therapeutic drug for cancer is described in patent reference 16, the following compound:

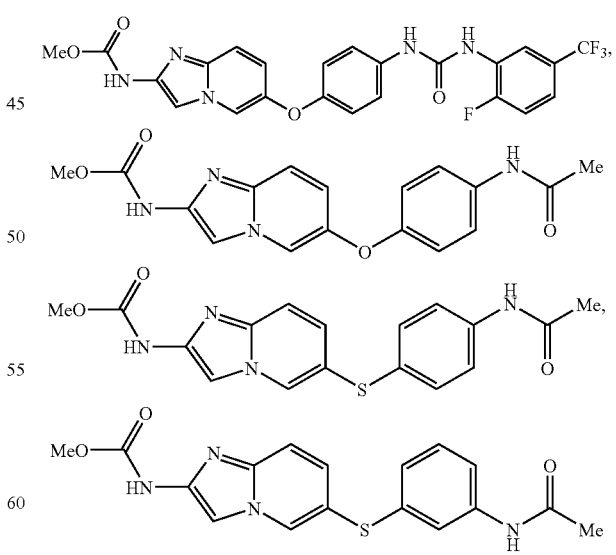

to be used as a therapeutic drug for parasitosis is described in patent reference 17, a compound to be used as a therapeutic drug for cancer is described in patent reference 18, a compound to be used as a therapeutic drug for cancer is described in patent reference 19, a compound to be used as a therapeutic drug for cancer is described in patent reference 20, and the following compound:

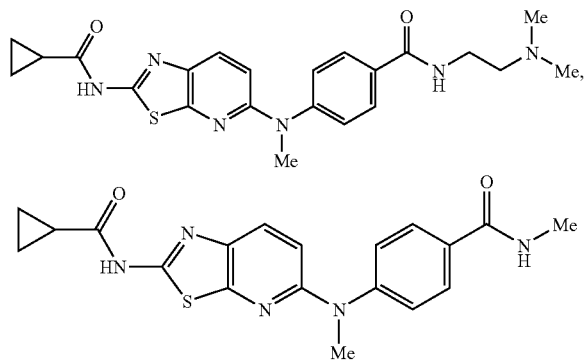

to be used as an agent for the prophylaxis or treatment of is cancer is described in patent reference 21.
patent reference 1: WO 2000/42012
patent reference 2: WO 2000/41698
patent reference 3: WO 2002/62763
patent reference 4: WO 99/10325
patent reference 5: WO 2002/94808
patent reference 6: WO 2002/24680
patent reference 7: WO 2001/66540
patent reference 8: WO 2001/66539
patent reference 9: WO 2003/22838
patent reference 10: WO 2003/22837
patent reference 11: WO 2003/22836
patent reference 12: WO 2003/22833
patent reference 13: WO 2003/082272
patent reference 14: WO 2005/032548
patent reference 15: WO 2007/030377
patent reference 16: WO 2002/44156
patent reference 17: JP-A-52-073896
patent reference 18: WO 2006/076376
patent reference 19: WO 2005/112932
patent reference 20: WO 2005/032548
patent reference 21: WO 2006/071035
non-patent reference 1: Current Pharmaceutical Design, 2000, 8, 2269-2278

DISCLOSURE OF THE INVENTION

Problems to be Solved by the Invention

A Raf inhibitor superior in the efficacy expression, pharmacokinetics, solubility, interaction with other pharmaceutical products, safety and stability is expected to show a therapeutically superior effect. At present, however, such inhibitor sufficiently satisfactory in the efficacy expression, pharmacokinetics, solubility, interaction with other pharmaceutical products, safety and stability has not been found. Thus, there is a demand for the development of a compound sufficiently satisfactory as a pharmaceutical product. Accordingly, an object of the present invention is to provide a compound having low toxicity and sufficiently satisfactory as a pharmaceutical product.

Means of Solving the Problems

The present inventors have conducted intensive studies in an attempt to solve the above-mentioned problems and found that a compound represented by the following formula and a salt thereof have a superior Raf inhibitory activity, which resulted in the completion of the present invention.
Accordingly, the present invention provides the following.
[1] A compound represented by the formula

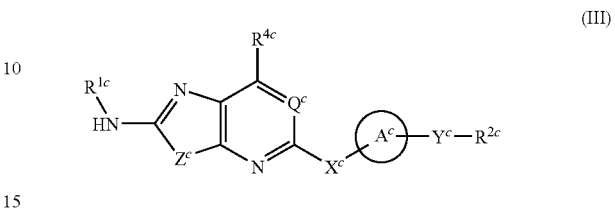

(III)

wherein
$R^{1c}$ is acyl, or a cyclic group optionally having substituent(s);
$R^{2c}$ is an aromatic hydrocarbon group optionally having substituent(s);
$R^{4c}$ is a hydrogen atom, a halogen atom, a group via a carbon atom, a group via a nitrogen atom, a group via an oxygen atom, or a group via a sulfur atom;
$X^c$ is —CO—, —$CR^{5c}R^{6c}$— wherein $R^{5c}$ and $R^{6c}$ are the same or different and each is a hydrogen atom, a group via a carbon atom, a group via a nitrogen atom, a group via an oxygen atom or a group via a sulfur atom, —$NR^{7c}$— wherein $R^{7c}$ is a hydrogen atom, or a group via a carbon atom, —O—, —S—, —S(O)— or —$S(O)_2$—;
$Y^c$ is —NH—, —NHCO—, —CONH— or —NHCONH—;
$Z^c$ is —S—, —O— or —$NR^{8c}$— wherein $R^{8c}$ is a hydrogen atom, or a group via a carbon atom;
$Q^c$ is =$CR^{3c}$— wherein $R^{3c}$ is a hydrogen atom, a halogen atom, a group via a carbon atom, a group via a nitrogen atom, a group via an oxygen atom, or a group via a sulfur atom, or =N—; and ring $A^c$ is a ring optionally further having substituent(s), provided that when $Z^c$ is —NH— and $Q^c$ is =CH—, then $Y^c$ is not —NHCONH—
(hereinafter sometimes to be abbreviated as compound (iii)) or a salt thereof,
[2] the compound of the above-mentioned [1], wherein $R^{1c}$ is acyl,
[3] the compound of the above-mentioned [1], wherein $R^{2c}$ is $C_{6-10}$ aryl optionally having substituent(s),
[4] the compound of the above-mentioned [1], wherein $R^{4c}$ is a hydrogen atom,
[5] the compound of the above-mentioned [1], wherein $X^c$ is —$NR^{7c}$— or —O—,
[6] the compound of the above-mentioned [1], wherein $Y^c$ is —NHCO— or —CONH—,
[7] the compound of the above-mentioned [1], wherein $Q^c$ is =CH—or =N—,
[8] the compound of the above-mentioned [1], wherein $Z^c$ is —S— or —$NR^{8c}$—,
[9] the compound of the above-mentioned [1], wherein $Z^c$ is —S— and $Q^c$ is =CH—,
[10] the compound of the above-mentioned [1], wherein $Z^c$ is —S— and $Q^c$ is =N—,
[11] the compound of the above-mentioned [1], wherein ring $A^c$ is a benzene ring optionally further having substituent(s),
[12] 2-chloro-3-(1-cyano-1-methylethyl)-N-[5-({2-[(cyclopropylcarbonyl)amino][1,3]thiazolo[5,4-b]pyridin-5-yl)oxy}-2-fluorophenyl]benzamide (Example C63);
N-(5-{[2-(acetylamino)[1,3]thiazolo[5,4-b]pyridin-5-yl]oxy}-2-fluorophenyl)-2-chloro-3-(1-cyanocyclopropyl)benzamide (Example C65);

2-chloro-3-(1-cyanocyclopropyl)-N-(5-({2-[(cyclopropyl-carbonyl)amino][1,3]thiazolo[5,4-b]pyridin-5-yl}oxy)-2-fluorophenyl]benzamide (Example C66);
2-chloro-3-(1-cyanocyclopropyl)-N-[5-({2-[(cyclopropyl-carbonyl)amino][1,3]thiazolo[5,4-b]pyridin-5-yl}oxy)-2,4-difluorophenyl]benzamide (Example C75);
2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide (Example C122);
2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide benzenesulfonate (Example C124);
2-chloro-3-(1-cyano-1-methylethoxy)-N-[5-({2-[(cyclopropylcarbonyl)amino][1,3]thiazolo[5,4-b]pyridin-5-yl}amino)-2-fluorophenyl]benzamide (Example C126);
3-(1-cyano-1-methylethyl)-N-{3-[methyl(2-{[(4-methylpiperazin-1-yl)acetyl]amino}[1,3]thiazolo[5,4-d]pyrimidin-5-yl)amino]phenyl}benzamide (Example D11); or
N-(3-{[2-(acetylamino)[1,3]thiazolo[5,4-d]pyrimidin-5-yl]amino}-4-methylphenyl)-2-chloro-3-(1-cyano-1-methylethyl)benzamide (Example D35);
or a salt thereof,

[13] a prodrug of the compound of the above-mentioned [1],
[14] a pharmaceutical agent comprising the compound of the above-mentioned [1] or a salt thereof or a prodrug thereof,
[15] the pharmaceutical agent of the above-mentioned [14], which is a Raf inhibitor,
[16] the pharmaceutical agent of the above-mentioned [14], which is a prophylactic or therapeutic drug for cancer,
[17] a method of inhibiting Raf, comprising administering an effective amount of the compound of the above-mentioned [1] or a salt thereof or a prodrug thereof to a mammal,
[18] a method for the prophylaxis or treatment of cancer, comprising administering an effective amount of the compound of the above-mentioned [1] or a salt thereof or a prodrug thereof to a mammal,
[19] use of the compound of the above-mentioned [1] or a salt thereof or a prodrug thereof for the production of a Raf inhibitor,
[20] use of the compound of the above-mentioned [1] or a salt thereof or a prodrug thereof for the production of a prophylactic or therapeutic drug for cancer,
[A1] a compound represented by the formula

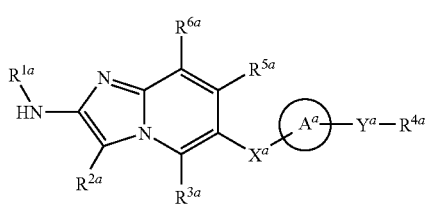

wherein
$R^{1a}$ is acyl, or a cyclic group optionally having substituent(s);
$R^{2a}$ is a hydrogen atom, a halogen atom, a group via a carbon atom, a group via a nitrogen atom, a group via an oxygen atom, or a group via a sulfur atom;
$R^{3a}$ is a hydrogen atom, a halogen atom, a group via a carbon atom, a group via a nitrogen atom, a group via an oxygen atom, or a group via a sulfur atom;
$R^{4a}$ is an aromatic hydrocarbon group optionally having substituent(s);
$R^{5a}$ is a hydrogen atom, a halogen atom, a group via a carbon atom, a group via a nitrogen atom, a group via an oxygen atom, or a group via a sulfur atom;
$R^{6a}$ is a hydrogen atom, a halogen atom, a group via a carbon atom, a group via a nitrogen atom, a group via an oxygen atom, or a group via a sulfur atom;
$X^a$ is —CO—, —$CR^{7a}R^{8a}$— wherein $R^{7a}$ and $R^{8a}$ are the same or different and each is a hydrogen atom, a group via a carbon atom, a group via a nitrogen atom, a group via an oxygen atom, or a group via a sulfur atom, —$NR^{9a}$— wherein $R^{9a}$ is a hydrogen atom, or a group via a carbon atom, —O—, —S—, —S(O)— or —S(O)$_2$—;
$Y^a$ is —NH—, —NHCO—, —CONH— or —NHCONH—; and
ring $A^a$ is a monocycle optionally further having substituent(s) (excluding the following 4 compounds)

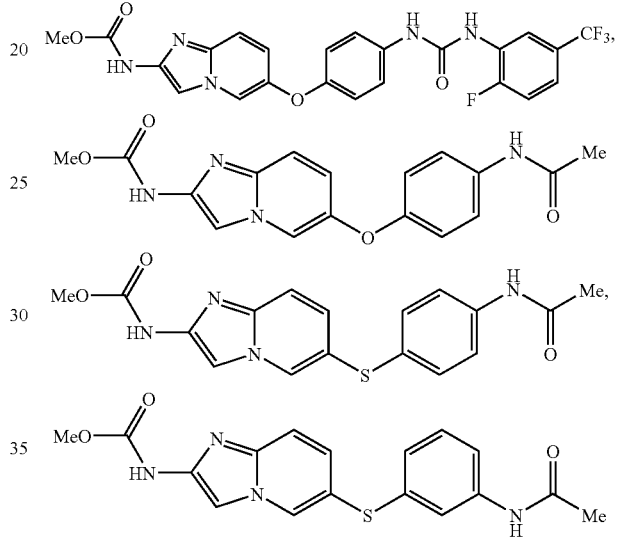

(hereinafter sometimes to be abbreviated as compound (i)) or a salt thereof,
[A2] a compound represented by the formula

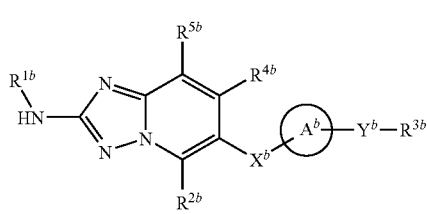

wherein
$R^{1b}$ is acyl, a cyclic group optionally having substituent(s);
$R^{2b}$ is a hydrogen atom, a halogen atom, a group via a carbon atom, a group via a nitrogen atom, a group via an oxygen atom, or a group via a sulfur atom;
$R^{3b}$ is an aromatic hydrocarbon group optionally having substituent(s);
$R^{4b}$ is a hydrogen atom, a halogen atom, a group via a carbon atom, a group via a nitrogen atom, a group via an oxygen atom, or a group via a sulfur atom;
$R^{5b}$ is a hydrogen atom, a halogen atom, a group via a carbon atom, a group via a nitrogen atom, a group via an oxygen atom, or a group via a sulfur atom;

$X^b$ is —CO—, —CR$^{6b}$R$^{7b}$— wherein R$^{6b}$ and R$^{7b}$ are the same or different and each is a hydrogen atom, a group via a carbon atom, a group via a nitrogen atom, a group via an oxygen atom, or a group via a sulfur atom, —NR$^{8b}$— wherein R$^{8b}$ is a hydrogen atom, or a group via a carbon atom, —O—, —S—, —S(O)— or —S(O)$_2$—;

$Y^b$ is —NH—, —NHCO—, —CONH— or —NHCONH—; and ring $A^b$ is a ring optionally further having substituent(s), (hereinafter sometimes to be abbreviated as compound (ii)) or a salt thereof,

[A3] a prodrug of the compound of the above-mentioned [A1] or [A2],

[A4] a pharmaceutical agent comprising the compound of the above-mentioned [A1] or [A2] or a salt thereof or a prodrug thereof,

[A5] the pharmaceutical agent of the above-mentioned [A4], which is a Raf inhibitor,

[A6] the pharmaceutical agent of the above-mentioned [A5], which is a prophylactic or therapeutic drug for cancer,

[A7] a method of inhibiting Raf, comprising administering an effective amount of the compound of the above-mentioned [A1] or [A2] or a salt thereof or a prodrug thereof to a mammal,

[A8] a method for the prophylaxis or treatment of cancer, comprising administering an effective amount of the compound of the above-mentioned [A1] or [A2] or a salt thereof or a prodrug thereof to mammal,

[A9] use of the compound of the above-mentioned [A1] or [A2] or a salt thereof or a prodrug thereof for the production of a Raf inhibitor, and

[A10] use of the compound of the above-mentioned [A1] or [A2] or a salt thereof or a prodrug thereof for the production of a prophylactic or therapeutic drug for cancer.

Effect of the Invention

Since the compound of the present invention or a salt thereof or a prodrug thereof has a strong Raf inhibitory action (particularly, B-Raf inhibitory action), it can provide a clinically useful agent for the prophylaxis or treatment of cancer, a cancer growth inhibitor and a cancer metastasis suppressive agent.

DETAILED DESCRIPTION OF THE INVENTION

The present invention is explained in detail in the following.

In the present specification, the "acyl" is
(1) formyl,
(2) alkyl-carbonyl (e.g., $C_{1-6}$ alkyl-carbonyl) optionally having substituent(s),
(3) alkenyl-carbonyl (e. $C_{2-6}$ alkenyl-carbonyl) optionally having substituent(s),
(4) alkynyl-carbonyl (e.g., $C_{2-6}$ alkynyl-carbonyl) optionally having substituent(s),
(5) cycloalkyl-carbonyl (e.g., $C_{3-8}$ cycloalkyl-carbonyl) optionally having substituent(s),
(6) cycloalkenyl-carbonyl (e.g., $C_{3-8}$ cycloalkenyl-carbonyl) optionally having substituent(s),
(7) aryl-carbonyl (e.g., $C_{6-10}$ aryl-carbonyl) optionally having substituent(s),
(8) heterocyclyl-carbonyl optionally having substituent(s),
(9) carboxyl,
(10) alkyloxy-carbonyl (e.g., $C_{1-6}$ alkyloxy-carbonyl) optionally having substituent(s),
(11) alkenyloxy-carbonyl (e.g., $C_{2-6}$ alkenyloxy-carbonyl) optionally having substituent(s),
(12) alkynyloxy-carbonyl (e.g., $C_{2-6}$ alkynyloxy-carbonyl) optionally having substituent(s),
(13) cycloalkyloxy-carbonyl (e.g., $C_{3-8}$ cycloalkyloxy-carbonyl) optionally having substituent(s),
(14) cycloalkenyloxy-carbonyl (e.g., $C_{3-8}$ cycloalkenyloxy-carbonyl) optionally having substituent(s),
(15) cycloalkynyloxy-carbonyl (e.g., $C_{3-8}$ cycloalkynyloxy-carbonyl) optionally having substituent(s),
(16) aryloxy-carbonyl (e.g., $C_{6-10}$ aryloxy-carbonyl) optionally having substituent(s),
(17) heterocyclyl-oxy-carbonyl optionally having substituent(s),
(18) carbamoyl optionally having substituent(s) and the like.

The "$C_{1-6}$ alkyl-carbonyl" of the above-mentioned "$C_{1-6}$ alkyl-carbonyl optionally having substituent(s)" is, for example, acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl and the like.

Examples of the "substituent" of the above-mentioned "$C_{1-6}$ alkyl-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

Substituent group A: a substituent group consisting of
(1) a halogen atom;
(2) cyano;
(3) nitro;
(4) hydroxy;
(5) $C_{3-8}$ cycloalkyl (e.g., cyclopropyl, cyclobutyl, cyclopentyl, cyclohexyl, cycloheptyl, cyclooctyl etc.) optionally having 1 to 3 substituents selected from a halogen atom and cyano;
(6) $C_{6-10}$ aryl (e.g., phenyl, 1-naphthyl, 2-naphthyl etc.) optionally having 1 to 3 substituents selected from a halogen atom and cyano;
(7) $C_{1-6}$ alkyl-oxy (e.g., methoxy, ethoxy, propoxy, isopropoxy, butoxy, isobutoxy, tert-butoxy etc.) optionally having 1 to 4 substituents selected from a halogen atom and cyano;
(8) $C_{2-6}$ alkenyloxy (e.g., ethenyloxy, propenyloxy, butenyloxy, pentenyloxy, hexenyloxy etc.) optionally having 1 to 3 halogen atoms;
(9) $C_{2-6}$ alkynyloxy (e.g., ethynyloxy, propynyloxy, butynyloxy, pentynyloxy, hexynyloxy etc.) optionally having 1 to 3 halogen atoms;
(10) $C_{3-8}$ cycloalkyl-oxy (e.g., cyclopropyloxy, cyclobutyloxy, cyclopentyloxy, cyclohexyloxy etc.) optionally having 1 to 3 halogen atoms;
(11) $C_{3-8}$ cycloalkenyloxy (e.g., cyclopropenyloxy, cyclobutenyloxy, cyclopentenyloxy, cyclohexenyloxy etc.) optionally having 1 to 3 halogen atoms;
(12) $C_{6-10}$ aryloxy (e.g., phenyloxy, 1-naphthyloxy, 2-naphthyloxy etc.) optionally having 1 to 3 halogen atoms;
(13) $C_{3-8}$ cycloalkyl-$C_{1-6}$ alkyl-oxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms;
(14) $C_{3-8}$ cycloalkenyl-$C_{1-6}$ alkyl-oxy (e.g., cyclopentenylmethyloxy, cyclohexenylmethyloxy, cyclohexenylethyloxy, cyclohexenylpropyloxy etc.) optionally having 1 to 3 halogen atoms;

(15) $C_{6-10}$ aryl-$C_{1-6}$ alkyl-oxy (e.g., phenylmethyloxy, phenylethyloxy etc.) optionally having 1 to 3 halogen atoms;
(16) $C_{1-6}$ alkyl-aminosulfonyl (e.g., methylaminosulfonyl, ethylaminosulfonyl, propylaminosulfonyl etc.);
(17) di-$C_{1-6}$ alkyl-aminosulfonyl (e.g., dimethylaminosulfonyl, diethylaminosulfonyl, dipropylaminosulfonyl etc.);
(18) $C_{1-6}$ alkyl-aminocarbonyl (e.g., methylaminocarbonyl, ethylaminocarbonyl, propylaminocarbonyl etc.);
(19) di-$C_{1-6}$ alkyl-aminocarbonyl (e.g., dimethylaminocarbonyl, diethylaminocarbonyl, dipropylaminocarbonyl etc.);
(20) formyl;
(21) $C_{1-6}$ alkyl-carbonyl (e.g., acetyl, ethylcarbonyl, propylcarbonyl, isopropylcarbonyl etc.);
(22) $C_{2-6}$ alkenyl-carbonyl (e.g., ethenylcarbonyl, propenylcarbonyl, butenylcarbonyl, pentenylcarbonyl, hexenylcarbonyl etc.);
(23) $C_{2-6}$ alkynyl-carbonyl (e.g., ethynylcarbonyl, propynylcarbonyl, butynylcarbonyl, pentynylcarbonyl, hexynylcarbonyl etc.);
(24) $C_{3-8}$ cycloalkyl-carbonyl (e.g., cyclopropylcarbonyl, cyclobutylcarbonyl, cyclopentylcarbonyl, cyclohexylcarbonyl etc.);
(25) $C_{3-8}$ cycloalkenyl-carbonyl (e.g., cyclopropenylcarbonyl, cyclobutenylcarbonyl, cyclopentenylcarbonyl, cyclohexenylcarbonyl etc.);
(26) $C_{6-10}$ aryl-carbonyl (e.g., benzoyl, 1-naphthylcarbonyl, 2-naphthylcarbonyl etc.);
(27) $C_{3-8}$ Cycloalkyl-$C_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);
(28) $C_{3-8}$ cycloalkenyl-$C_{1-6}$ alkyl-carbonyl (e.g., cyclopentenylmethylcarbonyl, cyclohexenylmethylcarbonyl, cyclohexenylethylcarbonyl, cyclohexenylpropylcarbonyl etc.);
(29) $C_{6-10}$ aryl-$C_{1-6}$ alkyl-carbonyl (e.g., benzylcarbonyl, phenylethylcarbonyl etc.);
(30) 5- or 6-membered monocyclic aromatic heterocyclyl-carbonyl (e.g., furylcarbonyl, thienylcarbonyl, pyrrolylcarbonyl, oxazolylcarbonyl, isooxazolylcarbonyl, thiazolylcarbonyl, isothiazolylcarbonyl, imidazolylcarbonyl, pyridylcarbonyl, pyrazolylcarbonyl etc.);
(31) 8- to 12-membered condensed aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.);
(32) 3- to 8-membered (preferably 5- or 6-membered) non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thioranylcarbonyl, piperidinylcarbonyl etc.);
(33) $C_{1-6}$ alkylsulfonyl (e.g., methylsulfonyl, ethylsulfonyl etc.);
(34) $C_{2-6}$ alkenylsulfonyl (e.g., ethenylsulfonyl, propenylsulfonyl etc.);
(35) $C_{2-6}$ alkynylsulfonyl (e.g., ethynylsulfonyl, propynylsulfonyl, butynylsulfonyl, pentynylsulfonyl, hexynylsulfonyl etc.);
(36) $C_{3-8}$ cycloalkylsulfonyl (e.g., cyclopropylsulfonyl, cyclobutylsulfonyl etc.);
(37) $C_{3-8}$ cycloalkenylsulfonyl (e.g., cyclopropenylsulfonyl, cyclobutenylsulfonyl etc.);
(38) $C_{6-10}$ arylsulfonyl (e.g., phenylsulfonyl etc.);
(39) $C_{3-8}$ cycloalkyl-$C_{1-6}$ alkyl-sulfonyl (e.g., cyclopropylmethylsulfonyl etc.);
(40) $C_{3-8}$ cycloalkenyl-$C_{1-6}$ alkyl-sulfonyl (e.g., cyclopentenylmethylsulfonyl etc.);
(41) $C_{6-10}$ aryl-$C_{1-6}$ alkyl-sulfonyl (e.g., benzylsulfonyl etc.);
(42) 5- or 6-membered monocyclic aromatic heterocyclylsulfonyl (e.g., furylsulfonyl, thienylsulfonyl, pyridylsulfonyl etc.);
(43) 8- to 12-membered condensed aromatic heterocyclylsulfonyl (e.g., benzofurylsulfonyl, isobenzofurylsulfonyl etc.);
(44) 3- to 8-membered (preferably 5- or 6-membered) non-aromatic heterocyclyl-sulfonyl (e.g., oxiranylsulfonyl, azetidinylsulfonyl etc.);
(45) amino;
(46) mono-$C_{1-6}$ alkylamino (e.g., methylamino, ethylamino, propylamino, isopropylamino, butylamino, isobutylamino, tert-butylamino etc.);
(47) di-$C_{1-6}$ alkylamino (e.g., dimethylamino, diethylamino, dipropylamino, diisopropylamino, dibutylamino, diisobutylamino, di-tert-butylamino etc.);
(48) mono($C_{1-6}$ alkyl-carbonyl)amino (e.g., acetylamino, ethylcarbonylamino, propylcarbonylamino, tert-butylcarbonylamino etc.) optionally having 1 to 3 halogen atoms;
(49) mono($C_{3-8}$ cycloalkyl-carbonyl)amino (e.g., cyclopropylcarbonylamino, cyclobutylcarbonylamino, cyclopentylcarbonylamino, cyclohexylcarbonylamino etc.);
(50) mono($C_{6-10}$ aryl-carbonyl)amino (e.g., benzoylamino etc.) optionally having 1 to 3 halogen atoms;
(51) mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isooxazolylcarbonylamino, thiazolylcarbonylamino, isothiazolylcarbonylamino, imidazolylcarbonylamino, pyridylcarbonylamino, pyrazolylcarbonylamino etc.);
(52) mono(8- to 12-membered condensed aromatic heterocyclyl-carbonyl)amino (e.g., benzofurylcarbonylamino, isobenzofurylcarbonylamino, benzothienylcarbonylamino, isobenzothienylcarbonylamino etc.);
(53) mono(3- to 8-membered (preferably 5- or 6-membered) non-aromatic heterocyclyl-carbonyl)amino (e.g., oxiranylcarbonylamino, azetidinylcarbonylamino, oxetanylcarbonylamino etc.);
(54) thiol;
(55) $C_{1-6}$ alkylsulfanyl (e.g., methylsulfanyl, ethylsulfanyl etc.);
(56) $C_{2-6}$ alkenylsulfanyl (e.g., ethenylsulfanyl, propenylsulfanyl etc.);
(57) $C_{2-6}$ alkynylsulfanyl (e.g., ethynylsulfanyl, propynylsulfanyl, butynylsulfanyl, pentynylsulfanyl, hexynylsulfanyl etc.);
(58) $C_{3-8}$ cycloalkylsulfanyl (e.g., cyclopropylsulfanyl, cyclobutylsulfanyl etc.);
(59) $C_{3-8}$ cycloalkenylsulfanyl (e.g., cyclopropenylsulfanyl, cyclobutenylsulfanyl etc.);
(60) $C_{6-10}$ arylsulfanyl (e.g., phenylsulfanyl etc.);
(61) $C_{3-8}$ cycloalkyl-$C_{1-6}$ alkyl-sulfanyl (e.g., cyclopropylmethylsulfanyl etc.);
(62) $C_{3-8}$ cycloalkenyl-$C_{1-6}$ alkyl-sulfanyl (e.g., cyclopentenylmethylsulfanyl etc.);
(63) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);
(64) a 8- to 12-membered condensed aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.);

(65) a 3- to 8-membered (preferably 5- or 6-membered) non-aromatic heterocyclic group (e.g., oxiranyl, azetidinyl, oxetanyl, thietanyl, pyrrolidinyl, tetrahydrofuryl, thioranyl, piperidinyl etc.);

(66) 5- or 6-membered monocyclic aromatic heterocyclyl-oxy (e.g., furyloxy, thienyloxy, pyrrolyloxy, oxazolyloxy, isooxazolyloxy, thiazolyloxy, isothiazolyloxy, imidazolyloxy, pyridyloxy, pyrazolyloxy etc.);

(67) 8- to 12-membered condensed aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.);

(68) 3- to 8-membered (preferably 5- or 6-membered) non-aromatic heterocyclyl-oxy (e.g., oxiranyloxy, azetidinyloxy, oxetanyloxy, thietanyloxy, pyrrolidinyloxy, tetrahydrofuryloxy, thioranyloxy, piperidinyloxy etc.);

(69) oxo;

(70) $C_{1-6}$ alkylsulfinyl (e.g., methylsulfinyl, ethylsulfinyl etc.);

(71) $C_{2-6}$ alkenylsulfinyl (e.g., ethenylsulfinyl, propenylsulfinyl etc.);

(72) $C_{2-6}$ alkynylsulfinyl (e.g., ethynylsulfinyl, propynylsulfinyl, butynylsulfinyl, pentynylsulfinyl, hexynylsulfinyl etc.);

(73) $C_{3-8}$ cycloalkylsulfinyl (e.g., cyclopropylsulfinyl, cyclobutylsulfinyl etc.);

(74) $C_{3-8}$ cycloalkenylsulfinyl (e.g., cyclopropenylsulfinyl, cyclobutenylsulfinyl etc.);

(75) $C_{6-10}$ arylsulfinyl (e.g., phenylsulfinyl etc.);

(76) $C_{3-8}$ cycloalkyl-$C_{1-6}$ alkyl-sulfinyl (e.g., cyclopropylmethylsulfinyl etc.);

(77) $C_{3-8}$ cycloalkenyl-$C_{1-6}$ alkyl-sulfinyl (e.g., cyclopentenylmethylsulfinyl etc.);

(78) $C_{1-6}$ alkyl-aminothiocarbonyl (e.g., methylaminothiocarbonyl, ethylaminothiocarbonyl, propylaminothiocarbonyl etc.);

(79) di-$C_{1-6}$ alkyl-aminothiocarbonyl (e.g., dimethylaminothiocarbonyl, diethylaminothiocarbonyl, dipropylaminothiocarbonyl etc.);

(80) carboxy;

(81) $C_{1-6}$ alkyl-oxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);

(82) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);

(83) $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);

(84) $C_{3-8}$ cycloalkyl-oxy-carbonyl (e.g., cyclopropyloxycarbonyl, cyclobutyloxycarbonyl, cyclopentyloxycarbonyl, cyclohexyloxycarbonyl etc.);

(85) $C_{3-8}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);

(86) $C_{6-10}$ aryloxy-carbonyl (e.g., phenyloxycarbonyl, 1-naphthyloxycarbonyl, 2-naphthyloxycarbonyl etc.);

(87) $C_{3-8}$ cycloalkyl-$C_{1-6}$ alkyl-oxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl etc.);

(88) $C_{3-8}$ cycloalkenyl-$C_{1-6}$ alkyl-oxy-carbonyl (e.g., cyclopentenylmethyloxycarbonyl, cyclohexenylmethyloxycarbonyl, cyclohexenylethyloxycarbonyl, cyclohexenylpropyloxycarbonyl etc.); and

(89) $C_{6-10}$ aryl-$C_{1-6}$ alkyl-oxy-carbonyl (e.g., phenylmethyloxycarbonyl, phenylethyloxycarbonyl etc.).

The "$C_{2-6}$ alkenyl-carbonyl" of the above-mentioned "$C_{2-6}$ alkenyl-carbonyl optionally having substituent(s)" is, for example, ethenylcarbonyl, propenylcarbonyl, butenylcarbonyl, pentenylcarbonyl, hexenylcarbonyl and the like.

Examples of the "substituent" of the above-mentioned "$C_{2-6}$ alkenyl-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{2-6}$ alkynyl-carbonyl" of the above-mentioned "$C_{2-6}$ alkynyl-carbonyl optionally having substituent(s)" is, for example, ethynylcarbonyl, propynylcarbonyl, butynylcarbonyl, pentynylcarbonyl, hexynylcarbonyl and the like.

Examples of the "substituent" of the above-mentioned "$C_{2-6}$ alkynyl-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{3-8}$ cycloalkyl-carbonyl" of the above-mentioned "$C_{3-8}$ cycloalkyl-carbonyl optionally having substituent(s)" is, for example, cyclopropylcarbonyl, cyclobutylcarbonyl, cyclopentylcarbonyl, cyclohexylcarbonyl, cycloheptylcarbonyl, cyclooctylcarbonyl and the like.

Examples of the "substituent" of the above-mentioned "$C_{3-8}$ cycloalkyl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkenyl-carbonyl" of the above-mentioned "$C_{3-8}$ cycloalkenyl-carbonyl optionally having substituent(s)" is, for example, cyclopropenylcarbonyl, cyclobutenylcarbonyl, cyclopentenylcarbonyl, cyclohexenylcarbonyl, cycloheptenylcarbonyl, cyclooctenylcarbonyl and the like.

Examples of the "substituent" of the above-mentioned "$C_{3-8}$ cycloalkenyl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{6-10}$ aryl-carbonyl" of the above-mentioned "$C_{6-10}$ aryl-carbonyl optionally having substituent(s)" is, for example, benzoyl, 1-naphthoyl, 2-naphthoyl and the like.

Examples of the "substituent" of the above-mentioned "$C_{6-10}$ aryl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "heterocycle" of the above-mentioned "heterocyclyl-carbonyl optionally having substituent(s)" is, for example, (1) 5- or 6-membered monocyclic aromatic heterocycle (e.g., furan, thiophene, pyrrole, oxazole, isoxazole, thiazole, isothiazole, imidazole, pyridine, pyrazole etc.), (2) 8- to 12-membered condensed aromatic heterocycle (e.g., benzofuran, isobenzofuran, benzothiophene, isobenzothiophene, indole, isoindole, 1H-indazole, benzimidazole, benzoxazole etc.), (3) 3- to 8-membered (preferably 5- or 6-membered) non-aromatic heterocycle (e.g., oxirane, azetidine, oxetane, pyrrolidine, tetrahydrofuran, thioran, piperidine etc.) and the like.

Examples of the "substituent" of the above-mentioned "heterocyclyl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{1-6}$ alkyloxy-carbonyl" of the above-mentioned "$C_{1-6}$ alkyloxy-carbonyl optionally having substituent(s)" is, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Examples of the "substituent" of the above-mentioned "$C_{1-6}$ alkyloxy-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{2-6}$ alkenyloxy-carbonyl" of the above-mentioned "$C_{2-6}$ alkenyloxy-carbonyl optionally having substituent(s)" is, for example, ethenyloxycarbonyl, propenyloxycarbonyl, butenyloxycarbonyl, pentenyloxycarbonyl, hexenyloxycarbonyl and the like.

Examples of the "substituent" of the above-mentioned "$C_{2-6}$ alkenyloxy-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{2-6}$ alkynyloxy-carbonyl" of the above-mentioned "$C_{2-6}$ alkynyloxy-carbonyl optionally having substituent(s)" is, for example, ethynyloxycarbonyl, propynyloxycarbonyl, butynyloxycarbonyl, pentynyloxycarbonyl, hexynyloxycarbonyl and the like.

Examples of the "substituent" of the above-mentioned "$C_{2-6}$ alkynyloxy-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{3-8}$ cycloalkyloxy-carbonyl" of the above-mentioned "$C_{3-8}$ cycloalkyloxy-carbonyl optionally having substituent(s)" is, for example, cyclopropyloxycarbonyl, cyclobutyloxycarbonyl, cyclopentyloxycarbonyl, cyclohexyloxycarbonyl, cycloheptyloxycarbonyl, cyclooctyloxycarbonyl and the like.

Examples of the "substituent" of the above-mentioned "$C_{3-8}$ cycloalkyloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkenyloxy-carbonyl" of the above-mentioned "$C_{3-8}$ cycloalkenyloxy-carbonyl optionally having substituent(s)" is, for example, cyclopropenyloxycarbonyl, cyclobutenyloxycarbonyl, cyclopentenyloxycarbonyl, cyclohexenyloxycarbonyl, cycloheptenyloxycarbonyl, cyclooctenyloxycarbonyl and the like.

Examples of the "substituent" of the above-mentioned "$C_{3-8}$ cycloalkenyloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkynyloxy-carbonyl" of the above-mentioned "$C_{3-8}$ cycloalkynyloxy-carbonyl optionally having substituent(s)" is, for example, cyclopropynyloxycarbonyl, cyclobutynyloxycarbonyl, cyclopentynyloxycarbonyl, cyclohexynyloxycarbonyl, cycloheptynyloxycarbonyl, cyclooctynyloxycarbonyl and the like.

Examples of the "substituent" of the above-mentioned "$C_{3-8}$ cycloalkynyloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{6-10}$ aryloxy-carbonyl" of the above-mentioned "$C_{6-10}$ aryloxy-carbonyl optionally having substituent(s)" is, for example, phenoxycarbonyl, 1-naphthyloxycarbonyl, 2-naphthyloxycarbonyl and the like.

Examples of the "substituent" of the above-mentioned "$C_{6-10}$ aryloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "heterocycle" of the above-mentioned "heterocyclyl-oxy-carbonyl optionally having substituent(s)" is, for example, (1) 5- or 6-membered monocyclic aromatic heterocycle (e.g., furan, thiophene, pyrrole, oxazole, isoxazole, thiazole, isothiazole, imidazole, pyridine, pyrazole etc.), (2) 8- to 12-membered condensed aromatic heterocycle (e.g., benzofuran, isobenzofuran, benzothiophene, isobenzothiophene, indole, isoindole, 1H-indazole, benzimidazole, benzoxazole etc.), (3) 3- to 8-membered (preferably 5- or 6-membered) non-aromatic heterocycle (e.g., oxirane, azetidine, oxetane, pyrrolidine, tetrahydrofuran, thioran, piperidine etc.) and the like.

Examples of the "substituent" of the above-mentioned "heterocyclyl-oxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The above-mentioned "carbamoyl optionally having substituent(s)" is carbamoyl optionally having 1 or 2 substituents selected from the following:
(1) cyano,
(2) $C_{1-6}$ alkyl optionally having substituent(s),
(3) $C_{2-6}$ alkenyl optionally having substituent(s),
(4) $C_{2-6}$ alkynyl optionally having substituent(s),
(5) $C_{3-8}$ cycloalkyl optionally having substituent(s),
(6) $C_{3-8}$ cycloalkenyl optionally having substituent(s),
(7) $C_{6-10}$ aryl optionally having substituent(s),
(8) a heterocyclic group optionally having substituent(s) (having a bond on the carbon atom),
(9) formyl,
(10) $C_{1-6}$ alkyl-carbonyl optionally having substituent(s),
(11) $C_{2-6}$ alkenyl-carbonyl optionally having substituent(s),
(12) $C_{2-6}$ alkynyl-carbonyl optionally having substituent(s),
(13) $C_{3-8}$ cycloalkyl-carbonyl optionally having substituent(s),
(14) $C_{3-8}$ cycloalkenyl-carbonyl optionally having substituent(s),
(15) $C_{6-10}$ aryl-carbonyl optionally having substituent(s),
(16) heterocyclyl-carbonyl optionally having substituent(s),
(17) carboxyl,
(18) $C_{1-6}$ alkyloxy-carbonyl optionally having substituent(s),
(19) $C_{2-6}$ alkenyloxy-carbonyl optionally having substituent(s),
(20) $C_{2-6}$ alkynyloxy-carbonyl optionally having substituent(s),
(21) $C_{3-8}$ cycloalkyloxy-carbonyl optionally having substituent(s),
(22) $C_{3-8}$ cycloalkenyloxy-carbonyl optionally having substituent(s),
(23) $C_{3-8}$ cycloalkynyloxy-carbonyl optionally having substituent(s),
(24) $C_{6-10}$ aryloxy-carbonyl optionally having substituent(s), and
(25) heterocyclyl-oxy-carbonyl optionally having substituent(s).

Examples of the above-mentioned "$C_{1-6}$ alkyl optionally having substituent(s)", "$C_{2-6}$ alkenyl optionally having substituent(s)", "$C_{2-6}$ alkynyl optionally having substituent(s)", "$C_{3-8}$ cycloalkyl optionally having substituent(s)", "$C_{3-8}$ cycloalkenyl optionally having substituent(s)", "$C_{6-10}$ aryl optionally having substituent(s)" and "heterocyclic group optionally having substituent(s) (having a bond on the carbon atom)" include those exemplified as the "group via a carbon atom" below.

Examples of the above-mentioned "$C_{1-6}$ alkyl-carbonyl optionally having substituent(s)", "$C_{2-6}$ alkenyl-carbonyl optionally having substituent(s)", "$C_{2-6}$ alkynyl-carbonyl optionally having substituent(s)", "$C_{3-8}$ cycloalkyl-carbonyl optionally having substituent(s)", "$C_{3-8}$ cycloalkenyl-carbonyl optionally having substituent(s)", "$C_{6-10}$ aryl-carbonyl optionally having substituent(s)", "heterocyclyl-carbonyl optionally having substituent(s)", "$C_{1-6}$ alkyloxy-carbonyl optionally having substituent(s)", "$C_{2-6}$ alkenyloxy-carbonyl optionally having substituent(s)", "$C_{2-6}$ alkynyloxy-carbonyl optionally having substituent(s)", "$C_{3-8}$ cycloalkyloxy-carbonyl optionally having substituent(s)", "$C_{3-8}$ cycloalkenyloxy-carbonyl optionally having substituent(s)", "$C_{3-8}$ cycloalkynyloxy-carbonyl optionally having substituent(s)", "$C_{6-10}$ aryloxy-carbonyl optionally having substituent(s)" and "heterocyclyl-oxy-carbonyl optionally having substituent(s)" include those exemplified as the aforementioned "acyl".

In the present specification, examples of the "cyclic group" of the "cyclic group optionally having substituent(s)" include an aromatic hydrocarbon group, an aromatic heterocyclic group (e.g., monocyclic aromatic heterocyclic group, condensed aromatic heterocyclic group), a nonaromatic cyclic hydrocarbon group, a nonaromatic heterocyclic group, a fused ring group thereof and the like.

Examples of the aromatic hydrocarbon group include $C_{6-10}$ aryl and the like. Specifically, phenyl, 1-naphthyl, 2-naphthyl and the like can be mentioned.

Examples of the monocyclic aromatic heterocyclic group include a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like.

Examples of the monocyclic aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,3,5-triazin-2-yl) and the like.

Examples of the "condensed aromatic heterocyclic group" include a group wherein a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like is condensed with $C_{6-10}$ aryl and the like; a group wherein the above-mentioned 5- to 7-membered monocyclic aromatic heterocyclic groups are condensed and the like.

Examples of the condensed aromatic heterocyclic group include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl), indolyl (e.g., indol-1-yl, indol-3-yl, indol-4-yl, indol-5-yl, indol-6-yl), indazolyl (e.g., 1H-indazol-3-yl), pyrrolopyrazinyl (e.g., 1H-pyrrolo[2, 3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisooxazolyl (e.g., 3-benzisooxazolyl), benzotriazolyl (e.g., 1H-1,2,3-benzotriazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the nonaromatic cyclic hydrocarbon group include cycloalkyl, cycloalkenyl, cycloalkadienyl and the like, each of which may be condensed with a benzene ring.

Examples of the nonaromatic cyclic hydrocarbon group include $C_{3-8}$ cycloalkyl (e.g., cyclopropyl, cyclobutyl, cyclopentyl, cyclohexyl, cycloheptyl, cyclooctyl), $C_{3-8}$ cycloalkenyl (e.g., cyclopropenyl, cyclobutenyl, cyclopentenyl, cyclohexenyl, cycloheptenyl, cyclooctenyl), $C_{4-10}$ cycloalkadienyl (e.g., cyclobutadienyl, cyclopentadienyl, cyclohexadienyl, cycloheptadienyl, cyclooctadienyl, cyclononadienyl, cyclodecadienyl), a fused ring group wherein these groups and a benzene ring are condensed (e.g., indanyl (e.g., 1-indanyl), tetrahydronaphthyl (e.g., 1,2,3,4-tetrahydronaphthalen-1-yl), fluorenyl (e.g., 9-fluorenyl) etc.) and the like.

Examples of the nonaromatic heterocyclic group include a 3- to 8-membered (preferably 5- or 6-membered) saturated or unsaturated (preferably saturated) nonaromatic heterocyclic group and the like.

Examples of the nonaromatic heterocyclic group include oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 1-pyrrolidinyl, 2-pyrrolidinyl, 3-pyrrolidinyl), tetrahydrofuryl (e.g., 2-tetrahydrofuryl, 3-tetrahydrofuryl), thioranyl (e.g., 2-thioranyl), piperidinyl (e.g., 1-piperidinyl, 2-piperidinyl, 3-piperidinyl, 4-piperidinyl), tetrahydropyranyl (e.g., 2-tetrahydropyranyl, 3-tetrahydropyranyl, 4-tetrahydropyranyl), thianyl (e.g., 2-thianyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 2-azepanyl), oxepanyl (e.g., 2-oxepanyl), thiepanyl (e.g., 2-thiepanyl), oxazepanyl (e.g., 1,4-oxazepan-5-yl), thiazepanyl (e.g., 1,4-thiazepan-5-yl), azocanyl (e.g., 2-azocanyl), oxocanyl (e.g., 2-oxocanyl), thiocanyl (e.g., 2-thiocanyl), oxazocanyl (e.g., 1,4-oxazocan-5-yl), thiazocanyl (e.g., 1,4-thiazocan-5-yl), dioxinyl (e.g., 2-dioxinyl) and the like.

In the present specification, examples of the "substituent" of the "cyclic group optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

In the present specification, the "halogen atom" is a fluorine atom, a chlorine atom, a bromine atom or an iodine atom.

In the present specification, the "group via a carbon atom" is
(1) cyano,
(2) alkyl (e.g., $C_{1-6}$ alkyl) optionally having substituent(s),
(3) alkenyl (e.g., $C_{2-6}$ alkenyl) optionally having substituent(s),
(4) alkynyl (e.g., $C_{2-6}$ alkynyl) optionally having substituent(s),
(5) cycloalkyl (e.g., $C_{3-8}$ cycloalkyl) optionally having substituent(s),
(6) cycloalkenyl (e.g., $C_{3-8}$ cycloalkenyl) optionally having substituent(s),
(7) aryl (e.g., $C_{6-10}$ aryl) optionally having substituent(s),
(8) acyl,
(9) a heterocyclic group optionally having substituent(s) (having a bond on the carbon atom), and the like.

The "$C_{1-6}$ alkyl" of the above-mentioned "$C_{1-6}$ alkyl optionally having substituent(s)" is, for example, methyl, ethyl, propyl, isopropyl, butyl, isobutyl, sec-butyl, tert-butyl, pentyl, hexyl and the like.

Examples of the "substituent" of the above-mentioned "$C_{1-6}$ alkyl optionally having substituent(s)" include a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{2-6}$ alkenyl" of the above-mentioned "$C_{2-6}$ alkenyl optionally having substituent(s)" is, for example, ethenyl, propenyl, butenyl, pentenyl, hexenyl and the like.

Examples of the "substituent" of the above-mentioned "$C_{2-6}$ alkenyl optionally having substituent(s)" include a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{2-6}$ alkynyl" of the above-mentioned "$C_{2-6}$ alkynyl optionally having substituent(s)" is, for example, ethynyl, propynyl, butynyl, pentynyl, hexynyl and the like.

Examples of the "substituent" of the above-mentioned "$C_{2-6}$ alkynyl optionally having substituent(s)" include a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkyl" of the above-mentioned "$C_{3-8}$ cycloalkyl optionally having substituent(s)" is, for example, cyclopropyl, cyclobutyl, cyclopentyl, cyclohexyl, cycloheptyl, cyclooctyl and the like.

Examples of the "substituent" of the above-mentioned "$C_{3-8}$ cycloalkyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkenyl" of the above-mentioned "$C_{3-8}$ cycloalkenyl optionally having substituent(s)" is, for example, cyclopropenyl, cyclobutenyl, cyclopentenyl, cyclohexenyl, cycloheptenyl, cyclooctenyl and the like.

Examples of the "substituent" of the above-mentioned "$C_{3-8}$ cycloalkenyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{6-10}$ aryl" of the above-mentioned "$C_{6-10}$ aryl optionally having substituent(s)" is, for example, phenyl, 1-naphthyl, 2-naphthyl and the like.

Examples of the "substituent" of the above-mentioned "$C_{6-10}$ aryl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom, $C_{2-6}$ alkynyl (e.g., ethynyl) and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

Examples of the above-mentioned "heterocyclic group optionally having substituent(s) (having a bond on the carbon atom)" include an aromatic heterocyclic group (e.g., monocyclic aromatic heterocyclic group, condensed aromatic heterocyclic group), a nonaromatic heterocyclic group and the like.

Examples of the monocyclic aromatic heterocyclic group include a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like.

Examples of the monocyclic aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 2-imidazolyl, 4-imidazolyl, 5-imidazolyl), pyrazolyl (e.g., 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-4-yl), tetrazolyl (e.g., tetrazol-5-yl), triazinyl (e.g., 1,3,5-triazin-2-yl) and the like.

Examples of the condensed aromatic heterocyclic group include a group wherein a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like is condensed with $C_{6-10}$ aryl and the like; a group wherein the above-mentioned 5- to 7-membered monocyclic aromatic heterocyclic groups are condensed and the like.

Examples of the condensed aromatic heterocyclic group include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-2-yl, benzimidazol-5-yl), indolyl (e.g., indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisooxazolyl (e.g., 3-benzisooxazolyl), benzotriazolyl (e.g., 1H-1,2,3-benzotriazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the nonaromatic heterocyclic group include a 3- to 8-membered (preferably 5- or 6-membered) saturated or unsaturated (preferably saturated) nonaromatic heterocyclic group and the like.

Examples of the nonaromatic heterocyclic group include oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 2-pyrrolidinyl, 3-pyrrolidinyl), tetrahydrofuryl (e.g., 2-tetrahydrofuryl, 3-tetrahydrofuryl), thioranyl (e.g., 2-thioranyl), piperidinyl (e.g., 2-piperidinyl, 3-piperidinyl, 4-piperidinyl), tetrahydropyranyl (e.g., 2-tetrahydropyranyl, 3-tetrahydropyranyl, 4-tetrahydropyranyl), thianyl (e.g., 2-thianyl), morpholinyl (e.g., 2-morpholinyl, 3-morpholinyl), thiomorpholinyl (e.g., 2-thiomorpholinyl, 3-thiomorpholinyl), piperazinyl (e.g., 2-piperazinyl), azepanyl (e.g., 2-azepanyl), oxepanyl (e.g., 2-oxepanyl), thiepanyl (e.g., 2-thiepanyl), oxazepanyl (e.g., 1,4-oxazepan-5-yl), thiazepanyl (e.g., 1,4-thiazepan-5-yl), azocanyl (e.g., 2-azocanyl), oxocanyl (e.g., 2-oxocanyl), thiocanyl (e.g., 2-thiocanyl), oxazocanyl (e.g., 1,4-oxazocan-5-yl), thiazocanyl (e.g., 1,4-thiazocan-5-yl), dioxinyl (e.g., 2-dioxinyl) and the like.

Examples of the "substituent" of the above-mentioned "heterocyclic group optionally having substituent(s) (having a bond on the carbon atom)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

In the present specification, examples of the "group via a nitrogen atom" include (1) nitro and (2) amino optionally having 1 or 2 of the above-mentioned "group via a carbon atom".

In the present specification, examples of the "group via an oxygen atom" include hydroxy optionally having one "group via a carbon atom" mentioned above.

In the present specification, examples of the "group via a sulfur atom" include thiol optionally having one "group via a carbon atom" or "group via a nitrogen atom" mentioned above, which group may be oxidized.

In the present specification, the "aromatic hydrocarbon group optionally having substituent(s)" is $C_{6-10}$ aryl optionally having substituent(s), and examples of the "$C_{6-10}$ aryl optionally having substituent(s)" include those similar to the "$C_{6-10}$ aryl optionally having substituent(s)" explained in the above-mentioned "group via a carbon atom".

In the present specification, the "monocycle optionally further having substituent(s)" for ring $A^a$ is monocycle optionally having substituent(s) other than the substituents shown in the formulas.

The "monocycle" is (1) $C_{3-8}$ cycloalkane (e.g., cyclopropane, cyclobutane, cyclopentane, cyclohexane, cycloheptane, cyclooctane), (2) $C_{3-8}$ cycloalkene (e.g., cyclopropene, cyclobutene, cyclopentene, cyclohexene, cycloheptene, cyclooctene), (3) benzene, (4) monocyclic aromatic heterocycle (e.g., furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine), (5) monocyclic non-aromatic heterocycle (e.g., oxirane, azetidine, oxetane, pyrrolidine, tetrahydrofuran, thioran, piperidine, tetrahydropyran, morpholine, thiomorpholine, piperazine, azepane, oxepane, thiepane, oxazepane, thiazepane) and the like.

Examples of the "substituent" of the "monocycle optionally further having substituent(s)" for ring $A^a$ include (1) $C_{1-8}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

In the present specification, the "ring optionally further having substituent(s)" for ring $A^b$ or ring $A^c$ is a ring optionally having substituent(s) other than the substituents shown in the formulas.

Examples of the "ring" include (1) an aromatic hydrocarbon ring, (2) a monocyclic aromatic heterocycle, (3) a condensed aromatic heterocycle, (4) a nonaromatic cyclic hydrocarbon ring, (5) a non-aromatic heterocycle, (6) a fused ring thereof and the like.

Examples of the "aromatic hydrocarbon ring" include a benzene ring, a naphthalene ring and the like.

Examples of the "monocyclic aromatic heterocycle" include a 5- to 7-membered monocyclic aromatic heterocycle containing, as ring-constituting atom(s) besides carbon atoms, 1 to 4 hetero atoms selected from an oxygen atom, a sulfur atom (optionally oxidized) and a nitrogen atom, and the like.

Specifically, furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazole and the like can be mentioned.

Examples of the "condensed aromatic heterocycle" include a condensed aromatic heterocycle wherein a 5- to 7-membered monocyclic aromatic heterocycle containing, as ring-constituting atom(s) besides carbon atoms, 1 to 4 hetero atoms selected from an oxygen atom, a sulfur atom (optionally oxidized) and a nitrogen atom, and the like and an aromatic hydrocarbon ring and the like are condensed; a condensed aromatic heterocycle wherein the above-mentioned 5- to 7-membered monocyclic aromatic heterocycles are condensed and the like.

Examples of the "condensed aromatic heterocycle" include quinoline, quinazoline, quinoxaline, benzofuran, benzothiophene, benzoxazole, benzothiazole, benzimidazole, indole, indazole, pyrrolopyrazine, imidazopyridine, imidazopyrazine, benzisoxazole, benzotriazole, pyrazolopyridine, pyrazolothiophene, pyrazolotriazine and the like.

Examples of the "nonaromatic cyclic hydrocarbon ring" include cycloalkane, cycloalkene, cycloalkadiene and the like, each of which may be condensed with a benzene ring.

Examples of the "nonaromatic cyclic hydrocarbon ring" include $C_{3-8}$ cycloalkane (e.g., cyclopropane, cyclobutane, cyclopentane, cyclohexane, cycloheptane, cyclooctane), $C_{3-8}$ cycloalkene (e.g., cyclopropene, cyclobutene, cyclopentene, cyclohexene, cycloheptene, cyclooctene), $C_{4-10}$ cycloalkadiene (e.g., cyclobutadiene, cyclopentadiene, cyclohexadiene, cycloheptadiene, cyclooctadiene, cyclononadiene, cyclodecadiene), a fused ring wherein these rings and a benzene ring are condensed (e.g., indane, tetrahydronaphthalene, fluorene etc.) and the like.

Examples of the "non-aromatic heterocycle" include a 3- to 8-membered (preferably 5- or 6-membered) saturated or unsaturated (preferably saturated) non-aromatic heterocycle and the like.

Examples of the "non-aromatic heterocycle" include oxirane, azetidine, oxetane, pyrrolidine, tetrahydrofuran, thioran, piperidine, tetrahydropyran, morpholine, thiomorpholine, piperazine, azepane, oxepane, thiepane, oxazepane, thiazepane and the like.

Examples of the "substituent" of the "ring optionally further having substituent(s)" for ring $A^b$ and ring $A^c$ include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

In the following, compound (i)-compound (iii) are explained in detail.

1. Compound (i)

$R^{1a}$ is acyl, or a cyclic group optionally having substituent(s).

Preferred as $R^{1a}$ is acyl. Especially,
(1) $C_{1-6}$ alkyl-carbonyl optionally having substituent(s), or
(2) $C_{3-8}$ cycloalkyl-carbonyl optionally having substituent(s) is preferable.

Particularly preferred as $R^{1a}$ is
(1) $C_{1-6}$ alkyl-carbonyl optionally having 1 to 3 halogen atoms (particularly, trifluoromethylcarbonyl), or
(2) $C_{3-8}$ cycloalkyl-carbonyl (particularly, cyclopropylcarbonyl).

$R^{2a}$ is a hydrogen atom, a halogen atom, a group via a carbon atom, a group via a nitrogen atom, a group via an oxygen atom or a group via a sulfur atom.

Preferred as $R^{2a}$ is a hydrogen atom.

$R^{3a}$ is a hydrogen atom, a halogen atom, a group via a carbon atom, a group via a nitrogen atom, a group via an oxygen atom or a group via a sulfur atom.

Preferred as $R^{3a}$ is a hydrogen atom.

$R^{4a}$ is an aromatic hydrocarbon group optionally having substituent(s).

Preferred as $R^{4a}$ is aryl (e.g., $C_{6-10}$ aryl) optionally having substituent(s). Especially, $C_{6-10}$ aryl (particularly, phenyl) optionally having 1 to 3 substituents selected from
(1) $C_{3-8}$ cycloalkyl (particularly, cyclopropyl) optionally having cyano, and
(2) $C_{1-6}$ alkyl (e.g., methyl, isopropyl) optionally having 1 to 3 substituents selected from a halogen atom and cyano are preferable.

$R^{5a}$ is a hydrogen atom, a halogen atom, a group via a carbon atom, a group via a nitrogen atom, a group via an oxygen atom or a group via a sulfur atom.

Preferred as $R^{5a}$ is a hydrogen atom.

$R^{6a}$ is a hydrogen atom, a halogen atom, a group via a carbon atom, a group via a nitrogen atom, a group via an oxygen atom or a group via a sulfur atom.

Preferred as $R^{6a}$ is a hydrogen atom.

$X^a$ is —CO—, —CR$^{7a}$R$^{8a}$— wherein R$^{7a}$ and R$^{8a}$ are the same or different and each is a hydrogen atom, a group via a carbon atom, a group via a nitrogen atom, a group via an oxygen atom or a group via a sulfur atom, —NR$^{9a}$— wherein R$^{9a}$ is a hydrogen atom, or a group via a carbon atom, —O—, —S—, —S(O)— or —S(O)$_2$—.

Preferred as $X^a$ is —O—.

$Y^a$ is —NH—, —NHCO—, —CONH— or —NHCONH—.

Preferred as $Y^a$ is —NHCO—.

Ring $A^a$ is a monocycle optionally further having substituent(s). Preferred as ring $A^a$ is a benzene ring optionally further having substituent(s), particularly preferably a benzene ring without additional substituents.

Preferred as compound (i) is the compounds described in Examples A1-A5 and the like.

2. Compound (ii)

$R^{1b}$ is acyl, or a cyclic group optionally having substituent(s).

Preferred as $R^{1b}$ is acyl. Especially, $C_{3-8}$ cycloalkyl-carbonyl optionally having substituent(s) is preferable. Particularly preferred as $R^{1b}$ is $C_{3-8}$ cycloalkyl-carbonyl (particularly, cyclopropylcarbonyl).

$R^{2b}$ is a hydrogen atom, a halogen atom, a group via a carbon atom, a group via a nitrogen atom, a group via an oxygen atom or a group via a sulfur atom.

Preferred as $R^{2b}$ is a hydrogen atom.

$R^{3b}$ is an aromatic hydrocarbon group optionally having substituent(s).

Preferred as $R^{3b}$ is aryl (e.g., $C_{8-10}$ aryl) optionally having substituent(s). Particularly, $C_{8-10}$ aryl (particularly, phenyl) optionally having a substituent selected from (1) $C_{3-8}$ cycloalkyl (particularly, cyclopropyl) optionally having cyano, and (2) $C_{1-8}$ alkyl (e.g., methyl, isopropyl) optionally having 1 to 3 substituents selected from a halogen atom and cyano are preferable.

$R^{4b}$ is a hydrogen atom, a halogen atom, a group via a carbon atom, a group via a nitrogen atom, a group via an oxygen atom or a group via a sulfur atom.

Preferred as $R^{4b}$ is a hydrogen atom.

$R^{5b}$ is a hydrogen atom, a halogen atom, a group via a carbon atom, a group via a nitrogen atom, a group via an oxygen atom or a group via a sulfur atom.

Preferred as $R^{5b}$ is a hydrogen atom.

$X^{b}$ is —CO—, —$CR^{6b}R^{7b}$— wherein $R^{6b}$ and $R^{7b}$ are the same or different and each is a hydrogen atom, a group via a carbon atom, a group via a nitrogen atom, a group via an oxygen atom or a group via a sulfur atom, —$NR^{8b}$— wherein $R^{8b}$ is a hydrogen atom or a group via a carbon atom, —O—, —S—, —S(O)— or —$S(O)_2$—.

Preferred as $X^{b}$ is —O—.

$Y^{b}$ is —NH—, —NHCO—, —CONH— or —NHCONH—.

Preferred as $Y^{b}$ is —NHCO—.

Ring $A^{b}$ is a monocycle optionally further having substituent(s). Preferred as ring $A^{b}$ is a benzene ring optionally further having substituent(s). Especially, a benzene ring optionally having one $C_{1-6}$ alkyl optionally having 1 to 3 substituents selected from a halogen atom and cyano is preferable, and a benzene ring optionally having one methyl is particularly preferable.

Preferred as the compound of the present invention is the compounds described in Examples B1-B6 and the like.

3. Compound (iii)

$R^{1c}$ is acyl, or a cyclic group optionally having substituent(s).

Preferred as $R^{1c}$ is acyl. Especially, (1) alkylcarbonyl (e.g., $C_{1-6}$ alkyl-carbonyl) optionally having substituent(s), (2) alkenyl-carbonyl (e.g., $C_{2-6}$ alkenyl-carbonyl) optionally having substituent(s), (3) cycloalkyl-carbonyl (e.g., $C_{3-8}$ cycloalkyl-carbonyl) optionally having substituent(s), or (4) heterocyclylcarbonyl optionally having substituent(s) is preferable. Particularly, (1) $C_{1-6}$ alkyl-carbonyl (particularly, acetyl, ethylcarbonyl, isopropylcarbonyl) optionally having 1 to 3 substituents selected from (i) hydroxy, (ii) $C_{1-6}$ alkyl-oxy (particularly, methoxy), (iii) di-$C_{1-6}$ alkylamino (particularly, dimethylamino), and (iv) a 5- or 6-membered nonaromatic heterocyclic group (particularly, piperidinyl, piperazinyl, morpholino, thiomorpholino wherein sulfur atom may be dioxidized) optionally having 1 or 2 substituents selected from (a) hydroxy, (b) a halogen atom (particularly, fluorine atom), (c) $C_{1-6}$ alkyl (particularly, methyl, ethyl) optionally substituted by hydroxy, and (d) $C_{3-8}$ cycloalkyl (particularly, cyclopropyl), and (v) a halogen atom (particularly, chlorine atom), (2) $C_{2-6}$ alkenyl-carbonyl (particularly, ethenylcarbonyl) having substituent(s) selected from (i) $C_{6-10}$ aryl (particularly, phenyl) optionally having 1 to 3 halogen atoms (particularly, chlorine atom), and (ii) a 5- or 6-membered monocyclic aromatic heterocyclic group (particularly, furyl), (3) $C_{3-8}$ cycloalkyl-carbonyl (particularly, cyclopropylcarbonyl) optionally having 1 to 3 $C_{1-6}$ alkyl (particularly, methyl, isopropyl), or (4) 5- or 6-membered monocyclic aromatic heterocyclyl-carbonyl (particularly, oxazolylcarbonyl, imidazolylcarbonyl, pyrazolylcarbonyl, pyridylcarbonyl) optionally having one $C_{1-6}$ alkyl (particularly, methyl, isopropyl) is preferable.

$R^{2c}$ is an aromatic hydrocarbon group optionally having substituent(s).

Preferred as $R^{2c}$ is aryl (e.g., $C_{6-10}$ aryl) optionally having substituent(s). Particularly, $C_{6-10}$ aryl (particularly phenyl) optionally having 1 or 2 substituents selected from (1) a halogen atom (particularly, chlorine atom), (2) $C_{3-8}$ cycloalkyl (particularly, cyclopropyl, cyclobutyl) optionally having cyano, (3) $C_{1-6}$ alkyl-oxy (particularly, methoxy, ethoxy, isopropoxy, tert-butoxy) optionally having 1 to 5 (especially 1 to 4, particularly 1 to 3) substituents selected from a halogen atom (particularly, fluorine atom) and cyano, and (4) $C_{1-6}$ alkyl (e.g., methyl, ethyl, propyl, isopropyl, isobutyl) optionally having 1 to 3 substituents selected from a halogen atom (particularly, fluorine atom), $C_{2-6}$ alkynyl (e.g., ethynyl) and cyano is preferable.

$R^{3c}$ is a hydrogen atom, a halogen atom, a group via a carbon atom, a group via a nitrogen atom, a group via an oxygen atom or a group via a sulfur atom.

Preferred as $R^{1a}$ is a hydrogen atom.

$R^{3c}$ is a hydrogen atom, a halogen atom, a group via a carbon atom, a group via a nitrogen atom, a group via an oxygen atom or a group via a sulfur atom.

Preferred as $R^{3c}$ is a hydrogen atom.

$X^{c}$ is —CO—, —$CR^{5c}R^{6c}$— wherein $R^{5c}$ and $R^{6c}$ are the same or different and each is a hydrogen atom, a group via a carbon atom, a group via a nitrogen atom, a group via an oxygen atom or a group via a sulfur atom, —$NR^{7c}$— wherein $R^{7c}$ is a hydrogen atom or a group via a carbon atom, —O—, —S—, —S(O)— or —$S(O)_2$—.

Preferred as $X^{c}$ is —O—, —$NR^{7c}$— wherein $R^{7c}$ is a hydrogen atom or a group via a carbon atom. Of these, —O—, —$NR^{7c'}$— wherein $R^{7c'}$ is a hydrogen atom, alkyl (e.g., $C_{1-6}$ alkyl) or cycloalkyl (e.g., $C_{3-6}$ cycloalkyl) is preferable. Furthermore, —O—, —NH—, —$N(CH_3)$—, —N(cyclopropyl)- is preferable, and particularly, —O—, —NH— or —$N(CH_3)$— is preferable.

$Y^{c}$ is —NH—, —NHCO—, —CONH— or —NHCONH—.

Preferred as $Y^c$ is —NHCO—, —CONH— or —NHCONH—, particularly preferably, —NHCO— or —CONH—.

$Z^c$ is —S—, —O— or —NR$^{8c}$— wherein R$^{8c}$ is a hydrogen atom or a group via a carbon atom. Preferred as $Z^c$ is —S—, —NR$^{8c}$— wherein R$^{8c}$ is a hydrogen atom or a group via a carbon atom. Of these, —S—, —NR$^{8c'}$— wherein R$^{8c'}$ is a hydrogen atom or alkyl (e.g., C$_{1-6}$ alkyl) is preferable, and particularly, —S— is preferable.

$Q^c$ is =CR$^{3c}$— wherein R$^{3c}$ is a hydrogen atom, a halogen atom, a group via a carbon atom, a group via a nitrogen atom, a group via an oxygen atom or a group via a sulfur atom, or =N—. Preferred as $Q^c$ is =CH— or =N—.

In a preferable embodiment, $Z^c$ and $Q^c$ are in the following combination:
(1) $Z^c$ is —S— and $Q^c$ is =CH—; or
(2) $Z^c$ is —S— and $Q^c$ is =N—.

Ring $A^c$ is a ring optionally further having substituent(s). Preferred as ring $A^c$ is a benzene ring optionally further having substituent(s). Particularly, a benzene ring optionally having 1 or 2 substituents selected from
(1) C$_{1-6}$ alkyl (e.g., methyl, ethyl) optionally having 1 to 3 halogen atoms (e.g., fluorine atom),
(2) cyano,
(3) a halogen atom (e.g., fluorine atom, chlorine atom), and
(4) C$_{1-6}$ alkyl-oxy (e.g., methoxy) is preferable.

As the compound of the present invention, the compounds described in Examples C1-C41, D1 and D2 are preferable.

As the compound of the present invention, the compounds described in C42-C45 and C47-C125 and the like are also preferable.

As the compound of the present invention, the compounds described in C126 and D3-D48 are also preferable.

As the compound of the present invention, the compounds described in C127-C130 are also preferable.

Preferable specific examples of compound (iii) or a salt thereof include the following.

(Compound III-a)
a compound represented by the formula (III) wherein R$^{1c}$ is acyl;
R$^{1c}$ is C$_{6-10}$ aryl optionally having substituent(s);
R$^{2c}$ is a hydrogen atom;
X$^c$ is —NR$^{7c}$— or —O—;
Y$^c$ is —NHCO— or —CONH—;
Q$^c$ is =CH— or =N—;
Z$^c$ is —S— or —NR$^{8c}$— (preferably —S—); and
ring A$^c$ is a benzene ring optionally further having substituent(s);
or a salt thereof.

(Compound III-b)
Compound (iii) wherein
R$^{1a}$
(1) C$_{1-6}$ alkyl-carbonyl (preferably acetyl) optionally having substituent(s) selected from (i) hydroxy and (ii) a 5- or 6-membered nonaromatic heterocyclic group (preferably, piperazinyl) optionally having C$_{1-6}$ alkyl (preferably methyl),
(2) C$_{3-8}$ cycloalkyl-carbonyl (preferably cyclopropylcarbonyl), or
(3) 5- or 6-membered monocyclic aromatic heterocyclyl-carbonyl (preferably oxazolylcarbonyl);
R$^{2c}$ is C$_{6-10}$ aryl (preferably phenyl) optionally having 1 or 2 substituents selected from
(1) a halogen atom (preferably chlorine atom),
(2) C$_{3-8}$ cycloalkyl (preferably cyclopropyl) optionally having cyano, and
(3) C$_{1-6}$ alkyl (preferably, methyl, isopropyl) optionally having 1 to 3 substituents selected from a halogen atom (preferably fluorine atom) and cyano;
R$^{4c}$ is a hydrogen atom;
X$^c$ is —O—, —NH— or —N(CH$_3$)—;
Y$^c$ is —NHCO— or —CONH—;
Z$^c$ is —S—;
Q$^c$ is =CH— or =N—; and
ring A$^c$ is a benzene ring optionally having one
(1) C$_{1-8}$ alkyl (preferably, methyl, ethyl), or
(2) C$_{1-8}$ alkyl-oxy (e.g., methoxy);
or a salt thereof.

(Compound III-c)
Compound (iii) wherein
R$^{1c}$ is
(1) C$_{1-8}$ alkyl-carbonyl (preferably, acetyl, ethylcarbonyl, isopropylcarbonyl) optionally having 1 to 3 substituents selected from
(i) hydroxy,
(ii) C$_{1-8}$ alkyl-oxy (preferably, methoxy),
(iii) di-C$_{1-6}$ alkylamino (preferably, dimethylamino) and
(iv) a 5- or 6-membered nonaromatic heterocyclic group (preferably, piperidinyl, piperazinyl, morpholino, thiomorpholino wherein sulfur atom may be dioxidized) optionally having 1 or 2 substituents selected from
(a) hydroxy,
(b) a halogen atom (preferably, fluorine atom),
(c) C$_{1-8}$ alkyl (preferably, methyl, ethyl) optionally substituted by hydroxy, and
(d) C$_{3-8}$ cycloalkyl (preferably, cyclopropyl),
(2) C$_{2-8}$ alkenyl-carbonyl (preferably, ethenylcarbonyl) having substituent(s) selected from
(i) C$_{8-10}$ aryl (preferably, phenyl) optionally having 1 to 3 halogen atoms (preferably, chlorine atom), and
(ii) 5- or 6-membered monocyclic aromatic heterocyclic group (preferably, furyl),
(3) C$_{3-8}$ cycloalkyl-carbonyl (preferably, cyclopropylcarbonyl) optionally having 1 to 3 C$_{1-8}$ alkyl (preferably, methyl), or
(4) 5- or 6-membered monocyclic aromatic heterocyclyl-carbonyl (preferably, oxazolylcarbonyl);
R$^{2c}$ is C$_{8-10}$ aryl (preferably, phenyl) optionally having 1 or 2 substituents selected from
(1) a halogen atom (preferably, chlorine atom),
(2) C$_{3-8}$ cycloalkyl (preferably, cyclopropyl, cyclobutyl) optionally having cyano,
(3) C$_{1-8}$ alkyl-oxy (preferably, methoxy, ethoxy, isopropoxy, tert-butoxy) optionally having 1 to 3 substituents selected from a halogen atom (preferably, fluorine atom) and cyano, and
(4) C$_{1-8}$ alkyl (preferably, methyl, isopropyl) optionally having 1 to 3 substituents selected from a halogen atom (preferably, fluorine atom), C$_{2-8}$ alkynyl (preferably, ethynyl) and cyano;
R$^{4c}$ is a hydrogen atom;
X$^c$ is —O—, —NH— or —N(CH$_3$)—;
Y$^c$ is —NHCO— or —CONH—;
Z$^c$ is —S—;
Q$^c$ is =CH— or =N—; and
ring A$^c$ is a benzene ring optionally having 1 or 2 substituents selected from
(1) C$_{1-8}$ alkyl (preferably, methyl, ethyl) optionally having 1 to 3 halogen atoms (preferably, fluorine atom),
(2) cyano,
(3) a halogen atom (preferably, fluorine atom, chlorine atom), and (4) $C_{1-6}$ alkyl-oxy (preferably, methoxy);
or a salt thereof.
(Compound III-d)
Compound (iii) wherein
$R^{1c}$ is
(1) $C_{1-8}$ alkyl-carbonyl (preferably, acetyl, ethylcarbonyl, isopropylcarbonyl) optionally having 1 to 3 substituents selected from
  (i) hydroxy,
  (ii) $C_{1-8}$ alkyl-oxy (preferably, methoxy),
  (iii) alkylamino (preferably, dimethylamino), and
  (iv) 5- or 6-membered nonaromatic heterocyclic group (preferably, piperidinyl, piperazinyl, morpholino, thiomorpholino wherein sulfur atom may be dioxidized) optionally having 1 or 2 substituents selected from
    (a) hydroxy,
    (b) a halogen atom (preferably, fluorine atom),
    (c) $C_{1-6}$ alkyl (preferably, methyl, ethyl) optionally substituted by hydroxy, and
    (d) $C_{3-8}$ cycloalkyl (preferably, cyclopropyl), and
  (v) a halogen atom (preferably, chlorine atom),
(2) $C_{2-6}$ alkenyl-carbonyl (preferably, ethenylcarbonyl) having substituent(s) selected from
  (i) $C_{6-10}$ aryl (preferably, phenyl) optionally having 1 to 3 halogen atoms (preferably, chlorine atom), and
  (ii) 5- or 6-membered monocyclic aromatic heterocyclic group (preferably, furyl),
(3) $C_{3-8}$ cycloalkyl-carbonyl (preferably, cyclopropylcarbonyl) optionally having 1 to 3 $C_{1-6}$ alkyl (preferably, methyl), or
(4) 5- or 6-membered monocyclic aromatic heterocyclyl-carbonyl (preferably, oxazolylcarbonyl, imidazolylcarbonyl, pyrazolylcarbonyl, pyridylcarbonyl) optionally having one $C_{1-6}$ alkyl (preferably, methyl, isopropyl);
$R^{2c}$ is $C_{6-10}$ aryl (preferably, phenyl) optionally having 1 or 2 substituents selected from
(1) a halogen atom (preferably, chlorine atom),
(2) $C_{3-8}$ cycloalkyl (preferably, cyclopropyl, cyclobutyl) optionally having cyano,
(3) $C_{1-6}$ alkyl-oxy (preferably, methoxy, ethoxy, isopropoxy, tert-butoxy)optionally having 1 to 5 (especially 1 to 4, particularly 1 to 3) substituents selected from a halogen atom (preferably, fluorine atom) and cyano, and
(4) $C_{1-6}$ alkyl (preferably, methyl, ethyl, propyl, isopropyl, isobutyl) optionally having 1 to 3 substituents selected from a halogen atom (preferably, fluorine atom), $C_{2-6}$ alkynyl (preferably, ethynyl) and cyano;
$R^{4c}$ is a hydrogen atom;
$X^c$ is —O—, —NH—, —N(CH_3)— or —N(cyclopropyl)—;
$Y^c$ is —NHCO— or —CONH—;
$Z^c$ is —S—;
$Q^c$ is =CH— or =N—; and
ring $A^c$ is a benzene ring optionally having 1 or 2 substituents selected from
(1) $C_{1-6}$ alkyl (preferably, methyl, ethyl) optionally having 1 to 3 halogen atoms (preferably, fluorine atom),
(2) cyano,
(3) a halogen atom (preferably, fluorine atom, chlorine atom), and
(4) $C_{1-6}$ alkyl-oxy (preferably, methoxy);
or a salt thereof.
(Compound III-e)
Compound (III-d) wherein
$Q^c$ is =CH—, or a salt thereof.
(Compound III-f)
Compound (III-d) wherein $Q^c$ is =N—, or a salt thereof.
(Compound III-g)
(1) 2-chloro-3-(1-cyano-1-methylethyl)-N-[5-({2-[(cyclopropylcarbonyl)amino][1,3]thiazolo[5,4-b]pyridin-5-yl}oxy)-2-fluorophenyl]benzamide (Example C63);
(2) N-(5-{[2-(acetylamino)[1,3]thiazolo[5,4-b]pyridin-5-yl]oxy}-2-fluorophenyl)-2-chloro-3-(1-cyanocyclopropyl)benzamide (Example C65);
(3) 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide (Example C66);
(4) 2-chloro-3-(1-cyanocyclopropyl)-N-[5-({2-[(cyclopropylcarbonyl)amino][1,3]thiazolo[5,4-b]pyridin-5-yl}oxy)-2,4-difluorophenyl]benzamide (Example C75);
(5) 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide (Example C122);
(6) 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide benzenesulfonate (Example C124);
(7) 2-chloro-3-(1-cyano-1-methylethoxy)-N-[5-({2-[(cyclopropylcarbonyl)amino][1,3]thiazolo[5,4-b]pyridin-5-yl}amino)-2-fluorophenyl]benzamide (Example C126);
(8) 3-(1-cyano-1-methylethyl)-N-{3-[methyl(2-{[(4-methylpiperazin-1-yl)acetyl]amino)[1,3]thiazolo[5,4-d]pyrimidin-5-yl)amino]phenyl}benzamide (Example D11); or
(9) N-(3-{[2-(acetylamino)[1,3]thiazolo[5,4-d]pyrimidin-5-yl]amino}-4-methylphenyl)-2-chloro-3-(1-cyano-1-methylethyl)benzamide (Example D35);
or a salt thereof.

Examples of the salt of compound (i), compound (ii) and compound (iii) (to be sometimes abbreviated as the compound of the present invention in the specification) include metal salt, ammonium salt, a salt with organic base, a salt with inorganic acid, a salt with organic acid, a salt with basic or acidic amino acid and the like. Preferable examples of the metal salt include alkali metal salt such as sodium salt, potassium salt and the like; alkaline earth metal salt such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like, and preferable examples of the salt with acidic amino acid include a salt with aspartic acid, glutamic acid and the like.

Of these, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

The production methods of the compound of the present invention are explained below.

In the present production methods, halogenated hydrocarbons, aromatic hydrocarbons, alcohols and ethanol as solvents are, for example, the following solvents.

halogenated hydrocarbons:

dichloromethane, chloroform, carbon tetrachloride, 1,2-dichloroethane etc.

aromatic hydrocarbons:

benzene, toluene, xylene etc.

alcohols:

methanol, ethanol, isopropanol, t-butanol etc.

ethers:

diethyl ether, tetrahydrofuran, dioxane etc.

In the present production methods, pyridine hydrochloride, pyridine hydrobromide, pyridine p-toluenesulfonate, quinoline hydrochloride, isoquinoline hydrochloride, pyrimidine hydrochloride, pyrazine hydrochloride, triazine hydrochloride, trimethylamine hydrochloride, triethylamine hydrochloride, N-ethyldiisopropylamine hydrochloride and the like are used as ammonium salts.

In the present production methods, an inorganic base, an organic base and the like are used as a base. Specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium t-butoxide, sodium hydride, sodium amide, diazabicycloundecene (DBU) and the like are used.

In the present production methods, palladium complexes described in, for example, J. Am. Chem. Soc. 1994, 116, 5969-5970, J. Am. Chem. Soc. 1994, 116, 7901-7902, Pure Appl. Chem., 71(8), 1417-1423, 1999 and the like, and the like are used as palladium complexes.

In the present production methods, lithium, sodium, potassium, cesium and the like are used as alkali metals.

In the present production methods, magnesium, calcium and the like are used as alkaline earth metals.

In the present production methods, for example, trityl, 4-methoxybenzyl, acetamidomethyl, tert-butyl and the like can be mentioned as mercapto-protecting groups.

In the present production methods, a starting material compound and a production intermediate may be salts. As such salt, those similar to the salts of the aforementioned compound of the present invention can be mentioned.

1. Production Method of Compound (i)

Compound (i) of the present invention can be obtained, for example, according to the following conversion reaction of compound (I-A) into (i), or a method analogous thereto, and the like. The reaction scheme is shown below. Each symbol in the compounds in the scheme is as defined above, and compound (I-A) encompasses compound (i).

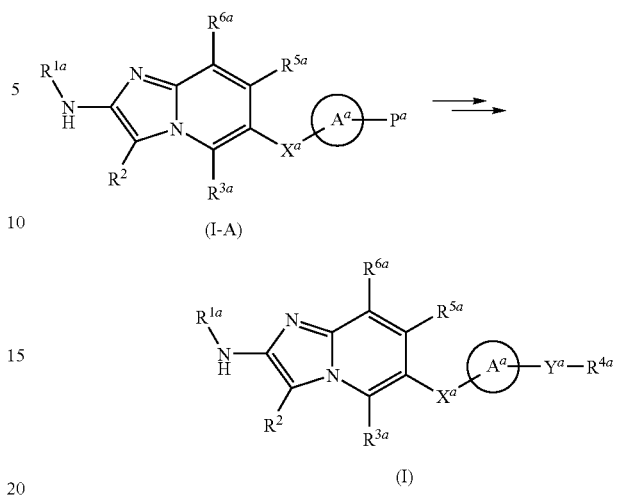

wherein $P^a$ is any functional group that can be converted to $Y^a$—$R^{4a}$, and may itself be $Y^a$—$R^{4a}$, and the other symbols are each as defined above.

In this production method, compound (i) can be obtained by converting $P^a$ of compound (I-A) to a suitable known general functional group as necessary.

Compound (i) [$Y^a$=CONH] can be obtained, for example, by subjecting compound (I-A) [$P^a$=COOH] to a known general amidation reaction, and compound (i) [$Y^a$=NHCO] or compound (i) [$Y^a$=NHCONH] can be obtained, for example, by subjecting compound (I-A) [$P^a$=COOH] to Curtius rearrangement reaction and a subsequent known general functional group conversion reaction, and a known general amidation reaction or ureation reaction.

Alternatively, compound (i) [$Y^a$=NHCO] or compound (i) [$Y^a$=NHCONH] can be obtained, for example, by converting compound (I-A) [$P^a$=NO_2$] to compound (I-A) [$P^a$=NH_2$] by a known general reduction reaction, and subjecting compound (I-A) [$P^a$=NH_2$] to a known general amidation reaction or ureation reaction. In addition, compound (i) [$Y^a$=NH] can be obtained, for example, by converting compound (I-A) [$P^a$=NO_2$] to compound (I-A) [$P^a$=NH_2$], and subjecting compound (I-A) [$P^a$=NH_2$] to a known general reductive amination reaction or a known general coupling reaction using a palladium catalyst, and the like.

Compound (I-A) can be obtained according to the following Method A, Method B, or Method C, or a method analogous thereto, and the like.

Method A:

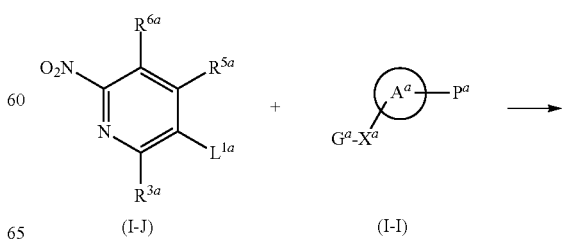

-continued

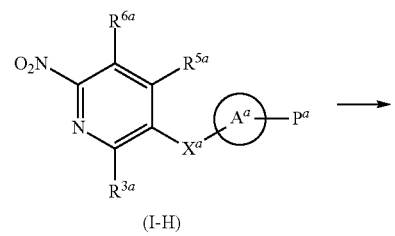

(I-H)

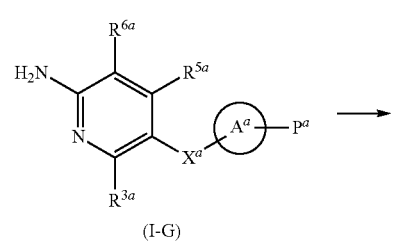

(I-G)

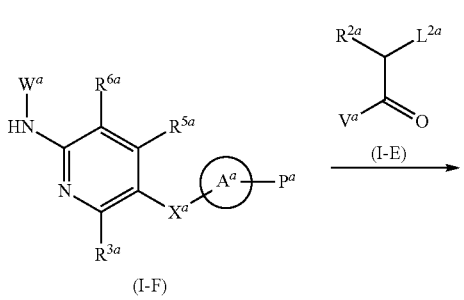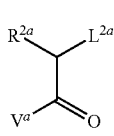

(I-F)

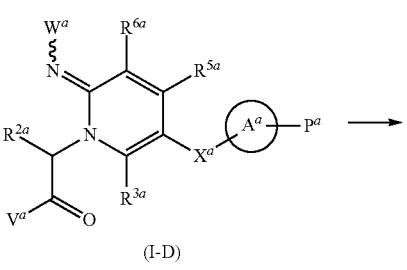

(I-D)

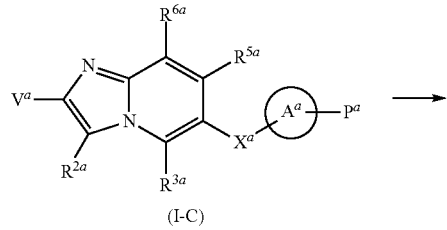

(I-C)

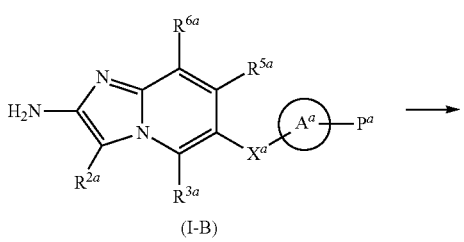

(I-B)

-continued

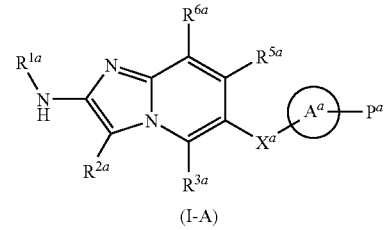

(I-A)

wherein $L^{1a}$ is a leaving group, $G^a$ is a hydrogen atom or a metal atom, $L^{2a}$ is a leaving group, $W^a$ is a hydrogen atom, alkylsulfonyl (e.g., methylsulfonyl etc.) or arylsulfonyl (e.g., p-toluenesulfonyl etc.), a wavy line means that two geometric isomers of imine are present in an optional ratio, $V^a$ is any substituent, and the other symbols are each as defined above.

Compound (I-A) ($R^{1a}$ is acyl), which is a starting material for this production method, can be produced, for example, by subjecting a compound represented by the formula:

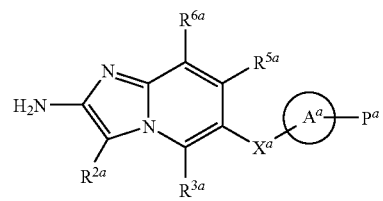

(I-B)

wherein each symbol is as defined above, or a salt thereof to a known general acylation reaction with a carboxylic acid represented by $R^{1a}$—OH ($R^{1a}$ is acyl) or a reactive derivative thereof.

Starting material compound (I-B) can be produced, for example, by subjecting a compound represented by the formula:

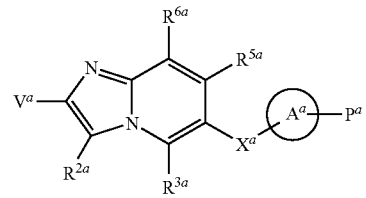

(I-C)

wherein each symbol is as defined above, to a suitable known general conversion of functional group to convert $V^a$ to an amino.

Compound (I-B) can be obtained, for example, by subjecting compound (I-C) [$V^a$=NHCOCF$_3$] to a known general deprotection of trifluoroacetyl.

Alternatively, compound (I-B) can be obtained, for example, by subjecting compound (I-C) [$V^a$=NHCOOR$^{10a}$ wherein $R^{10a}$ is $C_{1-4}$ alkyl (e.g., methyl, ethyl, propyl, t-butyl and the like)] to a known general hydrolysis of carbamate.

In addition, compound (I-B) can be obtained, for example, by subjecting compound (I-C) [$V^a$=COOR$^{11a}$ wherein $R^{11a}$ is $C_{1-4}$ alkyl (e.g., methyl, ethyl, propyl and the like), benzyl, $C_{6-10}$ aryl (e.g., phenyl, tolyl and the like)] to a known general hydrolysis of ester to give compound (I-C) [$V^a$=COOH], and subjecting the compound to Curtius rearrangement reaction and a subsequent known general functional group conversion reaction.

Starting material compound (I-C) can be produced, for example, from a compound represented by the formula:

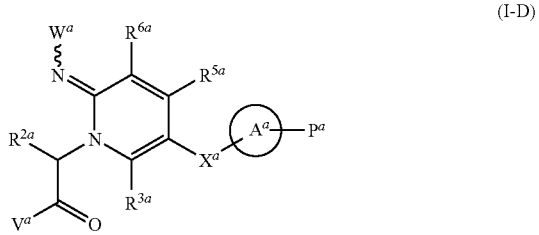

wherein each symbol is as defined above.

For example, compound (I-C) [$V^a$=NHCOCF$_3$] can be obtained, for example, by a method described in Synthesis (1998) 867-872 and the like, i.e., reacting compound (I-D) [$W^a$=SO$_2$C$_6$H$_4$(4-CH$_3$) and $V^a$=NH$_2$], with trifluoroacetic acid anhydride.

The reaction is preferably carried out in a solvent and using trifluoroacetic acid anhydride in an amount of 1 to 50 equivalents, preferably 1 to 30 equivalents, relative to compound (I-D) [$W^a$=SO$_2$C$_6$H$_4$ (4-CH$_3$) and $V^a$=NH$_2$].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under to cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr.

Starting material compound (I-D) can be produced, for example, by reacting a compound represented by the formula:

wherein each symbol is as defined above, or a salt thereof, with a compound represented by the formula:

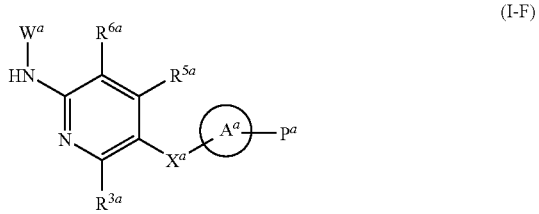

wherein each symbol is as defined above, or a salt thereof.

Compound (I-D) [$W^a$=alkylsulfonyl (e.g., methylsulfonyl etc.) or arylsulfonyl (p-toluenesulfonyl) and $V^a$=NH$_2$] can be obtained, for example, by reacting compound (I-F) [$W^a$=alkylsulfonyl (e.g., methylsulfonyl etc.) or arylsulfonyl (p-toluenesulfonyl)] with compound (I-E) [$V^a$=NH$_2$].

The reaction is preferably carried out in a solvent and using compound (I-E) [$V^a$=NH$_2$] in an amount of 1 to 5 equivalents, preferably 1 to 2 equivalents, relative to compound (I-F) [$W^a$=alkylsulfonyl (e.g., methylsulfonyl etc.) or arylsulfonyl (p-toluenesulfonyl)] or a salt thereof. In addition, a base may be used in an amount of about 1 to 10 equivalents, preferably 1 to 2 equivalents, relative to compound (I-F) [$W^a$=alkylsulfonyl (e.g., methylsulfonyl etc.) or arylsulfonyl (p-toluenesulfonyl)] or a salt thereof.

As the aforementioned leaving group for $L^{2a}$, a halogen atom such as chlorine, bromine, iodine and the like, a group represented by the formula: —S(O)$_k$R$^{12a}$ wherein k is 0, 1 or 2, and R$^{12a}$ is C$_{1-4}$ alkyl (e.g., methyl, ethyl, propyl etc.), benzyl, C$_{6-10}$ aryl (e.g., phenyl, tolyl etc.) and the like, and a group represented by the formula: —OR$^{12a}$ wherein R$^{12a}$ is as defined above, can be used.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling. (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

In addition, for example, it is known by WO2005/89763 and the like that compound (I-C) [$V^a$=NHCOR$^{10a}$ wherein R$^{10a}$ is as defined above] can be produced without going through compound (I-D) but by reacting compound (I-F) [$W^a$=H] with compound (I-E) [$V^a$=NHCOR$^{10a}$ wherein R$^{11a}$ is as defined above], and compound (I-C) [$V^a$=COOR$^{11a}$ wherein R$^{11a}$ is as defined above] can be produced without going through compound (I-D) but by reacting compound (I-F) [$W^a$=H] with compound (I-E) [$V^a$=COOR$^{11a}$ wherein R$^{11a}$ is as defined above].

Starting material compound (I-E) may be commercially available or can be produced from the corresponding starting material compound according to a method known per se.

Starting material compound (I-F) which is a compound represented by formula:

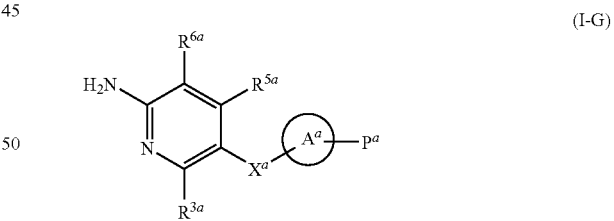

wherein each symbol is as defined above, or a salt thereof, may be directly used as compound (I-F) [$W^a$=H], or can be produced, for example, by introducing alkylsulfonyl or arylsulfonyl into compound (I-G) according to a method known per se.

The reaction is preferably carried out in a solvent and using alkylsulfonyl chloride or arylsulfonyl chloride in an amount of 1 to 5 equivalents, preferably 1 to 2 equivalents, relative to compound (I-G). In addition, a base may be used in an amount of about 1 to 10 equivalents, preferably 1 to 2 equivalents, relative to compound (I-G). As the solvent for aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (I-G) can be produced, for example, by subjecting a compound represented by the formula:

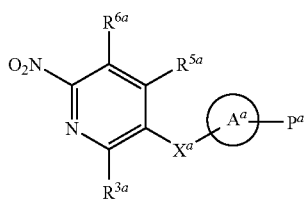

(I-H)

wherein each symbol is as defined above, to a general reduction reaction known per se to convert nitro to amino.

Compound (I-G) [$P^a$=$Y^a$—$R^{4a}$ wherein $Y^a$ is NHCO] or compound (I-G) [$P^a$=$Y^a$—$R^{4a}$ wherein $Y^a$ is NHCONH] can be obtained by converting compound (I-H) [$P^a$=$NO_2$] to compound (I-G) [$P^a$=$NH_2$] according to this reduction reaction, and subjecting the compound to a known general amidation reaction or ureation reaction.

Starting material compound (I-H) can be produced, for example, by reacting a compound represented by the formula:

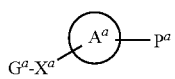

(I-I)

wherein each symbol is as defined above, or a salt thereof, with a compound represented by the formula:

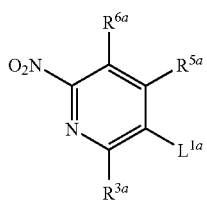

(I-J)

wherein each symbol is as defined above.

In compound (I-I), when $X^a$ is —$NR^{9a}$— [$R^{9a}$ is as defined above], —O— or —S—, $G^a$ is mainly a hydrogen atom but an alkali metal, or an alkaline earth metal can also be used.

In compound (I-J), as the leaving group represented by $L^{1a}$, those similar to the aforementioned leaving group represented by $L^{2a}$ can be mentioned.

The reaction is preferably performed in a solvent using compound (I-I) or a salt thereof in an amount of 1 to 5 equivalents, preferably 1 to 2 equivalents, relative to compound (I-J). In addition, a base or ammonium salt may be used in an amount of about 1 to 10 equivalents, preferably 1 to 2 equivalents, relative to compound (I-J).

A palladium complex may be used as a catalyst in an amount of 0.05-10 equivalents, preferably 0.05-2 equivalents, relative to compound (I-J).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The aforementioned reaction may be performed under microwave irradiation.

Starting material compound (I-I) and starting material compound (I-J) may be commercially available or can be produced from the corresponding starting material compound according to a method known per se.

Method B:

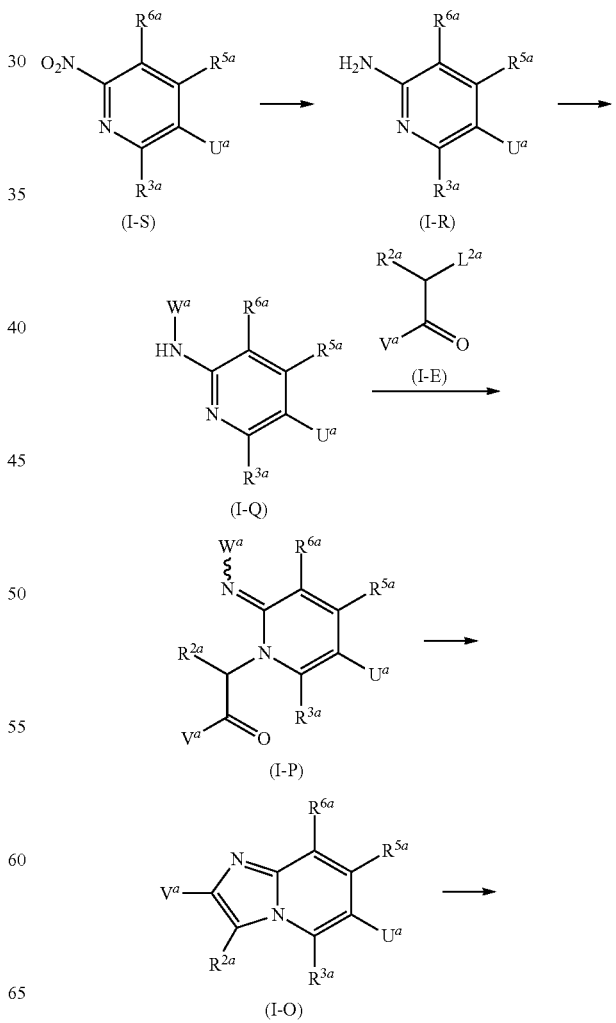

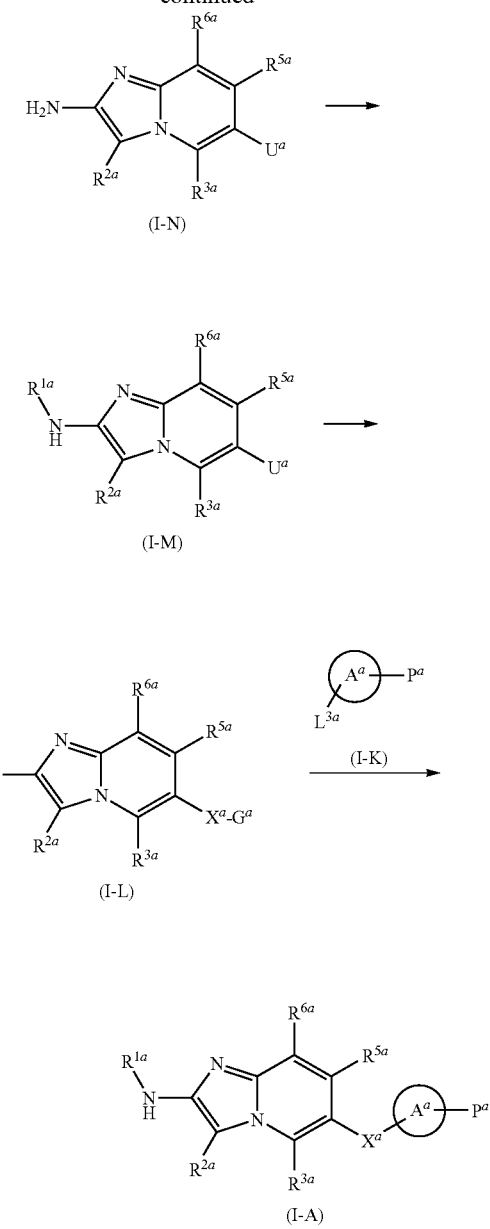

(I-N)

(I-M)

(I-L)

(I-A)

wherein $L^{3a}$ is a leaving group, $U^a$ is any functional group that can be converted to $X^a$-$G^a$ or may itself be $X^a$-$G^a$, a wavy line means that two geometric isomers of imine are present in an optional ratio, and the other symbols are each as defined above.

Compound (I-A) which is a starting material for this production method can also be produced, for example, by reacting a compound represented by the formula:

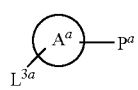

(I-K)

wherein each symbol is as defined above, with a compound represented by the formula:

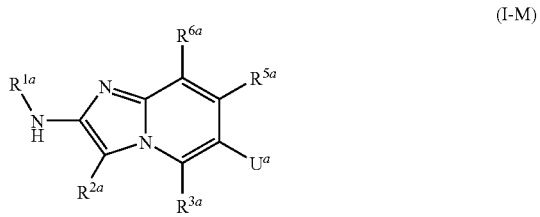

(I-L)

wherein each symbol is as defined above, or a salt thereof.

In compound (I-K), examples of the leaving group for $L^{3a}$ include a halogen atom such as fluorine, chlorine, bromine, iodine and the like, a group represented by the formula —S(O)$_k$R$^{12a}$ wherein k is 0, 1 or 2, and R$^{12a}$ is as defined above, and a group represented by the formula —OR$^{12a}$ wherein R$^{12a}$ is as defined above.

In compound (I-L), when $X^a$ is —NR$^{9a}$— [R$^{9a}$ is as defined above], —O— or —S—, $G^a$ is mainly a hydrogen atom, but may be an alkali metal or an alkaline earth metal.

The reaction is preferably carried out in a solvent and using compound (I-K) in an amount of 1 to 5 equivalents, preferably 1 to 2 equivalents, relative to compound (I-L) or a salt thereof. In addition, a base or ammonium salt may be used in an amount of about 1 to 10 equivalents, preferably 1 to 2 equivalents, relative to compound (I-L) or a salt thereof.

Moreover, a palladium complex may be used as a catalyst in an amount of 0.05 to 10 equivalents, preferably 0.05 to 2 equivalents, relative to compound (I-L) or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (I-K) may be commercially available or can be produced from the corresponding starting material compound according to a method known per se.

Starting material compound (I-L) can be produced, for example, by converting $U^a$ of a compound represented by the formula:

(I-M)

wherein each symbol is as defined above, to an suitable known general functional group as necessary. Compound (I-L) [$X^a$-$G^a$=NH—H] can be obtained, for example, by subjecting compound (I-M) [$U^a$=NO$_2$] to a known general reduction reaction, and compound (I-L) [$X^a$-$G^a$=NR$^{9a}$—H, R$^{9a}$ is as defined above] can be obtained, for example, by subjecting compound (I-L) [$X^a$-$G^a$=NH—H] to a known general reductive amination reaction, a known general coupling reaction using a palladium catalyst, and the like. In addition, compound (I-L) [$X^a$-$G^a$=S—H, O—H] can be obtained, for example, by subjecting compound (I-M) [$U^a$=$SR^{13a}$, $OR^{13a}$ wherein $R^{13a}$ is a protecting group such as methyl, benzyl and the like] to a known conventional deprotection as necessary.

Starting material compound (I-M) ($R^{1a}$ is acyl) can be produced, for example, by subjecting a compound represented by the formula:

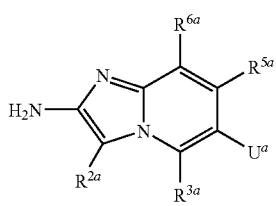

(I-N)

wherein each symbol is as defined above, or a salt thereof to a known general acylation reaction with a carboxylic acid represented by $R^{1a}$—OH ($R^{1a}$ is acyl) or a reactive derivative thereof.

Starting material compound (I-N) can be produced, for example, by subjecting a compound represented by the formula:

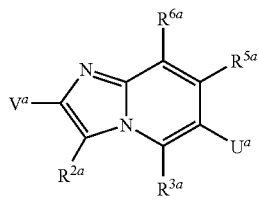

(I-O)

wherein each symbol is as defined above, to a to a suitable known general conversion of functional group to convert $V^a$ to amino.

Compound (I-N) can be obtained, for example, by subjecting compound (I-O) [$V^a$=NHCOCF$_3$] to a known general deprotection of trifluoroacetyl.

In addition, compound (I-N) can be obtained, for example, by subjecting compound (I-O) [$V^a$=NHCOOR$^{10a}$ wherein $R^{10a}$ is as defined above] to a known general hydrolysis of carbamate.

Moreover, compound (I-N) can be obtained, for example, by subjecting compound (I-O) [$V^a$=COOR$^{11a}$ wherein $R^{11a}$ is as defined above] to a known general hydrolysis of ester to give compound (I-O) [$V^a$=COOH], and subjecting the compound to Curtius rearrangement reaction and a subsequent known general functional group conversion reaction.

Starting material compound (I-O) can be produced, for example, from a compound represented by the formula:

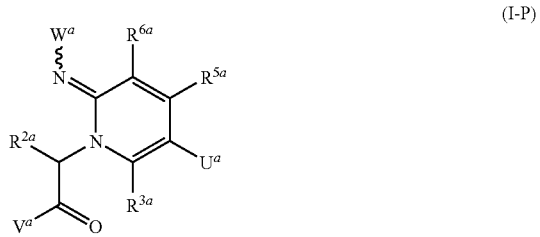

(I-P)

wherein each symbol is as defined above.

Compound (I-O) [$V^a$=NHCOCF$_3$] can be obtained, for example, by reacting compound (I-P) [$W^a$=SO$_2$C$_6$H$_4$(4-CH$_3$) and $V^a$=NH$_2$] with trifluoroacetic acid anhydride.

The reaction is preferably carried out in a solvent and using trifluoroacetic acid anhydride in an amount of 1 to 50 equivalents, preferably 1 to 30 equivalents, relative to compound (I-P) [$W^a$=SO$_2$C$_6$H$_4$ (4-CH$_3$) and $V^a$=NH$_2$].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr.

Starting material compound (I-P) can be produced, for example, by reacting a compound represented by the formula:

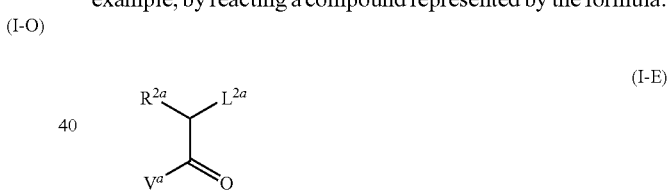

(I-E)

wherein each symbol is as defined above, with a compound represented by the formula:

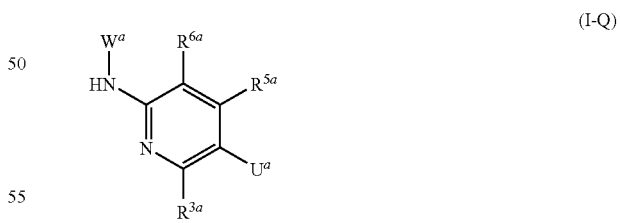

(I-Q)

wherein each symbol is as defined above, or a salt thereof.

Compound (I-P) [$W^a$=alkylsulfonyl (e.g., methylsulfonyl etc.) or arylsulfonyl (e.g., p-toluenesulfonyl) and $V^a$=NH$_2$] can be obtained, for example, by reacting compound (I-Q) [$W^a$=alkylsulfonyl (e.g., methylsulfonyl etc.) or arylsulfonyl (e.g., p-toluenesulfonyl)] with compound (I-E) [$V^a$=NH$_2$].

The reaction is preferably carried out in a solvent and using compound (I-E) [$V^a$=NH$_2$] in an amount of 1 to 5 equivalents, preferably 1 to 2 equivalents, relative to compound (I-Q) [$W^a$=alkylsulfonyl (e.g., methylsulfonyl etc.) or arylsulfonyl (e.g., p-toluenesulfonyl)] or a salt thereof. In addition, a base may be used in an amount of about 1 to 10 equivalents, preferably 1 to 2 equivalents, relative to compound (I-Q) [$W^a$=alkylsulfonyl (e.g., methylsulfonyl etc.) or arylsulfonyl (e.g., p-toluenesulfonyl)] or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

In addition, for example, it is known by WO2005/89763 and the like that compound (I-O) [$V^a$=NHCOR$^{10a}$ wherein R$^{10a}$ is as defined above] can be produced without going through compound (I-P) but by reacting compound (I-Q) [$W^a$=H] with compound (I-E) [$V^a$=NHCOR$^{10a}$ wherein R$^{10a}$ is as defined above], and compound (I-O) [$V^a$=COOR$^{11a}$ wherein R$^{11a}$ is as defined above] can be produced without going through compound (I-P) but by reacting compound (I-Q) [$W^a$=H] with compound (I-E) [$V^a$=COOR$^{11a}$ wherein R$^{11a}$ is as defined above].

Starting material compound (I-E) may be commercially available or can be produced from the corresponding starting material compound according to a method known per se.

As starting material compound (I-Q), a compound represented by the formula:

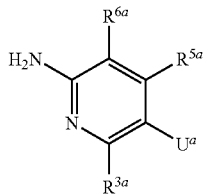

(I-R)

wherein each symbol is as defined above, or a salt thereof may be directly used as compound (I-Q) [$W^a$=H], or starting material compound (I-Q) can be produced, for example, by introducing alkylsulfonyl or arylsulfonyl into compound (I-R) according to a method known per se.

The reaction is preferably carried out in a solvent and using alkylsulfonyl chloride or arylsulfonyl chloride in an amount of 1 to 5 equivalents, preferably 1 to 2 equivalents, relative to compound (I-R) or a salt thereof. In addition, a base may be used in an amount of about 1 to 10 equivalents, preferably 1 to 2 equivalents, relative to compound (I-R) or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (I-R) can be produced, for example, by subjecting a compound represented by the formula:

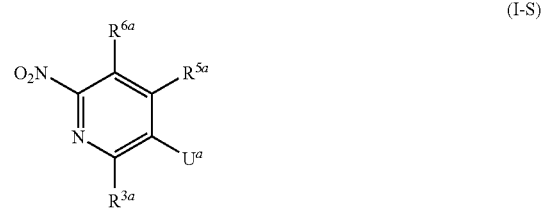

(I-S)

wherein each symbol is as defined above, to a general reduction reaction known per se to convert nitro to amino.

Starting material compound (I-S) may be commercially available or can be produced from the corresponding starting material compound according to a method known per se.

Method C:

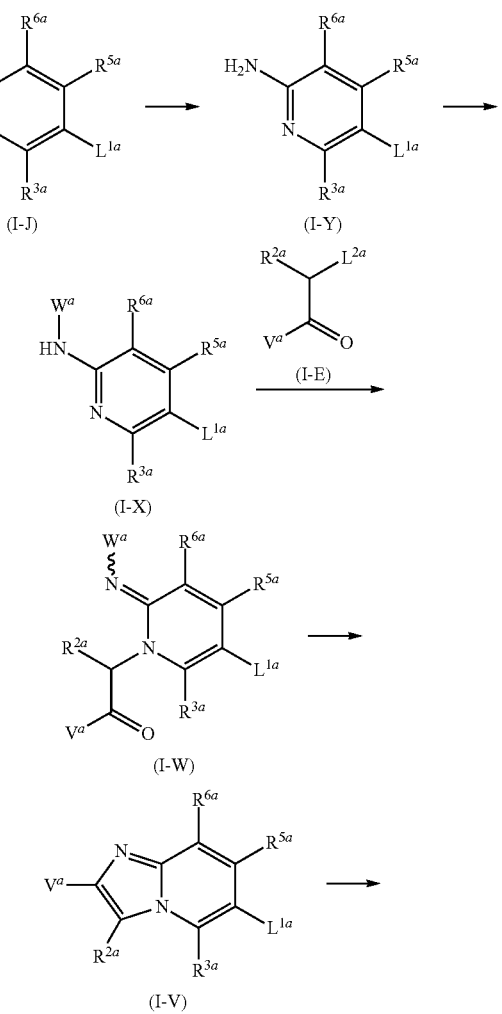

-continued

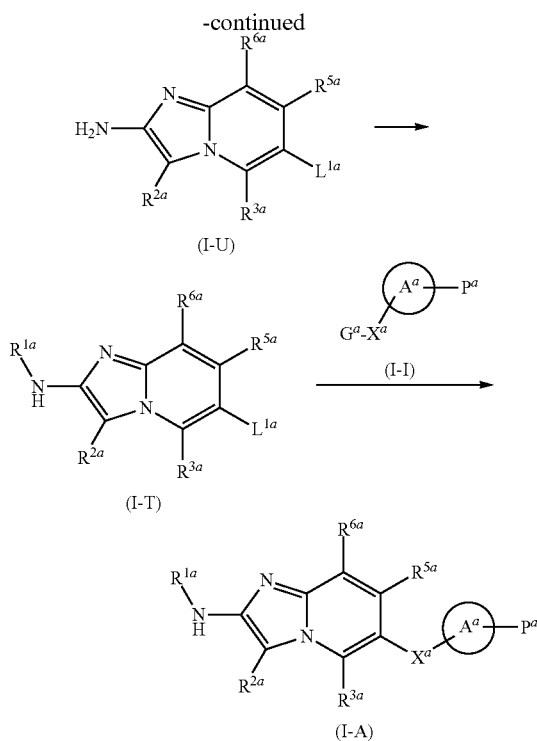

wherein each symbol is as defined above, and a wavy line means that two geometric isomers of imine are present in an optional ratio.

Starting material compound (I-A) can also be produced, for example, by reacting a compound represented by the formula:

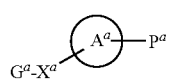

wherein each symbol is as defined above, or a salt thereof with a compound represented by the formula:

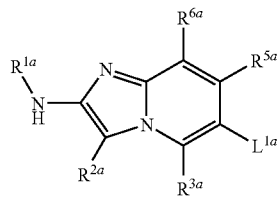

wherein each symbol is as defined above.

In compound (I-I), when $X^a$ is —$NR^{9a}$— [$R^{9a}$ is as defined above], —O— or —S—, $G^a$ is mainly a hydrogen atom, but may be an alkali metal or an alkaline earth metal.

The reaction is preferably carried out in a solvent and using compound (I-I) or a salt thereof in an amount of 1 to 5 equivalents, preferably 1 to 2 equivalents, relative to compound (I-T). In addition, a base or ammonium salt may be used in an amount of about 1 to 10 equivalents, preferably 1 to 2 equivalents, relative to compound (I-T). Moreover, a palladium complex may be used as a catalyst in an amount of 0.05 to 10 equivalents, preferably 0.05 to 2 equivalents, relative to compound (I-T).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (I-I) may be commercially available or can be produced from the corresponding starting material compound according to a method known per se.

Starting material compound (I-T) ($R^{1a}$ is acyl) can be produced, for example, by subjecting a compound represented by the formula:

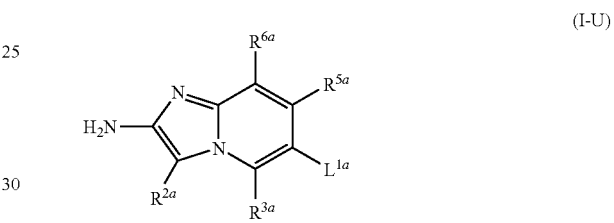

wherein each symbol is as defined above, or a salt thereof to a known general acylation reaction using a carboxylic acid represented by $R^{1a}$—OH ($R^{1a}$ is acyl) or a reactive derivative thereof.

Starting material compound (I-U) can be produced, for example, by subjecting a compound represented by the formula:

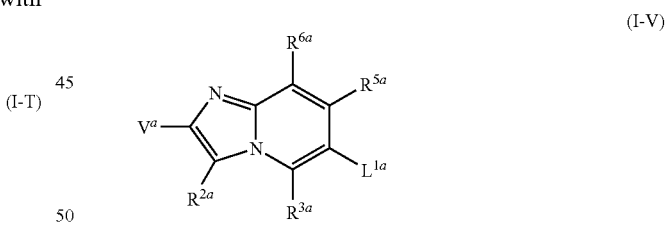

wherein each symbol is as defined above, to a suitable known general conversion of functional group to convert $V^a$ to amino Compound (I-U) can be obtained, for example, by subjecting compound (I-V) [$V^a$=NHCOCF$_3$] to a known general deprotection of trifluoroacetyl In addition, compound (I-U) can be obtained, for example, by subjecting compound (I-V) [$V^a$=NHCOCF$_3$] wherein $R^{10a}$ is as defined above] to a known general hydrolysis of carbamate.

Moreover, compound (I-U) can be obtained, for example, by subjecting compound (I-V) [$V^a$=COOR$^{11a}$ wherein $R^{11a}$ is as defined above] to a known general hydrolysis of ester to give compound (I-V) [$V^a$=COOH], and subjecting the compound to Curtius rearrangement reaction and a subsequent known general functional group conversion reaction.

Starting material compound (I-V) can be produced, for example, from a compound represented by the formula:

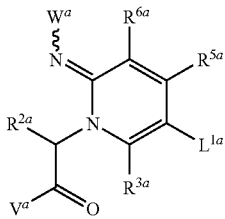

(I-W)

wherein each symbol is as defined above.

Compound (I-V) [$V^a$=NHCOCF$_3$] can be obtained, for example, by reacting compound (I-W) [$W^a$=SO$_2$C$_6$H$_4$(4-CH$_3$) and $V^a$=NH$_2$] with trifluoroacetic acid anhydride.

The reaction is preferably carried out in a solvent and using trifluoroacetic acid anhydride in an amount of 1 to 50 equivalents, preferably 1 to 30 equivalents, relative to compound (I-W) [$W^a$=SO$_2$C$_6$H$_4$(4-CH$_3$) and $V^a$=NH$_2$].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr.

Starting material compound (I-W) can be produced, for example, by reacting a compound represented by the formula:

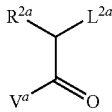

(I-E)

wherein each symbol is as defined above,
with a compound represented by the formula:

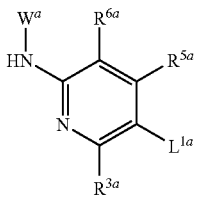

(I-X)

wherein each symbol is as defined above, or a salt thereof.

Compound (I-W) [$W^a$=alkylsulfonyl (e.g., methylsulfonyl etc.) or arylsulfonyl (e.g., p-toluenesulfonyl etc.) and $V^a$=NH$_2$] can be obtained, for example, by reacting compound (I-X) [$W^a$=alkylsulfonyl (e.g., methylsulfonyl etc.) or arylsulfonyl (e.g., p-toluenesulfonyl etc.)] with compound (I-E) [$V^a$=NH$_2$].

The reaction is preferably carried out in a solvent and using compound (I-E) [$V^a$=NH$_2$] in an amount of 1 to 5 equivalents, preferably 1 to 2 equivalents, relative to compound (I-X) [$W^a$=alkylsulfonyl (e.g., methylsulfonyl etc.) or arylsulfonyl (e.g., p-toluenesulfonyl etc.)] or a salt thereof. In addition, a base may be used in an amount of about 1 to 10 equivalents, preferably 1 to 2 equivalents, relative to compound (I-X) [$W^a$=alkylsulfonyl (e.g., methylsulfonyl etc.) or arylsulfonyl (e.g., p-toluenesulfonyl etc.)] or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

In addition, for example, it is known by WO2005/89763 and the like that compound (I-V) [$V^a$=NHCOR$^{10a}$ wherein $R^{10a}$ is as defined above] can be produced without going through compound (I-W) but by reacting compound (I-X) [$W^a$=H] with compound (I-E) [$V^a$=NHCOR$^{11a}$ wherein $R^{10a}$ is as defined above], and compound (I-V) [$V^a$=COOR$^{11a}$ wherein $R^{11a}$ is as defined above] can be produced without going through compound (I-W) but by reacting compound (I-X) [$W^a$=H] with compound (I-E) [$V^a$=COOR$^{11a}$ wherein $R^{11a}$ is as defined above].

Starting material compound (I-E) may be commercially available or can be produced from the corresponding starting material compound according to a method known per se.

As starting material compound (I-X), a compound represented by the formula:

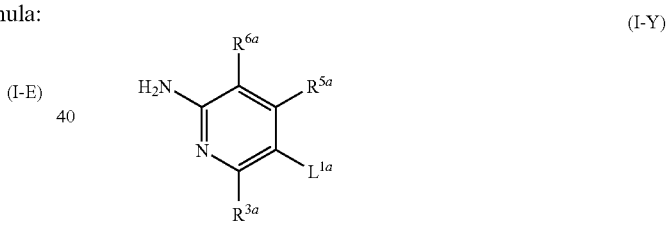

(I-Y)

wherein each symbol is as defined above, or a salt thereof may be directly used as compound (I-X) [$W^a$=H], or starting material compound (I-X) can be produced, for example, by introducing alkylsulfonyl or arylsulfonyl into compound (I-Y) according to a method known per se.

The reaction is preferably carried out in a solvent and using alkylsulfonyl chloride or arylsulfonyl chloride in an amount of 1 to 5 equivalents, preferably 1 to 2 equivalents, relative to compound (I-Y) or a salt thereof. In addition, a base may be used in an amount of about 1 to 10 equivalents, preferably 1 to 2 equivalents, relative to compound (I-Y) or a salt thereof. As the solvent for aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (I-Y) can be produced, for example, by subjecting a compound represented by the formula:

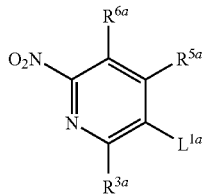

wherein each symbol is as defined above, to a general reduction reaction known per se to convert nitro to amino.

Starting material compound (I-J) may be commercially available or can be produced from the corresponding starting material compound according to a method known per se.

2. Production Method of Compound (ii)

Compound (ii) of the present invention can be obtained, for example, according to the following conversion reaction of compound (II-A) into compound (ii), or a method analogous thereto, and the like. The reaction scheme is shown below. Each symbol in the compounds in the scheme is as defined above, and compound (II-A) encompasses compound (ii).

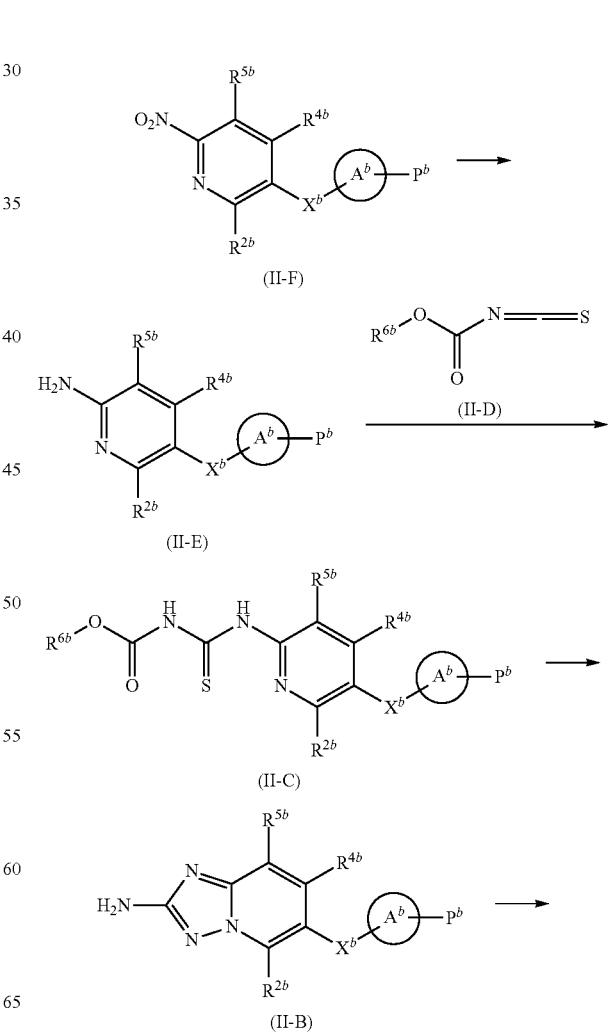

wherein $P^b$ is any functional group that can be converted to $Y^b$—$R^{3b}$, and may itself be $Y^b$—$R^{3b}$, and the other symbols are each as defined above.

In this production method, compound (ii) can be obtained by converting $P^b$ of compound (II-A) to a suitable known general functional group as necessary.

Compound (ii) [$Y^b$=CONH] can be obtained, for example, by subjecting compound (II-A) [$P^b$=COOH] to a known general amidation reaction, and compound (ii) [$Y^b$=NHCO] or compound (ii) [$Y^b$=NHCONH] can be obtained, for example, by subjecting compound (II-A) [$P^b$=COOH] to Curtius rearrangement reaction and a subsequent known general functional group conversion reaction, and a known general amidation reaction or ureation reaction.

Alternatively, compound (ii) [$Y^b$=NHCO] or compound (ii) [$Y^b$=NHCONH] can be obtained, for example, by subjecting compound (II-A) [$P^b$=NO$_2$] to a known general reduction reaction to give compound (II-A) [$P^b$=NH$_2$], and subjecting the compound to a known general amidation reaction or ureation reaction. In addition, compound (ii) [$Y^b$=NH] can be obtained, for example, by converting compound (II-A) [$P^b$=NO$_2$] to compound (II-A) [$P^b$=NH$_2$], and subjecting the compound to a known general reductive amination reaction or a known general coupling reaction using a palladium catalyst, and the like.

Compound (II-A) can be obtained according to the following Method A, Method B, or Method C, or a method analogous thereto, and the like.

Method A:

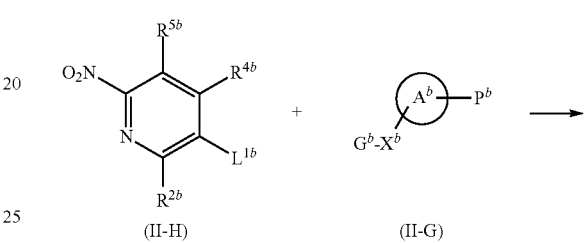

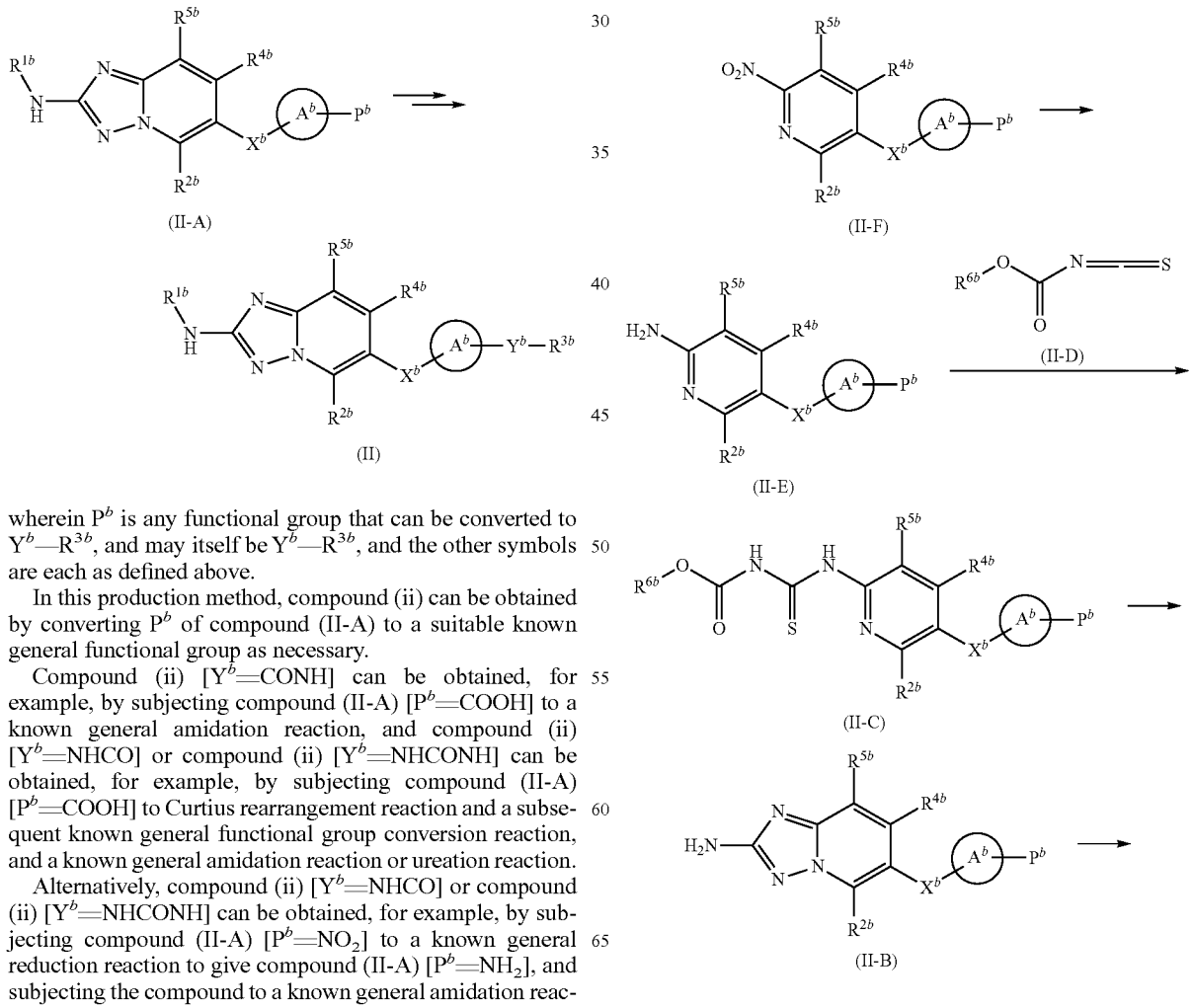

-continued

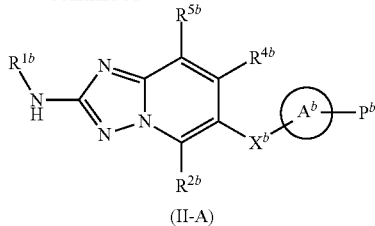

(II-A)

wherein $L^{1b}$ is a leaving group, $G^b$ is a hydrogen atom or a metal atom, $R^{9b}$ is $C_{1-4}$ alkyl (e.g., methyl, ethyl, propyl, t-butyl and the like), and the other symbols are each as defined above.

Compound (II-A) ($R^{1b}$ is acyl), which is a starting material for this production method, can be produced, for example, by subjecting a compound represented by the formula:

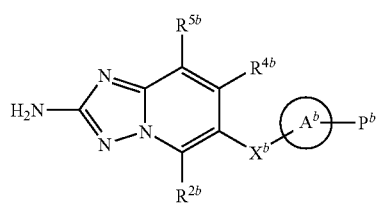

(II-B)

wherein each symbol is as defined above, or a salt thereof to a known general acylation reaction using a carboxylic acid represented by $R^{1b}$—OH ($R^{1b}$ is acyl) or a reactive derivative thereof.

Starting material compound (II-B) can be produced, for example, by reacting a compound represented by the formula:

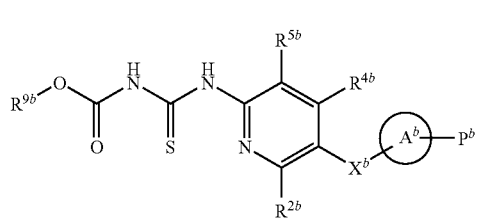

(II-C)

wherein each symbol is as defined above, with hydroxylamine or a salt thereof.

The reaction is preferably carried out according to the method shown in Synthesis (2003) 1649-1652 and the like in a solvent and using hydroxylamine or a salt thereof in an amount of 1 to 20 equivalents, preferably 1 to 10 equivalents, relative to (II-C). In addition, a base may be used in an amount of about 1 to 20 equivalents, preferably 1 to 10 equivalents, relative to (II-C).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (II-C) can be produced, for example, by reacting a compound represented by the formula:

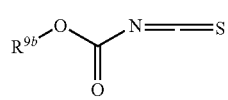

(II-D)

wherein each symbol is as defined above, with a compound represented by the formula:

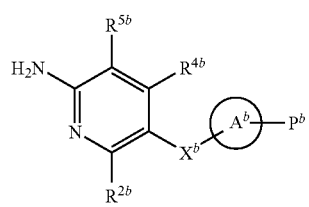

(II-E)

wherein each symbol is as defined above, or a salt thereof.

The reaction is preferably carried out in a solvent and using compound (II-D) in an amount of 1 to 5 equivalents, preferably 1 to 2 equivalents, relative to compound (II-E) or a salt thereof. In addition, a base may be used in an amount of about 1 to 10 equivalents, preferably 1 to 2 equivalents, relative to compound (II-E) or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (II-D) may be commercially available or can be produced from the corresponding starting material compound according to a method known per se.

Starting material compound (II-E) can be produced, for example, by subjecting a compound represented by the formula:

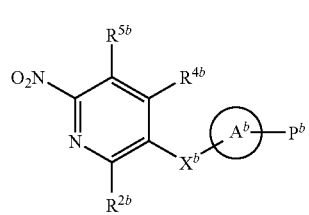

(II-F)

wherein each symbol is as defined above, to a general reduction reaction known per se to convert nitro to amino.

Starting material compound (II-F) can be produced, for example, by reacting a compound represented by the formula:

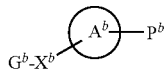
(II-G)

wherein each symbol is as defined above, or a salt thereof with a compound represented by the formula:

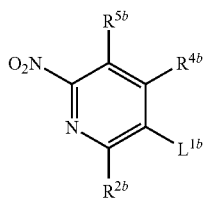
(II-H)

wherein each symbol is as defined above.

In compound (II-G), when $X^b$ is —$NR^{8b}$— as [$R^{8b}$ is as defined above], —O— or —S—, $G^b$ is mainly a hydrogen atom, but may be an alkali metal or an alkaline earth metal.

In compound (II-H), examples of the leaving group for $L^{1b}$ include a halogen atom such as fluorine, chlorine, bromine, iodine and the like, a group represented by the formula: —$S(O)_kR^{10b}$ wherein k is 0, 1 or 2, and $R^{10b}$ is $C_{1-4}$ alkyl (e.g., methyl, ethyl, propyl etc.), benzyl, $C_{6-10}$ aryl (e.g., phenyl, tolyl etc.) and the like, and a group represented by the formula: —$OR^{10b}$ wherein $R^{10b}$ is as defined above.

The reaction is preferably carried out in a solvent and using compound (II-G) or a salt thereof in an amount of 1 to 5 equivalents, preferably 1 to 2 equivalents, relative to compound (II-H). In addition, a base or ammonium salt may be used in an amount of about 1 to 10 equivalents, preferably 1 to 2 equivalents, relative to compound (II-H).

Moreover, a palladium complex may be used as a catalyst in an amount of 0.05 to 10 equivalents, preferably 0.05 to 2 equivalents, relative to compound (II-H).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The aforementioned reaction may be carried out under microwave irradiation.

Starting material compound (II-G) and starting material compound (II-H) may be commercially available or can be produced from the corresponding starting material compound according to a method known per se.

Method B:

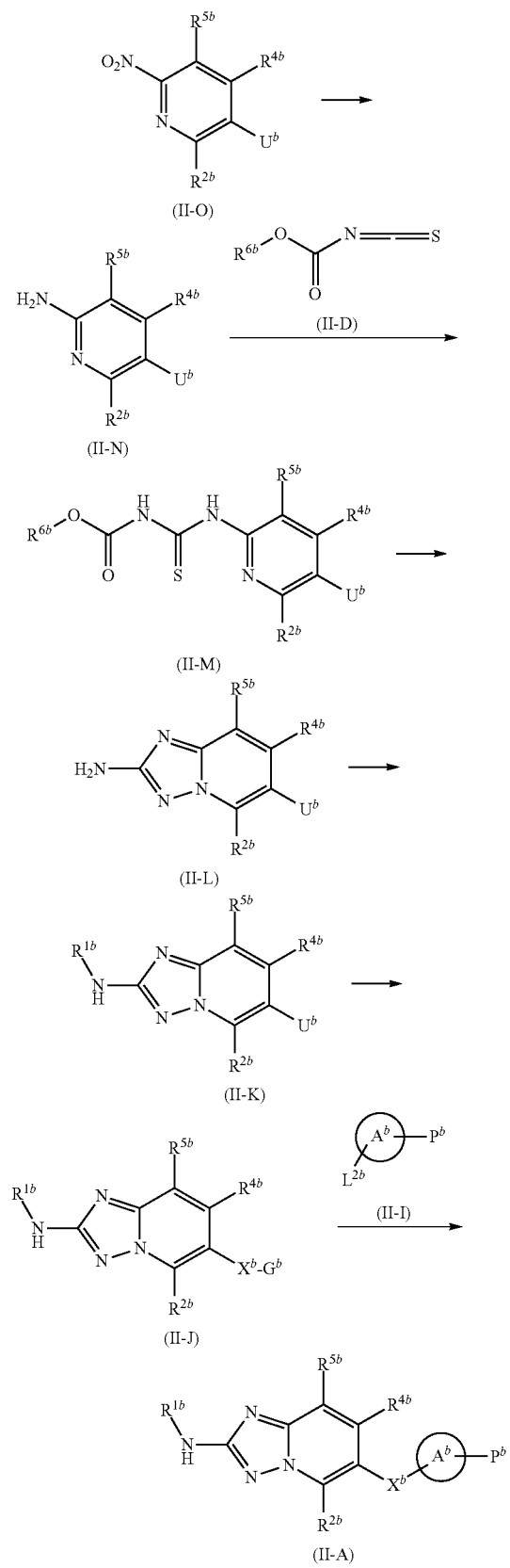

wherein $U^b$ is any functional group that can be converted to $X^b$-$G^b$, and may itself be $X^b$-$G^b$, $L^{2b}$ is a leaving group, and the other symbols are each as defined above.

Compound (II-A), which is a starting material for this production method, can also be produced, for example, by reacting a compound represented by the formula:

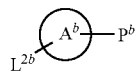

(II-I)

wherein $L^{2b}$ is a leaving group, and the other symbols are each as defined above, with a compound represented by the formula:

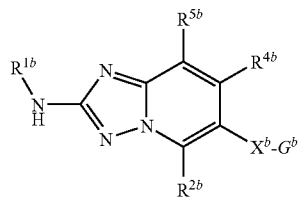

(II-J)

wherein each symbol is as defined above, or a salt thereof.

In compound (II-I), examples of the leaving group for $L^{2b}$ include those similar to the aforementioned leaving group for $L^{1b}$.

In compound (II-I), when $X^b$ is —$NR^{8b}$— [$R^{8b}$ is as defined above], —O— or —S—, $G^b$ is mainly a hydrogen atom, but may be an alkali metal or an alkaline earth metal.

The aforementioned reaction is preferably carried out in a solvent and using compound (II-I) in an amount of 1 to 5 equivalents, preferably 1 to 2 equivalents, relative to compound (II-J) or a salt thereof. In addition, a base or ammonium salt may be used in an amount of about 1 to 10 equivalents, preferably 1 to 2 equivalents, relative to compound (II-J) or a salt thereof.

Moreover, a palladium complex may be used as a catalyst in an amount of 0.05 to 10 equivalents, preferably 0.05 to 2 equivalents, relative to compound (II-J) or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (II-I) may be commercially available or can be produced from the corresponding starting material compound according to a method known per se.

Starting material compound (II-J) can be produced, for example, by converting $U^b$ of a compound represented by the formula:

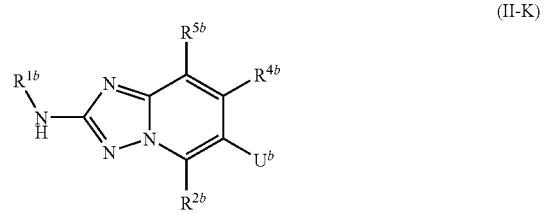

(II-K)

wherein each symbol is as defined above, to an suitable known general functional group as necessary. Compound (II-J) [$X^b$-$G^b$=NH—H] can be obtained, for example, by subjecting compound (II-K) [$U^b$=$NO_2$] to a known general reduction reaction, and compound (II-J) [$_LX^b$-$G^b$=$NR^{8b}$—H, $R^{8b}$ is as defined above] can be obtained, for example, by subjecting compound (II-J) [$X^b$-$G^b$=NH—H] to a known general reductive amination reaction, a known general coupling reaction using a palladium catalyst, and the like. In addition, compound (II-J) [$X^b$-$G^b$=S—H, O—H] can be obtained, for example, by subjecting compound (II-K) [$U^b$=$SR^{11b}$, $OR^{11b}$; $R^{11b}$ is a protecting group such as methyl, benzyl and the like] to a known conventional deprotection as necessary.

Starting material compound (II-K) ($R^{1b}$ is acyl) can be produced, for example, by subjecting a compound represented by the formula:

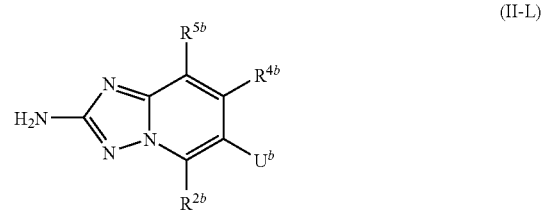

(II-L)

wherein each symbol is as defined above, or a salt thereof to a known general acylation reaction using a carboxylic acid represented by $R^{1b}$—OH ($R^{1b}$ is acyl) or a reactive derivative thereof.

Starting material compound (II-L) can be produced, for example, by reacting a compound represented by the formula:

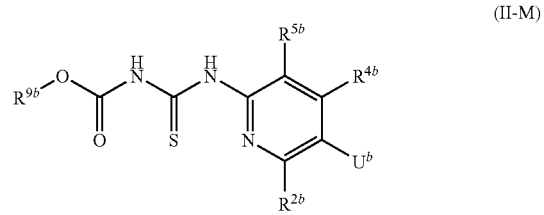

(II-M)

wherein each symbol is as defined above, with hydroxylamine or a salt thereof.

The reaction is preferably carried out in a solvent and using hydroxylamine or a salt thereof in an amount of 1 to 20 equivalents, preferably 1 to 10 equivalents, relative to compound (II-M). In addition, a base may be used in an amount of about 1 to 20 equivalents, preferably 1 to 10 equivalents, relative to compound (II-M).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (II-M) can be produced, for example, by reacting a compound represented by the formula:

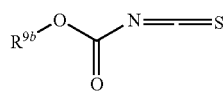

(II-D)

wherein each symbol is as defined above, with a compound represented by the formula:

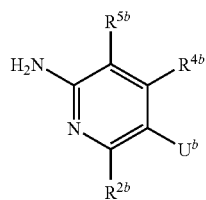

(II-N)

wherein each symbol is as defined above, or a salt thereof.

The reaction is preferably carried out in a solvent and using compound (II-D) in an amount of 1 to 5 equivalents, preferably 1 to 2 equivalents, relative to compound (II-N) or a salt thereof. In addition, a base may be used in an amount of about 1 to 10 equivalents, preferably 1 to 2 equivalents, relative to compound (II-N) or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (II-D) may be commercially available or can be produced from the corresponding starting material compound according to a method known per se.

Starting material compound (II-N) can be produced, for example, by subjecting a compound represented by the formula:

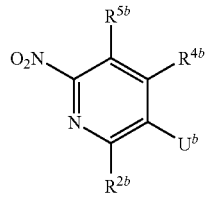

(II-O)

wherein each symbol is as defined above, to a general reduction reaction known per se to convert nitro to amino.

Starting material compound (II-O) may be commercially available or can be produced from the corresponding starting material compound according to a method known per se.

Method C:

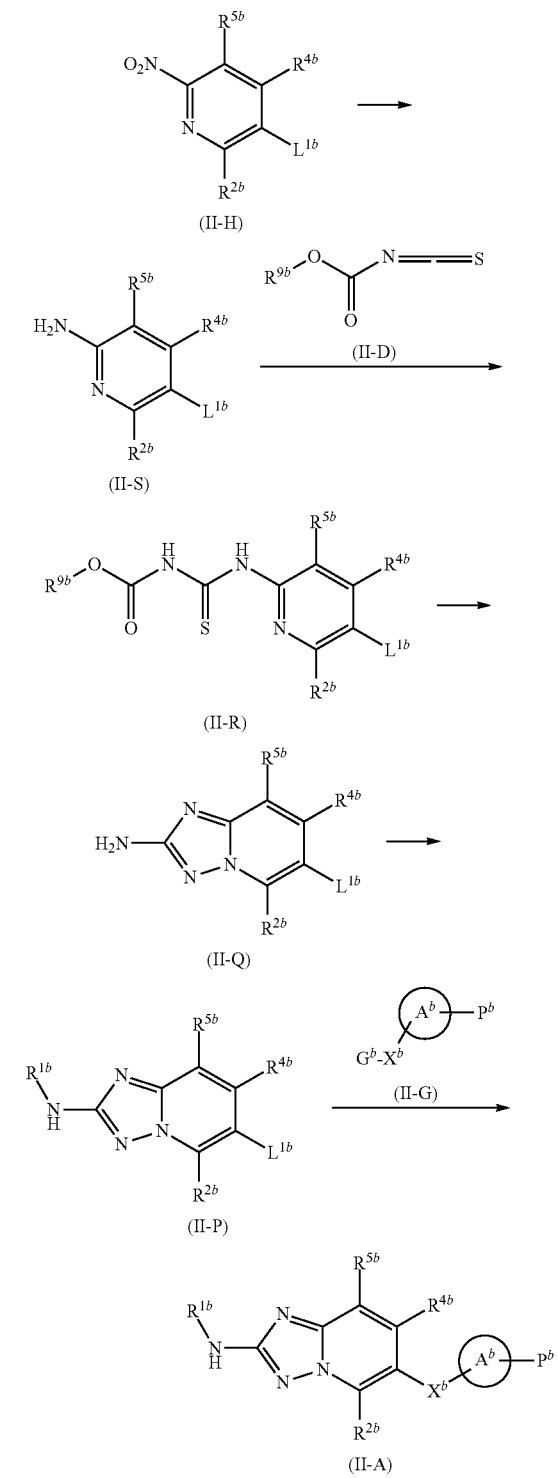

wherein each symbol is as defined above.

Compound (II-A), which is a starting material for this production method, can also be produced, for example, by reacting a compound represented by the formula:

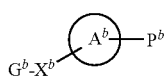
(II-G)

wherein each symbol is as defined above, or a salt thereof with a compound represented by the formula:

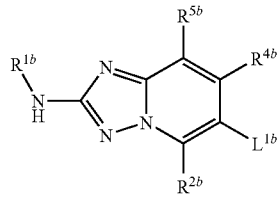
(II-P)

wherein each symbol is as defined above.

In compound (II-G), when $X^b$ is —$NR^{8b}$— [$R^{8b}$ is as defined above], —O— or —S—, $G^b$ is mainly a hydrogen atom, but may be an alkali metal or an alkaline earth metal.

The reaction is preferably carried out in a solvent and using compound (II-G) or a salt thereof in an amount of 1 to 5 equivalents, preferably 1 to 2 equivalents, relative to compound (II-P). In addition, a base or ammonium salt may be used in an amount of about 1 to 10 equivalents, preferably 1 to 2 equivalents, relative to compound (II-P). Moreover, a palladium complex may be used as a catalyst in an amount of 0.05 to 10 equivalents, preferably 0.05 to 2 equivalents, relative to compound (II-P).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (II-G) may be commercially available or can be produced from the corresponding starting material compound according to a method known per se.

Starting material compound (II-P) ($R^{1b}$ is acyl) can be produced, for example, by subjecting a compound represented by the formula:

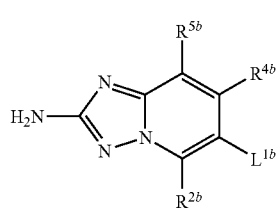
(II-Q)

wherein each symbol is as defined above, or a salt thereof to a known general acylation reaction using a carboxylic acid represented by $R^{1b}$—OH ($R^{1b}$ is acyl) or a reactive derivative thereof.

Starting material compound (II-Q) can be produced, for example, by reacting a compound represented by the formula:

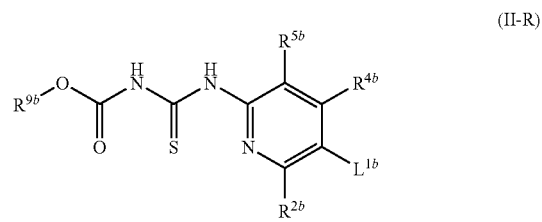
(II-R)

wherein each symbol is as defined above, with hydroxylamine or a salt thereof.

The reaction is preferably carried out in a solvent and using hydroxylamine or a salt thereof in an amount of 1 to 20 equivalents, preferably 1 to 10 equivalents, relative to compound (II-R). In addition, a base may be used in an amount of about 1 to 20 equivalents, preferably 1 to 10 equivalents, relative to compound (II-R).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (II-R) can be produced, for example, by reacting a compound represented by the formula:

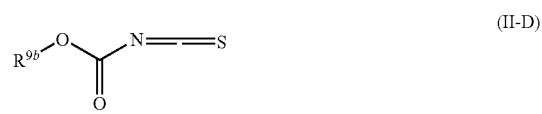
(II-D)

wherein each symbol is as defined above, with a compound represented by the formula:

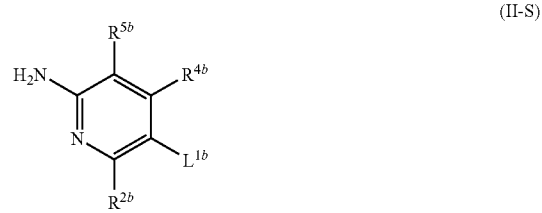
(II-S)

wherein each symbol is as defined above, or a salt thereof.

The reaction is preferably carried out in a solvent and using compound (II-D) in an amount of 1 to 5 equivalents, preferably 1 to 2 equivalents, relative to compound (II-S) or a salt thereof. In addition, a base may be used in an amount of about 1 to 10 equivalents, preferably 1 to 2 equivalents, relative to compound (II-S) or a salt thereof.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 50 hr, preferably about 1 to 20 hr.

Starting material compound (II-D) may be commercially available or can be produced from the corresponding starting material compound according to a method known per se.

Starting material compound (II-S) can be produced, for example, by subjecting a compound represented by the formula:

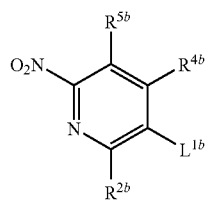

(II-H)

wherein each symbol is as defined above, to a general reduction reaction known per se to convert nitro to amino.

Starting material compound (II-H) may be commercially available or can be produced from the corresponding starting material compound according to a method known per se.

3. Production Method of Compound (iii)

Compound (iii) of the present invention can be obtained, for example, according to the following conversion reaction of compound (III-A) into compound (iii), or a method analogous thereto, and the like. The reaction scheme is shown below. Each symbol in the compounds in the scheme is as defined above, and compound (III-A) encompasses compound (iii).

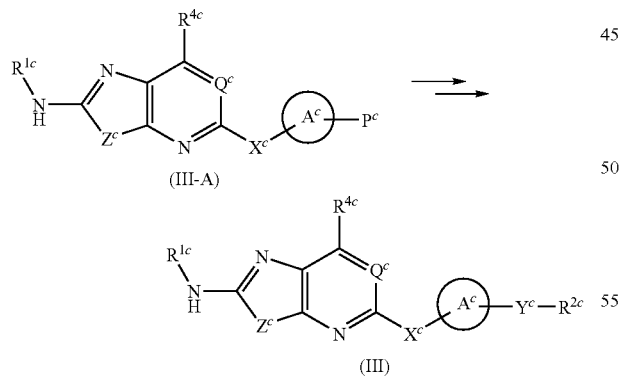

wherein $P^c$ is any functional group that can be converted to $Y^c$—$R^{2c}$, and may itself be $Y^c$—$R^{2c}$, and the other symbols are each as defined above.

In this production method, compound (iii) can be obtained by converting $P^c$ of compound (III-A) to a suitable known general functional group as necessary.

Compound (iii) [$Y^c$=CONH] can be obtained, for example, by subjecting compound (III-A) [$P^c$=COOH] to a known general amidation reaction, and compound (iii) [$Y^c$=NHCO] or compound (iii) [$Y^c$=NHCONH] can be obtained, for example, by subjecting compound (III-A) [$P^c$=COOH] to Curtius rearrangement reaction and a subsequent known general functional group conversion reaction, and a known general amidation reaction or ureation reaction.

Alternatively, compound (iii) [$Y^c$=NHCO] or compound (iii) [$Y^c$=NHCONH] can be obtained, for example, by subjecting compound (III-A) [$P^c$=NO$_2$] to a known general reduction reaction to give compound (III-A) [$P^c$=NH$_2$], and subjecting the compound to a known general amidation reaction or ureation reaction. In addition, compound (iii) [$Y^c$=NH] can be obtained, for example, by converting compound (III-A) [$P^c$=NO$_2$] to compound (III-A) [$P^c$=NH$_2$], and subjecting the compound to a known general reductive amination reaction or a known general coupling reaction using a palladium catalyst, and the like.

Compound (III-A) can be obtained according to the following Method A, Method B, or Method C, or a method analogous thereto, and the like.

Method A:

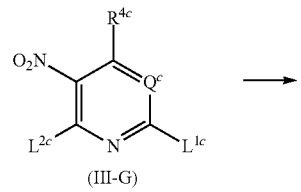

(III-G)

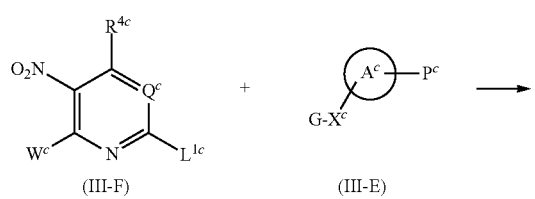

(III-F)    (III-E)

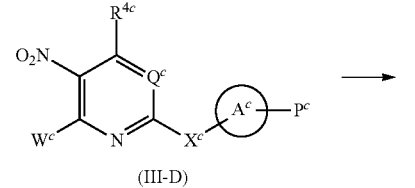

(III-D)

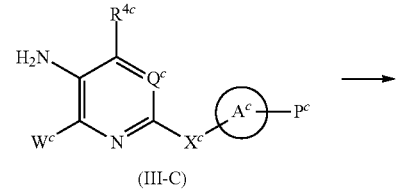

(III-C)

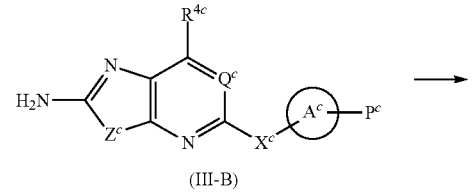

(III-B)

-continued

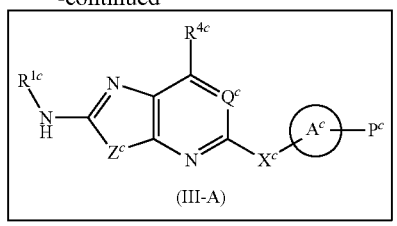

wherein $L^{1c}$ and $L^{2c}$ are each a leaving group, G is a hydrogen atom or a metal atom, $W^c$ is $SR^{9c}$, SCN or a hydrogen atom, $R^{9c}$ is a hydrogen atom or a protecting group, and the other symbols are each as defined above.

Compound (III-A) ($R^{1c}$ is acyl), which is a starting material for this production method, can be produced, for example, by subjecting a compound represented by the formula:

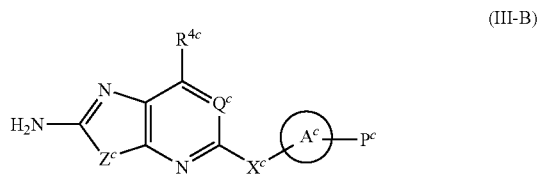

wherein each symbol is as defined above, to a known general acylation reaction using a carboxylic acid represented by $R^{1c}$—OH ($R^{1c}$ is acyl) or a reactive derivative thereof.

Starting material compound (III-B) can be produced, for example, from a compound represented by the formula:

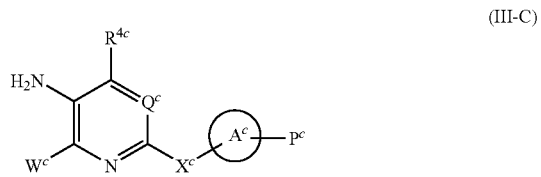

wherein each symbol is as defined above. Compound (III-B) can be obtained, for example, by subjecting compound (III-C) [$W^c$=$SR^{9c}$] to a known general deprotection as necessary to give compound (III-C) [$W^c$=SH], and reacting the compound with cyanogen bromide or 1,1-di-1H-imidazol-1-yl-methanimine.

The reaction is preferably carried out in a solvent and using cyanogen bromide or 1,1-di-1H-imidazol-1-ylmethanimine in an amount of 1 to 10 equivalents, preferably 1 to 5 equivalents, relative to compound (III-C) [$W^c$=SH]. In addition, a base may be used in an amount of 0 to 10 equivalents, preferably 0 to 2 equivalents, relative to compound (III-C) [$W^c$=SH].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, Compound (III-B) can also be obtained, for example, by reacting compound (III-C) [$W^c$=SCN] with an acid in an amount of 1 to 10 equivalents, sometimes a solvent amount, preferably 1 to 5 equivalents, relative to compound (III-C) [$W^c$=SCN].

As the acid for this reaction, hydrochloric acid, acetic acid, sulfuric acid and the like can be used. As the solvent for the above-mentioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, Compound (III-B) can also be obtained, for example, by reacting compound (III-C) [$W^c$=H] with potassium thiocyanate, sodium thiocyanate or ammonium thiocyanate and bromine. The reaction is preferably carried out in a solvent and using potassium thiocyanate, sodium thiocyanate or ammonium thiocyanate in an amount of 1 to 10 equivalents, preferably 1 to 5 equivalents, and bromine in an amount of 1 to 5 equivalents, preferably 1 to 2 equivalents, relative to compound (III-C) [$W^c$=H].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-C) can be produced, for example, by subjecting a compound represented by the formula:

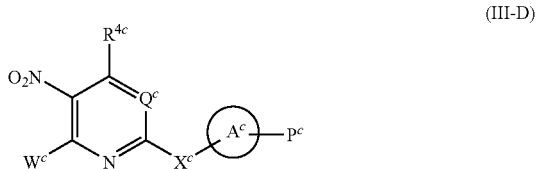

wherein each symbol is as defined above, to a known general reduction reaction to convert nitro to amino.

In addition, compound (III-B) can also be directly produced from compound (III-D) [$W^c$=SCN] without going through compound (III-C) [$W^c$=SCN] according to this reduction reaction.

For example, compound (III-B) can be directly produced without going through compound (III-C) [$W^c$=SCN] but by reacting compound (III-D) [$W^c$=SCN] with reduced iron in the presence of an acid.

The reaction is preferably carried out in a solvent and using reduced iron in an amount of 1 to 10 equivalents, preferably 1 to 5 equivalents, and an acid in an amount of 1 to 20 equivalents, sometimes a solvent amount, preferably 1 to 10 equivalents, relative to compound (III-D) [$W^c$=SCN].

As the acid for this reaction, hydrochloric acid, acetic acid, sulfuric acid and the like can be used. As the solvent for the above-mentioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-D) can be produced, for example, by reacting a compound represented by the formula:

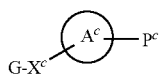

(III-E)

wherein each symbol is as defined above, or a salt thereof with a compound represented by the formula:

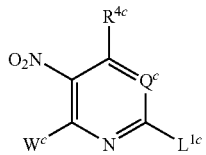

(III-F)

wherein each symbol is as defined above.

In compound (III-E), when $X^c$ is —$NR^{7c}$— [$R^{7c}$ is as defined above], —O— or —S—, G is mainly a hydrogen atom, but may be an alkali metal or an alkaline earth metal.

In compound (III-F), examples of the leaving group for $L^{1c}$ include a halogen atom such as fluorine, chlorine, bromine, iodine and the like, a group represented by the formula: —$S(O)_kR^{10c}$ wherein k is 0, 1 or 2, and $R^{10c}$ is $C_{1-4}$ alkyl (e.g., methyl, ethyl, propyl etc.), benzyl, $C_{6-10}$ aryl (e.g., phenyl, tolyl etc.), and a group represented by the formula: —$OR^{10c}$ wherein $R^{10c}$ is as defined above.

The reaction is preferably carried out in a solvent and using compound (III-E) or a salt thereof in an amount of 1 to 5 equivalents, preferably 1 to 2 equivalents, relative to compound (III-F). In addition, a base or ammonium salt may be used in an amount of about 1 to 10 equivalents, preferably 1 to 2 equivalents, relative to compound (III-F).

Moreover, a palladium complex may be used as a catalyst in an amount of 0.05 to 10 equivalents, preferably 0.05 to 2 equivalents, relative to compound (III-F).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (III-E) may be commercially available or can be produced from the corresponding starting material compound according to a method known per se.

Starting material compound (III-F) may be commercially available or can be produced by converting $L^{2c}$ of a compound represented by the formula:

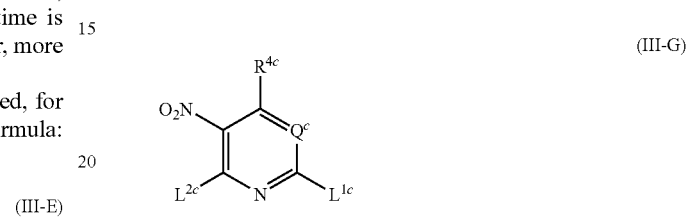

(III-G)

wherein each symbol is as defined above, to $W^c$ according to a known general organic chemical reaction.

In compound (III-G), examples of the leaving group for $L^{2c}$ include those similar to the aforementioned leaving group for $L^{1c}$.

Compound (III-F) [$W^c$=SCN] can be obtained, for example, by reacting compound (III-G) with potassium thiocyanate, sodium thiocyanate or ammonium thiocyanate.

The reaction is preferably carried out in a solvent and using potassium thiocyanate, sodium thiocyanate or ammonium thiocyanate in an amount of 1 to 5 equivalents, preferably 1 to 2 equivalents, relative to compound (III-G).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-G) may be commercially available or can be produced from the corresponding starting material compound according to a method known per se.

Method B:

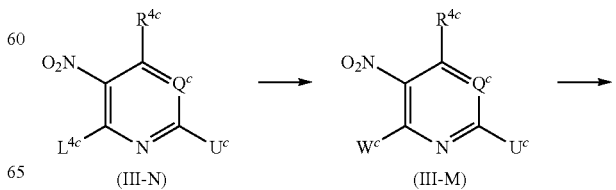

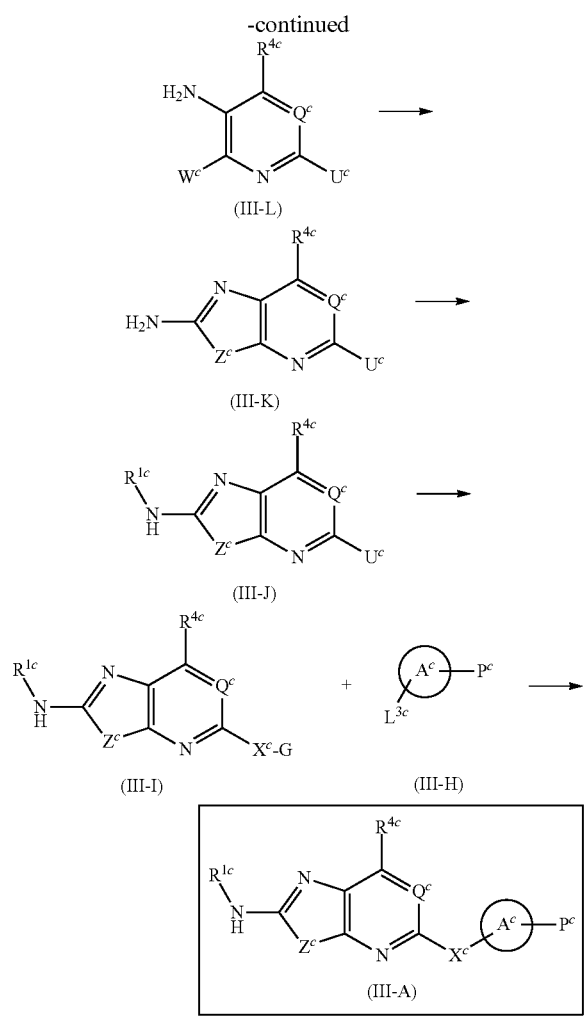

wherein $L^{3c}$ and $L^{4c}$ are each a leaving group, $U^c$ is any functional group that can be converted to $X^c$-G, and may itself be $X^c$-G, and the other symbols are each as defined above.

Starting material compound (III-A) can also be produced, for example, by reacting a compound represented by the formula:

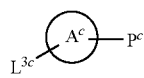

(III-H)

wherein each symbol is as defined above, with a compound represented by the formula:

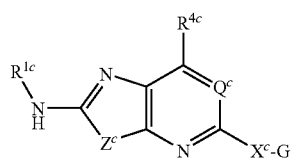

(III-I)

wherein each symbol is as defined above.

In compound (III-H), examples of the leaving group represented by $L^{3c}$ include those similar to the aforementioned leaving group for $L^{1c}$.

In compound (III-I), when $X^c$ is —$NR^{7c}$— [$R^{7c}$ is as defined above], —O— or —S—, G is mainly a hydrogen atom, but may be an alkali metal or an alkaline earth metal.

The reaction is preferably carried out in a solvent and using compound (III-I) or a salt thereof in an amount of 1 to 5 equivalents, preferably 1 to 2 equivalents, relative to compound (III-H). In addition, a base or ammonium salt may be used in an amount of about 1 to 10 equivalents, preferably 1 to 2 equivalents, relative to compound (III-H).

Moreover, a palladium complex may be used as a catalyst in an amount of 0.05 to 10 equivalents, preferably 0.05 to 2 equivalents, relative to compound (III-H).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (III-H) may be commercially available or can be produced from the corresponding starting material compound according to a method known per se.

Starting material compound (III-I) can be produced, for example, by converting $U^c$ of a compound represented by the formula:

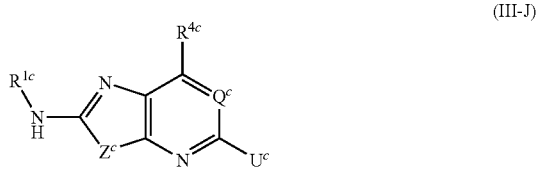

(III-J)

wherein each symbol is as defined above, to an suitable known general functional group as necessary. Compound (III-I) [$X^c$-G=NH—H] can be obtained, for example, by subjecting compound (III-J) [$U^c$=NO$_2$] to a known general reduction reaction, and compound (III-I) [$X^c$-G=NR$^{7c}$—H, $R^{7c}$ is as defined above] can be obtained, for example, by subjecting compound (III-I) [$X^c$-G=NH—H] to a known general reductive amination reaction, a known general coupling reaction using a palladium catalyst, and the like. In addition, compound (III-I) [$X^c$-G=S—H, O—H] can be obtained, for example, by subjecting compound (III-J) [$U^c$=SR$^{9c}$, OR$^{9c}$; R$^{9c}$ is as defined above] to a known conventional deprotection as necessary.

Starting material compound (III-J) ($R^{1c}$ is acyl) can be produced, for example, by subjecting a compound represented by the formula:

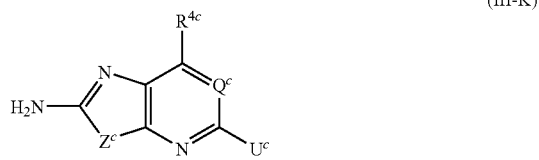
(III-K)

wherein each symbol is as defined above, to a known general acylation reaction using a carboxylic acid represented by $R^{1c}$—OH ($R^{1c}$ is acyl) or a reactive derivative thereof.

Starting material compound (III-K) can be produced, for example, from a compound represented by the formula:

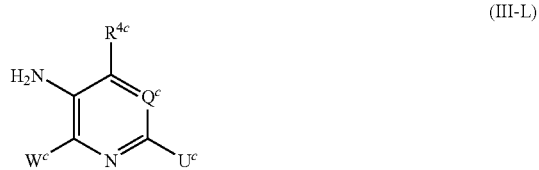
(III-L)

wherein each symbol is as defined above. Compound (III-K) can be obtained, for example, by subjecting compound (III-L) [$W^c$=$SR^{9c}$; $R^{9c}$ is as defined above] to a known general deprotection as necessary to give compound (III-L) [$W^c$=SH], and reacting the compound with cyanogen bromide or 1,1-di-1H-imidazol-1-ylmethanimine.

The reaction is preferably carried out in a solvent and using cyanogen bromide or 1,1-di-1H-imidazol-1-ylmethanimine in an amount of 1 to 10 equivalents, preferably 1 to 5 equivalents, relative to compound (III-L) [$W^c$=SH]. In addition, a base may be used in an amount of 0 to 10 equivalents, preferably 0 to 2 equivalents, relative to compound (III-L) [$W^c$=SH].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, compound (III-K) can also be obtained, for example, by reacting compound (III-L) [$W^c$=SCN] with an acid in an amount of 1 to 10 equivalents, sometimes a solvent amount, preferably 1 to 5 equivalents, relative to compound (III-L) [$W^c$=SCN].

As the acid for this reaction, hydrochloric acid, acetic acid, sulfuric acid and the like can be used. As the solvent for the above-mentioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, compound (III-K) can also be obtained, for example, by reacting compound (III-L) [$W^c$=H] with potassium thiocyanate, sodium thiocyanate or ammonium thiocyanate and bromine. The reaction is preferably carried out in a solvent and using potassium thiocyanate, sodium thiocyanate or ammonium thiocyanate in an amount of 1 to 10 equivalents, preferably 1 to 5 equivalents, and bromine in an amount of 1 to 5 equivalents, preferably 1 to 2 equivalents, relative to compound (III-L) [$W^c$=H].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-L) can be produced, for example, by subjecting a compound represented by the formula:

(III-M)

wherein each symbol is as defined above, to a known general reduction reaction to convert nitro to amino.

In addition, compound (III-K) can also be directly produced from compound (III-M) [$W^c$=SCN] without going through compound (III-L) [$W^c$=SCN] according to this reduction reaction.

For example, compound (III-K) can be directly produced without going through compound (III-L) [$W^c$=SCN] but by reacting compound (III-M) [$W^c$=SCN] with reduced iron in the presence of an acid.

The reaction is preferably carried out in a solvent and using reduced iron in an amount of 1 to 10 equivalents, preferably 1 to 5 equivalents, and an acid in an amount of 1 to 20 equivalents, sometimes a solvent amount, preferably 1 to 10 equivalents, relative to compound (III-M) [$W^c$=SCN].

As the acid for this reaction, hydrochloric acid, acetic acid, sulfuric acid and the like can be used. As the solvent for the above-mentioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-M) may be commercially available or can be produced by converting $L^{4c}$ of a compound represented by the formula:

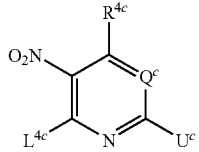

(III-N)

wherein each symbol is as defined above, to $W^c$ according to a known general organic chemical reaction.

In compound (III-N), examples of the leaving group for $L^{4c}$ include those similar to the aforementioned leaving group for $L^{2c}$.

Compound (III-M) [$W^c$=SCN] can be obtained, for example, by reacting compound (III-N) with potassium thiocyanate, sodium thiocyanate or ammonium thiocyanate.

The reaction is preferably carried out in a solvent and using potassium thiocyanate, sodium thiocyanate or ammonium thiocyanate in an amount of 1 to 5 equivalents, preferably 1 to 2 equivalents, relative to compound (III-N).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-N) may be commercially available or can be produced from the corresponding starting material compound according to a method known per se.

Method C:

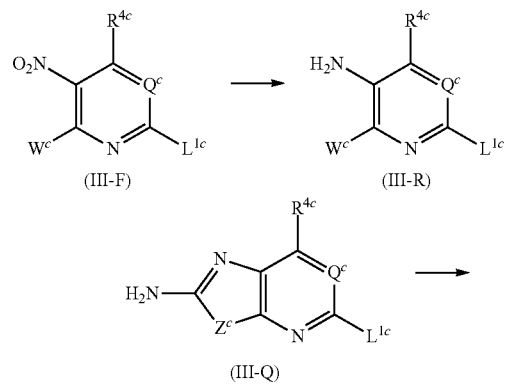

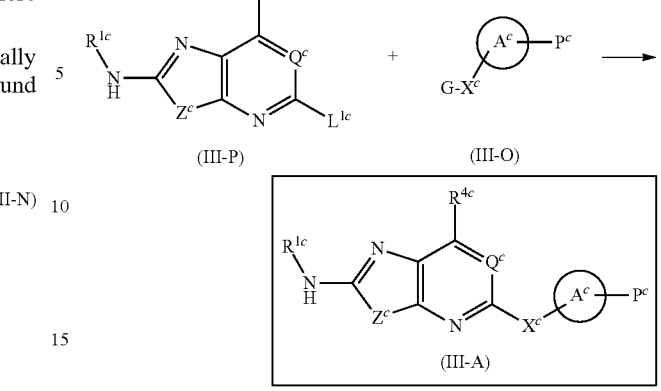

wherein each symbol is as defined above.

Starting material compound (III-A) can also be produced, for example, by reacting a compound represented by the formula:

(III-O)

wherein each symbol is as defined above, with a compound represented by the formula:

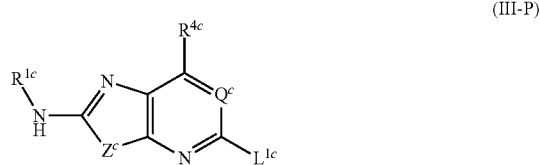

(III-P)

wherein each symbol is as defined above.

In compound (III-0), when $X^c$ is —$NR^{7c}$— [$R^{7c}$ is as defined above], —O— or —S—, G is mainly a hydrogen atom, but may be an alkali metal or an alkaline earth metal.

The reaction is preferably carried out in a solvent and using compound (III-O) or a salt thereof in an amount of 1 to 5 equivalents, preferably 1 to 2 equivalents, relative to compound (III-P). In addition, a base or ammonium salt may be used in an amount of about 1 to 10 equivalents, preferably 1 to 2 equivalents, relative to compound (III-P). Moreover, a palladium, complex may be used as a catalyst in an amount of 0.05 to 10 equivalents, preferably 0.05 to 2 equivalents, relative to compound (III-P).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The reaction may be carried out under microwave irradiation.

Starting material compound (III-O) may be commercially available or can be produced from the corresponding starting material compound according to a method known per se.

Starting material compound (III-P) ($R^{1c}$ is acyl) can be produced, for example, by subjecting a compound represented by the formula:

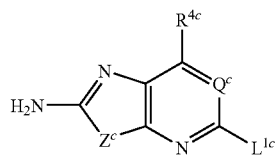

(III-Q)

wherein each symbol is as defined above, to a known general acylation reaction using a carboxylic acid represented by $R^{1c}$—OH ($R^{1c}$ is acyl) or a reactive derivative thereof.

Starting material compound (III-Q) can be produced, for example, from a compound represented by the formula:

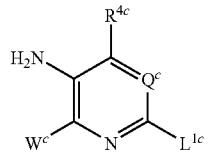

(III-R)

wherein each symbol is as defined above.

Compound (III-Q) can be obtained, for example, by subjecting compound (III-R) [$W^c$=$SR^{9c}$; $R^{9c}$ is as defined above] to a known general deprotection as necessary to give compound (III-R) [$W^c$=SH], and reacting the compound with cyanogen bromide or 1,1-di-1H-imidazol-1-ylmethanimine.

The reaction is preferably carried out in a solvent and using cyanogen bromide or 1,1-di-1H-imidazol-1-ylmethanimine in an amount of 1 to 10 equivalents, preferably 1 to 5 equivalents, relative to compound (III-R) [$W^c$=SH]. In addition, a base may be used in an amount of 0 to 10 equivalents, preferably 0 to 2 equivalents, relative to compound (III-R) [$W^c$=SH].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, compound (III-Q) can also be obtained, for example, by reacting compound (III-R) [$W^c$=SCN] with an acid in an amount of 1 to 10 equivalents, sometimes a solvent amount, preferably 1 to 5 equivalents, relative to compound (III-R) [$W^c$=SCN].

As the acid for this reaction, hydrochloric acid, acetic acid, sulfuric acid and the like can be used. As the solvent for the above-mentioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethyiphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, compound (III-Q) can also be obtained, for example, by reacting compound (III-R) [$W^c$=H] with potassium thiocyanate, sodium thiocyanate or ammonium thiocyanate and bromine. The reaction is preferably carried out in a solvent and using potassium thiocyanate, sodium thiocyanate or ammonium thiocyanate in an amount of 1 to 10 equivalents, preferably 1 to 5 equivalents, and bromine in an amount of 1 to 5 equivalents, preferably 1 to 2 equivalents, relative to compound (III-R) [$W^c$=H].

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

Starting material compound (III-R) may be commercially available or can be produced by subjecting a compound represented by the formula:

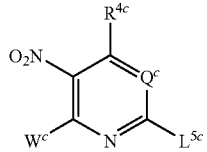

(III-F)

wherein each symbol is as defined above, to a known reduction reaction to convert nitro to amino.

In addition, compound (III-Q) can be directly produced from compound (III-F) [$W^c$=SCN] without going through compound (III-R) [$W^c$=SCN] according to this reduction reaction.

For example, compound (III-Q) can be directly produced without going through compound (III-R) [$W^c$=SCN] but by reacting compound (III-F) [$W^c$=SCN] with reduced iron in the presence of an acid.

The reaction is preferably carried out in a solvent and using reduced iron in an amount of 1 to 10 equivalents, preferably 1 to 5 equivalents, and an acid in an amount of 1 to 20 equivalents, sometimes a solvent amount, preferably 1 to 10 equivalents, relative to compound (III-F) [$W^c$=SCN].

As the acid for this reaction, hydrochloric acid, acetic acid, sulfuric acid and the like can be used. As the solvent for the above-mentioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be carried out under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The compound of the present invention can be isolated and purified by a means known per se, such as phase transfer, concentration, solvent extraction, fractionation, liquid conversion, crystallization, recrystallization, chromatography and the like. When the compound of the present invention is obtained as a free compound, it can be converted to a desired salt by a method known per se or a method analogous thereto. Conversely, when the compound is obtained as a salt, it can be converted to a free form or other desired salt by a method known per se or a method analogous thereto.

The compound of the present invention may be used as a prodrug. A prodrug of the compound of the present invention means a compound converted to the compound of the present invention by a reaction due to an enzyme, a gastric acid, etc. under the physiological condition in the living body, that is, a compound converted to the compound of the present invention by oxidation, reduction, hydrolysis, etc. due to an enzyme, a compound converted to the compound of the present invention by hydrolysis etc. due to gastric acid, and the like.

A prodrug of the compound of the present invention may be a compound obtained by subjecting an amino in the compound of the present invention to an acylation, alkylation or phosphorylation (e.g., a compound obtained by subjecting an amino in the compound of the present invention to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, ethoxycarbonylation, tert-butoxycarbonylation, acetylation or cyclopropylcarbonylation); a compound obtained by subjecting hydroxy in the compound of the present invention to acylation, alkylation, phosphorylation or boration (e.g., a compound obtained by subjecting hydroxy in the compound of the present invention to acetylation, palmitoylation, propanoylation, pivaloylation, succinylation, fumarylation, alanylation or dimethylaminomethylcarbonylation); a compound obtained by subjecting carboxy in the compound of the present invention to esterification or amidation (e.g., a compound obtained by subjecting carboxy in the compound of the present invention to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from the compound of the present invention by a method known per se.

A prodrug of the compound of the present invention may also be a compound converted into the compound of the present invention under physiological conditions, such as those described in IYAKUHIN no KAIHATSU (Development of Pharmaceuticals), Vol. 7, Design of Molecules, p. 163-198, Published by HIROKAWA SHOTEN (1990).

When the compound of the present invention has an isomer such as optical isomer, stereoisomer, positional isomer, rotational isomer and the like, any isomer and a mixture thereof are encompassed in the compound of the present invention. For example, when the compound of the present invention has an optical isomer, an optical isomer separated from a racemate is also encompassed in the compound of the present invention. Such isomers can be obtained as independent products by a synthesis means or a separation means (concentration, solvent extraction, column chromatography, recrystallization and the like) known per se.

The compound of the present invention may be a crystal, and both a single crystal and crystal mixtures are encompassed in the compound of the present invention. Crystals can be produced by crystallization according to crystallization methods known per se.

The compound of the present invention may be a solvate (e.g., hydrate etc.) or a non-solvate, both of which are encompassed in the compound of the present invention.

A compound labeled with an isotope (e.g., $^3$H, $^{14}$C, $^{35}$S, $^{125}$I etc.) is also encompassed in the compound of the present invention.

Furthermore, a deuterium conversion form wherein $^1$H is converted to $^2$H(D) is also encompassed in the compound of the present invention.

The compound of the present invention, or a salt thereof, or a prodrug thereof (in the specification, sometimes to be abbreviated as the compound of the present invention) has an Raf, particularly B-Raf, inhibitory activity, and can provide a clinically useful agent for the prophylaxis or treatment of cancer, and a cancer growth inhibitor, a cancer metastasis suppressive agent. In addition, it can be used for the prophylaxis or treatment of B-Raf dependent diseases in mammals.

The compound of the present invention also has an inhibitory activity on a vascular endothelial growth factor receptor (VEGFR; particularly, VEGFR2).

The compound of the present invention shows a strong inhibitory activity on Raf, particularly, B-Raf. Since the compound of the present invention is also superior in the efficacy, pharmacokinetics (absorption, distribution, metabolism, excretion etc.), solubility (water-solubility etc.), interaction with other pharmaceutical products, safety (acute toxicity, chronic toxicity, genetic toxicity, reproductive toxicity, cardiotoxicity, carcinogenicity etc.) and stability (chemical stability, stability to enzyme etc.), it is useful as a pharmaceutical agent.

Accordingly, the compound of the present invention is useful as Raf (specifically B-Raf) inhibitor for mammal (for example, mouse, rat, hamster, rabbit, cat, dog, bovine, sheep, monkey, human, etc.). The compound of the present invention is used as a pharmaceutical agent such as an agent for the prophylaxis or treatment of Raf-related diseases, for example, cancer [e.g., colorectal cancer (e.g., familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic duct cancer, etc.), gastric cancer (e.g., papillary adenocarcinoma, mucinous adenocarcinoma, adenosquamous cancer, etc.), breast cancer (e.g., invasive ductal carcinoma, ductal cancer in situ, inflammatory breast cancer, etc.), ovarian cancer (e.g., ovarian epithelial cancer, extragonadal germ cell tumor, ovarian germ cell tumor, ovarian low malignant potential tumor, etc.), prostate cancer (e.g., hormone-dependent prostate cancer, non-hormone dependent prostate cancer, etc.), liver cancer (e.g., primary liver cancer, extrahepatic bile duct cancer, etc.), thyroid cancer (e.g., medullary thyroid cancer, etc.), kidney cancer (e.g., renal cell carcinoma, renal pelvis and ureter transitional cell cancer, etc.), uterine cancer, brain tumor (e.g., pineal astrocytoma, pilocytic astrocytoma, diffuse astrocytoma, anaplastic astrocytoma, etc.), melanoma, sarcoma, urinary bladder cancer, blood cancer including multiple myeloma etc.], diabetic retinopathy, rheumatoid arthritis, psoriasis, atherosclerosis, Kaposi's sarcoma, COPD, pain, asthma, endometriosis, nephritis, inflammation such as osteoarthritis and the like and hypertension, a cancer growth inhibitor, a cancer metastasis suppressor, an apoptosis promoter and the like. Of these, it is effective, for example, for colorectal cancer, lung cancer, pancreatic cancer, gastric cancer, breast cancer, ovary cancer, prostate cancer, liver cancer, thyroid cancer, kidney cancer, brain tumor, melanoma, urinary bladder cancer and blood cancer. Particularly, the compound of the present invention is effective for patients with melanoma, thyroid cancer, lung cancer, colorectal cancer, ovary cancer, prostate cancer or kidney cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet, sublingual tablet, buccal tablet, mouth cavity quick-integrating tablet), pill, granule, powder, capsule (including soft capsule, microcapsule), oral preparation such as syrup, emulsion, suspension, films (e.g., mouth cavity mucous membrane adhesion film) and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method (e.g., the method described in the Japanese Pharmacopoeia) generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the preparation field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be blended. A prepared injection is generally filled in an ampoule.

While the content of the compound of the present invention in the pharmaceutical agent of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the pharmaceutical agent of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, pharmaceutical agents inhibiting the action of cell proliferation factors or cell proliferation factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, epristeride, and the like), aderenal cortex hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine, and the like), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell proliferation factors" in the "pharmaceutical agents inhibiting the action of cell proliferation factors or cell proliferation factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα, and the like], (2) insulin or substances possessing substantially the same activity as insulin [e.g., insulin, IGF (insulin-like growth factor)-1, IGF-2, and the like], (3) FGF (fibroblast growth factor) or substances possessing substantially the same activity as FGF [e.g., acidic FGF, basic FGF, KGF (keratinocyte growth factor), FGF-10, and the like], and (4) other cell proliferation factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin, and the like].

Examples of the "cell proliferation factor receptors" include any receptors capable of binding to the aforementioned cell proliferation factors, including EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

As the "pharmaceutical agents inhibiting the action of cell proliferation factors or cell proliferation factor receptors", EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK(MEK1/2) inhibitor, MET inhibitor, CDK inhibitor, Akt inhibitor, ERK inhibitor and the like are used. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl) butyl]ureido]isothiazole-4-carboxamide (CP-547632), Axitinib, N-(3,3-dimethyl-2,3-dihydro-1H-indol-6-yl)-2-

(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropoxy]-3,4-difluoro-2-(2-fluoro-4-iodophenylamino)benzamide (PD-0325901) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), other angiogenesis inhibitors (e.g., humagillin, shark extract, COX-2 inhibitor, and the like), α-blockers (e.g., tamsulosin hydrochloride, and the like), bisphosphonic acids (pamidronate, zoledronate, and the like), thalidomide, 5 azacytidine, decitabine, bortezomib, antitumor antibody such as anti-CD20 antibody and the like, toxin labeled antibody and the like can also be used.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods: (1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (e.g., the compound of the present invention and the concomitant drug are administered in this order, or in the reverse order). The dose of the concomitant drug is appropriately determined in accordance with its clinical dose. And the ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered by intravenous, intramuscular, subcutaneous or intra-tissue administration, or directly to the lesion.

As a pharmacologically acceptable carrier which may be used for preparing a preparation of the combination agent of the present invention, those similar to the aforementioned pharmacologically acceptable carriers, that can be used for the production of the pharmaceutical agent of the present invention, can be mentioned. Where necessary, the aforementioned additives that can be used for the production of pharmaceutical agent of the present invention, such as preservatives, antioxidants, colorants, sweetening agents, adsorbents, wetting agents and the like can also be appropriately used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the entire preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the entire preparation.

The content of additives in the combination agent of the present invention varies depending on the dosage faun, and is usually from about 1 to 99.99% by weight, preferably from about 10 to 90% by weight, based on the entire preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH adjuster (e.g., hydrochloric acid, sodium hydroxide and the like), a preservative (e.g., ethyl paraoxybenzoate, benzoic acid, methylparaben, propylparaben, benzyl alcohol and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch and the like), a disintegrating agent (e.g., starch, calcium carbonate and the like), a binder (e.g., starch, gum arabic, carboxymethylcellulose, polyvinylpyrrolidone, hydroxypropylcellulose and the like), a lubricant (e.g., talc, magnesium stearate, polyethylene glycol 6000 and the like) and the like may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid•acrylic acid copolymer, manufactured by Rohm, DE), pigment (e.g., iron oxide red, titanium dioxide, etc.) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acid [e.g., cacao butter, Witepsols (manufactured by Dynamit Nobel, Germany), etc.], glycerides of medium chain fatty acid [e.g., Miglyols (manufactured by Dynamit Nobel, Germany), etc.], or vegetable oils (e.g., sesame oil, soybean oil, cotton seed oil and the like), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se, for example, a method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as tromethamol and the like, etc. are listed.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

Into the injection of the present invention, additives usually used in an injection, for example, a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH regulator (e.g., hydrochloric acid, sodium hydroxide and the like), a preservative (e.g., ethyl p-oxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, can be appropriately blended. These additives are generally blended in a proportion usually used in an injection.

It is advantageous that pH of an injection is controlled from pH 2 to 12, preferably from pH 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-release Preparation, and Preparation Thereof A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (manufactured by Rohm Pharma) such as Eudoragit RS-100, RL-100, RS-30D, RL-30D, RL-PO, RS-PO (ethyl acrylate/methyl methacrylate/trimethylchloride methacrylate/ethyl ammonium), Eudoragit NE-30D (methyl methacrylate/ethyl acrylate copolymer), and the like, hydrogenated oils such as hydrogenated castor oil (e.g., Lubri wax (manufactured by Freund Corporation) and the like), waxes such as carnauba wax, fatty acid glycerin ester, paraffin and the like, polyglycerin fatty acid esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (last two are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 μm, further preferably, from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscaimelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned productions method, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral agents and parenteral agents such as an injection and the like are used, and oral agents are preferable.

The immediate-release preparation, usually, may contain, in addition to an active component drug, also carriers, additives and excipients conventionally used in the preparation field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95 w/w %, preferably from about 1 to about 60 w/w % based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (for example, Actisol, manufactured by Asahi Kasei Corporation), crospovidone (for example, Kollidon CL, manufactured by BASF), low substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by absorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the immediate-release preparation.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (for example, Aerosil (manufactured by Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one preparation for oral administration (e.g., granule, fine particle, tablet, capsule and the like) or made into one preparation for oral administration appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include gelatins, dextrins, animal proteins or vegetable proteins such as soybean, wheat and psyllium seed protein and the like; rubber substances such as gum Arabic, guar gum, agar, xanthan and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a coloring agent, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the administration subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin and the like, macrolide type such as clarithromycin and the like etc.) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administered 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administered repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is explained in more detail in the following by referring to Examples, Formulation Examples, Experimental Examples and Test Examples, which are not to be construed as limitative.

Example A1

Production of N-[3-({2-[(trifluoroacetyl)amino]imidazo[1,2-a]pyridin-6-yl}oxy)phenyl]-3-(trifluoromethyl)benzamide

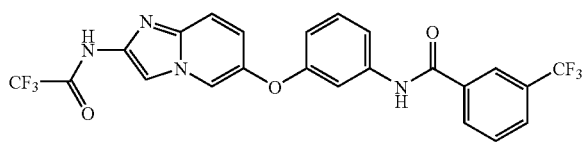 [SMILES: O=C(Nc1cccc(Oc2ccc3nc(NC(=O)C(F)(F)F)cn3c2)c1)c1cccc(C(F)(F)F)c1]

(i) Production of 2-nitro-5-(3-nitrophenoxy)pyridine

To a solution of 5-bromo-2-nitropyridine (20.5 g, 101 mmol) and cesium carbonate (50 g, 153 mmol) in N,N-dimethylformamide (200 mL) was added dropwise a solution of 3-nitrophenol (15.5 g, 111 mmol) in N,N-dimethylformamide (100 mL) for 1 hr, and the mixture was stirred at room temperature for 12 hr. The reaction mixture was concentrated under reduced pressure, and the obtained residue was diluted with water (300 mL) and extracted with ethyl acetate (600 mL). The organic layer was washed with 5% aqueous sodium hydrogen carbonate solution (300 mL) and saturated brine (300 mL), and dried over anhydrous sodium sulfate. The insoluble material was filtered off, and the filtrate was concentrated under reduced pressure. The obtained residue was purified by basic silica gel column chromatography (hexane/ethyl acetate=90/10→60/40), and fractions containing the object product was concentrated under reduced pressure to give the title compound (14.28 g, 54%) as colorless crystals.

$^1$H-NMR (DMSO-$d_6$, 300 MHz) δ 7.69-7.87 (3H, m), 8.10 (1H, t, J=2.1 Hz), 8.17 (1H, dt, J=1.8, 7.7 Hz), 8.38 (1H, d, J=9.0 Hz), 8.53 (1H, d, J=2.7 Hz).

(ii) Production of 5-(3-aminophenoxy)pyridine-2-amine dihydrochloride

To a solution of 2-nitro-5-(3-nitrophenoxy)pyridine (14.0 g, 53.6 mmol) in methanol (1000 mL)/tetrahydrofuran (200 mL)/ethyl acetate (200 mL) was added 10% palladium-carbon (1.4 g), and the mixture was stirred under a hydrogen atmosphere (1.0 pressure) at room temperature for 20 hr. The insoluble material was filtered off, and the filtrate was concentrated. The obtained residue was diluted with ethyl acetate (300 mL), and 4N hydrochloric acid/ethyl acetate (30 mL) was slowly added dropwise. The obtained colorless precipitate was collected by filtration, washed with diisopropyl ether and hexane on filter paper, and dried to give the title compound (15.2 g, quantitative) as a colorless powder. The obtained compound was used for the next reaction without further purification.

(iii) Production of N-{3-[(6-aminopyridin-3-yl)oxy]phenyl}-3-(trifluoromethyl)benzamide To a solution of 5-(3-aminophenoxy)pyridine-2-amine dihydrochloride (3.5 g, 12.7 mmol) in N,N-dimethylacetamide (30 mL) was added 3-(trifluoromethyl)benzoylchloride (2.80 g, 13.4 mmol), and the mixture was stirred at room temperature for 6 hr. The reaction mixture was concentrated under reduced pressure, 5% aqueous sodium hydrogen carbonate solution (100 mL) was added to the residue, and the mixture was extracted with ethyl acetate (200 mL). The organic layer was washed with water (100 mL) and saturated brine (100 mL), and dried over anhydrous sodium sulfate. The insoluble material was filtered off, and the filtrate was concentrated under reduced pressure. Ethyl acetate (30 mL)/hexane (20 mL) was added to the obtained residue, and the obtained precipitate was collected by filtration and air-dried to give the title compound (3.95 g, 83%) as a colorless powder.

$^1$H-NMR (DMSO-d$_6$, 300 MHz) δ 5.90 (2H, s), 6.51 (1H, d, J=8.9 Hz), 6.71 (1H, dd, J=2.4, 8.1 Hz), 7.23 (1H, dd, J=3.0, 8.9 Hz), 7.31 (1H, t, J=8.1 Hz), 7.36 (1H, t, J=2.1 Hz), 7.51 (1H, d, J=8.1 Hz), 7.69-7.83 (2H, m), 7.96 (1H, d, J=7.5 Hz), 8.15-8.29 (2H, m), 10.47 (1H, s).

(iv) Production of N-{3-[(6-{[(4-methylphenyl)sulfonyl]amino}pyridin-3-yl)oxy]phenyl}-3-(trifluoromethyl)benzamide To a solution of N-{3-[(6-aminopyridin-3-yl)oxy]phenyl}-3-(trifluoromethyl)benzamide (2.00 g, 5.36 mmol) in pyridine (60 mL) was added 4-methylbenzenesulfonyl chloride (1.12 g, 5.89 mmol) under ice-cooling, and the mixture was stirred with heating at 80° C. for 2 days. After cooling the reaction mixture to room temperature, water (200 mL) was added, and the mixture was extracted with ethyl acetate (300 mL). The organic layer was washed with saturated brine (300 mL), and dried over anhydrous sodium sulfate. The insoluble material was filtered off, and the filtrate was concentrated under reduced pressure to give the title compound (2.75 g, 99%) as a yellow oil. The obtained compound was used for the next reaction without further purification.

$^1$H-NMR (DMSO-d$_6$, 300 MHz) δ 2.34 (3H, s), 6.72-6.80 (1H, m), 7.14 (1H, d, J=9.0 Hz), 7.29-7.44 (4H, m), 7.50 (1H, dd, J=2.4, 9.0 Hz), 7.53-7.60 (1H, m), 7.75-7.83 (3H, m), 7.96 (1H, d, J=7.8 Hz), 8.02 (1H, d, J=2.4 Hz), 8.16-8.27 (2H, m), 10.50 (1H, s), 11.07 (1H, br s).

(v) Production of N-{3-[(1-(2-amino-2-oxoethyl)-6-{[(4-methylphenyl)sulfonyl]imino}-1,6-dihydropyridin-3-yl)oxy]phenyl}-3-(trifluoromethyl)benzamide To a solution of N-{3-[(6-{[(4-methylphenyl)sulfonyl]amino}pyridin-3-yl)oxy]phenyl}-3-(trifluoromethyl)benzamide (2.7 g, 5.12 mmol) in N,N-dimethylformamide (18 mL) was added N-ethyl-N-isopropylpropan-2-amine (0.94 mL, 5.38 mmol), and the mixture was stirred at room temperature for 15 min. 2-Iodoacetamide (995 mg, 5.38 mmol) was added to the reaction mixture, and the mixture was stirred at room temperature for 18 hr. Water (200 mL) was added to the reaction mixture, and the mixture was extracted with ethyl acetate (300 mL). The organic layer was washed with water (100 mL) and saturated brine (100 mL) and dried over anhydrous sodium sulfate. The insoluble material was filtered off, and the filtrate was concentrated under reduced pressure. The obtained residue was purified by silica gel column chromatography (hexane/ethyl acetate=60/40→0/100) and recrystallized from ethyl acetate and hexane to give the title compound (1.84 g, 61%) as a colorless solid.

$^1$H-NMR (DMSO-d$_6$, 300 MHz) δ 2.34 (3H, s), 4.83 (2H, s), 6.78 (1H, dd, J=2.7, 8.4 Hz), 7.28 (2H, d, J=8.4 Hz), 7.32-7.45 (3H, m), 7.47 (1H, t, J=2.1 Hz), 7.60 (1H, d, J=8.4 Hz), 7.68 (2H, d, J=8.4 Hz), 7.71-7.85 (3H, m), 7.98 (1H, d, J=7.8 Hz), 8.15 (1H, d, J=2.7 Hz), 8.19-8.30 (2H, m), 10.56 (1H, s).

(vi) Production of N-[3-({2-[(trifluoroacetyl)amino]imidazo[1,2-a]pyridin-6-yl}oxy)phenyl]-3-(trifluoromethyl)benzamide To a solution of N-{3-[(1-(2-amino-2-oxoethyl)-6-{[(4-methylphenyl)sulfonyl]imino}-1,6-dihydropyridin-3-yl)oxy]phenyl}-3-(trifluoromethyl)benzamide (1.00 g, 1.71 mmol) in dichloromethane (8.0 mL) was added trifluoroacetic acid anhydride (6.0 mL), and the mixture was stirred at room temperature for 4 hr. The reaction mixture was concentrated under reduced pressure, 5% aqueous sodium hydrogen carbonate solution (150 mL) was added to the residue, and the mixture was extracted with ethyl acetate (300 mL). The organic layer was washed with saturated brine (150 mL), and dried over anhydrous sodium sulfate. The insoluble material was filtered off, and the filtrate was concentrated under reduced pressure. The obtained residue was purified by silica gel column chromatography (hexane/ethyl acetate=70/30→40/60) and recrystallized from ethyl acetate and hexane to give the title compound (0.55 g, 64%) as a colorless solid.

$^1$H-NMR (DMSO-d$_6$, 300 MHz) δ 6.86 (1H, dd, J=1.8, 8.1 Hz), 7.22 (1H, dd, J=2.1, 9.6 Hz), 7.39 (1H, t, J=8.2 Hz), 7.50 (1H, t, J=2.1 Hz), 7.55-7.67 (2H, m), 7.76 (1H, t, J=7.8 Hz), 7.96 (1H, d, J=7.8 Hz), 8.15-8.33 (3H, m), 8.66 (1H, d, J=2.1 Hz), 10.51 (1H, s), 12.49 (1H, br s).

Example A2

Production of N-[3-({2-[(cyclopropylcarbonyl)amino]imidazo[1,2-a]pyridin-6-yl}oxy)phenyl]-3-(trifluoromethyl)benzamide

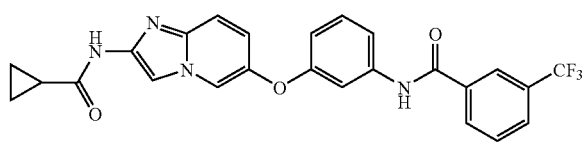 [SMILES: O=C(Nc1cccc(Oc2ccc3nc(NC(=O)C4CC4)cn3c2)c1)c1cccc(C(F)(F)F)c1]

(i) Production of N-{3-[(2-aminoimidazo[1,2-a]pyridin-6-yl)oxy]phenyl}-3-(trifluoromethyl)benzamide To a solution of N-[3-({2-[(trifluoroacetyl)amino]imidazo[1,2-a]pyridin-6-yl}oxy)phenyl]-3-(trifluoromethyl)benzamide (400 mg, 0.787 mmol) produced in Example A1(vi) in ethanol (4.0 mL) was added 1N aqueous sodium hydroxide solution (8.0 mL), and the mixture was stirred at room temperature for 12 hr. Water (100 mL) was added to the reaction mixture, and the mixture was extracted with ethyl acetate (200 mL). The organic layer was washed with saturated brine (100 mL) and dried over anhydrous sodium sulfate. The insoluble material was filtered off, and the filtrate was concentrated under reduced pressure. The obtained residue was purified by basic silica gel column chromatography (ethyl acetate/methanol=100/0→80/20), fractions containing the object product was concentrated under reduced pressure, and the residue was washed with ethyl acetate/diisopropyl ether (1:4) to give the title compound (350 mg, quantitative) as a colorless solid.

$^1$H-NMR (DMSO-$d_6$, 300 MHz) δ 5.09 (2H, br s), 6.80 (1H, dd, J=2.4, 8.1 Hz), 6.88 (1H, dd, J=2.1, 9.6 Hz), 7.02 (1H, s), 7.23 (1H, d, J=9.6 Hz), 7.35 (1H, t, J=8.1 Hz), 7.43 (1H, t, J=2.1 Hz), 7.53-7.60 (1H, m), 7.76 (1H, t, J=7.8 Hz), 7.96 (1H, d, J=7.8 Hz), 8.16-8.26 (2H, m), 8.34 (1H, d, J=2.1 Hz), 10.49 (1H, s).

(ii) Production of N-[3-({2-[(cyclopropylcarbonyl)amino]imidazo[1,2-a]pyridin-6-yl}oxy)phenyl]-3-(trifluoromethyl)benzamide To a solution of N-{3-[(2-aminoimidazo[1,2-a]pyridin-6-yl)oxy]phenyl}-3-(trifluoromethyl)benzamide (300 mg, 0.727 mmol) in N,N-dimethylacetamide (3.0 mL) was added cyclopropanecarbonyl chloride (69 μL, 0.763 mmol), and the mixture was stirred at room temperature for 2 hr. The reaction mixture was diluted with ethyl acetate (200 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was purified by basic silica gel column chromatography (hexane/ethyl acetate=60/40→0/100), fractions containing the object product was concentrated under reduced pressure, and the residue was triturated with ethyl acetate, diisopropyl ether and hexane to give the title compound (145 mg, 42%) as a colorless solid.

$^1$H-NMR (DMSO-$d_6$, 300 MHz) δ 0.57-0.93 (4H, m), 1.77-2.06 (1H, m), 6.83 (1H, dd, J=1.8, 8.1 Hz), 7.10 (1H, dd, J=2.1, 9.6 Hz), 7.37 (1H, t, J=8.2 Hz), 7.42-7.53 (2H, m), 7.58 (1H, d, J=8.4 Hz), 7.76 (1H, t, J=7.8 Hz), 7.95 (1H, d, J=7.8 Hz), 8.07 (1H, s), 8.16-8.30 (2H, m), 8.60 (1H, d, J=2.1 Hz), 10.49 (1H, s), 10.98 (1H, s).

Example A3

Production of 3-(1-cyano-1-methylethyl)-N-[3-({2-[(trifluoroacetyl)amino]imidazo[1,2-a]pyridin-6-yl}oxy)phenyl]benzamide

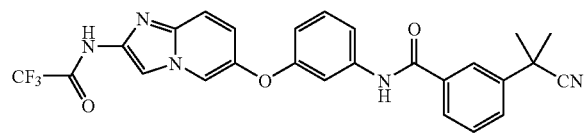 [SMILES: CC(C)(C#N)c1cccc(C(=O)Nc2cccc(Oc3ccc4nc(NC(=O)C(F)(F)F)cn4c3)c2)c1]

(i) Production of methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtrated, solvent was evaporated under reduced pressure, and the residue was purified by silica gel column chromatography (ethyl acetate/hexane=5/95→30/70). The combined solution was concentrated under reduced pressure to give the title compound (7.0 g, 91%) as a colorless oil.

$^1$H-NMR (DMSO-$d_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ii) Production of methyl 3-(1-cyano-1-methylethyl)benzoate

To a solution of methyl 3-(cyanomethyl)benzoate (7.0 g, 40 mmol) in dimethyl sulfoxide (80 mL) was added sodium hydride (60% in oil, 4.8 g, 120 mmol) while cooling the solution to a temperature of 25° C. or below at which the solution did not solidify. The reaction mixture was stirred at room temperature for 20 min, methyl iodide (7.5 mL, 120 mmol) was added, and the mixture was further stirred at room temperature for 16 hr. The reaction mixture was diluted with water (400 mL) and extracted with ethyl acetate (800 mL). The organic layer was washed with water (400 mL) and saturated brine (400 mL), dried over anhydrous sodium sulfate, and filtrated. The solvent was evaporated under reduced pressure, and the residue was purified by silica gel column chromatography (ethyl acetate/hexane=5/95→50/50). The combined solution was concentrated under reduced pressure to give the title compound (6.4 g, 79%) as a colorless oil.

$^1$H-NMR (DMSO-$d_6$, 300 MHz) δ 1.72 (6H, s), 3.89 (3H, s), 7.61 (1H, t, J=7.8 Hz), 7.84 (1H, ddd, J=1.2, 2.1, 7.8 Hz), 7.95 (1H, dt, J=7.8, 1.2 Hz), 8.08 (1H, t, J=1.5 Hz).

(iii) Production of 3-(1-cyano-1-methylethyl)benzoic acid

To a solution of methyl 3-(1-cyano-1-methylethyl)benzoate (2.8 g, 14 mmol) in tetrahydrofuran (30 mL) were added lithium hydroxide•monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). 1N Hydrochloric acid was slowly added to the mixture to adjust the pH to 3. The precipitated white precipitate was collected by filtration, washed with water, and dried to give the title compound (2.5 g, 98%) as a white powder.

$^1$H-NMR (DMSO-$d_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(iv) Production of N-{3-[(6-aminopyridin-3-yl)oxy]phenyl}-3-(1-cyano-1-methylethyl)benzamide To a solution of 3-(1-cyano-1-methylethyl)benzoic acid (2.66 g, 14.0 mmol) in tetrahydrofuran (28 mL) were added oxalyl chloride (1.63 mL, 19.1 mmol) and N,N-dimethylformamide (about 20 μL), and the mixture was stirred at room temperature for 1 hr. The reaction mixture was concentrated under reduced pressure to give 3-(1-cyano-1-methylethyl)benzoyl chloride as a pale-brown oil.

To a solution of 3-(1-cyano-1-methylethyl)benzoyl chloride synthesized above in N,N-dimethylacetamide (50 mL) was added 5-(3-aminophenoxy)pyridine-2-amine dihydrochloride (3.5 g, 12.7 mmol) produced in Example A1(ii), and the mixture was stirred at room temperature for 18 hr. 5% Aqueous sodium hydrogen carbonate solution (200 mL) was added to the reaction mixture, and the mixture was extracted with ethyl acetate (300 mL). The organic layer was washed with saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100) and triturated with ethyl acetate and hexane to give the title compound (3.44 g, 66%) as a colorless solid.

$^1$H-NMR (DMSO-$d_6$, 300 MHz) δ 1.74 (6H, s), 5.91 (2H, s), 6.51 (1H, d, J=8.9 Hz), 6.66-6.77 (1H, m), 7.23 (1H, dd, J=2.7, 8.9 Hz), 7.30 (1H, t, J=8.1 Hz), 7.38 (1H, t, J=2.1 Hz), 7.43-7.52 (1H, m), 7.58 (1H, t, J=7.8 Hz), 7.68-7.82 (2H, m), 7.84-7.94 (1H, m), 7.99 (1H, t, J=1.8 Hz), 10.33 (1H, s).

(v) Production of 3-(1-cyano-1-methylethyl)-N-{3-[(6-{[(4-methylphenyl)sulfonyl]amino}pyridin-3-yl)oxy]phenyl}benzamide To a solution of N-{3-[(6-aminopyridin-3-yl)oxy]phenyl}-3-(1-cyano-1-methylethyl)benzamide (2.5 g, 6.71 mmol) in pyridine (60 mL) was added 4-methylbenzenesulfonyl chloride (1.34 g, 7.05 mmol) under ice-cooling, and the mixture was 5 stirred with heating at 80° C. for 2 days. After the reaction mixture was cooled to room temperature, water (200 mL) was added, and the mixture was extracted with ethyl acetate (300 mL). The organic layer was washed with saturated brine (300 mL), and dried over anhydrous sodium sulfate. The insoluble material was filtered off, and the filtrate was concentrated under reduced pressure to give the title compound (3.48 g, 99%) as a colorless powder. The powder was used for the next reaction without further purification.

$^1$H-NMR (DMSO-$d_6$, 300 MHz) δ 1.74 (6H, s), 2.34 (3H, s), 6.75 (1H, dd, J=8.1, 2.4 Hz), 7.15 (1H, d, J=9.0 Hz), 7.27-7.45 (4H, m), 7.46-7.68 (3H, m), 7.71-7.83 (3H, m), 7.89 (1H, d, J=7.8 Hz), 7.99 (1H, s), 8.02 (1H, d, J=3.0 Hz), 10.37 (1H, s), 11.07 (1H, br s).

(vi) Production of N-{3-[(1-(2-amino-2-oxoethyl)-6-{[(4-methylphenyl)sulfonyl]imino}-1,6-dihydropyridin-3-yl)oxy]phenyl}-3-(1-cyano-1-methylethyl)benzamide To a solution of 3-(1-cyano-1-methylethyl)-N-{3-[(6-{[(4-methylphenyl)sulfonyl]amino}pyridin-3-yl)oxy]phenyl}benzamide (3.2 g, 6.08 mmol) in N,N-dimethylfoLmamide (20 mL) was added N-ethyl-N-isopropylpropan-2-amine (1.11 mL, 6.38 mmol), and the mixture was stirred at room temperature for 15 min. 2-Iodoacetamide (1.18 g, 6.38 mmol) was added to the reaction mixture, and the mixture was stirred at room temperature for 48 hr. The reaction mixture was concentrated under reduced pressure, 5% aqueous sodium hydrogen carbonate solution (150 mL) was added to the residue, and the mixture was extracted with ethyl acetate (300 mL). The organic layer was washed with saturated brine (150 ml), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and triturated with ethyl acetate, diisopropyl ether and hexane to give the title compound (2.23 g, 63%) as a colorless solid.

$^1$H-NMR (DMSO-$d_6$, 300 MHz) δ 1.74 (6H, s), 2.34 (3H, s), 4.83 (2H, s), 6.76 (1H, dd, J=2.4, 7.8 Hz), 7.28 (2H, d, J=8.1 Hz), 7.32-7.46 (3H, m), 7.48 (1H, t, J=2.1 Hz), 7.59 (2H, t, J=7.8 Hz), 7.68 (2H, d, J=8.1 Hz), 7.71-7.82 (3H, m), 7.86-7.94 (1H, m), 8.01 (1H, t, J=1.8 Hz), 8.13 (1H, J=2.4 Hz), 10.41 (1H, s).

(vii) Production of 3-(1-cyano-1-methylethyl)-N-[3-({2-[(trifluoroacetyl)amino]imidazo[1,2-a]pyridin-6-yl}oxy)phenyl]benzamide To a solution of N-{3-[(1-(2-amino-2-oxoethyl)-6-{[(4-methylphenyl)sulfonyl]imino}-1,6-dihydropyridin-3-yl) oxy]phenyl}-3-(1-cyano-1-methylethyl)benzamide (1.00 g, 1.72 mmol) in dichloromethane (8.0 mL) was added trifluoroacetic acid anhydride (6.0 mL), and the mixture was stirred at room temperature for 16 hr. The reaction mixture was concentrated under reduced pressure, 5% aqueous sodium hydrogen carbonate solution (150 mL) was added, and the mixture was extracted with ethyl acetate (150 mL). The organic layer was washed with saturated brine (150 mL), and dried over anhydrous sodium sulfate. The insoluble material was filtered off, and the filtrate was concentrated under reduced pressure. The obtained residue was purified by silica gel column chromatography (hexane/ethyl acetate=70/30→40/60) and triturated with diisopropyl ether and hexane to give the title compound (450 mg, 52%) as a colorless solid.

$^1$H-NMR (DMSO-$d_6$, 300 MHz) δ 1.73 (6H, s), 6.84 (1H, dd, J=2.4, 7.5 Hz), 7.22 (1H, dd, J=2.4, 9.6 Hz), 7.38 (1H, t, J=8.1 Hz), 7.51 (1H, t, J=2.4 Hz), 7.54-7.68 (3H, m), 7.70-7.79 (1H, m), 7.89 (1H, d, J=8.1 Hz), 7.99 (1H, t, J=1.8 Hz), 8.27 (1H, s), 8.66 (1H, d, J=2.4 Hz), 10.36 (1H, s), 12.48 (1H, s).

Example A4

Production of 3-(1-cyano-1-methylethyl)-N-[3-({2-[(cyclopropylcarbonyl)amino]imidazo[1,2-a]pyridin-6-yl}oxy)phenyl]benzamide

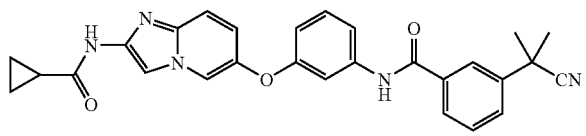 [SMILES: CC(C)(C#N)c1cccc(C(=O)Nc2cccc(Oc3ccc4nc(NC(=O)C5CC5)cn4c3)c2)c1]

(i) Production of N-{3-[(2-aminoimidazo[1,2-a]pyridin-6-yl)oxy]phenyl}-3-(1-cyano-1-methylethyl)benzamide To a solution of 3-(1-cyano-1-methylethyl)-N-[3-({2-[(trifluoroacetyl)amino]imidazo[1,2-a]pyridin-6-yl}oxy)phenyl]benzamide (400 mg, 0.788 mmol) produced in Example A3(vii) in ethanol (4.0 mL) was added 1N aqueous sodium hydroxide solution (8.0 mL), and the mixture was stirred at 45° C. for 12 hr. Water (100 mL) was added to the reaction mixture, and the mixture was extracted with ethyl acetate (200 mL). The organic layer was washed with saturated brine (100 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→80/20), and fractions containing the object product was concentrated under reduced pressure to give the title compound (0.35 g, quantitative) as a colorless solid.

$^1$H-NMR (DMSO-$d_6$, 300 MHz) δ 1.73 (6H, s), 5.08 (2H, s), 6.78 (1H, dd, J=2.1, 8.1 Hz), 6.87 (1H, dd, J=2.1, 9.6 Hz), 7.01 (1H, s), 7.22 (1H, d, J=9.6 Hz), 7.34 (1H, t, J=8.2 Hz), 7.44 (1H, s), 7.50-7.62 (2H, m), 7.74 (1H, d, J=8.1 Hz), 7.88 (1H, d, J=7.5 Hz), 7.98 (1H, s), 8.34 (1H, d, J=2.1 Hz), 10.34 (1H, s).

(ii) Production of 3-(1-cyano-1-methylethyl)-N-[3-({2-[(cyclopropylcarbonyl)amino]imidazo[1,2-a]pyridin-6-yl}oxy)phenyl]benzamide To a solution of N-{3-[(2-aminoimidazo[1,2-a]pyridin-6-yl)oxy]phenyl}-3-(1-cyano-1-methylethyl)benzamide (200 mg, 0.486 mmol) in N,N-dimethylacetamide (2.0 mL) was added cyclopropanecarbonyl chloride (46 µL, 0.510 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), fractions containing the object product was concentrated under reduced pressure, and the residue was triturated with ethyl acetate and diisopropyl ether to give the title compound (100 mg, 43%) as a colorless solid.

$^1$H-NMR (DMSO-d$_6$, 300 MHz) δ 0.73-0.85 (4H, m), 1.73 (6H, s), 1.86-2.03 (1H, m), 6.81 (1H, dd, J=2.4, 8.1 Hz), 7.10 (1H, dd, J=2.4, 9.6 Hz), 7.36 (1H, t, J=8.1 Hz), 7.44-7.52 (2H, m), 7.57 (2H, t, J=7.8 Hz), 7.69-7.78 (1H, m), 7.89 (1H, d, J=8.4 Hz), 7.98 (1H, t, J=1.5 Hz), 8.07 (1H, s), 8.59 (1H, d, J=2.4 Hz), 10.35 (1H, s), 10.98 (1H, s).

Example A5

Production of 3-(1-cyanocyclopropyl)-N-[3-({2-[(cyclopropylcarbonyl)amino]imidazo[1,2-a]pyridin-6-yl}oxy)phenyl]benzamide

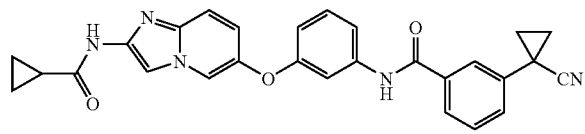 [SMILES: N#CC1(c2cccc(C(=O)Nc3cccc(Oc4ccc5nc(NC(=O)C6CC6)cn5c4)c3)c2)CC1]

(i) Production of methyl 3-(1-cyanocyclopropyl)benzoate

To a solution of methyl 3-(cyanomethyl)benzoate (1.5 g, 8.6 mmol) produced in Example A3(i) in dimethyl sulfoxide (30 mL) was added sodium hydride (60% in oil, 1.0 g, 26 mmol) while cooling the solution to a temperature of 25° C. or below at which the solution did not solidify. The reaction mixture was stirred at room temperature for 30 min, 1,2-dibromoethane (2.4 g, 12.8 mmol) was added, and the mixture was further at room temperature for 10 hr. The reaction mixture was diluted with water (100 mL), and extracted with ethyl acetate (300 mL). The organic layer was washed with saturated brine (100 mL) and dried over anhydrous sodium sulfate, and the insoluble material was filtered off. The solvent was evaporated under reduced pressure, the residue was purified by silica gel column chromatography (ethyl acetate/hexane=5/95→50/50), and fractions containing the object product was concentrated under reduced pressure to give the title compound (1.3 g, 76%) as a colorless oil.

$^1$H-NMR (CDCl$_3$, 300 MHz) δ 1.38-1.56 (2H, m), 1.74-1.82 (2H, m), 3.93 (3H, s), 7.40-7.49 (1H, m), 7.55-7.62 (1H, m), 7.88 (1H, t, J=1.5 Hz), 7.96 (1H, dt, J=7.8, 1.5 Hz).

(ii) Production of 3-(1-cyanocyclopropyl)benzoic acid

To a solution of methyl 3-(1-cyanocyclopropyl)benzoate (1.3 g, 6.4 mmol) in tetrahydrofuran (12 ml) were added lithium hydroxide•monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). 1N Hydrochloric acid was slowly added to the mixture to adjust the pH to 5. The precipitated white precipitate was collected by filtration, washed with water, and dried to give the title compound (0.73 g, 61%) as a white powder.

$^1$H-NMR (DMSO-d$_6$, 300 MHz) δ 1.50-1.62 (2H, m), 1.76-1.86 (2H, m), 7.41-7.59 (2H, m), 7.82-7.97 (2H, m), 13.19 (1H, br s).

(iii) Production of N-{3-[(6-aminopyridin-3-yl)oxy]phenyl}-3-(1-cyanocyclopropyl)benzamide To a solution of 3-(1-cyanocyclopropyl)benzoic acid (2.6 g, 13.9 mmol) in tetrahydrofuran (60 mL) were added oxalyl chloride (1.63 mL, 19.1 mmol) and N,N-dimethylformamide (about 20 µL), and the mixture was stirred at room temperature for 1 hr. The reaction mixture was concentrated under reduced pressure to give 3-(1-cyanocyclopropyl)benzoyl chloride as a colorless oil.

To a solution of 3-(1-cyanocyclopropyl)benzoyl chloride synthesized above in N,N-dimethylacetamide (50 mL) was added 5-(3-aminophenoxy)pyridine-2-amine dihydrochloride (3.5 g, 12.7 mmol) produced in Example A1(ii), and the mixture was stirred at room temperature for 18 hr. 5% Aqueous sodium hydrogen carbonate solution (200 mL) was added to the reaction mixture, and the mixture was extracted with ethyl acetate (300 mL). The organic layer was washed with saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and triturated with ethyl acetate and hexane to give the title compound (3.84 g, 75%) as a colorless solid.

$^1$H-NMR (DMSO-d$_6$, 300 MHz) δ 1.56-1.65 (2H, m), 1.75-1.86 (2H, m), 5.91 (2H, s), 6.51 (1H, d, J=8.9 Hz), 6.64-6.73 (1H, m), 7.23 (1H, dd, J=3.0, 8.9 Hz), 7.30 (1H, t, J=8.1 Hz), 7.37 (1H, t, J=2.1 Hz), 7.45-7.52 (1H, m), 7.52-7.60 (2H, m), 7.74-7.81 (2H, m), 7.85 (1H, dt, J=4.2, 2.1 Hz), 10.31 (1H, s).

(iv) Production of 3-(1-cyanocyclopropyl)-N-{3-[(6-{[(4-methylphenyl)sulfonyl]amino}pyridin-3-yl)oxy]phenyl}benzamide To a solution of N-{3-[(6-aminopyridin-3-yl)oxy]phenyl}-3-(1-cyanocyclopropyl)benzamide (2.0 g, 5.4 mmol) in pyridine (60 mL) was added 4-methylbenzenesulfonyl chloride (1.13 g, 5.94 mmol) under ice-cooling, and the mixture was stirred with heating at 80° C. for 2 days. After the reaction mixture was cooled to room temperature, water (200 mL) was added, and the mixture was extracted with ethyl acetate (400 mL). The organic layer was washed with saturated brine (200 mL), and dried over anhydrous sodium sulfate. The insoluble material was filtered off, the filtrate was concentrated under reduced pressure, and the obtained residue was washed with ethyl acetate and diisopropyl ether to give the title compound (2.61 g, 92%) as a colorless solid.

$^1$H-NMR (DMSO-d$_6$, 300 MHz) δ 1.56-1.65 (2H, m), 1.76-1.85 (2H, m), 2.34 (3H, s), 6.74 (1H, dd, J=2.1, 7.8 Hz), 7.13 (1H, d, J=9.0 Hz), 7.26-7.40 (3H, m), 7.41 (1H, t, J=2.1 Hz), 7.49 (1H, dd, J=3.0, 9.0 Hz), 7.52-7.61 (3H, m), 7.74-7.91 (4H, m), 8.01 (1H, d, J=3.0 Hz), 10.34 (1H, s), 11.05 (1H, br s).

(iii) Production of N-{3-[(1-(2-amino-2-oxoethyl)-6-{[(4-methylphenyl)sulfonyl]imino}-1,6-dihydropyridin-3-yl)oxy]phenyl}-3-(1-cyanocyclopropyl)benzamide To a solution of 3-(1-cyanocyclopropyl)-N-{3-[(6-{[(4-methylphenyl)sulfonyl]amino}pyridin-3-yl)oxy]phenyl}benzamide (2.5 g, 4.77 mmol) in N,N-dimethylformamide (15 mL) was added N-ethyl-N-isopropylpropan-2-amine (0.90 mL, 5.01 mmol), and the mixture was stirred at room temperature for 15 min. 2-Iodoacetamide (927 mg, 5.01 mmol) was added to the reaction mixture, and the mixture was stirred at room temperature for 48 hr. The reaction mixture was concentrated under reduced pressure, water (150 mL) was added to the residue, and the mixture was extracted with ethyl acetate (150 mL). The organic layer was washed with saturated brine (150 mL), and dried over anhydrous magnesium sulfate. The insoluble material was filtered off, and the filtrate was concentrated under reduced pressure. The obtained residue was recrystallized from ethyl acetate and hexane to give the title compound (2.14 g, 77%) as a pale-yellow solid.

$^1$H-NMR (DMSO-$d_6$, 300 MHz) δ 1.52-1.67 (2H, m), 1.76-1.87 (2H, m), 2.29-2.38 (3H, m), 4.83 (2H, s), 6.69-6.79 (1H, m), 7.28 (2H, d, J=8.1 Hz), 7.31-7.50 (4H, m), 7.50-7.62 (3H, m), 7.68 (2H, d, J=8.1 Hz), 7.71-7.91 (4H, m), 8.14 (1H, d, J=3.0 Hz), 10.39 (1H, s).

(iv) Production of 3-(1-cyanocyclopropyl)-N-[3-({2-[(trifluoroacetyl)amino]imidazo[1,2-a]pyridin-6-yl}oxy)phenyl]benzamide To a solution of N-{3-[(1-(2-amino-2-oxoethyl)-6-{[(4-methylphenyl)sulfonyl]imino}-1,6-dihydropyridin-3-yl)oxy]phenyl}-3-(1-cyanocyclopropyl)benzamide (1.5 g, 2.58 mmol) in dichloromethane (10 mL) was added trifluoroacetic acid anhydride (10 mL), and the mixture was stirred at room temperature for 12 hr. Water (200 mL) was added to the reaction mixture, and the mixture was extracted with ethyl acetate (200 mL). The organic layer was washed with 5% aqueous sodium hydrogen carbonate solution (200 mL) and saturated brine (200 mL), and dried over anhydrous sodium sulfate. The insoluble material was filtered off, and the filtrate was concentrated under reduced pressure. The obtained residue was purified by basic silica gel column chromatography (hexane/ethyl acetate=40/60→0/100), and fractions containing the object product was concentrated under reduced pressure to give the title compound (977 mg, 75%) as a pale-yellow oil.

$^1$H-NMR (DMSO-$d_6$, 300 MHz) δ 1.50-1.65 (2H, m), 1.76-1.87 (2H, m), 6.84 (1H, dt, J=1.2, 8.1 Hz), 7.22 (1H, dd, J=2.4, 9.6 Hz), 7.38 (1H, t, J=8.1 Hz), 7.50 (1H, t, J=2.1 Hz), 7.52-7.62 (4H, m), 7.75-7.89 (2H, m), 8.27 (1H, s), 8.66 (1H, dd, J=0.9, 2.4 Hz), 10.34 (1H, s), 12.48 (1H, br s).

(v) Production of 3-(1-cyanocyclopropyl)-N-[3-({2-[(cyclopropylcarbonyl)amino]imidazo[1,2-a]pyridin-6-yl}oxy)phenyl]benzamide To a solution of 3-(1-cyanocyclopropyl)-N-[3-({2-[(trifluoroacetyl)amino]imidazo[1,2-a]pyridin-6-yl}oxy)phenyl]benzamide (450 mg, 0.89 mmol) in ethanol (8.0 mL) was added 1N aqueous sodium hydroxide solution (8.9 mL), and the mixture was stirred at 45° C. for 8 hr. Water (100 mL) was added to the reaction mixture, and the mixture was extracted with ethyl acetate (200 mL). The organic layer was washed with saturated brine (100 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→80/20), and fractions containing the object product was concentrated under reduced pressure to give N-{3-[(2-aminoimidazo[1,2-a]pyridin-6-yl)oxy]phenyl}-3-(1-cyanocyclopropyl)benzamide (200 mg, 55%) as a colorless solid.

To a solution of N-{3-[(2-aminoimidazo[1,2-a]pyridin-6-yl)oxy]phenyl}-3-(1-cyanocyclopropyl)benzamide (200 mg, 0.488 mmol) obtained above in N,N-dimethylacetamide (4.0 mL) was added cyclopropanecarbonyl chloride (47 μL, 0.512 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=60/40→0/100), and further purified by reversed-phase column chromatography (ODS, 0.1% TFA, water/acetonitrile=95/5→5/95), and fractions containing the object product was concentrated under reduced pressure. The residue was diluted with ethyl acetate (100 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The residue was recrystallized from tetrahydrofuran and hexane to give the title compound (116 mg, 50%) as a colorless solid.

$^1$H-NMR (DMSO-$d_6$, 300 MHz) δ 0.56-0.89 (4H, m), 1.53-1.66 (2H, m), 1.74-1.87 (2H, m), 1.86-2.02 (1H, m), 6.81 (1H, dd, J=2.4, 8.4 Hz), 7.10 (1H, dd, J=2.4, 9.6 Hz), 7.36 (1H, t, J=8.1 Hz), 7.43-7.63 (5H, m), 7.70-7.89 (2H, m), 8.07 (1H, s), 8.60 (1H, d, J=2.4 Hz), 10.33 (1H, s), 10.99 (1H, s).

Preparation Example A1

A pharmaceutical agent containing the compound of the present invention as an active ingredient can be produced, for example, according to the following formulation.

1. Capsule

| | |
|---|---|
| (1) compound of Example A4 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added and the total amount is sealed in a gelatin capsule.

2. Tablet

| | |
|---|---|
| (1) compound of Example A4 | 40 mg |
| (2) lactose | 58 mg |

| | |
|---|---|
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The rest of (4) and (5) is added to the granules and the mixture is compression formed into a tablet.

Preparation Example A2

The compound (50 mg) obtained in Example A4 is dissolved in the Japanese Pharmacopoeia distilled water for injection (50 mL), and the Japanese Pharmacopoeia distilled water for injection is added to make the total amount 100 mL. This solution is aseptically filtered. The solution (1 mL) is aseptically filled in a vial for injection, sealed and freeze-dried.

Example B1

Production of N-[3-({2-[(cyclopropylcarbonyl)amino][1,2,4]triazolo[1,5-a]pyridin-6-yl}oxy)phenyl]-3-(trifluoromethyl)benzamide

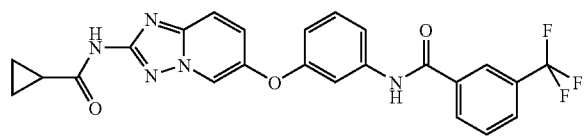 [SMILES: O=C(Nc1cccc(Oc2ccc3nc(NC(=O)C4CC4)nn3c2)c1)c1cccc(C(F)(F)F)c1]

(i) Production of 2-nitro-5-(3-nitrophenoxy)pyridine

To a solution of 5-bromo-2-nitropyridine (20.5 g, 101 mmol) and cesium carbonate (50 g, 153 mmol) in N,N-dimethylformamide (200 mL) was added dropwise a solution of 3-nitrophenol (15.5 g, 111 mmol) in N,N-dimethylformamide (100 mL) for 1 hr, and the mixture was stirred at room temperature for 12 hr. The reaction mixture was concentrated under reduced pressure, and the obtained residue was diluted with water (300 mL) and extracted with ethyl acetate (600 mL). The organic layer was washed with 5% aqueous sodium hydrogen carbonate solution (300 mL) and saturated brine (300 mL), and dried over anhydrous sodium sulfate. The insoluble material was filtered off, and the filtrate was concentrated under reduced pressure. The obtained residue was purified by basic silica gel column chromatography (hexane/ethyl acetate=90/10→60/40), and fractions containing the object product was concentrated under reduced pressure to give the title compound (14.28 g, 54%) as colorless crystals.
$^1$H-NMR (DMSO-$d_6$, 300 MHz) δ 7.69-7.87 (3H, m), 8.10 (1H, t, J=2.1 Hz), 8.17 (1H, dt, J=1.8, 7.7 Hz), 8.38 (1H, d, J=9.0 Hz), 8.53 (1H, d, J=2.7 Hz).

(ii) Production of 5-(3-aminophenoxy)pyridine-2-amine dihydrochloride

To a solution of 2-nitro-5-(3-nitrophenoxy)pyridine (14.0 g, 53.6 mmol) in methanol (1000 mL)/tetrahydrofuran (200 mL)/ethyl acetate (200 mL) was added 10% palladium-carbon (1.4 g), and the mixture was stirred under a hydrogen atmosphere (1.0 atm) at room temperature for 20 hr. The insoluble material was filtered off, and the filtrate was concentrated under reduced pressure. The obtained residue was diluted with ethyl acetate (300 mL), and 4N hydrogen chloride/ethyl acetate (30 mL) solution was slowly added dropwise. The obtained colorless precipitate was collected by filtration, washed with diisopropyl ether and hexane, and dried to give the title compound (15.2 g, quantitative) as a colorless powder. The obtained compound was used for the next reaction without further purification.
$^1$H-NMR (DMSO-$d_6$, 300 MHz) δ 6.69-6.83 (2H, m), 6.85-6.95 (1H, m), 7.09 (1H, d, J=9.6 Hz), 7.33 (1H, t, J=8.0 Hz), 7.86 (1H, dd, J=2.7, 9.6 Hz), 7.98 (1H, d, J=2.7 Hz), 8.15 (3H, br s), 10.02 (3H, br s).

(iii) Production of N-{3-[(6-aminopyridin-3-yl)oxy]phenyl}-3-(trifluoromethyl)benzamide To a solution of 5-(3-aminophenoxy)pyridine-2-amine dihydrochloride (3.5 g, 12.7 mmol) in N,N-dimethylacetamide (30 mL) was added 3-(trifluoromethyl)benzoyl chloride (2.8 g, 13.4 mmol), and the mixture was stirred at room temperature for 6 hr. The reaction mixture was concentrated under reduced pressure, 5% aqueous sodium hydrogen carbonate solution (100 mL) was added to the residue, and the mixture was extracted with ethyl acetate (200 mL). The organic layer was washed with water (100 mL) and saturated brine (100 mL), and dried over anhydrous sodium sulfate. The insoluble material was filtered off, and the filtrate was concentrated under reduced pressure. Ethyl acetate (30 mL)/hexane (20 mL) was added to the obtained residue, and the obtained precipitate was collected by filtration and dried to give the title compound (3.95 g, 83%) as a colorless powder.
$^1$H-NMR (DMSO-$d_6$, 300 MHz) δ 5.90 (2H, s), 6.51 (1H, d, J=8.9 Hz), 6.71 (1H, dd, J=2.4, 8.1 Hz), 7.23 (1H, dd, J=3.0, 8.9 Hz), 7.31 (1H, t, J=8.1 Hz), 7.36 (1H, t, J=2.1 Hz), 7.51 (1H, d, J=8.1 Hz), 7.69-7.83 (2H, m), 7.96 (1H, d, J=7.5 Hz), 8.15-8.29 (2H, m), 10.47 (1H, s).

(iv) Production of N-{3-[(2-amino[1,2,4]triazolo[1,5-a]pyridin-6-yl)oxy]phenyl}-3-(trifluoromethyl)benzamide To a solution of N-{3-[(6-aminopyridin-3-yl)oxy]phenyl}-3-(trifluoromethyl)benzamide (600 mg, 1.61 mmol) in dimethyl sulfoxide (30 mL) was added ethoxycarbonyl isothiocyanate (230 μL, 1.95 mmol), and the mixture was stirred at room temperature for 12 hr. Water (150 mL) was slowly added to the reaction mixture, and the mixture was extracted with ethyl acetate (300 mL). The organic layer was washed with water (100 mL) and saturated brine (100 mL), and dried over anhydrous sodium sulfate. The insoluble material was filtered off, and the filtrate was concentrated under reduced pressure to give ethyl ({[5-(3-{[3-(trifluoromethyl)benzoyl]amino}phenoxy)pyridin-2-yl]amino}carbonothioyl)carbamate (485 mg, 59%) as a brown oil.
To a solution of hydroxylamine hydrochloride (400 mg, 5.76 mmol) and N-ethyl-N-isopropylpropan-2-amine (1.20 mL, 6.88 mmol) in methanol (8.0 mL)/ethanol (8.0 mL) was added ethyl ({[5-(3-{[3-(trifluoromethyl)benzoyl]amino}phenoxy)pyridin-2-yl]amino}carbonothioyl)carbamate (480 mg, 0.95 mmol) obtained above, and the mixture was stirred with heating at 60° C. for 12 hr. The reaction mixture was concentrated under reduced pressure, and the residue was diluted with ethyl acetate (100 mL), washed with water (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and fractions containing the object product was concentrated under reduced pressure to give the title compound (0.48 g, quantitative) as a pale-yellow powder.

$^1$H-NMR (DMSO-d$_6$, 300 MHz) δ 6.02 (2H, s), 6.83 (1H, dd, J=1.8, 7.8 Hz), 7.24-7.51 (4H, m), 7.59 (1H, dd, J=0.9, 8.1 Hz), 7.77 (1H, t, J=7.8 Hz), 7.96 (1H, d, J=7.8 Hz), 8.11-8.31 (2H, m), 8.65 (1H, d, J=1.8 Hz), 10.50 (1H, s).

(v) Production of N-[3-({2-[(cyclopropylcarbonyl)amino][1,2,4]triazolo[1,5-a]pyridin-6-yl}oxy)phenyl]-3-(trifluoromethyl)benzamide To a solution of N-{3-[(2-amino[1,2,4]triazolo[1,5-a]pyridin-6-yl)oxy]phenyl}-3-(trifluoromethyl)benzamide (100 mg, 0.24 mmol) in N,N-dimethylacetamide (2.0 mL) was added cyclopropanecarbonyl chloride (33 µL, 0.36 mmol), and the mixture was stirred at room temperature for 4 hr. Cyclopropanecarbonyl chloride (15 µL, 0.17 mmol) was added to the reaction mixture, and the mixture was further stirred at room temperature for 2 hr. The reaction mixture was diluted with ethyl acetate (150 mL), washed with 1N hydrochloric acid (15 mL), 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), fractions containing the object product was concentrated under reduced pressure, and the residue was recrystallized from ethyl acetate, hexane and diisopropyl ether to give the title compound (108 mg, 92%) as a colorless powder.

$^1$H-NMR (DMSO-d$_6$, 300 MHz) δ 0.78-0.90 (4H, m), 2.03 (1H, br s), 6.87 (1H, dt, J=1.2, 8.1 Hz), 7.39 (1H, t, J=8.1 Hz), 7.49 (1H, t, J=2.1 Hz), 7.55 (1H, dd, J=2.4, 9.6 Hz), 7.61 (1H, dd, J=1.2, 8.1 Hz), 7.70-7.81 (2H, m), 7.96 (1H, d, J=7.8 Hz), 8.17-8.29 (2H, m), 8.95 (1H, d, J=1.8 Hz), 10.51 (1H, br s), 11.05 (1H, br s).

Example B2

Production of 3-(1-cyano-1-methylethyl)-N-[3-({2-[(cyclopropylcarbonyl)amino][1,2,4]triazolo[1,5-a]pyridin-6-yl}oxy)phenyl]benzamide

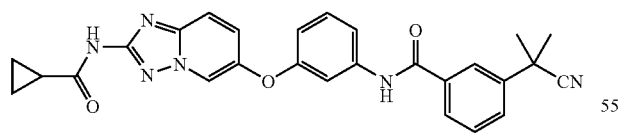

(i) Production of tert-butyl(3-hydroxyphenyl)carbamate

To a solution of di-tert-butyl-dicarbonate (39.9 g, 183 mmol) in tetrahydrofuran (600 mL) was added a solution of 3-aminophenol (20.0 g, 183 mmol) in tetrahydrofuran (400 mL), and the mixture was stirred at room temperature for 12 hr. Di-tert-butyl-dicarbonate (6.0 g, 27.4 mmol) was added to the reaction mixture, and the mixture was further stirred at room temperature for 7 hr. The reaction mixture was concentrated under reduced pressure, and the residue was recrystallized form diisopropyl ether (50 mL)/hexane (100 mL) to give the title compound (35.0 g, 91%) as colorless crystals.

$^1$H-NMR (DMSO-d$_6$, 300 MHz) δ 1.46 (9H, s), 6.27-6.40 (1H, m), 6.83 (1H, d, J=8.1 Hz), 6.92-7.05 (2H, m), 9.18 (1H, br s), 9.25 (1H, br s).

(ii) Production of tert-butyl{3-[(6-nitropyridin-3-yl)oxy]phenyl}carbamate

To a solution of 5-bromo-2-nitropyridine (20.0 g, 98.5 mmol) and cesium carbonate (48.1 g, 147 mmol) in N,N-dimethylformamide (150 mL) was added a solution of tert-butyl (3-hydroxyphenyl)carbamate (21.6 g, 103 mmol) in N,N-dimethylformamide (100 mL), and the mixture was stirred at room temperature for 2 days. The reaction mixture was concentrated under reduced pressure, the obtained residue was diluted with water (300 mL), and extracted with ethyl acetate (500 mL). The organic layer was washed with 5% aqueous sodium hydrogen carbonate solution (300 mL) and saturated brine (300 mL), and dried over anhydrous sodium sulfate. The insoluble material was filtered off, and the filtrate was concentrated under reduced pressure. The obtained residue was purified by basic silica gel column chromatography (hexane/ethyl acetate=90/10→60/40), and fractions containing the object product was concentrated under reduced pressure to give the title compound (19.4 g, 59%) as a pale-yellow oil.

$^1$H-NMR (DMSO-d$_6$, 300 MHz) δ 1.46 (9H, s), 6.82 (1H, ddd, J=1.5, 2.4, 7.5 Hz), 7.25-7.47 (3H, m), 7.62 (1H, dd, J=2.4, 9.0 Hz), 8.34 (1H, d, J=9.0 Hz), 8.42 (1H, d, J=2.4 Hz), 9.61 (1H, s).

(iii) Production of tert-butyl{3-[(6-aminopyridin-3-yl)oxy]phenyl}carbamate

To a solution of tert-butyl{3-[(6-nitropyridin-3-yl)oxy]phenyl}carbamate (6.00 g, 18.1 mmol) in ethyl acetate (500 mL)/tetrahydrofuran (150 mL) was added 10% palladium-carbon (600 mg), and the mixture was stirred at room temperature for 16 hr under a hydrogen atmosphere (1.0 atm). The insoluble material was filtered off, and the filtrate was concentrated under reduced pressure to give the title compound (5.9 g, quantitative) as a brown oil. The obtained compound was used for the next reaction without further purification.

$^1$H-NMR (DMSO-d$_6$, 300 MHz) δ 1.44 (9H, s), 5.86 (2H, s), 6.46-6.51 (2H, m), 7.04-7.39 (4H, m), 7.72 (1H, dd, J=0.6, 3.0 Hz), 9.35 (1H, s).

(iv) Production of ethyl{[(5-{3-[(tert-butoxycarbonyl)amino]phenoxy}pyridin-2-yl)amino]carbonothioyl}carbamate To a solution of tert-butyl{3-[(6-aminopyridin-3-yl)oxy]phenyl}carbamate (4.60 g, 15.2 mmol) in dimethyl sulfoxide (90 mL) was added ethoxycarbonyl isothiocyanate (2.00 mL, 16.7 mmol), and the mixture was stirred at room temperature for 5 days. Water (200 mL) was added to the reaction mixture, and the mixture was extracted with ethyl acetate (400 mL). The organic layer was washed with 5% aqueous ammonium chloride solution (200 mL), 5% aqueous sodium hydrogen carbonate solution (200 mL) and saturated brine (200 mL), and dried over anhydrous sodium sulfate. The insoluble material was filtered off, and the filtrate was concentrated under reduced pressure. The obtained residue was purified by silica gel column chromatography (hexane/ethyl acetate=90/10→50/50), and fractions containing the object product was concentrated under reduced pressure to give the title compound (4.56 g, 69%) as a colorless solid.

$^1$H-NMR (DMSO-d$_6$, 300 MHz) δ 1.26 (3H, t, J=7.2 Hz), 1.45 (9H, s) 4.22 (2H, q, J=7.2 Hz), 6.65 (1H, ddd, J=1.5, 1.8, 6.9 Hz), 7.14-7.32 (3H, m), 7.58 (1H, dd, J=2.7, 9.0 Hz), 8.19 (1H, d, J=2.7 Hz), 8.51-8.55 (1H, br s), 9.46 (1H, s).

(v) Production of tert-butyl{3-[(2-amino[1,2,4]triazolo[1,5-a]pyridin-6-yl)oxy]phenyl}carbamate To a solution of hydroxylamine hydrochloride (4.34 g, 62.4 mmol) and N-ethyl-N-isopropylpropan-2-amine (12.7 mL, 72.8 mmol) in methanol (70 mL)/ethanol (70 mL) was added ethyl{[(5-{3-[(tert-butoxycarbonyl)amino]phenoxy}pyridin-2-yl)amino]carbonothioyl}carbamate (4.50 g, 10.4 mmol), and the mixture was stirred with heating at 60° C. for 12 hr. The reaction mixture was concentrated under reduced pressure, and the residue was diluted with ethyl acetate (500 mL), and washed with water (200 mL) and saturated brine (200 mL). The organic layer was dried over anhydrous sodium sulfate, the insoluble material was filtered off, and the filtrate was concentrated under reduced pressure. The obtained residue was recrystallized from ethyl acetate, hexane and diisopropyl ether to give the title compound (2.98 g, 83%) as a colorless powder.

$^1$H-NMR (DMSO-d$_6$, 300 MHz) δ 1.43 (9H, s), 6.01 (2H, s), 6.60 (1H, ddd, J=7.2, 2.4, 2.1 Hz), 7.09-7.33 (4H, m), 7.37 (1H, d, J=0.6 Hz), 8.57 (1H, dd, J=2.4, 0.9 Hz), 9.39 (1H, s).

(vi) Production of tert-butyl[3-({2-[(cyclopropylcarbonyl)amino][1,2,4]triazolo[1,5-a]pyridin-6-yl}oxy)phenyl]carbamate To a solution of tert-butyl{3-[(2-amino[1,2,4]triazolo[1,5-a]pyridin-6-yl)oxy]phenyl}carbamate (1.5 g, 4.39 mmol) in N,N-dimethylacetamide (5.0 mL) was added cyclopropanecarbonyl chloride (480 µL, 5.27 mmol) under ice-cooling, and the mixture was stirred at room temperature for 12 hr. The reaction mixture was diluted with ethyl acetate (300 mL), washed with 5% aqueous sodium hydrogen carbonate solution (200 mL) and saturated brine (200 mL), and dried over anhydrous sodium sulfate. The insoluble material was filtered off, and the filtrate was concentrated under reduced pressure to give the title compound (1.79 g, 99%) as a pale-yellow oil. The obtained compound was used for the next reaction without further purification.

$^1$H-NMR (DMSO-d$_6$, 300 MHz) δ 0.75-0.90 (4H, m), 1.43 (9H, s), 1.95 (1H, br s), 6.59-6.68 (1H, m), 7.17-7.28 (3H, m), 7.49 (1H, dd, J=9.6, 1.8 Hz), 7.72 (1H, dd, J=0.9, 9.6 Hz), 8.86 (1H, d, J=1.8 Hz), 9.42 (1H, s), 11.03 (1H, s).

(vii) Production of N-[6-(3-aminophenoxy)[1,2,4]triazolo[1,5-a]pyridin-2-yl]cyclopropanecarboxamide To a mixture of tert-butyl[3-({2-[(cyclopropylcarbonyl)amino][1,2,4]triazolo[1,5-a]pyridin-6-yl}oxy)phenyl]carbamate (1.79 g, 4.39 mmol) and methoxybenzene (0.5 mL) was added trifluoroacetic acid (8.0 mL) under ice-cooling, and the mixture was stirred at room temperature for 2 hr. The reaction mixture was concentrated under reduced pressure, and 5% aqueous sodium hydrogen carbonate solution (200 mL) was added to the residue. The obtained precipitate was collected by filtration, and washed with water, diisopropyl ether and hexane to give the title compound (1.13 g, 83%) as a pale-yellow powder. The obtained compound was used for the next reaction without further purification.

$^1$H-NMR (DMSO-d$_6$, 300 MHz) δ 0.65-0.98 (4H, m), 2.03 (1H, br s), 5.24 (2H, s), 6.11-6.23 (2H, m), 6.26-6.38 (1H, m), 6.92-7.06 (1H, m), 7.46 (1H, dd, J=2.3, 9.6 Hz), 7.70 (1H, d, J=9.6 Hz), 8.79 (1H, d, J=2.3 Hz), 11.01 (1H, s).

(viii) Production of methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtrated, the solvent was evaporated under reduced pressure, and the residue was purified by silica gel column chromatography (ethyl acetate/hexane=5/95→30/70). The combined solution was concentrated under reduced pressure to give the title compound (7.0 g, 91%) as a colorless oil.

$^1$H-NMR (DMSO-d$_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ix) Production of methyl 3-(1-cyano-1-methylethyl)benzoate

To a solution of methyl 3-(cyanomethyl)benzoate (7.0 g, 40 mmol) in dimethyl sulfoxide (80 mL) was added sodium hydride (60% in oil, 4.8 g, 120 mmol) while cooling the solution to a temperature of 25° C. or below at which the solution did not solidify. The reaction mixture was stirred at room temperature for 20 min, methyl iodide (7.5 mL, 120 mmol) was added, and the mixture was further stirred at room temperature for 16 hr. The reaction mixture was diluted with water (400 mL), and extracted with ethyl acetate (800 mL). The organic layer was washed with water (400 mL) and saturated brine (400 mL), dried over anhydrous sodium sulfate, and filtrated. The solvent was evaporated under reduced pressure, and the residue was purified by silica gel column chromatography (ethyl acetate/hexane=5/95→50/50). The combined solution was concentrated under reduced pressure to give the title compound (6.4 g, 79%) as a colorless oil.

$^1$H-NMR (DMSO-d$_6$, 300 MHz) δ 1.72 (6H, s), 3.89 (3H, s), 7.61 (1H, t, J=7.8 Hz), 7.84 (1H, ddd, J=1.2, 2.1, 7.8 Hz), 7.95 (1H, dt, J=7.8, 1.2 Hz), 8.08 (1H, t, J=1.5 Hz).

(x) Production of 3-(1-cyano-1-methylethyl)benzoic acid

To a solution of methyl 3-(1-cyano-1-methylethyl)benzoate (2.8 g, 14 mmol) in tetrahydrofuran (30 mL) were added lithium hydroxide•monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). 1N Hydrochloric acid was slowly added to the mixture to adjust the pH to 3. The precipitated white precipitate was collected by filtration, washed with water, and dried to give the title compound (2.5 g, 98%) as a white powder.

$^1$H-NMR (DMSO-d$_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(xi) Production of 3-(1-cyano-1-methylethyl)-N-[3-({2-[(cyclopropylcarbonyl)amino][1,2,4]triazolo[1,5-a]pyridin-6-yl}oxy)phenyl]benzamide To a solution of 3-(1-cyano-1-methylethyl)benzoic acid (110 mg, 0.582 mmol) in tetrahydrofuran (5.0 mL) were added oxalyl chloride (62 µL, 0.728 mmol) and N,N-dimethylformamide (about 20 µL), and the mixture was stirred at room temperature for 1 hr. The reaction mixture was concentrated under reduced pressure to give 3-(1-cyano-1-methylethyl)benzoyl chloride as a pale-brown oil.

To a solution of 3-(1-cyano-1-methylethyl)benzoyl chloride synthesized above in N,N-dimethylacetamide (5.0 mL) was added N-[6-(3-aminophenoxy)[1,2,4]triazolo[1,5-a]pyridin-2-yl]cyclopropanecarboxamide (150 mg, 0.485 mmol) produced in Example B2(vii), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=60/40→0/100), and the obtained oil was triturated with ethyl acetate, toluene and diisopropyl ether to give the title compound (117 mg, 42%) as a colorless powder.

$^1$H-NMR (DMSO-$d_6$, 300 MHz) δ 0.74-0.94 (4H, m), 1.73 (6H, s), 2.00-2.12 (1H, m), 6.85 (1H, dd, J=2.4, 8.1 Hz), 7.38 (1H, t, J=8.1 Hz), 7.47-7.65 (4H, m), 7.69-7.79 (2H, m), 7.90 (1H, d, J=7.8 Hz), 7.99 (1H, s), 8.94 (1H, d, J=2.4 Hz), 10.37 (1H, s), 11.05 (1H, s).

Example B3

Production of 3-(1-cyanocyclopropyl)-N-[3-({2-[(cyclopropylcarbonyl)amino][1,2,4]triazolo[1,5-a]pyridin-6-yl}oxy)phenyl]benzamide

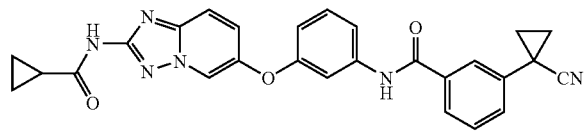 [SMILES: N#CC1(c2cccc(C(=O)Nc3cccc(Oc4ccc5nc(NC(=O)C6CC6)nn5c4)c3)c2)CC1]

(i) Production of methyl 3-(1-cyanocyclopropyl)benzoate

To a solution of methyl 3-(cyanomethyl)benzoate (1.5 g, 8.6 mmol) produced in Example B2(viii) in dimethyl sulfoxide (30 mL) was added sodium hydride (60% in oil, 1.0 g, 26 mmol) while cooling the solution to a temperature of 25° C. or below at which the solution did not solidify. The reaction mixture was stirred at room temperature for 30 min, 1,2-dibromoethane (2.4 g, 12.8 mmol) was added, and the mixture was further stirred at room temperature for 10 hr. The reaction mixture was diluted with water (100 mL), and extracted with ethyl acetate (300 mL). The organic layer was washed with saturated brine (100 mL), and dried over anhydrous sodium sulfate, and the insoluble material was filtered off. The solvent was evaporated under reduced pressure, and the residue was purified by silica gel column chromatography (ethyl acetate/hexane=5/95→50/50). The combined solution was concentrated under reduced pressure to give the title compound (1.3 g, 76%) as a colorless oil.

$^1$H-NMR (CDCl$_3$, 300 MHz) δ 1.38-1.56 (2H, m), 1.74-1.82 (2H, m), 3.93 (3H, s), 7.40-7.49 (1H, m), 7.55-7.62 (1H, m), 7.88 (1H, t, J=1.5 Hz), 7.96 (1H, dt, J=7.8, 1.5 Hz).

(ii) Production of 3-(1-cyanocyclopropyl)benzoic acid

To a solution of methyl 3-(1-cyanocyclopropyl)benzoate (1.3 g, 6.4 mmol) in tetrahydrofuran (12 mL) were added lithium hydroxide•monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). 1N Hydrochloric acid was slowly added to the mixture to adjust the pH to 5. The precipitated white precipitate was collected by filtration, washed with water, and dried to give the title compound (0.73 g, 61%) as a white powder.

$^1$H-NMR (DMSO-$d_6$, 300 MHz) δ 1.50-1.62 (2 H, m), 1.76-1.86 (2 H, m), 7.41-7.59 (2 H, m), 7.82-7.97 (2 H, m), 13.19 (1 H, br. s.).

(iii) Production of 3-(1-cyanocyclopropyl)-N-[3-({2-[(cyclopropylcarbonyl)amino][1,2,4]triazolo[1,5-a]pyridin-6-yl}oxy)phenyl]benzamide To a solution of 3-(1-cyanocyclopropyl)benzoic acid (109 mg, 0.582 mmol) in tetrahydrofuran (5.0 mL) were added oxalyl chloride (62 µL, 0.728 mmol) and N,N-dimethylformamide (about 20 µL), and the mixture was stirred at room temperature for 1 hr. The reaction mixture was concentrated under reduced pressure to give 3-(1-cyanocyclopropyl)benzoyl chloride as a pale-brown oil.

To a solution of 3-(1-cyanocyclopropyl)benzoyl chloride synthesized above in N,N-dimethylacetamide (5.0 mL) was added N-[6-(3-aminophenoxy)[1,2,4]triazolo[1,5-a]pyridin-2-yl]cyclopropanecarboxamide (150 mg, 0.485 mmol) produced in Example B2(vii), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=60/40→0/100), and the obtained oil was triturated with ethyl acetate, toluene and diisopropyl ether to give the title compound (175 mg, 63%) as a colorless powder.

$^1$H-NMR (DMSO-$d_6$, 300 MHz) δ 0.72-0.89 (4H, m), 1.55-1.65 (2H, m), 1.76-1.86 (2H, m), 1.97-2.11 (1H, m), 6.77-6.91 (1H, m), 7.38 (1H, t, J=8.1 Hz), 7.49 (1H, t, J=2.1 Hz), 7.51-7.63 (4H, m), 7.71-7.80 (2H, m), 7.80-7.88 (1H, m), 8.94 (1H, d, J=1.5 Hz), 10.35 (1H, s), 11.04 (1H, s).

Example B4

Production of 3-(1-cyano-1-methylethyl)-N-[3-({2-[(cyclopropylcarbonyl)amino][1,2,4]triazolo[1,5-a]pyridin-6-yl}oxy)-4-methylphenyl]benzamide

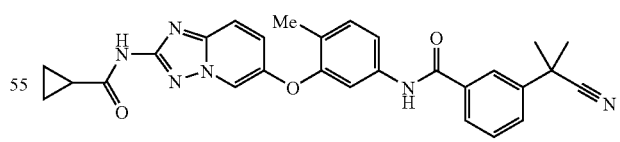

(i) Production of tert-butyl(3-hydroxy-4-methylphenyl)carbamate

To a solution of 5-amino-2-methylphenol (10.0 g, 81.2 mmol) and triethylamine (16.9 mL, 122 mmol) in tetrahydrofuran (75 mL) was added dropwise with stirring a solution of di-tert-butyl-dicarbonate (19.5 g, 89.3 mmol) in tetrahydrofuran (25 mL) under ice-cooling, and the mixture was stirred at room temperature for 15 hr. The reaction mixture was diluted with water, and extracted with ethyl acetate. The organic layer was washed with water and saturated brine, and dried over anhydrous magnesium sulfate, and the insoluble material was filtered off. The filtrate was concentrated under reduced pressure, and the residue was purified by column chromatography (silica gel, ethyl acetate/hexane=95/5→50/50) to give the title compound (3.25 g, 18%) as a colorless oil.

$^1$H-NMR (DMSO-$d_6$, 300 MHz) δ 1.46 (9H, s), 2.02 (3H, s), 6.71 (1H, dd, J=1.8, 8.2 Hz), 6.87 (1H, d, J=8.2 Hz), 7.07 (1H, d, J=1.8 Hz), 9.09 (1H, s), 9.16 (1H, s).

(ii) Production of tert-butyl{4-methyl-3-[(6-nitropyridin-3-yl)oxy]phenyl}carbamate A mixture of tert-butyl(3-hydroxy-4-methylphenyl)carbamate (3.14 g, 14.1 mmol), 5-bromo-2-nitropyridine (2.38 g, 11.7 mmol), cesium carbonate (5.72 g, 17.6 mmol) and N,N-dimethylformamide (25 mL) was stirred at room temperature for 15 hr. The reaction mixture was diluted with water, and extracted with ethyl acetate. The organic layer was washed with water and saturated brine, dried over anhydrous magnesium sulfate, and filtrated. The filtrate was concentrated under reduced pressure, and the residue was purified by column chromatography (basic silica gel, hexane/ethyl acetate=80/20→0/100) to give the title compound (1.86 g, 44%) as a colorless oil.

$^1$H-NMR (DMSO-$d_6$, 300 MHz) δ 1.45 (9H, s), 2.06 (3H, s), 7.24-7.34 (3H, m), 7.45 (1H, dd, J=2.9, 9.2 Hz), 8.32 (1H, d, J=9.2 Hz), 8.38 (1H, d, J=2.9 Hz), 9.50 (1H, s).

(iii) Production of tert-butyl{3-[(6-aminopyridin-3-yl)oxy]-4-methylphenyl}carbamate To a solution of tert-butyl{4-methyl-3-[(6-nitropyridin-3-yl)oxy]phenyl}carbamate (1.85 g, 5.35 mmol) in methanol (10 mL) was added palladium carbon (50% water-containing product, 100 mg), and the mixture was stirred at room temperature for 3 hr under a hydrogen atmosphere of 1.0 pressure. The reaction mixture was filtered through celite, the filtrate was concentrated under reduced pressure, and the residue was dried to give the title compound (1.69 g, 99%) as a colorless oil.

$^1$H-NMR (DMSO-$d_6$, 300 MHz) δ 1.40 (9H, s), 2.16 (3H, s), 5.80 (2H, s), 6.46 (1H, d, J=9.0 Hz), 6.89 (1H, s), 7.01-7.13 (3H, m), 7.66 (1H, d, J=3.0 Hz), 9.50 (1H, s).

(iv) Production of tert-butyl{3-[(2-amino[1,2,4]triazolo[1,5-a]pyridin-6-yl)oxy]-4-methylphenyl}carbamate In the same manner as in Example B1(iv), the title compound (1.55 g, 87%) was obtained as a white solid using tert-butyl{3-[(6-aminopyridin-3-yl)oxy]-4-methylphenyl}carbamate (1.69 g, 5.35 mmol), dimethyl sulfoxide (5 mL), ethoxycarbonyl isothiocyanate (843 mg, 6.42 mmol), ethanol (20 mL), methanol (20 mL), hydroxylammonium chloride (2.43 g, 35.0 mmol) and N-ethyl-N-isopropylpropan-2-amine (4.35 mL, 25.0 mmol) as starting materials.

$^1$H-NMR (DMSO-$d_6$, 300 MHz) δ 1.39 (9H, s), 2.19 (3H, s), 6.00 (2H, s), 6.98 (1H, s), 7.12-7.18 (2H, m), 7.24 (1H, dd, J=9.5, 2.3 Hz), 7.39 (1H, dd, J=0.3, 9.5 Hz), 8.43 (1H, d, J=1.8 Hz), 9.23 (1H, s).

(v) Production of tert-butyl[3-({2-[(cyclopropylcarbonyl)amino][1,2,4]triazolo[1,5-a]pyridin-6-yl}oxy)-4-methylphenyl]carbamate To a solution of tert-butyl{3-[(2-amino[1,2,4]triazolo[1,5-a]pyridin-6-yl)oxy]-4-methylphenyl}carbamate (1.50 g, 4.22 mmol) in N,N-dimethylacetamide (5 mL) was added with stirring cyclopropanecarbonyl chloride (1.15 mL, 12.7 mmol) under ice-cooling, and the mixture was stirred at room temperature for 2 hr. The reaction mixture was diluted with water, and extracted with ethyl acetate. The organic layer was washed with water and saturated brine, and dried over anhydrous magnesium sulfate, and the insoluble material was filtered off. The filtrate was concentrated under reduced pressure, and the residue was collected by filtration and washed with ethyl acetate and hexane to give the title compound (1.59 g, 89%) as a white compound.

$^1$H-NMR (DMSO-$d_6$, 300 MHz) δ 0.81-0.84 (4H, m), 1.39 (9H, s), 1.99-2.08 (1H, m), 2.19 (3H, s), 7.03 (1H, s), 7.16-7.22 (2H, m), 7.45 (1H, dd, J=2.1, 9.6 Hz), 7.72 (1H, dd, J=0.6, 9.6 Hz), 8.68 (1H, d, J=2.4 Hz), 9.26 (1H, s), 11.03 (1H, s).

(vi) Production of N-[6-(5-amino-2-methylphenoxy)[1,2,4]triazolo[1,5-a]pyridin-2-yl]cyclopropanecarboxamide A mixture of tert-butyl[3-({2-[(cyclopropylcarbonyl)amino][1,2,4]triazolo[1,5-a]pyridin-6-yl}oxy)-4-methylphenyl]carbamate (1.50 g, 3.54 mmol) and trifluoroacetic acid (5 mL) was stirred at 0° C. for 30 min. The solvent was evaporated under reduced pressure, the residue was dissolved in water, and the solution was neutralized with saturated aqueous sodium hydrogen carbonate solution and extracted with ethyl acetate. The organic layer was washed with water and saturated brine, and dried over anhydrous magnesium sulfate, the insoluble material was filtered off. The filtrate was concentrated under reduced pressure, the residue was collected by filtration and washed with ethyl acetate and hexane to give the title compound (1.04 g, 91%) as a white solid.

$^1$H-NMR (DMSO-$d_6$, 300 MHz) δ 0.81-0.84 (4H, m), 1.99-2.08 (1H, m), 2.09 (3H, s), 5.09 (2H, br s), 6.08 (1H, d, J=2.1 Hz), 6.30 (1H, dd, J=2.1, 8.2 Hz), 6.93 (1H, d, J=8.2 Hz), 7.42 (1H, dd, J=2.3, 9.6 Hz), 7.69 (1H, d, J=9.6 Hz), 8.61 (1H, d, J=2.3 Hz), 10.98 (1H, s).

(vii) Production of 3-(1-cyano-1-methylethyl)-N-[3-({2-[(cyclopropylcarbonyl)amino][1,2,4]triazolo[1,5-a]pyridin-6-yl}oxy)-4-methylphenyl]benzamide To a solution of 3-(1-cyano-1-methylethyl)benzoic acid (53 mg, 0.280 mmol) produced in Example B2(x) in tetrahydrofuran (2.0 mL) were added oxalyl chloride (35 μL, 0.42 mmol) and N,N-dimethylformamide (about 20 μL), and the mixture was stirred at room temperature for 1 hr. The reaction mixture was concentrated under reduced pressure to give 3-(1-cyano-1-methylethyl)benzoyl chloride as a pale-brown oil.

To a solution of 3-(1-cyano-1-methylethyl)benzoyl chloride synthesized above in N,N-dimethylacetamide (2.0 mL) was added N-[6-(5-amino-2-methylphenoxy)[1,2,4]triazolo[1,5-a]pyridin-2-yl]cyclopropanecarboxamide (75 mg, 0.233 mmol), and the mixture was stirred at room temperature for 10 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained oil was triturated with ethyl acetate and diisopropyl ether to give the title compound (40.8 mg, 35%) as a colorless powder.

$^1$H-NMR (DMSO-d$_6$, 300 MHz) δ 0.72-0.91 (4H, m), 1.71 (6H, s), 1.95-2.10 (1H, m), 2.28 (3H, s), 7.27-7.36 (2H, m), 7.48-7.60 (3H, m), 7.67-7.79 (2H, m), 7.82-7.89 (1H, m), 7.95 (1H, t, J=1.8 Hz), 8.80 (1H, dd, J=0.6, 2.4 Hz), 10.24 (1H, s), 11.03 (1H, s).

Example B5

Production of 3-(1-cyanocyclopropyl)-N-[3-({2-[(cyclopropylcarbonyl)amino][1,2,4]triazolo[1,5-a]pyridin-6-yl}oxy)-4-methylphenyl]benzamide

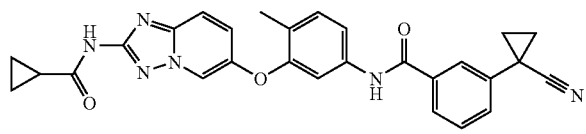 [SMILES: Cc1ccc(NC(=O)c2cccc(C3(C#N)CC3)c2)cc1Oc1ccc2nc(NC(=O)C3CC3)nn2c1]

To a solution of 3-(1-cyanocyclopropyl)benzoic acid (139 mg, 0.742 mmol) produced in Example B3(ii) in tetrahydrofuran (7.0 mL) were added oxalyl chloride (80 μL, 0.929 mmol) and N,N-dimethylformamide (about 20 μL), and the mixture was stirred at room temperature for 1 hr. The reaction mixture was concentrated under reduced pressure to give 3-(1-cyanocyclopropyl)benzoyl chloride as a pale-brown oil.

To a solution of 3-(1-cyanocyclopropyl)benzoyl chloride synthesized above in 1-methylpyrrolidin-2-one (7.0 mL) was added N-[6-(5-amino-2-methylphenoxy)[1,2,4]triazolo[1,5-a]pyridin-2-yl]cyclopropanecarboxamide (200 mg, 0.619 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and the obtained oil was triturated with toluene and diisopropyl ether to give the title compound (256 mg, 84%) as a colorless powder.

$^1$H-NMR (DMSO-d$_6$, 300 MHz) δ 0.72-0.90 (4H, m), 1.52-1.63 (2H, m), 1.74-1.83 (2H, m), 1.83-1.97 (1H, m), 2.28 (3H, s), 7.26-7.37 (2H, m), 7.44-7.61 (4H, m), 7.68-7.86 (3H, m), 8.79 (1H, d, J=1.5 Hz), 10.23 (1H, s), 11.02 (1H, s).

Example B6

Production of N-[3-({2-[(cyclopropylcarbonyl)amino][1,2,4]triazolo[1,5-a]pyridin-6-yl}oxy)-4-methylphenyl]-3-(trifluoromethyl)benzamide To a solution of N-[6-(3-amino-6-methylphenoxy)[1,2,4]triazolo[1,5-a]pyridin-2-yl]cyclopropanecarboxamide (100 mg, 0.309 mmol) in 1-methylpyrrolidin-2-one (2.0 mL) was added 3-(trifluoromethyl)benzoyl chloride (78 mg, 0.371 mmol), and the mixture was stirred at room temperature for 10 hr. The reaction mixture was concentrated under reduced pressure, and the residue was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained oil was triturated with ethyl acetate and hexane to give the title compound (100 mg, 65%) as a colorless powder.

$^1$H-NMR (DMSO-d$_6$, 300 MHz) δ 0.71-0.93 (4H, m), 2.03 (1H, br s), 2.29 (3H, s), 7.24-7.39 (2H, m), 7.52 (1H, dd, J=2.4, 9.6 Hz), 7.58 (1H, dd, J=1.8, 8.4 Hz), 7.68-7.81 (2H, m), 7.93 (1H, d, J=7.8 Hz), 8.10-8.26 (2H, m), 8.81 (1H, d, J=2.1 Hz), 10.39 (1H, s), 11.03 (1H,s).

Preparation Example B1

A pharmaceutical agent containing the compound of the present invention as an active ingredient can be produced, for example, according to the following formulation.

1. Capsule

| (1) compound of Example B1 | 40 mg |
|---|---|
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added and the total amount is sealed in a gelatin capsule.

2. tablet

| (1) compound of Example B1 | 40 mg |
|---|---|
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The rest of (4) and (5) is added to the granules and compression formed into a tablet.

Preparation Example B2

The compound (50 mg) obtained in Example B1 is dissolved in the Japanese Pharmacopoeia distilled water for injection (50 ml), and the Japanese Pharmacopoeia distilled water for injection is added to make the total amount 100 mL.

Example C1

Production of 3-(1-cyanocyclopropyl)-N-[3-({2-[(cyclopropylcarbonyl)amino][1,3]thiazolo[5,4-b]pyridin-5-yl}oxy)-4-methoxyphenyl]benzamide

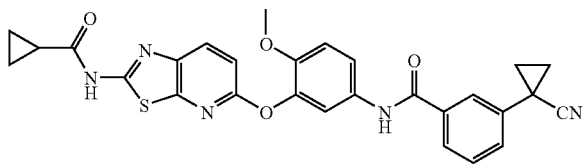 [SMILES: COc1ccc(NC(=O)c2cccc(C3(C#N)CC3)c2)cc1Oc1ccc2nc(NC(=O)C3CC3)sc2n1]

(i) Production of methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtrated, and the solvent was evaporated under reduced pressure. The residue was purified by silica gel column chromatography (ethyl acetate/hexane=5/95→30/70), and fractions containing the object product was concentrated under reduced pressure to give the title compound (7.0 g, 91%) as a colorless oil.

$^1$H-NMR (DMSO-d$_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ii) Production of methyl 3-(1-cyanocyclopropyl)benzoate

To a solution of methyl 3-(cyanomethyl)benzoate (1.5 g, 8.6 mmol) in dimethyl sulfoxide (30 mL) was added sodium hydride (60% in oil, 1.0 g, 26 mmol) while cooling the solution to a temperature of 25° C. or below at which the solution did not solidify. The reaction mixture was stirred at room temperature for 30 min, 1,2-dibromoethane (2.4 g, 12.8 mmol) was added, and the mixture was further stirred at room temperature for 10 hr. The reaction mixture was diluted with water (100 mL), and extracted with ethyl acetate (300 mL). The organic layer was washed with saturated brine (100 mL), and dried over anhydrous sodium sulfate, and the insoluble material was filtered off. The solvent was evaporated under reduced pressure, the residue was purified by silica gel column chromatography (ethyl acetate/hexane=5/95→50/50), and fractions containing the object product was concentrated under reduced pressure to give the title compound (1.3 g, 76%) as a colorless oil.

$^1$H-NMR (CDCl$_3$, 300 MHz) δ 1.38-1.56 (2H, m), 1.74-1.82 (2H, m), 3.93 (3H, s), 7.40-7.49 (1H, m), 7.55-7.62 (1H, m), 7.88 (1H, t, J=1.5 Hz), 7.96 (1H, dt, J=7.8, 1.5 Hz).

(iii) Production of 3-(1-cyanocyclopropyl)benzoic acid

To a solution of methyl 3-(1-cyanocyclopropyl)benzoate (1.3 g, 6.4 mmol) in tetrahydrofuran (12 mL) were added lithium hydroxide•monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). 1N Hydrochloric acid was slowly added to the mixture to adjust the pH to 5. The precipitated white precipitate was collected by filtration, washed with water, and dried to give the title compound (0.73 g, 61%) as a white powder.

$^1$H-NMR (DMSO-d$_6$, 300 MHz) δ 1.50-1.62 (2H, m), 1.76-1.86 (2H, m), 7.41-7.59 (2H, m), 7.82-7.97 (2H, m), 13.19 (1H, br s).

(iv) Production of 3-(1-cyanocyclopropyl)-N-(3-hydroxy-4-methoxyphenyl)benzamide To a suspension of 3-(1-cyanocyclopropyl)benzoic acid (9.40 g, 49.7 mmol) in toluene (150 mL) was added thionyl chloride (48.9 g, 411 mmol), and the mixture was heated under reflux for 2 hr. After cooling the obtained solution to room temperature, sodium chloride (1.5 g) was added, and the mixture was heated under reflux for 1.5 hr. After cooling the reaction solution to room temperature, the insoluble material was removed, and the solvent was evaporated under reduced pressure. The obtained brownish-red solid was successively used for the next reaction as 3-(1-cyanocyclopropyl)benzoyl chloride.

To a solution of 5-amino-2-methoxyphenol (7.20 g, 51.7 mmol) in tetrahydrofuran (200 mL) was added water (250 mL) in which sodium hydrogen carbonate (5.00 g, 59.5 mmol) had been dissolved, and the mixture was vigorously stirred at room temperature. The obtained reaction solution separated in two layers was vigorously stirred, during which a solution of 3-(1-cyanocyclopropyl)benzoyl chloride synthesized above in tetrahydrofuran (150 mL) was slowly added at room temperature, and the mixture was stirred for 1 hr. Sodium hydrogen carbonate was added to the reaction solution until generation of carbon dioxide ceased, and the reaction solution was further stirred for 12 hr. The aqueous layer was separated, and extracted with ethyl acetate (150 mL×2). The combined organic layer was washed with saturated brine (100 mL), dried over anhydrous magnesium sulfate, and decolorized with activated carbon. The insoluble material was filtered off through a pad with two layers of silica gel and celite, and the filtrate was concentrated. The obtained brown solid was recrystallized from a mixture of ethyl acetate, tetrahydrofuran and diisopropyl ether to give the title compound (14.2 g, 93%) as brownish-red crystals.

$^1$H-NMR (DMSO-d$_6$, 300 MHz) δ 1.60-1.64 (2H, m), 1.80-1.84 (2H, m), 3.75 (3H, s), 6.89 (1H, d, J=9.0 Hz), 7.11 (1H, dd, J=2.4, 8.7 Hz), 7.30 (1H, d, J=2.7 Hz), 7.53-7.55 (2H, m), 7.79-7.80 (1H, m), 7.84-7.87 (1H, m), 9.08 (1H, s), 10.06 (1H, br s).

(v) Production of 3-(1-cyanocyclopropyl)-N-{4-methoxy-3-[(5-nitropyridin-2-yl)oxy]phenyl}benzamide To a solution of 3-(1-cyanocyclopropyl)-N-(3-hydroxy-4-methoxyphenyl)benzamide (3.11 g, 10.1 mmol) and 2-chloro-5-nitropyridine (1.60 g, 10.1 mmol) in N,N-dimethylformamide (150 mL) was added potassium carbonate (4.24 g, 30.7 mmol), and the mixture was stirred at 60° C. for 16 hr. The reaction solution was cooled to room temperature, and diluted with a mixed solvent (250 mL) of ethyl acetate and hexane (1:1). The solution was washed with water (200 mL×3), and the combined m aqueous layer was extracted with a mixed solvent (100 mL×3) of ethyl acetate and hexane (1:1). The combined organic layer was washed with saturated brine (100 mL), and dried over anhydrous magnesium sulfate. The insoluble material was filtered off, and the filtrate was concentrated under reduced pressure to give the title compound (4.3 g, 99%) as pale-yellow crystals.

$^1$H-NMR (DMSO-$d_6$, 300 MHz) δ1.59-1.64 (2H, m), 1.80-1.84 (2H, m), 3.70 (3H, s), 7.21 (1H, d, J=9.0 Hz), 7.26 (1H, d, J=9.0 Hz), 7.55-7.57 (2H, m), 7.63 (1H, dd, J=2.4, 8.7 Hz), 7.70 (1H, d, J=2.4 Hz), 7.82-7.83 (1H, m), 7.86-7.89 (1H, m), 8.61 (1H, dd, J=2.7, 9.0 Hz), 9.01 (1H, d, J=2.7 Hz), 10.31 (1H, br s).

(vi) Production of N-{3-[(5-aminopyridin-2-yl)oxy]-4-methoxyphenyl}-3-(1-cyanocyclopropyl)benzamide To a solution of 3-(1-cyanocyclopropyl)-N-{4-methoxy-3-[(5-nitropyridin-2-yl)oxy]phenyl}benzamide (4.30 g, 9.99 mmol) in tetrahydrofuran (100 mL) were added methanol (50 mL) and 10% palladium-carbon (982 mg), and the mixture was stirred at room temperature for 14 hr under a hydrogen atmosphere (2.5 atm). The insoluble material was filtered off, and the filtrate was concentrated to give the title compound (4.1 g) as a brown syrup substance. The syrup substance was used for the next reaction without further purification.

$^1$H-NMR (DMSO-$d_6$, 300 MHz) δ 1.59-1.63 (2H, m), 1.79-1.83 (2H, m), 3.70 (3H, s), 4.97 (2H, br s), 6.72 (1H, d, J=8.7 Hz), 7.04-7.10 (2H, m), 7.41 (1H, d, J=2.4 Hz), 7.46 (1H, d, J=2.1 Hz), 7.51-7.56 (3H, m), 7.80 (1H, s), 7.84-7.87 (1H, m), 10.17 (1H, br s).

(vii) Production of N-{3-[(2-amino[1,3]thiazolo[5,4-b]pyridin-5-yl)oxy]-4-methoxyphenyl}-3-(1-cyanocyclopropyl)benzamide Potassium thiocyanate (4.44 g, 45.7 mmol) was suspended in acetic acid (100 mL), and the mixture was stirred at room temperature for 30 min. A solution of N-{3-[(5-aminopyridin-2-yl)oxy]-4-methoxyphenyl}-3-(1-cyanocyclopropyl)benzamide (4.1 g) in acetic acid (100 mL) was added to the obtained solution, and the mixture was further stirred at room temperature for 30 min. A solution of bromine (2.65 g, 16.6 mmol) in acetic acid (100 mL) was added dropwise to the obtained solution for 30 min or more. After the completion of the dropwise addition, the mixture was stirred at room temperature for 16 hr. The yielded yellow solid was filtered off, and washed with acetic acid, and the filtrate and the washing solution were combined and concentrated under reduced pressure. The residue was suspended in ethyl acetate (300 mL), and the suspension was washed with saturated aqueous sodium hydrogen carbonate solution (100 mL×2) and saturated brine (100 mL), and dried over anhydrous magnesium sulfate. The insoluble material was filtered off, and the filtrate was concentrated under reduced pressure to give the title compound (2.68 g, total of 2 steps 59%) as a yellow amorphous substance.

$^1$H-NMR (DMSO-$d_6$, 300 MHz) δ 1.59-1.63 (2H, m), 1.79-1.83 (2H, m), 3.70 (3H, s), 6.85 (1H, d, J=8.7 Hz), 7.16 (1H, d, J=9.0 Hz), 7.54-7.58 (5H, m), 7.61 (1H, dd, J=2.4, 8.7 Hz), 7.69 (1H, d, J=8.4 Hz), 7.80-7.81 (1H, m), 7.84-7.88 (1H, m), 10.23 (1H, br s).

(viii) Production of 3-(1-cyanocyclopropyl)-N-[3-({2-[(cyclopropylcarbonyl)amino][1,3]thiazolo[5,4-b]pyridin-5-yl}oxy)-4-methoxyphenyl]benzamide To a solution of N-{3-[(2-amino[1,3]thiazolo[5,4-b]pyridin-5-yl)oxy]-4-methoxyphenyl}-3-(1-cyanocyclopropyl)benzamide (528.0 mg, 1.15 mmol) in pyridine (10 mL) were added N,N-dimethylpyridine-4-amine (52.1 mg, 426 μmol) and cyclopropanecarbonyl chloride (1 mL, 11.0 mmol), and the mixture was stirred at room temperature for 6 hr. The reaction solution was concentrated under reduced pressure, and the residue was diluted with ethyl acetate (50 mL), washed with water (50 mL), 0.1N hydrochloric acid (50 mL) and saturated aqueous sodium hydrogen carbonate solution (50 mL), and dried over anhydrous magnesium sulfate. The insoluble material was filtered off, the filtrate was concentrated under reduced pressure, and the obtained residue was subjected to silica gel column chromatography (ethyl acetate/hexane=5/95→80/20) and recrystallized from acetone to give the title compound (280 mg, 46%) as colorless crystals.

$^1$H-NMR (DMSO-$d_6$, 300 MHz) δ 0.93-0.98 (4H, m), 1.61 (2H, dd, J=5.4, 8.1 Hz), 1.81 (2H, dd, J=5.4, 8.1 Hz), 1.96-2.02 (1H, m), 3.69 (3H, s), 7.09 (1H, d, J=8.7 Hz), 7.19 (1H, d, J=9.6 Hz), 7.54-7.56 (2H, m), 7.61-7.65 (2H, m), 7.81 (1H, br s), 7.85-7.88 (1H, m), 8.13 (1H, d, J=9.0 Hz), 10.28 (1H, br s), 12.67 (1H, br s).

Example C2

Production of 3-(1-cyanocyclopropyl)-N-{4-methoxy-3-[(2-{[(4-methylpiperazin-1-yl)acetyl]amino}[1,3]thiazolo[5,4-b]pyridin-5-yl)oxy]phenyl}benzamide

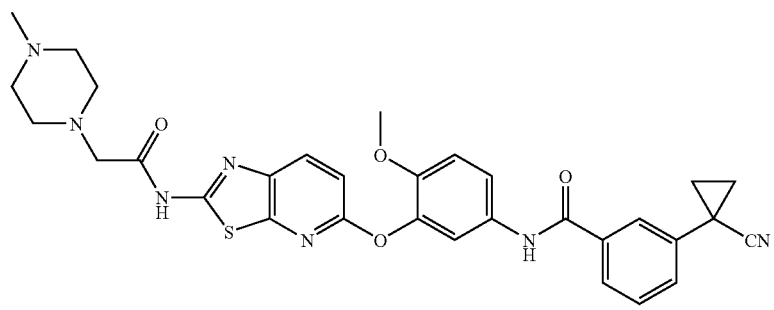 [SMILES: COc1ccc(NC(=O)c2cccc(C3(C#N)CC3)c2)cc1Oc1ccc2nc(NC(=O)CN3CCN(C)CC3)sc2n1]

(i) Production of tert-butyl(4-methylpiperazin-1-yl)acetate

To a suspension of tert-butyl chloroacetate (3.49 g, 34.9 mmol) and potassium carbonate (5.50 g, 39.8 mmol) in acetonitrile (300 mL) was added dropwise 1-methylpiperazine (5.00 g, 33.2 mmol), and the mixture was stirred with heating at 50° C. for 16 hr. The reaction mixture was cooled to room temperature, the insoluble material was filtered off, and the filtrate was concentrated. Water (150 mL) was added to the obtained residue, and the mixture was extracted with ethyl acetate (300 mL). The organic layer was washed with water (150 mL) and saturated brine (150 mL), and dried over anhydrous sodium sulfate. The insoluble material was filtered off, and the filtrate was concentrated to give the title compound (5.63 g, 79%) as a pale-yellow oil. The compound was used for the next reaction without further purification operation.

$^1$H-NMR (DMSO-$d_6$, 300 MHz) δ 1.40 (9H, s), 2.13 (3H, s), 2.21-2.36 (4H, m), 2.41-2.53 (4H, m), 3.06 (2H, s).

(ii) Production of (4-methylpiperazin-1-yl)acetic acid dihydrochloride tert-Butyl(4-methylpiperazin-1-yl)acetate (3.50 g, 16.3 mmol) was suspended in 4N hydrogen chloride/1,4-dioxane (35 mL) solution, trifluoroacetic acid (60 mL) was added to give a solution, and the solution was stirred at room temperature for 4 hr. The reaction mixture was concentrated under reduced pressure, 4N hydrogen chloride/ethyl acetate (30 mL) was added to the obtained oily residue to give a suspension, and the suspension was stirred at room temperature for 2 hr. The obtained precipitate was collected by filtration, washed with ethyl acetate and diisopropyl ether on filter paper, and dried to give the title compound (3.33 g, 88%) as a colorless powder. The compound was used for the next reaction without further purification operation.

$^1$H-NMR (DMSO-$d_6$, 300 MHz) δ 2.79 (3H, s), 3.10-3.73 (8H, m), 4.00 (2H, s), 11.67 (1H, br s).

(iii) Production of 3-(1-cyanocyclopropyl)-N-{4-methoxy-3-[(2-{[(4-methylpiperazin-1-yl)acetyl] amino}[1,3]thiazolo[5,4-b]pyridin-5-yl)oxy] phenyl}benzamide To a solution of N-{3-[(2-amino[1,3]thiazolo[5,4-b]pyridin-5-yl)oxy]-4-methoxyphenyl}-3-(1-cyanocyclopropyl) benzamide (457 mg, 998 μmol) produced in Example C1(vii) in pyridine (10 mL) were added (4-methylpiperazin-1-yl) acetic acid dihydrochloride (474 mg, 2.05 mmol), N,N-dimethylpyridine-4-amine (51.3 mg, 420 μmol) and 1-ethyl-3-(3-dimethylaminopropyl)carbodiimide hydrochloride (403 mg, 2.10 mmol), and the mixture was stirred at room temperature for 2 hr. Methanol (10 mL) was added to the reaction solution, and the mixture was stirred for 30 min. The solvent was evaporated under reduced pressure. The residue was dissolved in ethyl acetate (100 mL) and tetrahydrofuran (10 mL), and the solution was washed with 0.1N hydrochloric acid (50 mL), saturated aqueous sodium hydrogen carbonate solution (50 mL) and saturated brine (50 mL). The earlier 0.1N hydrochloric acid washing solution was neutralized (pH 7.0) with 1N aqueous sodium hydroxide solution, and extracted with ethyl acetate (50 mL×2). The combined organic layer was dried over anhydrous magnesium sulfate, the insoluble material was filtered off, and the filtrate was concentrated under reduced pressure. The residue was purified by basic silica gel column chromatography (ethyl acetate/methanol=100/0→80/20), and recrystallized from a mixture of ethyl acetate and diisopropyl ether to give the title compound (419 mg, 70%) as colorless crystals.

$^1$H-NMR (DMSO-$d_6$, 300 MHz) δ 1.61 (2H, dd, J=5.7, 8.4 Hz), 1.81 (2H, dd, J=5.7, 8.4 Hz), 2.15 (3H, s), 2.34 (4H, br s), 2.57 (4H, br s), 3.32 (2H, s), 3.69 (3H, s), 7.10 (1H, d, J=8.7 Hz), 7.20 (1H, d, J=9.6 Hz), 7.54-7.56 (2H, m), 7.61-7.65 (2H, m), 7.82 (1H, br s), 7.86 (1H, m), 8.15 (1H, d, J=8.7 Hz), 10.28 (1H, br s), 12.11 (1H, br s).

Example C3

Production of 3-(1-cyanocyclopropyl)-N-(3-{[2-(glycoloylamino)[1,3]thiazolo[5,4-b]pyridin-5-yl] oxy}-4-methoxyphenyl)benzamide

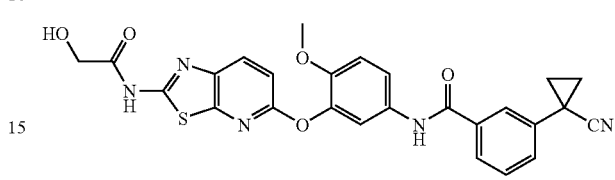

To a solution of N-{3-[(2-amino[1,3]thiazolo[5,4-b]pyridin-5-yl)oxy]-4-methoxyphenyl}-3-(1-cyanocyclopropyl) benzamide (313 mg, 683 μmol) produced in Example C1(vii) in pyridine (10 mL) were added 2-chloro-2-oxoethyl acetate (254 mg, 1.86 mmol) and N,N-dimethylpyridine-4-amine (85 mg, 696 μmol), and the mixture was stirred at room temperature for 2 hr. Methanol (10 mL) was added to the reaction solution, the mixture was stirred for 1 hr, conc. aqueous ammonia (4 mL) was added, and the mixture was further stirred for 1 hr. The reaction solution was concentrated under reduced pressure, and residue was dissolved in tetrahydrofuran (10 mL) and ethyl acetate (50 mL). The solution was washed with 0.1N hydrochloric acid (50 mL), saturated aqueous sodium hydrogen carbonate solution (50 mL) and saturated brine (50 mL), and dried over anhydrous magnesium sulfate. The insoluble material was filtered off, and the filtrate was concentrated under reduced pressure. The obtained residue was purified by basic silica gel column chromatography (ethyl acetate/methanol=100/0→80/20), and recrystallized from a mixture of ethyl acetate and diisopropyl ether to give the title compound (125 mg, 35%) as colorless crystals.

$^1$H-NMR (DMSO-$d_6$, 300 MHz) δ 1.61 (2H, dd, J=5.4, 8.1 Hz), 1.81 (2H, dd, J=5.4, 8.1 Hz), 3.70 (3H, s), 4.18 (2H, d, J=4.8 Hz), 5.53 (1H, t, J=4.8 Hz), 7.10 (1H, d, J=8.7 Hz), 7.20 (1H, d, J=9.6 Hz), 7.52-7.59 (2H, m), 7.61-7.64 (2H, m), 7.82 (1H, br s), 7.85-7.89 (1H, m), 8.15 (1H, d, J=9.0 Hz), 10.27 (1H, br s), 12.08 (1H, br s).

Example C4

Production of 3-({2-[(cyclopropylcarbonyl)amino] [1,3]thiazolo[5,4-b]pyridin-5-yl}oxy)-4-methoxy-N-[3-(trifluoromethyl)phenyl]benzamide

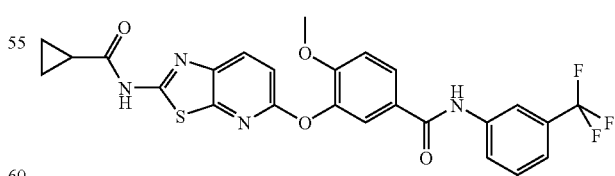

(i) Production of methyl 4-methoxy-3-[(5-nitropyridin-2-yl)oxy]benzoate

To a solution of methyl 3-hydroxy-4-methoxybenzoate (4.87 g, 26.7 mmol) and 2-chloro-5-nitropyridine (4.24 g, 26.7 mmol) in N,N-dimethylformamide (100 mL) was added potassium carbonate (8.13 g, 58.8 mmol), and the mixture was stirred at 60° C. for 14 hr. The reaction solution was cooled to room temperature, diluted with water, and extracted with a mixed solvent (1:1, 100 mL) of ethyl acetate and hexane. The combined organic layer was washed with saturated brine, and dried over anhydrous magnesium sulfate. The insoluble material was filtered off, and the filtrate was concentrated under reduced pressure to give the title compound (9.73 g) as an orange syrup substance.

$^1$H-NMR (CDCl$_3$, 300 MHz) δ 3.82 (3H, s), 3.90 (3H, s), 7.04-7.11 (2H, m), 7.84 (1H, d, J=2.1 Hz), 8.01 (1H, dd, J=2.4, 8.7 Hz), 8.49 (1H, dd, J=3.0, 9.0 Hz), 8.98 (1H, dd, J=0.6, 2.7 Hz).

(ii) Production of methyl 3-[(5-aminopyridin-2-yl)oxy]-4-methoxybenzoate

To a solution of methyl 4-methoxy-3-[(5-nitropyridin-2-yl)oxy]benzoate (26.7 mmol) in ethanol (250 mL) were added iron powder (5.6 g, 0.1 mol) and 6N hydrochloric acid (50 mL) with heating under reflux and vigorous stirring, and the mixture was vigorously stirred under refluxing condition for 1.5 hr. The reaction solution was filtered through celite, the insoluble material was filtered off, and the filtrate was concentrated under reduced pressure. The residue was diluted with ethyl acetate (350 mL), and washed with 1N aqueous sodium hydroxide solution (200 mL×2). The aqueous layer was extracted with ethyl acetate (150 mL×3), and the combined organic layer was washed with saturated aqueous ammonium chloride solution (100 mL×2), and dried over anhydrous magnesium sulfate. The insoluble material was filtered off, and the filtrate was concentrated to give the title compound (8.0 g) as a brownish-red syrup substance.

$^1$H-NMR (CDCl$_3$, 300 MHz) δ 3.85 (3H, s), 3.86 (3H, s), 6.81 (1H, d, J=8.7 Hz), 7.00 (1H, d, J=8.7 Hz), 7.09 (1H, dd, J=3.0, 8.4 Hz), 7.63 (1H, d, J=3.0 Hz), 7.73 (1H, d, J=2.1 Hz), 7.87 (1H, dd, J=2.1, 8.7 Hz).

(iii) Production of methyl 3-[(2-amino[1,3]thiazolo[5,4-b]pyridin-5-yl)oxy]-4-methoxybenzoate To a suspension of potassium thiocyanate (12.1 g, 125 mmol) in acetic acid (100 mL) was added a solution of methyl 3-[(5-aminopyridin-2-yl)oxy]-4-methoxybenzoate (26.7 mmol) in acetic acid (100 mL), and the mixture was stirred at room temperature for 15 min. The obtained solution was cooled to 0° C., a solution of bromine (6.55 g, 41.0 mmol) in acetic acid (80 mL) was added dropwise for 1 hr or more. After the completion of the dropwise addition, the mixture was stirred for 16 hr, during which the reaction temperature was allowed to gradually warm to room temperature. The yielded yellow solid was filtered off, and washed with water. The filtrate and the washing solution were combined, and concentrated under reduced pressure, and the residue was treated with saturated aqueous sodium hydrogen carbonate solution (200 mL). The obtained solution was extracted with ethyl acetate (100 mL×6), and the combined organic layer was dried over anhydrous magnesium sulfate. The insoluble material was filtered off, and the filtrate was concentrated under reduced pressure to give the title compound (6.0 g, total of 3 steps 67%) as a pale-brown solid.

$^1$H-NMR (DMSO-d$_6$, 300 MHz) δ 3.32 (6H, s), 6.89 (1H, d, J=8.4 Hz), 7.28 (1H, d, J=8.7 Hz), 7.55 (2H, br s), 7.60 (1H, d, J=2.1 Hz), 7.70 (1H, d, J=8.7 Hz), 7.85 (1H, dd, J=2.1, 8.4 Hz).

(iv) Production of methyl 3-({2-[(cyclopropylcarbonyl)amino][1,3]thiazolo[5,4-b]pyridin-5-yl}oxy)-4-methoxybenzoate In the same manner as in Example C1(viii), the title compound (4.0 g, 98%) was obtained as brown solid using methyl 3-[(2-amino[1,3]thiazolo[5,4-b]pyridin-5-yl)oxy]-4-methoxybenzoate (3.37 g, 10.2 mmol), pyridine (80 mL), N,N-dimethylpyridine-4-amine (111 mg, 904 µmol) and cyclopropanecarbonyl chloride (2.0 mL, 22.0 mmol) as starting materials.

$^1$H-NMR (DMSO-d$_6$, 300 MHz) δ 0.93-0.97 (4H, m), 1.97-1.99 (1H, m), 3.78 (3H, s), 3.82 (3H, s), 7.12 (1H, d, J=8.7 Hz), 7.31 (1H, d, J=8.7 Hz), 7.69 (1H, d, J=2.1 Hz), 7.90 (1H, dd, J=2.1, 8.4 Hz), 8.14 (1H, d, J=8.7 Hz), 12.66 (1H, br s).

(v) Production of 3-({2-[(cyclopropylcarbonyl)amino][1,3]thiazolo[5,4-b]pyridin-5-yl}oxy)-4-methoxybenzoic acid To a solution of methyl 3-({2-[(cyclopropylcarbonyl)amino][1,3]thiazolo[5,4-b]pyridin-5-yl}oxy)-4-methoxybenzoate (4.0 g, 9.96 mmol) in methanol (50 mL)-tetrahydrofuran (100 mL) was added 5N aqueous sodium hydroxide solution (80 mL), and the mixture was stirred at room temperature for 3 hr. 6N Hydrochloric acid was added to the reaction solution to adjust the pH to about 4.0, and the reaction solution was extracted with ethyl acetate (200 mL×3). The combined organic layer was dried over anhydrous magnesium sulfate, the insoluble material was filtered off, and the filtrate was concentrated to give the title compound (3.70 g, 96%) as a yellow solid.

$^1$H-NMR (DMSO-d$_6$, 300 MHz) δ 0.78-0.81 (4H, m), 1.95-2.03 (1H, m), 3.76 (3H, s), 7.10 (1H, d, J=8.7 Hz), 7.26 (1H, d, J=8.7 Hz), 7.64 (1H, d, J=2.1 Hz), 7.86 (1H, dd, J=2.1, 8.4 Hz), 8.14 (1H, d, J=8.7 Hz), 12.63 (1H, br s).

(vi) Production of 3-({2-[(cyclopropylcarbonyl)amino][1,3]thiazolo[5,4-b]pyridin-5-yl}oxy)-4-methoxy-N-[3-(trifluoromethyl)phenyl]benzamide In the same manner as in Example C2(iii), the title compound (94 mg, 55%) was obtained as colorless crystals using 3-({2-[(cyclopropylcarbonyl)amino][1,3]thiazolo[5,4-b]pyridin-5-yl}oxy)-4-methoxybenzoic acid (125 mg, 324 µmol), pyridine (5 mL), 3-(trifluoromethyl)aniline (300 mg, 1.86 mmol), N,N-dimethylpyridine-4-amine (58.1 mg, 476 µmol) and 1-ethyl-3-(3-dimethylaminopropyl)carbodiimide hydrochloride (324 mg, 1.69 mmol) as starting materials.

$^1$H-NMR (DMSO-d$_6$, 300 MHz) δ 0.92-0.94 (4H, m), 1.90-1.99 (1H, m), 3.79 (3H, s), 7.12 (1H, d, J=9.0 Hz), 7.35 (1H, d, J=8.7 Hz), 7.44 (1H, d, J=8.4 Hz), 7.59 (1H, t, J=7.8 Hz), 7.88 (1H, d, J=2.4 Hz), 7.98 (1H, dd, J=2.4, 8.4 Hz), 8.05

(1H, d, J=8.1 Hz), 8.13 (1H, d, J=8.7 Hz), 8.22 (1H, br s), 10.41 (1H, br s), 12.64 (1H, br s).

Example C5

Production of N-[3-({2-[(cyclopropylcarbonyl)amino][1,3]thiazolo[5,4-b]pyridin-5-yl}oxy)-4-methoxyphenyl]-3-(trifluoromethyl)benzamide

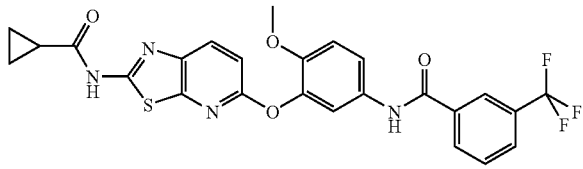 [SMILES: COc1ccc(NC(=O)c2cccc(C(F)(F)F)c2)cc1Oc1ccc2nc(NC(=O)C3CC3)sc2n1]

(i) Production of N-[5-(5-amino-2-methoxyphenoxy)[1,3]thiazolo[5,4-b]pyridin-2-yl]cyclopropanecarboxamide To a solution of 3-({2-[(cyclopropylcarbonyl)amino][1,3]thiazolo[5,4-b]pyridin-5-yl}oxy)-4-methoxybenzoic acid (1.92 g, 4.98 mmol) produced in Example C4(v) in N,N-dimethylformamide (50 mL) and 2-methylpropan-2-ol (50 mL) were added triethylamine (5 mL, 35.9 mmol) and diphenylphosphoryl azide (3 mL, 13.9 mmol), and the mixture was stirred at 120° C. for 2 hr. After cooling the reaction solution to room temperature, the reaction solution was diluted with water (200 mL). The yielded solid was collected by filtration to give tert-butyl[3-({2-[(cyclopropylcarbonyl)amino][1,3]thiazolo[5,4-b]pyridin-5-yl}oxy)-4-methoxyphenyl]carbamate (primary product, 1.16 g). The filtrate was extracted with ethyl acetate-hexane (1:1, 150 mL×3), and the combined organic layer was washed with saturated brine (150 mL), and dried over anhydrous magnesium sulfate. The insoluble material was filtered off, the filtrate was concentrated under reduced pressure, and the residue was subjected to silica gel column chromatography (ethyl acetate/hexane=2/98→80/20) to give tert-butyl[3-({2-[(cyclopropylcarbonyl)amino][1,3]thiazolo[5,4-b]pyridin-5-yl}oxy)-4-methoxyphenyl]carbamate (secondary product, 994 mg). These products contained structurally unknown impurities but used for the next reaction without further purification.

tert-Butyl[3-({2-[(cyclopropylcarbonyl)amino][1,3]thiazolo[5,4-b]pyridin-5-yl}oxy)-4-methoxyphenyl]carbamate (994 mg) obtained above was dissolved in trifluoroacetic acid (10 mL) at room temperature, and the mixture was heated under reflux for 2 hr. After cooling the reaction solution to room temperature, trifluoroacetic acid was evaporated under reduced pressure. The residue was diluted with methanol (15 mL) and ethyl acetate (100 mL), washed with saturated aqueous sodium hydrogen carbonate solution (50 mL), and dried over anhydrous magnesium sulfate. The insoluble material was filtered off, and the filtrate was concentrated under reduced pressure. The residue was purified by silica gel column chromatography (ethyl acetate/hexane=2/98→80/20) to give the title compound (411 mg, total yield of 2 steps 50%) as a colorless solid.

$^1$H-NMR (DMSO-$d_6$, 300 MHz) δ 0.94-1.00 (4H, m), 1.95-2.00 (1H, m), 3.54 (3H, s), 4.82 (2H, br s), 6.39 (1H, d, J=2.4 Hz), 6.43 (1H, dd, J=2.4, 8.7 Hz), 6.87 (1H, d, J=8.7 Hz), 6.97 (1H, d, J=8.7 Hz), 8.08 (1H, d, J=8.7 Hz), 12.63 (1H, br s).

(ii) Production of N-[3-({2-[(cyclopropylcarbonyl)amino][1,3]thiazolo[5,4-b]pyridin-5-yl}oxy)-4-methoxyphenyl]-3-(trifluoromethyl)benzamide To a suspension of 3-(trifluoromethyl)benzoic acid (260 mg, 1.37 mmol) in toluene (10 mL) was added thionyl chloride (1 mL, 13.7 mmol), and the mixture was heated under reflux for 2 hr. After cooling the obtained colorless solution to room temperature, the solvent was evaporated under reduced pressure. The obtained brown oil was used for next reaction as 3-(trifluoromethyl)benzoyl chloride.

To a solution of N-[5-(5-amino-2-methoxyphenoxy)[1,3]thiazolo[5,4-b]pyridin-2-yl]cyclopropanecarboxamide (93.0 mg, 261 μmol) in pyridine (2 mL) were added a solution of 3-(trifluoromethyl)benzoyl chloride prepared above in pyridine (3 mL) and N,N-dimethylpyridine-4-amine (28.9 mg, 237 μmol), and the mixture was stirred at room temperature for 14 hr. The reaction solution was concentrated under reduced pressure, and the residue was dissolved in ethyl acetate (50 mL). The solution was washed with 0.1N hydrochloric acid (30 mL) and saturated aqueous sodium hydrogen carbonate solution (30 mL), and dried over anhydrous magnesium sulfate, the insoluble material was filtered off, and the filtrate was concentrated under reduced pressure. The residue was subjected to silica gel column chromatography (ethyl acetate/hexane=2/98→80/20) to give the title compound (79 mg, 58%) as a white powder.

$^1$H-NMR (DMSO-$d_6$, 300 MHz) δ 0.94-0.97 (4H, m), 1.95-2.03 (1H, m), 3.70 (3H, s), 7.10 (1H, d, J=8.7 Hz), 7.19-7.23 (1H, m), 7.63-7.66 (2H, m), 7.78 (1H, t, J=8.1 Hz), 7.96 (1H, d, J=7.2 Hz), 8.14 (1H, d, J=8.7 Hz), 8.24-8.32 (2H, m), 10.45 (1H, br s), 12.66 (1H, br s).

Example C6

Production of 3-(1-cyano-1-methylethyl)-N-[3-({2-[(cyclopropylcarbonyl)amino][1,3]thiazolo[5,4-b]pyridin-5-yl}oxy)-4-methoxyphenyl]benzamide

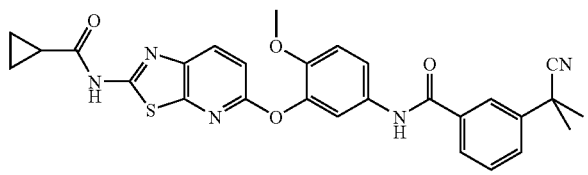 [SMILES: COc1ccc(NC(=O)c2cccc(C(C)(C)C#N)c2)cc1Oc1ccc2nc(NC(=O)C3CC3)sc2n1]

(i) Production of methyl 3-(1-cyano-1-methylethyl)benzoate

To a solution of methyl 3-(cyanomethyl)benzoate (7.0 g, 40 mmol) produced in Example C1(i) in dimethyl sulfoxide (80 mL) was added sodium hydride (60% in oil, 4.8 g, 120 mmol) while cooling the solution to a temperature of 25° C. or below at which the solution did not solidify. The reaction mixture was stirred at room temperature for 20 min, methyl iodide (7.5 mL, 120 mmol) was added, and the mixture was further stirred at room temperature for 16 hr. The reaction mixture was diluted with water (400 mL). After extraction with ethyl acetate (800 mL), the organic layer was washed with water (400 mL) and saturated brine (400 mL), and dried over anhydrous sodium sulfate, and the insoluble material was filtered off. The solvent was evaporated under reduced pressure, the residue was purified by silica gel column chromatography (ethyl acetate/hexane=5/95→50/50), and fractions containing the object product was concentrated under reduced pressure to give the title compound (6.4 g, 79%) as a colorless oil.

$^1$H-NMR (DMSO-$d_6$, 300 MHz) δ 1.72 (6H, s), 3.89 (3H, s), 7.61 (1H, t, J=7.8 Hz), 7.82-7.85 (1H, ddd, J=1.2, 2.1, 7.8 Hz), 7.95 (1H, dt, J=7.8, 1.2 Hz), 8.08 (1H, t, J=1.5 Hz).

(ii) Production of 3-(1-cyano-1-methylethyl)benzoic acid

To a solution of methyl 3-(1-cyano-1-methylethyl)benzoate (2.8 g, 14 mmol) in tetrahydrofuran (30 mL) were added lithium hydroxide•monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). 1N Hydrochloric acid was slowly added to the mixture to adjust the pH to 3. The precipitated white precipitate was collected by filtration, washed with water, and dried to give the title compound (2.5 g, 98%) as a white powder.

$^1$H-NMR (DMSO-$d_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(iii) Production of 3-(1-cyano-1-methylethyl)-N-[3-({2-[(cyclopropylcarbonyl)amino][1,3]thiazolo[5,4-b]pyridin-5-yl}oxy)-4-methoxyphenyl]benzamide In the same manner as in Example C5(ii), the title compound (95 mg, 53%) was obtained as colorless amorphous substance using 3-(1-cyano-1-methylethyl)benzoic acid (267 mg, 1.41 mmol), toluene (5 mL), thionyl chloride (1 mL, 13.7 mmol), N-[5-(5-amino-2-methoxyphenoxy)[1,3]thiazolo[5,4-b]pyridin-2-yl]cyclopropanecarboxamide (122 mg, 341 µmol) produced in Example C5(i), pyridine (5 mL), and N,N-dimethylpyridine-4-amine (19.8 mg, 162 µmol) as starting materials.

$^1$H-NMR (DMSO-$d_6$, 300 MHz) δ 0.87-1.00 (4H, m), 1.75 (6H, s), 1.92-2.03 (1H, m), 3.69 (3H, s), 7.09 (1H, d, J=8.7 Hz), 7.18-7.21 (1H, m), 7.52-7.65 (3H, m), 7.74 (1H, d, J=7.2 Hz), 7.89-7.94 (1H, m), 8.07 (1H, br s), 8.14 (1H, d, J=8.7 Hz), 10.29 (1H, br s), 12.64 (1H, br s).

Example C7

Production of 2,3-dichloro-N-[3-({2-[(cyclopropylcarbonyl)amino][1,3]thiazolo[5,4-b]pyridin-5-yl}oxy)-4-methoxyphenyl]benzamide

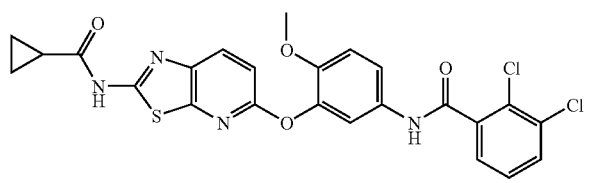 [SMILES: COc1ccc(NC(=O)c2cccc(Cl)c2Cl)cc1Oc1ccc2nc(NC(=O)C3CC3)sc2n1]

In the same manner as in Example C5(ii), the title compound (145 mg, 80%) was obtained as a pale-brown solid using 2,3-dichlorobenzoic acid (322 mg, 1.68 mmol), toluene (5 mL), thionyl chloride (1 mL, 13.7 mmol), N-[5-(5-amino-2-methoxyphenoxy)[1,3]thiazolo[5,4-b]pyridin-2-yl]cyclopropanecarboxamide (122 mg, 341 µmol) produced in Example C5(i), pyridine (5 mL), and N,N-dimethylpyridine-4-amine (58.9 mg, 482 µmol) as starting materials.

$^1$H-NMR (DMSO-$d_6$, 300 MHz) δ 0.94-0.97 (4H, m), 1.91-1.99 (1H, m), 3.67 (3H, s), 7.09 (1H, d, J=8.7 Hz), 7.18 (1H, d, J=9.0 Hz), 7.46-7.56 (3H, m), 7.59 (1H, t, J=2.7 Hz), 7.76 (1H, dd, J=1.8, 8.1 Hz), 8.14 (1H, d, J=8.7 Hz), 10.57 (1H, br s), 12.66 (1H, br s).

Example C8

Production of N-[3-({2-[(cyclopropylcarbonyl)amino][1,3]thiazolo[5,4-b]pyridin-5-yl}oxy)-4-methylphenyl]-3-(trifluoromethyl)benzamide

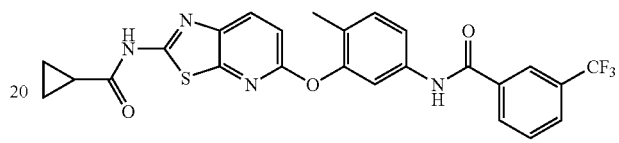

(i) Production of N-(3-hydroxy-4-methylphenyl)-3-(trifluoromethyl)benzamide

To a solution of 5-amino-2-methylphenol (7.38 g, 59.9 mmol) in tetrahydrofuran (30 mL) was added water (30 mL) in which sodium hydrogen carbonate (6.00 g, 71.9 mmol) has been suspended, and the mixture was vigorously stirred at room temperature. 3-(Trifluoromethyl)benzoyl chloride (15.0 g, 71.9 mmol) was added dropwise to the mixture under ice-cooling, and the mixture was stirred at room temperature for 24 hr. The aqueous layer of the reaction mixture was separated, and the organic layer was diluted with ethyl acetate, and washed with saturated brine. The organic layer was dried over anhydrous magnesium sulfate, and was filtrated, and the solvent was evaporated under reduced pressure. A mixture of the obtained residue, methanol (30 mL) and 2N aqueous sodium hydroxide solution (30 mL) was stirred at room temperature for 24 hr. Water was added to the reaction mixture, and the mixture was extracted with ethyl acetate. The extract was washed with saturated brine, dried over anhydrous magnesium sulfate, and decolorized with activated carbon. The insoluble material was filtered off through a pad with two layers of silica gel and celite. The solvent was evaporated under reduced pressure, and the obtained solid was washed with a mixed solvent of ethyl acetate and hexane to give the title compound (14.8 g, 84%) as a white powder.

$^1$H-NMR (DMSO-$d_6$, 300 MHz) δ 2.09 (3H, s), 6.98-7.08 (2H, m), 7.40 (1H, d, J=1.5 Hz), 7.77 (1H, t, J=7.7 Hz), 7.95 (1H, d, J=7.7 Hz), 8.21-8.28 (2H, m), 9.39 (1H, s), 10.29 (1H, s).

(ii) Production of N-{4-methyl-3-[(5-nitropyridin-2-yl)oxy]phenyl}-3-(trifluoromethyl)benzamide In the same method as in Example C1(v), the title compound (8.35 g, 98%) was obtained as an orange oil using N-(3-hydroxy-4-methylphenyl)-3-(trifluoromethyl)benzamide (6.00 g, 20.3 mmol), 2-chloro-5-nitropyridine (3.22 g, 20.3 mmol), potassium carbonate (8.43 g, 60.9 mmol) and N,N-dimethylformamide (150 mL) as starting materials. The title compound was used for the next reaction without further purification operation.

$^1$H-NMR (DMSO-d$_6$, 300 MHz) δ 2.07 (3H, s), 7.31 (1H, d, J=9.2 Hz), 7.36 (1H, d, J=8.3 Hz), 7.60 (1H, dd, J=2.1, 8.3 Hz), 7.69 (1H, d, J=2.1 Hz), 7.79 (1H, t, J=7.8 Hz), 7.93-8.01 (1H, m), 8.20-8.32 (2H, m), 8.65 (1H, dd, J=2.7 9.2 Hz), 9.04 (1H, d, J=2.7 Hz), 10.56 (1H, s).

(iii) Production of N-{3-[(5-aminopyridin-2-yl)oxy]-4-methylphenyl}-3-(trifluoromethyl)benzamide In the same method as in Example C1(vi), the title compound (7.34 g, 96%) was obtained as a white powder using N-{4-methyl-3-[(5-nitropyridin-2-yl)oxy]phenyl}-3-(trifluoromethyl)benzamide (8.25 g, 19.7 mmol), 10% palladium-carbon (380 mg), tetrahydrofuran (100 mL) and methanol (50 mL) as starting materials. The title compound was washed with a mixed solvent of ethyl acetate and hexane.

$^1$H-NMR (DMSO-d$_6$, 300 M Hz) δ 2.13 (3H, s), 5.06 (2H, s), 6.76 (1H, d, J=8.5 Hz), 7.09 (1H, dd, J=2.7, 8.5 Hz), 7.23 (1H, d, J=8.3 Hz), 7.33 (1H, d, J=2.1 Hz), 7.48 (1H, dd, J=2.1, 8.3 Hz), 7.52 (1H, d, J=2.7 Hz), 7.76 (1H, t, J=7.7 Hz), 7.95 (1H, d, J=7.7 Hz), 8.18-8.27 (2H, m), 10.38 (1H, s).

(iv) Production of N-{3-[(2-amino[1,3]thiazolo[5,4-b]pyridin-5-yl)oxy]-4-methylphenyl}-3-(trifluoromethyl)benzamide In the same method as in Example C1(vii), the title compound (7.76 g, 93%) was obtained as a white powder using N-{3-[(5-aminopyridin-2-yl)oxy]-4-methylphenyl}-3-(trifluoromethyl)benzamide (7.30 g, 18.8 mmol), potassium thiocyanate (7.33 g, 75.3 mmol), bromine (4.50 g, 28.2 mmol) and acetic acid (400 mL) as starting materials. The title to compound was washed with a mixed solvent of ethyl acetate and hexane.

$^1$H-NMR (DMSO-d$_6$, 300 MHz) δ 2.12 (3H, s), 6.90 (1H, d, J=8.5 Hz), 7.30 (1H, d, J=8.5 Hz), 7.47 (1H, d, J=2.1 Hz), 7.54-7.62 (3H, m), 7.70-7.80 (2H, m), 7.95 (1H, d, J=8.0 Hz), 8.23 (1H, d, J=8.0 Hz), 8.26 (1H, s), 10.45 (1H, s).

(v) Production of N-[3-({2-[(cyclopropylcarbonyl)amino][1,3]thiazolo[5,4-b]pyridin-5-yl}oxy)-4-methylphenyl]-3-(trifluoromethyl)benzamide To a solution of N-{3-[(2-amino[1,3]thiazolo[5,4-b]pyridin-5-yl)oxy]-4-methylphenyl}-3-(trifluoromethyl)benzamide (200 mg, 0.450 mmol) in pyridine (5 mL) was added cyclopropanecarbonyl chloride (77.5 μL, 1.12 mmol), and the mixture was stirred at room temperature for 16 hr. The reaction mixture was evaporated under reduced pressure, and a mixture of the obtained residue, methanol (3 mL) and 0.5N aqueous sodium hydroxide solution (3 mL) was stirred at room temperature for 30 min. Water was added to the reaction mixture, and the mixture was extracted with ethyl acetate. The extract was washed with saturated brine, dried over anhydrous magnesium sulfate, and filtrated. The solvent was evaporated under reduced pressure, and the residue was precipitated with tetrahydrofuran to give the title compound (130 mg, 56%) as a white powder.

$^1$H-NMR (DMSO-d$_6$, 300 MHz) δ 0.88-1.01 (4H, m), 1.93-2.04 (1H, m), 2.11 (3H, s), 7.13 (1H, d, J=8.7 Hz), 7.33 (1H, d, J=7.7 Hz), 7.54-7.64 (2H, m), 7.77 (1H, t, J=7.3 Hz), 7.96 (1H, d, J=7.3 Hz), 8.13-8.30 (3H, m), 10.49 (1H, s), 12.65 (1H, br s).

Example C9

Production of N-(3-{[2-(glycoloylamino)[1,3]thiazolo[5,4-b]pyridin-5-yl]oxy}-4-methylphenyl)-3-(trifluoromethyl)benzamide

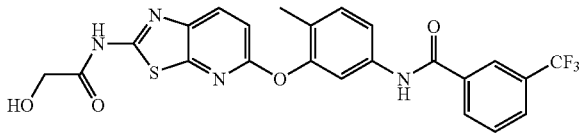 [SMILES: Cc1ccc(NC(=O)c2cccc(C(F)(F)F)c2)cc1Oc1ccc2nc(NC(=O)CO)sc2n1]

To a solution of N-{3-[(2-amino[1,3]thiazolo[5,4-b]pyridin-5-yl)oxy]-4-methylphenyl}-3-(trifluoromethyl)benzamide (200 mg, 0.450 mmol) produced in Example C8(iv) in pyridine (5 mL) was added acetoxyacetyl chloride (121 μL, 1.12 mmol), and the mixture was stirred at room temperature for 30 min. The reaction mixture was concentrated under reduced pressure, and a mixture of the obtained residue, methanol (3 mL), pyridine (2 mL) and 0.5N aqueous sodium hydroxide solution (3 mL) was stirred at room temperature for 16 hr. Water was added to the reaction mixture, and the mixture was extracted with ethyl acetate. The extract was washed with saturated brine, dried over anhydrous magnesium sulfate, and filtrated. The solvent was evaporated under reduced pressure, and the residue was precipitated with ethyl acetate and hexane to give the title compound (92 mg, 41%) as a white powder.

$^1$H-NMR (DMSO-d$_6$, 300 MHz) δ 2.11 (3H, s), 4.19 (2H, d, J=5.5 Hz), 5.55 (1H, t, J=5.5 Hz), 7.14 (1H, d, J=8.9 Hz), 7.34 (1H, d, J=7.7 Hz), 7.54-7.66 (2H, m), 7.77 (1H, t, J=7.4 Hz), 7.96 (1H, d, J=7.4 Hz), 8.14-8.32 (3H, m), 10.50 (1H, s), 12.13 (1H, br s).

Example C10

Production of N-[5-(2-methyl-5-{[3-(trifluoromethyl)benzoyl]amino}phenoxy)[1,3]thiazolo[5,4-b]pyridin-2-yl]-1,3-oxazole-4-carboxamide

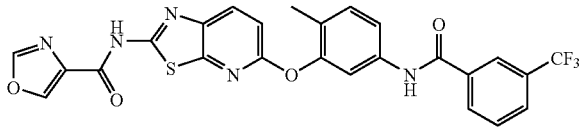 [SMILES: Cc1ccc(NC(=O)c2cccc(C(F)(F)F)c2)cc1Oc1ccc2nc(NC(=O)c3cocn3)sc2n1]

To a solution of 1,3-oxazole-4-carboxylic acid (126 mg, 1.12 mmol) in tetrahydrofuran (5 mL) were added oxalyl chloride (118 μL, 1.35 mmol) and N,N-dimethylformamide (20 μL), and the mixture was stirred at room temperature for 1 hr. The reaction mixture was concentrated under reduced pressure, the obtained residue and N-{3-[(2-amino[1,3]thiazolo[5,4-b]pyridin-5-yl)oxy]-4-methylphenyl}-3-(trifluoromethyl)benzamide (200 mg, 0.450 mmol) produced in Example C8(iv) were dissolved in pyridine (5 mL), and the solution was stirred at room temperature for 18 hr. Water was added to the reaction mixture, and the mixture was extracted with ethyl acetate. The extract was washed with saturated aqueous sodium hydrogen carbonate solution and saturated brine, dried over anhydrous magnesium sulfate, and filtrated. The solvent was evaporated under reduced pressure, and the residue was precipitated with tetrahydrofuran to give the title compound (205 mg, 84%) as a white powder.

$^1$H-NMR (DMSO-$d_6$, 300 MHz) δ 2.12 (3H, s), 7.18 (1H, d, J=8.7 Hz), 7.35 (1H, d, J=9.2 Hz), 7.58-7.64 (2H, m), 7.77 (1H, t, J=7.8 Hz), 7.96 (1H, d, J=7.8 Hz), 8.21-8.29 (3H, m), 8.66 (1H, d, J=0.9 Hz), 9.04 (1H, d, J=0.9 Hz), 10.50 (1H, s), 12.75 (1H, s).

Example C11

Production of N-{4-methyl-3-[(2-{[(4-methylpiperazin-1-yl)acetyl]amino}[1,3]thiazolo[5,4-b]pyridin-5-yl)oxy]phenyl}-3-(trifluoromethyl)benzamide

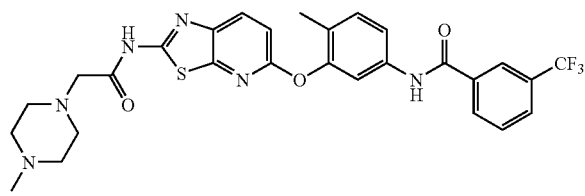 [SMILES: Cc1ccc(NC(=O)c2cccc(C(F)(F)F)c2)cc1Oc1ccc2nc(NC(=O)CN3CCN(C)CC3)sc2n1]

(i) Production of N-[3-({2-[(chloroacetyl)amino][1,3]thiazolo[5,4-b]pyridin-5-yl}oxy)-4-methylphenyl]-3-(trifluoromethyl)benzamide To a solution of N-{3-[(2-amino[1,3]thiazolo[5,4-b]pyridin-5-yl)oxy]-4-methylphenyl}-3-(trifluoromethyl)benzamide (200 mg, 0.450 mmol) produced in Example C8(iv) in N,N-dimethylformamide (5 mL) was added chloroacetyl chloride (104 μL, 0.900 mmol), and the mixture was stirred at room temperature for 2 hr. Saturated aqueous sodium hydrogen carbonate solution was added to the reaction mixture, and the mixture was extracted with ethyl acetate. The extract was washed with saturated brine, dried over anhydrous magnesium sulfate, and filtrated. The filtrate was concentrated under reduced pressure, and the obtained residue was washed with a mixed solution of ethyl acetate and hexane to give the title compound (218 mg, 93%) as a white powder. The powder was used for the next reaction without further purification operation.

$^1$H-NMR (DMSO-$d_6$, 300 MHz) δ 2.11 (3H, s), 4.45 (2H, s), 7.15 (1H, d, J=8.8 Hz), 7.34 (1H, d, J=8.8 Hz), 7.54-7.64 (2H, m), 7.77 (1H, t, J=7.8 Hz), 7.91-8.01 (1H, m), 8.17-8.32 (3H, m), 10.50 (1H, s), 12.78 (1H, br s).

(ii) Production of N-{4-methyl-3-[(2-{[(4-methylpiperazin-1-yl)acetyl]amino}[1,3]thiazolo[5,4-b]pyridin-5-yl)oxy]phenyl}-3-(trifluoromethyl)benzamide To a solution of N-[3-({2-[(chloroacetyl)amino][1,3]thiazolo[5,4-b]pyridin-5-yl}oxy)-4-methylphenyl]-3-(trifluoromethyl)benzamide (218 mg, 0.419 mmol) in tetrahydrofuran (5 mL) were added triethylamine (117 μL, 0.838 mmol) and 1-methylpiperazine (93.4 μL, 0.838 mmol), and the mixture was stirred at 60° C. for 14 hr. Saturated aqueous sodium hydrogen carbonate solution was added to the reaction mixture, and the mixture was extracted with ethyl acetate. The extract was washed with saturated brine, dried over anhydrous magnesium sulfate, and filtrated. The solvent was evaporated under reduced pressure, and the obtained residue was subjected to basic silica gel column chromatography (ethyl acetate/methanol=100/0→90/10), and precipitated with ethyl acetate to give the title compound (134 mg, 55%) as a white powder.

$^1$H-NMR (CDCl$_3$, 300 MHz) δ 2.19 (3H, s), 2.33 (3H, s), 2.47-2.60 (4H, m), 2.68 (4H, m), 3.27 (2H, s), 6.99 (1H, d, J=8.9 Hz), 7.28 (1H, d, J=9.0 Hz), 7.40 (1H, dd, J=2.1, 9.0 Hz), 7.50 (1H, d, J=2.1 Hz), 7.61 (1H, t, J=7.7 Hz), 7.79 (1H, d, J=7.7 Hz), 7.87 (1H, br s), 7.97-8.06 (2H, m), 8.10 (1H, s), 10.34 (1H, br s).

Example C12

Production of 3-(1-cyano-1-methylethyl)-N-[3-({2-[(cyclopropylcarbonyl)amino][1,3]thiazolo[5,4-b]pyridin-5-yl}oxy)-4-methylphenyl]benzamide

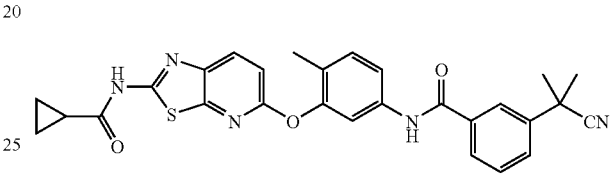

(i) Production of 3-(1-cyano-1-methylethyl)-N-(3-hydroxy-4-methylphenyl)benzamide To a solution of 3-(1-cyano-1-methylethyl)benzoic acid (5.00 g, 26.4 mmol) produced in Example C6(ii) in tetrahydrofuran (50 mL) were added N,N-dimethylformamide (40 μL) and oxalyl chloride (3.20 mL, 36.5 mmol), and the mixture was stirred at room temperature for 1.5 hr. The solvent was evaporated under reduced pressure to give 3-(1-cyano-1-methylethyl)benzoyl chloride. To a solution of 5-amino-2-methylphenol (3.00 g, 24.3 mmol) in tetrahydrofuran (20 mL) was added water (30 mL) in which sodium hydrogen carbonate (3.00 g, 36.5 mmol) has been suspended, and the mixture was vigorously stirred at room temperature. A solution of 3-(1-cyano-1-methylethyl)benzoyl chloride produced above in tetrahydrofuran (30 mL) was added dropwise to the mixture under ice-cooling, and the mixture was stirred at room temperature for 5 hr. The aqueous layer of the reaction mixture was separated, and the organic layer was diluted with ethyl acetate and washed with saturated brine. The organic layer was dried over anhydrous magnesium sulfate, and decolorized with activated carbon. The insoluble material was filtered off through a pad of two layers of silica gel and celite. The solvent was evaporated under reduced pressure, and the obtained solid was washed with a mixed solvent of ethyl acetate and hexane to give the title compound (6.75 g, 94%) as a white powder.

$^1$H-NMR (DMSO-$d_6$, 300 MHz) δ 1.75 (6H, s), 2.09 (3H, s), 6.97-7.06 (2H, m), 7.37 (1H, s), 7.58 (1H, t, J=7.7 Hz), 7.73 (1H, d, J=7.7 Hz), 7.90 (1H, d, J=7.7 Hz), 8.00 (1H, t, J=1.6 Hz), 9.36 (1H, s), 10.13 (1H, s).

(ii) Production of 3-(1-cyano-1-methylethyl)-N-{4-methyl-3-[(5-nitropyridin-2-yl)oxy]phenyl}benzamide In the same method as in Example C1(v), the title compound (4.20 g, 99%) was obtained as an orange oil using 3-(1-cyano-1-methylethyl)-N-(3-hydroxy-4-methylphenyl)

benzamide (3.00 g, 10.2 mmol), 2-chloro-5-nitropyridine (1.61 g, 10.2 mmol), potassium carbonate (4.22 g, 30.6 mmol) and N,N-dimethylformamide (75 mL) as starting materials. The obtained compound was used for the next reaction without further purification operation.

$^1$H-NMR (DMSO-$d_6$, 300 MHz) δ 1.74 (6H, s), 2.06 (3H, s), 7.30 (1H, d, J=9.0 Hz), 7.35 (1H, d, J=8.3 Hz), 7.55-7.64 (2H, m), 7.67 (1H, s), 7.75 (1H, d, J=7.6 Hz), 7.92 (1H, d, J=7.6 Hz), 8.02 (1H, s), 8.65 (1H, dd, J=2.6, 9.0 Hz), 9.04 (1H, d, J=2.6 Hz), 10.40 (1H, s).

(iii) Production of N-{3-[(5-aminopyridin-2-yl)oxy]-4-methylphenyl}-3-(1-cyano-1-methylethyl)benzamide In the same manner as in Example C1(vi), the title compound (3.79 g, 97%) was obtained as a white powder using 3-(1-cyano-1-methylethyl)-N-{4-methyl-3-[(5-nitropyridin-2-yl)oxy]phenyl}benzamide (4.20 g, 10.0 mmol), 10% palladium-carbon (260 mg), tetrahydrofuran (50 mL) and methanol (25 ml) as starting materials. The title compound was washed with a mixed solvent of ethyl acetate and hexane, and used for the next reaction without further purification operation.

$^1$H-NMR (DMSO-$d_6$, 300 MHz) δ 1.73 (6H, s), 2.12 (3H, s), 5.05 (2H, s), 6.76 (1H, d, J=8.5 Hz), 7.08 (1H, dd, J=2.7, 8.5 Hz), 7.22 (1H, d, J=8.4 Hz), 7.33 (1H, d, J=2.1 Hz), 7.46 (1H, dd, J=2.1, 8.4 Hz), 7.52 (1H, d, J=2.7 Hz), 7.57 (1H, t, J=7.7 Hz), 7.70-7.75 (1H, m), 7.86-7.91 (1H, m), 7.99 (1H, t, J=1.7 Hz), 10.23 (1H, s).

(iv) Production of N-{3-[(2-amino[1,3]thiazolo[5,4-b]pyridin-5-yl)oxy]-4-methylphenyl}-3-(1-cyano-1-methylethyl)benzamide In the same manner as in Example C1(vii), the title compound (2.90 g, 69%) was obtained as a white powder using N-{3-[(5-aminopyridin-2-yl)oxy]-4-methylphenyl}-3-(1-cyano-1-methylethyl)benzamide (3.67 g, 9.49 mmol), potassium thiocyanate (3.69 g, 37.9 mmol), bromine (2.27 g, 14.2 mmol) and acetic acid (175 mL) as starting materials. The title compound was washed with a mixed solvent of ethyl acetate and hexane, and used for the next reaction without further purification operation.

$^1$H-NMR (DMSO-$d_6$, 300 MHz) δ 1.73 (6H, s), 2.12 (3H, s), 6.90 (1H, d, J=8.5 Hz), 7.29 (1H, d, J=8.5 Hz), 7.47 (1H, d, J=2.1 Hz), 7.52-7.62 (4H, m), 7.70-7.77 (2H, m), 7.87-7.93 (1H, m), 8.00 (1H, t, J=1.7 Hz), 10.29 (1H, s).

(v) Production of 3-(1-cyano-1-methylethyl)-N-[3-({2-[(cyclopropylcarbonyl)amino][1,3]thiazolo[5,4-b]pyridin-5-yl}oxy)-4-methylphenyl]benzamide In the same manner as in Example C8(v), the title compound (154 mg, 66%) was obtained as a white powder using N-{3-[(2-amino[1,3]thiazolo[5,4-b]pyridin-5-yl)oxy]-4-methylphenyl}-3-(1-cyano-1-methylethyl)benzamide (200 mg, 0.450 mmol), pyridine (5 mL), cyclopropanecarbonyl chloride (77.5 µL, 1.12 mmol), methanol (3 mL) and 0.5N aqueous sodium hydroxide solution (3 mL) as starting materials.

$^1$H-NMR (DMSO-$d_6$, 300 MHz) δ 0.89-0.99 (4H, m), 1.73 (6H, s), 1.93-2.04 (1H, m), 2.10 (3H, s), 7.13 (1H, d, J=8.8 Hz), 7.32 (1H, d, J=8.3 Hz), 7.54-7.62 (3H, m), 7.74 (1H, d, J=7.8 Hz), 7.91 (1H, d, J=7.8 Hz), 8.00 (1H, s), 8.18 (1H, d, J=8.8 Hz), 10.34 (1H, s), 12.69 (1H, s).

Example C13

Production of 3-(1-cyano-1-methylethyl)-N-(3-{[2-(glycoloylamino)[1,3]thiazolo[5,4-b]pyridin-5-yl]oxy}-4-methylphenyl)benzamide

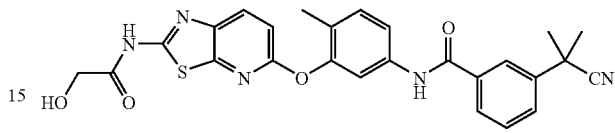

In the same manner as in Example C9, the title compound (106 mg, 47%) was obtained as a white powder using N-{3-[(2-amino[1,3]thiazolo[5,4-b]pyridin-5-yl)oxy]-4-methylphenyl}-3-(1-cyano-1-methylethyl)benzamide (200 mg, 0.450 mmol) produced in Example C12(iv), pyridine (6 mL), acetoxyacetyl chloride (121 µL, 1.12 mmol), methanol (2 mL) and 0.5N aqueous sodium hydroxide solution (2 mL) as starting materials. The title compound was precipitated with methanol and diethyl ether.

$^1$H-NMR (DMSO-$d_6$, 300 MHz) δ 1.73 (6H, s), 2.11 (3H, s), 4.18 (2H, d, J=6.3 Hz), 5.54 (1H, t, J=6.3 Hz), 7.14 (1H, d, J=8.7 Hz), 7.30-7.36 (1H, m), 7.54-7.62 (3H, m), 7.71-7.77 (1H, m), 7.88-7.94 (1H, m), 8.01 (1H, t, J=1.6 Hz), 8.19 (1H, d, J=8.7 Hz), 10.34 (1H, s), 12.13 (1H, s).

Example C14

Production of N-[5-(5-{[3-(1-cyano-1-methylethyl)benzoyl]amino}-2-methylphenoxy)[1,3]thiazolo[5,4-b]pyridin-2-yl]-1,3-oxazole-4-carboxamide

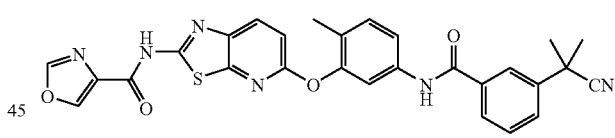

In the same manner as in Example C10, the title compound (46 mg, 19%) was obtained as a white powder using 1,3-oxazole-4-carboxylic acid (127 mg, 1.12 mmol), oxalyl chloride (118 µL, 1.35 mmol), tetrahydrofuran (5 mL), N,N-dimethylformamide (20 µL), N-{3-[(2-amino[1,3]thiazolo[5,4-b]pyridin-5-yl)oxy]-4-methylphenyl}-3-(1-cyano-1-methylethyl)benzamide (200 mg, 0.450 mmol) produced in Example C12(iv) and pyridine (5 mL) as starting materials. The title compound was purified by silica gel column chromatography (ethyl acetate/hexane=5/95→60/40), the obtained solid was further purified by reverse phase silica gel column chromatography (containing 0.1% TFA, water/acetonitrile=95/5→5/95), and fractions containing the object product was concentrated. The obtained trifluoroacetate was suspended in ethyl acetate, and the suspension was washed with saturated aqueous sodium hydrogen carbonate solution and saturated brine. The obtained organic layer was dried over anhydrous magnesium sulfate, and filtrated. The solvent was evaporated under reduced pressure, and the residue was precipitated with tetrahydrofuran.

$^1$H-NMR (DMSO-d$_6$, 300 MHz) δ 1.73 (6H, s), 2.12 (3H, s), 7.16 (1H, d, J=8.8 Hz), 7.34 (1H, d, J=8.8 Hz), 7.54-7.63 (3H, m), 7.71-7.77 (1H, m), 7.88-7.94 (1H, m), 8.01 (1H, t, J=1.7 Hz), 8.23 (1H, d, J=8.8 Hz), 8.65 (1H, s), 9.02 (1H, s), 10.35 (1H, s), 12.75 (1H, s).

Example C15

Production of 3-(1-cyano-1-methylethyl)-N-{4-methyl-3-[(2-{[(4-methylpiperazin-1-yl)acetyl]amino}[1,3]thiazolo[5,4-b]pyridin-5-yl)oxy]phenyl}benzamide

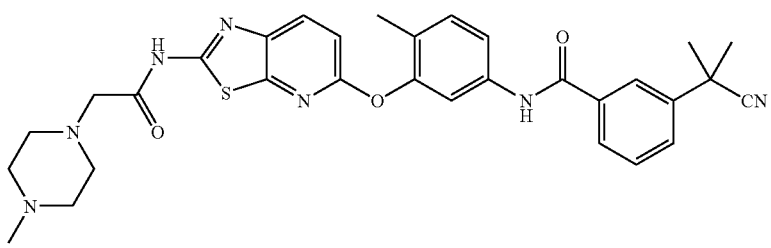 [SMILES: Cc1ccc(NC(=O)c2cccc(C(C)(C)C#N)c2)cc1Oc1ccc2nc(NC(=O)CN3CCN(C)CC3)sc2n1]

(i) Production of N-[3-({2-[(chloroacetyl)amino][1,3]thiazolo[5,4-b]pyridin-5-yl}oxy)-4-methylphenyl]-3-(1-cyano-1-methylethyl)benzamide In the same manner as in Example C11(i), the title compound (234 mg, quantitative) was obtained as a pale-yellow oil using N-{3-[(2-amino[1,3]thiazolo[5,4-b]pyridin-5-yl)oxy]-4-methylphenyl}-3-(1-cyano-1-methylethyl)benzamide (200 mg, 0.450 mmol) produced in Example C12(iv), chloroacetyl chloride (104 μL, 0.901 mmol) and N,N-dimethylformamide (5 mL) as starting materials. The obtained compound was purified by silica gel column chromatography (ethyl acetate/hexane=5/95→60/40).

$^1$H-NMR (DMSO-d$_6$, 300 MHz) δ 1.74 (6H, s), 2.11 (3H, s), 4.45 (2H, s), 7.15 (1H, d, J=8.8 Hz), 7.33 (1H, d, J=8.8 Hz), 7.55-7.61 (3H, m), 7.71-7.77 (1H, m), 7.89-7.94 (1H, m), 8.01 (1H, t, J=1.8 Hz), 8.21 (1H, d, J=8.8 Hz), 10.34 (1H, s), 12.77 (1H, s).

(ii) Production of 3-(1-cyano-1-methylethyl)-N-{4-methyl-3-[(2-{[(4-methylpiperazin-1-yol)acetyl]amino}[1,3]thiazolo[5,4-b]pyridin-5-yl)oxy]phenyl}benzamide In the same manner as in Example C11(ii), the title compound (142 mg, 54%) was obtained as a white powder using N-[3-({2-[(chloroacetyl)amino][1,3]thiazolo[5,4-b]pyridin-5-yl}oxy)-4-methylphenyl]-3-(1-cyano-1-methylethyl)benzamide (234 mg), triethylamine (125 μL, 0.901 mmol), 1-methylpiperazine (100 μL, 0.901 mmol) and tetrahydrofuran (5 mL) as starting materials.

$^1$H-NMR (CDCl$_3$, 300 MHz) δ 1.76 (6H, s), 2.20 (3H, s), 2.33 (3H, s), 2.47-2.61 (4H, m), 2.63-2.72 (4H, m), 3.27 (2H, s), 6.99 (1H, d, J=8.8 Hz), 7.24-7.31 (1H, m), 7.37-7.43 (1H, m), 7.46-7.54 (2H, m), 7.66-7.72 (1H, m), 7.73-7.78 (1H, m), 7.84 (1H, s), 7.95 (1H, t, J=1.8 Hz), 8.00 (1H, d, J=8.8 Hz), 10.31 (1H, br s).

Example C16

Production of 3-(1-cyanocyclopropyl)-N-[3-({2-[(cyclopropylcarbonyl)amino][1,3]thiazolo[5,4-b]pyridin-5-yl}oxy)-4-methylphenyl]benzamide

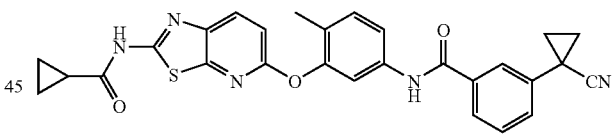

(i) Production of 3-(1-cyanocyclopropyl)-N-(3-hydroxy-4-methylphenyl)benzamide

In the same manner as in Example C12(i), the title compound (12.4 g, 87%) was obtained as a white powder using 5-amino-2-methylphenol (6.00 g, 48.5 mmol), 3-(1-cyanocyclopropyl)benzoic acid (6.00 g, 48.5 mmol), oxalyl chloride (6.40 mL, 73.0 mmol), N,N-dimethylformamide (40 μL), tetrahydrofuran (250 mL), sodium hydrogen carbonate (6.20 g, 73.0 mmol) and water (60 mL) as starting materials. The title compound was washed with a mixed solvent of ethyl acetate and hexane.

$^1$H-NMR (DMSO-d$_6$, 300 MHz) δ 1.58-1.65 (2H, m), 1.77-1.84 (2H, m), 2.08 (3H, s), 6.96-7.05 (2H, m), 7.35-7.40

(1H, m), 7.49-7.58 (2H, m), 7.77-7.81 (1H, m), 7.82-7.88 (1H, m), 9.34 (1H, s), 10.10 (1H, s).

(ii) Production of 3-(1-cyanocyclopropyl)-N-{4-methyl-3-[(5-nitropyridin-2-yl)oxy]phenyl}benzamide In the same manner as in Example C1(v), the title compound (7.82 g, 91%) was obtained as a white powder using 3-(1-cyanocyclopropyl)-N-(3-hydroxy-4-methylphenyl)benzamide (6.05 g, 20.6 mmol), 2-chloro-5-nitropyridine (3.28 g, 20.6 mmol), potassium carbonate (8.58 g, 62.0 mmol) and N,N-dimethylformamide (150 mL) as starting materials. The title compound was washed with a mixed solvent of ethyl acetate and hexane.
$^1$H-NMR (DMSO-$d_6$, 300 MHz) δ 1.57-1.65 (2H, m), 1.78-1.85 (2H, m), 2.06 (3H, s), 7.30 (1H, d, J=9.0 Hz), 7.34 (1H, d, J=8.5 Hz), 7.50-7.62 (3H, m), 7.66 (1H, d, J=1.9 Hz), 7.82 (1H, s), 7.84-7.90 (1H, m), 8.65 (1H, dd, J=2.7, 9.0 Hz), 9.04 (1H, d, J=2.7 Hz), 10.38 (1H, s).

(iii) Production of N-{3-[(5-aminopyridin-2-yl)oxy]-4-methylphenyl}-3-(1-cyanocyclopropyl)benzamide In the same manner as in Example C1(vi), the title compound (7.16 g, quantitative) was obtained as a white powder using 3-(1-cyanocyclopropyl)-N-{4-methyl-3-[(5-nitropyridin-2-yl)oxy]phenyl}benzamide (7.72 g, 18.6 mmol), tetrahydrofuran (100 mL), methanol (25 mL) and 10% palladium-carbon (430 mg) as starting materials. The title compound was washed with a mixed solvent of ethyl acetate and hexane, and used for the next reaction without further purification operation.
$^1$H-NMR (DMSO-$d_6$, 300 MHz) δ 1.57-1.63 (2H, m), 1.77-1.83 (2H, m), 2.12 (3H, s), 5.05 (2H, s), 6.75 (1H, d, J=8.7 Hz), 7.08 (1H, dd, J=3.0, 8.7 Hz), 7.21 (1H, d, J=8.7 Hz), 7.32 (1H, d, J=2.1 Hz), 7.46 (1H, dd, J=2.1, 8.3 Hz), 7.49-7.58 (3H, m), 7.77 (1H, s), 7.81-7.86 (1H, m), 10.21 (1H, s).

(iv) Production of N-{3-[(2-amino[1,3]thiazolo[5,4-b]pyridin-5-yl)oxy]-4-methylphenyl}-3-(1-cyanocyclopropyl)benzamide In the same manner as in Example C1(vii), the title compound (6.24 g, 76%) was obtained as pale-yellow powder using N-{3-[(5-aminopyridin-2-yl)oxy]-4-methylphenyl}-3-(1-cyanocyclopropyl)benzamide (7.10 g, 18.4 mmol), potassium thiocyanate (7.17 g, 73.8 mmol), bromine (4.42 g, 27.7 mmol) and acetic acid (180 mL) as starting materials. The title compound was washed with a mixed solvent of ethyl acetate and hexane, and used for the next reaction without further purification operation.
$^1$H-NMR (DMSO-$d_6$, 300 MHz) δ 1.58-1.63 (2H, m), 1.78-1.83 (2H, m), 2.11 (3H, s), 6.89 (1H, d, J=8.6 Hz), 7.28 (1H, d, J=8.5 Hz), 7.46 (1H, d, J=1.9 Hz), 7.50-7.61 (5H, m), 7.72 (1H, d, J=8.6 Hz), 7.77-7.80 (1H, m), 7.82-7.87 (1H, m), 10.28 (1H, s).

(v) Production of 3-(1-cyanocyclopropyl)-N-[3-({2-[(cyclopropylcarbonyl)amino][1,3]thiazolo[5,4-b]pyridin-5-yl}oxy)-4-methylphenyl]benzamide To a solution of N-{3-[(2-amino[1,3]thiazolo[5,4-b]pyridin-5-yl)oxy]-4-methylphenyl}-3-(1-cyanocyclopropyl)benzamide (200 mg, 0.452 mmol) in pyridine (5 mL) was added cyclopropanecarbonyl chloride (77.8 μL, 1.13 mmol), and the mixture was stirred at room temperature for 30 min. Saturated aqueous sodium hydrogen carbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was precipitated with tetrahydrofuran to give the title compound (140 mg, 61%) as a white powder.
$^1$H-NMR (DMSO-$d_6$, 300 MHz) δ 0.90-0.98 (4H, m), 1.57-1.64 (2H, m), 1.78-1.83 (2H, m), 1.95-2.02 (1H, m), 2.10 (3H, s), 7.12 (1H, d, J=8.7 Hz), 7.32 (1H, d, J=8.1 Hz), 7.50-7.60 (4H, m), 7.77-7.81 (1H, m), 7.82-7.88 (1H, m), 8.17 (1H, d, J=8.7 Hz), 10.32 (1H, s), 12.51 (1H, br s).

Example C17

Production of 3-(1-cyanocyclopropyl)-N-(3-{[2-(glycoloylamino)[1,3]thiazolo[5,4-b]pyridin-5-yl]oxy}-4-methylphenyl)benzamide

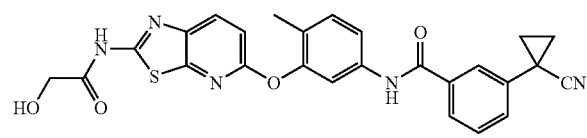 [SMILES: Cc1ccc(NC(=O)c2cccc(C3(C#N)CC3)c2)cc1Oc1ccc2nc(NC(=O)CO)sc2n1]

In the same manner as in Example C9, the title compound (79.7 mg, 35%) was obtained as a white powder using N-{3-[(2-amino[1,3]thiazolo[5,4-b]pyridin-5-yl)oxy]-4-methylphenyl}-3-(1-cyanocyclopropyl)benzamide (200 mg, 0.452 mmol) produced in Example C16(iv), acetoxyacetyl chloride (121 μL, 1.13 mmol), pyridine (6 mL), methanol (2 mL) and 0.5N aqueous sodium hydroxide solution (2 mL) as starting materials. The title compound was purified by reverse phase silica gel column chromatography (containing 0.1% TFA, water/acetonitrile=70/30→30/70), and fractions containing the object product was concentrated. The obtained trifluoroacetate was suspended in ethyl acetate, and the suspension was washed with saturated aqueous sodium hydrogen carbonate solution and m saturated brine. The obtained organic layer was dried over anhydrous magnesium sulfate, and filtrated. The solvent was evaporated under reduced pressure, and the residue was precipitated with ethyl acetate.
$^1$H-NMR (DMSO-$d_6$, 300 MHz) δ 1.57-1.64 (2H, m), 1.77-1.84 (2H, m), 2.11 (3H, s), 4.18 (2H, d, J=5.9 Hz), 5.54 (1H, t, J=5.9 Hz), 7.13 (1H, d, J=8.7 Hz), 7.33 (1H, d, J=9.0 Hz), 7.50-7.61 (4H, m), 7.79 (1H, s), 7.82-7.88 (1H, m), 8.19 (1H, d, J=8.7 Hz), 10.32 (1H, s), 12.13 (1H, br s).

Example C18

Production of N-[5-(5-{[3-(1-cyanocyclopropyl)benzoyl]amino}-2-methylphenoxy)[1,3]thiazolo[5,4-b]pyridin-2-yl]-1,3-oxazole-4-carboxamide

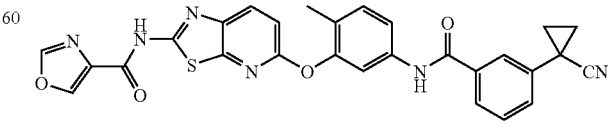

In the same manner as in Example C10, the title compound (79.3 mg, 32%) was obtained as a white powder using 1,3- oxazole-4-carboxylic acid (128 mg, 1.13 mmol), oxalyl chloride (118 μL, 1.35 mmol), tetrahydrofuran (5 mL), N,N-dimethylformamide (20 μL), N-{3-[(2-amino[1,3]thiazolo[5,4-b]pyridin-5-yl)oxy]-4-methylphenyl}-3-(1-cyanocyclopropyl)benzamide (200 mg, 0.452 mmol) and pyridine (5 mL) as starting materials. The title compound was purified by silica gel column chromatography (ethyl acetate/hexane=5/95→60/40), and precipitated with tetrahydrofuran.

$^1$H-NMR (DMSO-d$_6$, 300 MHz) δ 1.57-1.64 (2H, m), 1.77-1.84 (2H, m), 2.11 (3H, s), 7.16 (1H, d, J=8.8 Hz), 7.33 (1H, d, J=9.2 Hz), 7.48-7.62 (4H, m), 7.77-7.81 (1H, m), 7.83-7.89 (1H, m), 8.23 (1H, d, J=8.8 Hz), 8.65 (1H, d, J=0.8 Hz), 9.03 (1H, s), 10.33 (1H, s), 12.75 (1H, s).

Example C19

Production of 3-(1-cyanocyclopropyl)-N-{4-methyl-3-[(2-{[(4-methylpiperazin-1-yl)acetyl]amino}[1,3]thiazolo[5,4-b]pyridin-5-yl)oxy]phenyl}benzamide

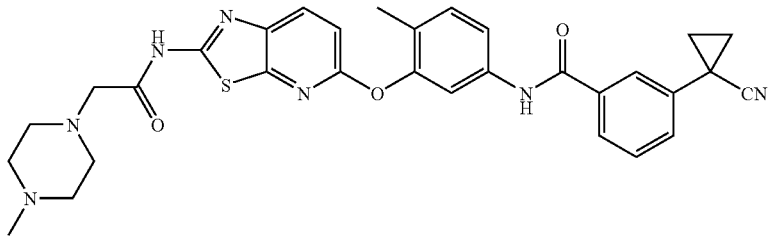 [SMILES: Cc1ccc(NC(=O)c2cccc(C3(C#N)CC3)c2)cc1Oc1ccc2nc(NC(=O)CN3CCN(C)CC3)sc2n1]

(i) Production of N-[3-({2-[(chloroacetyl)amino][1,3]thiazolo[5,4-b]pyridin-5-yl}oxy)-4-methylphenyl]-3-(1-cyanocyclopropyl)benzamide In the same manner as in Example C11(i), the title compound (234 mg, quantitative) was obtained as a colorless oil using N-{3-[(2-amino[1,3]thiazolo[5,4-b]pyridin-5-yl)oxy]-4-methylphenyl}-3-(1-cyanocyclopropyl)benzamide (200 mg, 0.452 mmol) produced in Example C16(iv), chloroacetyl chloride (104 μL, 0.905 mmol) and N,N-dimethylformamide (5 mL) as starting materials. The obtained compound was purified by silica gel column chromatography (ethyl acetate/hexane=5/95→60/40).

$^1$H-NMR (DMSO-d$_6$, 300 MHz) δ 1.58-1.63 (2H, m), 1.77-1.84 (2H, m), 2.11 (3H, s), 4.45 (2H, s), 7.15 (1H, d, J=8.8 Hz), 7.32 (1H, d, J=9.4 Hz), 7.52-7.61 (4H, m), 7.78-7.81 (1H, m), 7.83-7.88 (1H, m), 8.21 (1H, d, J=8.8 Hz), 10.32 (1H, s), 12.77 (1H, s).

(ii) Production of 3-(1-cyanocyclopropyl)-N-{4-methyl-3-[(2-{[(4-methylpiperazin-1-yl)acetyl]amino}[1,3]thiazolo[5,4-b]pyridin-5-yl)oxy]phenyl}benzamide In the same manner as in Example C11(ii), the title compound (98.4 mg, 37%) was obtained as a white powder using N-[3-({2-[(chloroacetyl)amino][1,3]thiazolo[5,4-b]pyridin-5-yl}oxy)-4-methylphenyl]-3-(1-cyanocyclopropyl)benzamide (234 mg), triethylamine (126 μL, 0.905 mmol), 1-methylpiperazine (100 μL, 0.905 mmol) and tetrahydrofuran (5 mL) as starting materials.

$^1$H-NMR (DMSO-d$_5$, 300 MHz) δ 1.43-1.51 (2H, m), 1.73-1.81 (2H, m), 2.20 (3H, s), 2.33 (3H, s), 2.47-2.60 (4H, m), 2.63-2.72 (4H, m), 3.27 (2H, s), 6.98 (1H, d, J=8.8 Hz), 7.24-7.30 (1H, m), 7.36-7.42 (1H, m), 7.42-7.52 (2H, m), 7.52-7.58 (1H, m), 7.68-7.75 (2H, m), 7.84 (1H, s), 8.00 (1H, d, J=8.8 Hz), 10.31 (1H, br s).

Example C20

Production of N-[3-({2-[(cyclopropylcarbonyl)amino][1,3]thiazolo[5,4-b]pyridin-5-yl}oxy)phenyl]-3-(trifluoromethyl)benzamide

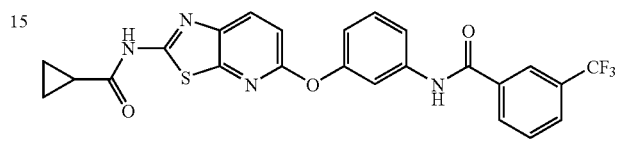

(i) Production of N-(3-hydroxyphenyl)-3-(trifluoromethyl)benzamide

To a solution of 3-aminophenol (11.3 g, 104 mmol) in tetrahydrofuran (250 mL) were added water (250 mL) in which sodium hydrogen carbonate (10.6 g, 126.4 mmol) has been dissolved and 3-(trifluoromethyl)benzoyl chloride (22.4 g, 107 mmol), and the mixture was vigorously stirred at room temperature for 2 hr. The aqueous layer was separated, and the organic layer was diluted with ethyl acetate (150 mL) and washed with saturated brine (150 mL). The combined aqueous layer was extracted with ethyl acetate (150 mL). The combined organic layer was dried over anhydrous magnesium sulfate, the insoluble material was filtered off, and the filtrate was concentrated under reduced pressure. The crude product was recrystallized from ethyl acetate and hexane to give title compound (31.7 g) as pale-brown crystals.

$^1$H-NMR (DMSO-d$_6$, 300 MHz) δ 6.54 (1H, dt, J=6.9, 2.4 Hz), 7.12-7.19 (2H, m), 7.36 (1H, d, J=2.1 Hz), 7.78 (1H, t, J=7.5 Hz), 7.96 (1H, d, J=7.8 Hz), 8.24-8.27 (2H, m), 9.48 (1H, s), 10.36 (1H, br s).

(ii) Production of N-{3-[(5-nitropyridin-2-yl)oxy]phenyl}-3-(trifluoromethyl)benzamide In the same method as in Example C1(v) and using N-(3-hydroxyphenyl)-3-(trifluoromethyl)benzamide (5.00 g, 17.7 mmol), 2-chloro-5-nitropyridine (2.81 g, 17.7 mmol), potassium carbonate (7.37 g, 30.6 mmol) and N,N-dimethylformamide (150 mL) as starting materials, the title compound (5.98 g, 83%) was obtained as a pale-brown powder.

$^1$H-NMR (DMSO-d$_6$, 300 MHz) δ 6.99-7.05 (1H, m), 7.30 (1H, dd, J=0.5, 9.0 Hz), 7.48 (1H, t, J=8.1 Hz), 7.65-7.70 (1H, m), 7.75 (1H, t, J=2.1 Hz), 7.80 (1H, t, J=8.0 Hz), 7.98 (1H, d, J=8.0 Hz), 8.26 (1H, d, J=8.0 Hz), 8.29 (1H, s), 8.65 (1H, dd, J=2.8, 9.0 Hz), 9.06 (1H, dd, J=0.5, 2.8 Hz), 10.63 (1H, s).

(iii) Production of N-{3-[(5-aminopyridin-2-yl)oxy]phenyl}-3-(trifluoromethyl)benzamide In the same manner as in Example C1(vi), the title compound (5.38 g, quantitative) was obtained as a white powder using N-{3-[(5-nitropyridin-2-yl)oxy]phenyl}-3-(trifluoromethyl)benzamide (5.82 g, 14.4 mmol), tetrahydrofuran (100 mL), methanol (50 mL) and 10% palladium-carbon (270 mg) as starting materials. The title compound was washed with a mixed solvent of ethyl acetate and hexane.

$^1$H-NMR (DMSO-d$_6$, 300 MHz) δ 5.15 (2H, s), 6.70-6.77 (1H, m), 6.80 (1H, d, J=8.6 Hz), 7.09 (1H, dd, J=2.8, 8.6 Hz), 7.32 (1H, t, J=8.2 Hz), 7.42 (1H, t, J=2.2 Hz), 7.49-7.55 (1H, m), 7.58 (1H, d, J=2.8 Hz), 7.77 (1H, t, J=7.8 Hz), 7.96 (1H, d, J=7.8 Hz), 8.20-8.28 (2H, m), 10.46 (1H, s).

(iv) Production of N-{3-[(2-amino[1,3]thiazolo[5,4-b]pyridin-5-yl)oxy]phenyl}-3-(trifluoromethyl)benzamide In the same manner as in Example C1(vii), the title compound (5.07 g, 83%) was obtained as a pale-yellow powder using N-{3-[(5-aminopyridin-2-yl)oxy]phenyl}-3-(trifluoromethyl)benzamide (5.30 g, 14.1 mmol), potassium thiocyanate (5.52 g, 56.7 mmol), bromine (3.40 g, 21.2 mmol) and acetic acid (100 mL) as starting materials. The title compound was washed with a mixed solvent of ethyl acetate and hexane, and used for the next reaction without further purification operation.

$^1$H-NMR (DMSO-d$_6$, 300 MHz) δ 6.84-6.89 (1H, m), 6.94 (1H, d, J=8.5 Hz), 7.39 (1H, t, J=8.1 Hz), 7.55 (1H, t, J=2.2 Hz), 7.59-7.66 (3H, m), 7.71-7.82 (2H, m), 7.97 (1H, d, J=7.7 Hz), 8.21-8.28 (2H, m), 10.52 (1H, s).

(v) Production of N-[3-({2-[(cyclopropylcarbonyl)amino][1,3]thiazolo[5,4-b]pyridin-5-yl}oxy)phenyl]-3-(trifluoromethyl)benzamide In the same manner as in Example C1(viii), the title compound (208 mg, 87%) was obtained as colorless crystals using N-{3-[(2-amino[1,3]thiazolo[5,4-b]pyridin-5-yl)oxy]phenyl}-3-(trifluoromethyl)benzamide (207 mg, 481 μmol), pyridine (5 mL), N,N-dimethylpyridine-4-amine (10.3 mg, 84.3 μmol) and cyclopropanecarbonyl chloride (200 μL, 2.20 mmol) as starting materials. The present compound was recrystallized from ethyl acetate-diisopropyl ether.

$^1$H-NMR (DMSO-d$_6$, 300 MHz) δ 0.91-0.98 (4H, m), 1.96-2.02 (1H, m), 6.95 (1H, ddd, J=0.9, 2.1, 8.1 Hz), 7.16 (1H, d, J=8.7 Hz), 7.44 (1H, t, J=8.7 Hz), 7.64-7.67 (2H, m), 7.78 (1H, t, J=7.8 Hz), 7.97 (1H, d, J=7.8 Hz), 8.19 (1H, d, J=8.7 Hz), 8.23-8.28 (2H, m), 10.56 (1H, br s), 12.71 (1H, br s).

Example C21

Production of N-(3-{[2-(glycoloylamino)[1,3]thiazolo[5,4-b]pyridin-5-yl]oxy}phenyl)-3-(trifluoromethyl)benzamide

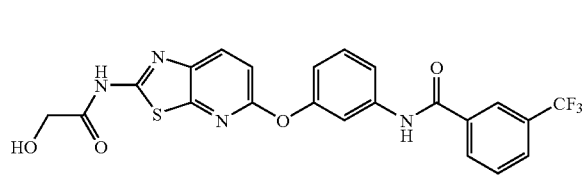 [SMILES: O=C(CO)Nc1nc2ccc(Oc3cccc(NC(=O)c4cccc(C(F)(F)F)c4)c3)nc2s1]

In the same manner as in Example C9, the title compound (119 mg, 52%) was obtained as a white powder using N-{3-[(2-amino[1,3]thiazolo[5,4-b]pyridin-5-yl)oxy]phenyl}-3-(trifluoromethyl)benzamide (200 mg, 0.464 mmol) produced in Example C20(iv), pyridine (5 mL+2 mL), acetoxyacetyl chloride (100 μL, 0.929 mmol), methanol (2 mL) and 0.5N aqueous sodium hydroxide solution (2 mL) as starting materials. The title compound was precipitated with ethyl acetate.

$^1$H-NMR (DMSO-d$_6$, 300 MHz) δ 4.15-4.22 (2H, m), 5.53 (1H, br s), 6.93-6.98 (1H, m), 7.17 (1H, d, J=8.7 Hz), 7.44 (1H, t, J=8.4 Hz), 7.63-7.68 (2H, m), 7.78 (1H, t, J=7.8 Hz), 7.97 (1H, d, J=7.8 Hz), 8.20 (1H, d, J=8.7 Hz), 8.22-8.29 (2H, m), 10.57 (1H, s), 12.15 (1H, br s).

Example C22

Production of N-{3-[(2-{[(4-methylpiperazin-1-yl)acetyl]amino}[1,3]thiazolo[5,4-b]pyridin-5-yl)oxy]phenyl}-3-(trifluoromethyl)benzamide

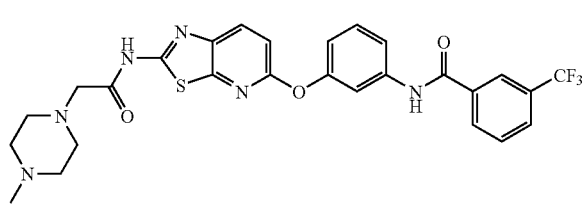 [SMILES: CN1CCN(CC(=O)Nc2nc3ccc(Oc4cccc(NC(=O)c5cccc(C(F)(F)F)c5)c4)nc3s2)CC1]

(i) Production of N-[3-({2-[(chloroacetyl)amino][1,3]thiazolo[5,4-b]pyridin-5-yl}oxy)phenyl]-3-(trifluoromethyl)benzamide In the same manner as in Example C11(i), the title compound (262 mg) was obtained as a white powder using N-{3-[(2-amino[1,3]thiazolo[5,4-b]pyridin-5-yl)oxy]phenyl}-3-(trifluoromethyl)benzamide (200 mg, 0.464 mmol) produced in Example C20(iv), chloroacetyl chloride (107 μL, 0.929 mmol) and N,N-dimethylformamide (5 mL) as starting materials. The obtained compound was purified by silica gel column chromatography (ethyl acetate/hexane=5/95→70/30).

$^1$H-NMR (DMSO-d$_6$, 300 MHz) δ 4.47 (2H, s), 6.93-7.00 (1H, m), 7.19 (1H, d, J=8.9 Hz), 7.45 (1H, t, J=8.3 Hz), 7.62-7.69 (2H, m), 7.79 (1H, t, J=7.8 Hz), 7.92-8.00 (1H, m), 8.21-8.30 (3H, m), 10.57 (1H, s), 12.80 (1H, s).

(ii) Production of N-{3-[(2-{[(4-methylpiperazin-1-yl)acetyl]amino}[1,3]thiazolo[5,4-b]pyridin-5-yl)oxy]phenyl}-3-(trifluoromethyl)benzamide In the same manner as in Example C11(ii), the title compound (165 mg, 62%) was obtained as a white powder using N-[3-({2-[(chloroacetyl)amino][1,3]thiazolo[5,4-b]pyridin-5-yl}oxy)phenyl]-3-(trifluoromethyl)benzamide (262 mg), triethylamine (129 μL, 0.929 mmol), 1-methylpiperazine (104 μL, 0.929 mmol) and tetrahydrofuran (5 mL) as starting materials.

$^1$H-NMR (CDCl$_3$, 300 MHz) δ 2.34 (3H, s), 2.55 (4H, br s), 2.62-2.73 (4H, m), 3.28 (2H, s), 6.98-7.08 (2H, m), 7.38-7.50 (2H, m), 7.58-7.68 (2H, m), 7.82 (1H, d, J=7.9 Hz), 7.87 (1H, s), 8.00-8.08 (2H, m), 8.12 (1H, s), 10.31 (1H, br s).

Example C23

Production of 3-(1-cyano-1-methylethyl)-N-[3-({2-[(cyclopropylcarbonyl)amino][1,3]thiazolo[5,4-b]pyridin-5-yl}oxy)phenyl]benzamide

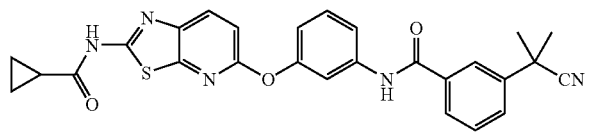 [SMILES: CC(C)(C#N)c1cccc(C(=O)Nc2cccc(Oc3ccc4nc(NC(=O)C5CC5)sc4n3)c2)c1]

(i) Production of 3-(1-cyano-1-methylethyl)-N-(3-hydroxyphenyl)benzamide

In the same manner as in Example C12(i), the title compound (13.0 g, 96%) was obtained as a white powder using 3-(1-cyano-1-methylethyl)benzoic acid (10.0 g, 52.8 mmol) produced in Example C6(ii), tetrahydrofuran (200 mL), N,N-dimethylformamide (80 μL), oxalyl chloride (6.28 mL, 72.0 mmol), 3-aminophenol (5.24 g, 48.0 mmol), sodium hydrogen carbonate (6.05 g, 72.0 mmol) and water (60 mL) as starting materials. The title compound was washed with a mixed solvent of ethyl acetate and hexane, and used for the next reaction without further purification operation.

$^1$H-NMR (DMSO-d$_6$, 300 MHz) δ 1.75 (6H, s), 6.49-6.55 (1H, m), 7.08-7.18 (2H, m), 7.30-7.34 (1H, m), 7.59 (1H, t, J=7.8 Hz), 7.72-7.77 (1H, m), 7.88-7.93 (1H, m), 8.01 (1H, t, J=1.7 Hz), 9.43 (1H, s), 10.18 (1H, s).

(ii) Production of 3-(1-cyano-1-methylethyl)-N-{3-[(5-nitropyridin-2-yl)oxy]phenyl}benzamide In the same method as in Example C1(v), the title compound (5.07 g, 95%) was obtained as a pale-brown powder using 3-(1-cyano-1-methylethyl)-N-(3-hydroxyphenyl)benzamide (4 g, 14.2 mmol), 2-chloro-5-nitropyridine (2.26 g, 14.2 mmol), potassium carbonate (5.91 g, 42.8 mmol) and N,N-dimethylformamide (100 mL) as starting materials. The title compound was washed with a mixed solvent of ethyl acetate and hexane.

$^1$H-NMR (DMSO-d$_6$, 300 MHz) δ 1.75 (6H, s), 7.00 (1H, d, J=7.8 Hz), 7.30 (1H, d, J=9.1 Hz), 7.47 (1H, t, J=7.8 Hz), 7.56-7.70 (2H, m), 7.70-7.80 (2H, m), 7.93 (1H, d, J=7.7 Hz), 8.02 (1H, s), 8.64 (1H, d, J=9.1 Hz), 9.06 (1H, s), 10.48 (1H, s).

(iii) Production of N-{3-[(5-aminopyridin-2-yl)oxy]phenyl}-3-(1-cyano-1-methylethyl)benzamide In the same manner as in Example C1(vi), a mixture (4.60 g) containing the title compound was obtained using 3-(1-cyano-1-methylethyl)-N-13-[(5-nitropyridin-2-yl)oxy]phenyl}benzamide (5.07 g, 12.5 mmol), tetrahydrofuran (100 mL), methanol (50 mL) and 10% palladium-carbon (190 mg) as starting materials. Next, to a solution of sodium hydrosulfite (4.32 g, 24.8 mmol) in water (30 mL) was added dropwise a mixed solution of the above-mentioned mixture (1.00 g) in tetrahydrofuran (30 mL) and ethanol (30 mL) with heating under reflux, and the mixture was stirred with heating under reflux for 1.5 hr. After cooling to room temperature, ethyl acetate was added to the reaction mixture, and the mixture was washed with saturated aqueous sodium hydrogen carbonate solution and saturated brine. The obtained organic layer was dried over anhydrous sodium sulfate, and filtrated. The filtrate was concentrated under reduced pressure, and the residue was washed with a mixed solvent of ethyl acetate and hexane to give the title compound (664 mg) as a pale-yellow powder.

$^1$H-NMR (DMSO-d$_6$, 300 MHz) δ 1.74 (6H, s), 5.13 (2H, s), 6.69-6.74 (1H, m), 6.79 (1H, d, J=8.7 Hz), 7.09 (1H, dd, J=2.9, 8.7 Hz), 7.31 (1H, t, J=8.1 Hz), 7.42 (1H, t, J=2.1 Hz), 7.47-7.53 (1H, m), 7.55-7.62 (2H, m), 7.72-7.77 (1H, m), 7.88-7.93 (1H, m), 8.00 (1H, t, J=1.6 Hz), 10.31 (1H, s).

(iv) Production of N-{3-[(2-amino[1,3]thiazolo[5,4-b]pyridin-5-yl)oxy]phenyl}-3-(1-cyano-1-methylethyl)benzamide In the same manner as in Example C1(vii), the title compound (359 mg, 59%) was obtained as a pale-yellow powder using N-{3-[(5-aminopyridin-2-yl)oxy]phenyl}-3-(1-cyano-1-methylethyl)benzamide (560 mg, 1.50 mmol), potassium thiocyanate (584 mg, 6.01 mmol), bromine (360 mg, 2.25 mmol) and acetic acid (9 mL) as starting materials. The title compound was purified by basic silica gel column chromatography (ethyl acetate/hexane=50/50→100/0) and washed with diethyl ether.

$^1$H-NMR (DMSO-d$_6$, 300 MHz) δ 1.74 (6H, s), 6.82-6.88 (1H, m), 6.94 (1H, d, J=8.7 Hz), 7.38 (1H, t, J=8.1 Hz), 7.52-7.66 (5H, m), 7.71-7.78 (2H, m), 7.88-7.94 (1H, m), 8.01 (1H, t, J=1.7 Hz), 10.37 (1H, s).

(v) Production of 3-(1-cyano-1-methylethyl)-N-[3-({2-[(cyclopropylcarbonyl)amino][1,3]thiazolo[5,4-b]pyridin-5-yl}oxy)phenyl]benzamide In the same manner as in Example C1(viii), the title compound (58.2 mg, 48%) was obtained as colorless crystals using N-{3-[(2-amino[1,3]thiazolo[5,4-b]pyridin-5-yl)oxy]phenyl}-3-(1-cyano-1-methylethyl)benzamide (104 mg, 242 μmol), pyridine (3 mL), N,N-dimethylpyridine-4-amine (51.2 mg, 419 μmol) and cyclopropanecarbonyl chloride (200 μL, 2.20 mmol) as starting materials. The present compound was recrystallized from ethyl acetate-diisopropyl ether.

$^1$H-NMR (DMSO-d$_6$, 300 MHz) δ 0.94-0.97 (4H, m), 1.74 (6H, s), 1.95-2.04 (1H, m), 6.93 (1H, ddd, J=0.9, 2.4, 8.1 Hz), 7.15 (1H, d, J=8.1 Hz), 7.43 (1H, t, J=8.4 Hz), 7.57-7.65 (3H,

Example C24

Production of 3-(1-cyano-1-methylethyl)-N-(3-{[2-(glycoloylamino)[1,3]thiazolo[5,4-b]pyridin-5-yl]oxy}phenyl)benzamide

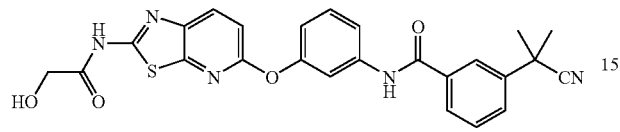

In the same manner as in Example C9, the title compound (79.7 mg, 35%) was obtained as a white powder using N-{3-[(2-amino[1,3]thiazolo[5,4-b]pyridin-5-yl)oxy]phenyl}-3-(1-cyano-1-methylethyl)benzamide (200 mg, 0.465 mmol) produced in Example C23(iv), pyridine (5 mL), acetoxyacetyl chloride (100 μL, 0.931 mmol), methanol (2 mL) and 0.5N aqueous sodium hydroxide solution (2 mL) as starting materials. The title compound was purified by reverse phase silica gel column chromatography (containing 0.1% TFA, water/acetonitrile=95/5→5/95), and fractions containing the object product was concentrated. The obtained trifluoroacetate was suspended in ethyl acetate, and the suspension was washed with saturated aqueous sodium hydrogen carbonate solution and saturated brine. The obtained organic layer was dried over anhydrous magnesium sulfate, and filtrated. The solvent was evaporated under reduced pressure, and the reside was precipitated with ethyl acetate.

$^1$H-NMR (DMSO-d$_6$, 300 MHz) δ 1.57-1.64 (2H, m), 1.77-1.84 (2H, m), 2.11 (3H, s), 4.18 (2H, d, J=5.9 Hz), 5.54 (1H, t, J=5.9 Hz), 7.13 (1H, d, J=8.7 Hz), 7.33 (1H, d, J=9.0 Hz), 7.50-7.61 (4H, m), 7.79 (1H, s), 7.82-7.88 (1H, m), 8.19 (1H, d, J=8.7 Hz), 10.32 (1H, s), 12.13 (1H, br s).

Example C25

Production of 3-(1-cyano-1-methylethyl)-N-{3-[(2-{[(4-methylpiperazin-1-yl)acetyl]amino}[1,3]thiazolo[5,4-b]pyridin-5-yl)oxy]phenyl}benzamide

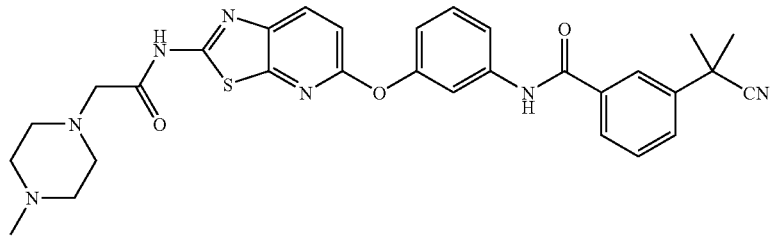 [SMILES: CN1CCN(CC(=O)Nc2nc3ccc(Oc4cccc(NC(=O)c5cccc(C(C)(C)C#N)c5)c4)nc3s2)CC1]

(i) Production of N-[3-({2-[(chloroacetyl)amino][1,3]thiazolo[5,4-b]pyridin-5-yl}oxy)phenyl]-3-(1-cyano-1-methylethyl)benzamide In the same manner as in Example C11(i), the title compound (235 mg, quantitative) was obtained as a yellow oil using N-{3-[(2-amino[1,3]thiazolo[5,4-b]pyridin-5-yl)oxy]phenyl}-3-(1-cyano-1-methylethyl)benzamide (200 mg, 0.465 mmol) produced in Example C23(iv), chloroacetyl chloride (107 μL, 0.931 mmol) and N,N-dimethylformamide (5 mL) as starting materials. The obtained compound was purified by silica gel column chromatography (ethyl acetate/hexane=0/100→70/30).

$^1$H-NMR (DMSO-d$_6$, 300 MHz) δ 1.74 (6H, s), 4.47 (2H, s), 6.95 (1H, dd, J=1.5, 8.1 Hz), 7.19 (1H, d, J=8.8 Hz), 7.44 (1H, t, J=8.1 Hz), 7.56-7.68 (3H, m), 7.72-7.78 (1H, m), 7.90-7.95 (1H, m), 8.02 (1H, t, J=1.5 Hz), 8.23 (1H, d, J=8.8 Hz), 10.42 (1H, s), 12.80 (1H, br s).

(ii) Production of 3-(1-cyano-1-methylethyl)-N-{3-[(2-{[(4-methylpiperazin-1-yl)acetyl]amino}[1,3]thiazolo[5,4-b]pyridin-5-yl)oxy]phenyl}benzamide In the same manner as in Example C11(ii), the title compound (142 mg, 54%) was obtained as a white powder using N-[3-({2-[(chloroacetyl)amino][1,3]thiazolo[5,4-b]pyridin-5-yl}oxy)phenyl]-3-(1-cyano-1-methylethyl)benzamide (235 mg), triethylamine (130 μL, 0.931 mmol), 1-methylpiperazine (104 μL, 0.931 mmol) and tetrahydrofuran (5 mL) as starting materials. The title compound was precipitated with ethyl acetate.

$^1$H-NMR (CDCl$_3$, 300 MHz) δ 1.77 (6H, s), 2.33 (3H, s), 2.47-2.61 (4H, m), 2.64-2.72 (4H, m), 3.28 (2H, s), 6.96-7.02 (1H, m), 7.03 (1H, d, J=8.7 Hz), 7.37-7.48 (2H, m), 7.51 (1H, t, J=7.8 Hz), 7.61 (1H, t, J=2.0 Hz), 7.67-7.73 (1H, m), 7.74-7.79 (1H, m), 7.90-7.98 (2H, m), 8.01 (1H, d, J=8.7 Hz), 10.36 (1H, br s).

Example C26

Production of 3-(1-cyanocyclopropyl)-N-[3-({2-[(cyclopropylcarbonyl)amino][1,3]thiazolo[5,4-b]pyridin-5-yl}oxy)phenyl]benzamide

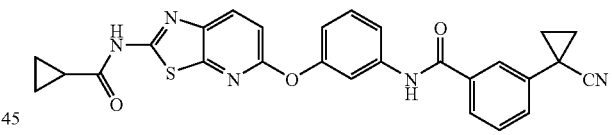

(i) Production of 3-(1-cyanocyclopropyl)-N-(3-hydroxyphenyl)benzamide

In the same method as in Example C1(iv) except that ethyl acetate and diisopropyl ether were used as a recrystallization solvent, the title compound (28.0 g, 100%) was obtained as colorless crystals using 3-(1-cyanocyclopropyl)benzoic acid (18.9 g, 101 mmol) produced in Example C1(iii), toluene (350 thionyl chloride (50.0 g, 420 mmol), 3-aminophenol (11.8 g, 108 mmol), tetrahydrofuran (400 mL), sodium hydrogen carbonate (9.20 g, 110 mmol), and water (300 mL) as starting materials.

$^1$-NMR (DMSO-$d_6$, 300 MHz) δ 1.60-1.65 (2H, m), 1.80-1.84 (2H, m), 6.52 (1H, dt, J=6.6, 2.4 Hz), 7.09-7.14 (2H, m), 7.32-7.33 (1H, m), 7.54-7.56 (2H, m), 7.80 (1H, s), 7.84-7.88 (1H, m), 9.43 (1H, s), 10.16 (1H, br s).

(ii) Production of 3-(1-cyanocyclopropyl)-N-{3-[(5-nitropyridin-2-yl)oxy]phenyl}benzamide In the same method as in Example C1(v), the title compound (6.27 g, 87%) was obtained as a pale-brown powder using 3-(1-cyanocyclopropyl)-N-(3-hydroxyphenyl)benzamide (5.00 g, 17.9 mmol), 2-chloro-5-nitropyridine (2.85 g, 17.9 mmol), potassium carbonate (7.45 g, 53.8 mmol) and N,N-dimethylformamide (150 mL) as starting materials. The title compound was washed with a mixed solvent of ethyl acetate and hexane.

$^1$H-NMR (DMSO-$d_6$, 300 MHz) δ 1.58-1.65 (2H, m), 1.78-1.85 (2H, m), 6.96-7.03 (1H, m), 7.29 (1H, dd, J=0.5, 9.0 Hz), 7.47 (1H, t, J=8.1 Hz), 7.52-7.60 (2H, m), 7.63-7.69 (1H, m), 7.74 (1H, t, J=2.2 Hz), 7.81-7.84 (1H, m), 7.85-7.90 (1H, m), 8.65 (1H, dd, J=2.8, 9.0 Hz), 9.06 (1H, dd, J=0.5, 2.8 Hz), 10.46 (1H, s).

(iii) Production of N-{3-[(5-aminopyridin-2-yl)oxy]-4-methylphenyl}-3-(1-cyanocyclopropyl)benzamide In the same manner as in Example C1(vi), the title compound (5.71 g, quantitative) was obtained as a pale-brown powder using 3-(1-cyanocyclopropyl)-N-{3-[(5-nitropyridin-2-yl)oxy]phenyl}benzamide (6.18 g, 15.4 mmol), tetrahydrofuran (100 mL), methanol (50 mL) and 10% palladium-carbon (330 mg) as starting materials. The title compound was washed with a mixed solvent of ethyl acetate and hexane, and used for the next reaction without further purification operation.

$^1$H-NMR (DMSO-$d_6$, 300 MHz) δ 1.57-1.65 (2H, m), 1.76-1.85 (2H, m), 5.14 (2H, s), 6.68-6.74 (1H, m), 6.80 (1H, d, J=8.7 Hz), 7.09 (1H, dd, J=2.9, 8.7 Hz), 7.30 (1H, t, J=8.1 Hz), 7.42 (1H, t, J=2.2 Hz), 7.46-7.61 (4H, m), 7.77-7.81 (1H, m), 7.83-7.89 (1H, m), 10.30 (1H, s).

(iv) Production of N-{3-[(2-amino[1,3]thiazolo[5,4-b]pyridin-5-yl)oxy]phenyl}-3-(1-cyanocyclopropyl)benzamide In the same manner as in Example C1(vii), the title compound (4.74 g, 72%) was obtained as a pale-yellow powder using N-{3-[(5-aminopyridin-2-yl)oxy]-4-methylphenyl}-3-(1-cyanocyclopropyl)benzamide (5.70 g, 15.3 mmol), potassium thiocyanate (5.98 g, 61.5 mmol), bromine (3.68 g, 23.0 mmol) and acetic acid (100 mL) as starting materials. The title compound was washed with a mixed solvent of ethyl acetate and hexane, and used for the next reaction without further purification operation.

$^1$H-NMR (DMSO-$d_6$, 300 MHz) δ 1.58-1.65 (2H, m), 1.77-1.85 (2H, m), 6.82-6.87 (1H, m), 6.94 (1H, d, J=8.7 Hz), 7.38 (1H, t, J=8.1 Hz), 7.51-7.66 (6H, m), 7.73 (1H, d, J=8.7 Hz), 7.80 (1H, s), 7.83-7.89 (1H, m), 10.35 (1H, s).

(v) Production of 3-(1-cyanocyclopropyl)-N-[3-({2-[(cyclopropylcarbonyl)amino][1,3]thiazolo[5,4-b]pyridin-5-yl}oxy)phenyl]benzamide In the same manner as in Example C1(viii), the title compound (116 mg, 94%) was obtained as colorless crystals using N-{3-[(2-amino[1,3]thiazolo[5,4-b]pyridin-5-yl)oxy]phenyl}-3-(1-cyanocyclopropyl)benzamide (106 mg, 248 μmol), pyridine (3 mL), N,N-dimethylpyridine-4-amine (15.2 mg, 124 μmol) and cyclopropanecarbonyl chloride (200 μL, 2.20 mmol) as starting materials. The present compound was recrystallized from ethyl acetate-diisopropyl ether.

$^1$H-NMR (DMSO-$d_6$, 300 MHz) δ 0.94-0.97 (4H, m), 1.61 (2H, dd, J=5.4, 8.4 Hz), 1.81 (2H, dd, J=5.4, 8.4 Hz), 1.97-2.01 (1H, m), 6.91-6.95 (1H, m), 7.15 (1H, d, J=8.7 Hz), 7.42 (1H, t, J=8.4 Hz), 7.52-7.59 (2H, m), 7.62-7.64 (2H, m), 7.81 (1H, br s), 7.86 (1H, dt, J=6.0, 2.4 Hz), 8.18 (1H, d, J=8.7 Hz), 10.40 (1H, br s), 12.70 (1H, br s).

Example C27

Production of 3-(1-cyanocyclopropyl)-N-(3-{[2-(glycoloylamino)[1,3]thiazolo[5,4-b]pyridin-5-yl]oxy}phenyl)benzamide

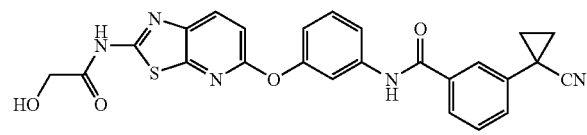 [SMILES: N#CC1(c2cccc(C(=O)Nc3cccc(Oc4ccc5nc(NC(=O)CO)sc5n4)c3)c2)CC1]

In the same manner as in Example C9, the title compound (125 mg, 55%) was obtained as a pale-yellow powder using N-{3-[(2-amino[1,3]thiazolo[5,4-b]pyridin-5-yl)oxy]phenyl}-3-(1-cyanocyclopropyl)benzamide (200 mg, 0.467 mmol) produced in Example C26(iv), acetoxyacetyl chloride (100 μL, 0.935 mmol), pyridine (7 mL), methanol (2 mL) and 0.5N aqueous sodium hydroxide solution (2 mL) as starting materials. The title compound was precipitated with ethyl acetate.

$^1$H-NMR (DMSO-$d_6$, 300 MHz) δ 1.58-1.64 (2H, m), 1.78-1.84 (2H, m), 4.19 (2H, d, J=5.9 Hz), 5.55 (1H, t, J=5.9 Hz), 6.91-6.97 (1H, m), 7.16 (1H, d, J=8.7 Hz), 7.43 (1H, t, J=8.2 Hz), 7.51-7.60 (2H, m), 7.61-7.67 (2H, m), 7.81 (1H, s), 7.84-7.90 (1H, m), 8.20 (1H, d, J=8.7 Hz), 10.40 (1H, s), 12.15 (1H, br s).

Example C28

Production of 3-(1-cyanocyclopropyl)-N-{3-[(2-{[(4-methylpiperazin-1-yl)acetyl]amino}[1,3]thiazolo[5,4-b]pyridin-5-yl)oxy]phenyl}benzamide

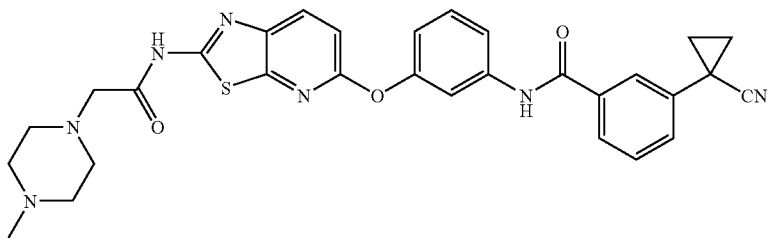 [SMILES: CN1CCN(CC(=O)Nc2nc3ccc(Oc4cccc(NC(=O)c5cccc(C6(C#N)CC6)c5)c4)nc3s2)CC1]

(i) Production of N-[3-({2-[(chloroacetyl)amino][1,3]thiazolo[5,4-b]pyridin-5-yl}oxy)phenyl]-3-(1-cyanocyclopropyl)benzamide In the same manner as in Example C11(i), the title compound (272 mg) was obtained as a yellow oil using N-{3-[(2-amino[1,3]thiazolo[5,4-b]pyridin-5-yl)oxy]phenyl}-3-(1-cyanocyclopropyl)benzamide (200 mg, 0.467 mmol) produced in Example C26(iv), chloroacetyl chloride (108 μL, 0.935 mmol) and N,N-dimethylformamide (5 mL) as starting materials. The obtained compound was purified by silica gel column chromatography (ethyl acetate/hexane=0/100→70/30).

$^1$H-NMR (DMSO-d$_6$, 300 MHz) δ 1.58-1.65 (2H, m), 1.78-1.85 (2H, m), 4.47 (2H, s), 6.92-6.98 (1H, m), 7.18 (1H, d, J=8.7 Hz), 7.43 (1H, t, J=8.1 Hz), 7.51-7.60 (2H, m), 7.60-7.68 (2H, m), 7.79-7.83 (1H, m), 7.84-7.90 (1H, m), 8.23 (1H, d, J=8.7 Hz), 10.40 (1H, s), 12.80 (1H, s).

(ii) Production of 3-(1-cyanocyclopropyl)-N-{3-[(2-{[(4-methylpiperazin-1-yl)acetyl]amino}[1,3]thiazolo[5,4-b]pyridin-5-yl)oxy]phenyl}benzamide In the same manner as in Example C11(ii), the title compound (124 mg, 47%) was obtained as a white powder using N-[3-({2-[(chloroacetyl)amino][1,3]thiazolo[5,4-b]pyridin-5-yl}oxy)phenyl]-3-(1-cyanocyclopropyl)benzamide (272 mg), triethylamine (130 μL, 0.935 mmol), 1-methylpiperazine (104 μL, 0.935 mmol) and tetrahydrofuran (5 mL) as starting materials. The title compound was precipitated with ethyl acetate.

$^1$H-NMR (CDCl$_3$, 300 MHz) δ 1.45-1.52 (2H, m), 1.75-1.83 (2H, m), 2.34 (3H, s), 2.55 (4H, br s), 2.63-2.73 (4H, m), 3.28 (2H, s), 6.96-7.07 (2H, m), 7.37-7.52 (3H, m), 7.54-7.62 (2H, m), 7.70-7.76 (2H, m), 7.89 (1H, s), 8.02 (1H, d, J=8.9 Hz), 10.38 (1H, br s).

Example C29

Production of 3-(1-cyanocyclopropyl)-N-[5-({2-[(cyclopropylcarbonyl)amino][1,3]thiazolo[5,4-b]pyridin-5-yl}oxy)-2-methylphenyl]benzamide

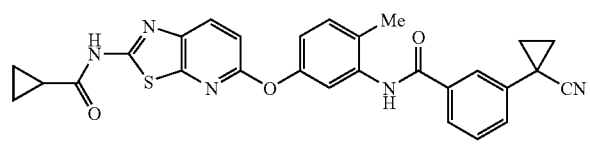 [SMILES: Cc1ccc(Oc2ccc3nc(NC(=O)C4CC4)sc3n2)cc1NC(=O)c1cccc(C2(C#N)CC2)c1]

(i) Production of 3-(1-cyanocyclopropyl)-N-(5-hydroxy-2-methylphenyl)benzamide

To a solution of 3-(1-cyanocyclopropyl)benzoic acid (10 g, 53.4 mmol) produced in Example C1(iii) in tetrahydrofuran (130 mL) were added oxalyl chloride (5.47 mL, 64.1 mmol) and N,N-dimethylformamide (40 μL), and the mixture was stirred at room temperature for 3 hr. The reaction mixture was concentrated under reduced pressure to give 3-(1-cyanocyclopropyl)benzoyl chloride as a colorless oil.

To a two-layer solution of 3-amino-4-methylphenol (5.92 g, 48.0 mmol) in tetrahydrofuran (40 mL)/1N aqueous sodium hydrogen carbonate solution (54 mL) was added a solution of 3-(1-cyanocyclopropyl)benzoyl chloride synthesized above in tetrahydrofuran (20 mL), and the mixture was stirred at room temperature for 2 hr. Since the pH of the reaction mixture was 4-5, sodium hydrogen carbonate (900 mg, 10.7 mmol) was added to the mixture to adjust the pH to 8-9, and the reaction mixture was further stirred at room temperature for 1 hr. The aqueous layer was separated, and extracted with ethyl acetate (150 mL). The combined organic layer was washed with saturated brine (150 mL), and dried over anhydrous sodium sulfate. The insoluble material was filtered off, and the filtrate was concentrated under reduced pressure. Ethyl acetate (25 mL)/hexane (50 mL) was added to the obtained suspension, and the mixture was stirred at room temperature for 20 min. The precipitate was collected by filtration, washed repeatedly with diisopropyl ether/hexane (1:1), and air-dried to give the title compound (12.2 g, 87%) as a pale-yellow powder.

¹H-NMR (DMSO-d₆, 300 MHz) δ 1.56-1.67 (2H, m), 1.76-1.89 (2H, m), 2.10 (3H, s), 6.59 (1H, dd, J=2.4, 8.1 Hz), 6.80 (1H, d, J=2.4 Hz), 7.04 (1H, d, J=8.1 Hz), 7.45-7.64 (2H, m), 7.80-8.00 (2H, m), 9.26 (1H, s), 9.81 (1H, br s).

(ii) Production of 3-(1-cyanocyclopropyl)-N-{2-methyl-5-[(5-nitropyridin-2-yl)oxy]phenyl}benzamide To a solution of 2-chloro-5-nitropyridine (3.25 g, 20.5 mmol) and 3-(1-cyanocyclopropyl)-N-(5-hydroxy-2-methylphenyl)benzamide (6.0 g, 20.5 mmol) in N,N-dimethylformamide (50 mL) was added potassium carbonate (7.08 g, 51.3 mmol), and the mixture was stirred at 60° C. for 12 hr. The reaction mixture was cooled to room temperature, and concentrated under reduced pressure. The obtained residue was diluted with ethyl acetate (300 mL), washed with water (300 mL), 5% aqueous sodium hydrogen carbonate solution (200 mL) and saturated brine (200 mL), and dried over anhydrous sodium sulfate. The insoluble material was filtered off, and the filtrate was concentrated under reduced pressure. The obtained residue was purified by silica gel column chromatography (hexane/ethyl acetate=80/20→30/70). The obtained solution was concentrated under reduced pressure to give the title compound (8.8 g, quantitative) as a yellow oil.

¹H-NMR (DMSO-d₆, 300 MHz) δ 1.54-1.66 (2H, m), 1.78-1.90 (2H, m), 2.28 (3H, s), 7.07 (1H, dd, J=2.4, 8.4 Hz), 7.20-7.32 (2H, m), 7.38 (1H, d, J=8.4 Hz), 7.49-7.63 (2H, m), 7.79-7.99 (2H, m), 8.63 (1H, dd, J=2.7, 9.0 Hz), 9.03 (1H, d, J=2.7 Hz), 10.04 (1H, s).

(iii) Production of N-{5-[(5-aminopyridin-2-yl)oxy]-2-methylphenyl}-3-(1-cyanocyclopropyl)benzamide A suspension of 3-(1-cyanocyclopropyl)-N-{2-methyl-5-[(5-nitropyridin-2-yl)oxy]phenyl}benzamide (8.5 g, 20.5 mmol), calcium chloride (5.55 g, 50 mmol) and reduced iron (14.5 g, 260 mmol) in ethanol (500 mL)/water (50 mL) was stirred with heating at 80° C. for 4 hr. After the reaction mixture was cooled to room temperature, the insoluble material was filtered off through a pad filled with celite, and washed with ethanol. The filtrate and washing solution were combined, and concentrated under reduced pressure. The obtained residue was diluted with ethyl acetate (300 mL), washed with 5% aqueous sodium hydrogen carbonate solution (300 mL) and saturated brine (300 mL), and dried over anhydrous sodium sulfate. The insoluble material was filtered off, and the filtrate was concentrated under reduced pressure to give the title compound (6.57 g, 83%) as a green amorphous substance. The amorphous substance was used for the next reaction without further purification.

¹H-NMR (DMSO-d₆, 300 MHz) δ 1.56-1.66 (2H, m), 1.76-1.85 (2H, m), 2.19 (3H, s), 5.11 (2H, s), 6.71-6.84 (2H, m), 6.96 (1H, d, J=2.4 Hz), 7.07 (1H, dd, J=2.4, 8.4 Hz), 7.22 (1H, d, J=8.4 Hz), 7.47-7.63 (3H, m), 7.78-7.96 (2H, m), 9.94 (1H, s).

(iv) Production of N-{5-[(2-amino[1,3]thiazolo[5,4-b]pyridin-5-yl)oxy]-2-methylphenyl}-3-(1-cyanocyclopropyl)benzamide Potassium thiocyanate (506 mg, 5.2 mmol) was suspended in acetic acid (10 mL), and the mixture was stirred at room temperature for 10 min. A solution of N-{5-[(5-aminopyridin-2-yl)oxy]-2-methylphenyl}-3-(1-cyanocyclopropyl)benzamide (500 mg, 1.3 mmol) in acetic acid (10 mL) was added to the obtained solution, and the mixture was further stirred at room temperature for 15 min. A solution of bromine (230 mg, 1.43 mmol) in acetic acid (7.0 mL) was slowly added dropwise to the obtained solution. After the completion of the dropwise addition, the mixture was stirred at room temperature for 4 hr. The yielded yellow insoluble material was filtered off, and washed with acetic acid. The filtrate and washing solution were combined, and concentrated under reduced pressure. The obtained residue was suspended in ethyl acetate (200 mL), and the suspension was washed with 5% aqueous sodium hydrogen carbonate solution (200 mL) and saturated brine (200 mL), and dried over anhydrous sodium sulfate. The insoluble material was filtered off, and the filtrate was concentrated under reduced pressure to give the title compound (350 mg, 61%) as a pale-yellow amorphous substance. The amorphous substance was used for the next reaction without further purification.

¹H-NMR (DMSO-d₆, 300 MHz) δ 1.57-1.66 (2H, m), 1.76-1.87 (2H, m), 2.24 (3H, s), 6.91 (1H, d, J=8.4 Hz), 6.91-6.98 (1H, m), 7.11 (1H, d, J=2.4 Hz), 7.30 (1H, d, J=8.4 Hz), 7.48-7.65 (4H, m), 7.72 (1H, d, J=8.4 Hz), 7.81-7.97 (2H, m), 9.98 (1H, s).

(v) Production of 3-(1-cyanocyclopropyl)-N-[5-({2-[(cyclopropylcarbonyl)amino][1,3]thiazolo[5,4-b]pyridin-5-yl}oxy)-2-methylphenyl]benzamide To a solution of N-{5-[(2-amino[1,3]thiazolo[5,4-b]pyridin-5-yl)oxy]-2-methylphenyl}-3-(1-cyanocyclopropyl)benzamide (47 mg, 0.124 mmol) in pyridine (2.0 mL) was added cyclopropanecarbonyl chloride (25 μL, 0.273 mmol), and the mixture was stirred at room temperature for 2 hr. The reaction mixture was concentrated under reduced pressure, and the residue was dissolved in methanol (1.0 mL)/water (1.0 mL). 1N Aqueous sodium hydroxide solution (1.0 mL) was added, and the mixture was stirred at room temperature for 30 min. The reaction mixture was concentrated under reduced pressure, and the residue was diluted with ethyl acetate (100 mL), washed with water (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=70/30→0/100), and the obtained solution was concentrated under reduced pressure. The residue was triturated with ethyl acetate/hexane to give the title compound (40 mg, 64%) as a colorless powder.

¹H-NMR (DMSO-d₆, 300 MHz) δ 0.88-1.00 (4H, m), 1.53-1.65 (2H, m), 1.75-1.86 (2H, m), 1.93-2.06 (1H, m), 2.26 (3H, s), 7.01 (1H, dd, J=2.4, 8.4 Hz), 7.12 (1H, d, J=8.7 Hz), 7.19 (1H, d, J=2.4 Hz), 7.34 (1H, d, J=8.4 Hz), 7.46-7.64

(2H, m), 7.86 (1H, s), 7.87-7.96 (1H, m), 8.16 (1H, d, J=8.7 Hz), 10.00 (1H, s), 12.68 (1H, br s).

Example C30

Production of N-[5-(3-{[3-(1-cyanocyclopropyl)benzoyl]amino}-4-methylphenoxy)[1,3]thiazolo[5,4-b]pyridin-2-yl]-1,3-oxazole-4-carboxamide

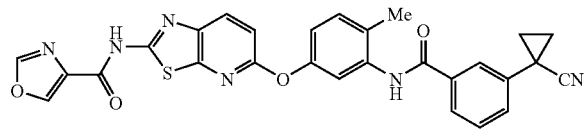 [SMILES: Cc1ccc(Oc2ccc3nc(NC(=O)c4cocn4)sc3n2)cc1NC(=O)c1cccc(C2(C#N)CC2)c1]

To a solution of 1,3-oxazole-4-carboxylic acid (137 mg, 1.22 mmol) in tetrahydrofuran (2.0 mL) were added oxalyl chloride (130 μL, 1.52 mmol) and N,N-dimethylformamide (20 μL), and the mixture was stirred at room temperature for 2 hr. The reaction mixture was concentrated under reduced pressure to give 1,3-oxazole-4-carbonyl chloride as a yellow oil.

1,3-Oxazole-4-carbonyl chloride synthesized above was suspended in pyridine (2.0 mL) at 0° C., N-{5-[(2-amino[1,3]thiazolo[5,4-b]pyridin-5-yl)oxy]-2-methylphenyl}-3-(1-cyanocyclopropyl)benzamide (200 mg, 0.452 mmol) produced in Example C29(iv) was added, and the mixture was stirred at room temperature for 8 hr. The reaction mixture was concentrated under reduced pressure, 1% aqueous citric acid solution (50 mL) was added, and the mixture was extracted with ethyl acetate (100 mL). The organic layer was washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was recrystallized from ethyl acetate/hexane to give the title compound (125 mg, 77%) as a colorless powder.

$^1$H-NMR (DMSO-d$_6$, 300 MHz) δ 1.54-1.67 (2H, m), 1.77-1.88 (2H, m), 2.27 (3H, s), 6.98-7.08 (1H, m), 7.17 (1H, dd, J=1.5, 8.7 Hz), 7.22 (1H, s), 7.36 (1H, d, J=8.4 Hz), 7.50-7.64 (2H, m), 7.81-7.98 (2H, m), 8.23 (1H, dd, J=1.5, 8.7 Hz), 8.66 (1H, d, J=1.2 Hz), 9.04 (1H, d, J=1.2 Hz), 10.03 (1H, s), 12.77 (1H, br s).

Example C31

Production of 3-(1-cyanocyclopropyl)-N-{2-methyl-5-[(2-{[(4-methylpiperazin-1-yl)acetyl]amino}[1,3]thiazolo[5,4-b]pyridin-5-yl)oxy]phenyl}benzamide

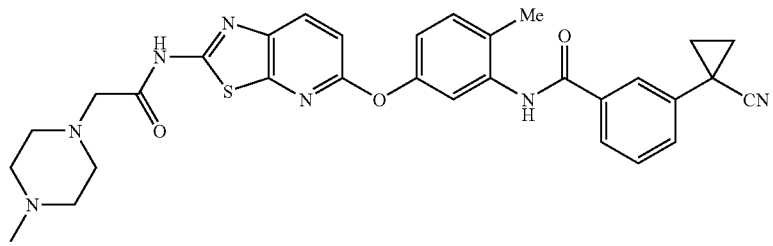 [SMILES: Cc1ccc(Oc2ccc3nc(NC(=O)CN4CCN(C)CC4)sc3n2)cc1NC(=O)c1cccc(C2(C#N)CC2)c1]

To a solution of N-{5-[(2-amino[1,3]thiazolo[5,4-b]pyridin-5-yl)oxy]-2-methylphenyl}-3-(1-cyanocyclopropyl)benzamide (200 mg, 0.453 mmol) produced in Example C29 (iv) in N,N-dimethylformamide (4.0 mL) was added chloroacetyl chloride (54 μL, 0.68 mmol), and the mixture was stirred at room temperature for 2 hr. The reaction mixture was diluted with ethyl acetate (100 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and the obtained solution was concentrated under reduced pressure to give N-[5-({2-[(chloroacetyl)amino][1,3]thiazolo[5,4-b]pyridin-5-yl}oxy)-2-methylphenyl]-3-(1-cyanocyclopropyl)benzamide as a colorless solid.

N-[5-({2-[(Chloroacetyl)amino][1,3]thiazolo[5,4-b]pyridin-5-yl}oxy)-2-methylphenyl]-3-(1-cyanocyclopropyl)benzamide produced above was dissolved in tetrahydrofuran (8.0 mL), triethylamine (155 μL, 1.13 mmol) and 1-methylpiperazine (100 ∞L, 0.902 mmol) were added, and the mixture was stirred at 80° C. for 8 hr. The reaction mixture was cooled to room temperature, diluted with ethyl acetate (100 mL), washed with 5% aqueous sodium hydrogen carbonate solution (100 mL), water (100 mL) and saturated brine (100 mL), and dried over anhydrous sodium sulfate. The insoluble material m was filtered off, and the filtrate was concentrated under reduced pressure. The obtained residue was purified by basic silica gel column chromatography (ethyl acetate/methanol=100/0→80/20), and the obtained solution was concentrated under reduced pressure. The residue was triturated with ethyl acetate/hexane to give the title compound (169 mg, 64%) as a colorless solid.

$^1$H-NMR (DMSO-d$_6$, 300 MHz) δ 1.55-1.66 (2H, m), 1.76-1.86 (2H, m), 2.15 (3H, s), 2.22-2.40 (7H, m), 2.45-2.58 (6H, m), 7.02 (1H, dd, J=8.4, 2.4 Hz), 7.13 (1H, d, J=8.7 Hz), 7.20 (1H, d, J=2.4 Hz), 7.34 (1H, d, J=8.4 Hz), 7.49-7.67 (2H, m), 7.86 (1H, s), 7.87-7.94 (1H, m), 8.17 (1H, d, J=8.7 Hz), 10.00 (1H, s), 12.12 (1H, br s).

Example C32

Production of 3-(1-cyanocyclopropyl)-N-(5-{[2-(glycoloylamino)[1,3]thiazolo[5,4-b]pyridin-5-yl]oxy}-2-methylphenyl)benzamide

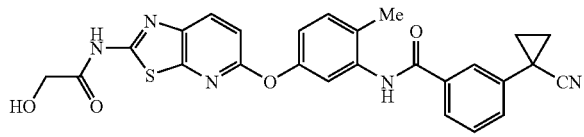 [SMILES: Cc1ccc(Oc2ccc3nc(NC(=O)CO)sc3n2)cc1NC(=O)c1cccc(C2(C#N)CC2)c1]

To a solution of N-{5-[(2-amino[1,3]thiazolo[5,4-b]pyridin-5-yl)oxy]-2-methylphenyl}-3-(1-cyanocyclopropyl)benzamide (200 mg, 0.453 mmol) produced in Example C29 (iv) in pyridine (4.0 mL) was added 2-chloro-2-oxoethyl acetate (73 µL, 0.68 mmol), and the mixture was stirred at room temperature for 2 hr. The reaction mixture was concentrated under reduced pressure, and the residue was diluted with methanol (2.0 mL). 1N Aqueous sodium hydroxide solution (2.0 mL) was added, and the mixture was stirred at room temperature for 1 hr. The reaction mixture was concentrated under reduced pressure, 1N hydrochloric acid was added to neutralize the residue, and the mixture was extracted with ethyl acetate (100 mL). The organic layer was washed with water (100 mL) and saturated brine (100 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→80/20), and the obtained solution was concentrated under reduced pressure. The residue was crystallized from ethyl acetate/tetrahydrofuran/hexane to give the title compound (104 mg, 46%) as a colorless powder.

$^1$H-NMR (DMSO-$d_6$, 300 MHz) δ 1.54-1.66 (2H, m), 1.77-1.86 (2H, m), 2.26 (3H, s), 4.18 (2H, s), 5.52 (1H, br s), 7.02 (1H, dd, J=2.4, 8.4 Hz), 7.13 (1H, d, J=8.7 Hz), 7.20 (1H, d, J=2.4 Hz), 7.34 (1H, d, J=8.4 Hz), 7.45-7.63 (2H, m), 7.86 (1H, s), 7.87-8.03 (1H, m), 8.17 (1H, d, J=8.7 Hz), 10.00 (1H, s), 12.12 (1H, br s).

Example C33

Production of 3-(1-cyano-1-methylethyl)-N-[5-({2-[(cyclopropylcarbonyl)amino][1,3]thiazolo[5,4-b]pyridin-5-yl}oxy)-2-methylphenyl]benzamide

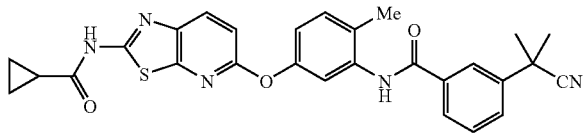 [SMILES: Cc1ccc(Oc2ccc3nc(NC(=O)C4CC4)sc3n2)cc1NC(=O)c1cccc(C(C)(C)C#N)c1]

(i) Production of 3-(1-cyano-1-methylethyl)-N-(5-hydroxy-2-methylphenyl)benzamide To a solution of 3-(1-cyano-1-methylethyl)benzoic acid (5.0 g, 26.4 mmol) produced in Example C6(ii) in tetrahydrofuran (50 mL) were added oxalyl chloride (2.7 mL, 31.7 mmol) and N,N-dimethylformamide (40 µL), and the mixture was stirred at room temperature for 1 hr. The reaction mixture was concentrated under reduced pressure to give 3-(1-cyano-1-methylethyl)benzoyl chloride as a pale-yellow oil.

To a two-layer solution of 3-amino-4-methylphenol (3.25 g, 26.4 mmol) in tetrahydrofuran (20 mL)/1N aqueous sodium hydrogen carbonate solution (39 mL) was added a solution of 3-(1-cyano-1-methylethyl)benzoyl chloride synthesized above in tetrahydrofuran (20 mL), and the mixture was stirred at room temperature for 3 hr. The aqueous layer was separated, and extracted with ethyl acetate (100 mL). The combined organic layer was washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was recrystallized from ethyl acetate (45 mL)/hexane (45 mL) to give the title compound (5.95 g, 77%) as a colorless powder.

$^1$H-NMR (DMSO-$d_6$, 300 MHz) δ 1.75 (6H, s), 2.11 (3H, s), 6.59 (1H, dd, J=2.4, 8.1 Hz), 6.81 (1H, d, J=2.4 Hz), 7.04 (1H, d, J=8.1 Hz), 7.59 (1H, t, J=7.8 Hz), 7.65-7.85 (1H, m), 7.94 (1H, d, J=7.8 Hz), 8.07 (1H, s), 9.27 (1H, s), 9.84 (1H, s).

(ii) Production of 3-(1-cyano-1-methylethyl)-N-{2-methyl-5-[(5-nitropyridin-2-yl)oxy]phenyl}benzamide To a solution of 2-chloro-5-nitropyridine (1.41 g, 8.92 mmol) and 3-(1-cyano-1-methylethyl)-N-(5-hydroxy-2-methylphenyl)benzamide (2.5 g, 8.5 mmol) in N,N-dimethylformamide (20 mL) was added potassium carbonate (1.85 g, 13.3 mmol), and the mixture was stirred at 80° C. for 18 hr. The reaction mixture was cooled to room temperature, the insoluble material was filtered off, and the filtrate was concentrated under reduced pressure. The obtained residue was diluted with ethyl acetate (200 mL), and washed with water (200 mL). The aqueous layer was extracted with ethyl acetate (100 mL), and the combined organic layer was washed with water (200 mL) and saturated brine (200 mL), and dried over anhydrous sodium sulfate. The insoluble material was filtered off, the filtrate was concentrated under reduced pressure, and the obtained residue was purified by silica gel column chromatography (hexane/ethyl acetate=70/30→20/80). The obtained solution was concentrated under reduced pressure to give the title compound (2.68 g, 76%) as a yellow amorphous substance.

$^1$H-NMR (DMSO-$d_6$, 300 MHz) δ 1.74 (6H, s), 2.28 (3H, s), 7.07 (1H, dd, J=2.4, 8.4 Hz), 7.20-7.33 (2H, m), 7.38 (1H, d, J=8.4 Hz), 7.60 (1H, t, J=7.8 Hz), 7.70-7.81 (1H, m), 7.96 (1H, d, J=7.8 Hz), 8.08 (1H, s), 8.63 (1H, dd, J=2.7, 9.1 Hz), 9.03 (1H, d, J=2.7 Hz), 10.05 (1H, s).

(iii) Production of N-{5-[(5-aminopyridin-2-yl)oxy]-2-methylphenyl}-3-(1-cyano-1-methylethyl)benzamide A suspension of 3-(1-cyano-1-methylethyl)-N-{2-methyl-5-[(5-nitropyridin-2-yl)oxy]phenyl}benzamide (2.5 g, 6.0 mmol), calcium chloride (1.75 g, 15 mmol) and reduced iron (4.03 g, 72 mmol) in ethanol (300 mL)/water (30 mL) was stirred with heating at 80° C. for 2 days. After the reaction mixture was cooled to room temperature, the insoluble material was filtered off through a pad filled with celite, and washed with ethanol. The filtrate and washing solution were combined, and concentrated under reduced pressure. The obtained residue was diluted with ethyl acetate (300 mL), washed with 5% aqueous sodium hydrogen carbonate solution (300 mL×2), water (300 mL) and saturated brine (300 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and the obtained solution was concentrated under reduced pressure to give the title compound (2.31 g, 99%) as a pale-yellow amorphous substance.

$^1$H-NMR (DMSO-$d_6$, 300 MHz) δ 1.74 (6H, s), 2.20 (3H, s), 5.10 (2H, s), 6.73-6.86 (2H, m), 6.97 (1H, d, J=2.4 Hz), 7.08 (1H, dd, J=2.7, 8.7 Hz), 7.23 (1H, d, J=8.4 Hz), 7.50-7.66 (2H, m), 7.75 (1H, ddd, J=0.9, 1.8, 7.8 Hz), 7.94 (1H, d, J=7.8 Hz), 8.06 (1H, s), 9.96 (1H, s).

(iv) Production of N-{5-[(2-amino[1,3]thiazolo[5,4-b]pyridin-5-yl)oxy]-2-methylphenyl}-3-(1-cyano-1-methylethyl)benzamide Potassium thiocyanate (2.02 g, 20.8 mmol) was suspended in acetic acid (40 mL), and the mixture was stirred at room temperature for 10 min. A solution of N-{5-[(5-aminopyridin-2-yl)oxy]-2-methylphenyl}-3-(1-cyano-1-methylethyl)benzamide (2.0 g, 5.20 mmol) in acetic acid (40 mL) was added to the obtained solution, and the mixture was further stirred at room temperature for 10 min. A solution of bromine (914 mg, 5.72 mmol) in acetic acid (28 mL) was slowly added dropwise to the obtained solution. After the completion of the dropwise addition, the mixture was stirred at room temperature for 4 hr. The yielded yellow insoluble material was filtered off, and washed with acetic acid. The filtrate and washing solution were combined, and concentrated under reduced pressure. The obtained residue was suspended in ethyl acetate (300 mL), and the suspension was washed with 5% aqueous sodium hydrogen carbonate solution (300 mL), water (300 mL) and saturated brine (300 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the obtained solution was concentrated under reduced pressure to give the title compound (2.20 g, 95%) as a colorless amorphous substance.

$^1$H-NMR (DMSO-$d_6$, 300 MHz) δ 1.74 (6H, s), 2.24 (3H, s), 6.86-6.98 (2H, m), 7.12 (1H, d, J=2.4 Hz), 7.30 (1H, d, J=8.4 Hz), 7.54-7.64 (3H, m), 7.66-7.79 (2H, m), 7.91-7.98 (1H, m), 8.06 (1H, t, J=1.8 Hz), 9.99 (1H, s).

(v) Production of 3-(1-cyano-1-methylethyl)-N-[5-({2-[(cyclopropylcarbonyl)amino][1,3]thiazolo[5,4-b]pyridin-5-yl}oxy)-2-methylphenyl]benzamide To a solution of N-{5-[(2-amino[1,3]thiazolo[5,4-b]pyridin-5-yl)oxy]-2-methylphenyl}-3-(1-cyano-1-methylethyl)benzamide (300 mg, 0.676 mmol) in pyridine (6.0 mL) was added cyclopropanecarbonyl chloride (80 µL, 0.879 mmol), and the mixture was stirred at room temperature for 2 hr. The reaction mixture was concentrated under reduced pressure, and the obtained residue was diluted with ethyl acetate (200 mL), washed with 5% aqueous sodium hydrogen carbonate solution (200 mL), water (200 mL) and saturated brine (200 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained solution was concentrated under reduced pressure. The residue was recrystallized from ethyl acetate to give the title compound (234 mg, 68%) as a colorless powder.

$^1$H-NMR (DMSO-$d_6$, 300 MHz) δ 0.82-1.02 (4H, m), 1.74 (6H, s), 1.92-2.07 (1H, m), 2.26 (3H, s), 7.01 (1H, dd, J=2.4, 8.4 Hz), 7.12 (1H, d, J=8.7 Hz), 7.20 (1H, d, J=2.4 Hz), 7.34 (1H, d, J=8.4 Hz), 7.59 (1H, t, J=7.8 Hz), 7.75 (1H, ddd, J=1.2, 2.1, 7.8 Hz), 7.95 (1H, d, J=7.8 Hz), 8.07 (1H, t, J=1.8 Hz), 8.16 (1H, d, J=8.7 Hz), 10.02 (1H, s), 12.69 (1H, s).

Example C34

Production of N-[5-(3-{[3-(1-cyano-1-methylethyl)benzoyl]amino}-4-methylphenoxy)[1,3]thiazolo[5,4-b]pyridin-2-yl]-1,3-oxazole-4-carboxamide

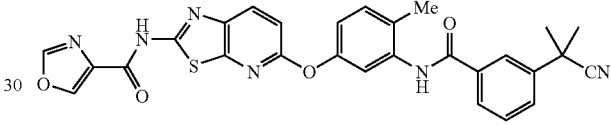

To a solution of 1,3-oxazole-4-carboxylic acid (66 mg, 0.586 mmol) in tetrahydrofuran (4.0 mL) were added oxalyl chloride (60 µL, 0.704 mmol) and N,N-dimethylformamide (20 µL), and the mixture was stirred at room temperature for 1 hr. The reaction mixture was concentrated under reduced pressure to give 1,3-oxazole-4-carbonyl chloride as a yellow oil.

1,3-Oxazole-4-carbonyl chloride synthesized above was suspended in pyridine (4.0 mL) at 0° C., N-{5-[(2-amino[1,3]thiazolo[5,4-b]pyridin-5-yl)oxy]-2-methylphenyl}-3-(1-cyano-1-methylethyl)benzamide (200 mg, 0.451 mmol) produced in Example C33(iv) was added, and the mixture was stirred at room temperature for 2 hr. The reaction mixture was concentrated under reduced pressure. 5% Aqueous sodium hydrogen carbonate solution (20 mL), ethyl acetate (20 mL) and hexane (20 mL) were added to the residue, and the yielded pale-yellow precipitate was collected by filtration. The obtained precipitate was purified by basic silica gel column chromatography (ethyl acetate/methanol=100/0→80/20), and the obtained solution was concentrated under reduced pressure. The residue was recrystallized from ethyl acetate to give the title compound (108 mg, 45%) as a colorless powder.

$^1$H-NMR (DMSO-$d_6$, 300 MHz) δ 1.74 (6H, s), 2.27 (3H, s), 7.04 (1H, dd, J=2.4, 8.4 Hz), 7.16 (1H, d, J=8.7 Hz), 7.23 (1H, d, J=2.4 Hz), 7.35 (1H, d, J=8.4 Hz), 7.59 (1H, t, J=7.8 Hz), 7.69-7.80 (1H, m), 7.96 (1H, d, J=7.8 Hz), 8.08 (1H, t, J=1.5 Hz), 8.21 (1H, d, J=8.7 Hz), 8.64 (1H, d, J=0.8 Hz), 9.02 (1H, d, J=0.8 Hz), 10.03 (1H, s), 12.74 (1H, s).

Example C35

Production of 3-(1-cyano-1-methylethyl)-N-{2-methyl-5-[(2-{[(4-methylpiperazin-1-yl)acetyl]amino}[1,3]thiazolo[5,4-b]pyridin-5-yl)oxy]phenyl}benzamide

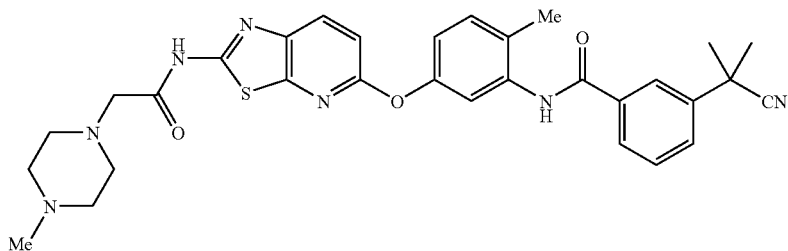 [SMILES: Cc1ccc(Oc2ccc3nc(NC(=O)CN4CCN(C)CC4)sc3n2)cc1NC(=O)c1cccc(C(C)(C)C#N)c1]

To a solution of N-{5-[(2-amino[1,3]thiazolo[5,4-b]pyridin-5-yl)oxy]-2-methylphenyl}-3-(1-cyano-1-methylethyl)benzamide (200 mg, 0.451 mmol) produced in Example C33(iv) in N,N-dimethylformamide (4.0 mL) was added chloroacetyl chloride (50 µL, 0.631 mmol), and the mixture was stirred at room temperature for 2 hr. Chloroacetyl chloride (25 µL, 0.314 mmol) was added to the reaction mixture, and the mixture was further stirred at room temperature for 2 hr. The reaction mixture was diluted with ethyl acetate (100 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure to give N-[5-({2-[(chloroacetyl)amino][1,3]thiazolo[5,4-b]pyridin-5-yl}oxy)-2-methylphenyl]-3-(1-cyano-1-methylethyl)benzamide as a colorless solid.

N-[5-({2-[(Chloroacetyl)amino][1,3]thiazolo[5,4-b]pyridin-5-yl}oxy)-2-methylphenyl]-3-(1-cyano-1-methylethyl)benzamide produced above was dissolved in tetrahydrofuran (8.0 mL), triethylamine (155 µL, 1.13 mmol) and 1-methylpiperazine (100 µL, 0.902 mmol) were added, and the mixture was stirred at 80° C. for 8 hr. The reaction mixture was cooled to room temperature, diluted with ethyl acetate (100 mL), washed with water (100 mL) and saturated brine (100 mL), and dried over anhydrous sodium sulfate. The insoluble material was filtered off, and the filtrate was concentrated under reduced pressure. The residue was purified by basic silica gel column chromatography (ethyl acetate/methanol=100/0→80/20), and the obtained solution was concentrated under reduced pressure. The residue was triturated with ethyl acetate/diisopropyl ether to give the title compound (92 mg, 35%) as a colorless solid.

$^1$H-NMR (DMSO-d$_6$, 300 MHz) δ 1.74 (6H, s), 2.15 (3H, s), 2.23-2.40 (7H, m), 2.46-2.59 (6H, m), 7.02 (1H, dd, J=2.4, 8.4 Hz), 7.13 (1H, d, J=8.7 Hz), 7.21 (1H, d, J=2.4 Hz), 7.35 (1H, d, J=8.4 Hz), 7.59 (1H, t, J=7.8 Hz), 7.75 (1H, ddd, J=0.9, 2.1, 7.8 Hz), 7.95 (1H, d, J=7.8 Hz), 8.07 (1H, t, J=1.8 Hz), 8.17 (1H, d, J=8.7 Hz), 10.02 (1H, s), 12.12 (1H, br s).

Example C36

Production of 3-(1-cyano-1-methylethyl)-N-(5-{[2-(glycoloylamino)[1,3]thiazolo[5,4-b]pyridin-5-yl]oxy}-2-methylphenyl)benzamide

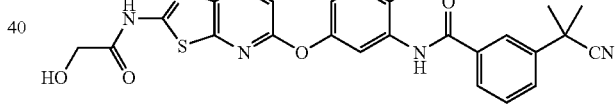

To a solution of N-{5-[(2-amino-1,3-benzothiazol-6-yl)oxy]-2-methylphenyl}-3-(1-cyano-1-methylethyl)benzamide (200 mg, 0.451 mmol) produced in Example C33(iv) in pyridine (4.0 mL) was added 2-chloro-2-oxoethyl acetate (78 µL, 0.722 mmol), and the mixture was stirred at room temperature for 4 hr. The reaction mixture was concentrated under reduced pressure, ethyl acetate (100 mL) was added, and the mixture was washed with water (50 mL), 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was dissolved in methanol (4.0 mL), 1N aqueous sodium hydroxide solution (4.0 mL) was added, and the mixture was stirred at room temperature for 1 hr. The reaction mixture was concentrated under reduced pressure, neutralized with 1N hydrochloric acid, and extracted with ethyl acetate (100 ml×2). The organic layer was washed with water (100 mL) and saturated brine (100 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained solution was concentrated under reduced pressure. The residue was triturated with ethyl acetate/hexane to give the title compound (112 mg, 50%) as a colorless solid.

¹H-NMR (DMSO-d₆, 300 MHz) δ 1.74 (6H, s), 2.27 (3H, s), 4.18 (2H, d, J=5.1 Hz), 5.51 (1H, br s), 7.02 (1H, dd, J=2.7, 8.4 Hz), 7.13 (1H, d, J=8.7 Hz), 7.21 (1H, d, J=2.7 Hz), 7.34 (1H, d, J=8.4 Hz), 7.59 (1H, t, J=7.8 Hz), 7.70-7.79 (1H, m), 7.93-7.98 (1H, m), 8.07 (1H, t, J=1.8 Hz), 8.17 (1H, d, J=8.7 Hz), 10.02 (1H, s), 12.11 (1H, s).

Example C37

Production of 3-(1-cyano-1-methylethyl)-N-[3-({2-[(cyclopropylcarbonyl)amino][1,3]thiazolo[5,4-b]pyridin-5-yl}oxy)-4-ethylphenyl]benzamide

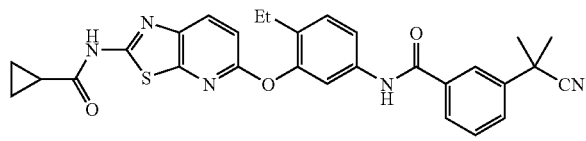 [SMILES: CCc1ccc(NC(=O)c2cccc(C(C)(C)C#N)c2)cc1Oc1ccc2nc(NC(=O)C3CC3)sc2n1]

(i) Production of
N-(4-acetyl-3-hydroxyphenyl)acetamide

A solution of 3-aminophenol (10.0 g, 91.6 mmol) in acetic anhydride (40 mL) was stirred with heating at 80° C. for 2 hr. The reaction mixture was cooled to room temperature, and concentrated under reduced pressure. The obtained oily residue was again heated to 110° C., triturated aluminum chloride (30.5 g, 229 mmol) was slowly added, and the mixture was heated at the same temperature for 30 min. The solidified reaction mixture was poured into ice water, and the mixture was extracted with ethyl acetate (300 mL×2). The combined organic layer was washed with water (200 mL) and saturated brine (200 mL), and dried over anhydrous sodium sulfate. The insoluble material was filtered off, and the filtrate was concentrated under reduced pressure. The obtained residue was purified by silica gel column chromatography (hexane/ethyl acetate=80/20→20/80), and the obtained solution was concentrated under reduced pressure to give the title compound (2.56 g, 14%) as pale-yellow crystals.

¹H-NMR (DMSO-d₆, 300 MHz) δ 2.08 (3H, s), 2.56 (3H, s), 7.05 (1H, dd, J=2.1, 8.7 Hz), 7.35 (1H, d, J=2.1 Hz), 7.84 (1H, d, J=8.7 Hz), 10.27 (1H, s), 12.32 (1H, s).

(ii) Production of
N-(4-ethyl-3-hydroxyphenyl)acetamide

To a solution of N-(4-acetyl-3-hydroxyphenyl)acetamide (4.0 g, 20.7 mmol) in methanol (50 mL)/acetic acid (50 mL) was added 10% palladium-carbon powder (2.0 g), and the mixture was stirred at room temperature for 6 hr under a hydrogen atmosphere of 2.8 pressure. 10% Palladium-carbon powder was filtered off by celite filtration, the filtrate was concentrated under reduced pressure, and the obtained residue was washed with diisopropyl ether/hexane (1:1) to give the title compound (3.07 g, 83%) as a colorless powder.

¹H-NMR (DMSO-d₆, 300 MHz) δ 1.08 (3H, t, J=7.5 Hz), 1.99 (3H, s), 2.38-2.48 (2H, m), 6.82 (1H, dd, J=2.1, 8.1 Hz), 6.92 (1H, d, J=8.1 Hz), 7.23 (1H, d, J=2.1 Hz), 9.23 (1H, br s), 9.69 (1H, br s).

(iii) Production of 5-amino-2-ethylphenol
hydrochloride

N-(4-Ethyl-3-hydroxyphenyl)acetamide (3.5 g, 19.5 mmol) was suspended in 5N hydrochloric acid, and the suspension was stirred with heating at 100° C. for 2 hr. The reaction mixture was cooled to room temperature, and the yielded crystals were collected by filtration, and air-dried to give the title compound (2.66 g, 79%) as pale-gray crystals.

¹H-NMR (DMSO-d₆, 300 MHz) δ 1.10 (3H, t, J=7.5 Hz), 2.40-2.58 (2H, m), 6.68 (1H, dd, J=2.4, 7.8 Hz), 6.80 (1H, d, J=2.4 Hz), 7.13 (1H, d, J=7.8 Hz), 9.65-10.95 (4 H, m).

(iv) Production of 3-(1-cyano-1-methylethyl)-N-(4-ethyl-3-hydroxyphenyl)benzamide To a solution of 3-(1-cyano-1-methylethyl)benzoic acid (2.62 g, 13.9 mmol) in tetrahydrofuran (30 mL) were added oxalyl chloride (1.4 mL, 16.4 mmol) and N,N-dimethylformamide (40 µL), and the mixture was stirred at room temperature for 1 hr. The reaction mixture was concentrated under reduced pressure to give 3-(1-cyano-1-methylethyl)benzoyl chloride as a pale-yellow oil.

To a two-layer solution of 5-amino-2-ethylphenol hydrochloride (2.2 g, 12.6 mmol) in tetrahydrofuran (20 mL)/1N aqueous sodium hydrogen carbonate solution (38 mL) was added a solution of 3-(1-cyano-1-methylethyl)benzoyl chloride synthesized above in tetrahydrofuran (20 mL), and the mixture was stirred at room temperature for 12 hr. The aqueous layer was separated, and extracted with ethyl acetate (80 mL). The combined organic layer was washed with water (40 mL) and saturated brine (40 mL), and dried over anhydrous sodium sulfate. The insoluble material was filtered off, and the filtrate was concentrated under reduced pressure. Ethyl acetate (45 mL)/hexane (25 mL) was added to the obtained residue, and the obtained solid was collected by filtration to give the title compound (3.48 g, 90%) as a colorless powder.

¹H-NMR (DMSO-d₆, 300 MHz) δ 1.12 (3H, t, J=7.5 Hz), 1.75 (6H, s), 2.47-2.53 (2H, m), 6.87-7.12 (2H, m), 7.37 (1H, d, J=1.8 Hz), 7.58 (1H, t, J=7.8 Hz), 7.73 (1H, ddd, J=1.2, 1.8, 7.8 Hz), 7.87-7.93 (1H, m), 8.00 (1H, t, J=1.8 Hz), 9.34 (1H, s), 10.12 (1H, s).

(v) Production of 3-(1-cyano-1-methylethyl)-N-{4-ethyl-3-[(5-nitropyridin-2-yl)oxy]phenyl}benzamide To a solution of 2-chloro-5-nitropyridine (1.07 g, 6.81 mmol) and 3-(1-cyano-1-methylethyl)-N-(4-ethyl-3-hydroxyphenyl)benzamide (2.0 g, 6.48 mmol) in N,N-dimethylformamide (15 mL) was added potassium carbonate (1.34 g, 9.72 mmol), and the mixture was stirred at 80° C. for 12 hr. The reaction mixture was cooled to room temperature, the insoluble material was filtered off, and the filtrate was concentrated under reduced pressure. The obtained residue was diluted with ethyl acetate (200 mL), washed with water (150 mL), 5% aqueous sodium hydrogen carbonate solution (150 mL) and saturated brine (150 mL), and dried over anhydrous sodium sulfate. The insoluble material was filtered off, the filtrate was concentrated under reduced pressure, and the obtained residue was purified by silica gel column chromatography (hexane/ethyl acetate=80/20→30/70). The obtained solution was concentrated under reduced pressure to give the title compound (3.3 g, quantitative) as a yellow amorphous substance.

¹H-NMR (DMSO-d₆, 300 MHz) δ 1.09 (3H, t, J=7.6 Hz), 1.74 (6H, s), 2.44 (2H, q, J=7.6 Hz), 7.30 (1H, dd, J=0.6, 9.0 Hz), 7.37 (1H, d, J=8.4 Hz), 7.54-7.68 (3H, m), 7.75 (1H, ddd, J=0.9, 2.1, 7.8 Hz), 7.89-7.95 (1H, m), 8.02 (1H, t, J=1.8 Hz), 8.64 (1H, dd, J=3.0, 9.0 Hz), 9.05 (1H, dd, J=0.6, 2.7 Hz), 10.40 (1H, br s).

(vi) Production of N-{3-[(5-aminopyridin-2-yl)oxy]-4-ethylphenyl}-3-(1-cyano-1-methylethyl)benzamide To a solution of 3-(1-cyano-1-methylethyl)-N-{4-ethyl-3-[(5-nitropyridin-2-yl)oxy]phenyl}benzamide (2.78 g, 6.48 mmol) in methanol (70 mL) was added 10% palladium-carbon powder (640 mg), and the mixture was stirred at room temperature for 5 hr under a hydrogen atmosphere of 3.0 pressure. Palladium-carbon powder was filtered off by celite filtration, the filtrate was concentrated under reduced pressure, and the obtained residue was washed with ethyl acetate/tetrahydrofuran (10:1) to give the title compound (2.18 g, 84%) as a gray powder.

$^1$H-NMR (DMSO-$d_6$, 300 MHz) δ 1.12 (3H, t, J=7.5 Hz), 1.73 (6H, s), 2.46-2.60 (2H, m), 5.05 (2H, s), 6.76 (1H, d, J=8.4 Hz), 7.08 (1H, dd, J=2.7, 8.4 Hz), 7.23 (1H, d, J=8.4 Hz), 7.31 (1H, d, J=2.1 Hz), 7.45-7.60 (3H, m), 7.73 (1H, ddd, J=0.9, 1.8, 7.8 Hz), 7.85-7.93 (1H, m), 7.99 (1H, t, J=1.8 Hz), 10.23 (1H, s).

(vii) Production of N-{3-[(2-amino[1,3]thiazolo[5,4-b]pyridin-5-yl)oxy]-4-ethylphenyl}-3-(1-cyano-1-methylethyl)benzamide Potassium thiocyanate (972 mg, 10 mmol) was suspended in acetic acid (20 mL), and the mixture was stirred at room temperature for 10 min. A solution of N-{3-[(5-aminopyridin-2-yl)oxy]-4-ethylphenyl}-3-(1-cyano-1-methylethyl)benzamide (1.0 g, 2.50 mmol) in acetic acid (20 mL) was added to the obtained solution, and the mixture was further stirred at room temperature for 15 min. A solution of bromine (439 mg, 2.75 mmol) in acetic acid (14 mL) was slowly added dropwise to the obtained solution. After the completion of the dropwise addition, the mixture was stirred at room temperature for 12 hr. The yielded yellow insoluble material was filtered off, and washed with acetic acid. The filtrate and washing solution were combined and concentrated under reduced pressure. The obtained residue was suspended in ethyl acetate (250 mL), and the suspension was washed with 5% aqueous sodium hydrogen carbonate solution (200 mL) and saturated brine (200 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and the obtained solution was concentrated under reduced pressure to give the title compound (1.0 g, 87%) as a pale-yellow amorphous substance.

$^1$H-NMR (DMSO-$d_6$, 300 MHz) δ 1.12 (3H, t, J=7.6 Hz), 1.73 (6H, s), 2.46-2.59 (2H, m), 6.90 (1H, d, J=8.4 Hz), 7.31 (1H, d, J=8.4 Hz), 7.44 (1H, d, J=2.1 Hz), 7.51-7.66 (4 H, m), 7.68-7.78 (2H, m), 7.85-7.94 (1H, m), 8.00 (1H, t, J=1.8 Hz), 10.29 (1H, s).

(viii) Production of 3-(1-cyano-1-methylethyl)-N-[3-({2-[(cyclopropylcarbonyl)amino][1,3]thiazolo[5,4-b]pyridin-5-yl}oxy)-4-ethylphenyl]benzamide To a solution of N-{3-[(2-amino[1,3]thiazolo[5,4-b]pyridin-5-yl)oxy]-4-ethylphenyl}-3-(1-cyano-1-methylethyl)benzamide (270 mg, 0.59 mmol) in pyridine (6.0 mL) was added cyclopropanecarbonyl chloride (70 μL, 0.767 mmol), and the mixture was stirred at room temperature for 12 hr. Cyclopropanecarbonyl chloride (35 μL, 0.383 mmol) was added to the reaction mixture, and the mixture was further stirred at room temperature for 1 hr. The reaction mixture was concentrated under reduced pressure, and the obtained residue was diluted with ethyl acetate (50 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained solution was concentrated under reduced pressure. The residue was recrystallized from ethyl acetate to give the title compound (188 mg, 61%) as a colorless powder.

$^1$H-NMR (DMSO-$d_6$, 300 MHz) δ 0.79-0.98 (4 H, m), 1.11 (3H, t, J=7.5 Hz), 1.73 (6H, s), 1.90-1.98 (1H, m), 2.42-2.57 (2H, m), 7.09 (1H, d, J=8.7 Hz), 7.34 (1H, d, J=8.4 Hz), 7.47-7.66 (3H, m), 7.69-7.79 (1H, m), 7.85-7.96 (1H, m), 8.00 (1H, t, J=1.8 Hz), 8.13 (1H, d, J=8.7 Hz), 10.32 (1H, s), 12.63 (1H, br s).

Example C38

Production of 3-(1-cyano-1-methylethyl)-N-(4-ethyl-3-{[2-(glycoloylamino)[1,3]thiazolo[5,4-b]pyridin-5-yl]oxy}phenyl)benzamide

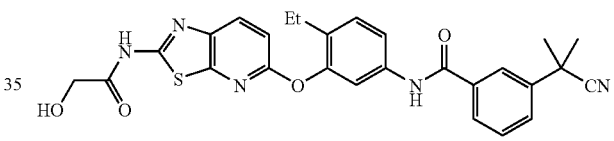

To a solution of N-{3-[(2-amino[1,3]thiazolo[5,4-b]pyridin-5-yl)oxy]-4-ethylphenyl}-3-(1-cyano-1-methylethyl)benzamide (150 mg, 0.327 mmol) in pyridine (4.0 mL) was added 2-chloro-2-oxoethyl acetate (56 μL, 0.523 mmol), and the mixture was stirred at room temperature for 12 hr. The reaction mixture was concentrated under reduced pressure, the obtained residue was dissolved in methanol (10 mL), potassium carbonate (45 mg, 0.327 mmol) was added, and the mixture was stirred at room temperature for 4 hr. The reaction mixture was concentrated under reduced pressure, neutralized with 1% aqueous citric acid solution, and extracted with ethyl acetate (100 mL). The organic layer was washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→85/15), and the obtained solution was concentrated under reduced pressure. The residue was triturated with ethyl acetate/diisopropyl ether/hexane to give the title compound (73.6 mg, 44%) as a colorless solid.

$^1$H-NMR (DMSO-$d_6$, 300 MHz) δ 1.11 (3H, t, J=7.8 Hz), 1.73 (6H, s), 2.43-2.56 (2H, m), 4.17 (2H, s), 5.46 (1H, br s), 7.12 (1H, d, J=8.7 Hz), 7.35 (1H, d, J=8.4 Hz), 7.50-7.66 (3H, m), 7.68-7.78 (1H, m), 7.91 (1H, d, J=7.8 Hz), 8.00 (1H, t, J=1.8 Hz), 8.17 (1H, d, J=8.7 Hz), 10.33 (1H, s), 12.11 (1H, br s).

Example C39

Production of 3-(1-cyano-1-methylethyl)-N-{4-ethyl-3-[(2-{[(4-methylpiperazin-1-yl)acetyl]amino}[1,3]thiazolo[5,4-b]pyridin-5-yl)oxy]phenyl}benzamide

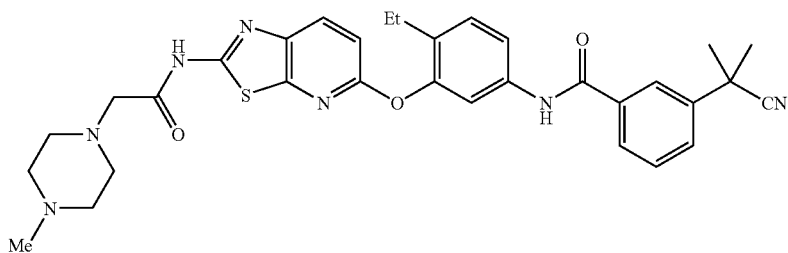 [SMILES: CCc1ccc(NC(=O)c2cccc(C(C)(C)C#N)c2)cc1Oc1ccc2nc(NC(=O)CN3CCN(C)CC3)sc2n1]

To a solution of N-{3-[(2-amino[1,3]thiazolo[5,4-b]pyridin-5-yl)oxy]-4-ethylphenyl}-3-(1-cyano-1-methylethyl)benzamide (150 mg, 0.327 mmol) in N,N-dimethylformamide (4.0 mL) was added chloroacetyl chloride (34 μL, 0.425 mmol), and the mixture was stirred at room temperature for 2 hr. The reaction mixture was diluted with ethyl acetate (100 mL), washed with 5% aqueous sodium hydrogen carbonate solution (100 mL) and saturated brine (50 mL), and dried over anhydrous sodium sulfate. The insoluble material was filtered off, and the filtrate was concentrated under reduced pressure to give N-[3-({2-[(chloroacetyl)amino][1,3]thiazolo[5,4-b]pyridin-5-yl}oxy)-4-ethylphenyl]-3-(1-cyano-1-methylethyl)benzamide as a colorless solid.

N-[3-({2-[(Chloroacetyl)amino][1,3]thiazolo[5,4-b]pyridin-5-yl}oxy)-4-ethylphenyl]-3-(1-cyano-1-methylethyl)benzamide synthesized above was dissolved in tetrahydrofuran (4.0 mL), triethylamine (135 μL, 0.98 mmol) and 1-methylpiperazine (108 μL, 0.98 mmol) were added, and the mixture was stirred at 60° C. for 8 hr. The reaction mixture was cooled to room temperature, diluted with ethyl acetate (100 mL), washed with water (100 mL) and saturated brine (100 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concentrated under reduced pressure. The residue was triturated with ethyl acetate/diisopropyl ether/hexane to give the title compound (114 mg, 59%) as a colorless solid.

$^1$H-NMR (DMSO-$d_6$, 300 MHz) δ 1.11 (3H, t, J=7.5 Hz), 1.73 (6H, s), 2.15 (3H, s), 2.23-2.60 (12H, m), 7.10 (1H, d, J=8.7 Hz), 7.34 (1H, d, J=8.7 Hz), 7.50-7.65 (3H, m), 7.68-7.78 (1H, m), 7.87-7.96 (1H, m), 8.00 (1H, t, J=1.8 Hz), 8.13 (1H, d, J=8.7 Hz), 10.32 (1H, s), 12.09 (1H, br s).

Example C40

Production of N-{3-[{2-[(cyclopropylcarbonyl)amino][1,3]thiazolo[5,4-b]pyridin-5-yl}(methyl)amino]phenyl}-3-(trifluoromethyl)benzamide

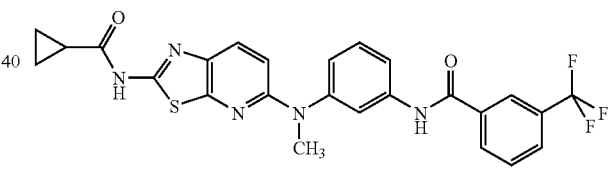

(i) Production of N-(3-nitrophenyl)-3-(trifluoromethyl)benzamide

To a solution of 3-nitroaniline (13.8 g, 99.9 mmol) in pyridine (200 mL) were added 3-(trifluoromethyl)benzoyl chloride (21.4 g, 103 mmol) and N,N-dimethylpyridine-4-amine (69.1 mg, 566 μmol), and the mixture was stirred at room temperature for 1.5 hr. Methanol (50 mL) was added to the reaction solution to stop the reaction, and the solvent was evaporated under reduced pressure. The residue was suspended in ethyl acetate (300 mL), washed with water (200 mL×2), 0.1N hydrochloric acid (200 mL×2), saturated aqueous sodium hydrogen carbonate solution (200 mL) and saturated brine (100 mL), and dried over anhydrous magnesium sulfate. The insoluble material was filtered off, and the filtrate was concentrated under reduced pressure to give the title compound (31.0 g, 100%) as a colorless solid.

$^1$H-NMR (DMSO-$d_6$, 300 MHz) δ 7.69 (1H, t, J=8.4 Hz), 7.82 (1H, t, J=7.8 Hz), 7.98-8.03 (2H, m), 8.21 (1H, ddd, J=0.9, 1.8, 8.1 Hz), 8.29-8.34 (2H, m), 8.78 (1H, t, J=2.1 Hz), 10.90 (1H, br s).

(ii) Production of N-(3-aminophenyl)-3-(trifluoromethyl)benzamide

To a solution of N-(3-nitrophenyl)-3-(trifluoromethyl)benzamide (30.0 g, 96.7 mmol) in tetrahydrofuran (300 mL) was slowly added with heating under reflux, a solution (500 mL) of sodium hydrosulfite (97.8 g, 562 mmol) in water, and the obtained two-layer solution was vigorously stirred with heating under reflux for 2 days. After cooling the reaction solution to room temperature, the aqueous layer was separated, and extracted with ethyl acetate (150 mL×2). The organic layer separated earlier was diluted with ethyl acetate (350 mL), and washed with saturated aqueous sodium hydrogen carbonate solution (150 mL×2) and saturated brine (100 mL). The combined organic layer was washed with saturated aqueous sodium hydrogen carbonate solution (150 mL×2) and saturated brine (150 mL), and dried over anhydrous magnesium sulfate. The insoluble material was filtered off, and the filtrate was concentrated under reduced pressure to give the title compound (17.8 g, 66%) as a pale-brown solid.

$^1$H-NMR (DMSO-$d_6$, 300 MHz) δ 5.14 (2H, br s), 6.34 (1H, ddd, J=1.2, 2.1, 8.1 Hz), 6.85-6.88 (1H, m), 6.99 (1H, t, J=8.1 Hz), 7.09 (1H, t, J=1.8 Hz), 7.77 (1H, t, J=7.8 Hz), 7.94 (1H, d, J=7.8 Hz), 8.22-8.26 (2H, m), 10.19 (1H, br s).

(iii) Production of N-[3-(methylamino)phenyl]-3-(trifluoromethyl)benzamide

Formic acid (2.5 mL, 66.3 mmol) and acetic anhydride (5 mL, 52.9 mmol) were mixed, and stirred with heating at 50° C. for 3 hr. The reaction mixture was cooled to room temperature, diluted with tetrahydrofuran (50 mL), and cooled to 0° C. A solution of N-(3-aminophenyl)-3-(trifluoromethyl)benzamide (5.65 g, 20.2 mmol) in tetrahydrofuran (50 mL) was added to the reaction mixture, and the mixture was stirred at the same temperature for 16 hr, during which the reaction temperature was allowed to gradually warm to room temperature. The reaction solution was concentrated under reduced pressure, and the residue was dissolved in tetrahydrofuran (50 mL) and ethyl acetate (250 mL). The solution was washed with saturated aqueous sodium hydrogen carbonate solution (150 mL×2) and saturated aqueous ammonium chloride solution (150 mL), and dried over anhydrous magnesium sulfate. The insoluble material was filtered off, and the filtrate was concentrated under reduced pressure to give N-[3-(formylamino)phenyl]-3-(trifluoromethyl)benzamide as a yellow amorphous substance. To a solution of N-[3-(formylamino)phenyl]-3-(trifluoromethyl)benzamide produced above in tetrahydrofuran (100 mL) was added a 1.9M solution (21 mL, 39.9 mmol) of borane-dimethylsulfide complex in tetrahydrofuran, and the mixture was stirred at room temperature for 1.5 hr. Since the starting materials were not completely consumed, a 1.9M solution (2 mL, 3.8 mmol) of borane-dimethylsulfide complex in tetrahydrofuran was added, and the mixture was further stirred at room temperature for 1 hr. Methanol (30 mL) and acetic acid (10 mL) were added to the reaction solution, the mixture was stirred at room temperature for 14 hr, and the reaction solution was concentrated under reduced pressure. The residue was dissolved in ethyl acetate (250 mL), and the solution was washed with saturated aqueous sodium hydrogen carbonate solution (100 mL×2) and saturated brine (100 mL), and dried over anhydrous magnesium sulfate. The insoluble material was filtered off, and the filtrate was concentrated under reduced pressure. The residue was recrystallized from ethyl acetate and hexane to give the title compound (5.54 g, total yield of 2 steps 93%) as yellow crystals.

$^1$H-NMR (DMSO-$d_6$, 300 MHz) δ 2.68 (3H, s), 5.71 (1H, br s), 6.32 (1H, ddd, J=1.2, 2.1, 8.4 Hz), 6.95-7.08 (3H, m), 7.77 (1H, t, J=7.8 Hz), 7.95 (1H, dd, J=0.6, 7.8 Hz), 8.23-8.27 (2H, m), 10.22 (1H, br s).

(iv) Production of 5-bromo[1,3]thiazolo[5,4-b]pyridin-2-amine

To a suspension of potassium thiocyanate (33.8 g, 348 mmol) in acetic acid (150 mL) was added 6-bromopyridin-3-amine (15.2 g, 88.1 mmol), and the mixture was stirred at room temperature for 15 min. A solution of bromine (18.4 g, 115 mmol) in acetic acid (200 mL) was added dropwise to the obtained solution at room temperature for 30 min or more. After the completion of the dropwise addition, the mixture was stirred at room temperature for 6 hr. The yielded yellow solid was filtered off, and the filtrate was concentrated under reduced pressure. The residue was suspended in tetrahydrofuran (200 mL) and ethyl acetate (200 mL), the suspension was washed with saturated aqueous sodium hydrogen carbonate solution (300 mL×2) and saturated brine (200 mL), dried over anhydrous magnesium sulfate, and decolorized with activated carbon. The insoluble material was filtered off, and the filtrate was concentrated under reduced pressure. The obtained crude product was recrystallized from tetrahydrofuran and diisopropyl ether to give the title compound (15.8 g, 78%) as a pale-brown solid.

$^1$H-NMR (DMSO-$d_6$, 300 MHz) δ 7.43 (1H, d, J=8.4 Hz), 7.58 (1H, J=8.4 Hz), 7.96 (2H, br s).

(v) Production of N-(5-bromo[1,3]thiazolo[5,4-b]pyridin-2-yl)cyclopropanecarboxamide In the same manner as in Example C1(viii), the title compound (3.8 g, 65%) was obtained as a brownish-red solid using 5-bromo[1,3]thiazolo[5,4-b]pyridin-2-amine (4.50 g, 19.6 mmol), pyridine (150 mL), N,N-dimethylpyridine-4-amine (58.9 mg, 482 µmol) and cyclopropanecarbonyl chloride (3.5 mL, 38.6 mmol) as starting materials. Recrystallization was carried out using tetrahydrofuran and ethyl acetate.

$^1$H-NMR (DMSO-$d_6$, 300 MHz) δ 0.97-1.02 (4H, m), 2.00-2.05 (1H, m), 7.67 (1H, d, J=8.4 Hz), 8.05 (1H, J=8.4 Hz), 12.91 (1H, br s).

(vi) Production of N-{3-[{2-[(cyclopropylcarbonyl)amino][1,3]thiazolo[5,4-b]pyridin-5-yl}(methyl)amino]phenyl}-3-(trifluoromethyl)benzamide To a suspension of N-(5-bromo[1,3]thiazolo[5,4-b]pyridin-2-yl)cyclopropanecarboxamide (298 mg, 1.00 mmol) in 2-methylpropan-2-ol (10 mL) were added N-[3-(methylamino)phenyl]-3-(trifluoromethyl)benzamide (306 mg, 1.04 mmol), tris(dibenzylideneacetone)dipalladium(0)(55.2 mg, 60.3 µmol), dicyclohexyl(2',4',6'-triisopropylbiphenyl-2-yl)phosphine (X-phos) (63.1 mg, 132 µmol) and t-butoxy potassium (283 mg, 2.52 mmol), and the mixture was stirred at 130° C. for 2.5 hr under microwave irradiation in a sealed tube. After the reaction solution was allowed to cool to room temperature, the insoluble material was filtered off, and washed with ethyl acetate, tetrahydrofuran and methanol. The filtrate and the washing solution were combined and diluted with ethyl acetate (200 mL), washed with saturated aqueous ammonium chloride solution (100 mL×2), and dried over anhydrous magnesium sulfate. The insoluble material was filtered off, and concentrated. The residue was purified by silica gel column chromatography (ethyl acetate/hexane=5/

95→50/50), and further purified by reverse phase silica gel column chromatography (containing 0.1% TFA, water/acetonitrile=5/95→95/5), fractions containing the object product was concentrated, and the residue was dissolved in saturated aqueous sodium hydrogen carbonate solution. The aqueous solution was extracted with ethyl acetate (100 mL×2), the combined organic layer was dried over anhydrous magnesium sulfate, and concentrated. The obtained crude product was recrystallized from ethyl acetate and diisopropyl ether to give the title compound (81.2 mg, 16%) as colorless crystals.

$^1$H-NMR (DMSO-$d_6$, 300 MHz) δ 0.93-0.95 (4H, m), 1.96-2.00 (1H, m), 3.46 (3H, s), 6.72 (1H, d, J=9.0 Hz), 7.09-7.12 (1H, m), 7.45 (1H, t, J=8.1 Hz), 7.67-7.70 (1H, m), 7.77-7.82 (3H, m), 7.98 (1H, d, J=7.8 Hz), 8.25-8.29 (2H, m), 10.53 (1H, br s), 12.46 (1H, br s).

Example C41

Production of N-[3-({2-[(cyclopropylcarbonyl)amino][1,3]thiazolo[5,4-b]pyridin-5-yl}amino)phenyl]-3-(trifluoromethyl)benzamide

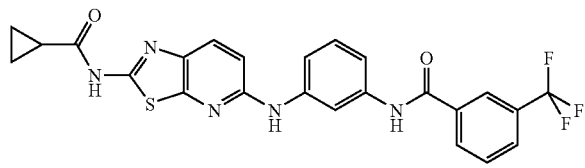 [SMILES: O=C(Nc1cccc(Nc2ccc3nc(NC(=O)C4CC4)sc3n2)c1)c1cccc(C(F)(F)F)c1]

In the same manner as in Example C40(vi), the title compound (78.3 mg, 16%) was obtained as colorless crystals using N-(5-bromo[1,3]thiazolo[5,4-b]pyridin-2-yl)cyclopropanecarboxamide (307 mg, 1.00 mmol) produced in Example C40(v), 1-methyl-2-pyrrolidone (4 mL), N-(3-aminophenyl)-3-(trifluoromethyl)benzamide (279 mg, 996 μmol) produced in Example C40(ii), tris(dibenzylideneacetone)dipalladium(0) (94 mg, 103 μmol), dicyclohexyl(2',4',6'-triisopropylbiphenyl-2-yl)phosphine (X-phos) (96.1 mg, 202 μmol) and t-butoxy potassium (386 mg, 3.44 mmol) as starting materials.

$^1$H-NMR (DMSO-d6, 300 MHz) δ 0.93-0.99 (4H, m), 1.95-2.03 (1H, m), 7.99 (1H, d, J=9.0 Hz), 7.25-7.32 (2H, m), 7.51-7.55 (1H, m), 7.80 (1H, t, J=7.8 Hz), 7.91 (1H, d, J=9.0 Hz), 7.97 (1H, d, J=8.1 Hz), 8.19 (1H, br s), 8.27-8.29 (2H, m), 9.36 (1H, br s), 10.45 (1H, br s), 12.45 (1H, br s).

Example C42

Production of N-(3-{[2-(acetylamino)[1,3]thiazolo[5,4-b]pyridin-5-yl]oxy}-4-methoxyphenyl)-3-(1-cyano-1-methylethyl)benzamide

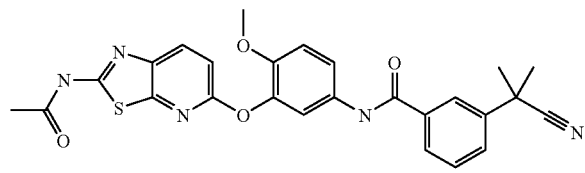 [SMILES: COc1ccc(NC(=O)c2cccc(C(C)(C)C#N)c2)cc1Oc1ccc2nc(NC(C)=O)sc2n1]

(i) Production of 3-(1-cyano-1-methylethyl)-N-(3-hydroxy-4-methoxyphenyl)benzamide To a solution of 3-(1-cyano-1-methylethyl)benzoic acid (4.92 g, 26.0 mmol) produced in Example C6(ii) in oxalyl chloride (20 mL) was added N,N-dimethylformamide (0.1 mL), and the mixture was stirred at room temperature for 30 min. Excessive reagent was evaporated under reduced pressure, the obtained residue was dissolved in tetrahydrofuran (20 mL), and 5-amino-2-methoxyphenol (4.17 g, 30.0 mmol) and N-ethyl-N-(1-methylethyl)propan-2-amine (6.46 g, 50.0 mmol) were sequentially added dropwise under ice-cooling. The reaction solution was stirred at room temperature for 18 hr, and poured into water. The mixture was extracted with ethyl acetate, the organic layer was dried over anhydrous magnesium sulfate, and the solvent was evaporated under reduced pressure. The residue was dissolved in methanol (5 mL)/tetrahydrofuran (5 mL), 8N aqueous sodium hydroxide solution (1 mL) was added under ice-cooling, and the mixture was stirred at room temperature for 18 hr. The reaction solution was poured into water, and the mixture was extracted with ethyl acetate. The organic layer was dried over anhydrous magnesium sulfate, and the solvent was evaporated under reduced pressure. The residue was purified by silica gel chromatography (hexane/ethyl acetate=5:1) and triturated with diethyl ether to give the title compound (4.70 g, 58%) as a pale-yellow solid.

$^1$H-NMR (CDCl$_3$, 300 MHz) δ 1.77 (6H, s), 3.90 (3H, s), 5.71 (1H, s), 6.85 (1H, d, J=8.7 Hz), 7.15-7.22 (2H, m), 7.52 (1H, t, J=3.6 Hz), 7.68-7.78 (3H, m), 7.96 (1H, br s).

(ii) Production of N-{3-[(2-amino[1,3]thiazolo[5,4-b]pyridin-5-yl)oxy]-4-methoxyphenyl}-3-(1-cyano-1-methylethyl)benzamide To a solution of 2-chloro-5-nitropyridine (547 mg, 3.45 mmol) and 3-(1-cyano-1-methylethyl)-N-(3-hydroxy-4-methoxyphenyl)benzamide (1.03 g, 3.33 mmol) in N,N-dimethylformamide (50 mL) was added potassium carbonate (1.92 g, 13.9 mmol), and the mixture was stirred at 80° C. for 4 hr. The reaction mixture was cooled to room temperature, and diluted with ethyl acetate (75 mL)/hexane (75 mL). The obtained suspension was washed with water (50 mL×3), and the combined aqueous layer was extracted with ethyl acetate (75 mL)/hexane (75 mL). The organic layer were combined, washed with saturated aqueous ammonium chloride solution (100 mL), and dried over anhydrous magnesium sulfate. The insoluble material was filtered off, and the filtrate was concentrated under reduced pressure to give 3-(1-cyano-1-methylethyl)-N-{4-methoxy-3-[(5-nitropyridin-2-yl)oxy]phenyl}benzamide as a brown oil. This was used for the next reaction without further purification.

To a solution of 3-(1-cyano-1-methylethyl)-N-{4-methoxy-3-[(5-nitropyridin-2-yl)oxy]phenyl}benzamide obtained above in acetic acid (25 mL) was added 10% palladium-carbon (208 mg), and the mixture was stirred at room temperature for 2 hr under a hydrogen atmosphere (2.5 atm). The insoluble material was filtered off, and the filtrate was concentrated under reduced pressure. The obtained residue was diluted with ethyl acetate (100 mL), washed with saturated aqueous sodium hydrogen carbonate solution (50 mL) and saturated aqueous ammonium chloride solution (50 mL), and dried over anhydrous magnesium sulfate. The insoluble material was filtered off, and the filtrate was concentrated under reduced pressure to give N-{3-[(5-aminopyridin-2-yl)oxy]-4-methoxyphenyl}-3-(1-cyano-1-methylethyl)benzamide as a colorless amorphous substance. This was used for the next reaction without further purification.

Potassium thiocyanate (1.26 g, 13.0 mmol) was suspended in acetic acid (15 mL), and the mixture was stirred at room temperature for 15 min. To the obtained solution was added a solution of N-{3-[(5-aminopyridin-2-yl)oxy]-4-methoxyphenyl}-3-(1-cyano-1-methylethyl)benzamide obtained above in acetic acid (25 mL), and the mixture was further stirred at room temperature for 15 min. A solution of bromine (690 mg, 4.32 mmol) in acetic acid (30 mL) was added dropwise to the obtained solution for 30 min or more. After the completion of the dropwise addition, the mixture was stirred at room temperature for 10 hr. The yielded yellow insoluble material was filtered off, and washed with acetic acid. The filtrate and the washing fluid were combined, and concentrated under reduced pressure. The obtained residue was suspended in ethyl acetate (100 mL)/tetrahydrofuran (10 mL), and the suspension was washed with saturated aqueous sodium hydrogen carbonate solution (50 mL) and aqueous ammonium chloride solution (50 mL), and dried over anhydrous magnesium sulfate. The insoluble material was filtered off, and the filtrate was concentrated under reduced pressure. The obtained residue was purified by silica gel column chromatography (hexane/ethyl acetate=20/80→0/100), and the obtained solution was concentrated under reduced pressure to give the title compound (1.00 g, 65%, 3 step yield) as a colorless amorphous substance.

$^1$H-NMR (DMSO-d$_6$, 300 MHz) δ 1.74 (6H, s), 3.70 (3H, s), 6.86 (1H, d, J=8.7 Hz), 7.16 (1H, d, J=8.7 Hz), 7.55-7.56 (3H, m), 7.58-7.63 (2H, m), 7.69 (1H, d, J=8.7 Hz), 7.72-7.76 (1H, m), 7.92 (1H, dt, J=5.4, 1.2 Hz), 8.02 (1H, t, J=1.8 Hz), 10.26 (1H, s).

(iii) Production of N-(3-{([2-(acetylamino)[1,3]thiazolo[5,4-b]pyridin-5-yl]oxy}-4-methoxyphenyl)-3-(1-cyano-1-methylethyl)benzamide To a solution of N-{3-[(2-amino[1,3]thiazolo[5,4-b]pyridin-5-yl)oxy]-4-methoxyphenyl}-3-(1-cyano-1-methylethyl)benzamide (167 mg, 363 µmol) in pyridine (5.0 mL) were added acetyl chloride (200 µL, 2.813 mmol) and N,N-dimethylpyridin-4-amine (28.5 mg, 233 µmol), and the mixture was stirred at room temperature for 2 hr. Methanol (10 mL) was added to the reaction mixture, and the mixture was concentrated under reduced pressure. The obtained residue was diluted with tetrahydrofuran (10 mL)/ethyl acetate (50 mL), washed with 0.1N hydrochloric acid (50 mL), saturated aqueous sodium hydrogen carbonate solution (50 mL) and saturated aqueous ammonium chloride solution (50 mL), and dried over anhydrous magnesium sulfate. The insoluble material was filtered off, and the filtrate was concentrated under reduced pressure. The obtained residue was recrystallized from ethyl acetate/diethyl ether to give the title compound (166 mg, 91%) as colorless crystals.

$^1$H-NMR (DMSO-d$_6$, 300 MHz) δ 1.74 (6H, s), 2.18 (3H, s), 3.61 (3H, s), 7.08 (1H, d, J=8.7 Hz), 7.20 (1H, d, J=9.6 Hz), 7.56-7.66 (3H, m), 7.73-7.76 (1H, m), 7.91-7.93 (1H, m), 8.02-8.03 (1H, m), 8.13 (1H, d, J=8.7 Hz), 10.29 (1H, s), 12.35 (1H, br s).

Example C43

Production of N-[4-cyano-3-({2-[(cyclopropylcarbonyl)amino][1,3]thiazolo[5,4-b]pyridin-5-yl}oxy)phenyl]-3-(1-cyano-1-methylethyl)benzamide

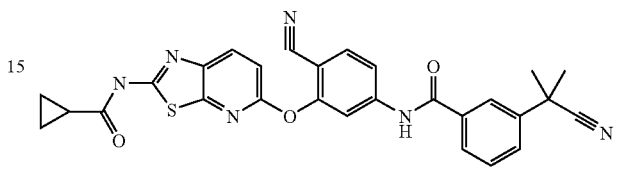

(i) Production of 2-hydroxy-4-nitrobenzonitrile

To a solution of 2-methoxy-4-nitrobenzonitrile (5.0 g, 28.1 mmol) in N,N-dimethylformamide (28 mL) was added lithium chloride (2.38 g, 56.2 mmol), and the mixture was stirred at 160° C. for 16 hr. The reaction solution was cooled to room temperature, diluted with ethyl acetate (300 mL), washed with 1% aqueous citric acid solution (150 mL), water (150 mL) and saturated brine (150 mL×2), and dried over anhydrous sodium sulfate. The insoluble material was filtered off, and the filtrate was concentrated under reduced pressure. The residue was purified by silica gel column chromatography (hexane/ethyl acetate=80/20→30/70), and the obtained solution was concentrated under reduced pressure. The residue was triturated with ethyl acetate to give the title compound (3.98 g, 86%) as a yellow-brown solid.

$^1$H-NMR (DMSO-d$_6$, 300 MHz) δ 7.65-7.79 (2H, m), 7.91-8.01 (1H, m), 12.21 (1H, br s).

(ii) Production of 4-amino-2-hydroxybenzonitrile

To a solution of 2-hydroxy-4-nitrobenzonitrile (3.98 g, 24.25 mmol) in tetrahydrofuran (17 mL) were added methanol (70 mL) and 10% palladium-carbon (460 mg), and the mixture was stirred at room temperature for 14 hr under a hydrogen atmosphere (2.5 atm). The insoluble material was filtered off, and the filtrate was concentrated under reduced pressure to give the title compound (3.16 g, 97%) as a brown oil. This was used for the next reaction without further purification.

$^1$H-NMR (DMSO-d$_6$, 300 MHz) δ 5.95 (2H, br s), 6.02-6.13 (2H, m), 7.11 (1H, d, J=8.4 Hz), 10.11 (1H, br s).

(iii) Production of N-(4-cyano-3-hydroxyphenyl)-3-(1-cyano-1-methylethyl)benzamide To a solution of 3-(1-cyano-1-methylethyl)benzoic acid (5.10 g, 27.0 mmol) produced in Example C6(ii) in tetrahydrofuran (80 mL) were added oxalyl chloride (2.76 mL, 32.4 mmol) and N,N-dimethylformamide (20 µL), and the mixture was stirred at room temperature for 1 hr. The reaction mixture was concentrated under reduced pressure to give 3-(1-cyano-1-methylethyl)benzoyl chloride as a pale-yellow solid.

To a two-layer solution of 4-amino-2-hydroxybenzonitrile (3.16 g, 23.5 mmol) in tetrahydrofuran (80 mL)/1N aqueous sodium hydrogen carbonate solution (80 mL) was added a solution of 3-(1-cyano-1-methylethyl)benzoyl chloride synthesized above in tetrahydrofuran (20 mL), and the mixture was stirred at room temperature for 18 hr. The aqueous layer was separated, and extracted with ethyl acetate (100 mL). The combined organic layer was washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was dissolved in methanol (300 mL), anhydrous potassium carbonate (3.5 g) was added, and the mixture was stirred at room temperature for 2 hr. The reaction mixture was concentrated under reduced pressure, ethyl acetate (300 mL) was added to the obtained residue, and the mixture was washed with water (150 mL) and saturated brine (150 mL), and dried over anhydrous sodium sulfate. The insoluble material was filtered off, and the filtrate was concentrated under reduced pressure. The obtained residue was recrystallized from ethyl acetate (50 mL)/hexane (50 mL) to give the title compound (3.10 g, 44%) as a pale-brown powder.

$^1$H-NMR (DMSO-d$_6$, 300 MHz) δ 1.75 (6H, s), 7.26 (1H, dd, J=1.8, 8.7 Hz), 7.53-7.67 (2H, m), 7.72 (1H, d, J=1.8 Hz), 7.75-7.81 (1H, m), 7.87-7.95 (1H, m), 8.00 (1H, t, J=1.5 Hz), 10.55 (1H, s), 11.20 (1H, br s).

(iv) Production of 3-(1-cyano-1-methylethyl)-N-{4-cyano-3-[(5-nitropyridin-2-yl)oxy]
phenyl}benzamide To a solution of 2-chloro-5-nitropyridine (1.06 g, 6.68 mmol) and N-(4-cyano-3-hydroxyphenyl)-3-(1-cyano-1-methylethyl)benzamide (2.0 g, 6.55 mmol) in N,N-dimethylformamide (15 mL) was added potassium carbonate (1.35 g, 9.82 mmol), and the mixture was stirred at 80° C. for 20 hr. The reaction mixture was cooled to room temperature, the insoluble material was filtered off, and the filtrate was concentrated under reduced pressure. The obtained residue was diluted with ethyl acetate (300 mL), washed with water (150 mL) and saturated brine (150 mL×2), and dried over anhydrous sodium sulfate. The insoluble material was filtered off, and the filtrate was concentrated under reduced pressure. The obtained residue was purified by silica gel column chromatography (hexane/ethyl acetate=80/20→40/60), and further purified by basic silica gel column chromatography (hexane/ethyl acetate=70/30→0/100). The obtained solution was concentrated under reduced pressure to give the title compound (0.68 g, 24%) as a pale-yellow oil.

$^1$H-NMR (DMSO-d$_6$, 300 MHz) δ1.74 (6H, s), 7.53 (1H, d, J=9.1 Hz), 7.62 (1H, t, J=7.8 Hz), 7.79 (1H, ddd, J=0.9, 2.1, 7.8 Hz), 7.84 (1H, dd, J=1.8, 8.4 Hz), 7.91-8.00 (3H, m), 8.03 (1H, t, J=1.8 Hz), 8.73 (1H, dd, J=2.7, 9.1 Hz), 9.08 (1H, d, J=2.7 Hz), 10.86 (1H, br s).

(v) Production of N-{3-[(5-aminopyridin-2-yl)oxy]-4-cyanophenyl}-3-(1-cyano-1-methylethyl)benzamide To a solution of 3-(1-cyano-1-methylethyl)-N-{4-cyano-3-[(5-nitropyridin-2-yl)oxy]phenyl}benzamide (0.65 g, 1.59 mmol) in methanol (20 mL) was added 10% palladium-carbon (130 mg), and the mixture was stirred at room temperature for 20 hr under a hydrogen atmosphere (2.8 atm). The insoluble material was filtered off, and the filtrate was concentrated under reduced pressure to give the title compound (0.57 g, 90%) as a pale-yellow oil. This was used for the next reaction without further purification.

$^1$H-NMR (DMSO-d$_6$, 300 MHz) δ1.73 (6H, s), 5.31 (2H, br s), 6.96 (1H, d, J=8.4 Hz), 7.15 (1H, dd, J=3.0, 8.4 Hz), 7.53 (1H, d, J=1.8 Hz), 7.55-7.63 (2H, m), 7.68 (1H, dd, J=1.8, 8.7 Hz), 7.76 (1H, ddd, J=0.9, 1.8, 7.8 Hz), 7.79-7.84 (1H, m), 7.86-7.93 (1H, m), 7.97 (1H, t, J=1.8 Hz), 10.65 (1H, br s).

(vi) Production of N-{3-[(2-amino[1,3]thiazolo[5,4-b]pyridin-5-yl)oxy]-4-cyanophenyl}-3-(1-cyano-1-methylethyl)benzamide Potassium thiocyanate (536 mg, 5.52 mmol) was suspended in acetic acid (10 mL), and the mixture was stirred at room temperature for 10 min. A solution of N-{3-[(5-aminopyridin-2-yl)oxy]-4-cyanophenyl}-3-(1-cyano-1-methylethyl)benzamide (550 mg, 1.38 mmol) in acetic acid (10 mL) was added to the obtained solution, and the mixture was further stirred at room temperature for 10 min. A solution of bromine (242 mg, 1.51 mmol) in acetic acid (7 mL) was slowly added dropwise to the obtained solution. After the completion of the dropwise addition, the mixture was stirred at room temperature for 12 hr. The yielded yellow insoluble material was filtered off, and washed with acetic acid. The filtrate and the washing fluid were combined, and concentrated under reduced pressure. The obtained residue was suspended in ethyl acetate (100 mL), and the suspension was washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100). The obtained solution was concentrated under reduced pressure to give the title compound (0.51 g, 81%) as a pale-yellow amorphous substance.

$^1$H-NMR (DMSO-d$_6$, 300 MHz) δ1.73 (6H, s), 7.13 (1H, d, J=8.4 Hz), 7.59 (1H, t, J=7.8 Hz), 7.65 (1H, d, J=1.8 Hz), 7.70-7.85 (5H, m), 7.84-7.93 (2H, m), 7.98 (1H, t, J=1.8 Hz), 10.70 (1H, s).

(vii) Production of N-[4-cyano-3-({2-[(cyclopropylcarbonyl)amino][1,3]thiazolo[5,4-b]pyridin-5-yl}oxy)phenyl]-3-(1-cyano-1-methylethyl)benzamide To a solution of N-13-[(2-amino[1,3]thiazolo[5,4-b]pyridin-5-yl)oxy]-4-cyanophenyl}-3-(1-cyano-1-methylethyl) benzamide (190 mg, 0.418 mmol) in pyridine (4.0 mL) was added cyclopropanecarbonyl chloride (57 μL, 0.627 mmol), and the mixture was stirred at room temperature for 4 hr. Cyclopropanecarbonyl chloride (57 μL, 0.627 mmol) was further added to the reaction mixture, and the mixture was further stirred at room temperature for 12 hr. The reaction mixture was concentrated under reduced pressure, and the obtained residue was diluted with 10% tetrahydrofuran/ethyl acetate (100 mL), and washed with 5% aqueous sodium hydrogen carbonate solution (100 mL). The aqueous layer was extracted with 10% tetrahydrofuran/ethyl acetate (100 mL). The combined organic layer was washed with saturated brine (200 mL), and dried over anhydrous sodium sulfate. The insoluble material was filtered off, and the filtrate was concentrated under reduced pressure. The obtained residue was purified by silica gel column chromatography (hexane/ethyl acetate=60/40→20/80). The obtained solution was concentrated under reduced pressure. The residue was recrystallized from ethyl acetate to give the title compound (160 mg, 73%) as a colorless powder.

$^1$H-NMR (DMSO-d$_6$, 300 MHz) δ0.88-1.03 (4H, m), 1.73 (6H, s), 1.94-2.07 (1H, m), 7.35 (1H, d, J=8.7 Hz), 7.60 (1H, t, J=7.8 Hz), 7.72-7.85 (3H, m), 7.86-7.96 (2H, m), 7.99 (1H, t, J=1.8 Hz), 8.27 (1H, d, J=8.7 Hz), 10.74 (1H, s), 12.78 (1 H, br s).

Example C44

Production of 3-(1-cyano-1-methylethyl)-N-{4-cyano-3-[(2-{[(4-methylpiperazin-1-yl)acetyl]amino}[1,3]thiazolo[5,4-b]pyridin-5-yl)oxy]phenyl}benzamide

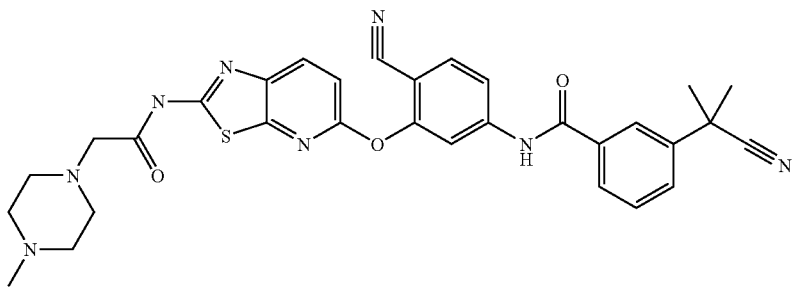 [SMILES: CN1CCN(CC(=O)Nc2nc3ccc(Oc4cc(NC(=O)c5cccc(C(C)(C)C#N)c5)ccc4C#N)nc3s2)CC1]

To a solution of N-{3-[(2-amino[1,3]thiazolo[5,4-b]pyridin-5-yl)oxy]-4-cyanophenyl}-3-(1-cyano-1-methylethyl)benzamide (150 mg, 0.330 mmol) produced in Example C43 (vi) in N,N-dimethylformamide (3.0 mL) was added chloroacetyl chloride (42 μL, 0.528 mmol), and the mixture was stirred at room temperature for 4 hr. Chloroacetyl chloride (21 μL, 0.264 mmol) was further added, and the mixture was stirred at room temperature for 12 hr. The reaction mixture was diluted with ethyl acetate (100 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure to give N-[3-({2-[(chloroacetyl)amino][1,3]thiazolo[5,4-b]pyridin-5-yl}oxy)-4-cyanophenyl]-3-(1-cyano-1-methylethyl)benzamide as a colorless solid.

N-[3-({2-[(Chloroacetyl)amino][1,3]thiazolo[5,4-b]pyridin-5-yl}oxy)-4-cyanophenyl]-3-(1-cyano-1-methylethyl)benzamide synthesized above was dissolved in tetrahydrofuran (3.0 mL), triethylamine (136 μL, 0.99 mmol) and 1-methylpiperazine (109 μL, 0.99 mmol) were added, and the mixture was stirred at 60° C. for 8 hr. The reaction mixture was cooled to room temperature, diluted with ethyl acetate (100 mL), washed with water (100 mL) and saturated brine (100 mL), and dried over anhydrous sodium sulfate. The insoluble material was filtered off, and the filtrate was concentrated under reduced pressure. The residue was purified by basic silica gel column chromatography (ethyl acetate/methanol=100/0→80/20), and the obtained solution was concentrated under reduced pressure. The residue was triturated with ethyl acetate/diisopropyl ether/hexane to give the title compound (93 mg, 47%) as a colorless solid.

$^1$H-NMR (DMSO-d$_6$, 300 MHz) δ1.73 (6H, s), 2.16 (3H, s), 2.25-2.45 (4H, m), 2.48-2.60 (6H, m), 7.36 (1H, d, J=8.7 Hz), 7.60 (1H, t, J=7.8 Hz), 7.74-7.85 (3H, m), 7.88-7.97 (2H, m), 7.99 (1H, t, J=1.8 Hz), 8.29 (1H, d, J=8.7 Hz), 10.75 (1H, s), 12.23 (1 H, br s).

Example C45

Production of 3-(1-cyano-1-methylethyl)-N-{3-[(2-{[(4-methylpiperazin-1-yl)acetyl]amino)[1,3]thiazolo[5,4-b]pyridin-5-yl)oxy]-4-(trifluoromethyl)phenyl}benzamide

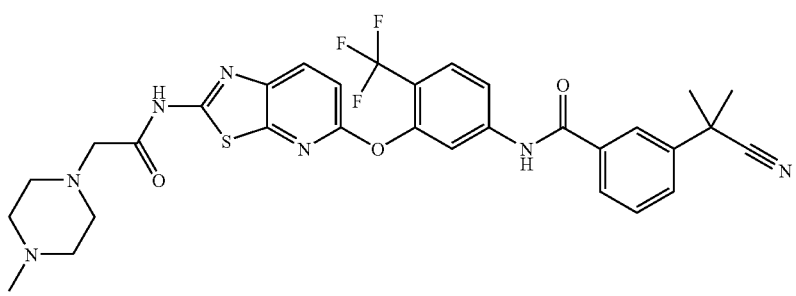 [SMILES: CN1CCN(CC(=O)Nc2nc3ccc(Oc4cc(NC(=O)c5cccc(C(C)(C)C#N)c5)ccc4C(F)(F)F)nc3s2)CC1]

(i) Production of 2-methoxy-4-nitro-1-(trifluoromethyl)benzene

To a solution of 1-bromo-2-methoxy-4-nitrobenzene (10.0 g, 43.0 mmol) in N,N-dimethylformamide (200 mL) were added potassium trifluoroacetate (13.0 g, 86.0 mmol), copper iodide(I) and toluene (40 mL), and the mixture was stirred at 155° C. for 20 hr while removing the produced water drops by a Dean-Stark trap. The reaction mixture was cooled to room temperature, and concentrated under reduced pressure. The residue was suspended in ethyl acetate (300 mL), the insoluble material was filtered off, and the filtrate was washed with water (150 mL) and saturated brine (150 mL), and dried over anhydrous sodium sulfate. The insoluble material was filtered off, and the filtrate was concentrated under reduced pressure. The obtained residue was purified by silica gel column chromatography (hexane/ethyl acetate=98/2→88/12). The obtained solution was concentrated under reduced pressure to give the title compound (6.86 g, 72%) as a pale-yellow oil.

$^1$H-NMR (DMSO-$d_6$, 300 MHz) δ 4.04 (3H, s), 7.92-7.96 (2H, m), 8.00 (1H, s).

(ii) Production of 5-nitro-2-(trifluoromethyl)phenol

To a solution of 2-methoxy-4-nitro-1-(trifluoromethyl) benzene (5.0 g, 22.6 mmol) in N,N-dimethylformamide (23 mL) was added lithium chloride (2.40 g, 56.5 mmol), and the mixture was stirred at 120° C. for 2 hr. The reaction temperature was heated to 155° C., and the mixture was further stirred for 12 hr. The reaction mixture was cooled to room temperature, diluted with ethyl acetate (150 mL)/hexane (75 mL), and washed with 1% aqueous citric acid solution (100 mL). The aqueous layer was extracted with ethyl acetate (50 mL)/hexane (25 mL), and the combined organic layer was washed with water (100 mL) and saturated brine (100 mL×2), and dried over anhydrous sodium sulfate. The insoluble material was filtered off, and the filtrate was concentrated under reduced pressure. The obtained residue was purified by silica gel column chromatography (hexane/ethyl acetate=98/2→90/10). The obtained solution was concentrated under reduced pressure to give the title compound (2.22 g, 47%) as a yellow oil.

$^1$H-NMR (DMSO-$d_6$, 300 MHz) δ 7.69-7.87 (3H, m) 11.73 (1H, br s).

(iii) Production of 5-amino-2-(trifluoromethyl)phenol

To a solution of 5-nitro-2-(trifluoromethyl)phenol (2.22 g, 10.7 mmol) in methanol (30 mL) was added 10% palladium-carbon (440 mg), and the mixture was stirred at room temperature for 8 hr under a hydrogen atmosphere (1 atm). The insoluble material was filtered off, and the filtrate was concentrated under reduced pressure. The obtained residue was crystallized from ethyl acetate/hexane to give the title compound (1.59 g, 84%) as a pale-brown solid.

$^1$H-NMR (DMSO-d6, 300 MHz) δ 5.60 (2H, s), 6.04 (1H, dd, J=1.5, 8.4 Hz), 6.13 (1H, d, J=1.5 Hz), 7.06 (1H, d, J=8.4 Hz), 9.82 (1H, br s).

(iv) Production of 3-(1-cyano-1-methylethyl)-N-[3-hydroxy-4-(trifluoromethyl)phenyl]benzamide To a solution of 3-(1-cyano-1-methylethyl)benzoic acid (1.75 g, 9.30 mmol) produced in Example C6(ii) in tetrahydrofuran (20 mL) were added oxalyl chloride (0.943 mL, 11.0 mmol) and N,N-dimethylformamide (20 μL), and the mixture was stirred at room temperature for 1 hr. The reaction mixture was concentrated under reduced pressure to give 3-(1-cyano-1-methylethyl)benzoyl chloride as a pale-yellow oil.

To a two-layer solution of 5-amino-2-(trifluoromethyl) phenol (1.50 g, 8.46 mmol) in tetrahydrofuran (25 mL)/1N aqueous sodium hydrogen carbonate solution (25 mL) was added a solution of 3-(1-cyano-1-methylethyl)benzoyl chloride synthesized above in tetrahydrofuran (15 mL), and the mixture was stirred at room temperature for 4 hr. The aqueous layer was separated, and extracted with ethyl acetate (200 mL). The combined organic layer was washed with saturated brine (200 mL), and dried over anhydrous sodium sulfate. The insoluble material was filtered off, and the filtrate was concentrated under reduced pressure. The obtained residue was triturated with ethyl acetate/hexane to give the title compound (2.03 g, 69%) as a colorless powder.

$^1$H-NMR (DMSO-$d_6$, 300 MHz) δ1.75 (6H, s), 7.25 (1H, dd, J=1.2, 8.7 Hz), 7.48 (1H, d, J=8.7 Hz), 7.61 (1H, t, J=7.8 Hz), 7.71 (1H, br s), 7.77 (1H, ddd, J=1.2, 1.8, 7.8 Hz), 7.93 (1H, dd, J=1.2, 9.0 Hz), 8.02 (1H, t, J=1.8 Hz), 10.49 (1H, s), 10.62 (1H, br s).

(v) Production of 3-(1-cyano-1-methylethyl)-N-{3-[(5-nitropyridin-2-yl)oxy]-4-(trifluoromethyl)phenyl}benzamide To a solution of 2-chloro-5-nitropyridine (2.00 g, 5.74 mmol) and 3-(1-cyano-1-methylethyl)-N-[3-hydroxy-4-(trifluoromethyl)phenyl]benzamide (955 mg, 6.02 mmol) in N,N-dimethylformamide (15 mL) was added potassium carbonate (1.18 g, 8.61 mmol), and the mixture was stirred at 80° C. for 20 hr. After the reaction mixture was cooled to room temperature, water (150 mL) was added, and the mixture was twice extracted with ethyl acetate/hexane (75 mL/75 mL). The combined organic layer was washed with saturated brine (150 mL), and dried over anhydrous sodium sulfate. The insoluble material was filtered off, and the filtrate was concentrated under reduced pressure. The obtained residue was purified by silica gel column chromatography (hexane/ethyl acetate=80/20→30/70). The obtained solution was concentrated under reduced pressure to give the title compound (1.79 g, 66%) as a yellow amorphous substance.

$^1$H-NMR (DMSO-$d_6$, 300 MHz) δ1.75 (6H, s), 7.44 (1H, dd, J=0.6, 9.0 Hz), 7.62 (1H, t, J=7.8 Hz), 7.79 (1H, ddd, J=0.9, 2.1, 7.8 Hz), 7.87 (2H, d, J=0.9 Hz), 7.91-7.99 (2H, m), 8.04 (1H, t, J=1.8 Hz), 8.69 (1H, dd, J=2.8, 9.0 Hz), 9.07 (1H, d, J=2.8 Hz), 10.74 (1H, br s).

(vi) Production of N-{3-[(5-aminopyridin-2-yl)oxy]-4-(trifluoromethyl)phenyl}-3-(1-cyano-1-methylethyl)benzamide To a solution of 3-(1-cyano-1-methylethyl)-N-{3-[(5-nitropyridin-2-yl)oxy]-4-(trifluoromethyl)phenyl}benzamide (1.78 g, 3.78 mmol) in methanol (50 mL) was added 10% palladium-carbon powder (350 mg), and the mixture was stirred at room temperature for 11 hr under a hydrogen atmosphere of 2.4 atm. 10% Palladium-carbon powder was filtered off by celite filtration, and the filtrate was concentrated under reduced pressure to give the title compound (1.44 g, 87%) as a brown amorphous substance.

$^1$H-NMR (DMSO-$d_6$, 300 MHz) δ1.73 (6H, s), 5.24 (2H, s), 6.87 (1H, d, J=8.4 Hz), 7.13 (1H, dd, J=3.0, B.4 Hz), 7.48-7.65 (3H, m), 7.67-7.82 (3H, m), 7.91 (1H, dt, J=7.8, 1.2 Hz), 7.99 (1H, t, J=1.8 Hz), 10.58 (1H, br s).

(vii) Production of N-{3-[(5-aminopyridin-2-yl)oxy]-4-(trifluoromethyl)phenyl}-3-(1-cyano-1-methylethyl)benzamide Potassium thiocyanate (1.25 g, 12.9 mmol) was suspended in acetic acid (25 mL), and the mixture was stirred at room temperature for 10 min. A solution of N-{3-[(5-aminopyridin-2-yl)oxy]-4-(trifluoromethyl)phenyl}-3-(1-cyano-1-methylethyl)benzamide (1.42 g, 3.22 mmol) in acetic acid (25 mL) was added to the obtained solution, and the mixture was further stirred at room temperature for 10 min. A solution of bromine (566 mg, 3.54 mmol) in acetic acid (20 mL) was slowly added dropwise to the obtained solution. After the completion of the dropwise addition, the mixture was stirred at room temperature for 6 hr. The yielded yellow insoluble material was filtered off, and washed with acetic acid. The filtrate and the washing fluid were combined, and concentrated under reduced pressure. The obtained residue was dissolved in ethyl acetate (150 mL), washed with 5% aqueous sodium hydrogen carbonate solution (150 mL) and saturated brine (150 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100). The obtained solution was concentrated under reduced pressure to give the title compound (1.50 g, 94%) as a pale-yellow amorphous substance.

$^1$H-NMR (DMSO-d$_6$, 300 MHz) δ1.73 (6H, s), 7.03 (1H, d, J=8.4 Hz), 7.59 (1H, t, J=7.8 Hz), 7.64 (1H, br s), 7.70 (2H, s), 7.73-7.83 (4H, m), 7.91 (1H, ddd, J=1.2, 1.5, 7.8 Hz), 7.99 (1H, t, J=1.8 Hz), 10.61 (1H, s).

(viii) Production of 3-(1-cyano-1-methylethyl)-N-{3-[(2-{[(4-methylpiperazin-1-yl)acetyl]amino}[1,3]thiazolo[5,4-b]pyridin-5-yl)oxy]-4-(trifluoromethyl)phenyl}benzamide To a solution of N-{3-[(5-aminopyridin-2-yl)oxy]-4-(trifluoromethyl)phenyl}-3-(1-cyano-1-methylethyl)benzamide (200 mg, 0.402 mmol) in N,N-dimethylformamide (3.0 mL) was added chloroacetyl chloride (64 μL, 0.804 mmol), and the mixture was stirred at room temperature for 2 hr. The reaction mixture was diluted with ethyl acetate (50 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure to give N-[3-({2-[(chloroacetyl)amino][1,3]thiazolo[5,4-b]pyridin-5-yl}oxy)-4-(trifluoromethyl)phenyl]-3-(1-cyano-1-ethylethyl)benzamide as a colorless solid.

N-[3-({2-[(Chloroacetyl)amino][1,3]thiazolo[5,4-b]pyridin-5-yl}oxy)-4-(trifluoromethyl)phenyl]-3-(1-cyano-1-methylethyl)benzamide produced above was dissolved in tetrahydrofuran (3.0 mL), triethylamine (165 μL, 1.20 mmol) and 1-methylpiperazine (133 μL, 1.20 mmol) were added, and the mixture was stirred at 60° C. for 4 hr. The reaction mixture was cooled to room temperature, diluted with ethyl acetate (50 mL), washed with water (50 mL) and saturated brine (50 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concentrated under reduced pressure. The residue was triturated with ethyl acetate/diisopropyl ether to give the title compound (85 mg, 33%) as a colorless solid.

$^1$H-NMR (DMSO-d$_6$, 300 MHz) δ1.73 (6H, s), 2.15 (3H, s), 2.25-2.41 (4H, m), 2.43-2.61 (6H, m), 7.25 (1H, d, J=8.7 Hz), 7.59 (1H, t, J=7.8 Hz), 7.72-7.88 (4H, m), 7.92 (1H, ddd, J=1.2, 1.5, 7.8 Hz), 8.00 (1H, t, J=1.8 Hz), 8.24 (1H, d, J=8.7 Hz), 10.66 (1H, s), 12.18 (1H, br s).

Example C46

Production of tert-butyl [3-({2-[(clopropylcarbonyl)amino][1,3]thiazolo[5,4-b]pyridin-5-yl}oxy)-4-methylphenyl]carbamate

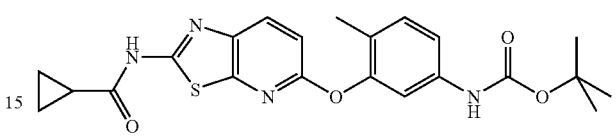

(i) Production of tert-butyl (3-hydroxy-4-methylphenyl)carbamate

To a solution of 3-amino-6-methylphenol (22.0 g, 178 mmol) in tetrahydrofuran (800 mL) was added di-tert-butyl bicarbonate (39.7 g, 182 mmol), and the mixture was stirred at room temperature for 12 hr. The reaction mixture was diluted with ethyl acetate (400 mL), washed with water (400 mL), and dried over anhydrous sodium sulfate. The insoluble material was filtered off, and the filtrate was concentrated under reduced pressure to give the title compound (37.1 g, 94%) as a colorless solid. This was used for the next reaction without further purification.

$^1$H-NMR (DMSO-d$_6$, 300 MHz) δ 1.46 (9H, s), 2.01 (3H, s), 6.70 (1H, dd, J=1.8, 8.4 Hz), 6.86 (1H, d, J=8.4 Hz), 7.07 (1H, d, J=1.8 Hz), 9.08 (1 H, s), 9.15 (1 H, s).

(ii) Production of tert-butyl {4-methyl-3-[(5-nitropyridin-2-yl)oxy]phenyl}carbamate To a solution of 2-chloro-5-nitropyridine (15.0 g, 94.5 mmol) and tert-butyl (3-hydroxy-4-methylphenyl)carbamate (20.0 g, 90.0 mmol) in N,N-dimethylformamide (200 mL) was added potassium carbonate (18.6 g, 135 mmol), and the mixture was stirred at 70° C. for 18 hr. The reaction mixture was cooled to room temperature, the insoluble material was filtered off, and the filtrate was concentrated under reduced pressure. Water (400 mL) was added to the obtained residue, and the mixture was extracted with ethyl acetate (400 mL×2). The combined organic layer was washed with saturated brine (300 mL×2), and dried over anhydrous magnesium sulfate. The insoluble material was filtered off, and the filtrate was concentrated under reduced pressure. The obtained residue was purified by basic silica gel column chromatography (ethyl acetate), and the obtained solution was concentrated under reduced pressure. The residue was triturated with hexane to give the title compound (28.6 g, 92%) as a pale-yellow solid.

$^1$H-NMR (DMSO-d$_6$, 300 MHz) δ1.45 (9H, s), 1.98 (3H, s), 7.16-7.28 (3H, m), 7.33 (1H, s), 8.62 (1H, dd, J=2.7, 9.0 Hz), 9.02 (1H, d, J=2.7 Hz), 9.45 (1H, s).

(iii) Production of tert-butyl {3-[(5-aminopyridin-2-yl)oxy]-4-methylphenyl}carbamate To a solution of tert-butyl {4-methyl-3-[(5-nitropyridin-2-yl)oxy]phenyl}carbamate (2.20 g, 6.37 mmol) in methanol (50 mL)/N-methylpyrrolidone (10 mL) was added 10% palladium-carbon powder (440 mg), and the mixture was stirred at room temperature for 4 hr under a hydrogen atmosphere (3.0 atm). 10% Palladium-carbon powder was filtered off by celite filtration, and water (20 mL) was added to the filtrate. The obtained precipitate was collected by filtration, and repeatedly washed with water to give the title compound (1.87 g, 93%) as a pale-gray powder.

$^1$H-NMR (DMSO-$d_6$, 300 MHz) δ1.43 (9H, s), 2.03 (3H, s), 5.00 (2H, s), 6.69 (1H, d, J=8.7 Hz), 6.93-7.17 (4H, m), 7.48 (1H, d, J=2.4 Hz), 9.24 (1H, br s).

(iv) Production of tert-butyl {3-[(2-amino[1,3]thiazolo[5,4-b]pyridin-5-yl)oxy]-4-methylphenyl}carbamate Potassium thiocyanate (1.23 g, 12.7 mmol) was suspended in acetic acid (25 mL), and the mixture was stirred at room temperature for 10 min. A solution of tert-butyl {3-[(5-aminopyridin-2-yl)oxy]-4-methylphenyl}carbamate (1.00 g, 3.17 mmol) in acetic acid (25 mL) was added to the obtained solution, and the mixture was further stirred at room temperature for 10 min. A solution of bromine (531 mg, 3.32 mmol) in acetic acid (20 mL) was slowly added dropwise to the obtained solution. After the completion of the dropwise addition, the mixture was stirred at room temperature for 22 hr. The yielded yellow insoluble material was filtered off, and washed with acetic acid. The filtrate and the washing fluid were combined, and concentrated under reduced pressure. The obtained residue was dissolved in ethyl acetate (50 mL), and the solution was washed with water (50 mL), 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (ethyl acetate), and the obtained solution was concentrated under reduced pressure to give the title compound (0.97 g, 82%) as a colorless powder.

$^1$H-NMR (DMSO-$d_6$, 300 MHz) δ1.44 (9H, s), 2.03 (3H, s), 6.83 (1H, d, J=8.7 Hz), 7.09-7.23 (3H, m), 7.57 (2H, s), 7.70 (1H, d, J=8.7 Hz), 9.33 (1H, br s).

(v) Production of tent-butyl [3-({2-[(cyclopropylcarbonyl)amino][1,3]thiazolo[5,4-b]pyridin-5-yl}oxy)-4-methylphenyl]carbamate To a solution of tert-butyl {3-[(2-amino[1,3]thiazolo[5,4-b]pyridin-5-yl)oxy]-4-methylphenyl}carbamate (800 mg, 2.14 mmol) in pyridine (10 mL) was added cyclopropanecarbonyl chloride (390 μL, 4.29 mmol), and the mixture was stirred at room temperature for 1 hr. The reaction mixture was diluted with methanol (20 mL), anhydrous sodium carbonate (1.0 g, 9.43 mmol) was added, and the mixture was stirred at room temperature for 6 hr. The insoluble material was filtered off, and the filtrate was concentrated under reduced pressure. The obtained residue was diluted with ethyl acetate (100 mL)/tetrahydrofuran (10 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was triturated with ethyl acetate and diisopropyl ether to give the title compound (880 mg, 93%) as a pale-yellow powder.

$^1$H-NMR (DMSO-$d_6$, 300 MHz) δ 0.89-0.99 (4H, m), 1.44 (9H, s), 1.88-2.07 (4H, m), 7.04 (1H, d, J=8.7 Hz), 7.14-7.28 (3H, m), 8.13 (1H, d, J=8.7 Hz), 9.37 (1H, s), 12.66 (1H, br s).

Example C47

Production of 3-tert-butoxy-N-[3-({2-[(cyclopropylcarbonyl)amino][1,3]thiazolo[5,4-b]pyridin-5-yl}oxy)-4-methylphenyl]benzamide

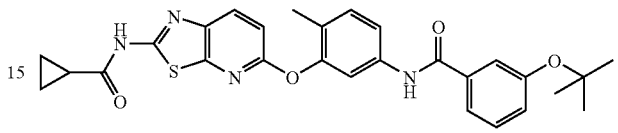

(i) Production of N-[5-(5-amino-2-methylphenoxy)[1,3]thiazolo[5,4-b]pyridin-2-yl]cyclopropanecarboxamide To tert-butyl [3-({2-[(cyclopropylcarbonyl)amino][1,3]thiazolo[5,4-b]pyridin-5-yl}oxy)-4-methylphenyl]carbamate (0.80 g, 1.82 mmol) produced in Example C46(v) were added anisole (0.5 mL) and trifluoroacetic acid (5.0 mL) at 4° C. to give a solution, and the solution was stirred at the same temperature for 2 hr. The reaction mixture was concentrated under reduced pressure, saturated aqueous sodium hydrogen carbonate solution (80 mL) was added to the obtained oily residue, and the mixture was extracted with ethyl acetate (80 mL)/tetrahydrofuran (8 mL). The organic layer was washed with saturated brine (80 mL), and dried over anhydrous sodium sulfate. The insoluble material was filtered off, and the filtrate was concentrated under reduced pressure. The obtained residue was purified by basic silica gel column chromatography (ethyl acetate), and the obtained solution was concentrated under reduced pressure. The residue was triturated with hexane to give the title compound (525 mg, 85%) as a colorless powder.

$^1$H-NMR (DMSO-$d_6$, 300 MHz) δ0.85-1.01 (4H, m), 1.89-2.09 (4H, m), 5.01 (2H, s), 6.25 (1H, d, J=2.4 Hz), 6.38 (1H, dd, J=2.4, 8.1 Hz), 6.84-7.03 (2H, m), 8.08 (1H, d, J=8.7 Hz), 12.62 (1H, br s).

(ii) Production of 3-tert-butoxy-N-[3-({2-[(cyclopropylcarbonyl)amino][1,3]thiazolo[5,4-b]pyridin-5-yl}oxy)-4-methylphenyl]benzamide To a solution of 3-tert-butoxybenzoic acid (64 mg, 0.330 mmol) in pyridine (3.0 mL) was added O-(7-azabenzotriazol-1-yl)-N,N,N',N'-tetramethyluronium hexafluorophosphate (125 mg, 0.330 mmol), and the mixture was stirred at room temperature for 10 min. N-[5-(5-Amino-2-methylphenoxy)[1,3]thiazolo[5,4-b]pyridin-2-yl]cyclopropanecarboxamide (102 mg, 0.30 mmol) was added to the obtained solution, and the mixture was stirred at 70° C. for 4 hr. The reaction mixture was concentrated under reduced pressure, and the obtained residue was diluted with ethyl acetate (100 mL)/tetrahydrofuran (10 mL), washed with 1% aqueous citric acid solution (100 mL), 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was triturated with diisopropyl ether to give the title compound (88 mg, 57%) as a colorless powder.

¹H-NMR (DMSO-d₆, 300 MHz) δ0.88-0.99 (4H, m), 1.32 (9H, s), 1.93-2.05 (1H, m), 2.09 (3H, s), 7.11 (1H, d, J=8.7 Hz), 7.16-7.22 (1H, m), 7.27-7.34 (1H, m), 7.42 (1H, t, J=8.1 Hz), 7.49 (1H, t, J=1.8 Hz), 7.54-7.61 (2H, m), 7.61-7.67 (1H, m), 8.17 (1H, d, J=8.7 Hz), 10.23 (1H, s), 12.67 (1H, br s).

Example C48

Production of N-[3-({2-[(cyclopropylcarbonyl)amino][1,3]thiazolo[5,4-b]pyridin-5-yl}oxy)-4-methylphenyl]-3-(trifluoromethoxy)benzamide

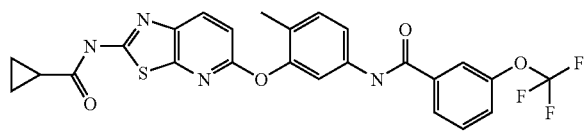 [SMILES: Cc1ccc(NC(=O)c2cccc(OC(F)(F)F)c2)cc1Oc1ccc2nc(NC(=O)C3CC3)sc2n1]

To a solution of 3-(trifluoromethoxy)benzoic acid (37.5 mg, 0.185 mmol) in pyridine (2.0 mL) was added O-(7-azabenzotriazol-1-yl)-N,N,N',N'-tetramethyluronium hexafluorophosphate (70 mg, 0.185 mmol), and the mixture was stirred at room temperature for 10 min. N-[5-(5-Amino-2-methylphenoxy)[1,3]thiazolo[5,4-b]pyridin-2-yl]cyclopropanecarboxamide (60 mg, 0.176 mmol) produced in Example C47(i) was added to the obtained solution, and the mixture was stirred at 70° C. for 20 hr. After the reaction mixture was cooled to room temperature, water (2 mL) was added, and the obtained yellow precipitate was collected by filtration, washed with water and ethyl acetate, and dried to give the title compound (48.5 mg, 52%) as a yellow powder.

¹H-NMR (DMSO-d₆, 300 MHz) δ0.80-1.05 (4H, m), 1.94-2.05 (1H, m), 2.11 (3H, s), 7.12 (1H, d, J=8.7 Hz), 7.32 (1H, d, J=7.8 Hz), 7.52-7.63 (3H, m), 7.67 (1H, t, J=7.8 Hz), 7.88 (1H, s), 7.98 (1H, dt, J=7.8, 1.2 Hz), 8.17 (1H, d, J=8.7 Hz), 10.39 (1H, s), 12.66 (1H, br s).

Example C49

Production of N-[3-({2-[(cyclopropylcarbonyl)amino][1,3]thiazolo[5,4-b]pyridin-5-yl}oxy)-4-methylphenyl]-3-(1,1,2,2-tetrafluoroethoxy)benzamide

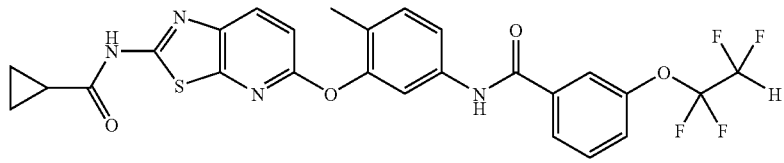 [SMILES: Cc1ccc(NC(=O)c2cccc(OC(F)(F)C(F)F)c2)cc1Oc1ccc2nc(NC(=O)C3CC3)sc2n1]

To a solution of 3-(1,1,2,2-tetrafluoroethoxy)benzoic acid (44 mg, 0.185 mmol) in pyridine (2.0 mL) was added O-(7-azabenzotriazol-1-yl)-N,N,N',N'-tetramethyluronium hexafluorophosphate (70 mg, 0.185 mmol), and the mixture was stirred at room temperature for 10 min. N-[5-(5-Amino-2-methylphenoxy)[1,3]thiazolo[5,4-b]pyridin-2-yl]cyclopropanecarboxamide (60 mg, 0.176 mmol) produced in Example C47(i) was added to the obtained solution, and the mixture was stirred at 70° C. for 20 hr. After the reaction mixture was cooled to room temperature, water (2 mL) was added, and the obtained precipitate was collected by filtration, washed with water and ethyl acetate, and dried to give the title compound (55 mg, 56%) as a colorless powder.

¹H-NMR (DMSO-d₆, 300 MHz) δ0.87-1.01 (4H, m), 1.92-2.04 (1H, m), 2.10 (3H, s), 6.84 (1H, tt, J=3.0, 51.8 Hz), 7.11 (1H, d, J=8.7 Hz), 7.32 (1H, d, J=8.1 Hz), 7.46-7.54 (1H, m), 7.54-7.68 (3H, m), 7.81 (1H, s), 7.91-8.00 (1H, m), 8.16 (1H, d, J=8.7 Hz), 10.38 (1H, s), 12.67 (1H, br s).

Example C50

Production of N-[4-chloro-3-({2-[(cyclopropylcarbonyl)amino][1,3]thiazolo[5,4-b]pyridin-5-yl}oxy)phenyl]-3-(1-cyano-1-methylethyl)benzamide

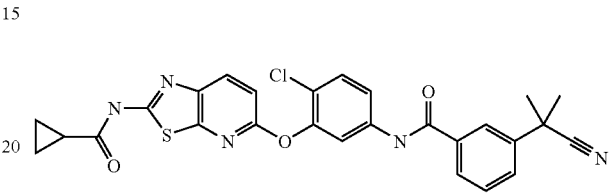

(i) Production of 5-amino-2-chlorophenol

A suspension of 2-chloro-5-nitrophenol (25.0 g, 144 mmol), calcium chloride (40 g, 360 mmol) and reduced iron (40.2 g, 720 mmol) in ethanol (500 mL)/water (50 mL) was stirred with heating at 90° C. for 4 hr. After the reaction mixture was cooled to room temperature, the insoluble material was filtered off through a pad filled with celite, and washed with ethanol. The filtrate and the washing fluid were combined, and concentrated under reduced pressure. The obtained residue was diluted with ethyl acetate (400 mL), washed with water (250 mL×2), 5% aqueous sodium hydrogen carbonate solution (250 mL×2) and saturated brine (250 mL), and dried over anhydrous sodium sulfate. The insoluble material was filtered off, and the filtrate was concentrated under reduced pressure to give the title compound (19.1 g, 92%) as a brown powder. This was used for the next reaction without further purification.

¹H-NMR (DMSO-d₆, 300 MHz) δ5.06 (2H, br s), 6.01 (1H, dd, J=2.6, 8.5 Hz), 6.19 (1H, d, J=2.6 Hz), 6.87 (1H, d, J=8.5 Hz), 9.52 (1H, br s).

(ii) Production of N-(4-chloro-3-hydroxyphenyl)-3-(1-cyano-1-methylethyl)benzamide To a solution of 3-(1-cyano-1-methylethyl)benzoic acid (4.2 g, 22.2 mmol) produced in Example C6(ii) in tetrahydrofuran (44 mL) were added oxalyl chloride (2.28 mL, 28.2 mmol) and N,N-dimethylformamide (20 μL), and the mixture was stirred at room temperature for 1 hr. The reaction mixture was concentrated under reduced pressure to give 3-(1-cyano-1-methylethyl)benzoyl chloride as a pale-yellow oil.

To a two-layer solution of 5-amino-2-chlorophenol (3.19 g, 22.2 mmol) in tetrahydrofuran (50 mL)/1N aqueous sodium hydrogen carbonate solution (66 mL) was added a solution of 3-(1-cyano-1-methylethyl)benzoyl chloride synthesized above in tetrahydrofuran (16 mL), and the mixture was stirred at room temperature for 6 hr. The aqueous layer was separated, and extracted with ethyl acetate (66 mL). The combined organic layer was washed with 5% aqueous sodium hydrogen carbonate solution (100 mL) and saturated brine (100 mL), and dried over anhydrous sodium sulfate. The insoluble material was filtered off, the filtrate was concentrated under reduced pressure, and the obtained residue was triturated with ethyl acetate/hexane to give the title compound (6.65 g, 95%) as a colorless powder.

$^1$H-NMR (DMSO-d$_6$, 300 MHz) δ1.75 (6H, s), 7.16 (1H, dd, J=2.5, 8.7 Hz), 7.28 (1H, d, J=8.7 Hz), 7.52-7.65 (2H, m), 7.69-7.79 (1H, m), 7.91 (1H, dt, J=7.8, 1.2 Hz), 8.00 (1H, t, J=1.8 Hz), 10.30 (2H, br s).

(iii) Production of N-{4-chloro-3-[(5-nitropyridin-2-yl)oxy]phenyl}-3-(1-cyano-1-methylethyl)benzamide To a solution of 2-chloro-5-nitropyridine (1.00 g, 6.35 mmol) and N-(4-chloro-3-hydroxyphenyl)-3-(1-cyano-1-methylethyl)benzamide (2.00 g, 6.35 mmol) in N,N-dimethylformamide (15 mL) was added potassium carbonate (1.31 g, 9.52 mmol), and the mixture was stirred at 70° C. for 16 hr. The reaction mixture was cooled to room temperature, the insoluble material was filtered off, and the filtrate was concentrated under reduced pressure. Water (100 mL) was added to the obtained residue, and the mixture was twice extracted with ethyl acetate (50 mL)/hexane (50 mL). The combined organic layer was washed with water (150 mL) and saturated brine (150 mL), and dried over anhydrous sodium sulfate. The insoluble material was filtered off, the filtrate was concentrated under reduced pressure, and the obtained residue was purified by basic silica gel column chromatography (ethyl acetate). The obtained solution was concentrated under reduced pressure to give the title compound (2.57 g, 93%) as a yellow oil.

$^1$H-NMR (DMSO-d$_6$, 300 MHz) δ1.75 (6H, s), 7.42 (1H, d, J=9.1 Hz), 7.54-7.68 (2H, m), 7.69-7.81 (2H, m), 7.88-7.98 (2H, m), 8.03 (1H, t, J=1.8 Hz), 8.69 (1H, dd, J=2.7, 9.1 Hz), 9.05 (1H, d, J=2.7 Hz), 10.59 (1H, br s).

(iv) Production of N-{3-[(5-aminopyridin-2-yl)oxy]-4-chlorophenyl}-3-(1-cyano-1-methylethyl)benzamide A suspension of N-{4-chloro-3-[(5-nitropyridin-2--yl)oxy]phenyl}-3-(1-cyano-1-methylethyl)benzamide (2.5 g, 5.72 mmol), calcium chloride (2.00 g, 17.2 mmol) and reduced iron (1.43 g, 25.7 mmol) in ethanol (35 mL)/water (5 mL) was stirred with heating at 90° C. for 4 hr. After the reaction mixture was cooled to room temperature, the insoluble material was filtered off through a pad filled with celite, and washed with ethyl acetate. The filtrate and the washing fluid were combined, and concentrated under reduced pressure. The obtained residue was diluted with ethyl acetate (100 mL), washed with water (50 mL×2), 5% aqueous sodium hydrogen carbonate solution (50 mL×2) and saturated brine (50 mL), and dried over anhydrous sodium sulfate. The insoluble material was filtered off, and the filtrate was concentrated under reduced pressure. The obtained residue was purified by basic silica gel column chromatography (ethyl acetate), and the obtained solution was concentrated under reduced pressure to give the title compound (1.45 g, 62%) as a beige amorphous substance.

$^1$H-NMR (DMSO-d$_6$, 300 MHz) δ1.73 (6H, s), 5.13 (2H, s), 6.85 (1H, d, J=8.7 Hz), 7.11 (1H, dd, J=3.0, 8.7 Hz), 7.44-7.65 (5H, m), 7.71-7.79 (1H, m), 7.86-7.93 (1H, m), 7.99 (1H, t, J=1.7 Hz), 10.41 (1H, s).

(v) Production of N-{3-[(2-amino[1,3]thiazolo[5,4-b]pyridin-5-yl)oxy]-4-chlorophenyl}-3-(1-cyano-1-methylethyl)benzamide Potassium thiocyanate (1.33 g, 13.7 mmol) was suspended in acetic acid (30 mL), and the mixture was stirred at room m temperature for 10 min. N-{3-[(5-Aminopyridin-2-yl)oxy]-4-chlorophenyl}-3-(1-cyano-1-methylethyl)benzamide (1.40 g, 3.44 mmol) was added to the obtained solution, and the mixture was further stirred at room temperature for 10 min. A solution of bromine (576 mg, 3.61 mmol) in acetic acid (10 mL) was slowly added dropwise to the obtained solution. After the completion of the dropwise addition, the mixture was stirred at room temperature for 12 hr. The yielded yellow insoluble material was filtered off, and washed with acetic acid. The filtrate and the washing fluid were combined, and concentrated under reduced pressure. The obtained residue was dissolved in ethyl acetate (200 mL), and the solution was washed with saturated aqueous sodium hydrogen carbonate solution (200 mL×2), water (200 mL) and saturated brine (200 mL), and dried over anhydrous sodium sulfate. The insoluble material was filtered off, and the filtrate was concentrated under reduced pressure. The obtained residue was purified by basic silica gel column chromatography (ethyl acetate), and the obtained solution was concentrated under reduced pressure to give the title compound (1.58 g, 99%) as a yellow amorphous substance.

$^1$H-NMR (DMSO-d$_6$, 300 MHz) δ 1.74 (6H, s), 7.00 (1H, d, J=8.5 Hz), 7.48-7.81 (8H, m), 7.91 (1H, d, J=7.7 Hz), 8.00 (1H, s), 10.47 (1H, s).

(vi) Production of N-[4-chloro-3-({2-[(cyclopropylcarbonyl)amino][1,3]thiazolo[5,4-b]pyridin-5-yl}oxy)phenyl]-3-(1-cyano-1-methylethyl)benzamide To a solution of N-{3-[(2-amino[1,3]thiazolo[5,4-b]pyridin-5-yl)oxy]-4-chlorophenyl}-3-(1-cyano-1-methylethyl) benzamide (464 mg, 1.00 mmol) in pyridine (10 mL) was added cyclopropanecarbonyl chloride (181 μL, 2.00 mmol), and the mixture was stirred at room temperature for 12 hr. The reaction mixture was concentrated under reduced pressure, and the residue was diluted with ethyl acetate (50 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=60/40→0/100), and the obtained solution was concentrated under reduced pressure. The residue was crystallized from ethyl acetate/hexane to give the title compound (246 mg, 46%) as a colorless powder.

$^1$H-NMR (DMSO-d$_6$, 300 MHz) δ0.89-1.01 (4H, m), 1.74 (6H, s), 1.92-2.03 (1H, m), 7.21 (1H, d, J=8.7 Hz), 7.54-7.63 (2H, m), 7.67-7.78 (2H, m), 7.80 (1H, d, J=2.4 Hz), 7.91 (1H, dt, J=7.9, 1.2 Hz), 8.01 (1H, t, J=1.8 Hz), 8.19 (1H, d, J=8.7 Hz), 10.51 (1H, s), 12.69 (1H, br s).

Example C51

Production of N-{4-chloro-3-[(2-{[(4-methylpiperazin-1-yl)acetyl]amino}[1,3]thiazolo[5,4-b]pyridin-5-yl)oxy]phenyl}-3-(1-cyano-1-methylethyl)benzamide

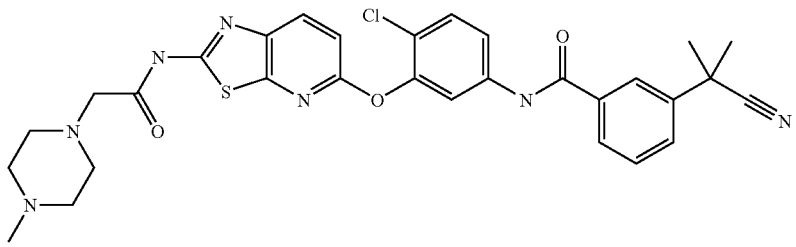 [SMILES: CN1CCN(CC(=O)Nc2nc3ccc(Oc4cc(NC(=O)c5cccc(C(C)(C)C#N)c5)ccc4Cl)nc3s2)CC1]

To a solution of N-{3-[(2-amino[1,3]thiazolo[5,4-b]pyridin-5-yl)oxy]-4-chlorophenyl}-3-(1-cyano-1-methylethyl)benzamide (200 mg, 0.431 mmol) produced in Example C50 (v) in N,N-dimethylacetamide (3.0 mL) was added chloroacetyl chloride (75.4 µL, 0.948 mmol), and the mixture was stirred at room temperature for 4 hr. The reaction mixture was diluted with ethyl acetate (20 mL), washed with 5% aqueous sodium hydrogen carbonate solution (20 mL) and saturated brine (20 mL), and dried over anhydrous sodium sulfate. The insoluble material was filtered off, and the filtrate was concentrated under reduced pressure to give N-[4-chloro-3-({2-[(chloroacetyl)amino][1,3]thiazolo[5,4-b]pyridin-5-yl}oxy)phenyl]-3-(1-cyano-1-methylethyl)benzamide as an oily residue.

N-[4-Chloro-3-({2-[(chloroacetyl)amino][1,3]thiazolo[5,4-b]pyridin-5-yl}oxy)phenyl]-3-(1-cyano-1-methylethyl)benzamide synthesized above was dissolved in tetrahydrofuran (3.0 mL), triethylamine (178 µL, 1.29 mmol) and 1-methylpiperazine (143 µL, 1.29 mmol) were added, and the mixture was stirred at 60° C. for 4 hr. The reaction mixture was cooled to room temperature, diluted with ethyl acetate (20 mL), washed with 5% aqueous sodium hydrogen carbonate solution (20 mL) and saturated brine (20 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concentrated under reduced pressure. The residue was recrystallized from ethyl acetate/hexane to give the title compound (179 mg, 69%) as a colorless powder.

$^1$H-NMR (DMSO-$d_6$, 300 MHz) δ1.74 (6H, s), 2.15 (3H, s), 2.33 (4H, br s), 2.46-2.59 (6H, m), 7.23 (1H, d, J=8.7 Hz), 7.54-7.65 (2H, m), 7.69-7.79 (2H, m), 7.82 (1H, d, J=2.4 Hz), 7.88-7.96 (1H, m), 8.01 (1H, t, J=1.7 Hz), 8.21 (1H, d, J=8.7 Hz), 10.52 (1H, s), 12.15 (1H, br s).

Example C52

Production of N-{4-chloro-2-fluoro-5-[(2-{[(4-methylpiperazin-1-yl)acetyl]amino}[1,3]thiazolo[5,4-b]pyridin-5-yl)oxy]phenyl}-3-(1-cyano-1-methylethyl)benzamide

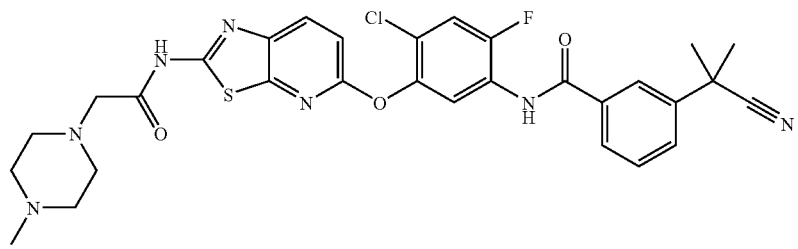 [SMILES: CN1CCN(CC(=O)Nc2nc3ccc(Oc4cc(NC(=O)c5cccc(C(C)(C)C#N)c5)c(F)cc4Cl)nc3s2)CC1]

(i) Production of 5-amino-2-chloro-4-fluorophenol

A suspension of 2-chloro-4-fluoro-5-nitrophenol (21.8 g, 124 mmol), calcium chloride (30.6 g, 248 mmol) and reduced iron (20.8 g, 372 mmol) in ethanol (500 mL)/water (50 mL) was stirred with heating at 90° C. for 4 hr. After the reaction mixture was cooled to room temperature, the insoluble material was filtered off through a pad filled with celite, and washed with ethyl acetate. The filtrate and the washing fluid were combined, and concentrated under reduced pressure. The obtained residue was diluted with ethyl acetate (500 mL), washed with water (250 mL×2), 5% aqueous sodium hydrogen carbonate solution (250 mL×2) and saturated brine (250 mL), and dried over anhydrous sodium sulfate. The insoluble material was filtered off, and the filtrate was concentrated under reduced pressure to give the title compound (15.5 g, 77%) as a black powder. This was used for the next reaction without further purification.

$^1$H-NMR (DMSO-$d_6$, 300 MHz) δ5.15 (2H, s), 6.38 (1H, d, J=8.5 Hz), 6.97 (1H, d, J=11.0 Hz), 9.55 (1H, s).

(ii) Production of N-(4-chloro-2-fluoro-5-hydroxyphenyl)-3-(1-cyano-1-methylethyl)benzamide To a solution of 3-(1-cyano-1-methylethyl)benzoic acid (4.29 g, 22.7 mmol) produced in Example C6(ii) in tetrahydrofuran (45 mL) were added oxalyl chloride (2.41 mL, 28.2 mmol) and N,N-dimethylformamide (20 μL), and the mixture was stirred at room temperature for 1 hr. The reaction mixture was concentrated under reduced pressure to give 3-(1-cyano-1-methylethyl)benzoyl chloride as a pale-yellow oil.

To a two-layer solution of 5-amino-2-chloro-4-fluorophenol (3.50 g, 21.7 mmol) in tetrahydrofuran (35 mL)/1N aqueous sodium hydrogen carbonate solution (65 mL) was added a solution of 3-(1-cyano-1-methylethyl)benzoyl chloride synthesized above in tetrahydrofuran (30 mL), and the mixture was stirred at room temperature for 4 hr. The aqueous layer was separated, and extracted with ethyl acetate (200 mL). The combined organic layer was washed with water (100 mL) and saturated brine (100 mL), and dried over anhydrous sodium sulfate. The insoluble material was filtered off, and the filtrate was concentrated under reduced pressure to give the title compound (5.18 g, 72%) as a gray powder.

$^1$H-NMR (DMSO-d$_6$, 300 MHz) δ1.75 (6H, s), 7.29 (1H, d, J=7.4 Hz), 7.40 (1H, d, J=10.0 Hz), 7.59 (1H, t, J=7.7 Hz), 7.72-7.82 (1H, m), 7.86-7.98 (1H, m), 8.06 (1H, t, J=1.7 Hz), 10.17 (1H, s), 10.38 (1H, br s).

(iii) Production of N-{4-chloro-2-fluoro-5-[(5-nitropyridin-2-yl)oxy]phenyl}-3-(1-cyano-1-methylethyl)benzamide To a solution of 2-chloro-5-nitropyridine (952 mg, 6.01 mmol) and N-(4-chloro-2-fluoro-5-hydroxyphenyl)-3-(1-cyano-1-methylethyl)benzamide (2.00 g, 6.01 mmol) in N,N-dimethylformamide (20 mL) was added potassium carbonate (1.24 g, 9.01 mmol), and the mixture was stirred at 80° C. for 16 hr. The reaction mixture was cooled to room temperature, the insoluble material was filtered off, and the filtrate was concentrated under reduced pressure. Water (100 mL) was added to the obtained residue, and the mixture was extracted with ethyl acetate (200 mL and 100 mL). The combined organic layer was washed with 5% aqueous sodium hydrogen carbonate solution (200 mL) and saturated brine (200 mL×2), and dried over anhydrous sodium sulfate. The insoluble material was filtered off, the filtrate was concentrated under reduced pressure, and the obtained residue was purified by basic silica gel column chromatography (ethyl acetate). The obtained solution was concentrated under reduced pressure to give the title compound (2.28 g, 83%) as a yellow oil.

$^1$H-NMR (DMSO-d$_6$, 300 MHz) δ1.74 (6H, s), 7.44 (1H, dd, J=9.1, 0.6 Hz), 7.61 (1H, t, J=7.8 Hz), 7.74-7.83 (3H, m), 7.94 (1H, dt, J=7.8, 1.2 Hz), 8.08 (1H, t, J=1.8 Hz), 8.68 (1H, dd, J=2.8, 9.1 Hz), 9.05 (1H, dd, J=0.6, 2.8 Hz), 10.43 (1H, br s).

(iv) Production of N-{5-[(5-aminopyridin-2-yl)oxy]-4-chloro-2-fluorophenyl}-3-(1-cyano-1-methylethyl)benzamide A suspension of N-{4-chloro-2-fluoro-5-[(5-nitropyridin-2-yl)oxy]phenyl}-3-(1-cyano-1-methylethyl)benzamide (2.28 g, 5.01 mmol), calcium chloride (1.23 g, 10.0 mmol) and reduced iron (840 mg, 15.0 mmol) in ethanol (35 mL)/water (5 mL) was stirred with heating at 90° C. for 12 hr. After the reaction mixture was cooled to room temperature, the insoluble material was filtered off through a pad filled with celite, and washed with ethyl acetate. The filtrate and the washing fluid were combined, and concentrated under reduced pressure. The obtained residue was diluted with ethyl acetate (200 mL), washed with water (100 mL×2), 5% aqueous sodium hydrogen carbonate solution (100 mL×2) and saturated brine (100 mL), and dried over anhydrous sodium sulfate. The insoluble material was filtered off, the filtrate was concentrated under reduced pressure, and the obtained residue was purified by basic silica gel column chromatography (ethyl acetate). The obtained solution was concentrated under reduced pressure to give the title compound (1.58 g, 74%) as a beige amorphous substance.

$^1$H-NMR (DMSO-d$_6$, 300 MHz) δ1.74 (6H, s), 5.09 (2H, s), 6.85 (1H, d, J=8.6 Hz), 7.11 (1H, dd, J=2.7, 8.6 Hz), 7.41 (1H, d, J=7.2 Hz), 7.47 (1H, d, J=2.7 Hz), 7.59 (1H, t, J=7.8 Hz), 7.65 (1H, d, J=10.2 Hz), 7.73-7.79 (1H, m), 7.92 (1H, ddd, J=1.2, 1.5, 7.8 Hz), 8.05 (1H, t, J=1.8 Hz), 10.30 (1H, br s).

(v) Production of N-{5-[(2-amino[1,3]thiazolo[5,4-b]pyridin-5-yl)oxy]-4-chloro-2-fluorophenyl}-3-(1-cyano-1-methylethyl)benzamide Potassium thiocyanate (1.50 g, 3.53 mmol) was suspended in acetic acid (15 mL), and the mixture was stirred at room temperature for 10 min. A solution of N-{5-[(5-aminopyridin-2-yl)oxy]-4-chloro-2-fluorophenyl}-3-(1-cyano-1-methylethyl)benzamide (1.42 g, 3.22 mmol) in acetic acid (15 mL) was added to the obtained solution, and the mixture was further stirred at room temperature for 10 min. A solution of bromine (591 mg, 3.70 mmol) in acetic acid (10 mL) was slowly added dropwise to the obtained solution. After the completion of the dropwise addition, the mixture was stirred at room temperature for 20 hr. The yielded yellow insoluble material was filtered off, and washed with acetic acid. The filtrate and the washing fluid were combined, and concentrated under reduced pressure. The obtained residue was dissolved in ethyl acetate (150 mL), and the solution was washed with saturated aqueous sodium hydrogen carbonate solution (150 mL) and saturated brine (150 mL), and dried over anhydrous sodium sulfate. The insoluble material was filtered off, and the filtrate was concentrated under reduced pressure. The obtained residue was purified by basic silica gel column chromatography (hexane/ethyl acetate=70/30→20/80), and the obtained solution was concentrated under reduced pressure to give the title compound (1.41 g, 83%) as a yellow amorphous substance.

$^1$H-NMR (DMSO-d$_6$, 300 MHz) δ1.74 (6H, s), 7.00 (1H, d, J=8.7 Hz), 7.49-7.82 (7H, m), 7.93 (1H, d, J=7.9 Hz), 8.06 (1H, t, J=1.6 Hz), 10.35 (1H, s).

(vi) Production of N-{4-chloro-2-fluoro-5-[(2-{[(4-methylpiperazin-1-yl)acetyl]amino}[1,3]thiazolo[5,4-b]pyridin-5-yl)oxy]phenyl}-3-(1-cyano-1-methylethyl)benzamide To a solution of N-{5-[(2-amino[1,3]thiazolo[5,4-b]pyridin-5-yl)oxy]-4-chloro-2-fluorophenyl}-3-(1-cyano-1-methylethyl)benzamide (200 mg, 0.415 mmol) in N,N-dimethylacetamide (3.0 mL) was added chloroacetyl chloride (52.8 μL, 0.664 mmol), and the mixture was stirred at room temperature for 4 hr. Chloroacetyl chloride (26.4 μL, 0.332 mmol) was further added, and the mixture was stirred at room temperature for 2 hr. The reaction mixture was diluted with ethyl acetate (30 mL), washed with water (15 mL), 5% aqueous sodium hydrogen carbonate solution (15 mL) and saturated brine (15 mL), and dried over anhydrous sodium sulfate. The insoluble material was filtered off, and the filtrate was concentrated under reduced pressure to give N-[4-chloro-5-

({2-[(chloroacetyl)amino][1,3]thiazolo[5,4-b]pyridin-5-yl}oxy)-2-fluorophenyl]-3-(1-cyano-1-methylethyl)benzamide as an oily residue.

N-[4-Chloro-5-({2-[(chloroacetyl)amino][1,3]thiazolo[5,4-b]pyridin-5-yl}oxy)-2-fluorophenyl]-3-(1-cyano-1-methylethyl)benzamide synthesized above was dissolved in tetrahydrofuran (3.0 mL), triethylamine (171 μL, 1.25 mmol) and 1-methylpiperazine (138 μL, 1.25 mmol) were added, and the mixture was stirred at 60° C. for 4 hr. The reaction mixture was cooled to room temperature, diluted with ethyl acetate (30 mL), washed with water (30 mL) and saturated brine (30 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concentrated under reduced pressure. The residue was recrystallized from ethyl acetate/hexane to give the title compound (193 mg, 75%) as a colorless powder.

$^1$H-NMR (DMSO-$d_5$, 300 MHz) δ1.74 (6H, s), 2.15 (3H, s), 2.34 (4H, br s), 2.46-2.61 (6H, m), 7.24 (1H, d, J=8.7 Hz), 7.60 (1H, t, J=7.8 Hz), 7.69 (1H, d, J=7.2 Hz), 7.73-7.81 (2H, m), 7.89-7.98 (1H, m), 8.07 (1H, t, J=1.7 Hz), 8.21 (1H, d, J=8.7 Hz), 10.39 (1H, s), 12.16 (1H, br s).

Example C53

Production of N-[4-chloro-2-fluoro-5-({2-[(methoxyacetyl)amino][1,3]thiazolo[5,4-b]pyridin-5-yl}oxy)phenyl]-3-(1-cyano-1-methylethyl)benzamide

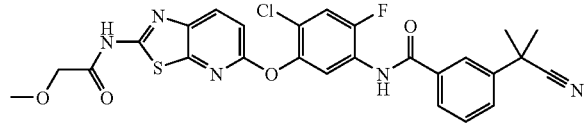 [SMILES: COCC(=O)Nc1nc2ccc(Oc3cc(NC(=O)c4cccc(C(C)(C)C#N)c4)c(F)cc3Cl)nc2s1]

To a solution of N-{5-[(2-amino[1,3]thiazolo[5,4-b]pyridin-5-yl)oxy]-4-chloro-2-fluorophenyl}-3-(1-cyano-1-methylethyl)benzamide (100 mg, 0.207 mmol) produced in Example C52(v) in pyridine (2.0 mL) was added methoxyacetyl chloride (30 μL, 0.331 mmol), and the mixture was stirred at room temperature for 2 hr. Methoxyacetyl chloride (15 μL, 0.165 mmol) was further added, and the mixture was stirred at room temperature for 2 hr. The reaction mixture was diluted with ethyl acetate (25 mL), washed with 5% aqueous sodium hydrogen carbonate solution (25 mL) and saturated brine (25 mL), and dried over anhydrous sodium sulfate. The insoluble material was filtered off, and the filtrate was concentrated under reduced pressure. The residue was purified by basic silica gel column chromatography (hexane/ethyl acetate=70/30→20/80), and the obtained solution was concentrated under reduced pressure. The residue was recrystallized from ethyl acetate/hexane to give the title compound (74.5 mg, 65%) as a colorless powder.

$^1$H-NMR (DMSO-$d_6$, 300 MHz) δ1.74 (6H, s), 3.36 (3H, s), 4.18 (2H, s), 7.23 (1H, d, J=8.7 Hz), 7.60 (1H, t, J=7.8 Hz), 7.69 (1H, d, J=7.2 Hz), 7.74-7.82 (2H, m), 7.89-7.99 (1H, m), 8.07 (1H, t, J=1.7 Hz), 8.20 (1H, d, J=8.7 Hz), 10.38 (1H, s), 12.37 (1H, br s).

Example C54

Production of N-[4-chloro-2-fluoro-5-({2-[(hydroxyacetyl)amino][1,3]thiazolo[5,4-b]pyridin-5-yl}oxy)phenyl]-3-(1-cyano-1-methylethyl)benzamide

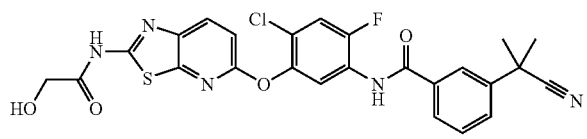 [SMILES: CC(C)(C#N)c1cccc(C(=O)Nc2cc(Oc3ccc4nc(NC(=O)CO)sc4n3)c(Cl)cc2F)c1]

To a solution of N-{5-[(2-amino[1,3]thiazolo[5,4-b]pyridin-5-yl)oxy]-4-chloro-2-fluorophenyl}-3-(1-cyano-1-methylethyl)benzamide (100 mg, 0.207 mmol) produced in Example C52(v) in pyridine (2.0 mL) was added acetoxyacetyl chloride (48.9 μL, 0.455 mmol), and the mixture was stirred at room temperature for 4 hr. The reaction mixture was diluted with ethyl acetate (10 mL), washed with 5% aqueous sodium hydrogen carbonate solution (10 mL) and saturated brine (10 mL), and dried over anhydrous sodium sulfate. The insoluble material was filtered off, and the filtrate was concentrated under reduced pressure. The obtained residue was dissolved in methanol (2.0 mL), sodium carbonate (100 mg, 0.943 mmol) was added, and the mixture was stirred at room temperature for 2 hr. The reaction mixture was concentrated under reduced pressure, and the residue was suspended in ethyl acetate (10 mL). The obtained suspension was washed with 5% aqueous ammonium chloride solution (10 mL), 5% aqueous sodium hydrogen carbonate solution (10 mL) and saturated brine (10 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concentrated under reduced pressure. The residue was recrystallized from ethyl acetate/hexane to give the title compound (63.0 mg, 56%) as a colorless powder.

$^1$H-NMR (DMSO-$d_6$, 300 MHz) δ 1.74 (6H, s), 4.18 (2H, d, J=2.6 Hz), 5.50 (1H, br s), 7.24 (1H, d, J=8.7 Hz), 7.60 (1H, t, J=7.7 Hz), 7.70 (1H, d, J=7.2 Hz), 7.78 (2H, d, J=10.0 Hz), 7.94 (1H, d, J=7.7 Hz), 8.07 (1H, t, J=1.6 Hz), 8.22 (1H, d, J=8.7 Hz), 10.39 (1H, s), 12.15 (1H, br s).

Example C55

Production of N-[4-chloro-2-fluoro-5-({2-[(morpholin-4-ylacetyl)amino][1,3]thiazolo[5,4-b]pyridin-5-yl}oxy)phenyl]-3-(1-cyano-1-methylethyl)benzamide

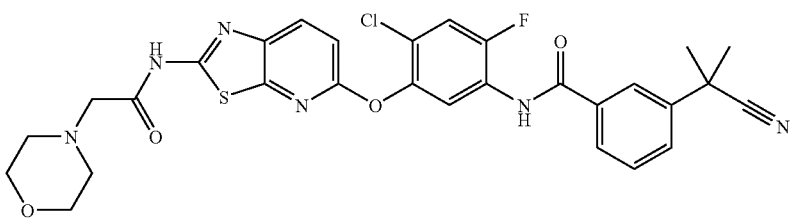 [SMILES: CC(C)(C#N)c1cccc(C(=O)Nc2cc(Oc3ccc4nc(NC(=O)CN5CCOCC5)sc4n3)c(Cl)cc2F)c1]

To a solution of N-{5-[(2-amino[1,3]thiazolo[5,4-b]pyridin-5-yl)oxy]-4-chloro-2-fluorophenyl}-3-(1-cyano-1-methylethyl)benzamide (100 mg, 0.207 mmol) produced in Example C52(v) in N,N-dimethylacetamide (1.0 mL) was added chloroacetyl chloride (36 μL, 0.455 mmol), and the mixture was stirred at room temperature for 2 hr. The reaction mixture was diluted with ethyl acetate (10 mL), washed with 5% aqueous sodium hydrogen carbonate solution (10 mL) and saturated brine (10 mL), and dried over anhydrous sodium sulfate. The insoluble material was filtered off, and the filtrate was concentrated under reduced pressure to give N-[4-chloro-5-({2-[(chloroacetyl)amino][1,3]thiazolo[5,4-b]pyridin-5-yl}oxy)-2-fluorophenyl]-3-(1-cyano-1-methylethyl)benzamide as an oily residue.

N-[4-Chloro-5-({2-[(chloroacetyl)amino][1,3]thiazolo[5,4-b]pyridin-5-yl}oxy)-2-fluorophenyl]-3-(1-cyano-1-methylethyl)benzamide synthesized above was dissolved in tetrahydrofuran (3.0 mL), triethylamine (85.6 μL, 0.621 mmol) and morpholine(54.3 μL, 0.621 mmol) were added, and the mixture was stirred at 80° C. for 8 hr. The reaction mixture was cooled to room temperature, diluted with ethyl acetate (10 mL), washed with water (10 mL) and saturated brine (10 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concentrated under reduced pressure. The residue was triturated with ethyl acetate/hexane to give the title compound (101 mg, 80%) as a colorless amorphous powder.

$^1$H-NMR (DMSO-$d_6$, 300 MHz) δ 1.74 (6H, s), 2.43-2.60 (6H, m), 3.51-3.71 (4H, m), 7.24 (1H, d, J=8.7 Hz), 7.60 (1H, t, J=7.7 Hz), 7.69 (1H, d, J=7.2 Hz), 7.77 (2H, d, J=9.8 Hz), 7.94 (1H, d, J=7.6 Hz), 8.07 (1H, s), 8.21 (1H, d, J=8.7 Hz), 10.39 (1H, s), 12.20 (1H, br s).

Example C56

Production of N-(4-chloro-2-fluoro-5-{[2-(propanoylamino)[1,3]thiazolo[5,4-b]pyridin-5-yl]oxy}phenyl)-3-(1-cyano-1-methylethyl)benzamide

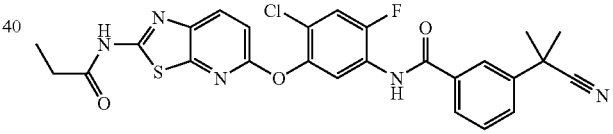

To a solution of N-{5-[(2-amino[1,3]thiazolo[5,4-b]pyridin-5-yl)oxy]-4-chloro-2-fluorophenyl}-3-(1-cyano-1-methylethyl)benzamide produced in Example C52(v) in pyridine (1.0 mL) was added propionyl chloride (29 μL, 0.332 mmol), and the mixture was stirred at room temperature for 2 hr. The reaction mixture was diluted with ethyl acetate (10 mL), washed with 5% aqueous sodium hydrogen carbonate solution (10 mL) and saturated brine (10 mL), and dried over anhydrous sodium sulfate. The insoluble material was filtered off, and the filtrate was concentrated under reduced pressure. The obtained residue was purified by basic silica gel column chromatography (hexane/ethyl acetate=70/30→0/100), and the obtained solution was concentrated under reduced pressure. The residue was crystallized from ethyl acetate/hexane to give the title compound (46.7 mg, 52%) as a colorless powder.

$^1$H-NMR (DMSO-$d_6$, 300 MHz) δ1.09 (3H, t, J=7.5 Hz), 1.74 (6H, s), 2.42-2.55 (2H, m), 7.23 (1H, d, J=8.7 Hz), 7.60 (1H, t, J=7.8 Hz), 7.69 (1H, d, J=7.2 Hz), 7.73-7.83 (2H, m), 7.90-7.97 (1H, m), 8.07 (1H, t, J=1.7 Hz), 8.19 (1H, d, J=8.7 Hz), 10.40 (1H, br s), 12.37 (1H, br s).

Example C57

Production of N-{4-chloro-2-fluoro-5-[(2-{[(2E)-3-phenylprop-2-enoyl]amino}[1,3]thiazolo[5,4-b]pyridin-5-yl)oxy]phenyl}-3-(1-cyano-1-methylethyl)benzamide

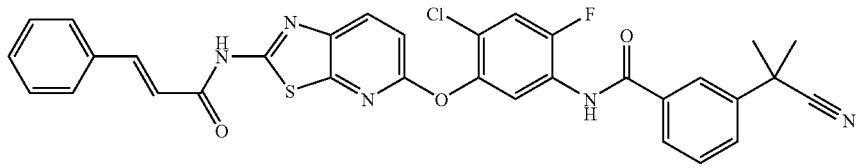 [SMILES: CC(C)(C#N)c1cccc(C(=O)Nc2cc(Oc3ccc4nc(NC(=O)/C=C/c5ccccc5)sc4n3)c(Cl)cc2F)c1]

To a suspension of N-{5-[(2-amino[1,3]thiazolo[5,4-b]pyridin-5-yl)oxy]-4-chloro-2-fluorophenyl}-3-(1-cyano-1-methylethyl)benzamide (80 mg, 0.166 mmol) produced in Example C52(v) in pyridine (1.0 mL) were added dimethylacetamide (0.5 mL) and (2E)-3-phenylprop-2-enoyl chloride (55 mg, 0.332 mmol), and the mixture was stirred at room temperature for 2 hr. The reaction mixture was diluted with ethyl acetate (20 mL), washed with 5% aqueous sodium hydrogen carbonate solution (10 mL) and saturated brine (10 mL), and dried over anhydrous sodium sulfate. The insoluble material was filtered off, and the filtrate was concentrated under reduced pressure. The obtained residue was purified by basic silica gel column chromatography (hexane/ethyl acetate=70/30→0/100), and the obtained solution was concentrated under reduced pressure. The residue was crystallized from ethyl acetate/hexane to give the title compound (87.5 mg, 86%) as a colorless powder.

$^1$H-NMR (DMSO-$d_6$, 300 MHz) δ 1.74 (6H, s), 6.93 (1H, d, J=15.9 Hz), 7.24 (1H, d, J=8.7 Hz), 7.40-7.52 (3H, m), 7.54-7.73 (4H, m), 7.73-7.87 (3H, m), 7.90-8.01 (1H, m), 8.08 (1H, t, J=1.6 Hz), 8.22 (1H, d, J=8.7 Hz), 10.40 (1H, s), 12.69 (1H, br s).

Example C58

Production of N-{4-chloro-2-fluoro-5-[(2-{[(2E)-3-furan-2-ylprop-2-enoyl]amino}[1,3]thiazolo[5,4-b]pyridin-5-yl)oxy]phenyl}-3-(1-cyano-1-methylethyl)benzamide To a solution of (2E)-3-furan-2-ylprop-2-enoic acid (24 mg, 0.173 mmol) in pyridine (1.0 mL) was added O-(7-azabenzotriazol-1-yl)-N,N,N',N'-tetramethyluronium hexafluorophosphate (65.7 mg, 0.173 mmol), and the mixture was stirred at room temperature for 10 min. N-{5-[(2-Amino[1,3]thiazolo[5,4-b]pyridin-5-yl)oxy]-4-chloro-2-fluorophenyl}-3-(1-cyano-1-methylethyl)benzamide (80 mg, 0.166 mmol) produced in Example C52(v) was added to the obtained solution, and the mixture was stirred at 80° C. for 12 hr. The reaction mixture was diluted with ethyl acetate (10 mL), washed with 5% aqueous sodium hydrogen carbonate solution (10 mL) and saturated brine (100 mL), and dried over anhydrous sodium sulfate. The insoluble material was filtered off, and the filtrate was concentrated under reduced pressure. The obtained residue was purified by basic silica gel column chromatography (hexane/ethyl acetate=70/30→0/100), and the obtained solution was concentrated under reduced pressure. The residue was crystallized from ethyl acetate/hexane to give the title compound (37.2 mg, 87%) as a colorless powder.

$^1$H-NMR (DMSO-$d_6$, 300 MHz) δ 1.74 (6H, s), 6.61-6.76 (2H, m), 6.96 (1H, d, J=3.3 Hz), 7.24 (1H, d, J=8.7 Hz), 7.48-7.64 (2H, m), 7.69 (1H, d, J=7.2 Hz), 7.74-7.82 (2H, m), 7.89 (1H, d, J=1.5 Hz), 7.91-7.99 (1H, m), 8.07 (1H, t, J=1.5 Hz), 8.21 (1H, d, J=8.7 Hz), 10.40 (1H, s), 12.65 (1H, br s).

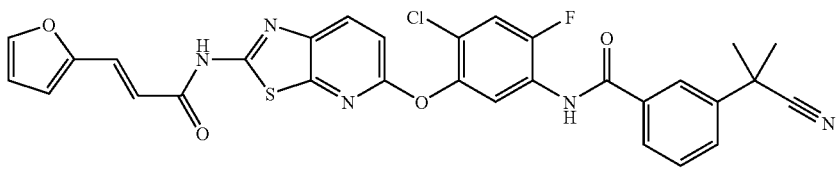 [SMILES: CC(C)(C#N)c1cccc(C(=O)Nc2cc(Oc3ccc4nc(NC(=O)/C=C/c5ccco5)sc4n3)c(Cl)cc2F)c1]

Example C59

Production of N-{4-chloro-5-[(2-{[(4-ethylpiperazin-1-yl)acetyl]amino}[1,3]thiazolo[5,4-b]pyridin-5-yl)oxy]-2-fluorophenyl}-3-(1-cyano-1-methylethyl)benzamide trated under reduced pressure. The residue was triturated with ethyl acetate/hexane to give the title compound (133 mg, 67%) as a colorless powder.

$^1$H-NMR (DMSO-$d_6$, 300 MHz) δ0.97 (3H, t, J=7.2 Hz), 1.74 (6H, s), 2.20-2.45 (6H, m), 2.45-2.62 (4H, m), 3.30 (2H, s), 7.23 (1H, d, J=8.8 Hz), 7.60 (1H, t, J=7.8 Hz), 7.69 (1H, d,

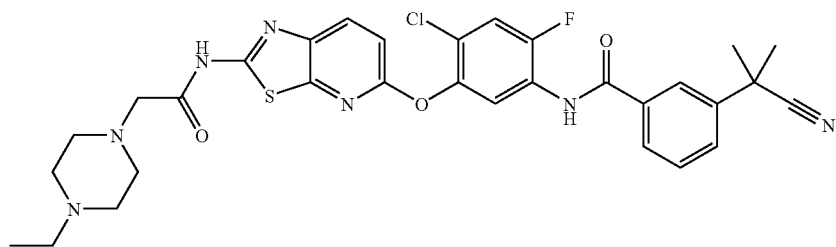 [SMILES: CCN1CCN(CC(=O)Nc2nc3ccc(Oc4cc(NC(=O)c5cccc(C(C)(C)C#N)c5)c(F)cc4Cl)nc3s2)CC1]

To a solution of N-{5-[(2-amino[1,3]thiazolo[5,4-b]pyridin-5-yl)oxy]-4-chloro-2-fluorophenyl}-3-(1-cyano-1-methylethyl)benzamide (150 mg, 0.311 mmol) produced in Example C52(v) in N,N-dimethylacetamide (2.0 mL) was added chloroacetyl chloride (50 μL, 0.622 mmol), and the mixture was stirred at room temperature for 2 hr. The reaction mixture was diluted with ethyl acetate (20 mL), washed with 5% aqueous sodium hydrogen carbonate solution (10 mL) and saturated brine (10 mL), and dried over anhydrous sodium sulfate. The insoluble material was filtered off, and the filtrate was concentrated under reduced pressure to give N-[4-chloro-5-({2-[(chloroacetyl)amino][1,3]thiazolo[5,4-b]pyridin-5-yl}oxy)-2-fluorophenyl]-3-(1-cyano-1-methylethyl)benzamide as an oily residue.

N-[4-Chloro-5-({2-[(chloroacetyl)amino][1,3]thiazolo[5,4-b]pyridin-5-yl}oxy)-2-fluorophenyl]-3-(1-cyano-1-methylethyl)benzamide synthesized above was dissolved in tetrahydrofuran (3.0 mL), triethylamine (128 μL, 0.933 mmol) and N-ethylpiperazine (118 μL, 0.933 mmol) were added, and the mixture was stirred at 70° C. for 4 hr. The reaction mixture was cooled to room temperature, diluted with ethyl acetate (10 mL), washed with water (10 mL) and saturated brine (10 mL), and dried over anhydrous sodium sulfate. The insoluble material was filtered off, and the filtrate was concentrated under reduced pressure. The residue was purified by basic silica gel column chromatography (ethyl acetate/methanol=100/0→85/15), and the obtained solution was concenJ=7.2 Hz), 7.73-7.82 (2H, m), 7.89-7.98 (1H, m), 8.07 (1H, t, J=1.7 Hz), 8.19 (1H, d, J=8.8 Hz), 10.39 (1H, s), 12.14 (1H, br s).

Example C60

Production of N-[4-chloro-5-({2-[(cyclopropylcarbonyl)amino][1,3]thiazolo[5,4-b]pyridin-5-yl}oxy)-2-fluorophenyl]-3-(1-cyano-1-methylethyl)benzamide

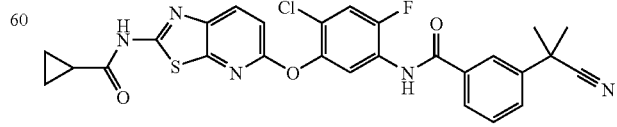

To a solution of N-{5-[(2-amino[1,3]thiazolo[5,4-b]pyridin-5-yl)oxy]-4-chloro-2-fluorophenyl}-3-(1-cyano-1-methylethyl)benzamide (400 mg, 0.83 mmol) produced in Example C52(v) in pyridine (4.0 mL) was added cyclopropanecarbonyl chloride (112 µL, 1.24 mmol), and the mixture was stirred at room temperature for 6 hr. Cyclopropanecarbonyl chloride (112 µL, 1.24 mmol) was further added, and the mixture was stirred at room temperature for 2 hr. The reaction mixture was diluted with ethyl acetate (100 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was purified by basic silica gel column chromatography (hexane/ethyl acetate=70/30→0/100), and the obtained solution was concentrated under reduced pressure. The residue was crystallized from ethyl acetate/hexane to give the title compound (190 mg, 44%) as a colorless powder.

$^1$H-NMR (DMSO-d$_6$, 300 MHz) δ0.85-1.02 (4H, m), 1.74 (6H, s), 1.92-2.05 (1H, m), 7.22 (1H, d, J=8.7 Hz), 7.60 (1H, t, J=7.8 Hz), 7.68 (1H, d, J=7.2 Hz), 7.73-7.83 (2H, m), 7.87-7.99 (1H, m), 8.07 (1H, t, J=1.7 Hz), 8.19 (1H, d, J=8.7 Hz), 10.39 (1H, s), 12.70 (1H, br s).

Example C61

Production of N-(5-{[2-(acetylamino)[1,3]thiazolo[5,4-b]pyridin-5-yl]oxy}-4-chloro-2-fluorophenyl)-2-chloro-3-(1-cyano-1-methylethyl)benzamide

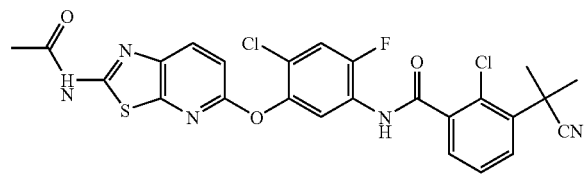 [SMILES: CC(=O)Nc1nc2ccc(Oc3cc(NC(=O)c4cccc(C(C)(C)C#N)c4Cl)c(F)cc3Cl)nc2s1]

(i) Production of methyl 2-chloro-3-methylbenzoate

A mixture of 2-chloro-3-methylbenzoic acid (25.0 g, 0.146 mol), conc. sulfuric acid (2 mL) and methanol (160 mL) was stirred 80° C. for 3 hr. The reaction mixture was concentrated, and the residue was diluted with ethyl acetate, and neutralized with 8N aqueous sodium hydroxide solution. The organic layer was separated, washed with saturated brine, dried over anhydrous magnesium sulfate, and filtered through a pad filled with basic silica gel. The solvent was concentrated under reduced pressure to give the title compound (18.0 g, 66%) as a pale-orange oil. The obtained compound was used for the next reaction without further purification operation.

$^1$H-NMR (CDCl$_3$, 300 MHz) δ 2.42 (3H, s), 3.93 (3H, s), 7.19 (1H, t, J=7.6 Hz), 7.32-7.38 (1H, m), 7.56 (1H, dd, J=1.2, 7.6 Hz).

(ii) Production of methyl 3-(bromomethyl)-2-chlorobenzoate

To a solution of methyl 2-chloro-3-methylbenzoate (3.60 g, 19.4 mmol) in acetonitrile (60 mL) were added 1-bromopyrrolidine-2,5-dione (11.46 g, 64.3 mmol) and 2,2'-(E)-diazen-1,2-diylbis(2-methylpropanenitrile) (960 mg, 5.84 mmol), and the mixture was stirred at 90° C. for 26 hr. The reaction mixture was concentrated, the insoluble material was filtered off, and the filtrate was concentrated. The obtained residue was purified by silica gel column chromatography (ethyl acetate/hexane=0/100→5/95) to give the title compound (3.42 g, 66%) as a colorless oil.

$^1$H-NMR (CDCl$_3$, 300 MHz) δ 3.94 (3H, s), 4.64 (2H, s), 7.31 (1H, t, J=7.7 Hz), 7.58 (1H, dd, J=1.7, 7.7 Hz), 7.71 (1H, dd, J=1.7, 7.7 Hz).

(iii) Production of methyl 2-chloro-3-(cyanomethyl)benzoate

To a solution of methyl 3-(bromomethyl)-2-chlorobenzoate (748 mg, 2.84 mmol) in N,N-dimethylformamide (7 mL) was added sodium cyanate (412 mg, 8.41 mmol), and the mixture was stirred at 80° C. for 1 hr under nitrogen stream. The reaction mixture was diluted with a mixed solvent of ethyl acetate and hexane (1:1). The solution was washed with water and saturated brine, dried over anhydrous magnesium sulfate, and filtrated. The solvent was evaporated under reduced pressure, and the obtained residue was purified by silica gel column chromatography (ethyl acetate/hexane=2/98→20/80), and recrystallized from ethyl acetate and hexane to give the title compound (470 mg, 79%) as white crystals.

$^1$H-NMR (CDCl$_3$, 300 MHz) δ 3.91 (2H, s), 3.95 (3H, s), 7.39 (1H, t, J=7.8 Hz), 7.66-7.72 (1H, m), 7.76-7.81 (1H, m).

(iv) Production of methyl 2-chloro-3-(1-cyano-1-methylethyl)benzoate

In the same manner as in Example C6(i), the title compound (1.99 g, 88%) was obtained as a colorless oil using methyl 2-chloro-3-(cyanomethyl)benzoate (2.00 g, 9.54 mmol), sodium hydride (60% in oil, 1.14 g, 28.6 mmol), methyl iodide (1.78 mL, 28.6 mmol) and dimethyl sulfoxide (20 mL) as starting materials.

$^1$H-NMR (CDCl$_3$, 300 MHz) δ 1.90 (6H, s), 3.95 (3H, s), 7.33-7.40 (1H, m), 7.57-7.64 (2H, m).

(v) Production of 2-chloro-3-(1-cyano-1-methylethyl)benzoic acid

In the same manner as in Example C6(ii), the title compound (1.43 g, 91%) was obtained as a white powder using methyl 2-chloro-3-(1-cyano-1-methylethyl)benzoate (1.67 g, 7.02 mmol), lithium hydroxide.monohydrate (501 mg, 11.9 mmol), tetrahydrofuran (24 mL), methanol (8 mL) and water (8 mL) as starting materials.

$^1$H-NMR (CDCl$_3$, 300 MHz) δ 1.92 (6H, s), 7.41 (1H, t, J=7.8 Hz), 7.67 (1H, dd, J=1.6, 7.8 Hz), 7.85 (1H, dd, J=1.6, 7.8 Hz).

(vi) Production of 5-amino-2-chloro-4-fluorophenol

A mixture of 2-chloro-4-fluoro-5-nitrophenol (28.6 g, 0.150 mol), reduced iron (41.6 g, 0.745 mol), calcium chloride (8.28 g, 74.6 mmol) and ethanol (540 mL)/water (60 mL) was stirred with heating under reflux for 3.5 hr. The reaction mixture was filtered through celite, the filtrate was concentrated under reduced pressure, and ethyl acetate (700 mL) was added to the residue. The solution was washed with water (200 mL) and saturated brine (100 mL), and dried over anhydrous magnesium sulfate, and concentrated under reduced pressure. The residue was purified by silica gel column chromatography (hexane/ethyl acetate=95/5→50/50) to give the title compound (19.3 g, 80%) as a brown powder.

$^1$H-NMR (CDCl$_3$, 300 MHz) δ 3.73 (2H, br s), 5.22 (1H, s), 6.44 (1H, d, J=8.1 Hz), 6.96 (1H, d, J=10.2 Hz).

(vii) Production of 4-chloro-2-fluoro-5-[(5-nitropyridin-2-yl)oxy]aniline

A mixture of 5-amino-2-chloro-4-fluorophenol (5.00 g, 30.9 mmol), 2-chloro-5-nitropyridine (5.09 g, 32.1 mmol), potassium carbonate (4.51 g, 32.6 mmol) and N,N-dimethylformamide (50 mL) was stirred at room temperature for 13 hr. To the reaction mixture was added aqueous ammonium chloride solution (50 mL), and the mixture was extracted with ethyl acetate (80 mL×3). The organic layer was washed with water (50 mL) and saturated brine (30 mL), dried over anhydrous magnesium sulfate, and concentrated under reduced pressure. The precipitate was collected by filtration to give the title compound (6.31 g, 72%) as a yellow powder.

$^1$H-NMR (CDCl$_3$, 300 MHz) δ 3.86 (2H, br s), 6.65 (1H, d, J=8.1 Hz), 7.08 (1H, d, J=9.1 Hz), 7.14 (1H, d, J=10.2 Hz), 8.50 (1H, dd, J=2.8, 9.1 Hz), 9.02 (1H, dd, J=0.6, 2.8 Hz).

(viii) Production of N-{4-chloro-2-fluoro-5-[(5-nitropyridin-2-yl)oxy]phenyl}-2,2,2-trifluoroacetamide To a solution of 4-chloro-2-fluoro-5-[(5-nitropyridin-2-yl)oxy]aniline (499 mg, 1.76 mmol) in tetrahydrofuran (5 mL) was added trifluoroacetic acid anhydride (268 μL, 1.94 mmol), and the mixture was stirred at room temperature for 1 hr. The reaction mixture was concentrated under reduced pressure, and the residue was dissolved in ethyl acetate (10 mL). The solution was washed successively with saturated aqueous sodium hydrogen carbonate solution (5 mL×2) and saturated brine (2 mL), dried over anhydrous magnesium sulfate, and concentrated under reduced pressure. The precipitate was collected by filtration to give the title compound (614 mg, 92%) as a pale-brown powder.

$^1$H-NMR (CDCl$_3$, 300 MHz) δ 7.18 (1H, d, J=9.0 Hz), 7.38 (1H, d, J=10.0 Hz), 8.11 (1H, br s), 8.31 (1H, d, J=7.2 Hz), 8.55 (1H, dd, J=2.8, 9.0 Hz), 8.97 (1H, d, J=2.8 Hz).

(ix) Production of N-{5-[(5-aminopyridin-2-yl)oxy]-4-chloro-2-fluorophenyl}-2,2,2-trifluoroacetamide A mixture of N-{4-chloro-2-fluoro-5-[(5-nitropyridin-2-yl)oxy]phenyl}-2,2,2-trifluoroacetamide (600 mg, 1.58 mmol), reduced iron (452 mg, 8.09 mmol) and acetic acid (10 mL) was stirred at 60° C. for 1.5 hr. The reaction mixture was filtered through celite, and the filtrate was concentrated under reduced pressure. The residue was dissolved in ethyl acetate (20 mL), washed with saturated aqueous sodium hydrogen carbonate solution (10 mL) and saturated brine (10 mL), dried over anhydrous magnesium sulfate, and concentrated under reduced pressure. The residue was purified by silica gel column chromatography (hexane/ethyl acetate=80/20→34/66) to give the title compound (357 mg, 65%) as a white powder.

$^1$H-NMR (CDCl$_3$, 300 MHz) δ 3.52 (2H, br s), 6.86 (1H, d, J=8.7 Hz), 7.12 (1H, dd, J=3.0, 8.7 Hz), 7.30 (1H, d, J=10.2 Hz), 7.61 (1H, d, J=3.0 Hz), 8.03 (1H, br s), 8.15 (1H, d, J=7.4 Hz).

(x) Production of N-{5-[(2-amino[1,3]thiazolo[5,4-b]pyridin-5-yl)oxy]-4-chloro-2-fluorophenyl}-2,2,2-trifluoroacetamide Potassium thiocyanate (5.98 g, 61.5 mmol) was dissolved in acetic acid (280 mL), N-{5-[(5-aminopyridin-2-yl)oxy]-4-chloro-2-fluorophenyl}-2,2,2-trifluoroacetamide (5.20 g, 14.9 mmol) was added thereto, and the mixture was stirred at room temperature for 30 min. To the solution was added dropwise a solution (40 mL) of bromine (2.54 g, 15.9 mmol) in acetic acid, and the mixture was stirred at room temperature overnight. The reaction mixture was filtered through celite, and the filtrate was concentrated under reduced pressure. The residue was dissolved in ethyl acetate (500 mL), the solution was washed with saturated aqueous sodium hydrogen carbonate solution (200 mL×3) and saturated brine (100 mL), and dried over anhydrous magnesium sulfate. The dried organic layer was concentrated under reduced pressure. The precipitate was collected by filtration to give the title compound (5.78 g, 96%) as a pale-yellow powder.

$^1$H-NMR (CDCl$_3$, 300 MHz) δ 5.12 (2H, s), 6.96 (1H, d, J=8.5 Hz), 7.33 (1H, d, J=10.2 Hz), 7.79 (1H, d, J=8.5 Hz), 8.05 (1H, br s), 8.22 (1H, d, J=7.4 Hz).

(xi) Production of N-(5-{[2-(acetylamino)[1,3]thiazolo[5,4-b]pyridin-5-yl]oxy}-4-chloro-2-fluorophenyl)-2,2,2-trifluoroacetamide To a solution of N-{5-[(2-amino[1,3]thiazolo[5,4-b]pyridin-5-yl)oxy]-4-chloro-2-fluorophenyl}-2,2,2-trifluoroacetamide (2.03 g, 5 mmol) and N,N-dimethylpyridine-4-amine (0.61 g, 5 mmol) in pyridine (10 mL) was added dropwise acetyl chloride (0.78 g, 10 mmol) under ice-cooling, and the mixture was stirred at room temperature for 3 hr. The reaction solution was concentrated under reduced pressure, and the residue was diluted with ethyl acetate (50 mL), washed with water (50 mL×2), and dried over anhydrous magnesium sulfate. The insoluble material was filtered off, and the filtrate was concentrated under reduced pressure. The obtained residue was washed with diethyl ether, collected by filtration, and dried under reduced pressure to give the title compound (2.16 g, 96%) as white powder crystals.

$^1$H-NMR (DMSO-d$_6$, 300 MHz) δ 2.26.(3H, s), 7.04 (1H, d, J=8.7 Hz), 7.34 (1H, d, J=6.9 Hz), 7.80 (1H, d, J=7.2 Hz), 7.99 (1H, d, J=8.7 Hz), 10.02 (1H, br s), 11.77 (1H, br s).

(xii) Production of N-[5-(5-amino-2-chloro-4-fluorophenoxy)[1,3]thiazolo[5,4-b]pyridin-2-yl]acetamide To a solution of sodium borohydride (3.38 g, 100 mmol) in ethanol (60 mL) was added dropwise methanol (40 mL) under ice-cooling, and N-(5-{[2-(acetylamino)[1,3]thiazolo[5,4-b]pyridin-5-yl]oxy}-4-chloro-2-fluorophenyl)-2,2,2-trifluoroacetamide (2.16 g, 4.81 mmol) was added in portions thereto under ice-cooling. The reaction mixture was stirred at room temperature for 1 hr, and poured into water (400 mL), and the mixture was extracted with ethyl acetate (200 mL×2). The ethyl acetate layers were combined, and dried over anhydrous sodium sulfate. The insoluble material was filtered off, and the filtrate was concentrated under reduced pressure. The obtained residue was washed with diethyl ether, collected by filtration, and dried under reduced pressure to give the title compound (3.26 g, 68%) as white powder crystals.

$^1$H-NMR (DMSO-d$_6$, 300 MHz) δ 2.35 (3H, s), 4.02 (2H, br s), 6.70 (1H, d, J=8.4 Hz), 6.94 (1H, d, J=8.7 Hz), 7.00 (1H, d, J=10.5 Hz), 7.40 (1H, d, J=8.7 Hz), 11.50 (1H, br s).

(xiii) Production of N-(5-{[2-(acetylamino)[1,3]thiazolo[5,4-b]pyridin-5-yl]oxy}-4-chloro-2-fluorophenyl)-2-chloro-3-(1-cyano-1-methylethyl)benzamide To a solution of 2-chloro-3-(1-cyano-1-methylethyl)benzoic acid (0.11 g, 0.5 mmol) produced in Example C61(v) in oxalyl chloride (0.5 mL) was added N,N-dimethylformamide (40 μL), and the mixture was stirred at room temperature for 30 min, and concentrated to dryness under reduced pressure.

This was dissolved in a mixture of N,N-dimethylacetamide (1 mL) and tetrahydrofuran (1 mL), and the solution was added dropwise to a solution of N-[5-(5-amino-2-chloro-4-fluorophenoxy)[1,3]thiazolo[5,4-b]pyridin-2-yl]acetamide (0.12 g, 0.33 mmol) in N,N-dimethylacetamide (1 mL) under ice-cooling. The reaction mixture was stirred at room temperature for 3 hr, and poured into water (50 mL), and the mixture was extracted with ethyl acetate (50 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50), and recrystallized from methanol to give the title compound (40 mg, 22%) as colorless crystals.

$^1$H-NMR (DMSO-$d_6$, 300 MHz) δ 1.55 (6H, s), 2.30 (3H, s), 7.10 (1H, d, J=8.7 Hz), 7.31 (1H, d, J=9.0 Hz), 7.43 (1H, t, J=7.5 Hz), 7.52-7.68 (2H, m), 7.81 (1H, d, J=6.9 Hz), 8.01 (1H, d, J=8.7 Hz), 8.49 (1H, d, J=7.5 Hz), 9.01 (1H, br s).

Example C62

Production of N-(5-{[2-(acetylamino)[1,3]thiazolo[5,4-b]pyridin-5-yl]oxy}-4-chloro-2-fluorophenyl)-2-chloro-3-(1-cyanocyclopropyl)benzamide

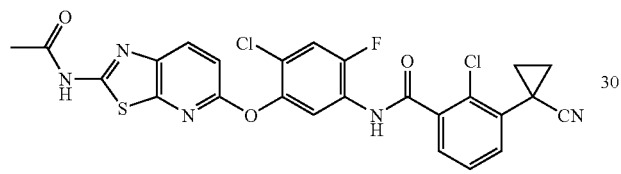

(i) Production of methyl 2-chloro-3-(1-cyanocyclopropyl)benzoate

In the same manner as in Example C1(ii), the title compound (787 mg, 35%) was obtained as a colorless oil using methyl 2-chloro-3-(cyanomethyl)benzoate (2.00 g, 9.54 mmol) produced in Example C61(iii), sodium hydride (60% in oil, 1.14 g, 28.6 mmol), 1,2-dibromoethane (1.18 mL, 14.3 mmol) and dimethyl sulfoxide (20 mL) as starting materials.

$^1$H-NMR (CDCl$_3$, 300 MHz) δ 1.33-1.39 (2H, m), 1.76-1.83 (2H, m), 3.95 (3H, s), 7.32 (1H, t, J=7.7 Hz), 7.50 (1H, dd, J=1.7, 7.7 Hz), 7.74 (1H, dd, J=1.7, 7.7 Hz).

(ii) Production of 2-chloro-3-(1-cyanocyclopropyl)benzoic acid

In the same manner as in Example C6(ii), the title compound (457 mg, 71%) was obtained as a white powder using methyl 2-chloro-3-(1-cyanocyclopropyl)benzoate (684 mg, 2.90 mmol), lithium hydroxide.monohydrate (207 mg, 4.93 mmol), tetrahydrofuran (10 mL), methanol (3 mL) and water (3 mL) as starting materials.

$^1$H-NMR (CDCl$_3$, 300 MHz) δ 1.32-1.42 (2H, m), 1.79-1.87 (2H, m), 4.47 (1H, br s), 7.37 (1H, t, J=7.7 Hz), 7.56 (1H, dd, J=1.7, 7.7 Hz), 7.95 (1H, dd, J=1.7, 7.7 Hz).

(iii) Production of N-(5-{[2-(acetylamino)[1,3]thiazolo[5,4-b]pyridin-5-yl]oxy}-4-chloro-2-fluorophenyl)-2-chloro-3-(1-cyanocyclopropyl)benzamide In the same manner as in Example C61(xiii), the title compound (30 mg, 16%) was obtained as colorless crystals using N-[5-(5-amino-2-chloro-4-fluorophenoxy)[1,3]thiazolo[5,4-b]pyridin-2-yl]acetamide (0.12 g, 0.33 mmol) produced in Example C61(xii), 2-chloro-3-(1-cyanocyclopropyl)benzoic acid (0.11 g, 0.5 mmol), oxalyl chloride (0.5 mL), N,N-dimethylformamide, tetrahydrofuran and N,N-dimethylacetamide.

$^1$H-NMR (DMSO-$d_6$, 300 MHz) δ 1.38 (2H, dd, J=5.1, 7.5 Hz), 1.83 (2H, dd, J=5.4, 7.5 Hz), 2.30 (3H, s), 7.10 (1H, d, J=8.7 Hz), 7.32 (1H, d, J=8.7 Hz), 7.40 (1H, t, J=8.7 Hz), 7.51 (1H, dd, J=1.8, 7.8 Hz), 7.69 (1H, dd, J=1.8, 7.5 Hz), 8.01 (1H, d, J=8.7 Hz), 8.05 (1H, d, J=2.7 Hz), 8.51 (1H, d, J=7.8 Hz), 9.02 (1H, br s).

Example C63

Production of 2-chloro-3-(1-cyano-1-methylethyl)-N-[5-({2-[(cyclopropylcarbonyl)amino][1,3]thiazolo[5,4-b]pyridin-5-yl}oxy)-2-fluorophenyl]benzamide

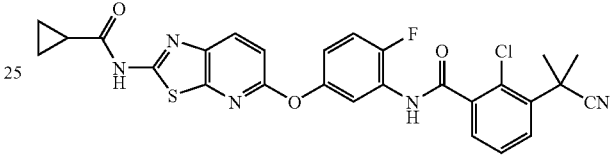

(i) Production of 2-fluoro-5-[(5-nitropyridin-2-yl)oxy]aniline

A mixture of 2-chloro-5-nitropyridine (6.34 g, 40 mmol), 3-amino-4-fluorophenol (5.08 g, 40 mmol) and potassium carbonate (5.52 g, 40 mmol) in N,N-dimethylformamide (20 mL) was stirred at room temperature overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50), and crystallized from diethyl ether to give the title compound (7.90 g, 79%) as a yellow powder.

$^1$H-NMR (DMSO-$d_6$, 300 MHz) δ 3.88 (2H, br s), 6.43-6.48 (1H, m), 6.57 (1H, dd, J=2.7 Hz, 9.0 Hz), 6.99 (1H, dd, J=0.6 Hz, 9.0 Hz), 7.04 (1H, dd, J=8.7 Hz, 10.5 Hz), 8.46 (1H, dd, J=3.0 Hz, 9.0 Hz), 9.06 (1H, dd, J=0.3 Hz, 2.7 Hz).

(ii) Production of tert-butyl{2-fluoro-5-[(5-nitropyridin-2-yl)oxy]phenyl}carbamate A solution of 2-fluoro-5-[(5-nitropyridin-2-yl)oxy]aniline (7.43 g, 30 mmol) and di-tert-butyl bicarbonate (10.9 g, 50 mmol) in tetrahydrofuran (50 mL) was refluxed overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was triturated with diethyl ether to give the title compound (9.41 g, 90%) as a white amorphous.

$^1$H-NMR (DMSO-$d_6$, 300 MHz) δ 1.51 (9H, s), 6.73-6.79 (1H, m), 6.81 (1H, br s), 7.03 (1H, d, J=9.0 Hz), 7.13 (1H, dd,

J=9.0, 10.5 Hz), 8.02 (1H, d, J=4.5 Hz), 8.47 (1H, dd, J=3.0, 9.0 Hz), 9.04 (1H, d, J=2.7 Hz).

(iii) Production of tert-butyl{5-[(5-aminopyridin-2-yl)oxy]-2-fluorophenyl}carbamate A suspension of tert-butyl{2-fluoro-5-[(5-nitropyridin-2-yl)oxy]phenyl}carbamate (3.49 g, 10 mmol) and 10% palladium-carbon (1.0 g) in methanol (20 mL)-tetrahydrofuran (20 mL) was vigorously stirred at room temperature under a hydrogen atmosphere overnight. The insoluble material was filtered off, and the filtrate was concentrated under reduced pressure. The residue was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure, and the residue was triturated with diethyl ether to give the title compound (3.00 g, 94%) as a white amorphous.

$^1$H-NMR (DMSO-$d_6$, 300 MHz) δ 1.50 (9H, s), 3.49 (2H, br s), 6.65-6.70 (1H, m), 6.71 (1H, br s), 6.75 (1H, d, J=8.7 Hz), 7.02 (1H, dd, J=9.0, 10.5 Hz), 7.07 (1H, dd, J=3.0, 8.4 Hz), 7.68 (1H, d, J=3.0 Hz), 7.88 (1H, d, J=2.7 Hz).

(iv) Production of tert-butyl{5-[(2-amino[1,3]thiazolo[5,4-b]pyridin-5-yl)oxy]-2-fluorophenyl}carbamate To a solution of tert-butyl{5-[(5-aminopyridin-2-yl)oxy]-2-fluorophenyl}carbamate (3.00 g, 9.4 mmol) and potassium thiocyanate (3.93 g, 40 mmol) in acetic acid (40 mL) was added dropwise bromine (2.40 g, 15 mmol) under ice-cooling, and the mixture was stirred at room temperature overnight. The yellow insoluble material was filtered off, and the filtrate was concentrated under reduced pressure. To residue was added saturated aqueous sodium hydrogen carbonate solution (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was triturated with diethyl ether to give the title compound (3.20 g, 90%) as a pale-yellow amorphous.

$^1$H-NMR (DMSO-$d_6$, 300 MHz) δ 1.51 (9H, s), 5.49 (2H, br s), 6.71-6.76 (2H, m), 6.85 (1H, d, J=8.4 Hz), 7.06 (1H, dd, J=9.0, 10.5 Hz), 7.73 (1H, d, J=8.7 Hz), 8.30 (1H, br s).

(v) Production of tert-butyl(5-{[2-(cyclopropylcarbonyl)amino[1,3]thiazolo[5,4-b]pyridin-5-yl]oxy}-2-fluorophenyl)carbamate To a solution of tert-butyl{5-[(2-amino[1,3]thiazolo[5,4-b]pyridin-5-yl)oxy]-2-fluorophenyl}carbamate (1.13 g, 3.0 mmol) and N,N-dimethylpyridine-4-amine (1.22 g, 10 mmol) in pyridine (10 mL) was added dropwise cyclopropanecarbonyl chloride (1.05 g, 10 mmol) under ice-cooling, and the mixture was stirred at room temperature overnight. To the reaction mixture was added water (200 mL), and the mixture was extracted with ethyl acetate (100 mL×2). The ethyl acetate layers were combined, and dried over anhydrous magnesium sulfate. The insoluble material was filtered off, and the filtrate was concentrated under reduced pressure. The obtained residue was triturated with diethyl ether to give the title compound (0.78 g, 59%) as a pale-yellow amorphous.

$^1$H-NMR (DMSO-$d_6$, 300 MHz) δ 1.02-1.10 (2H, m), 1.21-1.28 (2H, m), 1.50 (9H, s), 1.58-1.67 (1H, m), 6.76-6.81 (2H, m), 6.95 (1H, d, J=8.7 Hz), 7.08 (1H, dd, J=9.0, 10.8 Hz), 7.96 (1H, d, J=3.6 Hz), 7.97 (1H, br s), 10.12 (1H, br s).

(vi) Production of N-[5-(3-amino-4-fluorophenoxy)[1,3]thiazolo[5,4-b]pyridin-2-yl]cyclopropanecarboxamide A solution of tert-butyl(5-{[2-(cyclopropylcarbonyl)amino[1,3]thiazolo[5,4-b]pyridin-5-yl]oxy}-2-fluorophenyl)carbamate (0.78 g, 1.75 mmol) in trifluoroacetic acid (5 mL) was stirred at room temperature for 30 min. The reaction mixture was concentrated under reduced pressure, and the residue was diluted with ethyl acetate (100 mL), washed with 0.1N aqueous sodium hydroxide solution (100 mL), and dried over anhydrous magnesium sulfate. The insoluble material was filtered off, and the filtrate was concentrated under reduced pressure. The obtained residue was triturated with diethyl ether to give the title compound (0.60 g, quantitatively) as a white amorphous.

$^1$H-NMR (DMSO-$d_6$, 300 MHz) δ 0.91-0.99 (2H, m), 1.11-1.19 (2H, m), 1.90-1.98 (1H, m), 4.03 (2H, br s), 6.40-6.44 (1H, m), 6.60 (1H, dd, J=2.7, 7.5 Hz), 6.88 (1H, d, J=8.7 Hz), 6.97 (1H, dd, J=9.0, 10.5 Hz), 7.92 (1H, d, J=8.7 Hz), 11.85 (1H, br s).

(vii) Production of 2-chloro-3-(1-cyano-1-methylethyl)-N-[5-({2-[(cyclopropylcarbonyl)amino][1,3]thiazolo[5,4-b]pyridin-5-yl}oxy)-2-fluorophenyl]benzamide To a solution of 2-chloro-3-(1-cyano-1-methylethyl)benzoic acid (0.33 g, 1.5 mmol) produced in Example C61(v) in oxalyl chloride (1.5 mL) was added N,N-dimethylformamide (100 μL), and the mixture was stirred at room temperature for 30 min, and concentrated to dryness under reduced pressure. This was dissolved in a mixture of N,N-dimethylacetamide (1.5 mL) and tetrahydrofuran (1.5 mL), and the solution was added dropwise to a solution of N-[5-(3-amino-4-fluorophenoxy)[1,3]thiazolo[5,4-b]pyridin-2-yl]cyclopropanecarboxamide (0.345 g, 1.00 mmol) in N,N-dimethylacetamide (3 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (430 mg, 78%) as colorless crystals.

$^1$H-NMR (DMSO-$d_6$, 300 MHz) δ 1.02-1.10 (2H, m), 1.22-1.30 (2H, m), 1.59 (6H, s), 1.61-1.69 (1H, m), 6.94-6.99 (1H, m), 7.03 (1H, d, J=8.7 Hz), 7.18 (1H, dd, J=9.0, 10.5 Hz), 7.42

(1H, t, J=7.8 Hz), 7.56-7.64 (2H, m), 7.82 (1H, d, J=3.0 Hz), 7.99 (1H, d, J=8.7 Hz), 8.38 (1H, dd, J=2.7, 6.6 Hz), 9.46 (1H, br s).

Example C64

Production of N-(5-{[2-(acetylamino)[1,3]thiazolo[5,4-b]pyridin-5-yl]oxy}-2-fluorophenyl)-2-chloro-3-(1-cyano-1-methylethyl)benzamide

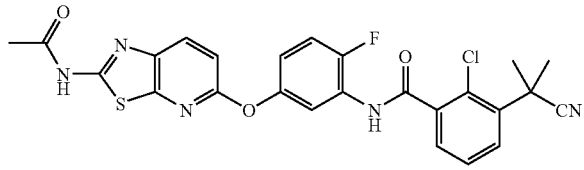 [SMILES: CC(=O)Nc1nc2ccc(Oc3ccc(F)c(NC(=O)c4cccc(C(C)(C)C#N)c4Cl)c3)nc2s1]

(i) Production of tert-butyl(5-{[2-(acetylamino)[1,3]thiazolo[5,4-b]pyridin-5-yl]oxy}-2-fluorophenyl)carbamate To a solution of tert-butyl{5-[(2-amino[1,3]thiazolo[5,4-b]pyridin-5-yl)oxy]-2-fluorophenyl}carbamate (1.13 g, 3.0 mmol) produced in Example C63(iv) and N,N-dimethylpyridine-4-amine (1.22 g, 10 mmol) in pyridine (10 mL) was added dropwise acetyl chloride (0.79 g, 10 mmol) under ice-cooling, and the mixture was stirred at room temperature overnight. To the reaction mixture was added water (200 mL), and the mixture was extracted with ethyl acetate (100 mL×2). The ethyl acetate layers were combined, and dried over anhydrous magnesium sulfate. The insoluble material was filtered off, and the filtrate was concentrated under reduced pressure. The obtained residue was purified by silica gel column chromatography (ethyl acetate/hexane=0/100→100/0), and triturated with diethyl ether to give the title compound (0.65 g, 52%) as a white amorphous.

$^1$H-NMR (DMSO-$d_6$, 300 MHz) δ 1.52 (9H, s), 2.24 (3H, s), 6.76-6.80 (1H, m), 6.81-6.89 (1H, m), 6.97 (1H, dd, J=4.5, 8.7 Hz), 7.09 (1H, dd, J=9.0, 10.5 Hz), 7.93 (1H, d, J=8.7 Hz), 7.98 (1H, br s), 10.45 (1H, br s).

(ii) Production of N-[5-(3-amino-4-fluorophenoxy)[1,3]thiazolo[5,4-b]pyridin-2-yl]acetamide A solution of tert-butyl(5-{[2-(acetylamino)[1,3]thiazolo[5,4-b]pyridin-5-yl]oxy}-2-fluorophenyl)carbamate (0.65 g, 1.54 mmol) in trifluoroacetic acid (5 mL) was stirred at room temperature for 30 min. The reaction mixture was concentrated under reduced pressure, and the residue was diluted with ethyl acetate (100 mL), washed with 0.1N aqueous sodium hydroxide solution (100 mL), and dried over anhydrous magnesium sulfate. The insoluble material was filtered off, and the filtrate was concentrated under reduced pressure. The obtained residue was triturated with diethyl ether to give the title compound (0.49 g, quantitatively) as a white amorphous.

$^1$H-NMR (DMSO-$d_6$, 300 MHz) δ 2.27 (3H, s), 4.03 (2H, br s), 6.40-6.46 (1H, m), 6.61 (1H, dd, J=3.0, 7.5 Hz), 6.89 (1H, d, J=8.7 Hz), 6.97 (1H, dd, J=8.7, 10.8 Hz), 7.92 (1H, d, J=8.7 Hz), 11.66 (1H, br s).

(iii) Production of N-(5-{[2-(acetylamino)[1,3]thiazolo[5,4-b]pyridin-5-yl]oxy}-2-fluorophenyl)-2-chloro-3-(1-cyano-1-methylethyl)benzamide To a solution of 2-chloro-3-(1-cyano-1-methylethyl)benzoic acid (0.33 g, 1.5 mmol) produced in Example C61(v) in oxalyl chloride (1.5 mL) was added N,N-dimethylformamide (100 μL), and the mixture was stirred at room temperature for 30 min, and concentrated to dryness under reduced pressure. This was dissolved in a mixture of N,N-dimethylacetamide (1.5 mL) and tetrahydrofuran (1.5 mL), and the solution was added dropwise to a solution of N-[5-(3-amino-4-fluorophenoxy)[1,3]thiazolo[5,4-b]pyridin-2-yl]acetamide (0.33 g, 1.00 mmol) in N,N-dimethylacetamide (3 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (320 mg, 61%) as colorless crystals.

$^1$H-NMR (DMSO-$d_6$, 300 MHz) δ 1.59 (6H, s), 2.30 (3H, s), 6.94-6.99 (1H, m), 7.03 (1H, d, J=8.7 Hz), 7.18 (1H, dd, J=9.0, 10.5 Hz), 7.43 (1H, t, J=7.8 Hz), 7.57-7.63 (2H, m), 7.83 (1H, d, J=3.0 Hz), 7.97 (1H, d, J=9.0 Hz), 8.38 (1H, dd, J=2.7, 6.6 Hz), 9.21 (1H, br s).

Example C65

Production of N-(5-{[2-(acetylamino)[1,3]thiazolo[5,4-b]pyridin-5-yl]oxy}-2-fluorophenyl)-2-chloro-3-(1-cyanocyclopropyl)benzamide

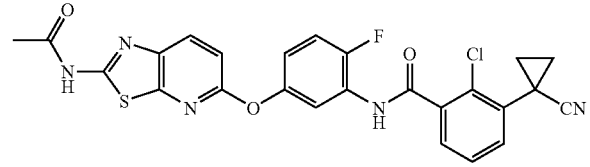 [SMILES: CC(=O)Nc1nc2ccc(Oc3ccc(F)c(NC(=O)c4cccc(C5(C#N)CC5)c4Cl)c3)nc2s1]

To a solution of 2-chloro-3-(1-cyanocyclopropyl)benzoic acid (0.33 g, 1.5 mmol) produced in Example C62(ii) in oxalyl chloride (1.5 mL) was added N,N-dimethylformamide (100 μL), and the mixture was stirred at room temperature for 30 min, and concentrated to dryness under reduced pressure. This was dissolved in a mixture of N,N-dimethylacetamide (1.5 mL) and tetrahydrofuran (1.5 mL), and the solution was added dropwise to a solution of N-[5-(3-amino-4-fluorophenoxy)[1,3]thiazolo[5,4-b]pyridin-2-yl]acetamide (0.33 g, 1.00 mmol) produced in Example C64(ii) in N,N-dimethylacetamide (3 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (280 mg, 54%) as colorless crystals.

$^1$H-NMR (DMSO-d$_6$, 300 MHz) δ 1.39 (2H, dd, J=5.1, 7.5 Hz), 1.82 (2H, dd, J=5.4, 7.5 Hz), 2.30 (3H, s), 6.94-6.99 (1H, m), 7.03 (1H, d, J=8.7 Hz), 7.19 (1H, dd, J=9.0, 10.5 Hz), 7.39 (1H, t, J=7.8 Hz), 7.50 (1H, dd, J=1.8, 7.8 Hz), 7.68 (1H, dd, J=1.8, 7.8 Hz), 7.97 (1H, d, J=8.7 Hz), 8.06 (1H, d, J=3.0 Hz), 8.39 (1H, dd, J=2.7, 6.6 Hz), 9.18 (1H, br s).

Example C66

Production of 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide

To a solution of 2-chloro-3-(1-cyanocyclopropyl)benzoic acid (0.11 g, 0.5 mmol) produced in Example C62(ii) in oxalyl chloride (0.5 mL) was added N,N-dimethylformamide (40 μL), and the mixture was stirred at room temperature for 30 min, and concentrated to dryness under reduced pressure. This was dissolved in N,N-dimethylacetamide (1.0 mL), and the solution was added dropwise to a solution of N-[5-(3-amino-4-fluorophenoxy)[1,3]thiazolo[5,4-b]pyridin-2-yl]cyclopropanecarboxamide (0.115 g, 0.33 mmol) produced in Example C63(vi) in N,N-dimethylacetamide (1 mL) under ice-cooling. The reaction mixture was stirred at room temperature for 1 hr, and poured into water (50 μL), and the mixture was extracted with ethyl acetate (50 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (80 mg, 44%) as colorless crystals.

$^1$H-NMR (DMSO-d$_6$, 300 MHz) δ 1.01-1.09 (2H, m), 1.21-1.29 (2H, m), 1.39 (2H, dd, J=5.4, 7.5 Hz), 1.62-1.70 (1H, m), 1.81 (2H, dd, J=5.4, 7.5 Hz), 6.94-6.99 (1H, m), 7.03 (1H, d, J=8.7 Hz), 7.19 (1H, dd, J=9.0, 10.2 Hz), 7.39 (1H, t, J=7.8 Hz), 7.50 (1H, dd, J=1.5, 7.5 Hz), 7.68 (1H, dd, J=1.5, 7.5 Hz), 7.98 (1H, d, J=8.7 Hz), 8.06 (1H, d, J=3.0 Hz), 8.39 (1H, dd, J=2.7, 6.6 Hz), 9.99 (1H, br s).

Example C67

Production of N-[5-({2-[(cyclopropylcarbonyl)amino][1,3]thiazolo[5,4-b]pyridin-5-yl}oxy)-2-fluorophenyl]-3-(1,1-dimethylprop-2-yn-1-yl)benzamide

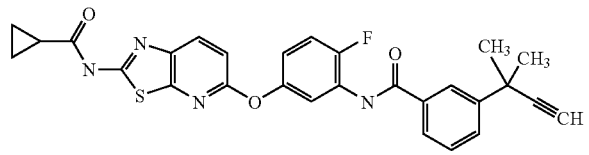 [SMILES: C#CC(C)(C)c1cccc(C(=O)Nc2cc(Oc3ccc4nc(NC(=O)C5CC5)sc4n3)ccc2F)c1]

(i) Production of 3-(1,1-dimethyl-2-oxoethyl)benzoic acid

To a solution of 3-(1-cyano-1-methylethyl)benzoic acid (8.60 g, 45.5 mmol) produced in Example C6(ii) in toluene (60 mL)/tetrahydrofuran (40 mL) was added dropwise a 1.0M solution (100 mL, 100 mmol) of diisobutylaluminum hydride in hexane at −78° C. for 1 hr. After the completion of the dropwise addition, the mixture was stirred at −78° C. for 1 hr and at 0° C. for 1 hr. The reaction mixture was poured into a mixture of ethyl acetate (200 mL) and 3N hydrochloric acid (300 mL), the organic layer and the aqueous layer were separated, and the aqueous layer was extracted with ethyl acetate (2×100 ml). The combined organic layer was washed with saturated brine (50 mL), and dried over anhydrous magnesium sulfate. The insoluble material was filtered off, and the filtrate was concentrated under reduced pressure. The obtained residue was recrystallized from ethyl acetate and hexane to give the title compound (6.39 g, 73%) as colorless crystals.

$^1$H-NMR (DMSO-d$_6$, 300 MHz) δ 1.43 (6H, s), 7.53 (1H, dt, J=0.6, 7.5 Hz), 7.58 (1H, dt, J=7.5, 1.6 Hz), 7.83-7.85 (1H, m), 7.88 (1H, dt, J=7.5, 1.6 Hz), 9.54 (1H, s), 13.06 (1H, br s).

(ii) Production of methyl 3-(1,1-dimethylprop-2-yn-1-yl)benzoate

To a solution of 3-(1,1-dimethyl-2-oxoethyl)benzoic acid in acetone (60 mL) were added potassium carbonate (3.78 g, 27.3 mmol) and methyl iodide (3.40 mL, 54.6 mmol), and the mixture was stirred at 60° C. for 5 hr. The insoluble material was filtered off, and the filtrate was concentrated under reduced pressure. To the obtained residue was added saturated aqueous sodium hydrogen carbonate solution (50 mL), and the mixture was extracted with ethyl acetate (100 mL, 30 mL). The combined organic layer was washed with saturated brine (20 mL), and dried over anhydrous magnesium sulfate. The insoluble material was filtered off, and the filtrate was concentrated under reduced pressure to give methyl 3-(1,1-dimethyl-2-oxoethyl)benzoate as a yellow oil.

To a suspension of p-acetamidobenzenesulfonyl azide (5.25 g, 21.9 mmol) and potassium carbonate (7.55 g, 54.6 mmol) in acetonitrile (100 mL) was added dimethyl(2-oxopropyl)phosphonate (3.00 mL, 21.9 mmol), and the mixture was stirred at room temperature for 2 hr. Then, to the reaction mixture was added a solution of methyl(1,1-dimethyl-2-oxoethyl)benzoate synthesized above in methanol (20 mL), and the mixture was stirred at room temperature for 16 hr. The insoluble material was filtered off, and the filtrate was concentrated under reduced pressure. To the obtained residue was added saturated aqueous sodium hydrogen carbonate solution (70 mL), and the mixture was extracted with ethyl acetate (100 mL). The combined organic layer was washed with saturated brine (20 mL), and dried over anhydrous magnesium sulfate. The insoluble material was filtered off, and the filtrate was concentrated under reduced pressure. The obtained residue was purified by basic silica gel column chromatography (hexane/ethyl acetate=100/0→90/10), and fractions containing the object product were concentrated under reduced pressure to give the title compound (2.26 g, 61%) as a colorless oil.

$^1$H-NMR (DMSO-d$_6$, 300 MHz) δ 1.56 (6H, s), 3.34 (1H, s), 3.66 (3H, s), 7.51 (1H, dt, J=0.6, 7.8 Hz), 7.80-7.88 (2H, m), 8.17 (1H, dt, J=0.6, 1.8 Hz).

(iii) Production of 3-(1,1-dimethylprop-2-yn-1-yl)benzoic acid

To a solution of methyl 3-(1,1-dimethylprop-2-yn-1-yl)benzoate (2.26 g, 11.2 mmol) in methanol (15 mL)/tetrahydrofuran (10 mL) was added 2N aqueous sodium hydroxide solution (11.2 mL, 22.4 mmol), and the mixture was stirred at 60° C. for 3 hr. The reaction mixture was neutralized with 6N hydrochloric acid (5 mL), 1N hydrochloric acid (50 mL) was added, and the mixture was extracted with ethyl acetate (100 mL, 20 mL). The combined organic layer was washed with saturated brine (10 mL), and dried over anhydrous magnesium sulfate. The insoluble material was filtered off, and the filtrate was concentrated under reduced pressure. The obtained residue was recrystallized from ethyl acetate and hexane to give the title compound (1.94 g, 92%) as colorless crystals.

$^1$H-NMR (DMSO-d$_6$, 300 MHz) δ 1.56 (6H, s), 3.33 (1H, s), 7.48 (1H, t, J=7.6 Hz), 7.72-7.88 (2H, m), 8.16 (1H, t, J=1.6 Hz), 13.01 (1H, br s).

(iv) Production of N-[5-({2-[(cyclopropylcarbonyl) amino][1,3]thiazolo[5,4-b]pyridin-5-yl}oxy)-2-fluorophenyl]-3-(1,1-dimethylprop-2-yn-1-yl)benzamide To a solution of 3-(1,1-dimethylprop-2-yn-1-yl)benzoic acid (0.10 g, 0.5 mmol) in oxalyl chloride (1 mL) was added N,N-dimethylformamide (40 μL), and the mixture was stirred at room temperature for 30 min, and concentrated to dryness under reduced pressure. This was dissolved in a mixed solution of N,N-dimethylacetamide (1 mL) and tetrahydrofuran (1 mL), and the solution was added dropwise to a solution of N-[5-(3-amino-4-fluorophenoxy)[1,3]thiazolo[5,4-b]pyridin-2-yl]cyclopropanecarboxamide (0.12 g, 0.33 mmol) produced in Example C63(vi) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (62 mg, 37%) as colorless crystals.

$^1$H-NMR (DMSO-d$_6$, 300 MHz) δ 0.96-1.04 (2H, m), 1.19-1.27 (2H, m), 1.62 (6H, s), 1.58-1.66 (1H, m), 2.40 (1H, s), 6.90-6.97 (1H, m), 7.00 (1H, d, J=8.7 Hz), 7.18 (1H, dd, J=8.7, 10.5 Hz), 7.47 (1H, t, J=7.8 Hz), 7.68-7.72 (1H, m), 7.76-7.81 (1H, m), 7.97 (1H, d, J=9.0 Hz), 8.09-8.13 (2H, m), 8.39 (1H, dd, J=2.7, 6.6 Hz), 10.23 (1H, br s).

Example C68

Production of N-(5-{[2-(acetylamino)[1,3]thiazolo[5,4-b]pyridin-5-yl]oxy}-2-fluorophenyl)-3-(1-cyano-1-methylethoxy)benzamide

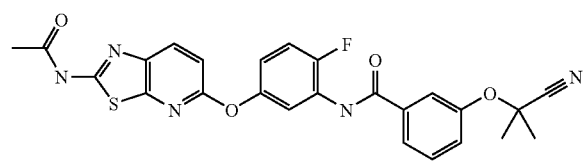 [SMILES: CC(=O)Nc1nc2ccc(Oc3ccc(F)c(NC(=O)c4cccc(OC(C)(C)C#N)c4)c3)nc2s1]

(i) Production of methyl 3-(cyanomethoxy)benzoate

To a solution of methyl 3-hydroxybenzoate (5.00 g, 32.9 mmol) in acetone (60 mL) were added bromoacetonitrile (2.63 mL, 39.4 mmol) and potassium carbonate (6.81 g, 49.3 mmol), and the mixture was stirred at 60° C. for 4 hr. To the reaction mixture was added saturated aqueous sodium hydrogen carbonate solution (100 mL), and the mixture was extracted with ethyl acetate (100 mL, 30 mL). The combined organic layer was washed with saturated brine (10 mL), and dried over anhydrous magnesium sulfate. The insoluble material was filtered off, and the filtrate was concentrated under reduced pressure. The obtained residue was purified by basic silica gel column chromatography (hexane/ethyl acetate=90/10→80/20), and fractions containing the object product were concentrated under reduced pressure to give the title compound (5.43 g, 86%) as a colorless oil.

$^1$H-NMR (DMSO-d$_6$, 300 MHz) δ 3.87 (3H, s), 5.27 (2H, s), 7.37 (1H, ddd, J=7.8, 2.6, 1.3 Hz), 7.54 (1H, t, J=7.8 Hz), 7.59 (1H, dd, J=2.6, 1.3 Hz), 7.68 (1H, dt, J=7.8, 1.3 Hz).

(ii) Production of methyl 3-(1-cyano-1-methylethoxy)benzoate

To a solution of methyl 3-(cyanomethoxy)benzoate (6.00 g, 31.4 mmol) in tetrahydrofuran (200 mL) was added methyl iodide (15.6 mL, 251 mmol), and a 1.1M solution (62.8 mL, 69.0 mmol) of lithium hexamethyl disilazide in tetrahydrofuran was added dropwise at −78° C. for 1.5 hr. After the completion of the dropwise addition, the mixture was stirred at −78° C. for 2 hr. The reaction mixture was poured into a mixture of ethyl acetate (150 mL) and aqueous ammonium chloride solution (150 mL), the organic layer and the aqueous layer were separated, and the aqueous layer was extracted with ethyl acetate (50 mL). The combined organic layer was washed with saturated brine (50 mL), and dried over anhydrous magnesium sulfate. The insoluble material was filtered off, and the filtrate was concentrated under reduced pressure. The obtained residue was purified by silica gel column chromatography (hexane/ethyl acetate=100/0→90/10), and fractions containing the object product were concentrated under reduced pressure to give the title compound (2.07 g, 30%) as a yellow oil.

$^1$H-NMR (DMSO-d$_6$, 300 MHz) δ 1.71 (6H, s), 3.86 (3H, s), 7.46 (1H, ddd, J=7.8, 2.4, 1.2 Hz), 7.56 (1H, dt, J=7.8, 0.3 Hz), 7.69-7.72 (1H, m), 7.79 (1H, ddd, J=7.8, 1.5, 1.2 Hz).

(iii) Production of 3-(1-cyano-1-methylethoxy)benzoic acid

To a solution of methyl 3-(1-cyano-1-methylethoxy)benzoate (2.07 g, 9.44 mmol) in methanol (12 mL)/tetrahydrofuran (4 mL) was added 2N aqueous sodium hydroxide solution (9.44 mL, 18.9 mmol), and the mixture was stirred at room temperature for 30 min. The reaction mixture was neutralized with 6N hydrochloric acid (5 mL), 1N hydrochloric acid (50 mL) was added, and the mixture was extracted with ethyl acetate (50 mL, 20 mL). The combined organic layer was washed with saturated brine (10 mL), and dried over anhydrous magnesium sulfate. The insoluble material was filtered off, and the filtrate was concentrated under reduced pressure. The obtained residue was purified by silica gel column chromatography (hexane/ethyl acetate=90/10→50/50), and fractions containing the object product were concentrated under reduced pressure. The obtained residue was recrystallized from ethyl acetate and hexane to give the title compound (1.01 g, 51%) as colorless crystals.

$^1$H-NMR (DMSO-d$_6$, 300 MHz) δ 1.72 (6H, s), 7.42 (1H, ddd, J=7.9, 2.5, 1.2 Hz), 7.54 (1H, t, J=7.9 Hz), 7.70-7.73 (1H, m), 7.78 (1H, dt, J=7.9, 1.2 Hz), 13.18 (1H, br s). cl (iv)

Production of N-(5-{[2-(acetylamino)[1,3]thiazolo[5,4-b]pyridin-5-yl]oxy}-2-fluorophenyl)-3-(1-cyano-1-methylethoxy)benzamide To a solution of 3-(1-cyano-1-methylethoxy)benzoic acid (0.10 g, 0.5 mmol) in oxalyl chloride (0.5 mL) was added N,N-dimethylformamide (40 µL), and the mixture was stirred at room temperature for 30 min, and concentrated to dryness under reduced pressure. This was dissolved in a mixture of N,N-dimethylacetamide (1 mL) and tetrahydrofuran (1 mL), and the solution was added dropwise to a solution of N-[5-(3-amino-4-fluorophenoxy)[1,3]thiazolo[5,4-b]pyridin-2-yl]acetamide (0.11 g, 0.33 mmol) produced in Example C64 (ii) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from diethyl ether to give the title compound (85 mg, 51%) as colorless crystals.

$^1$H-NMR (DMSO-$d_6$, 300 MHz) δ 1.75 (6H, s), 2.30 (3H, s), 6.91-6.97 (1H, m), 7.02 (1H, d, J=8.7 Hz), 7.18 (1H, dd, J=8.7, 10.5 Hz), 7.43-7.48 (1H, m), 7.50 (1H, t, J=7.8 Hz), 7.62-7.67 (2H, m), 7.97 (1H, d, J=8.7 Hz), 8.08 (1H, d, J=3.3 Hz), 8.37 (1H, dd, J=2.7, 6.6 Hz), 9.14 (1H, br s).

Example C69

Production of N-(5-{[2-(acetylamino)[1,3]thiazolo[5,4-b]pyridin-5-yl]oxy}-2-fluorophenyl)-4-chloro-3-(1-cyano-1-methylethyl)benzamide

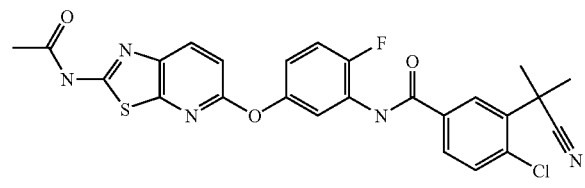 [SMILES: CC(=O)Nc1nc2ccc(Oc3ccc(F)c(NC(=O)c4ccc(Cl)c(C(C)(C)C#N)c4)c3)nc2s1]

(i) Production of methyl 4-chloro-3-(1-cyano-1-methylethyl)benzoate

To a solution of methyl 4-chloro-3-(cyanomethyl)benzoate (14.0 g, 67 mmol) in dimethylsulfoxide (300 mL) was added sodium hydride (60% in oil, 9.6 g, 240 mmol), and the reaction mixture was stirred at room temperature for 20 min. Methyl iodide (15 mL, 240 mmol) was added, and the mixture was further stirred at room temperature for 15 hr. The reaction mixture was diluted with water (500 mL), extracted with ethyl acetate (800 mL), washed with saturated brine (100 mL), and dried over anhydrous sodium sulfate, and the insoluble material was filtered off. The solvent was evaporated under reduced pressure, the residue was purified by silica gel column chromatography (ethyl acetate/hexane=5/95→50/50), and fractions containing the object product were concentrated under reduced pressure to give the title compound (8.4 g, 53%) as a colorless oil.

$^1$H-NMR (DMSO-$d_6$, 300 MHz) δ 1.81 (6H, s), 3.91 (3H, s), 7.64-8.01 (2H, m), 8.08 (1H, d, J=1.9 Hz).

(ii) Production of 4-chloro-3-(1-cyano-1-methylethyl)benzoic acid

To a solution of methyl 4-chloro-3-(1-cyano-1-methylethyl)benzoate (8.0 g, 34 mmol) in tetrahydrofuran (30 mL) were added lithium hydroxide.monohydrate (2.13 g, 51 mmol), methanol (100 mL) and water (5 mL), and the mixture was stirred at room temperature for 4 hr. The solvent was evaporated under reduced pressure, and the residue was diluted with water (200 mL). 1N Hydrochloric acid was slowly added to the mixture to adjust the pH to 3. The precipitated white precipitate was collected by filtration, washed with water, and dried to give the title compound (7.4 g, 99%) as a white powder.

$^1$H-NMR (DMSO-$d_6$, 300 MHz) δ 1.85 (6H, s), 7.70 (1H, d, J=8.3 Hz), 7.94 (1H, dd, J=8.3, 2.1 Hz), 8.07 (1H, d, J=2.1 Hz), 12.70 (1H, br s).

(iii) Production of N-(5-{[2-(acetylamino)[1,3]thiazolo[5,4-b]pyridin-5-yl]oxy}-2-fluorophenyl)-4-chloro-3-(1-cyano-1-methylethyl)benzamide To a solution of 4-chloro-3-(1-cyano-1-methylethyl)benzoic acid (0.11 g, 0.5 mmol) in oxalyl chloride (0.5 mL) was added N,N-dimethylformamide (40 µL), and the mixture was stirred at room temperature for 30 min, and concentrated to dryness under reduced pressure. This was dissolved in a mixture of N,N-dimethylacetamide (1 mL) and tetrahydrofuran (1 mL), and a solution was added dropwise to a solution of N-[5-(3-amino-4-fluorophenoxy)[1,3]thiazolo[5,4-b]pyridin-2-yl]acetamide (0.11 g, 0.33 mmol) produced in Example C64(ii) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (37 mg, 21%) as colorless crystals.

$^1$H-NMR (DMSO-$d_6$, 300 MHz) δ 1.91 (6H, s), 2.27 (3H, s), 6.94-7.10 (1H, m), 7.00 (1H, d, J=8.7 Hz), 7.14-7.24 (1H, m), 7.58 (1H, d, J=8.4 Hz), 7.78 (1H, dd, J=2.7, 8.4 Hz), 7.96 (1H, d, J=8.7 Hz), 7.97 (1H, d, J=2.7 Hz), 8.18 (1H, dd, J=2.7, 6.3 Hz), 8.47 (1H, d, J=2.7 Hz), 11.10 (1H, br s).

Example C70

Production of N-(5-{[2-(acetylamino)[1,3]thiazolo[5,4-b]pyridin-5-yl]oxy}-2-fluorophenyl)-2-chloro-3-(1-cyano-1-methylethoxy)benzamide

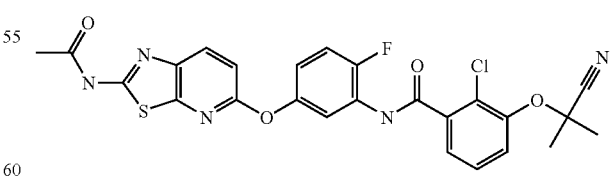

(i) Production of methyl 2-chloro-3-(cyanomethoxy)benzoate

To a solution of 2-chloro-3-methoxybenzoic acid (52.1 g, 279 mmol) in acetic acid (200 mL) was added 40% hydrobromic acid (50 mL), and the mixture was heated under reflux for 4 days. The reaction mixture was cooled to room temperature, and concentrated under reduced pressure to give 2-chloro-3-hydroxybenzoic acid as a colorless solid.

2-Chloro-3-hydroxybenzoic acid obtained above was dissolved in methanol (300 mL), conc. sulfuric acid (3 mL) was added, and the mixture was stirred at room temperature for 8 days, and at 80° C. for 6 hr. The reaction mixture was cooled to room temperature, and concentrated under reduced pressure. The obtained residue was dissolved in ethyl acetate (300 mL), and the solution was washed with saturated aqueous sodium hydrogen carbonate solution (200 mL). The aqueous layer was separated, and extracted with ethyl acetate (50 mL×2). The combined organic layer was washed with saturated brine (50 mL), and dried over anhydrous magnesium sulfate. The insoluble material was filtered off, and the filtrate was concentrated under reduced pressure to give methyl 2-chloro-3-hydroxybenzoate as a pale-brown powder.

To a suspension of methyl 2-chloro-3-hydroxybenzoate obtained above, potassium carbonate (57.9 mmol, 419 mmol) and sodium iodide (62.8 g, 419 mmol) in acetone (300 mL) was added chloroacetonitrile (19.5 mL, 307 mmol), and the mixture was stirred at 70° C. for 13 hr. The reaction mixture was cooled to room temperature, the insoluble material was filtered off, and the filtrate was concentrated under reduced pressure. The residue was dissolved in ethyl acetate (300 mL), and the solution was washed with saturated aqueous sodium hydrogen carbonate solution (200 mL). The aqueous layer was separated, and extracted with ethyl acetate (50 mL). The combined organic layer was washed with saturated brine (30 mL), and dried over anhydrous magnesium sulfate. The insoluble material was filtered off, and the filtrate was concentrated under reduced pressure. The obtained residue was triturated with ethyl acetate/hexane to give methyl 2-chloro-3-(cyanomethoxy)benzoate (57.8 g, 92%, 3 step yield) as a colorless powder.

$^1$H-NMR (DMSO-$d_6$, 300 MHz) δ 3.87 (3H, s), 5.34 (2H, s), 7.43-7.52 (3H, m).

(ii) Production of methyl
2-chloro-3-(1-cyano-1-methylethoxy)benzoate

To a solution of methyl 2-chloro-3-(cyanomethoxy)benzoate (15.2 g, 67.4 mmol) and methyl iodide (12.6 mL, 202 mmol) in tetrahydrofuran (200 mL) was added dropwise a 1.9M solution (78.0 mL, 148 mmol) of sodium hexamethyldisilazide in tetrahydrofuran at 0° C. for 1 hr. After the completion of the dropwise addition, the reaction mixture was stirred at 0° C. for 30 min, and at room temperature for 30 min. To the reaction mixture was added saturated aqueous ammonium chloride solution (150 mL), and the separated aqueous layer was extracted with ethyl acetate (50 mL). The combined organic layer was washed with saturated brine (30 mL), and dried over anhydrous magnesium sulfate. The insoluble material was filtered off, and the filtrate was concentrated under reduced pressure, and the residue was purified by basic silica gel column chromatography (hexane/ethyl acetate=100/0→85/15). The obtained solution was concentrated under reduced pressure to give the title compound (8.55 g, 50%) as a pale-yellow oil.

$^1$H-NMR (DMSO-$d_6$, 300 MHz) δ 1.77 (6H, s), 3.87 (3H, s), 7.51 (1H, t, J=7.8 Hz), 7.59 (1H, dd, J=1.8, 7.8 Hz), 7.66 (1H, dd, J=1.8, 7.8 Hz).

(iii) Production of
2-chloro-3-(1-cyano-1-methylethoxy)benzoic acid

To a solution of methyl 2-chloro-3-(1-cyano-1-methylethoxy)benzoate (19.0 g, 74.7 mmol) in 2-propanol (250 mL) was added 2N aqueous sodium hydroxide solution (44.8 mL, 89.7 mmol), and the mixture was stirred at room temperature for 2 hr. The reaction mixture was concentrated under reduced pressure, and the residue was dissolved in ethyl acetate (300 mL). To the obtained solution was added water (60 mL) to give a two-layer mixture, and 1N hydrochloric acid (90 mL) was added with stirring to neutralize the mixture. The organic layer was separated, washed with saturated brine (30 mL), and dried over anhydrous magnesium sulfate. The insoluble material was filtered off, and the filtrate was concentrated under reduced pressure, and the obtained powder was crystallized from ethanol/water to give the title compound (13.88 g, 77%) as colorless crystals.

$^1$H-NMR (DMSO-$d_6$, 300 MHz) δ 1.77 (6H, s), 7.47 (1H, t, J=7.8 Hz), 7.55 (1H, dd, J=1.8, 7.8 Hz), 7.61 (1H, dd, J=1.8, 7.8 Hz), 13.55 (1H, br s).

(iv) Production of N-(5-{[2-(acetylamino)[1,3]thiazolo[5,4-b]pyridin-5-yl]oxy}-2-fluorophenyl)-2-chloro-3-(1-cyano-1-methylethoxy)benzamide To a solution of 2-chloro-3-(1-cyano-1-methylethoxy)benzoic acid (0.12 g, 0.5 mmol) in oxalyl chloride (0.5 mL) was added N,N-dimethylformamide (40 μL), and the mixture was stirred at room temperature for 30 min, and concentrated to dryness under reduced pressure. This was dissolved in a mixture of N,N-dimethylacetamide (1 mL) and tetrahydrofuran (1 mL), and a solution was added dropwise to a solution of N-[5-(3-amino-4-fluorophenoxy)[1,3]thiazolo[5,4-b]pyridin-2-yl]acetamide (0.11 g, 0.33 mmol) produced in Example C64(ii) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (24 mg, 14%) as colorless crystals.

$^1$H-NMR (DMSO-$d_6$, 300 MHz) δ 1.80 (6H, s), 2.29 (3H, s), 6.92-6.98 (1H, m), 7.03 (1H, d, J=8.7 Hz), 7.18 (1H, dd, J=9.0, 10.5 Hz), 7.40 (1H, t, J=7.8 Hz), 7.52 (1H, dd, J=1.5, 8.1 Hz), 7.68 (1H, dd, J=1.5, 8.1 Hz), 7.98 (1H, d, J=8.7 Hz), 8.10 (1H, d, J=2.7 Hz), 8.39 (1H, dd, J=2.7, 6.6 Hz), 9.45 (1H, br s).

Example C71

Production of 2-chloro-3-(1-cyanocyclopropyl)-N-(2-fluoro-5-{[2-(propanoylamino)[1,3]thiazolo[5,4-b]pyridin-5-yl]oxy}phenyl)benzamide

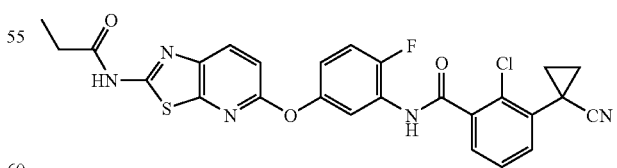

(i) Production of 2-chloro-3-(1-cyanocyclopropyl)-N-(2-fluoro-5-hydroxyphenyl)benzamide To a solution of 2-chloro-3-(1-cyanocyclopropyl)benzoic acid (4.42 g, 20 mmol) produced in Example C62(ii) in oxalyl chloride (10 mL) was added N,N-dimethylformamide (100 μL), and the mixture was stirred at room temperature for 1 hr, and concentrated to dryness under reduced pressure. This was dissolved in tetrahydrofuran (10 mL), and the solution was added dropwise with vigorous stirring to a two-layer mixture of a solution of 3-amino-4-fluorophenol (2.54 g, 20 mmol) in tetrahydrofuran (10 mL) and a solution (10 mL) of sodium hydrogen carbonate (2.70 g, 30 mmol) in water under ice-cooling. The reaction mixture was stirred at room temperature for 1 hr, and poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50) to give the title compound (6.50 g, 98%) as white crystals.

$^1$H-NMR (DMSO-$d_6$, 300 MHz) δ 1.40 (2H, dd, J=5.4, 7.8 Hz), 1.82 (2H, dd, J=5.4, 7.8 Hz), 6.49 (1H, br s), 6.56-6.62 (1H, m), 7.01 (1H, dd, J=9.0, 10.5 Hz), 7.42 (1H, t, J=7.8 Hz), 7.53 (1H, dd, J=1.8, 7.5 Hz), 7.69 (1H, dd, J=1.8, 7.5 Hz), 8.04 (1H, d, J=3.0 Hz), 8.27 (1H, dd, J=3.0, 6.3 Hz).

(ii) Production of 2-chloro-3-(1-cyanocyclopropyl)-N-{2-fluoro-5-[(5-nitropyridin-2-yl)oxy]phenyl}benzamide A mixture of 2-chloro-3-(1-cyanocyclopropyl)-N-(2-fluoro-5-hydroxyphenyl)benzamide (6.50 g, 19.7 mmol), 2-chloro-5-nitropyridine (3.17 g, 20 mmol) and potassium carbonate (2.76 g, 20 mmol) in N,N-dimethylformamide (20 mL) was stirred at room temperature overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50), and crystallized from diethyl ether to give the title compound (6.60 g, 74%) as a yellow powder.

$^1$H-NMR (DMSO-$d_6$, 300 MHz) δ 1.40 (2H, dd, J=5.4, 7.5 Hz), 1.83 (2H, dd, J=5.4, 7.5 Hz), 6.92-6.98 (1H, m), 7.10 (1H, d, J=9.0 Hz), 7.19-7.24 (1H, m), 7.41 (1H, t, J=7.8 Hz), 7.52 (1H, dd, J=1.8, 7.5 Hz), 7.69 (1H, dd, J=1.8, 7.5 Hz), 8.10 (1H, br s), 8.43 (1H, dd, J=3.0, 6.6 Hz), 7.66 (1H, dd, J=2.7, 9.0 Hz), 9.06 (1H, d, J=2.7 Hz).

(iii) Production of N-{5-[(5-aminopyridin-2-yl)oxy]-2-fluorophenyl}-2-chloro-3-(1-cyanocyclopropyl)benzamide A suspension of 2-chloro-3-(1-cyanocyclopropyl)-N-{2-fluoro-5-[(5-nitropyridin-2-yl)oxy]phenyl}benzamide (6.60 g, 14.6 mmol), iron powder (1.68 g, 30 mmol) and calcium chloride (3.33 g, 30 mmol) in ethanol (80 mL)-water (20 mL) was stirred at 80° C. overnight. The reaction mixture was poured into 0.5N aqueous sodium hydroxide solution (500 mL), ethyl acetate (300 mL) was added, the mixture was stirred, and the insoluble material was filtered through celite. The ethyl acetate layer was separated from the filtrate, and dried over anhydrous sodium sulfate. The insoluble material was filtered off, and the filtrate was concentrated under reduced pressure. The obtained residue was triturated with diethyl ether to give the title compound (4.23 g, 69%) as a pale-yellow amorphous.

$^1$H-NMR (DMSO-$d_6$, 300 MHz) δ 1.39 (2H, dd, J=5.4, 7.5 Hz), 1.80 (2H, dd, J=5.4, 7.5 Hz), 3.52 (2H, br s), 6.82 (1H, d, J=9.4 Hz), 6.82-6.88 (1H, m), 7.10 (1H, d, J=8.7 Hz), 7.12 (1H, dd, J=7.8, 8.7 Hz), 7.38 (1H, t, J=7.8 Hz), 7.50 (1H, dd, J=1.8, 7.8 Hz), 7.66 (1H, dd, J=1.8, 7.8 Hz), 7.70 (1H, d, J=3.0 Hz), 8.00 (1H, d, J=3.0 Hz), 8.29 (1H, dd, J=3.0, 6.6 Hz).

(iv) Production of N-{5-[(2-amino[1,3]thiazolo[5,4-b]pyridin-5-yl)oxy]-2-fluorophenyl}-2-chloro-3-(1-cyanocyclopropyl)benzamide To a solution of N-{5-[(5-aminopyridin-2-yl)oxy]-2-fluorophenyl}-2-chloro-3-(1-cyanocyclopropyl)benzamide (4.23 g, 10 mmol) and potassium thiocyanate (3.89 g, 40 mmol) in acetic acid (50 mL) was added dropwise bromine (2.40 g, 15 mmol) under ice-cooling, and the mixture was stirred at room temperature overnight. The yellow insoluble material was filtered off, and the filtrate was concentrated under reduced pressure. To the residue was added saturated aqueous sodium hydrogen carbonate solution (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and triturated with diethyl ether to give the title compound (3.32 g, 69%) as a pale-yellow amorphous.

$^1$H-NMR (DMSO-$d_6$, 300 MHz) δ 1.40 (2H, dd, J=5.4, 7.5 Hz), 1.80 (2H, dd, J=5.4, 7.5 Hz), 5.14 (2H, br s), 6.88-6.95 (2H, m), 7.16 (1H, dd, J=9.0, 10.2 Hz), 7.39 (1H, t, J=7.8 Hz), 7.50 (1H, dd, J=1.8, 7.8 Hz), 7.68 (1H, dd, J=1.8, 7.8 Hz), 7.77 (1H, d, J=8.7 Hz), 8.04 (1H, d, J=3.0 Hz), 8.39 (1H, dd, J=2.7, 6.6 Hz).

(v) Production of 2-chloro-3-(1-cyanocyclopropyl)-N-(2-fluoro-5-{[2-(propanoylamino)[1,3]thiazolo[5,4-b]pyridin-5-yl]oxy}phenyl)benzamide To a solution of N-{5-[(2-amino[1,3]thiazolo[5,4-b]pyridin-5-yl)oxy]-2-fluorophenyl}-2-chloro-3-(1-cyanocyclopropyl)benzamide (0.16 g, 0.33 mmol) and N,N-dimethylpyridine-4-amine (0.12 g, 1.00 mmol) in pyridine (2 mL) was added dropwise propionyl chloride (0.09 g, 1.00 mmol) under ice-cooling, and the mixture was stirred at room temperature for 2 hr. To the reaction mixture was added water (50 mL), and the mixture was extracted with ethyl acetate (50 mL×2). The ethyl acetate layers were combined, and dried over anhydrous magnesium sulfate. The insoluble material was filtered off, and the filtrate was concentrated under reduced pressure. The obtained residue was dissolved in methanol (5 mL), 8N aqueous sodium hydroxide solution (1 mL) was added, and the mixture was stirred at room temperature for 1 hr. The reaction mixture was poured into water (50 mL), and the mixture was extracted with ethyl acetate (50 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (80 mg, 45%) as white crystals.

$^1$H-NMR (DMSO-$d_6$, 300 MHz) δ 1.29 (3H, t, J=7.5 Hz), 1.39 (2H, dd, J=5.4, 7.5 Hz), 1.82 (2H, dd, J=5.4, 7.5 Hz), 2.53 (2H, q, J=7.5 Hz), 6.94-7.00 (1H, m), 7.03 (1H, d, J=8.7 Hz), 7.19 (1H, dd, J=9.0, 10.5 Hz), 7.39 (1H, t, J=7.5 Hz), 7.50 (1H, dd, J=1.5, 7.8 Hz), 7.68 (1H, dd, J=1.8, 7.8 Hz), 7.98 (1H, d, J=8.7 Hz), 8.06 (1H, d, J=3.0 Hz), 8.39 (1H, dd, J=3.0, 6.6 Hz), 9.08 (1H, br s).

Example C72

Production of 2-chloro-3-(1-cyanocyclopropyl)-N-[2-fluoro-5-({2-[(2-methylpropanoyl)amino][1,3]thiazolo[5,4-b]pyridin-5-yl}oxy)phenyl]benzamide

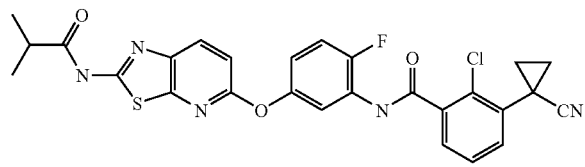 [SMILES: CC(C)C(=O)Nc1nc2ccc(Oc3ccc(F)c(NC(=O)c4cccc(C5(C#N)CC5)c4Cl)c3)nc2s1]

To a solution of N-{5-[(2-amino[1,3]thiazolo[5,4-b]pyridin-5-yl)oxy]-2-fluorophenyl}-2-chloro-3-(1-cyanocyclopropyl)benzamide (0.16 g, 0.33 mmol) produced in Example C71(iv) and N,N-dimethylpyridine-4-amine (0.12 g, 1.00 mmol) in pyridine (2 mL) was added dropwise 2-methylpropanoyl chloride (0.12 g, 1.00 mmol) under ice-cooling, and the mixture was stirred at room temperature for 2 hr. To the reaction mixture was added water (50 mL), and the mixture was extracted with ethyl acetate (50 mL×2). The ethyl acetate layers were combined, and dried over anhydrous magnesium sulfate. The insoluble material was filtered off, and the filtrate was concentrated under reduced pressure. The obtained residue was dissolved in methanol (5 mL), 8N aqueous sodium hydroxide solution (1 mL) was added, and the mixture was stirred at room temperature for 1 hr. The reaction mixture was poured into water (50 mL), and the mixture was extracted with ethyl acetate (50 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (114 mg, 63%) as white crystals.

$^1$H-NMR (DMSO-d$_6$, 300 MHz) δ 1.29 (6H, d, J=6.9 Hz), 1.39 (2H, dd, J=5.4, 7.5 Hz), 1.82 (2H, dd, J=5.4, 7.5 Hz), 2.66 (1H, m), 6.94-7.00 (1H, m), 7.03 (1H, d, J=8.7 Hz), 7.19 (1H, dd, J=9.0, 10.2 Hz), 7.39 (1H, t, J=7.8 Hz), 7.50 (1H, dd, J=1.8, 7.8 Hz), 7.68 (1H, dd, J=1.8, 7.8 Hz), 7.97 (1H, d, J=8.7 Hz), 8.08 (1H, d, J=3.0 Hz), 8.39 (1H, dd, J=3.0, 6.6 Hz), 9.18 (1H, br s).

Example C73

Production of N-(3-{([2-(acetylamino)[1,3]thiazolo[5,4-b]pyridin-5-yl]oxy}-4-fluorophenyl)-2-chloro-3-(1-cyano-1-methylethyl)benzamide

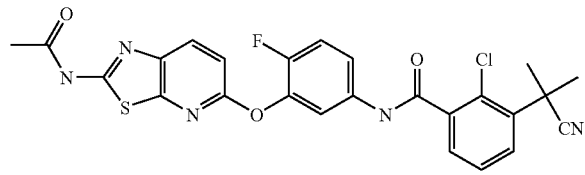 [SMILES: CC(=O)Nc1nc2ccc(Oc3cc(NC(=O)c4cccc(C(C)(C)C#N)c4Cl)ccc3F)nc2s1]

(i) Production of 4-fluoro-3-[(5-nitropyridin-2-yl)oxy]aniline

A mixture of 2-chloro-5-nitropyridine (3.17 g, 20 mmol), 5-amino-2-fluorophenol hydrobromide (4.16 g, 20 mmol) and potassium carbonate (5.52 g, 40 mmol) in N,N-dimethylformamide (20 mL) was stirred at room temperature overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50), and crystallized from diethyl ether to give the title compound (4.36 g, 88%) as an orange powder.

$^1$H-NMR (DMSO-d$_6$, 300 MHz) δ 3.66 (2H, br s), 6.52-6.60 (2H, m), 7.00 (1H, t, J=9.9 Hz), 7.09 (1H, d, J=9.0 Hz), 8.54 (1H, dd, J=3.0, 6.6 Hz), 9.03 (1H, t, J=2.7 Hz).

(ii) Production of tert-butyl{4-fluoro-3-[(5-nitropyridin-2-yl)oxy]phenyl}carbamate A solution of 4-fluoro-3-[(5-nitropyridin-2-yl)oxy]aniline (4.36 g, 17.5 mmol) and di-tert-butyl bicarbonate (5.73 g, 26.3 mmol) in tetrahydrofuran (25 mL) was refluxed overnight. The reaction mixture was poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was triturated with diethyl ether to give the title compound (3.75 g, 61%) as a pale-yellow amorphous.

$^1$H-NMR (DMSO-d$_6$, 300 MHz) δ 1.50 (9H, s), 6.52 (1H, br s), 7.01-7.09 (2H, m), 7.13 (1H, t, J=9.0 Hz), 7.54 (1H, d, J=4.8 Hz), 8.50 (1H, dd, J=2.7, 9.0 Hz), 9.01 (1H, dd, J=0.3, 2.7 Hz).

(iii) Production of tert-butyl{3-[(5-aminopyridin-2-yl)oxy]-4-fluorophenyl}carbamate A suspension of tert-butyl{4-fluoro-3-[(5-nitropyridin-2-yl)oxy]phenyl}carbamate (3.75 g, 10.7 mmol) and 10% palladium-carbon (0.5 g) in methanol (10 mL)-tetrahydrofuran (10 mL) was vigorously stirred at room temperature under a hydrogen atmosphere overnight. The insoluble material was filtered off, and the filtrate was concentrated under reduced pressure. The residue was poured into water (100 mL), and the mixture was extracted with ethyl acetate (100 mL×2). The ethyl acetate layers were combined and dried over anhydrous sodium sulfate, and the insoluble material was filtered off. The filtrate was concentrated under reduced pressure, and the residue was triturated with diethyl ether to give the title compound (2.50 g, 73%) as a pale-yellow amorphous.

$^1$H-NMR (DMSO-d$_6$, 300 MHz) δ 1.50 (9H, s), 3.48 (2H, br s), 6.42 (1H, br s), 6.81 (1H, dd, J=0.6, 8.7 Hz), 7.04-7.08 (2H, m), 7.23-7.28 (1H, m), 8.50 (1H, dd, J=3.0, 8.7 Hz), 7.63 (1H, dd, J=0.6, 3.0 Hz).

(iv) Production of tert-butyl{3-[(2-amino[1,3]thiazolo[5,4-b]pyridin-5-yl)oxy]-4-fluorophenyl}carbamate To a solution of tert-butyl{3-[(5-aminopyridin-2-yl)oxy]-4-fluorophenyl}carbamate (2.50 g, 7.8 mmol) and potassium thiocyanate (2.92 g, 30 mmol) in acetic acid (30 mL) was added dropwise bromine (1.93 g, 12 mmol) under ice-cooling, and the mixture was stirred at room temperature overnight. The yellow insoluble material was filtered off, and the filtrate was concentrated under reduced pressure. To the residue was added saturated aqueous sodium hydrogen carbonate solution (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was triturated with diethyl ether to give the title compound (1.92 g, 65%) as a pale-yellow amorphous.

$^1$H-NMR (DMSO-$d_6$, 300 MHz) δ 1.49 (9H, s), 5.20 (2H, br s), 6.58 (1H, br s), 6.91 (1H, d, J=8.4 Hz), 7.04-7.14 (2H, m), 8.30 (1H, d, J=5.7 Hz), 7.75 (1H, d, J=8.7 Hz).

(v) Production of tert-butyl(3-{[2-(acetylamino)[1,3]thiazolo[5,4-b]pyridin-5-yl]oxy}-4-fluorophenyl)carbamate To a solution of tert-butyl{3-[(2-amino[1,3]thiazolo[5,4-b]pyridin-5-yl)oxy]-4-fluorophenyl}carbamate (0.94 g, 2.5 mmol) and N,N-dimethylpyridine-4-amine (0.31 g, 2.5 mmol) in pyridine (5 mL) was added dropwise acetyl chloride (0.40 g, 5 mmol) under ice-cooling, and the mixture was stirred at room temperature overnight. To the reaction mixture was added water (100 mL), and the mixture was extracted with ethyl acetate (100 mL×2). The ethyl acetate layers were combined, and dried over anhydrous magnesium sulfate. The insoluble material was filtered off, and the filtrate was concentrated under reduced pressure. The obtained residue was triturated with diethyl ether to give the title compound (1.05 g, quantitatively) as a white amorphous.

$^1$H-NMR (DMSO-$d_6$, 300 MHz) δ 1.50 (9H, s), 2.30 (3H, s), 6.60 (1H, br s), 7.02-7.10 (2H, m), 7.05 (1H, d, J=8.7 Hz), 7.30 (1H, d, J=5.7 Hz), 7.98 (1H, d, J=8.7 Hz), 9.15 (1H, br s).

(vi) Production of N-[5-(5-amino-2-fluorophenoxy)[1,3]thiazolo[5,4-b]pyridin-2-yl]acetamide A solution of tert-butyl(3-{[2-(acetylamino)[1,3]thiazolo[5,4-b]pyridin-5-yl]oxy}-4-fluorophenyl)carbamate (1.05 g, 2.5 mmol) in trifluoroacetic acid (5 mL) was stirred at room temperature for 30 min. The reaction mixture was concentrated under reduced pressure, and the residue was diluted with ethyl acetate (100 mL), washed with 0.1N aqueous sodium hydroxide solution (100 mL), and dried over anhydrous magnesium sulfate. The insoluble material was filtered off, and the filtrate was concentrated under reduced pressure. The obtained residue was triturated with diethyl ether to give the title compound (0.78 g, 98%) as a pale-yellow amorphous.

$^1$H-NMR (DMSO-$d_6$, 300 MHz) δ 2.29 (3H, s), 3.82 (2H, br s), 6.47-6.53 (1H, m), 6.58 (1H, dd, J=2.7, 6.6 Hz), 6.98 (1H, dd, J=9.0, 10.2 Hz), 7.02 (1H, d, J=8.7 Hz), 7.96 (1H, d, J=8.7 Hz), 9.37 (1H, br s).

(vii) Production of N-(3-{[2-(acetylamino)[1,3]thiazolo[5,4-b]pyridin-5-yl]oxy}-4-fluorophenyl)-2-chloro-3-(1-cyano-1-methylethyl)benzamide To a solution of 2-chloro-3-(1-cyano-1-methylethyl)benzoic acid (0.11 g, 0.5 mmol) produced in Example C61(v) in oxalyl chloride (0.5 ml) was added N,N-dimethylformamide (40 μL), and the mixture was stirred at room temperature for 30 min, and concentrated to dryness under reduced pressure. This was dissolved in a mixture of N,N-dimethylacetamide (1 mL) and tetrahydrofuran (1 mL), and the solution was added dropwise to a solution of N-[5-(5-amino-2-fluorophenoxy)[1,3]thiazolo[5,4-b]pyridin-2-yl]acetamide (0.11 g, 0.33 mmol) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (52 mg, 30%) as colorless crystals.

$^1$H-NMR (DMSO-$d_6$, 300 MHz) δ 1.90 (6H, s), 2.29 (3H, s), 7.09 (1H, d, J=9.0 Hz), 7.21 (1H, dd, J=9.0, 9.6 Hz), 7.40 (1H, t, J=7.5 Hz), 7.40-7.46 (1H, m), 7.55-7.61 (2H, m), 7.63 (1H, br s), 7.72 (1H, dd, J=2.4, 6.9 Hz), 7.99 (1H, d, J=8.7 Hz), 9.26 (1H, br s).

Example C74

Production of N-(3-{[2-(acetylamino)[1,3]thiazolo[5,4-b]pyridin-5-yl]oxy}-4-fluorophenyl)-2-chloro-3-(1-cyanocyclopropyl)benzamide

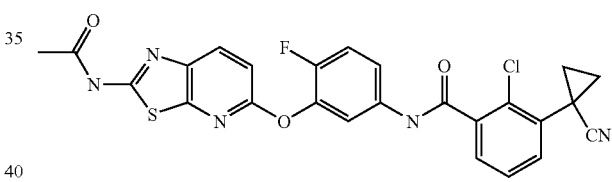

To a solution of 2-chloro-3-(1-cyanocyclopropyl)benzoic acid (0.11 g, 0.5 mmol) produced in Example C62(ii) in oxalyl chloride (0.5 mL) was added N,N-dimethylformamide (40 μL), and the mixture was stirred at room temperature for 30 min, and concentrated to dryness under reduced pressure. This was dissolved in a mixture of N,N-dimethylacetamide (1 mL) and tetrahydrofuran (1 mL), and the solution was added dropwise to a solution of N-[5-(5-amino-2-fluorophenoxy)[1,3]thiazolo[5,4-b]pyridin-2-yl]acetamide (0.11 g, 0.33 mmol) produced in Example C73(vi) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (50 mg, 29%) as colorless crystals.

$^1$H-NMR (DMSO-$d_6$, 300 MHz) δ 1.38 (2H, dd, J=5.4, 7.5 Hz), 1.81 (2H, dd, J=5.4, 7.5 Hz), 2.29 (3H, s), 7.09 (1H, d, J=8.7 Hz), 7.21 (1H, t, J=9.3 Hz), 7.32-7.46 (2H, m), 7.47

(1H, dd, J=1.8, 7.8 Hz), 7.65 (1H, dd, J=1.8, 7.8 Hz), 7.74 (1H, dd, J=2.7, 6.9 Hz), 7.76 (1H, br s), 7.99 (1H, d, J=8.7 Hz), 9.12 (1H, br s).

Example C75

Production of 2-chloro-3-(1-cyanocyclopropyl)-N-[5-({2-[(cyclopropylcarbonyl)amino][1,3]thiazolo[5,4-b]pyridin-5-yl}oxy)-2,4-difluorophenyl]benzamide

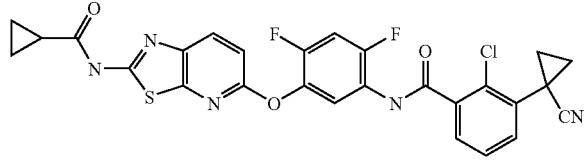 [SMILES: N#CC1(c2cccc(C(=O)Nc3cc(Oc4ccc5nc(NC(=O)C6CC6)sc5n4)c(F)cc3F)c2Cl)CC1]

(i) Production of 2-chloro-3-(1-cyanocyclopropyl)-N-(2,4-difluoro-5-hydroxyphenyl)benzamide To a solution of 2-chloro-3-(1-cyanocyclopropyl)benzoic acid (4.42 g, 20 mmol) produced in Example C62(ii) in oxalyl chloride (10 mL) was added N,N-dimethylformamide (100 µL)), and the mixture was stirred at room temperature for 1 hr, and concentrated to dryness under reduced pressure. This was dissolved in tetrahydrofuran (10 mL), and the solution was added dropwise with vigorous stirring to a two-layer mixture of a solution of 5-amino-2,4-difluorophenol (2.90 g, 20 mmol) in tetrahydrofuran (5 mL) and a solution (10 mL) of sodium hydrogen carbonate (2.70 g, 30 mmol) in water under ice-cooling. The reaction mixture was stirred at room temperature for 1 hr, and poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50) to give the title compound (4.90 g, 70%) as white crystals.
$^1$H-NMR (DMSO-$d_6$, 300 MHz) δ 1.40 (2H, dd, J=5.1, 7.8 Hz), 1.83 (2H, dd, J=5.1, 7.5 Hz), 6.08 (1H, d, J=2.4 Hz), 6.96 (1H, t, J=10.2 Hz), 7.41 (1H, t, J=7.8 Hz), 7.52 (1H, dd, J=1.8, 7.8 Hz), 7.69 (1H, dd, J=1.8, 7.5 Hz), 7.91 (1H, br s), 8.30 (1H, dd, J=7.8, 9.0 Hz).

(ii) Production of 2-chloro-3-(1-cyanocyclopropyl)-N-{2,4-difluoro-5-[(5-nitropyridin-2-yl)oxy]phenyl}benzamide A suspension of 2-chloro-3-(1-cyanocyclopropyl)-N-(2,4-difluoro-5-hydroxyphenyl)benzamide (4.20 g, 12 mmol), 2-chloro-5-nitropyridine (1.9 g, 12 mmol) and potassium carbonate (1.66 g, 12 mmol) in N,N-dimethylformamide (20 mL) was stirred at room temperature overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→50/50), and crystallized from diethyl ether to give the title compound (5.20 g, 92%) as a yellow powder.
$^1$H-NMR (DMSO-$d_6$, 300 MHz) δ 1.40 (2H, dd, J=5.4, 7.5 Hz), 1.83 (2H, dd, J=5.4, 7.5 Hz), 7.11 (1H, t, J=9.9 Hz), 7.18 (1H, d, J=9.0 Hz), 7.41 (1H, t, J=7.8 Hz), 7.52 (1H, dd, J=1.8, 7.8 Hz), 7.69 (1H, dd, J=1.8, 7.8 Hz), 8.01 (1H, d, J=3.0 Hz), 8.53 (1H, t, J=7.5 Hz), 8.54 (1H, dd, J=3.0, 9.0 Hz), 9.02 (1H, d, J=2.7 Hz).

(iii) Production of N-{5-[(5-aminopyridin-2-yl)oxy]-2,4-difluorophenyl}-2-chloro-3-(1-cyanocyclopropyl)benzamide A mixed solution of 2-chloro-3-(1-cyanocyclopropyl)-N-{2,4-difluoro-5-[(5-nitropyridin-2-yl)oxy]phenyl}benzamide (5.20 g, 11 mmol), iron powder (1.24 g, 22 mmol) and calcium chloride (2.45 g, 22 mmol) in ethanol (80 mL)-water (20 mL) was stirred at 80° C. overnight. The reaction mixture was poured into 0.5N aqueous sodium hydroxide solution (500 mL), ethyl acetate (300 mL) was added, the mixture was stirred, and the insoluble material was filtered through celite. The ethyl acetate layer was separated from the filtrate, and dried over anhydrous sodium sulfate. The insoluble material was filtered off, and the filtrate was concentrated under reduced pressure. The obtained residue was triturated with diethyl ether to give the title compound (4.25 g, 88%) as a pale-yellow amorphous.
$^1$H-NMR (DMSO-$d_6$, 300 MHz) δ 1.39 (2H, dd, J=5.4, 7.8 Hz), 1.83 (2H, dd, J=5.4, 7.8 Hz), 3.50 (2H, br s), 6.87 (1H, d, J=8.4 Hz), 7.03 (1H, t, J=9.9 Hz), 7.11 (1H, dd, J=3.0, 8.7 Hz), 7.38 (1H, t, J=7.8 Hz), 7.50 (1H, dd, J=1.5, 7.5 Hz), 7.61 (1H, d, J=2.7 Hz), 7.65 (1H, dd, J=1.5, 7.5 Hz), 7.94 (1H, br s), 8.39 (1H, t, J=8.1 Hz).

(iv) Production of N-{5-[(2-amino[1,3]thiazolo[5,4-b]pyridin-5-yl)oxy]-2,4-difluorophenyl}-2-chloro-3-(1-cyanocyclopropyl)benzamide To a solution of N-{5-[(5-aminopyridin-2-yl)oxy]-2,4-difluorophenyl}-2-chloro-3-(1-cyanocyclopropyl)benzamide (4.25 g, 9.64 mmol) and potassium thiocyanate (3.75 g, 38.6 mmol) in acetic acid (50 mL) was added dropwise bromine (2.11 g, 13.1 mmol) under ice-cooling, and the mixture was stirred at room temperature overnight. The yellow insoluble material was filtered off, and the filtrate was concentrated under reduced pressure. To the residue was added saturated aqueous sodium hydrogen carbonate solution (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and triturated with diethyl ether to give the title compound (4.05 g, 84%) as a pale-yellow amorphous.
$^1$H-NMR (DMSO-$d_6$, 300 MHz) δ 1.39 (2H, dd, J=5.4, 7.5 Hz), 1.82 (2H, dd, J=5.4, 7.5 Hz), 5.14 (2H, br s), 6.98 (1H, d, J=8.4 Hz), 7.06 (1H, t, J=9.9 Hz), 7.39 (1H, t, J=7.8 Hz, 10.2 Hz), 7.50 (1H, dd, J=1.5, 7.5 Hz), 7.68 (1H, dd, J=1.8, 7.5 Hz), 7.78 (1H, d, J=8.7 Hz), 7.97 (1H, d, J=3.0 Hz), 8.43 (1H, t, J=8.1 Hz).

(v) Production of 2-chloro-3-(1-cyanocyclopropyl)-N-[5-({2-[(cyclopropylcarbonyl)amino][1,3]thiazolo[5,4-b]pyridin-5-yl}oxy)-2,4-difluorophenyl]benzamide To a solution of N-{5-[(2-amino[1,3]thiazolo[5,4-b]pyridin-5-yl)oxy]-2,4-difluorophenyl}-2-chloro-3-(1-cyanocyclopropyl)benzamide (0.17 g, 0.33 mmol) and N,N-dimethylpyridine-4-amine (0.12 g, 1.00 mmol) in pyridine (2 mL) was added dropwise cyclopropanecarbonyl chloride (0.11 g, 1.00 mmol) under ice-cooling, and the mixture was stirred at room temperature for 2 hr. To the reaction mixture was added water (50 mL), and the mixture was extracted with ethyl acetate (50 mL×2). The ethyl acetate layers were combined, and dried over anhydrous magnesium sulfate. The insoluble material was filtered off, and the filtrate was concentrated under reduced pressure. The obtained residue was dissolved in methanol (5 mL), 8N aqueous sodium hydroxide solution (1 mL) was added, and the mixture was stirred at room temperature for 1 hr. The reaction mixture was poured into water (50 mL), and the mixture was extracted with ethyl acetate (50 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (88 mg, 47%) as white crystals.

$^1$H-NMR (DMSO-$d_6$, 300 MHz) δ 0.98-1.05 (2H, m), 1.20-1.26 (2H, m), 1.39 (2H, dd, J=5.4, 7.5 Hz), 1.60-1.67 (1H, m), 1.82 (2H, dd, J=5.4, 7.5 Hz), 7.08 (1H, t, J=9.9 Hz), 7.09 (1H, d, J=8.7 Hz), 7.39 (1H, t, J=7.8 Hz), 7.50 (1H, dd, J=1.8, 7.8 Hz), 7.68 (1H, dd, J=1.8, 7.5 Hz), 7.97 (1H, d, J=3.0 Hz), 7.99 (1H, d, J=8.7 Hz), 8.48 (1H, t, J=7.8 Hz), 9.86 (1H, br s).

Example C76

Production of N-(5-{[2-(acetylamino)[1,3]thiazolo[5,4-b]pyridin-5-yl]oxy}-2,4-difluorophenyl)-2-chloro-3-(1-cyano-1-methylethyl)benzamide

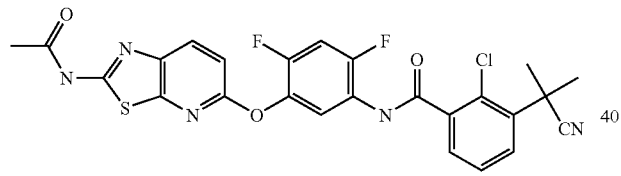

(i) Production of 2,4-difluoro-5-[(5-nitropyridin-2-yl)oxy]aniline

A suspension of 2-chloro-5-nitropyridine (5.55 g, 35 mmol), 5-amino-2,4-difluorophenol (5.08 g, 35 mmol) and potassium carbonate (4.84 g, 35 mmol) in N,N-dimethylformamide (20 mL) was stirred at room temperature overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was crystallized from diethyl ether to give the title compound (9.35 g, quantitatively) as a white powder.

$^1$H-NMR (CDCl$_3$, 300 MHz) δ 3.71 (2H, br s), 6.66 (1H, dd, J=7.5, 8.4 Hz), 6.94 (1H, t, J=7.2 Hz), 7.10 (1H, d, J=9.0 Hz), 8.49 (1H, dd, J=3.0, 9.0 Hz), 8.50 (1H, d, J=2.7 Hz).

(ii) Production of tert-butyl{2,4-difluoro-5-[(5-nitropyridin-2-yl)oxy]phenyl}carbamate A solution of 2,4-difluoro-5-[(5-nitropyridin-2-yl)oxy]aniline (9.35 g, 35 mmol) and di-tert-butyl bicarbonate (10.9 g, 50 mmol) in tetrahydrofuran (50 mL) was heated under reflux overnight. The reaction mixture was poured into water (200 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was triturated with diethyl ether to give the title compound (10.15 g, 79%) as a white amorphous.

$^1$H-NMR (CDCl$_3$, 300 MHz) δ 1.51 (9H, s), 6.69 (1H, br s), 7.01 (1H, dd, J=9.6, 10.5 Hz), 7.12 (1H, dd, J=0.3, 9.0 Hz), 8.12 (1H, t, J=7.5 Hz), 8.50 (1H, dd, J=3.0, 9.0 Hz), 9.00 (1H, dd, J=0.3, 2.7 Hz).

(iii) Production of tert-butyl{5-[(5-aminopyridin-2-yl)oxy]-2,4-difluorophenyl}carbamate A suspension of tert-butyl{2,4-difluoro-5-[(5-nitropyridin-2-yl)oxy]phenyl}carbamate (10.10 g, 27.5 mmol) and 10% palladium-carbon (5.0 g) in methanol (50 mL)-tetrahydrofuran (50 mL) was vigorously stirred at room temperature under a hydrogen atmosphere overnight. The insoluble material was filtered through celite, and the filtrate was concentrated under reduced pressure. The residue was poured into water (200 mL), and the mixture was extracted with ethyl acetate (100 mL×2). The ethyl acetate layers were combined dried over anhydrous sodium sulfate, and the insoluble material was filtered off. The filtrate was concentrated under reduced pressure, and the residue was crystallized from acetonitrile to give the title compound (8.70 g, 94%) as a white powder.

$^1$H-NMR (CDCl$_3$, 300 MHz) δ 1.52 (9H, s), 3.47 (2H, br s), 6.61 (1H, br s), 6.81 (1H, dd, J=0.6, 8.7 Hz), 6.94 (1H, dd, J=9.9, 10.5 Hz), 7.08 (1H, dd, J=6.0, 8.7 Hz), 7.60 (1H, dd, J=0.6, 3.0 Hz), 7.92-8.07 (1H, m).

(iv) Production of tert-butyl{5-[(2-amino[1,3]thiazolo[5,4-b]pyridin-5-yl)oxy]-2,4-difluorophenyl}carbamate To a solution of tert-butyl{5[(5-aminopyridin-2-yl)oxy]-2,4-difluorophenyl}carbamate (8.70 g, 25.8 mmol) and potassium thiocyanate (9.72 g, 100 mmol) in acetic acid (100 mL) was added dropwise bromine (6.39 g, 40 mmol) under ice-cooling, and the mixture was stirred at room temperature overnight. The yellow insoluble material was filtered off, and the filtrate was concentrated under reduced pressure. To the residue was added saturated aqueous sodium hydrogen carbonate solution (400 mL), and the mixture was extracted with ethyl acetate (300 mL×2). The ethyl acetate layers were combined, and dried over anhydrous sodium sulfate. The insoluble material was filtered off, and the filtrate was concentrated under reduced pressure. The obtained residue was triturated with diethyl ether to give the title compound (9.00 g, 88%) as a pale-yellow amorphous.

$^1$H-NMR (CDCl$_3$, 300 MHz) δ 1.50 (9H, s), 5.24 (2H, br s), 6.64 (1H, br s), 6.91 (1H, d, J=8.7 Hz), 6.96 (1H, dd, J=9.9, 10.8 Hz), 7.75 (1H, d, J=8.4 Hz), 7.97-8.09 (1H, m).

(v) Production of tert-butyl{5-[(2-acetylamino[1,3]thiazolo[5,4-b]pyridin-5-yl)oxy]-2,4-difluorophenyl}carbamate To a solution of tert-butyl{5-[(2-amino[1,3]thiazolo[5,4-b]pyridin-5-yl)oxy]-2,4-difluorophenyl}carbamate (3.94 g, 10.0 mmol) and N,N-dimethylpyridine-4-amine (1.22 g, 10 mmol) in pyridine (20 mL) was added dropwise acetyl chloride (0.94 g, 12 mmol) under ice-cooling, and the mixture was stirred at room temperature overnight. To the reaction mixture was added water (200 mL), and the mixture was extracted with ethyl acetate (100 mL×2). The ethyl acetate layers were combined, and dried over anhydrous magnesium sulfate. The insoluble material was filtered off, and the filtrate was concentrated under reduced pressure. The obtained residue was triturated with diethyl ether to give the title compound (4.36 g, quantitatively) as a pale-yellow amorphous.

$^1$H-NMR (DMSO-d$_6$, 300 MHz) δ 1.50 (9H, s), 2.24 (3H, s), 6.64 (1H, br s), 6.71 (1H, dd, J=7.8, 10.2 Hz), 6.90 (1H, t, J=10.2 Hz), 6.97 (1H, d, J=8.7 Hz), 7.75 (1H, d, J=8.7 Hz), 10.45 (1H, br s).

(vi) Production of N-[5-(5-amino-2,4-difluorophenoxy)[1,3]thiazolo[5,4-b]pyridin-2-yl]acetamide A solution of tert-butyl{5-[(2-acetylamino[1,3]thiazolo[5,4-b]pyridin-5-yl)oxy]-2,4-difluorophenyl}carbamate (4.36 g, 10.0 mmol) in trifluoroacetic acid (20 mL) was stirred at room temperature for 30 min. The reaction mixture was concentrated under reduced pressure, and the residue was diluted with ethyl acetate (200 mL), washed with 0.1N aqueous sodium hydroxide solution (200 mL), and dried over anhydrous magnesium sulfate. The insoluble material was filtered off, and the filtrate was concentrated under reduced pressure. The obtained residue was triturated with diethyl ether to give the title compound (3.37 g, quantitatively) as a white amorphous.

$^1$H-NMR (DMSO-d$_6$, 300 MHz) δ 2.27 (3H, s), 4.46 (2H, br s), 6.71 (1H, dd, J=7.8, 10.2 Hz), 6.90 (1H, t, J=10.2 Hz), 6.97 (1H, d, J=8.7 Hz), 7.93 (1H, d, J=8.7 Hz), 11.38 (1H, br s).

(vii) Production of N-(5-{[2-(acetylamino)[1,3]thiazolo[5,4-b]pyridin-5-yl]oxy}-2,4-difluorophenyl)-2-chloro-3-(1-cyano-1-methylethyl)benzamide To a solution of 2-chloro-3-(1-cyano-1-methylethyl)benzoic acid (0.11 g, 0.5 mmol) produced in Example C61(v) in oxalyl chloride (0.5 mL) was added N,N-dimethylformamide (40 μL), and the mixture was stirred at room temperature for 30 min, and concentrated to dryness under reduced pressure. This was dissolved in a mixture of N,N-dimethylacetamide (1 mL) and tetrahydrofuran (1 mL), and the solution was added dropwise to a solution of N-[5-(3-amino-2,4-difluorophenoxy)[1,3]thiazolo[5,4-b]pyridin-2-yl]acetamide (0.11 g, 0.33 mmol) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (70 mg, 39%) as colorless crystals.

$^1$H-NMR (DMSO-d$_6$, 300 MHz) δ 1.91 (6H, s), 2.27 (3H, s), 7.06 (1H, d, J=8.7 Hz), 7.07 (1H, t, J=9.9 Hz), 7.42 (1H, t, J=7.8 Hz), 7.54-7.62 (2H, m), 7.97 (1H, d, J=8.7 Hz), 8.34 (1H, t, J=7.8 Hz), 8.48 (1H, br s), 11.34 (1H, br s).

Example C77

Production of N-(5-{[2-(acetylamino)[1,3]thiazolo[5,4-b]pyridin-5-yl]oxy}-2,4-difluorophenyl)-2-chloro-3-(1-cyanocyclopropyl)benzamide

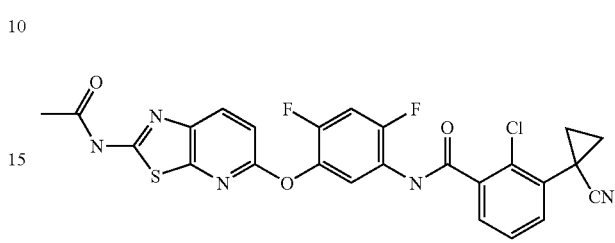

To a solution of 2-chloro-3-(1-cyanocyclopropyl)benzoic acid (0.11 g, 0.5 mmol) produced in Example C62(ii) in oxalyl chloride (0.5 mL) was added N,N-dimethylformamide (40 μL), and the mixture was stirred at room temperature for 30 min, and concentrated to dryness under reduced pressure. This was dissolved in a mixture of N,N-dimethylacetamide (1 mL) and tetrahydrofuran (1 mL), and the solution was added dropwise to a solution of N-[5-(3-amino-2,4-difluorophenoxy)[1,3]thiazolo[5,4-b]pyridin-2-yl]acetamide (0.11 g, 0.33 mmol) produced in Example C76(vi) in N,N-dimethylacetamide (1 mL) under ice-cooling. The reaction mixture was stirred at room temperature for 3 hr, and poured into water (100 mL), and the mixture was extracted with ethyl acetate (100 mL×2). The ethyl acetate layers were combined, and dried over anhydrous sodium sulfate. The insoluble material was filtered off, and the filtrate was concentrated under reduced pressure. The obtained residue was purified by silica gel column chromatography (ethyl acetate/hexane=0/100→100/0), and recrystallized from methanol to give the title compound (60 mg, 34%) as colorless crystals.

$^1$H-NMR (DMSO-d$_6$, 300 MHz) δ 1.40 (2H, dd, J=5.4, 7.5 Hz), 1.83 (2H, dd, J=5.4, 7.5 Hz), 2.27 (3H, s), 7.05 (1H, d, J=11.1 Hz), 7.07 (1H, t, J=9.0 Hz), 7.39 (1H, t, J=7.5 Hz), 7.50 (1H, dd, J=1.8, 7.8 Hz), 7.65 (1H, dd, J=1.8, 7.5 Hz), 7.97 (1H, d, J=8.7 Hz), 8.37 (1H, d, J=7.8 Hz), 8.57 (1H, br s), 11.19 (1H, br s).

Example C78

Production of 2-chloro-N-[3-({2-[(cyclopropylcarbonyl)amino][1,3]thiazolo[5,4-b]pyridin-5-yl}oxy)-4-methylphenyl]-3-(trifluoromethyl)benzamide

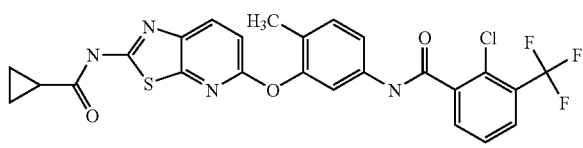 [SMILES: Cc1ccc(NC(=O)c2cccc(C(F)(F)F)c2Cl)cc1Oc1ccc2nc(NC(=O)C3CC3)sc2n1]

(i) Production of 2-chloro-N-(3-hydroxy-4-methylphenyl)-3-(trifluoromethyl)benzamide To a solution of 2-chloro-3-(trifluoromethyl)benzoic acid (5.26 g, 23.4 mmol) in tetrahydrofuran (50 mL) were added N,N-dimethylformamide (40 μL) and oxalyl chloride (2.8 mL, 31.9 mmol), and the mixture was stirred at room temperature for 2 hr. The solvent was evaporated under reduced pressure to give 2-chloro-3-(trifluoromethyl)benzoyl chloride. To a solution of 5-amino-2-methylphenol (2.62 g, 21.2 mmol) in tetrahydrofuran (20 mL) was added water (30 mL) in which sodium hydrogen carbonate (2.68 g, 31.9 mmol) has been suspended, and the mixture was vigorously stirred at room temperature. To the mixture was added dropwise a solution of 2-chloro-3-(trifluoromethyl)benzoyl chloride produced above in tetrahydrofuran (30 mL) under ice-cooling, and the mixture was stirred at room temperature for 18 hr. The aqueous layer of the reaction mixture was separated, and the organic layer was diluted with ethyl acetate, and washed with saturated brine. The extract was dried over anhydrous magnesium sulfate, and filtered through a pad filled with silica gel. The solvent was concentrated under reduced pressure, and the obtained solid was washed with a mixed solvent of ethyl acetate and hexane to give the title compound (6.37 g, 91%) as a pale-brown powder. The obtained compound was used for the next reaction without further purification operation.

$^1$H-NMR (DMSO-$d_6$, 300 MHz) δ 2.08 (3H, s), 6.91-7.02 (2H, m), 7.37 (1H, d, J=1.7 Hz), 7.66 (1H, t, J=7.7 Hz), 7.87 (1H, dd, J=1.1, 7.7 Hz), 7.96 (1H, dd, J=1.1, 7.7 Hz), 9.39 (1H, s), 10.43 (1H, s).

(ii) Production of 2-chloro-N-{4-methyl-3-[(5-nitropyridin-2-yl)oxy]phenyl}-3-(trifluoromethyl)benzamide In the same manner as in Example C1(v), the title compound (8.18 g, 95%) was obtained as a pale-yellow powder using 2-chloro-N-(3-hydroxy-4-methylphenyl)-3-(trifluoromethyl)benzamide (6.24 g, 18.9 mmol), 2-chloro-5-nitropyridine (3.00 g, 18.9 mmol), potassium carbonate (7.84 g, 56.7 mmol) and N,N-dimethylformamide (100 mL) as starting materials. The obtained compound was used for the next reaction without further purification operation.

$^1$H-NMR (DMSO-$d_6$, 300 MHz) δ 2.05 (3H, s), 7.27-7.37 (2H, m), 7.43-7.48 (1H, m), 7.62-7.72 (2H, m), 7.89-8.01 (2H, m), 8.65 (1H, dd, J=2.8, 9.1 Hz), 9.04 (1H, d, J=2.8 Hz), 10.78 (1H, s).

(iii) Production of N-{3-[(5-aminopyridin-2-yl)oxy]-4-methylphenyl}-2-chloro-3-(trifluoromethyl)benzamide To a solution of 2-chloro-N-{4-methyl-3-[(5-nitropyridin-2-yl)oxy]phenyl}-3-(trifluoromethyl)benzamide (7.15 g, 15.8 mmol) in acetic acid (150 mL) was added reduced iron (8.84 g, 15.8 mmol), and the mixture was stirred at 100° C. for 1.5 hr. The insoluble material was filtered off, and the solvent was evaporated. The obtained residue was diluted with ethyl acetate, and washed with saturated aqueous sodium hydrogen carbonate solution, saturated aqueous ammonium chloride solution and saturated brine. The extract was dried over anhydrous magnesium sulfate, and filtered through a pad with two layers of silica gel and celite. The solvent was concentrated under reduced pressure to give brownish-red solid (7.69 g).

To a solution of the obtained solid in methanol (80 mL) was added 4N hydrochloric acid-ethyl acetate solution (40 mL), and the mixture was stirred at 60° C. for 2 hr. To the reaction mixture was added 8N aqueous sodium hydroxide solution, and the mixture was extracted with ethyl acetate. The extract was washed with saturated brine, dried over anhydrous magnesium sulfate, and filtered through a pad filled with silica gel. The filtrate was concentrated under reduced pressure, and the obtained residue was purified by silica gel column chromatography (ethyl acetate/hexane=40/60→80/20) to give the title compound (5.75 g, 86%) as a pale-brown powder.

$^1$H-NMR (DMSO-$d_6$, 300 MHz) δ 2.11 (3H, s), 5.05 (2H, s), 6.76 (1H, d, J=8.7 Hz), 7.08 (1H, dd, J=2.8, 8.7 Hz), 7.21 (1H, d, J=8.3 Hz), 7.24 (1H, d, J=2.1 Hz), 7.37 (1H, dd, J=2.1, 8.3 Hz), 7.51 (1H, d, J=2.8 Hz), 7.65 (1H, t, J=7.8 Hz), 7.86 (1H, dd, J=1.1, 7.8 Hz), 7.96 (1H, dd, J=1.1, 7.8 Hz), 10.57 (1H, s).

(iv) Production of N-{3-[(2-amino[1,3]thiazolo[5,4-b]pyridin-5-yl)oxy]-4-methylphenyl}-2-chloro-3-(trifluoromethyl)benzamide In the same manner as in Example C1(vii), the title compound (6.09 g, 93%) was obtained as a pale-yellow solid using N-{3-[(5-aminopyridin-2-yl)oxy]-4-methylphenyl}-2-chloro-3-(trifluoromethyl)benzamide (5.75 g, 13.6 mmol), potassium thiocyanate (5.30 g, 54.5 mmol), bromine (3.26 g, 20.4 mmol) and acetic acid (100 mL) as starting materials. The title compound was washed with a mixed solvent of ethyl acetate and hexane.

$^1$H-NMR (DMSO-$d_6$, 300 MHz) δ 2.10 (3H, s), 6.90 (1H, d, J=8.5 Hz), 7.29 (1H, d, J=8.3 Hz), 7.40 (1H, d, J=1.9 Hz), 7.45 (1H, dd, J=1.9, 8.3 Hz), 7.60 (2H, s), 7.66 (1H, t, J=7.5 Hz), 7.72 (1H, d, J=8.5 Hz), 7.89 (1H, d, J=7.5 Hz), 7.97 (1H, dd, J=0.8, 7.5 Hz), 10.65 (1H, s).

(v) Production of 2-chloro-N-[3-({2-[(cyclopropylcarbonyl)amino][1,3]thiazolo[5,4-b]pyridin-5-yl}oxy)-4-methylphenyl]-3-(trifluoromethyl)benzamide To a solution of N-{3-[(2-amino[1,3]thiazolo[5,4-b]pyridin-5-yl)oxy]-4-methylphenyl}-2-chloro-3-(trifluoromethyl)benzamide (200 mg, 0.417 mmol) in pyridine (5 mL) was added cyclopropanecarbonyl chloride (57.4 μL, 0.835 mmol), and the mixture was stirred at room temperature for 18 hr. The reaction mixture was diluted with ethyl acetate, washed with saturated aqueous sodium hydrogen carbonate solution and saturated brine, and dried over anhydrous magnesium sulfate. The residue was filtered through a pad filled with silica gel, and the filtrate was concentrated under reduced pressure. The obtained residue was purified by silica gel column chromatography (ethyl acetate/hexane=10/90→70/30), and recrystallized from tetrahydrofuran to give the title compound (115 mg, 50%) as white crystals.

$^1$H-NMR (DMSO-$d_6$, 300 MHz) δ 0.90-0.99 (4H, m), 1.92-2.03 (1H, m), 2.09 (3H, s), 7.12 (1H, d, J=8.7 Hz), 7.32 (1H, d, J=8.3 Hz), 7.43-7.49 (1H, m), 7.51 (1H, d, J=2.1 Hz), 7.66 (1H, t, J=7.8 Hz), 7.90 (1H, dd, J=1.1, 7.8 Hz), 7.97 (1H, dd, J=1.1, 7.8 Hz), 8.16 (1H, d, J=8.7 Hz), 10.70 (1H, s), 12.64 (1H, br s).

Example C79

Production of 2-chloro-N-{4-methyl-3-[(2-{[(4-methylpiperazin-1-yl)acetyl]amino}[1,3]thiazolo[5,4-b]pyridin-5-yl)oxy]phenyl}-3-(trifluoromethyl)benzamide

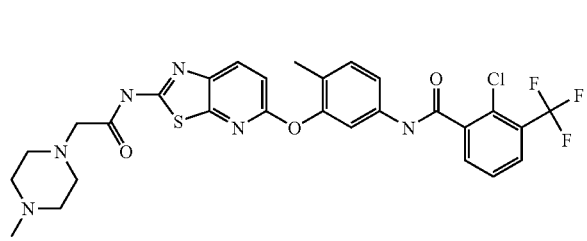 [SMILES: Cc1ccc(NC(=O)c2cccc(C(F)(F)F)c2Cl)cc1Oc1ccc2nc(NC(=O)CN3CCN(C)CC3)sc2n1]

(i) Production of 2-chloro-N-[3-({2-[(chloroacetyl)amino][1,3]thiazolo[5,4-b]pyridin-5-yl}oxy)-4-methylphenyl]-3-(trifluoromethyl)benzamide In the same manner as in Example C11(i), the title compound (279 mg, quantitatively) was obtained as an orange oil using N-{3-[(2-amino[1,3]thiazolo[5,4-b]pyridin-5-yl)oxy]-4-methylphenyl}-2-chloro-3-(trifluoromethyl)benzamide (200 mg, 0.417 mmol) produced in Example C78(iv), chloroacetyl chloride (96.5 μL, 1.20 mmol) and N,N-dimethylformamide (5 mL) as starting materials. The obtained compound was purified by silica gel column chromatography (ethyl acetate/hexane=0/100→70/30).

$^1$H-NMR (DMSO-d$_6$, 300 MHz) δ 2.09 (3H, s), 4.45 (2H, s), 7.15 (1H, d, J=8.8 Hz), 7.33 (1H, d, J=8.5 Hz), 7.43-7.49 (1H, m), 7.54 (1H, d, J=1.9 Hz), 7.67 (1H, t, J=7.7 Hz), 7.87-8.00 (2H, m), 8.21 (1H, d, J=8.8 Hz), 10.71 (1H, s), 12.77 (1H, br s).

(ii) Production of 2-chloro-N-{4-methyl-3-[(2-{[(4-methylpiperazin-1-yl)acetyl]amino}[1,3]thiazolo[5,4-b]pyridin-5-yl)oxy]phenyl}-3-(trifluoromethyl)benzamide In the same manner as in Example C11(ii), the title compound (146 mg, 56%) was obtained as white crystals using 2-chloro-N-[3-({2-[(chloroacetyl)amino][1,3]thiazolo[5,4-b]pyridin-5-yl}oxy)-4-methylphenyl]-3-(trifluoromethyl)benzamide (279 mg, 5.03 mmol), 1-methylpiperazine (93.0 μL, 0.835 mmol), triethylamine (116 μL, 0.835 mmol) and tetrahydrofuran (5 mL) as starting materials. The obtained compound was recrystallized from ethyl acetate and tetrahydrofuran.

$^1$H-NMR (CDCl$_3$, 300 MHz) δ 2.20 (3H, s), 2.33 (3H, s), 2.48-2.61 (4H, m), 2.63-2.73 (4H, m), 3.27 (2H, s), 7.00 (1H, d, J=8.8 Hz), 7.23-7.34 (1H, m), 7.34-7.41 (1H, m), 7.43-7.52 (2H, m), 7.63 (1H, s), 7.75-7.84 (2H, m), 8.00 (1H, d, J=8.8 Hz), 10.29 (1H, br s).

Example C80

Production of 2-chloro-N-(3-{[2-(glycoloylamino)[1,3]thiazolo[5,4-b]pyridin-5-yl]oxy}-4-methylphenyl)-3-(trifluoromethyl)benzamide

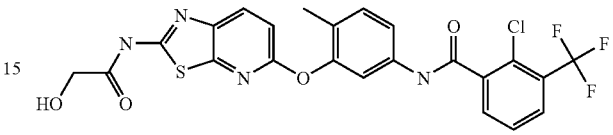

In the same manner as in Example C9, the title compound (97.3 mg, 43%) was obtained as a white powder using N-{3-[(2-amino[1,3]thiazolo[5,4-b]pyridin-5-yl)oxy]-4-methylphenyl}-2-chloro-3-(trifluoromethyl)benzamide (200 mg, 0.417 mmol) produced in Example C78(iv), acetoxyacetyl chloride (89.8 μL, 0.835 mmol), pyridine (5 mL), 0.5N aqueous sodium hydroxide solution (2 mL) and methanol (2 mL) as starting materials. The compound was purified by reverse phase silica gel column chromatography (containing 0.1% TFA, water/acetonitrile=60/40→40/60), and precipitated from ethyl acetate and hexane.

$^1$H-NMR (DMSO-d$_6$, 300 MHz) δ 2.10 (3H, s), 4.18 (2H, s), 5.53 (1H, br s), 7.14 (1H, d, J=8.9 Hz), 7.33 (1H, d, J=8.3 Hz), 7.43-7.50 (1H, m), 7.53 (1H, d, J=1.3 Hz), 7.66 (1H, t, J=7.6 Hz), 7.91 (1H, d, J=7.6 Hz), 7.97 (1H, d, J=7.6 Hz), 8.19 (1H, d, J=8.9 Hz), 10.71 (1H, s), 12.11 (1H, br s).

Example C81

Production of N-{3-[(2-acetylamino[1,3]thiazolo[5,4-b]pyridin-5-yl)oxy]-4-methylphenyl}-2-chloro-3-(trifluoromethyl)benzamide

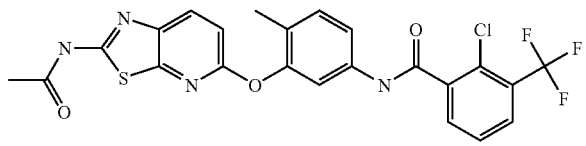 [SMILES: CC(=O)Nc1nc2ccc(Oc3cc(NC(=O)c4cccc(C(F)(F)F)c4Cl)ccc3C)nc2s1]

To a solution of N-{3-[(2-amino[1,3]thiazolo[5,4-b]pyridin-5-yl)oxy]-4-methylphenyl}-2-chloro-3-(trifluoromethyl)benzamide (200 mg, 0.417 mmol) produced in Example C78(iv) in pyridine (5 mL) were added acetyl chloride (118 μL, 1.67 mmol) and N,N-dimethylpyridine-4-amine (6.2 mg, 0.0507 mmol), and the mixture was stirred at room temperature for 28 hr. To the reaction mixture was added saturated aqueous sodium hydrogen carbonate solution, and the mixture was extracted with ethyl acetate. The extract was washed with saturated brine, and dried over anhydrous magnesium sulfate, and filtered through a pad filled with basic silica gel. The solvent was concentrated under reduced pressure, and the obtained crude product was recrystallized from ethyl acetate to give the title compound (162 mg, 74%) as white crystals.

$^1$H-NMR (DMSO-d$_6$, 300 MHz) δ 2.09 (3H, s), 2.19 (3H, s), 7.12 (1H, d, J=8.7 Hz), 7.32 (1H, d, J=8.3 Hz), 7.46 (1H, dd, J=1.9, 8.3 Hz), 7.52 (1H, d, J=1.9 Hz), 7.66 (1H, t, J=7.6 Hz), 7.88-7.93 (1H, m), 7.95-8.00 (1H, m), 8.17 (1H, d, J=8.7 Hz), 10.70 (1H, s), 12.38 (1H, br s).

Example C82

Production of 2-chloro-N-[3-({2-[(cyclopropylcarbonyl)amino][1,3]thiazolo[5,4-b]pyridin-5-yl}oxy)phenyl]-3-(trifluoromethyl)benzamide

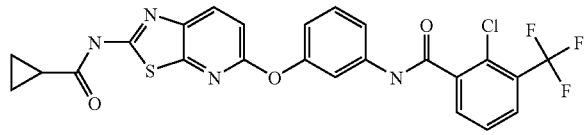 [SMILES: O=C(Nc1cccc(Oc2ccc3nc(NC(=O)C4CC4)sc3n2)c1)c1cccc(C(F)(F)F)c1Cl]

(i) Production of 2-chloro-N-(3-hydroxyphenyl)-3-(trifluoromethyl)benzamide

In the same manner as in Example C78(i), the title compound (6.07 g, 96%) was obtained as a white powder using 2-chloro-3-(trifluoromethyl)benzoic acid (4.96 g, 22.0 mmol), N,N-dimethylformamide (40 μL), oxalyl chloride (2.6 mL, 30.1 mmol), 3-aminophenol (2.19 g, 20.0 mmol), sodium hydrogen carbonate (2.52 g, 30.1 mmol), tetrahydrofuran (80 mL) and water (30 mL) as starting materials.

$^1$H-NMR (DMSO-d$_6$, 300 MHz) δ 6.49-6.56 (1H, m), 7.02-7.17 (2H, m), 7.30 (1H, t, J=2.1 Hz), 7.67 (1H, t, J=7.7 Hz), 7.88 (1H, dd, J=1.1, 7.7 Hz), 7.97 (1H, dd, J=1.1, 7.7 Hz), 9.48 (1H, s), 10.52 (1H, s).

(ii) Production of 2-chloro-N-{3-[(5-nitropyridin-2-yl)oxy]phenyl}-3-(trifluoromethyl)benzamide In the same manner as in Example C1(v), the title compound (7.99 g, 98%) was obtained as a pale-yellow solid using 2-chloro-N-(3-hydroxyphenyl)-3-(trifluoromethyl) benzamide (5.85 g, 18.5 mmol), 2-chloro-5-nitropyridine (2.94 g, 18.5 mmol), potassium carbonate (7.68 g, 55.5 mmol) and N,N-dimethylformamide (100 mL) as starting materials. The obtained compound was used for the next reaction without further purification operation.

$^1$H-NMR (DMSO-d$_6$, 300 MHz) δ 6.99-7.05 (1H, m), 7.30 (1H, d, J=9.0 Hz), 7.44-7.57 (2H, m), 7.65-7.73 (2H, m), 7.90-7.95 (1H, m), 7.97-8.03 (1H, m), 8.64 (1H, dd, J=2.8, 9.0 Hz), 9.06 (1H, d, J=2.8 Hz), 10.87 (1H, s).

(iii) Production of N-{3-[(5-aminopyridin-2-yl)oxy]phenyl}-2-chloro-3-(trifluoromethyl)benzamide In the same manner as in Example C78(iii), the title compound (4.57 g, 71%) was obtained as a pale-yellow powder using 2-chloro-N-{3-[(5-nitropyridin-2-yl)oxy]phenyl}-3-(trifluoromethyl)benzamide, reduced iron (4.40 g, 78.8 mmol), acetic acid (100 mL), 4N hydrochloric acid-ethyl acetate solution (15 mL) and methanol (30 mL) as starting materials.

$^1$H-NMR (DMSO-d$_6$, 300 MHz) δ 5.14 (2H, s), 6.73 (1H, dd, J=1.4, 8.0 Hz), 6.80 (1H, d, J=8.6 Hz), 7.09 (1H, dd, J=2.8, 8.6 Hz), 7.26-7.36 (2H, m), 7.37-7.45 (1H, m), 7.57 (1H, d, J=2.8 Hz), 7.67 (1H, t, J=7.7 Hz), 7.89 (1H, d, J=7.7 Hz), 7.98 (1H, d, J=7.7 Hz), 10.67 (1H, s).

(iv) Production of N-{3-[(2-amino[1,3]thiazolo[5,4-b]pyridin-5-yl)oxy]phenyl}-2-chloro-3-(trifluoromethyl)benzamide In the same manner as in Example C1(vii), the title compound (4.59 g, 88%) was obtained as a pale-yellow solid using N-{3-[(5-aminopyridin-2-yl)oxy]phenyl}-2-chloro-3-(trifluoromethyl)benzamide (4.55 g, 11.1 mmol), potassium thiocyanate (4.34 g, 44.6 mmol), bromine (2.67 g, 16.7 mmol) and acetic acid (100 mL) as starting materials. The title compound was washed with a mixed solvent of ethyl acetate and hexane.

$^1$H-NMR (DMSO-d$_6$, 300 MHz) δ 6.83-6.89 (1H, m), 6.94 (1H, d, J=8.5 Hz), 7.38 (1H, t, J=8.0 Hz), 7.45-7.52 (2H, m), 7.61-7.71 (3H, m), 7.73 (1H, d, J=8.5 Hz), 7.91 (1H, dd, J=1.2, 7.8 Hz), 7.98 (1H, dd, J=1.2, 7.8 Hz), 10.74 (1H, s).

(v) Production of 2-chloro-N-[3-({2-[(cyclopropylcarbonyl)amino][1,3]thiazolo[5,4-b]pyridin-5-yl}oxy)phenyl]-3-(trifluoromethyl)benzamide In the same manner as in Example C81, the title compound (113 mg, 49%) was obtained as white crystals using N-{3-[(2-amino[1,3]thiazolo[5,4-b]pyridin-5-yl)oxy]phenyl}-2-chloro-3-(trifluoromethyl)benzamide (200 mg, 0.430 mmol), cyclopropanecarbonyl chloride (59.1 μL, 0.860 mmol) and pyridine (5 mL) as starting materials. The present compound was recrystallized from ethyl acetate and tetrahydrofuran.

$^1$H-NMR (DMSO-d$_6$, 300 MHz) δ 0.91-0.99 (4H, m), 1.93-2.04 (1H, m), 6.90-6.97 (1H, m), 7.15 (1H, d, J=8.7 Hz), 7.42 (1H, t, J=8.0 Hz), 7.49-7.54 (1H, m), 7.58 (1H, t, J=2.1 Hz), 7.68 (1H, t, J=8.0 Hz), 7.88-7.94 (1H, m), 7.98 (1H, dd, J=1.1, 8.0 Hz), 8.17 (1H, d, J=8.7 Hz), 10.78 (1H, s), 12.71 (1H, br s).

Example C83

Production of N-{3-[(2-acetylamino[1,3]thiazolo[5,4-b]pyridin-5-yl)oxy]phenyl}-2-chloro-3-(trifluoromethyl)benzamide

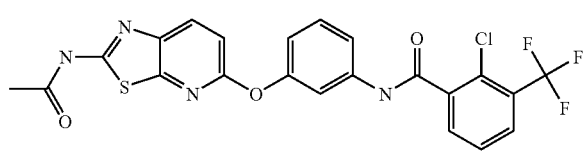 [SMILES: CC(=O)Nc1nc2ccc(Oc3cccc(NC(=O)c4cccc(C(F)(F)F)c4Cl)c3)nc2s1]

In the same manner as in Example C81, the title compound (125 mg, 57%) was obtained as white crystals using N-{3-[(2-amino[1,3]thiazolo[5,4-b]pyridin-5-yl)oxy]phenyl}-2-chloro-3-(trifluoromethyl)benzamide (200 mg, 0.430 mmol) produced in Example C82(iv), acetyl chloride (61.1 μL, 0.860 mmol), N,N-dimethylpyridine-4-amine (22.5 mg, 0.184 mmol) and pyridine (5 mL) as starting materials.

$^1$H-NMR (DMSO-d$_6$, 300 MHz) δ 2.19 (3H, s), 6.92-6.98 (1H, m), 7.15 (1H, d, J=8.8 Hz), 7.42 (1H, t, J=8.1 Hz), 7.49-7.55 (1H, m), 7.59 (1H, t, J=2.1 Hz), 7.68 (1H, t, J=7.7

Hz), 7.92 (1H, dd, J=1.1, 7.7 Hz), 7.98 (1H, dd, J=1.1, 7.7 Hz), 8.18 (1H, d, J=8.8 Hz), 10.79 (1H, s), 12.41 (1H, br s).

Example C84

Production of 2-chloro-N-{3-[(2-{[(4-methylpiperazin-1-yl)acetyl]amino}[1,3]thiazolo[5,4-b]pyridin-5-yl)oxy]phenyl}-3-(trifluoromethyl)benzamide

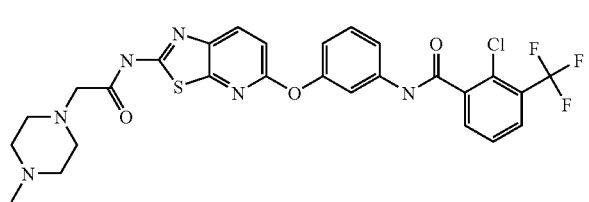 [SMILES: CN1CCN(CC(=O)Nc2nc3ccc(Oc4cccc(NC(=O)c5cccc(C(F)(F)F)c5Cl)c4)nc3s2)CC1]

(i) Production of 2-chloro-N-[3-({2-[(chloroacetyl)amino][1,3]thiazolo[5,4-b]pyridin-5-yl}oxy)phenyl]-3-(trifluoromethyl)benzamide In the same manner as in Example C11(i), the title compound (294 mg, quantitatively) was obtained as a pale-yellow oil using N-{3-[(2-amino[1,3]thiazolo[5,4-b]pyridin-5-yl)oxy]phenyl}-2-chloro-3-(trifluoromethyl)benzamide (200 mg, 0.430 mmol) produced in Example C82(iv), chloroacetyl chloride (99.4 µL, 1.24 mmol) and N,N-dimethylformamide (5 mL) as starting materials. The obtained compound was purified by silica gel column chromatography (ethyl acetate/hexane=0/100→70/30).

$^1$H-NMR (DMSO-d$_6$, 300 MHz) δ 4.47 (2H, s), 6.94-6.99 (1H, m), 7.19 (1H, d, J=8.7 Hz), 7.44 (1H, t, J=8.1 Hz), 7.50-7.56 (1H, m), 7.61 (1H, t, J=2.1 Hz), 7.68 (1H, t, J=7.8 Hz), 7.89-8.01 (2H, m), 8.23 (1H, d, J=8.7 Hz), 10.80 (1H, s), 12.80 (1H, s).

(ii) Production of 2-chloro-N-{3-[(2-{[(4-methylpiperazin-1-yl)acetyl]amino}[1,3]thiazolo[5,4-b]pyridin-5-yl)oxy]phenyl}-3-(trifluoromethyl)benzamide In the same manner as in Example C11(ii), the title compound (158 mg, 61%) was obtained as white crystals using 2-chloro-N-[3-({2-[(chloroacetyl)amino][1,3]thiazolo[5,4-b]pyridin-5-yl}oxy)phenyl]-3-(trifluoromethyl)benzamide (294 mg, 0.544 mmol), 1-methylpiperazine (95.8 µL, 0.860 mmol), triethylamine (119 µL, 0.860 mmol) and tetrahydrofuran (5 mL) as starting materials. The obtained compound was recrystallized from ethyl acetate and tetrahydrofuran.

$^1$H-NMR (CDCl$_3$, 300 MHz) δ 2.33 (3H, s), 2.45-2.64 (4H, m), 2.64-2.73 (4H, m), 3.28 (2H, s), 6.99-7.07 (2H, m), 7.38-7.52 (3H, m), 7.58-7.62 (1H, m), 7.71 (1H, s), 7.78-7.84 (2H, m), 8.02 (1H, d, J=8.7 Hz), 10.35 (1H, br s).

Example C85

Production of 2-chloro-3-(1-cyano-1-methylethyl)-N-[3-({2-[(cyclopropylcarbonyl)amino][1,3]thiazolo[5,4-b]pyridin-5-yl}oxy)-4-methylphenyl]benzamide

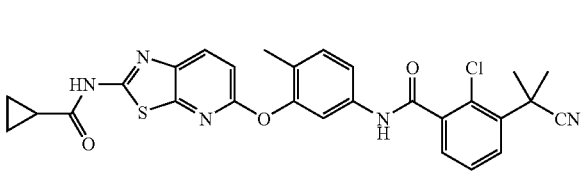 [SMILES: Cc1ccc(NC(=O)c2cccc(C(C)(C)C#N)c2Cl)cc1Oc1ccc2nc(NC(=O)C3CC3)sc2n1]

To a solution of 2-chloro-3-(1-cyano-1-methylethyl)benzoic acid (157 mg, 0.705 mmol) produced in Example C61(v) in tetrahydrofuran (5 mL) were added N,N-dimethylformamide (20 µL) and oxalyl chloride (103 µL, 1.17 mmol), and the mixture was stirred at room temperature for 1.5 hr. The solvent was concentrated under reduced pressure to give 2-chloro-3-(1-cyano-1-methylethyl)benzoyl chloride. The present compound was dissolved in dimethylacetamide (5 mL), N-[5-(5-amino-2-methylphenoxy)[1,3]thiazolo[5,4-b]pyridin-2-yl]cyclopropanecarboxamide (200 mg, 0.587 mmol) produced in Example C47(i) was added, and the mixture was stirred at room temperature for 20 hr. To the reaction mixture was added saturated aqueous sodium hydrogen carbonate solution, and the mixture was extracted with ethyl acetate. The extract was washed with saturated brine, and dried over anhydrous magnesium sulfate, and filtered through a pad filled with silica gel. The solvent was concentrated under reduced pressure, and the obtained the residue was purified by silica gel column chromatography (ethyl acetate/hexane=0/100→70/30), and recrystallized from ethyl acetate and tetrahydrofuran to give the title compound (204 mg, 64%) as white crystals.

$^1$H-NMR (DMSO-d$_6$, 300 MHz) δ 0.89-1.01 (4H, m), 1.83 (6H, s), 1.93-2.04 (1H, m), 2.09 (3H, s), 7.12 (1H, d, J=8.7 Hz), 7.31 (1H, d, J=8.3 Hz), 7.43-7.69 (5H, m), 8.17 (1H, d, J=8.7 Hz), 10.62 (1H, s), 12.68 (1H, s).

Example C86

Production of 2-chloro-3-(1-cyanocyclopropyl)-N-[3-({2-[(cyclopropylcarbonyl)amino][1,3]thiazolo[5,4-b]pyridin-5-yl}oxy)-4-methylphenyl]benzamide

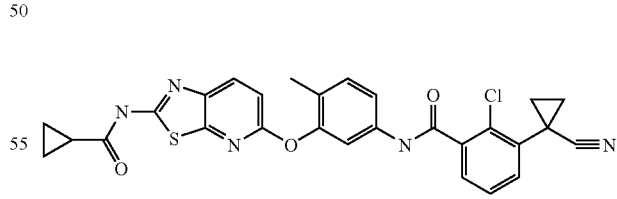

In the same manner as in Example C85(vi), the title compound (200 mg, 63%) was obtained as white crystals using 2-chloro-3-(1-cyanocyclopropyl)benzoic acid (156 mg, 0.705 mmol), N-[5-(5-amino-2-methylphenoxy)[1,3]thiazolo[5,4-b]pyridin-2-yl]cyclopropanecarboxamide (200 mg, 0.587 mmol) produced in Example C47(i), oxalyl chloride (103 µL, 1.17 mmol), N,N-dimethylformamide (20 µL), tetrahydrofuran (5 mL) and dimethylacetamide (5 mL) as starting materials.

¹H-NMR (DMSO-d₆, 300 MHz) δ 0.89-0.99 (4H, m), 1.40-1.48 (2H, m), 1.71-1.83 (2H, m), 1.93-2.04 (1H, m), 2.09 (3H, s), 7.12 (1H, d, J=8.7 Hz), 7.31 (1H, d, J=8.1 Hz), 7.41-7.69 (5H, m), 8.16 (1H, d, J=8.7 Hz), 10.61 (1H, s), 12.69 (1H, br s).

Example C87

Production of N-{3-[(2-acetylamino[1,3]thiazolo[5,4-b]pyridin-5-yl)oxy]-4-methylphenyl}-3-(1-cyano-1-methylethyl)benzamide

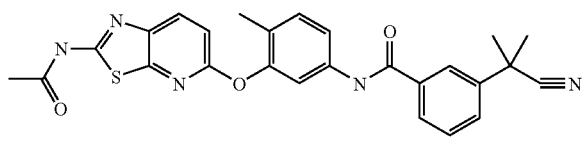 [SMILES: CC(=O)Nc1nc2ccc(Oc3cc(NC(=O)c4cccc(C(C)(C)C#N)c4)ccc3C)nc2s1]

To a solution of N-{3-[(2-amino[1,3]thiazolo[5,4-b]pyridin-5-yl)oxy]-4-methylphenyl}-3-(1-cyano-1-methylethyl)benzamide (200 mg, 0.450 mmol) produced in Example C12 (iv) in pyridine (5 mL) were added acetyl chloride (128 μL, 1.80 mmol) and N,N-dimethylpyridine-4-amine (8.8 mg, 0.0720 mmol), and the mixture was stirred at room temperature for 28 hr. The title compound (157 mg, 72%) was obtained as white crystals by operation in the same manner as in Example C81. The present compound was recrystallized from ethyl acetate and tetrahydrofuran.

¹H-NMR (DMSO-d₆, 300 MHz) δ 1.73 (6H, s), 2.11 (3H, s), 2.19 (3H, s), 7.11 (1H, d, J=8.8 Hz), 7.32 (1H, d, J=8.1 Hz), 7.54-7.62 (3H, m), 7.71-7.77 (1H, m), 7.88-7.93 (1H, m), 7.98-8.02 (1H, m), 8.17 (1H, d, J=8.8 Hz), 10.33 (1H, s), 12.38 (1H, s).

Example C88

Production of 3-(1-cyano-1-methylethyl)-N-{3-[(2-{[(4-ethylpiperazin-1-yl)acetyl]amino}[1,3]thiazolo[5,4-b]pyridin-5-yl)oxy]-4-methylphenyl}benzamide

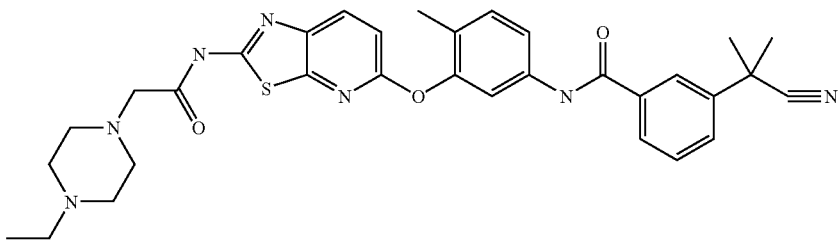 [SMILES: CCN1CCN(CC(=O)Nc2nc3ccc(Oc4cc(NC(=O)c5cccc(C(C)(C)C#N)c5)ccc4C)nc3s2)CC1]

A mixture of N-[3-({2-[(chloroacetyl)amino][1,3]thiazolo[5,4-b]pyridin-5-yl}oxy)-4-methylphenyl]-3-(1-cyano-1-methylethyl)benzamide (284 mg, 0.547 mmol) produced in Example C15(i), 1-ethylpiperazine (114 μL, 0.901 mmol) triethylamine (125 μL, 0.901 mmol) and tetrahydrofuran (5 mL) was stirred at 60° C. for 2 hr. To the reaction mixture was added saturated aqueous sodium hydrogen carbonate solution, and the mixture was extracted with ethyl acetate. The extract was washed with saturated brine, and dried over anhydrous magnesium sulfate, and filtered through a pad filled with basic silica gel. The filtrate was concentrated under reduced pressure, and the obtained residue was recrystallized from ethyl acetate to give the title compound (138 mg, 51%) as white crystals.

¹H-NMR (CDCl₃, 300 MHz) δ 1.11 (3H, t, J=7.2 Hz), 1.76 (6H, s), 2.21 (3H, s), 2.47 (2H, q, J=7.2 Hz), 2.52-2.74 (8H, m), 3.27 (2H, s), 6.99 (1H, d, J=8.8 Hz), 7.29 (1H, d, J=8.5 Hz), 7.37-7.42 (1H, m), 7.48-7.54 (2H, m), 7.67-7.72 (1H, m), 7.73-7.78 (1H, m), 7.83 (1H, br s), 7.95 (1H, t, J=1.7 Hz), 8.00 (1H, d, J=8.8 Hz).

Example C89

Production of 3-(1-cyano-1-methylethyl)-N-[4-methyl-3-({2-[(morpholin-4-ylacetyl)amino][1,3]thiazolo[5,4-b]pyridin-5-yl}oxy)phenyl]benzamide

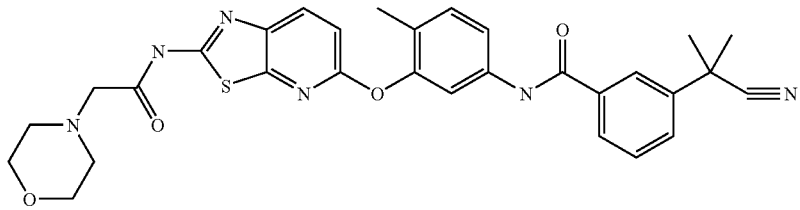 [SMILES: Cc1ccc(NC(=O)c2cccc(C(C)(C)C#N)c2)cc1Oc1ccc2nc(NC(=O)CN3CCOCC3)sc2n1]

To a solution of N-[3-({2-[(chloroacetyl)amino][1,3]thiazolo[5,4-b]pyridin-5-yl}oxy)-4-methylphenyl]-3-(1-cyano-1-methylethyl)benzamide (304 mg, 0.584 mmol) produced in Example C15(i) in tetrahydrofuran (5 mL) were added morpholine (78.8 μL, 0.901 mmol) and triethylamine (125 μL, 0.901 mmol), and the mixture was stirred at 60° C. for 4 hr. The title compound (141 mg, 55%) was obtained as white crystals by operation in the same manner as in Example C88. The present compound was recrystallized from ethyl acetate and tetrahydrofuran.

$^1$H-NMR (CDCl$_3$, 300 MHz) δ 1.76 (6H, s), 2.20 (3H, s), 2.62-2.68 (4H, m), 3.28 (2H, s), 3.77-3.84 (4H, m), 6.99 (1H, d, J=8.8 Hz), 7.25-7.31 (1H, m), 7.37-7.42 (1H, m), 7.47-7.55 (2H, m), 7.66-7.72 (1H, m), 7.73-7.78 (1H, m), 7.85 (1H, s), 7.95 (1H, t, J=1.7 Hz), 8.00 (1H, d, J=8.8 Hz), 10.28 (1H, br s).

Example C90

Production of 3-(1-cyano-1-methylethyl)-N-[4-methyl-3-({2-[(thiomorpholin-4-ylacetyl)amino][1,3]thiazolo[5,4-b]pyridin-5-yl}oxy)phenyl]benzamide

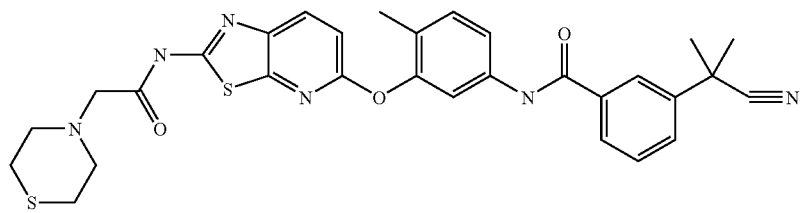

In the same manner as in Example C88, the title compound (114 mg, 43%) was obtained as white crystals using a solution of N-[3-({2-[(chloroacetyl)amino][1,3]thiazolo[5,4-b]pyridin-5-yl}oxy)-4-methylphenyl]-3-(1-cyano-1-methylethyl)benzamide (295 mg, 0.569 mmol) produced in Example C15 (i) in tetrahydrofuran (5 mL), thiomorpholine (85.3 μL, 0.901 mmol) and triethylamine (125 μL, 0.901 mmol) as starting materials. The present compound was recrystallized from tetrahydrofuran.

$^1$H-NMR (DMSO-d$_6$, 300 MHz) δ 1.76 (6H, s), 2.20 (3H, s), 2.73-2.82 (4H, m), 2.84-2.93 (4H, m), 3.27 (2H, s), 6.99 (1H, d, J=8.7 Hz), 7.25-7.31 (1H, m), 7.36-7.42 (1H, m), 7.47-7.55 (2H, m), 7.66-7.72 (1H, m), 7.72-7.78 (1H, m), 7.84 (1H, s), 7.95 (1H, t, J=1.7 Hz), 8.00 (1H, d, J=8.7 Hz), 10.25 (1H, br s).

Example C91

Production of 3-(1-cyano-1-methylethyl)-N-{3-[(2-{[(4-fluoropiperidin-1-yl)acetyl]amino}[1,3]thiazolo[5,4-b]pyridin-5-yl)oxy]-4-methylphenyl}benzamide

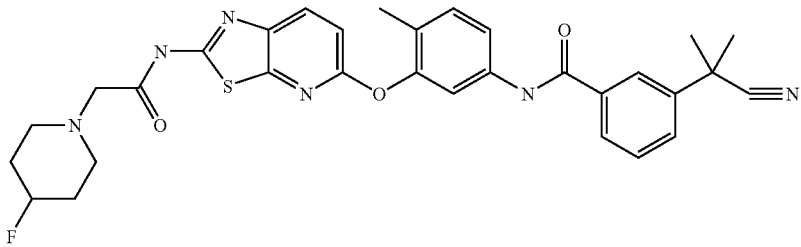 [SMILES: Cc1ccc(NC(=O)c2cccc(C(C)(C)C#N)c2)cc1Oc1ccc2nc(NC(=O)CN3CCC(F)CC3)sc2n1]

In the same manner as in Example C88, the title compound (118 mg, 52%) was obtained as white crystals using a solution of N-[3-({2-[(chloroacetyl)amino][1,3]thiazolo[5,4-b]pyridin-5-yl}oxy)-4-methylphenyl]-3-(1-cyano-1-methylethyl)benzamide (200 mg, 0.384 mmol) produced in Example C15 (i) in tetrahydrofuran (5 mL), 4-fluoropiperidine hydrochloride (107 mg, 0.769 mmol) and triethylamine (214 µL, 1.53 mmol) as starting materials. The present compound was recrystallized from ethyl acetate and tetrahydrofuran.

$^1$H-NMR (CDCl$_3$, 300 MHz) δ 1.76 (6H, s), 1.90-2.06 (4H, m), 2.20 (3H, s), 2.55-2.65 (2H, m), 2.71-2.83 (2H, m), 3.27 (2H, s), 4.65-4.90 (1H, m), 6.99 (1H, d, J=8.8 Hz), 7.26-7.31 (1H, m), 7.37-7.42 (1H, m), 7.47-7.54 (2H, m), 7.67-7.72 (1H, m), 7.72-7.78 (1H, m), 7.81 (1H, s), 7.95 (1H, t, J=1.7 Hz), 7.99 (1H, d, J=8.8 Hz), 10.32 (1H, br s).

Example C92

Production of 3-(1-cyano-1-methylethyl)-N-{3-[(2-{[(4,4-difluoropiperidin-1-yl)acetyl]amino}[1,3]thiazolo[5,4-b]pyridin-5-yl)oxy]-4-methylphenyl}benzamide In the same manner as in Example C88, the title compound (133 mg, 57%) was obtained as white crystals using a solution of N-[3-({2-[(chloroacetyl)amino][1,3]thiazolo[5,4-b]pyridin-5-yl}oxy)-4-methylphenyl]-3-(1-cyano-1-methylethyl)benzamide (200 mg, 0.384 mmol) produced in Example C15 (i) in tetrahydrofuran (5 mL), 4,4-difluoropiperidine hydrochloride (121 mg, 0.769 mmol) and triethylamine (214 µL, 1.53 mmol) as starting materials. The present compound was recrystallized from ethyl acetate and tetrahydrofuran.

$^1$H-NMR (CDCl$_3$, 300 MHz) δ 1.76 (6H, s), 2.04-2.19 (4H, m), 2.20 (3H, s), 2.74-2.81 (4H, m), 3.33 (2H, s), 7.00 (1H, d, J=8.8 Hz), 7.26-7.31 (1H, m), 7.36-7.41 (1H, m), 7.47-7.54 (2H, m), 7.67-7.72 (1H, m), 7.73-7.77 (1H, m), 7.82 (1H, s), 7.95 (1H, t, J=1.8 Hz), 8.00 (1H, d, J=8.8 Hz), 10.21 (1H, br s).

Example C93

Production of 3-(1-cyano-1-methylethyl)-N-{3-[(2-{[(1,1-dioxidothiomorpholin-4-yl)acetyl]amino}[1,3]thiazolo[5,4-b]pyridin-5-yl)oxy]-4-methylphenyl}benzamide

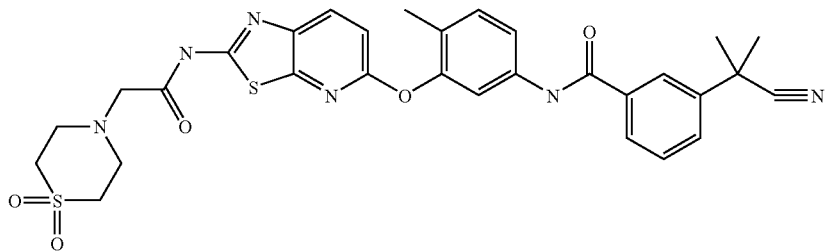 [SMILES: Cc1ccc(NC(=O)c2cccc(C(C)(C)C#N)c2)cc1Oc1ccc2nc(NC(=O)CN3CCS(=O)(=O)CC3)sc2n1]

In the same manner as in Example C88, the title compound (79.7 mg, 33%) was obtained as white crystals using a solution of N-[3-({2-[(chloroacetyl)amino][1,3]thiazolo[5,4-b]pyridin-5-yl}oxy)-4-methylphenyl]-3-(1-cyano-1-methylethyl)benzamide (200 mg, 0.384 mmol) produced in Example C15(i) in tetrahydrofuran (5 mL), thiomorpholine 1,1-dioxide (259 mg, 0.769 mmol) and triethylamine (214 μL, 0.769 mmol) as starting materials. The present compound was recrystallized from ethyl acetate and ethanol.

$^1$H-NMR (CDCl$_3$, 300 MHz) δ 1.76 (6H, s), 2.20 (3H, s), 3.15-3.27 (8H, m), 3.46 (2H, s), 7.01 (1H, d, J=8.7 Hz), 7.29 (1H, d, J=8.5 Hz), 7.36 (1H, dd, J=1.9, 8.5 Hz), 7.51 (1H, t, J=7.8 Hz), 7.56 (1H, d, J=1.9 Hz), 7.66-7.72 (1H, m), 7.73-7.78 (1H, m), 7.83 (1H, s), 7.95 (1H, t, J=1.7 Hz), 8.00 (1H, d, J=8.7 Hz), 10.01 (1H, s).

Example C94

Production of 3-(1-cyano-1-methylethyl)-N-(3-{[2-({[4-(2-hydroxyethyl)piperazin-1-yl]acetyl}amino)[1,3]thiazolo[5,4-b]pyridin-5-yl]oxy}-4-methylphenyl)benzamide trihydrochloride To a solution of N-{3-[(2-amino[1,3]thiazolo[5,4-b]pyridin-5-yl)oxy]-4-methylphenyl}-3-(1-cyano-1-methylethyl)benzamide (200 mg, 0.450 mmol) produced in Example C12 (iv) in N,N-dimethylacetamide (3 mL) was added chloroacetyl chloride (68.6 μL, 0.863 mmol), and the mixture was stirred at room temperature for 3 hr. To the reaction mixture was added aqueous sodium hydrogen carbonate solution (5 mL), and the mixture was extracted with ethyl acetate (5 mL×3). The organic layers were combined, and dried over anhydrous magnesium sulfate, and concentrated under reduced pressure. The residue was dissolved in tetrahydrofuran (3 mL), triethylamine (0.2 mL, 1.43 mmol) and 1-(2-hydroxyethyl)piperazine (160 μL, 1.30 mmol) were added, and the mixture was stirred at 60° C. for 14 hr. To the reaction mixture was added water (5 mL), and the mixture was extracted with ethyl acetate (5 mL×4). The organic layers were combined was washed successively with water (3 mL) and saturated brine (3 mL), and dried over anhydrous magnesium sulfate, and concentrated under reduced pressure. The residue was purified by silica gel column chromatography (hexane/ethyl acetate=20/80→0/100), and fractions containing the object product were concentrated under reduced pressure. The residue was dissolved in ethyl acetate (3 mL), 4N hydrochloric acid/ethyl acetate (0.3 mL, 1.20 mmol) was added, and the mixture was stirred at room temperature for 3 hr. The reaction mixture was concentrated under reduced pressure to give the title compound (200 mg, 61%) as a white amorphous.

$^1$H-NMR (DMSO-d$_6$, 300 MHz) δ 1.74 (6H, s), 2.10 (3H, s), 3.02-3.26 (4H, m), 3.47-3.70 (2H, m), 3.73-3.83 (2H, m), 3.83-3.99 (2H, m), 4.14-4.93 (5H, m), 7.16 (1H, d, J=8.8 Hz),

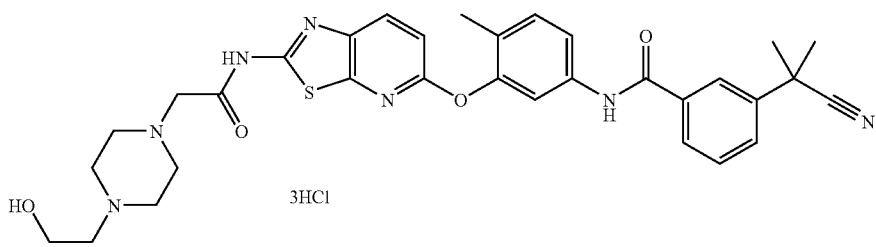 [SMILES: Cc1ccc(NC(=O)c2cccc(C(C)(C)C#N)c2)cc1Oc1ccc2nc(NC(=O)CN3CCN(CCO)CC3)sc2n1 ; "3HCl"]

7.33 (1H, d, J=8.3 Hz), 7.53-7.67 (3H, m), 7.70-7.78 (1H, m), 7.93 (1H, dt, J=7.8, 1.3 Hz), 8.04 (1H, t, J=1.3 Hz), 8.23 (1H, d, J=8.8 Hz), 10.43 (1H, s), 10.60 (1H, br s), 12.67 (1H, br s).

Example C95

Production of 3-(1-cyano-1-methylethyl)-N-(3-{[2-({[4-(hydroxymethyl)piperidin-1-yl]acetyl}amino)[1,3]thiazolo[5,4-b]pyridin-5-yl]oxy}-4-methylphenyl)benzamide dihydrochloride

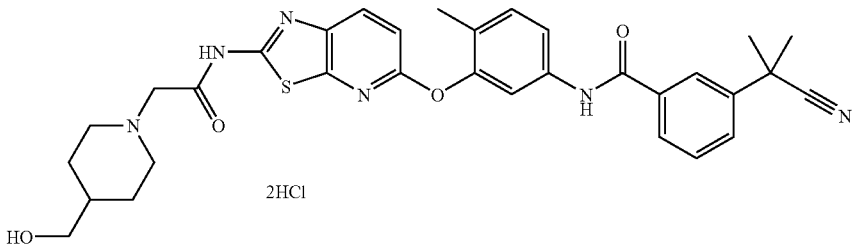 [SMILES: Cc1ccc(NC(=O)c2cccc(C(C)(C)C#N)c2)cc1Oc1ccc2nc(NC(=O)CN3CCC(CO)CC3)sc2n1 ; "2HCl"]

In the same manner as in Example C104, the title compound (89.8 mg, 42%) was obtained as a white amorphous using N-{3-[(2-amino[1,3]thiazolo[5,4-b]pyridin-5-yl)oxy]-4-methylphenyl}-3-(1-cyano-1-methylethyl)benzamide (141 mg, 0.317 mmol) produced in Example C12(iv), chloroacetyl chloride (50 μL, 0.624 mmol), N,N-dimethylacetamide (3 mL), 4-piperidinemethanol (93.8 mg, 0.814 mmol), triethylamine (120 μL, 0.861 mmol) and tetrahydrofuran (3 mL) as starting materials.

$^1$H-NMR (DMSO-d$_6$, 300 MHz) δ 1.28-1.70 (3H, m), 1.74 (6H, s), 1.76-1.90 (2H, m), 2.10 (3H, s), 2.92-3.18 (2H, m), 3.19-3.40 (2H, m), 3.41-3.65 (2H, m), 4.13-4.43 (2H, m), 4.64 (1H, br s), 7.19 (1H, d, J=8.8 Hz), 7.33 (1H, d, J=8.7 Hz), 7.53-7.68 (3H, m), 7.74 (1H, ddd, J=0.9, 1.6, 8.0 Hz), 7.92 (1H, d, J=8.0 Hz), 8.02 (1H, t, J=1.6 Hz), 8.26 (1H, d, J=8.8 Hz), 9.98 (1H, br s), 10.39 (1H, s), 13.09 (1H, br s).

Example C96

Production of 3-(1-cyano-1-methylethyl)-N-{3-[(2-{[(4-hydroxypiperidin-1-yl)acetyl]amino}[1,3]thiazolo[5,4-b]pyridin-5-yl)oxy]-4-methylphenyl}benzamide dihydrochloride

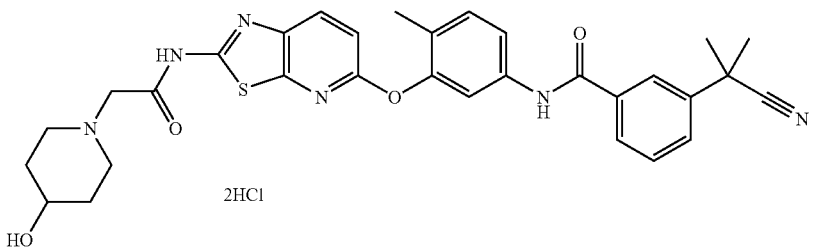 [SMILES: Cc1ccc(NC(=O)c2cccc(C(C)(C)C#N)c2)cc1Oc1ccc2nc(NC(=O)CN3CCC(O)CC3)sc2n1 ; "2HCl"]

In the same manner as in Example C104, the title compound (142 mg, 69%) was obtained as a white amorphous using N-{3-[(2-amino[1,3]thiazolo[5,4-b]pyridin-5-yl)oxy]-4-methylphenyl}-3-(1-cyano-1-methylethyl)benzamide (139 mg, 0.313 mmol) produced in Example C12(iv), chloroacetyl chloride (50 μL, 0.624 mmol), N,N-dimethylacetamide (3 mL), 4-hydroxypiperidine (82.4 mg, 0.815 mmol), triethylamine (120 μL, 0.861 mmol) and tetrahydrofuran (3 mL) as starting materials.

$^1$H-NMR (DMSO-d$_6$, 300 MHz) δ 1.62-1.80 (2H, m), 1.74 (6H, s), 1.85-2.02 (2H, m), 2.10 (3H, s), 2.99-3.58 (5H, m), 4.18-4.40 (2H, m), 4.94-5.14 (1H, m), 7.19 (1H, d, J=8.7 Hz), 7.33 (1H, d, J=8.5 Hz), 7.52-7.69 (3H, m), 7.74 (1H, ddd, J=0.9, 1.9, 7.7 Hz), 7.92 (1H, d, J=7.9 Hz), 8.02 (1H, t, J=1.6 Hz), 8.26 (1H, d, J=8.7 Hz), 10.06 (1H, br s), 10.39 (1H, s), 13.08 (1H, br s).

Example C97

Production of 3-(1-cyano-1-methylethyl)-N-[3-({2-[(N,N-dimethylglycyl)amino][1,3]thiazolo[5,4-b]pyridin-5-yl}oxy)-4-methylphenyl]benzamide

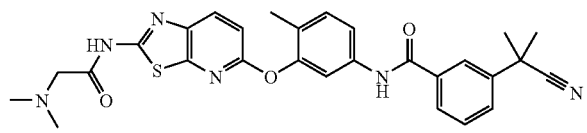 [SMILES: Cc1ccc(NC(=O)c2cccc(C(C)(C)C#N)c2)cc1Oc1ccc2nc(NC(=O)CN(C)C)sc2n1]

A mixture of N-{3-[(2-amino[1,3]thiazolo[5,4-b]pyridin-5-yl)oxy]-4-methylphenyl}-3-(1-cyano-1-methylethyl)benzamide (153 mg, 0.344 mmol) produced in Example C12(iv), N,N-dimethylglycine (79.5 mmol, 0.771 mmol), O-(7-azabenzotriazol-1-yl)-N,N,N',N'-tetramethyluronium hexafluorophosphate (321 mg, 0.843 mmol) and pyridine (3 mL) was stirred at 100° C. for 15 hr. To the reaction mixture was added aqueous sodium hydrogen carbonate solution (5 mL), and the mixture was extracted with ethyl acetate (5 mL×4). The organic layers were combined, and dried over anhydrous magnesium sulfate, and concentrated under reduced pressure.

The residue was purified by silica gel column chromatography (hexane/ethyl acetate=50/50→0/100), and crystallized from diisopropyl ether/ethyl acetate to give the title compound (25.4 mg, 14%) as pale-orange crystals.

$^1$H-NMR (DMSO-d$_6$, 300 MHz) δ 1.73 (6H, s), 2.11 (3H, s), 2.30 (6H, s), 3.30 (2H, s), 7.12 (1H, d, J=8.7 Hz), 7.33 (1H, d, J=8.9 Hz), 7.53-7.64 (3H, m), 7.74 (1H, ddd, J=1.0, 2.0, 7.9 Hz), 7.86-7.95 (1H, m), 8.01 (1H, t, J=2.0 Hz), 8.17 (1H, d, J=8.7 Hz), 10.34 (1H, s), 12.09 (1H, br s).

Example C98

Production of N-[3-({2-[(6-azaspiro[2.5]oct-6-ylacetyl)amino][1,3]thiazolo[5,4-b]pyridin-5-yl}oxy)-4-methylphenyl]-3-(1-cyano-1-methylethyl)benzamide

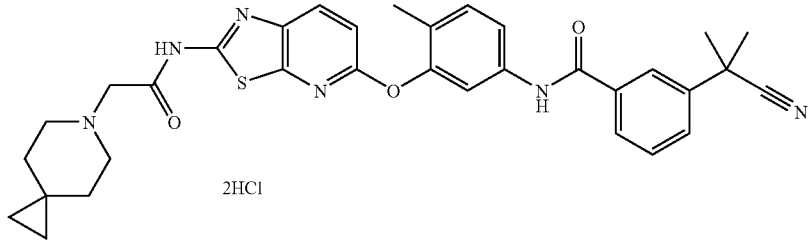 [SMILES: Cc1ccc(NC(=O)c2cccc(C(C)(C)C#N)c2)cc1Oc1ccc2nc(NC(=O)CN3CCC4(CC3)CC4)sc2n1 ; "2HCl"]

(i) Production of tert-butyl 4-methylidenepiperidine-1-carboxylate

Methyltriphenylphosphonium bromide (11.7 g, 32.7 mmol) was suspended in tetrahydrofuran (50 mL), and the suspension was cooled to 0° C. Potassium tert-butoxide (3.61 g, 37.6 mmol) was added, and the mixture was stirred for 1 hr. To the mixture was added dropwise a solution (25 mL) of tert-butyl 4-oxopiperidine-1-carboxylate (5.02 g, 25.2 mmol) in tetrahydrofuran, and the mixture was stirred for 2.5 hr with warming to room temperature. To the reaction mixture was added aqueous ammonium chloride solution (100 mL), and the mixture was extracted with a mixture of diethyl ether/ethyl acetate=1/1 (200 mL×2). The organic layers were combined, washed with saturated brine (50 mL), and dried over anhydrous magnesium sulfate, and concentrated under reduced pressure. The residue was purified by silica gel column chromatography (hexane/ethyl acetate=100/0→90/10) to give the title compound (4.71 g, 95%) as a colorless oil.

$^1$H-NMR (CDCl$_3$, 300 MHz) δ 1.47 (9H, s), 2.18 (4H, t, J=5.8 Hz), 3.34-3.51 (4H, m), 4.74 (2H, s).

(ii) Production of tert-butyl 6-azaspiro[2.5]octane-6-carboxylate

To a mixture of diethyl ether (25 mL) and 30% aqueous potassium hydroxide solution (5 mL) was added 1-methyl-3-nitro-1-nitrosoguanidine (containing 50% water, 2.17 g), and the mixture was stirred at room temperature for 10 min. To a solution (25 mL) of tert-butyl 4-methylidenepiperidine-1-carboxylate (1.00 g, 5.07 mmol) in tetrahydrofuran was added dropwise the above-mentioned ether layer, and the mixture was stirred at room temperature for 16 hr. To the reaction mixture was added a ether layer prepared from diethyl ether (25 mL), 30% aqueous potassium hydroxide solution (5 mL), and 1-methyl-3-nitro-1-nitrosoguanidine (containing 50% water, 3.77 g), and the mixture was further stirred for 16 hr. To the reaction mixture was added acetic acid (1 mL), and the mixture was concentrated under reduced pressure. The residue was purified by silica gel column chromatography (hexane/ethyl acetate=100/0→90/10) to give the title compound (261 mg, 24%) as a white powder.

$^1$H-NMR (CDCl$_3$, 300 MHz) δ 0.32 (4H, s), 1.33 (4H, d, J=5.6 Hz), 1.47 (9H, s), 3.42 (4H, d, J=5.6 Hz).

(iii) Production of 6-azaspiro[2.5]octane hydrochloride

Tert-butyl 6-azaspiro[2.5]octane-6-carboxylate (261 mg, 1.23 mmol) was dissolved in tetrahydrofuran (5 mL), 4N hydrochloric acid/ethyl acetate solution (2 mL, 8.00 mmol) was added, and the mixture was stirred at 50° C. for 24 hr. The reaction mixture was concentrated under reduced pressure to give the title compound (155 mg, 85%) as white crystals.

$^1$H-NMR (DMSO-d$_6$, 300 MHz) δ 0.37 (4H, s), 1.53 (4H, d, J=5.8 Hz), 3.03 (4H, d, J=5.8 Hz), 8.85 (2H, br s).

(iv) Production of N-[3-({2-[(6-azaspiro[2.5]oct-6-ylacetyl)amino][1,3]thiazolo[5,4-b]pyridin-5-yl}oxy [-4-methylphenyl]-3-(1-cyano-1-methylethyl)benzamide In the same manner as in Example C104, the title compound (113 mg, 68%) was obtained as a white amorphous using N-{3-[(2-amino[1,3]thiazolo[5,4-b]pyridin-5-yl)oxy]-4-methylphenyl}-3-(1-cyano-1-methylethyl)benzamide (110 mg, 0.248 mmol) produced in Example C12(iv), chloroacetyl chloride (40 µL, 0.499 mmol), N,N-dimethylacetamide (2 mL), 6-azaspiro[2.5]octane hydrochloride (55.0 mg, 0.373 mmol), triethylamine (0.1 mL, 0.717 mmol) and tetrahydrofuran (3 mL) as starting materials.

$^1$H-NMR (DMSO-d$_6$, 300 MHz) δ 0.29-0.52 (4H, m), 1.02-1.20 (2H, m), 1.74 (6H, s), 2.10 (3H, s), 2.13-2.31 (2H, m), 3.09-3.31 (2H, m), 3.38-3.61 (2H, m), 4.39 (2H, br s), 7.20 (1H, d, J=8.8 Hz), 7.33 (1H, d, J=8.5 Hz), 7.53-7.62 (2H, m), 7.65 (1H, d, J=1.9 Hz), 7.74 (1H, ddd, J=0.9, 1.7, 7.8 Hz), 7.88-7.96 (1H, m), 8.03 (1H, t, J=1.7 Hz), 8.27 (1H, d, J=8.8 Hz), 10.17 (1H, br s), 10.41 (1H, s), 13.13 (1H, br s).

Example C99

Production of N-{3-[(2-{[(2E)-3-(4-chlorophenyl)prop-2-enoyl]amino}[1,3]thiazolo[5,4-b]pyridin-5-yl)oxy]-4-methylphenyl}-3-(1-cyano-1-methylethyl)benzamide

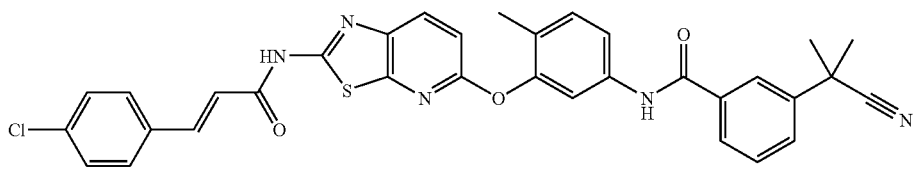 [SMILES: Cc1ccc(NC(=O)c2cccc(C(C)(C)C#N)c2)cc1Oc1ccc2nc(NC(=O)/C=C/c3ccc(Cl)cc3)sc2n1]

In the same manner as in Example C97, the title compound (140 mg, 70%) was obtained as pale-yellow crystals using N-{3-[(2-amino[1,3]thiazolo[5,4-b]pyridin-5-yl)oxy]-4-methylphenyl}-3-(1-cyano-1-methylethyl)benzamide (145 mg, 0.327 mmol) produced in Example C12(iv), p-chlorocinnamic acid (125 mg, 0.682 mmol), O-(7-azabenzotriazol-1-yl)-N,N,N',N'-tetramethyluronium hexafluorophosphate (299 mg, 0.787 mmol) and pyridine (3 mL) as starting materials.

$^1$H-NMR (DMSO-d$_6$, 300 MHz) δ 1.73 (6H, s), 2.12 (3H, s), 6.93 (1H, d, J=15.9 Hz), 7.15 (1H, d, J=8.7 Hz), 7.33 (1H, d, J=9.1 Hz), 7.50-7.63 (5H, m), 7.65-7.71 (2H, m), 7.71-7.83 (2H, m), 7.91 (1H, ddd, J=1.1, 1.5, 7.8 Hz), 8.01 (1H, t, J=1.5 Hz), 8.20 (1H, d, J=8.7 Hz), 10.34 (1H, s), 12.68 (1H, br s).

Example C100

Production of 3-(1-cyano-1-methylethyl)-N-{4-methyl-3-[(2-{[(1-methylcyclopropyl)carbonyl]amino}[1,3]thiazolo[5,4-b]pyridin-5-yl)oxy]phenyl}benzamide

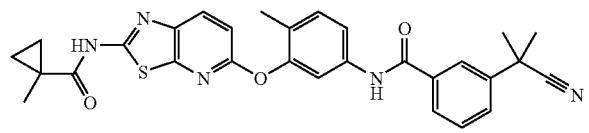 [SMILES: Cc1ccc(NC(=O)c2cccc(C(C)(C)C#N)c2)cc1Oc1ccc2nc(NC(=O)C3(C)CC3)sc2n1]

In the same manner as in Example C97, the title compound (79.6 mg, 45%) was obtained as white crystals using N-{3-[(2-amino[1,3]thiazolo[5,4-b]pyridin-5-yl)oxy]-4-methylphenyl}-3-(1-cyano-1-methylethyl)benzamide (151 mg, 0.339 mmol) produced in Example C12(iv), 1-methylcyclopropane-1-carboxylic acid (70.0 mg, 0.699 mmol), O-(7-azabenzotriazol-1-yl)-N,N,N',N'-tetramethyluronium hexafluorophosphate (325 mg, 0.853 mmol) and pyridine (3 mL) as starting materials.

$^1$H-NMR (DMSO-d$_6$, 300 MHz) δ 0.74-0.82 (2H, m), 1.19-1.29 (2H, m), 1.41 (3H, s), 1.73 (6H, s), 2.11 (3H, s), 7.13 (1H, d, J=8.7 Hz), 7.32 (1H, d, J=7.9 Hz), 7.53-7.64 (3H, m), 7.74 (1H, ddd, J=0.9, 1.8, 7.9 Hz), 7.87-7.94 (1H, m), 8.00 (1H, t, J=1.8 Hz), 8.15 (1H, d, J=8.7 Hz), 10.34 (1H, s), 11.88 (1H, s).

Example C101

Production of 2-chloro-N-[4-chloro-5-({2-[(cyclopropylcarbonyl)amino][1,3]thiazolo[5,4-b]pyridin-5-yl}oxy)-2-fluorophenyl]-3-(1-cyano-1-methylethyl)benzamide

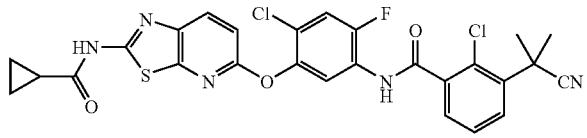

(i) Production of tert-butyl(4-chloro-2-fluoro-5-hydroxyphenyl)carbamate

A mixture of 5-amino-2-chloro-4-fluorophenol (4.05 g, 25.1 mmol) produced in Example C61(vi), di-tert-butyl bicarbonate (6.3 mL, 27.4 mmol) and tetrahydrofuran (60 mL) was stirred with heating under reflux for 24 hr. Di-tert-butyl bicarbonate (5 mL, 21.8 mmol) was further added, and the mixture was stirred with heating under reflux for 6 hr. The reaction mixture was concentrated under reduced pressure, and the residue was purified by silica gel column chromatography (hexane/ethyl acetate=95/5→50/50) to give the title compound (5.64 g, 86%) as an orange oil.

$^1$H-NMR (CDCl$_3$, 300 MHz) δ 1.52 (9H, s), 5.31 (1H, s), 6.64 (1H, br s), 7.05 (1H, d, J=10.4 Hz), 7.86 (1H, d, J=7.6 Hz).

(ii) Production of tert-butyl{4-chloro-2-fluoro-5-[(5-nitropyridin-2-yl)oxy]phenyl}carbamate A mixture of tert-butyl(4-chloro-2-fluoro-5-hydroxyphenyl)carbamate (6.70 g, 25.6 mmol), 2-chloro-5-nitropyridine (4.06 g, 25.6 mmol), potassium carbonate (3.89 g, 28.1 mmol) and N,N-dimethylformamide (70 mL) was stirred at room temperature for 30 min. To the reaction mixture was added aqueous ammonium chloride solution (100 mL), and the mixture was extracted with ethyl acetate (150 mL×3). The organic layers were combined, and washed successively with water (100 mL) and saturated brine (50 mL), and dried over anhydrous magnesium sulfate, and concentrated under reduced pressure to give the title compound (4.52 g, 46%) as a white powder.

$^1$H-NMR (CDCl$_3$, 300 MHz) δ 1.50 (9H, s), 6.77 (1H, br s), 7.11 (1H, d, J=9.1 Hz), 7.23 (1H, d, J=10.4 Hz), 8.13 (1H, d, J=7.6 Hz), 8.50 (1H, dd, J=2.8, 9.1 Hz), 9.00 (1H, d, J=2.8 Hz).

(iii) Production of tert-butyl{5-[(5-aminopyridin-2-yl)oxy]-4-chloro-2-fluorophenyl}carbamate A mixture of tert-butyl{4-chloro-2-fluoro-5-[(5-nitropyridin-2-yl)oxy]phenyl}carbamate (4.66 g, 12.1 mmol), reduced iron (61.2 mmol), calcium chloride (680 mg, 6.13 mmol) and ethanol (90 mL)/water (10 mL)/1-methyl-2-pyrrolidone (40 mL) was stirred with heating under reflux for 5 hr. Reduced iron (5.00 g, 89.5 mmol) and calcium chloride (700 mg, 6.31 mmol) were further added, and the mixture was stirred with heating under reflux for 16 hr. The reaction mixture was filtered through celite, and the filtrate was concentrated under reduced pressure. The residue was diluted with ethyl acetate (300 mL), washed with water (100 mL×2) and saturated brine (50 mL). The obtained organic layer was dried over anhydrous magnesium sulfate, and concentrated under reduced pressure. The residue was purified by basic silica gel column chromatography (hexane/ethyl acetate=90/10→10/90), and fractions containing the object product were concentrated under reduced pressure to give the title compound (2.45 g, 57%) as a yellow powder.

$^1$H-NMR (DMSO-d$_6$, 300 MHz) δ 1.43 (9H, s), 5.07 (2H, s), 6.81 (1H, d, J=8.6 Hz), 7.09 (1H, dd, J=2.9, 8.6 Hz), 7.40-7.48 (2H, m), 7.51 (1H, d, J=10.6 Hz), 9.17 (1H, s).

(iv) Production of tert-butyl{5-[(2-amino[1,3]thiazolo[5,4-b]pyridin-5-yl)oxy]-4-chloro-2-fluorophenyl}carbamate Potassium thiocyanate (2.70 g, 27.8 mmol) was dissolved in acetic acid (190 mL), tert-butyl{5-[(5-aminopyridin-2-yl)oxy]-4-chloro-2-fluorophenyl}carbamate (2.40 g, 6.78 mmol) was added, and the mixture was stirred at room temperature for 30 min. To the solution was added dropwise a solution (20 mL) of bromine (1.13 g, 7.07 mmol) in acetic acid, and the mixture was stirred at room temperature for 13 hr. The reaction mixture was filtered through celite, and the filtrate was concentrated under reduced pressure. The residue was dissolved in ethyl acetate (300 mL), washed with saturated aqueous sodium hydrogen carbonate solution (100 mL×2) and saturated brine (50 mL), and dried over anhydrous magnesium sulfate. The dried organic layer was purified by basic silica gel chromatography (ethyl acetate), and the eluted fraction was concentrated under reduced pressure to give the title compound (2.69 g, 97%) as a white powder.

$^1$H-NMR (DMSO-d$_6$, 300 MHz) δ 1.43 (9H, s), 6.95 (1H, d, J=8.6 Hz), 7.54-7.67 (4H, m), 7.73 (1H, d, J=8.6 Hz), 9.27 (1H, s).

(v) Production of tert-butyl[4-chloro-5-({2-[(cyclopropylcarbonyl)amino][1,3]thiazolo[5,4-b]pyridin-5-yl}oxy)-2-fluorophenyl]carbamate To a solution of tert-butyl{5-[(2-amino[1,3]thiazolo[5,4-b]pyridin-5-yl)oxy]-4-chloro-2-fluorophenyl}carbamate (1.30 g, 3.16 mmol) in pyridine (20 mL) was added cyclopropanecarbonyl chloride (345 μL, 3.80 mmol), and the mixture was stirred at room temperature for 4 hr. To the reaction mixture was added aqueous sodium hydrogen carbonate solution (30 mL), and the mixture was extracted with ethyl acetate (50 mL×3). The organic layer was washed successively with water (50 mL) and saturated brine (30 mL), and dried over anhydrous magnesium sulfate, and concentrated under reduced pressure. The residue was dissolved in a mixed solvent of methanol (10 mL)/tetrahydrofuran (10 mL), sodium carbonate (335 mg, 3.16 mmol) was added, and the mixture was stirred at room temperature for 17 hr. To the reaction mixture was added aqueous ammonium chloride solution (30 mL), and the mixture was extracted with ethyl acetate (50 mL×3). The organic layer was washed with saturated brine (20 mL), and dried over anhydrous magnesium sulfate, and concentrated under reduced pressure. The residue was purified by silica gel column chromatography (hexane/ethyl acetate=95/5→50/50) to give the title compound (1.22 g, 81%) as a white powder.

$^1$H-NMR (CDCl$_3$, 300 MHz) δ 0.95-1.07 (2H, m), 1.18-1.28 (2H, m), 1.49 (9H, s), 1.58-1.68 (1H, m), 6.75 (1H, d, J=3.0 Hz), 7.01 (1H, d, J=8.7 Hz), 7.21 (1H, d, J=10.6 Hz), 7.97 (1H, d, J=8.7 Hz), 8.09 (1H, d, J=7.0 Hz), 9.84 (1H, s).

(vi) Production of N-[5-(5-amino-2-chloro-4-fluorophenoxy)[1,3]thiazolo[5,4-b]pyridin-2-yl]cyclopropanecarboxamide A mixture of tert-butyl[4-chloro-5-({2-[(cyclopropylcarbonyl)amino][1,3]thiazolo[5,4-b]pyridin-5-yl}oxy)-2-fluorophenyl]carbamate (1.20 g, 2.51 mmol) and trifluoroacetic acid (10 mL) was stirred at room temperature for 30 min. The reaction mixture was concentrated under reduced pressure, and the residue was dissolved in ethyl acetate (100 mL). The solution was washed successively with saturated aqueous sodium hydrogen carbonate solution (50 mL×2) and saturated brine (10 mL), dried over anhydrous magnesium sulfate, and concentrated under reduced pressure to give the title compound (886 mg, 93%) as a white powder.

$^1$H-NMR (DMSO-d$_6$, 300 MHz) δ 0.81-1.11 (4H, m), 1.87-2.12 (1H, m), 5.49 (2H, s), 6.66 (1H, d, J=8.5 Hz), 7.11 (1H, d, J=8.7 Hz), 7.30 (1H, d, J=11.0 Hz), 8.16 (1H, d, J=8.7 Hz), 12.68 (1H, br s).

(vii) Production of 2-chloro-N-[4-chloro-5-({2-[(cyclopropylcarbonyl)amino][1,3]thiazolo[5,4-b]pyridin-5-yl}oxy)-2-fluorophenyl]-3-(1-cyano-1-methylethyl)benzamide 2-Chloro-3-(1-cyano-1-methylethyl)benzoic acid (71.6 mg, 0.320 mmol) produced in Example C61(v) was dissolved in tetrahydrofuran (2 mL)/N,N-dimethylformamide (40 μL), oxalyl chloride (36 μL, 0.420 mmol) was added, and the mixture was stirred at room temperature for 45 min. The reaction mixture was concentrated under reduced pressure, and the residue was dissolved in N,N-dimethylacetamide (2 mL). N-[5-(5-Amino-2-chloro-4-fluorophenoxy)[1,3]thiazolo[5,4-b]pyridin-2-yl]cyclopropanecarboxamide (79.8 mg, 0.211 mmol) was added, and the mixture was stirred at room temperature for 15 hr. To the reaction mixture was added aqueous sodium hydrogen carbonate solution (5 mL), and the mixture was extracted with ethyl acetate (5 mL×4). The organic layer was washed successively with water (5 mL) and saturated brine (5 mL), dried over anhydrous magnesium sulfate, and concentrated under reduced pressure. The residue was purified by silica gel column chromatography (hexane/ethyl acetate=80/20→10/90), and crystallized from diisopropyl ether/ethyl acetate to give the title compound (63.4 mg, 51%) as white crystals.

$^1$H-NMR (DMSO-$d_6$, 300 MHz) δ 0.88-1.01 (4H, m), 1.84 (6H, s), 1.92-2.06 (1H, m), 7.23 (1H, d, J=8.7 Hz), 7.47-7.56 (1H, m), 7.56-7.62 (1H, m), 7.63-7.69 (1H, m), 7.75 (1H, d, J=10.2 Hz), 7.98 (1H, d, J=7.4 Hz), 8.21 (1H, d, J=8.7 Hz), 10.72 (1H, s), 12.70 (1H, br s).

Example C102

Production of N-[4-chloro-5-({2-[(cyclopropylcarbonyl)amino][1,3]thiazolo[5,4-b]pyridin-5-yl}oxy)-2-fluorophenyl]-3-(trifluoromethoxy)benzamide

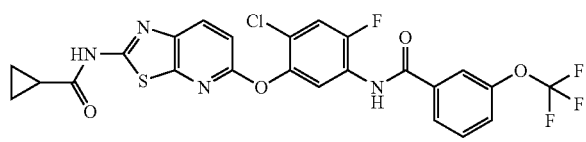 [SMILES: O=C(Nc1cc(Oc2ccc3nc(NC(=O)C4CC4)sc3n2)c(Cl)cc1F)c1cccc(OC(F)(F)F)c1]

In the same manner as in Example C101, the title compound (78.9 mg, 66%) was obtained as white crystals using 3-(trifluoromethoxy)benzoic acid (65.3 mg, 0.317 mmol), tetrahydrofuran (2 mL)/N,N-dimethylformamide (40 μL), oxalyl chloride (36 μL, 0.420 mmol), N-[5-(5-amino-2-chloro-4-fluorophenoxy)[1,3]thiazolo[5,4-b]pyridin-2-yl]cyclopropanecarboxamide (80.4 mg, 0.212 mmol) produced in Example C101(vi) and N,N-dimethylacetamide (2 mL) as starting is materials.

$^1$H-NMR (DMSO-$d_6$, 300 MHz) δ 0.89-1.01 (4H, m), 1.86-2.08 (1H, m), 7.23 (1H, d, J=8.7 Hz), 7.59-7.73 (3H, m), 7.77 (1H, d, J=10.0 Hz), 7.91 (1H, s), 8.00 (1H, dt, J=7.5, 1.4 Hz), 8.20 (1H, d, J=8.7 Hz), 10.47 (1H, br s), 12.71 (1H, br s).

Example C103

Production of N-[4-chloro-5-({2-[(cyclopropylcarbonyl)amino][1,3]thiazolo[5,4-b]pyridin-5-yl}oxy)-2-fluorophenyl]-2-fluoro-3-(trifluoromethyl)benzamide

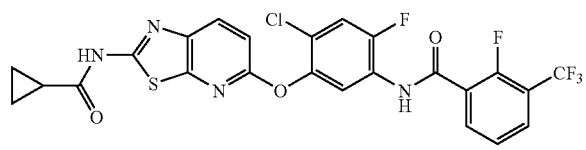 [SMILES: O=C(Nc1cc(Oc2ccc3nc(NC(=O)C4CC4)sc3n2)c(Cl)cc1F)c1cccc(C(F)(F)F)c1F]

In the same manner as in Example C97, the title compound (49.9 mg, 41%) was obtained as white crystals using N-[5-(5-amino-2-chloro-4-fluorophenoxy)[1,3]thiazolo[5,4-b]pyridin-2-yl]cyclopropanecarboxamide (80.1 mg, 0.211 mmol) produced in Example C101(vi), 2-fluoro-3-(trifluoromethyl)benzoic acid (72.9 mg, 0.350 mmol), O-(7-azabenzotriazol-1-yl)-N,N,N',N'-tetramethyluronium hexafluorophosphate (167 mg, 0.439 mmol) and pyridine (2 mL) as starting materials.

$^1$H-NMR (DMSO-$d_6$, 300 MHz) δ 0.86-1.02 (4H, m), 1.91-2.04 (1H, m), 7.23 (1H, d, J=8.8 Hz), 7.53 (1H, t, J=7.8 Hz), 7.78 (1H, d, J=10.2 Hz), 7.89-8.08 (3H, m), 8.20 (1H, d, J=8.8 Hz), 10.69 (1H, br s), 12.70 (1H, br s).

Example C104

Production of N-(4-chloro-2-fluoro-5-{[2-(propanoylamino)[1,3]thiazolo[5,4-b]pyridin-5-yl]oxy}phenyl)-3-(trifluoromethoxy)benzamide

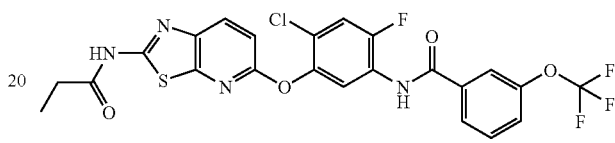

(i) Production of tert-butyl(4-chloro-2-fluoro-5-hydroxyphenyl)carbamate

A mixture of 5-amino-2-chloro-4-fluorophenol (4.05 g, 25.1 mmol), di-tert-butyl bicarbonate (6.3 mL, 27.4 mmol) and tetrahydrofuran (60 mL) was stirred with heating under reflux for 24 hr. Di-tert-butyl bicarbonate (5 mL, 21.8 mmol) was further added, and the mixture was stirred with heating under reflux for 6 hr. The reaction mixture was concentrated under reduced pressure, and the residue was purified by silica gel column chromatography (hexane/ethyl acetate=95/5→50/50) to give the title compound (5.64 g, 86%) as an orange oil.

$^1$H-NMR (CDCl$_3$, 300 MHz) δ 1.52 (9H, s), 5.31 (1H, s), 6.64 (1H, br s), 7.05 (1H, d, J=10.4 Hz), 7.86 (1H, d, J=7.6 Hz).

(ii) Production of tert-butyl{4-chloro-2-fluoro-5-[(5-nitropyridin-2-yl)oxy]phenyl}carbamate A mixture of tert-butyl(4-chloro-2-fluoro-5-hydroxyphenyl)carbamate (6.70 g, 25.6 mmol), 2-chloro-5-nitropyridine (4.06 g, 25.6 mmol), potassium carbonate (3.89 g, 28.1 mmol) and N,N-dimethylformamide (70 mL) was stirred at room temperature for 30 min. To the reaction mixture was added aqueous ammonium chloride solution (100 mL), and the mixture was extracted with ethyl acetate (150 mL×3). The organic layers were combined, washed successively with water (100 mL) and saturated brine (50 mL), dried over anhydrous magnesium sulfate, and concentrated under reduced pressure to give the title compound (4.52 g, 46%) as a white powder.

$^1$H-NMR (CDCl$_3$, 300 MHz) δ 1.50 (9H, s), 6.77 (1H, br s), 7.11 (1H, d, J=9.1 Hz), 7.23 (1H, d, J=10.4 Hz), 8.13 (1H, d, J=7.6 Hz), 8.50 (1H, dd, J=2.8, 9.1 Hz), 9.00 (1H, d, J=2.8 Hz).

(iii) Production of tert-butyl{5-[(5-aminopyridin-2-yl)oxy]-4-chloro-2-fluorophenyl}carbamate A mixture of tert-butyl{4-chloro-2-fluoro-5-[(5-nitropyridin-2-yl)oxy]phenyl}carbamate (4.66 g, 12.1 mmol), reduced iron (61.2 mmol), calcium chloride (680 mg, 6.13 mmol) and ethanol (90 mL)/water (10 mL)/1-methyl-2-pyrrolidone (40 mL) was stirred with heating under reflux for 5 hr. Reduced iron (5.00 g, 89.5 mmol) and calcium chloride (700 mg, 6.31 mmol) were further added, and the mixture was stirred with heating under reflux for 16 hr. The reaction mixture was filtered through celite, and the filtrate was concentrated under reduced pressure. The residue was diluted with ethyl acetate (300 mL), and washed with water (100 mL×2) and saturated brine (50 mL). The obtained organic layer was dried over anhydrous magnesium sulfate, and concentrated under reduced pressure. The residue was purified by basic silica gel column chromatography (hexane/ethyl acetate=90/10→10/90) to give the title compound (2.45 g, 57%) as a yellow powder.

$^1$H-NMR (DMSO-$d_6$, 300 MHz) δ 1.43 (9H, s), 5.07 (2H, s), 6.81 (1H, d, J=8.6 Hz), 7.09 (1H, dd, J=2.9, 8.6 Hz), 7.40-7.48 (2H, m), 7.51 (1H, d, J=10.6 Hz), 9.17 (1H, s).

(iv) Production of tert-butyl{5-[(2-amino[1,3]thiazolo[5,4-b]pyridin-5-yl)oxy]-4-chloro-2-fluorophenyl}carbamate Potassium thiocyanate (2.70 g, 27.8 mmol) was dissolved in acetic acid (190 mL), tert-butyl{5-[(5-aminopyridin-2-yl)oxy]-4-chloro-2-fluorophenyl}carbamate (2.40 g, 6.78 mmol) was added, and the mixture was stirred at room temperature for 30 min. To the solution was added dropwise a solution (20 mL) of bromine (1.13 g, 7.07 mmol) in acetic acid, and the mixture was stirred at room temperature for 13 hr. The reaction mixture was filtered through celite, and the filtrate was concentrated under reduced pressure. The residue was dissolved in ethyl acetate (300 mL), and the solution was washed with saturated aqueous sodium hydrogen carbonate solution (100 mL×2) and saturated brine (50 mL), and dried over anhydrous magnesium sulfate. The dried organic layer was purified by basic silica gel chromatography (15 g, ethyl acetate), and the eluted fraction was concentrated under reduced pressure to give the title compound (2.69 g, 97%) as a white powder.

$^1$H-NMR (DMSO-$d_6$, 300 MHz) δ 1.43 (9H, s), 6.95 (1H, d, J=8.6 Hz), 7.54-7.67 (4H, m), 7.73 (1H, d, J=8.6 Hz), 9.27 (1H, s).

(v) Production of tert-butyl(4-chloro-2-fluoro-5-{[2-(propanoylamino)[1,3]thiazolo[5,4-b]pyridin-5-yl]oxy}phenyl)carbamate To a solution of tert-butyl{5-[(2-amino[1,3]thiazolo[5,4-b]pyridin-5-yl)oxy]-4-chloro-2-fluorophenyl}carbamate (1.30 g, 3.16 mmol) in pyridine (20 mL) was added propionyl chloride (330 µL, 3.80 mmol), and the mixture was stirred at room temperature for 4.5 hr. To the reaction mixture was added aqueous sodium hydrogen carbonate solution (30 mL), and the mixture was extracted with ethyl acetate (50 mL×3). The organic layer was washed successively with water (20 mL) and saturated brine (20 mL), dried over anhydrous magnesium sulfate, and concentrated under reduced pressure. The residue was purified by silica gel column chromatography (hexane/ethyl acetate=90/10→34/66) to give the title compound (1.30 g, 88%) as white crystals.

$^1$H-NMR (CDCl$_3$, 300 MHz) δ 1.28 (3H, t, J=7.6 Hz), 1.49 (9H, s), 2.52 (2H, q, J=7.6 Hz), 6.77 (1H, d, J=3.0 Hz), 7.02 (1H, d, J=8.7 Hz), 7.22 (1H, d, J=10.6 Hz), 7.96 (1H, d, J=8.7 Hz), 8.09 (1H, d, J=7.4 Hz), 9.15 (1H, s).

(vi) Production of N-[5-(5-amino-2-chloro-4-fluorophenoxy)[1,3]thiazolo[5,4-b]pyridin-2-yl]propanamide A mixture of tert-butyl(4-chloro-2-fluoro-5-{[2-(propanoylamino)[1,3]thiazolo[5,4-b]pyridin-5-yl]oxy}phenyl)carbamate (1.26 g, 2.70 mmol) and trifluoroacetic acid (10 mL) was stirred at room temperature for 2 hr. The reaction mixture was concentrated under reduced pressure, and the residue was dissolved in ethyl acetate (100 mL). The solution was washed with aqueous sodium hydrogen carbonate solution (30 mL×2) and saturated brine (10 mL), dried over anhydrous magnesium sulfate, and concentrated under reduced pressure. The residue was purified by silica gel column chromatography (hexane/ethyl acetate=67/33→0/100) to give the title compound (787 mg, 79%) as white crystals.

$^1$H-NMR (DMSO-$d_6$, 300 MHz) δ 1.10 (3H, t, J=7.6 Hz), 2.31-2.67 (2H, m), 5.50 (2H, s), 6.66 (1H, d, J=8.3 Hz), 7.10 (1H, d, J=8.7 Hz), 7.31 (1H, d, J=10.8 Hz), 8.15 (1H, d, J=8.7 Hz), 12.35 (1H, s).

(vii) Production of N-(4-chloro-2-fluoro-5-{[2-(propanoylamino)[1,3]thiazolo[5,4-b]pyridin-5-yl]oxy}phenyl)-3-(trifluoromethoxy)benzamide In the same manner as in Example C101, the title compound (87.8 mg, 72%) was obtained as white crystals using 3-(trifluoromethoxy)benzoic acid (89.3 mg, 0.433 mmol), tetrahydrofuran (2 mL)/N,N-dimethylformamide (40 µL), oxalyl chloride (47 µL, 0.548 mmol), N-[5-(5-amino-2-chloro-4-fluorophenoxy)[1,3]thiazolo[5,4-b]pyridin-2-yl]propanamide (80.7 mg, 0.220 mmol) and N,N-dimethylacetamide (2 mL) as starting materials.

$^1$H-NMR (DMSO-$d_6$, 300 MHz) δ 1.09 (3H, t, J=7.5 Hz), 2.43-2.56 (2H, m), 7.23 (1H, d, J=8.7 Hz), 7.57-7.74 (3H, m), 7.77 (1H, d, J=9.8 Hz), 7.91 (1H, s), 8.01 (1H, dt, J=7.5, 1.4 Hz), 8.19 (1H, d, J=8.7 Hz), 10.47 (1H, br s), 12.36 (1H, br s).

Example C105

Production of 2-chloro-N-(4-chloro-2-fluoro-5-{[2-(propanoylamino)[1,3]thiazolo[5,4-b]pyridin-5-yl]oxy}phenyl)-3-(1-cyano-1-methylethyl)benzamide

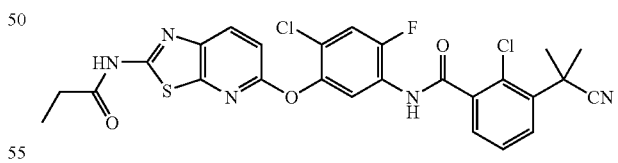

In the same manner as in Example C101, the title compound (95.0 mg, 76%) was obtained as white crystals using 2-chloro-3-(1-cyano-1-methylethyl)benzoic acid (99.9 mg, 0.447 mmol) produced in Example C61(v), tetrahydrofuran (2 mL)/N,N-dimethylformamide (40 µL), oxalyl chloride (47 µL, 0.548 mmol), N-[5-(5-amino-2-chloro-4-fluorophenoxy)[1,3]thiazolo[5,4-b]pyridin-2-yl]propanamide (80.0 mg, 0.218 mmol) produced in Example C104(vi) and N,N-dimethylacetamide (2 mL) as starting materials.

$^1$H-NMR (DMSO-$d_6$, 300 MHz) δ 1.10 (3H, t, J=7.6 Hz), 1.84 (6H, s), 2.42-2.57 (2H, m), 7.23 (1H, d, J=8.7 Hz), 7.46-7.70 (3H, m), 7.75 (1H, d, J=10.2 Hz), 7.98 (1H, d, J=7.2 Hz), 8.20 (1H, d, J=8.7 Hz), 10.72 (1H, s), 12.36 (1H, br s).

Example C106

Production of 2-chloro-N-(4-chloro-2-fluoro-5-{[2-(propanoylamino)[1,3]thiazolo[5,4-b]pyridin-5-yl]oxy}phenyl)-3-(1-cyanocyclopropyl)benzamide

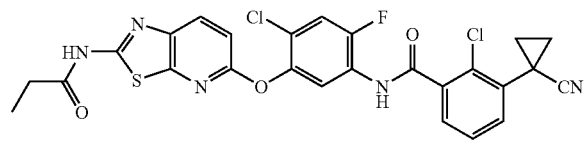 [SMILES: CCC(=O)Nc1nc2ccc(Oc3cc(NC(=O)c4cccc(C5(C#N)CC5)c4Cl)c(F)cc3Cl)nc2s1]

In the same manner as in Example C101, the title compound (85.9 mg, 69%) was obtained as white crystals using 2-chloro-3-(1-cyanocyclopropyl)benzoic acid (99.0 mg, 0.447 mmol) produced in Example C62(ii), tetrahydrofuran (2 mL)/N,N-dimethylformamide (40 μL), oxalyl chloride (47 μL, 0.548 mmol), N-[5-(5-amino-2-chloro-4-fluorophenoxy)[1,3]thiazolo[5,4-b]pyridin-2-yl]propanamide (79.6 mg, 0.217 mmol) produced in Example C104(vi) and N,N-dimethylacetamide (2 mL) as starting materials.

$^1$H-NMR (DMSO-$d_6$, 300 MHz) δ 1.10 (3H, t, J=7.5 Hz), 1.39-1.51 (2H, m), 1.75-1.85 (2H, m), 2.43-2.57 (2H, m), 7.23 (1H, d, J=8.7 Hz), 7.47 (1H, t, J=7.6 Hz), 7.61 (1H, dd, J=1.6, 7.6 Hz), 7.65 (1H, dd, J=1.6, 7.6 Hz), 7.76 (1H, d, J=10.0 Hz), 7.99 (1H, d, J=7.2 Hz), 8.20 (1H, d, J=8.7 Hz), 10.69 (1H, s), 12.36 (1H, br s).

Example C107

Production of N-(4-chloro-2-fluoro-5-{[2-(propanoylamino)[1,3]thiazolo[5,4-b]pyridin-5-yl]oxy}phenyl)-3-(1,1-dimethylprop-2-yn-1-yl)benzamide

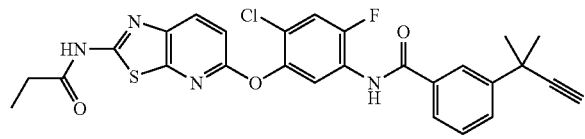 [SMILES: C#CC(C)(C)c1cccc(C(=O)Nc2cc(Oc3ccc4nc(NC(=O)CC)sc4n3)c(Cl)cc2F)c1]

In the same manner as in Example C101, the title compound (54.7 mg, 46%) was obtained as white crystals using 3-(1,1-dimethylprop-2-yn-1-yl)benzoic acid (67.4 mg, 0.358 mmol) produced in Example C67(iii), tetrahydrofuran (1 mL)/N,N-dimethylformamide (10 μL), oxalyl chloride (38 μL, 0.443 mmol), N-[5-(5-amino-2-chloro-4-fluorophenoxy)[1,3]thiazolo[5,4-b]pyridin-2-yl]propanamide (80.7 mg, 0.220 mmol) produced in Example C104(vi) and N,N-dimethylacetamide (2 mL) as starting materials.

$^1$H-NMR (DMSO-$d_6$, 300 MHz) δ 1.09 (3H, t, J=7.5 Hz), 1.58 (6H, s), 2.42-2.56 (2H, m), 3.31 (1H, s), 7.22 (1H, d, J=8.7 Hz), 7.51 (1H, t, J=7.8 Hz), 7.68 (1H, d, J=7.2 Hz), 7.76 (1H, d, J=10.0 Hz), 7.78-7.82 (1H, m), 7.82-7.88 (1H, m), 8.11 (1H, t, J=1.7 Hz), 8.19 (1H, d, J=8.7 Hz), 10.31 (1H, s), 12.36 (1H, br s).

Example C108

Production of 2-chloro-N-[4-chloro-5-({2-[(cyclopropylcarbonyl)amino][1,3]thiazolo[5,4-b]pyridin-5-yl}oxy)-2-fluorophenyl]-3-(1-cyanocyclopropyl)benzamide

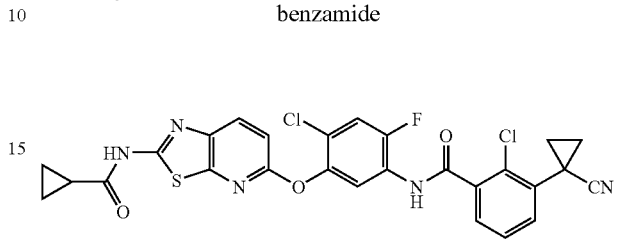

In the same manner as in Example C101, the title compound (39.0 mg, 31%) was obtained as white crystals using 2-chloro-3-(1-cyanocyclopropyl)benzoic acid (92.5 mg, 0.417 mmol) produced in Example C62(ii), tetrahydrofuran (2 mL)/N,N-dimethylformamide (10 μL), oxalyl chloride (45 μL, 0.525 mmol), N-[5-(5-amino-2-chloro-4-fluorophenoxy)[1,3]thiazolo[5,4-b]pyridin-2-yl]propanamide (80.1 mg, 0.211 mmol) produced in Example C104(vi) and N,N-dimethylacetamide (2 mL) as starting materials.

$^1$H-NMR (DMSO-$d_6$, 300 MHz) δ 0.86-1.02 (4H, m), 1.38-1.51 (2H, m), 1.73-1.85 (2H, m), 1.91-2.07 (1H, m), 7.23 (1H, d, J=8.7 Hz), 7.47 (1H, t, J=7.6 Hz), 7.61 (1H, dd, J=1.5, 7.6 Hz), 7.65 (1H, dd, J=1.5, 7.6 Hz), 7.76 (1H, d, J=10.2 Hz), 7.98 (1H, d, J=7.2 Hz), 8.20 (1H, d, J=8.7 Hz), 10.70 (1H, s), 12.71 (1H, br s).

Example C109

Production of N-(5-{[2-(acetylamino)[1,3]thiazolo[5,4-b]pyridin-5-yl]oxy}-2-fluorophenyl)-2-chloro-3-(1-cyanocyclobutyl)benzamide

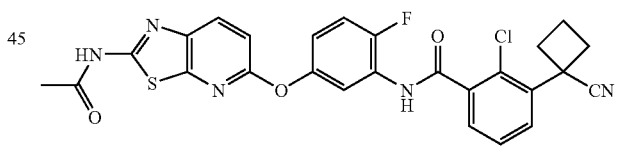

(i) Production of methyl 2-chloro-3-(1-cyanocyclobutyl)benzoate

A solution (15 mL) of methyl 2-chloro-3-(cyanomethyl)benzoate (1.50, 7.16 mmol) produced in Example C61(iii) in dimethylsulfoxide was cooled at which the solution did not solidify, sodium hydride (60%, 869 mg, 21.7 mmol) was slowly added, and the mixture was stirred at room temperature for 30 min. To the suspension was added dropwise 1,3-dibromopropane (1.45 mL, 14.3 mmol), and the mixture was stirred at room temperature for 1.5 hr. To the reaction mixture was slowly added water (50 mL), and the mixture was extracted with ethyl acetate (50 mL×3). The organic layer was washed successively with water (50 mL) and saturated brine (50 mL), dried over anhydrous magnesium sulfate, and concentrated under reduced pressure. The residue was purified by silica gel column chromatography (hexane/ethyl acetate=95/5→50/50) to give the title compound (714 mg, 40%) as a white powder.

$^1$H-NMR (CDCl$_3$, 300 MHz) δ 1.88-2.10 (1H, m), 2.40-2.76 (3H, m), 2.85-3.09 (2H, m), 3.95 (3H, s), 7.28-7.50 (2H, m), 7.70 (1H, dd, J=2.6, 6.8 Hz).

(ii) Production of 2-chloro-3-(1-cyanocyclobutyl)benzoic acid

Methyl 2-chloro-3-(1-cyanocyclobutyl)benzoate (710 mg, 2.84 mmol) was dissolved in a mixed solvent of tetrahydrofuran (9 mL)/methanol (3 mL)/water (3 mL), lithium hydroxide monohydrate (192 mg, 4.56 mmol) was added, and the mixture was stirred at room temperature for 19 hr. The reaction mixture was concentrated under reduced pressure, and 1N hydrochloric acid (5 mL) was added dropwise to the residue. The precipitate was collected by filtration, and washed with water to give the title compound (435 mg, 65%) as a white powder.

$^1$H-NMR (DMSO-d$_6$, 300 MHz) δ 1.83-2.02 (1H, m), 2.20-2.43 (1H, m), 2.59-2.76 (2H, m), 2.77-2.92 (2H, m), 7.49 (1H, t, J=7.6 Hz), 7.58 (1H, dd, J=1.7, 7.6 Hz), 7.70 (1H, dd, J=1.7, 7.6 Hz), 13.59 (1H, br s).

(iii) Production of N-(5-{[2-(acetylamino)[1,3]thiazolo[5,4-b]pyridin-5-yl]oxy}-2-fluorophenyl)-2-chloro-3-(1-cyanocyclobutyl)benzamide In the same manner as in Example C101, the title compound (67.3 mg, 40%) was obtained as white crystals using 2-chloro-3-(1-cyanocyclobutyl)benzoic acid (126 mg, 0.536 mmol), tetrahydrofuran (1 mL)/N,N-dimethylformamide (10 μL), oxalyl chloride (67 μL, 0.782 mmol), N-[5-(3-amino-4-fluorophenoxy)[1,3]thiazolo[5,4-b]pyridin-2-yl]acetamide (101 mg, 0.316 mmol) produced in Example C64(ii) and N,N-dimethylacetamide (2 mL) as starting materials.

$^1$H-NMR (DMSO-d$_6$, 300 MHz) δ 1.84-2.03 (1H, m), 2.20 (3H, s), 2.24-2.40 (1H, m), 2.60-2.78 (2H, m), 2.79-2.94 (2H, m), 7.04-7.12 (1H, m), 7.16 (1H, d, J=8.7 Hz), 7.38 (1H, dd, J=10.2, 9.1 Hz), 7.46-7.64 (3H, m), 7.76 (1H, dd, J=6.5, 2.9 Hz), 8.19 (1H, d, J=8.7 Hz), 10.60 (1H, s), 12.41 (1H, s).

Example C110

Production of N-(5-{[2-(acetylamino)[1,3]thiazolo[5,4-b]pyridin-5-yl]oxy}-2,4-difluorophenyl)-2-chloro-3-(1-cyanocyclobutyl)benzamide In the same manner as in Example C101, the title compound (43.3 mg, 26%) was obtained as white crystals using 2-chloro-3-(1-cyanocyclobutyl)benzoic acid (119 mg, 0.505 mmol), tetrahydrofuran (1 mL)/N,N-dimethylformamide (10 μL), oxalyl chloride (56 μL, 0.653 mmol), N-[5-(5-amino-2,4-difluorophenoxy)[1,3]thiazolo[5,4-b]pyridin-2-yl]acetamide (102 mg, 0.303 mmol) produced in Example C76(vi) and N,N-dimethylacetamide (2 mL) as starting materials.

$^1$H-NMR (DMSO-d$_6$, 300 MHz) δ 1.85-2.03 (1H, m), 2.19 (3H, s), 2.24-2.45 (1H, m), 2.60-2.79 (2H, m), 2.78-2.96 (2H, m), 7.26 (1H, d, J=8.7 Hz), 7.45-7.75 (4H, m), 7.88 (1H, t, J=8.1 Hz), 8.21 (1H, d, J=8.7 Hz), 10.60 (1H, s), 12.42 (1H, br s).

Example C111

Production of 2-chloro-3-(1-cyano-1-methylethyl)-N-[3-({2-[(cyclopropylcarbonyl)amino][1,3]thiazolo[5,4-b]pyridin-5-yl}oxy)phenyl]benzamide

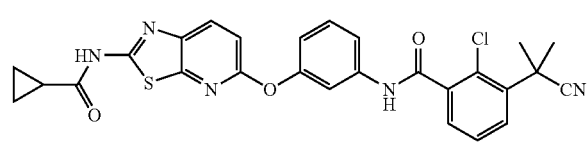 [SMILES: CC(C)(C#N)c1cccc(C(=O)Nc2cccc(Oc3ccc4nc(NC(=O)C5CC5)sc4n3)c2)c1Cl]

(i) Production of tert-butyl(3-hydroxyphenyl)carbamate

To a solution of 3-aminophenol (25.5 g, 234 mmol) in tetrahydrofuran (300 mL) was added di-tert-butyl-dicarbonate (59.8 g, 274 mmol), and the mixture was stirred at 60° C. for 14 hr. The reaction mixture was concentrated under reduced pressure, 1N hydrochloric acid (150 mL) was added to the obtained residue, and the mixture was extracted with ethyl acetate (250 mL). The organic layer was washed with water (150 mL), aqueous ammonium chloride solution (150 mL) and saturated brine (150 mL), and dried over anhydrous magnesium sulfate. The insoluble material was filtered off, and the filtrate was concentrated under reduced pressure. The obtained residue was triturated with diisopropyl ether and hexane to give the title compound (36.0 g, 73%) as a colorless powder.

$^1$H-NMR (CDCl$_3$, 300 MHz) δ 1.53 (9H, s), 5.79 (1H, br s), 6.52-6.57 (1H, m), 6.72-6.78 (1H, m), 7.09-7.17 (2H, m).

(ii) Production of tert-butyl{3-[(5-aminopyridin-2-yl)oxy]phenyl}carbamate

To a suspension of tert-butyl(3-hydroxyphenyl)carbamate (3.02 g, 14.4 mmol) and potassium carbonate (2.99 g, 21.7 mmol) in N,N-dimethylformamide (35 mL) was added 2-chloro-5-nitropyridine (2.52 g, 15.9 mmol), and the mixture was stirred at 70° C. for 2 hr. To the reaction mixture was added water (100 mL), and the mixture was extracted with ethyl acetate (100 mL, 50 mL). The organic layer was washed with saturated brine (20 mL), and dried over anhydrous magnesium sulfate. The insoluble material was filtered off, and the filtrate was concentrated under reduced pressure to give tert-butyl{3-[(5-nitropyridin-2-yl)oxy]phenyl}carbamate as a yellow solid. The obtained compound was used for the next reaction without further purification operation.

To a solution of the above-mentioned crude product tert-butyl{3-[(5-nitropyridin-2-yl)oxy]phenyl}carbamate in ethanol (80 mL)/tetrahydrofuran (20 mL) was added 10% palladium-carbon (1.54 g), and the mixture was stirred at room temperature for 7 hr under a hydrogen atmosphere (1.0 pressure). The insoluble material was filtered off, and the filtrate was concentrated under reduced pressure. The obtained residue was recrystallized from methanol to give the title compound (3.35 g, 77%) as brown crystals.

¹H-NMR (DMSO-d₆, 300 MHz) δ 1.45 (9H, s), 5.11 (2H, br s), 6.52 (1H, dd, J=1.5, 7.4 Hz), 6.74 (1H, d, J=8.7 Hz), 7.07 (1H, dd, J=2.2, 8.7 Hz), 7.10-7.23 (3H, m), 7.55 (1H, d, J=2.2 Hz), 9.36 (1H, br s).

(iii) Production of tert-butyl{3-[(2-amino[1,3]thiazolo[5,4-b]pyridin-5-yl)oxy]phenyl}carbamate Potassium thiocyanate (4.30 g, 44.2 mmol) was suspended in acetic acid (50 mL), and the suspension was stirred at room temperature for 30 min. To the obtained solution was added tert-butyl{3-[(5-aminopyridin-2-yl)oxy]phenyl}carbamate (3.33 g, 11.1 mmol), and the mixture was further stirred at room temperature for 10 min. To the obtained solution was added dropwise a solution of bromine (1.85 g, 11.6 mmol) in acetic acid (10 mL) for 10 min or more. After the completion of the dropwise addition, the mixture was stirred at room temperature for 1.5 hr. The yielded yellow solid was filtered off, and washed with acetic acid. The filtrate and the washing solution were combined, and concentrated under reduced pressure. The residue was suspended in ethyl acetate (200 mL), and the suspension was washed with saturated aqueous sodium hydrogen carbonate solution (50 mL) and saturated brine (30 mL), and dried over anhydrous sodium sulfate. The insoluble material was filtered off, and the filtrate was concentrated under reduced pressure. The obtained residue was washed with ethyl acetate to give the title compound (3.51 g, 88%) as a pale-yellow solid.

¹H-NMR (DMSO-d₆, 300 MHz) δ 1.45 (9H, s), 6.62-6.70 (1H, m), 6.88 (1H, d, J=8.9 Hz), 7.18-7.29 (3H, m), 7.62 (2H, br s), 7.71 (1H, d, J=8.9 Hz), 9.43 (1H, br s).

(iv) Production of tert-butyl[3-({2-[(cyclopropylcarbonyl)amino][1,3]thiazolo[5,4-b]pyridin-5-yl}oxy)phenyl]carbamate To a solution of tert-butyl{3-[(2-amino[1,3]thiazolo[5,4-b]pyridin-5-yl)oxy]phenyl}carbamate (1.00 g, 2.79 mmol) in pyridine (30 mL) was added cyclopropanecarbonyl chloride (327 μL, 3.63 mmol), and the mixture was stirred at room temperature for 1 hr. To the reaction mixture was added water (100 mL), and the mixture was extracted with ethyl acetate (100 mL, 30 mL). The combined organic layer was washed with saturated brine (20 mL), and dried over anhydrous sodium sulfate. The insoluble material was filtered off, and the filtrate was concentrated under reduced pressure. The obtained residue was recrystallized from tetrahydrofuran and hexane to give the title compound (1.02 g, 86%) as pale-yellow crystals.

¹H-NMR (DMSO-d₆, 300 MHz) δ0.86-1.03 (4H, m), 1.45 (9H, s), 1.92-2.05 (1H, m), 6.68-6.79 (1H, m), 7.08 (1H, d, J=8.7 Hz), 7.20-7.38 (3H, m), 8.15 (1H, d, J=8.7 Hz), 9.48 (1H, br s), 12.66 (1H, br s).

(v) Production of N-[5-(3-aminophenoxy)[1,3]thiazolo[5,4-b]pyridin-2-yl]cyclopropanecarboxamide A solution of tert-butyl[3-({2-[(cyclopropylcarbonyl)amino][1,3]thiazolo[5,4-b]pyridin-5-yl}oxy)phenyl]carbamate (900 mg, 2.11 mmol) and anisole (1 mL) in trifluoroacetic acid (10 mL) was stirred at 0° C. for 1 hr. The reaction mixture was concentrated under reduced pressure, saturated aqueous sodium hydrogen carbonate solution (50 mL) was added to the residue, and the mixture was extracted with tetrahydrofuran-ethyl acetate mixture (1:1, 50 mL, 15 mL). The combined organic layer was washed with saturated brine (5 mL), and dried over anhydrous sodium sulfate. The insoluble material was filtered off, and the filtrate was concentrated under reduced pressure. The obtained residue was washed with a tetrahydrofuran-ethyl acetate mixture to give the title compound (542 mg, 79%) as a pale-yellow solid.

¹H-NMR (DMSO-d₆, 300 MHz) δ 0.87-1.03 (4H, m), 1.92-2.05 (1H, m), 5.25 (2H, br s), 6.23 (1H, ddd, J=7.9, 2.4, 0.8 Hz), 6.28 (1H, t, J=2.4 Hz), 6.40 (1H, ddd, J=7.9, 2.4, 0.8 Hz), 6.97-7.08 (2H, m), 8.11 (1H, d, J=8.7 Hz), 12.67 (1H, br s).

(vi) Production of 2-chloro-3-(1-cyano-1-methylethyl)-N-[3-({2-[(cyclopropylcarbonyl)amino][1,3]thiazolo[5,4-b]pyridin-5-yl}oxy)phenyl]benzamide A solution of N-[5-(3-aminophenoxy)[1,3]thiazolo[5,4-b]pyridin-2-yl]cyclopropanecarboxamide (120 mg, 3.68 μmol), 2-chloro-3-(1-cyano-1-methylethyl)benzoic acid produced in Example C61(v) (87 mg, 386 μmol) and O-(7-azabenzotriazol-1-yl)-N,N,N',N'-tetramethyluronium hexafluorophosphate (168 mg, 442 μmol) in pyridine (3 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=40/60→20/80), and fractions containing the object product were concentrated under reduced pressure. The obtained residue was recrystallized from tetrahydrofuran and ethanol to give the title compound (60 mg, 31%) as colorless crystals.

¹H-NMR (DMSO-d₆, 300 MHz) δ 0.85-0.98 (4H, m), 1.84 (6H, s), 1.92-2.03 (1H, m), 6.92 (1H, ddd, J=1.0, 2.4, 8.1 Hz), 7.13 (1H, d, J=8.7 Hz), 7.41 (1H, t, J=8.1 Hz), 7.49-7.63 (4H, m), 7.66 (1H, dd, J=7.8, 1.8 Hz), 8.15 (1H, d, J=8.7 Hz), 10.71 (1H, br s), 12.69 (1H, br s).

Example C112

Production of 2-chloro-3-(1-cyanocyclopropyl)-N-[3-({2-[(cyclopropylcarbonyl)amino][1,3]thiazolo[5,4-b]pyridin-5-yl}oxy)phenyl]benzamide

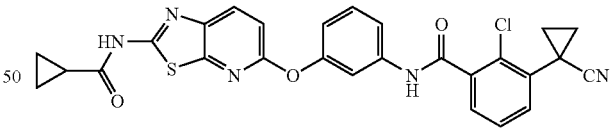

A solution of N-[5-(3-aminophenoxy)[1,3]thiazolo[5,4-b]pyridin-2-yl]cyclopropanecarboxamide (120 mg, 3.68 μmol) produced in Example C111(v), 2-chloro-3-(1-cyclopropyl)benzoic acid (90 mg, 405 μmol) produced in Example C62(ii) and O-(7-azabenzotriazol-1-yl)-N,N,N',N'-tetramethyluronium hexafluorophosphate (154 mg, 405 μmol) in pyridine (3 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=30/70→10/90), and fractions containing the object product were concentrated under reduced pressure. The obtained residue was recrystallized from tetrahydrofuran and ethanol to give the title compound (169 mg, 87%) as colorless crystals.

$^1$H-NMR (DMSO-d$_6$, 300 MHz) δ 0.88-0.99 (4H, m), 1.38-1.49 (2H, m), 1.78-1.84 (2H, m), 1.93-2.04 (1H, m), 6.93 (1H, ddd, J=0.9, 2.3, 8.1 Hz), 7.15 (1H, d, J=8.7 Hz), 7.41 (1H, t, J=8.1 Hz), 7.48 (1H, t, J=7.6 Hz), 7.51-7.56 (1H, m), 7.58-7.63 (2H, m), 7.66 (1H, dd, J=7.6, 1.7 Hz), 8.17 (1H, d, J=8.7 Hz), 10.70 (1H, br s), 12.70 (1H, br s).

Example C113

Production of N-[3-({2-[(cyclopropylcarbonyl)amino][1,3]thiazolo[5,4-b]pyridin-5-yl}oxy)phenyl]-3-(1,1-dimethylprop-2-yn-1-yl)benzamide

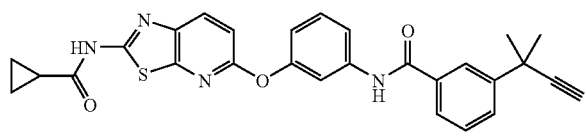 [SMILES: C#CC(C)(C)c1cccc(C(=O)Nc2cccc(Oc3ccc4nc(NC(=O)C5CC5)sc4n3)c2)c1]

In the same manner as in Example C101, the title compound (65.4 mg, 49%) was obtained as white crystals using 3-(1,1-dimethylprop-2-yn-1-yl)benzoic acid (81.4 mg, 0.432 mmol) produced in Example C67(iii), tetrahydrofuran (1 mL)/N,N-dimethylformamide (10 μL), oxalyl chloride (46 μL, 0.537 mmol), N-[5-(3-aminophenoxy)[1,3]thiazolo[5,4-b]pyridin-2-yl]cyclopropanecarboxamide (79.3 mg, 0.243 mmol) produced in Example C111(v) and N,N-dimethylacetamide (2 mL) as starting materials.

$^1$H-NMR (DMSO-d$_6$, 300 MHz) δ 0.87-1.01 (4H, m), 1.58 (6H, s), 1.92-2.06 (1H, m), 3.31 (1H, s), 6.92 (1H, ddd, J=1.0, 2.2, 8.4 Hz), 7.15 (1H, d, J=8.7 Hz), 7.41 (1H, t, J=8.4 Hz), 7.50 (1H, t, J=7.8 Hz), 7.59-7.69 (2H, m), 7.77 (1H, ddd, J=1.1, 1.8, 7.8 Hz), 7.80-7.86 (1H, m), 8.06 (1H, t, J=1.8 Hz), 8.18 (1H, d, J=8.7 Hz), 10.36 (1H, s), 12.70 (1H, br s).

Example C114

Production of N-(5-{[2-(acetylamino)[1,3]thiazolo[5,4-b]pyridin-5-yl]oxy)-2-chlorophenyl)-2-chloro-3-(1-cyano-1-methylethyl)benzamide

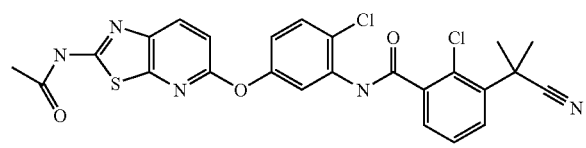 [SMILES: CC(=O)Nc1nc2ccc(Oc3ccc(Cl)c(NC(=O)c4cccc(C(C)(C)C#N)c4Cl)c3)nc2s1]

(i) Production of 2-chloro-5-[(5-nitropyridin-2-yl)oxy]aniline

To a solution of 2-chloro-5-nitropyridine (4.76 g, 30 mmol) and 3-amino-4-chlorophenol (4.31 g, 30 mmol) in N,N-dimethylformamide (15 mL) was added potassium carbonate (4.15 g, 30 mmol), and the mixture was stirred at room temperature for 16 hr. To the reaction mixture was added ethyl acetate (80 mL), and the mixture was washed successively with water (50 mL) and saturated brine (50 mL). The organic layer was dried over anhydrous magnesium sulfate, and concentrated under reduced pressure. The residual solid was recrystallized from ethyl acetate (15 mL)/n-hexane (15 mL), and the precipitated crystals were collected by filtration, washed with diisopropyl ether (20 mL), and dried under reduced pressure to give the title compound (6.74 g, 85%) as brown crystals.

$^1$H-NMR (CDCl$_3$, 300 MHz) δ 4.19 (2H, br s), 6.48 (1H, dd, J=2.7, 8.6 Hz), 6.58 (1H, d, J=2.7 Hz), 7.01 (1H, d, J=9.0 Hz), 7.29 (1H, d, J=8.6 Hz), 8.47 (1H, dd, J=2.7, 9.0 Hz), 9.05 (1H, d, J=2.7 Hz).

(ii) Production of N-{2-chloro-5-[(5-nitropyridin-2-yl)oxy]phenyl}-2,2,2-trifluoroacetamide 2-Chloro-5-[(5-nitropyridin-2-yl)oxy]aniline (6.5 g, 24.5 mmol) was dissolved in tetrahydrofuran (5.0 mL), trifluoroacetic acid anhydride (3.73 mL, 26.9 mmol) was added, and the mixture was stirred at room temperature for 1 hr. The reaction mixture was concentrated under reduced pressure, the residue was dissolved in ethyl acetate (80 mL), and the solution was washed with aqueous sodium hydrogen carbonate solution (50 mL). The organic layer was dried over anhydrous magnesium sulfate, and concentrated under reduced pressure. The residual solid was collected by filtration using diisopropyl ether (30 mL), and dried to give the title compound (7.73 g, 87%) as a white solid.

$^1$H-NMR (CDCl$_3$, 300 MHz) δ 6.95-7.19 (2H, m), 7.52 (1H, dd, J=1.5, 9.0 Hz), 8.20-8.30 (1H, m), 8.40-8.60 (2H, m), 9.00-9.10 (1H, m).

(iii) Production of N-{5-[(5-aminopyridin-2-yl)oxy]-2-chlorophenyl}-2,2,2-trifluoroacetamide N-{2-Chloro-5-[(5-nitropyridin-2-yl)oxy]phenyl}-2,2,2-trifluoroacetamide (13 g, 35.9 mmol) was dissolved in acetic acid (200 mL), reduced iron (10 g, 179 mmol) was added, and the mixture was stirred at 60° C. for 3 hr. After cooling to room temperature, the reaction mixture was concentrated under reduced pressure. The concentrated solution was diluted with ethyl acetate (150 mL), aqueous sodium hydrogen carbonate solution (200 mL) was slowly added, and the mixture was filtered through celite. The organic layer was collected, and dried over anhydrous magnesium sulfate, and concentrated under reduced pressure. The residual oil was dissolved in toluene, and the solution was purified by silica gel column chromatography (ethyl acetate/hexane=20/80→20/80) to give the title compound (10.9 g, 91%) as a brown oil.

$^1$H-NMR (CDCl$_3$, 300 MHz) δ 3.57 (2H, br s), 6.83 (1H, d, J=8.7 Hz), 6.93 (1H, dd, J=2.8, 8.7 Hz), 7.11 (1H, dd, J=2.8, 8.7 Hz), 7.39 (1H, d, J=8.7 Hz), 7.69 (1H, d, J=3.0 Hz), 8.11 (1H, d, J=3.0 Hz), 8.41 (1H, br s).

(iv) Production of N-{5-[(2-amino[1,3]thiazolo[5,4-b]pyridin-5-yl)oxy]-2-chlorophenyl}-2,2,2-trifluoroacetamide N-{5-[(5-Aminopyridin-2-yl)oxy]-2-chlorophenyl}-2,2,2-trifluoroacetamide (12 g, 36.2 mmol) and potassium thiocyanate (14.1 g, 145 mmol) were suspended in acetic acid (145 mL), bromine (8.67 g, 54.3 mmol) was added dropwise under ice-cooling, and the reaction mixture was stirred at room temperature for 16 hr. The reaction mixture was filtered through celite, and the filtrate was concentrated under reduced pressure. The residual oil was dissolved in ethyl acetate (100 mL), aqueous sodium hydrogen carbonate solution (150 mL) was slowly added, and the mixture was partitioned. The organic layer was dried over anhydrous magnesium sulfate, and concentrated under reduced pressure. The residual solid was collected by filtration using diisopropyl ether (100 mL), and dried to give the title compound (10.1 g, 72%) as a pale-yellow solid.

$^1$H-NMR (DMSO-$d_6$, 300 MHz) δ 6.98 (1H, d, J=8.5 Hz), 7.16 (1H, dd, J=2.8, 8.8 Hz), 7.27 (1H, d, J=2.8 Hz), 7.61 (1H, d, J=8.8 Hz), 7.66 (2H, br s), 7.75 (1H, d, J=8.5 Hz), 11.30 (1H, br s).

(v) Production of N-(5-{[2-(acetylamino)[1,3]thiazolo[5,4-b]pyridin-5-yl]oxy}-2-chlorophenyl)-2,2,2-trifluoroacetamide N-{5-[(2-Amino[1,3]thiazolo[5,4-b]pyridin-5-yl)oxy]-2-chlorophenyl}-2,2,2-trifluoroacetamide (1.8 g, 4.63 mmol) and N,N-dimethylpyridine-4-amine (566 mg, 4.63 mmol) were dissolved in pyridine (9.25 mL), acetyl chloride (0.658 mL, 9.25 mmol) was added dropwise under ice-cooling, and the mixture was stirred at room temperature for 16 hr. The reaction mixture was diluted with ethyl acetate (80 mL)/water (50 mL), and the organic layer was collected, and washed with saturated brine (50 mL). The mixture was dried over anhydrous magnesium sulfate, and concentrated under reduced pressure. The residual solid was crystallized from toluene/diisopropyl ether (1:3), collected by filtration, and dried to give the title compound (1.69 g, 85%) as a pale-yellow solid.

$^1$H-NMR (DMSO-$d_6$, 300 MHz) δ 2.20 (3H, s), 7.20 (1H, d, J=8.7 Hz), 7.26 (1H, dd, J=2.8, 8.9 Hz), 7.38 (1H, d, J=2.8 Hz), 7.66 (1H, d, J=8.9 Hz), 8.20 (1H, d, J=8.7 Hz), 11.30 (1H, br s), 12.42 (1H, br s).

(vi) Production of N-[5-(3-amino-4-chlorophenoxy)[1,3]thiazolo[5,4-b]pyridin-2-yl]acetamide Sodium borohydride (2.45 g, 64.8 mmol) was suspended in ethanol (43 mL), and methanol (29 mL) was slowly added. To the obtained reaction mixture was added N-(5-{[2-(acetylamino)[1,3]thiazolo[5,4-b]pyridin-5-yl]oxy}-2-chlorophenyl)-2,2,2-trifluoroacetamide (1.5 g, 3.48 mmol) powder in small portions under cooling in a water bath, and then, the mixture was stirred at room temperature for 1 hr. The reaction mixture was diluted with ethyl acetate (100 mL), and partitioned with water (50 mL), and the organic layer was concentrated under reduced pressure. The residue was diluted with ethyl acetate (80 mL), and washed with saturated brine (80 mL). The organic layer was dried over anhydrous magnesium sulfate, and concentrated under reduced pressure. The residue was purified by silica gel column chromatography (ethyl acetate/hexane=40/60→100/0), and triturated with diisopropyl ether to give the title compound (0.58 g, 50%) as a white solid.

$^1$H-NMR (DMSO-$d_6$, 300 MHz) δ 2.20 (3H, s), 5.50 (2H, br s), 6.32 (1H, dd, J=2.7, 8.5 Hz), 6.55 (1H, d, J=2.7 Hz), 7.08 (1H, d, J=8.70 Hz), 7.21 (1H, d, J=8.5 Hz), 8.15 (1H, d, J=8.7 Hz), 12.39 (1H, br s).

(vii) Production of N-(5-{[2-(acetylamino)[1,3]thiazolo[5,4-b]pyridin-5-yl]oxy}-2-chlorophenyl)-2-chloro-3-(1-cyano-1-methylethyl)benzamide 2-Chloro-3-(1-cyano-1-methylethyl)benzoic acid (120 mg, 0.537 mmol) produced in Example C61(v) was dissolved in tetrahydrofuran (3.0 mL) and N,N-dimethylformamide (0.01 mL), oxalyl chloride (56.87 μL, 0.672 mmol) was added, and the mixture was stirred at room temperature for 1 hr. The reaction mixture was concentrated under reduced pressure, toluene (10 mL) was added to the residue, and the mixture was again concentrated under reduced pressure. The residue was dissolved in N,N-dimethylacetamide (3.0 mL), N-[5-(3-amino-4-chlorophenoxy)[1,3]thiazolo[5,4-b]pyridin-2-yl]acetamide (90 mg, 0.269 mmol) was added to the reaction mixture, and the mixture was stirred at room temperature for 2 hr. The reaction mixture was diluted with ethyl acetate (80 mL), the organic layer was washed with aqueous sodium hydrogen carbonate solution (50 mL), dried over anhydrous magnesium sulfate, and concentrated under reduced pressure. The residue was purified by silica gel column chromatography (ethyl acetate/hexane=40/60→100/0), further purified by basic silica gel column chromatography (ethyl acetate/hexane=50/50→100/0→ethyl acetate/methanol=90/10), and crystallized from diethyl ether to give the title compound (81 mg, 56%) as white crystals.

$^1$H-NMR (DMSO-$d_6$, 300 MHz) δ 1.84 (6H, s), 2.20 (3H, s), 7.15 (1H, dd, J=2.8, 8.9 Hz), 7.20 (1H, d, J=8.7 Hz), 7.44-7.72 (5H, m), 8.20 (1H, d, J=8.7 Hz), 10.42 (1H, br s), 12.42 (1H, br s).

Example C115

Production of N-(5-{[2-(acetylamino)[1,3]thiazolo[5,4-b]pyridin-5-yl]oxy}-2-chlorophenyl)-2-chloro-3-(1-cyanocyclopropyl)benzamide

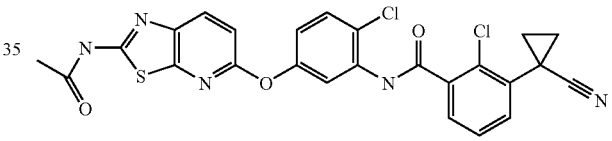

In the same reaction as in Example C114(vii), the title compound (113 mg, 78%) was obtained as white crystals using 2-chloro-3-(1-cyanocyclopropyl)benzoic acid (119 mg, 0.537 mmol) produced in Example C62(ii).

$^1$H-NMR (DMSO-$d_6$, 300 MHz) δ 1.34-1.54 (2H, m), 1.63-1.90 (2H, m), 2.20 (3H, s), 7.15 (1H, dd, J=2.9, 8.8 Hz), 7.20 (1H, d, J=8.7 Hz), 7.40-7.70 (5H, m), 8.20 (1H, d, J=8.7 Hz), 10.38 (1H, br s), 12.42 (1H, br s).

Example C116

Production of N-(5-{([2-(acetylamino)[1,3]thiazolo[5,4-b]pyridin-5-yl]oxy}-2-chlorophenyl)-3-(1-cyano-1-methylethyl)benzamide

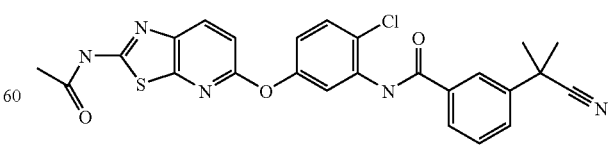

In the same reaction as in Example C114(vii), the title compound (105 mg, 77%) was obtained as white crystals using 3-(1-cyano-1-methylethyl)benzoic acid (102 mg, 0.537 mmol) produced in Example C6(ii).

$^1$H-NMR (DMSO-d$_6$, 300 MHz) δ 1.74 (6H, s), 2.20 (3H, s), 7.10-7.27 (2H, m), 7.47 (1H, d, J=2.6 Hz), 7.50-7.70 (2H, m), 7.75-7.80 (1H, m), 7.85-8.00 (1H, m), 8.09 (1H, t, J=1.70 Hz), 8.20 (1H, d, J=8.70 Hz), 10.22 (1H, br s), 12.42 (1H, br s).

Example C117

Production of N-(5-{[2-(acetylamino)[1,3]thiazolo[5,4-b]pyridin-5-yl]oxy)-2-chlorophenyl)-3-(1-cyanocyclopropyl)benzamide

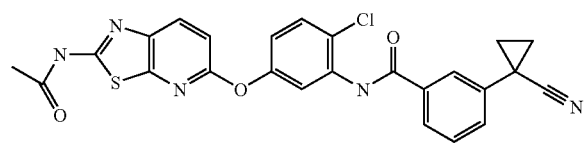 [SMILES: CC(=O)Nc1nc2ccc(Oc3ccc(Cl)c(NC(=O)c4cccc(C5(C#N)CC5)c4)c3)nc2s1]

In the same reaction as in Example C114(vii), the title compound (101 mg, 75%) was obtained as white crystals using 3-(1-cyanocyclopropyl)benzoic acid (101 mg, 0.537 mmol) produced in Example C1(iii).

$^1$H-NMR (DMSO-d$_6$, 300 MHz) δ 1.47-1.71 (2H, m), 1.71-1.91 (2H, m), 2.20 (3H, s), 7.16 (1H, dd, J=2.8, 8.8 Hz), 7.19 (1H, d, J=8.7 Hz), 7.46 (1H, d, J=2.8 Hz), 7.50-7.68 (3H, m), 7.77-7.99 (2H, m), 8.20 (1H, d, J=8.7 Hz), 10.20 (1H, br s), 12.42 (1H, br s).

Example C118

Production of 2-chloro-N-[2-chloro-5-({2-[(cyclopropylcarbonyl)amino][1,3]thiazolo[5,4-b]pyridin-5-yl}oxy)phenyl]-3-(1-cyanocyclopropyl)benzamide

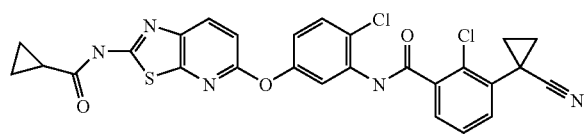 [SMILES: N#CC1(c2cccc(C(=O)Nc3cc(Oc4ccc5nc(NC(=O)C6CC6)sc5n4)ccc3Cl)c2Cl)CC1]

(i) Production of N-(5-{4-chloro-3-[(trifluoroacetyl)amino]phenoxy}[1,3]thiazolo[5,4-b]pyridin-2-yl)cyclopropanecarboxamide N-{5-[(2-Amino[1,3]thiazolo[5,4-b]pyridin-5-yl)oxy]-2-chlorophenyl}-2,2,2-trifluoroacetamide (5.0 g, 12.86 mmol) produced in Example C114(iv) was dissolved in pyridine (25 mL), cyclopropanecarbonyl chloride (1.284 mL, 14.15 mmol) was added dropwise under ice-cooling, and the mixture was stirred at room temperature for 1 hr. The reaction mixture was treated with aqueous sodium hydrogen carbonate solution (100 mL), and diluted with ethyl acetate (100 mL), and the organic layer was collected. The organic layer was dried over anhydrous magnesium sulfate, and concentrated under reduced pressure. The residual solid was crystallized from ethyl acetate (30 mL), collected by filtration, and dried to give the title compound (3.46 g, 59%) as a white solid.

$^1$H-NMR (DMSO-d$_6$, 300 MHz) δ 0.86-1.07 (4H, m), 1.90-2.10 (1H, m), 7.20 (1H, d, J=8.7 Hz), 7.26 (1H, dd, J=2.7, 8.9 Hz), 7.38 (1H, d, J=2.7 Hz), 7.66 (1H, d, J=8.9 Hz), 8.20 (1H, d, J=8.7 Hz), 11.34 (1H, br s), 12.72 (1H, br s).

(ii) Production of N-[5-(3-amino-4-chlorophenoxy)[1,3]thiazolo[5,4-b]pyridin-2-yl]cyclopropanecarboxamide Sodium borohydride (5.63 g, 149 mmol) was suspended in ethanol (100 mL), and methanol (66 mL) was slowly added. To the obtained reaction mixture was added N-(5-{4-chloro-3-[(trifluoroacetyl)amino]phenoxy}[1,3]thiazolo[5,4-b]pyridin-2-yl)cyclopropanecarboxamide (3.4 g, 7.44 mmol) powder in a small portions under cooling in a water bath, and then, the mixture was stirred at room temperature for 1 hr. The reaction mixture was diluted with ethyl acetate (150 mL), and partitioned with water (200 mL), and the organic layer was concentrated under reduced pressure. The residue was diluted with ethyl acetate (200 mL), washed with saturated brine (100 mL), the organic layer was dried over anhydrous magnesium sulfate, and concentrated under reduced pressure. The residue was purified by basic silica gel column chromatography (ethyl acetate/methanol=100/0), and triturated with diisopropyl ether to give the title compound (2.00 g, 75%) as a white solid.

$^1$H-NMR (DMSO-d$_6$, 300 MHz) δ 0.88-1.10 (4H, m), 1.90-2.10 (1H, m), 5.49 (2H, br s), 6.32 (1H, dd, J=2.7, 8.6 Hz), 6.54 (1H, d, J=2.7 Hz), 7.08 (1H, d, J=8.6 Hz), 7.21 (1H, d, J=8.6 Hz), 8.15 (1H, d, J=8.6 Hz), 12.69 (1H, br s).

(iii) Production of 2-chloro-N-[2-chloro-5-({2-[(cyclopropylcarbonyl)amino][1,3]thiazolo[5,4-b]pyridin-5-yl}oxy)phenyl]-3-(1-cyanocyclopropyl)benzamide In the same reaction as in Example C114(vii), the title compound (151 mg, 64%) was obtained as white crystals using N-[5-(3-amino-4-chlorophenoxy)[1,3]thiazolo[5,4-b]pyridin-2-yl]cyclopropanecarboxamide (150 mg, 0.416 mmol) and 2-chloro-3-(1-cyanocyclopropyl)benzoic acid (184 mg, 0.830 mmol) produced in Example C62(ii).

$^1$H-NMR (DMSO-d$_6$, 300 MHz) δ 0.90-1.00 (4H, m), 1.40-1.50 (2H, m), 1.75-1.82 (2H, m), 1.95-2.05 (1H, m), 7.15 (1H, dd, J=3.0, 9.0 Hz), 7.21 (1H, d, J=8.7 Hz), 7.40-7.55 (1H, m), 7.55-7.70 (4H, m), 8.20 (1H, d, J=8.7 Hz), 10.38 (1H, br s), 12.71 (1H, br s).

Example C119

Production of 2-chloro-N-[2-chloro-5-({2-[(cyclopropylcarbonyl)amino][1,3]thiazolo[5,4-b]pyridin-5-yl}oxy)phenyl]-3-(1-cyano-1-methylethyl)benzamide

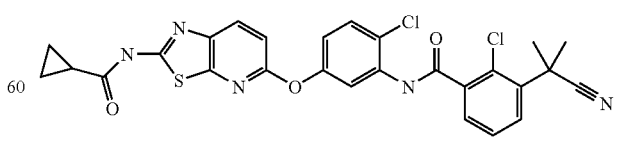

In the same reaction as in Example C114(vii), the title compound (154 mg, 65%) was obtained as white crystals using N-[5-(3-amino-4-chlorophenoxy)[1,3]thiazolo[5,4-b]pyridin-2-yl]cyclopropanecarboxamide (150 mg, 0.416 mmol) produced in Example C118(ii) and 2-chloro-3-(1-cyano-1-methylethyl)benzoic acid (186 mg, 0.830 mmol) produced in Example C61(v).

$^1$H-NMR (DMSO-d$_6$, 300 MHz) δ 0.86-1.05 (4H, m), 1.84 (6H, s), 1.90-2.10 (1H, m), 7.15 (1H, dd, J=2.7, 8.8 Hz), 7.21 (1H, d, J=8.7 Hz), 7.46-7.76 (5H, m), 8.20 (1H, d, J=8.7 Hz), 10.42 (1H, br s), 12.72 (1H, br s).

Example C120

Production of N-[2-chloro-5-({2-[(cyclopropylcarbonyl)amino][1,3]thiazolo[5,4-b]pyridin-5-yl}oxy)phenyl]-3-(trifluoromethoxy)benzamide

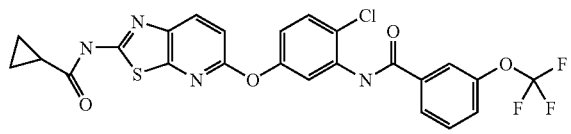 [SMILES: O=C(Nc1cc(Oc2ccc3nc(NC(=O)C4CC4)sc3n2)ccc1Cl)c1cccc(OC(F)(F)F)c1]

In the same reaction as in Example C114(vii), the title compound (90 mg, 39%) was obtained as white crystals using N-[5-(3-amino-4-chlorophenoxy)[1,3]thiazolo[5,4-b]pyridin-2-yl]cyclopropanecarboxamide (150 mg, 0.416 mmol) produced in Example C118(ii) and 3-trifluoromethoxybenzoic acid (171 mg, 0.830 mmol).

$^1$H-NMR (DMSO-d$_6$, 300 MHz) δ 0.85-1.05 (4H, m), 1.85-2.14 (1H, m), 7.17 (1H, dd, J=2.7, 8.7 Hz), 7.20 (1H, d, J=8.7 Hz), 7.46 (1H, d, J=2.7 Hz), 7.56-7.78 (3H, m), 7.91 (1H, m), 8.00-8.05 (1H, m), 8.20 (1H, d, J=8.7 Hz), 10.32 (1H, br s), 12.72 (1H, br s).

Example C121

Production of 2-chloro-N-[2-chloro-5-({2-[(cyclopropylcarbonyl)amino][1,3]thiazolo[5,4-b]pyridin-5-yl}oxy)phenyl]-3-(1-cyano-1-methylethoxy)benzamide

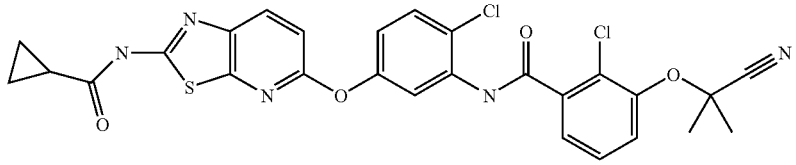 [SMILES: CC(C)(C#N)Oc1cccc(C(=O)Nc2cc(Oc3ccc4nc(NC(=O)C5CC5)sc4n3)ccc2Cl)c1Cl]

N-[5-(3-Amino-4-chlorophenoxy)[1,3]thiazolo[5,4-b]pyridin-2-yl]cyclopropanecarboxamide (200 mg, 0.554 mmol) produced in Example C118(ii), 2-chloro-3-(1-cyano-1-methylethoxy)benzoic acid (199 mg, 0.830 mmol) produced in Example C70(i) and O-(7-azabenzotriazol-1-yl)-N,N,N',N'-tetramethyluronium hexafluorophosphate (422 mg, 1.11 mmol) were suspended in pyridine (2 mL), and the suspension was stirred at 60° C. for 16 hr. After cooling to room temperature, ethyl acetate (100 mL) and water (80 mL) were added, and the mixture was partitioned. The organic layer was washed with saturated brine (50 mL), dried over anhydrous magnesium sulfate, and dried under reduced pressure. The residue was purified by silica gel column chromatography (ethyl acetate/hexane=40/60→100/0) and basic silica gel column chromatography (ethyl acetate/methanol=100/0→90/10), and triturated with diisopropyl ether to give the title compound (78 mg, 24%) as white crystals.

$^1$H-NMR (DMSO-d$_6$, 300 MHz) δ 0.86-1.00 (4H, m), 1.79 (6H, s), 1.90-2.10 (1H, m), 7.13 (1H, dd, J=3.0, 8.8 Hz), 7.20 (1H, d, J=8.7 Hz), 7.40-7.70 (5H, m), 8.20 (1H, d, J=8.7 Hz), 10.32 (1H, br s), 12.71 (1H, br s).

Example C122

Production of 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide

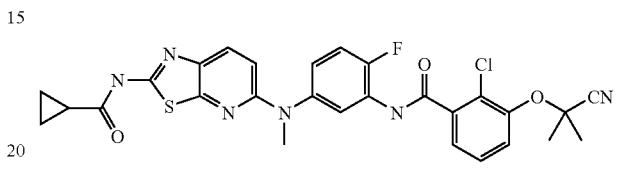

(i) Production of tert-butyl(4-fluoro-3-nitrophenyl)carbamate

To a solution of 4-fluoro-3-nitroaniline (1.56 g, 10 mmol) in tert-butanol (15 mL) was added di-tert-butyl bicarbonate (2.40 g, 11 mmol), and the mixture was stirred at 60° C. for 22 hr. The reaction mixture was concentrated under reduced pressure, and the obtained residue was triturated with hexane to give the title compound (2.38 g, 93%) as a yellow-brown solid.

$^1$H-NMR (DMSO-d$_6$, 300 MHz) δ1.49 (9H, s), 7.50 (1H, t, J=10.2 Hz), 7.65-7.81 (1H, m), 8.36 (1H, d, J=6.8 Hz), 9.87 (1H, s).

(ii) Production of tert-butyl(4-fluoro-3-nitrophenyl)methylcarbamate

To a suspension of tert-butyl(4-fluoro-3-nitrophenyl)carbamate (2.00 g, 6.35 mmol) and cesium carbonate (1.53 g, 4.7 mmol) in N,N-dimethylformamide (5 mL) was added methyl iodide (0.37 mL, 5.94 mmol), and the mixture was stirred at room temperature for 6 hr. The reaction mixture was suspended in ethyl acetate (5 mL), and the suspension was washed with water (5 mL) and saturated brine (5 mL), and dried over anhydrous magnesium sulfate. The insoluble material was filtered off, and the filtrate was concentrated under reduced pressure to give the title compound (1.0 g, 95%) as a brown oil. This was used for the next reaction without further purification operation.

$^1$H-NMR (DMSO-d$_6$, 300 MHz) δ1.42 (9H, s), 3.23 (3H, s), 7.57 (1H, dd, J=9.1, 11.0 Hz), 7.76 (1H, ddd, J=2.8, 4.0, 9.1 Hz), 8.10 (1H, dd, J=2.8, 6.8 Hz).

(iii) Production of tert-butyl(3-amino-4-fluorophenyl)methylcarbamate

To a solution of tert-butyl(4-fluoro-3-nitrophenyl)methylcarbamate (1.0 g, 3.70 mmol) in methanol (4 mL) was added 10% palladium-carbon (150 mg), and the mixture was stirred under a hydrogen atmosphere (1 atm) at room temperature for 18 hr. The insoluble material was filtered off, and the filtrate was concentrated under reduced pressure. The obtained residue was purified by silica gel column chromatography (ethyl acetate), and the obtained solution was concentrated under reduced pressure to give the title compound (0.88 g, 99%) as a brown oil.

$^1$H-NMR (DMSO-$d_6$, 300 MHz) δ1.37 (9H, s), 3.08 (3H, s), 5.14 (2H, s), 6.36 (1H, ddd, J=2.7, 4.0, 8.6 Hz), 6.64 (1H, dd, J=2.7, 8.6 Hz), 6.91 (1H, dd, J=8.6, 11.1 Hz).

(iv) Production of tert-butyl{4-fluoro-3-[(trifluoroacetyl)amino]phenyl}methylcarbamate To a solution of tert-butyl(3-amino-4-fluorophenyl)methylcarbamate (44 g, 183 mmol) in tetrahydrofuran (440 mL) was added trifluoroacetic acid anhydride (30.5 mL, 220 mmol) at 4° C. After the completion of the dropwise addition, the mixture was stirred at 10° C. for 18 hr. The reaction mixture was diluted with ethyl acetate (440 mL), and washed with saturated aqueous sodium hydrogen carbonate solution (440 mL), and the obtained aqueous layer was extracted with ethyl acetate (100 mL). The combined organic layer was washed with saturated brine (440 mL), and dried over anhydrous magnesium sulfate. The obtained solution was purified by silica gel column chromatography (ethyl acetate). The obtained solution was concentrated under reduced pressure to give the title compound (60.3 g, 98%) as a pale-yellow solid.

$^1$H-NMR (DMSO-$d_6$, 300 MHz) δ1.39 (9H, s), 3.17 (3H, s), 7.24-7.38 (2H, m), 7.42 (1H, dd, J=1.9, 6.8 Hz), 11.29 (1H, s).

(v) Production of 2,2,2-trifluoro-N-[2-fluoro-5-(methylamino)phenyl]acetamide To tert-butyl{4-fluoro-3-[(trifluoroacetyl)amino]phenyl}methylcarbamate (2.5 g, 7.43 mmol) was added trifluoroacetic acid (6 mL) at 4° C. to give a solution, and the solution was stirred at 10° C. for 2 hr. The reaction mixture was concentrated under reduced pressure, and the obtained residue was diluted with ethyl acetate (10 mL), washed with saturated aqueous sodium hydrogen carbonate solution (10 mL) and saturated brine (10 mL), and dried over anhydrous magnesium sulfate. The obtained solution was purified by silica gel column chromatography (ethyl acetate). The obtained solution was concentrated under reduced pressure to give the title compound (1.75 g, 99%) as a pale-yellow amorphous substance.

$^1$H-NMR (DMSO-$d_6$, 300 MHz) δ2.64 (3H, d, J=5.1 Hz), 5.74 (1H, q, J=5.1 Hz), 6.47 (1H, ddd, J=3.0, 3.9, 9.0 Hz), 6.54 (1H, dd, J=3.0, 6.2 Hz), 7.05 (1H, dd, J=9.0, 10.2 Hz), 11.05 (1H, s).

(vi) Production of 2,2,2-trifluoro-N-{2-fluoro-5-[methyl(5-nitropyridin-2-yl)amino]phenyl}acetamide A solution of 2-chloro-5-nitropyridine (201 mg, 1.27 mmol) and 2,2,2-trifluoro-N-[2-fluoro-5-(methylamino)phenyl]acetamide (300 mg, 1.27 mmol) in N,N-dimethylformamide (1.5 mL) was stirred at 140° C. for 22 hr. The reaction mixture was cooled to room temperature, and suspended in ethyl acetate (5 mL), and the suspension was washed with saturated aqueous sodium hydrogen carbonate solution (5 mL) and saturated brine (5 mL), and dried over anhydrous sodium sulfate. The insoluble material was filtered off, and the filtrate was concentrated under reduced pressure, and the obtained residue was crystallized from ethyl acetate/hexane to give the title compound (221 mg, 49%) as yellow crystals.

$^1$H-NMR (DMSO-$d_6$, 300 MHz) δ3.50 (3H, s), 6.53 (1H, d, J=9.4 Hz), 7.37-7.66 (3H, m), 8.21 (1H, dd, J=2.7, 9.4 Hz), 9.03 (1H, d, J=2.7 Hz), 11.43 (1H, s).

(vii) Production of N-{5-[(5-aminopyridin-2-yl)(methyl)amino]-2-fluorophenyl}-2,2,2-trifluoroacetamide To a solution of 2,2,2-trifluoro-N-{2-fluoro-5-[methyl(5-nitropyridin-2-yl)amino]phenyl}acetamide (18.0 g, 50.2 mmol) in ethanol (100 mL)/tetrahydrofuran (20 mL) was added 10% palladium-carbon (1.8 g), and the mixture was stirred under a hydrogen atmosphere (1 atm) at room temperature for 14 hr. The insoluble material was filtered off, and the filtrate was concentrated under reduced pressure. The obtained residue was crystallized from ethyl acetate/hexane to give the title compound (21.2 g, 68%) as colorless crystals.

$^1$H-NMR (DMSO-$d_6$, 300 MHz) δ 3.23 (3H, s), 4.94 (2H, br s), 6.71 (1H, d, J=8.7 Hz), 6.88-6.99 (2H, m), 7.03 (1H, dd, J=2.4, 6.6 Hz), 7.21 (1H, dd, J=9.0, 10.0 Hz), 7.69 (1H, d, J=2.4 Hz), 11.15 (1H, br s).

(viii) Production of N-{5-[(2-amino[1,3]thiazolo[5,4-b]pyridin-5-yl)(methyl)amino]-2-fluorophenyl)-2,2,2-trifluoroacetamide Potassium thiocyanate (2.96 g, 30.5 mmol) was suspended in acetic acid (20 mL), and the suspension was stirred at room temperature for 10 min. To the obtained solution was added N-{5-[(5-aminopyridin-2-yl)(methyl)amino]-2-fluorophenyl}-2,2,2-trifluoroacetamide (2.0 g, 6.96 mmol), and the mixture was further stirred at room temperature for 10 min. To the obtained solution was slowly added dropwise a solution of bromine (1.17 g, 7.30 mmol) in acetic acid (10 mL). After the completion of the dropwise addition, the mixture was stirred at room temperature for 20 hr. The yielded black insoluble material was filtered off, and washed with acetic acid. The filtrate and the washing solution were combined, and concentrated under reduced pressure. The obtained residue was suspended in ethyl acetate (100 mL), and the suspension was washed with saturated aqueous sodium hydrogen carbonate solution (70 mL) and saturated brine (100 mL), and dried over anhydrous magnesium sulfate. The insoluble material was filtered off, and the filtrate was concentrated under reduced pressure. The obtained residue was purified by basic silica gel column chromatography (hexane/ethyl acetate=40/60→0/100), and the obtained solution was concentrated under reduced pressure. The residue was crystallized from ethyl acetate/hexane to give the title compound (1.00 g, 43%) as a colorless powder.

$^1$H-NMR (DMSO-$d_6$, 300 MHz) δ3.34 (3H, s), 6.57 (1H, d, J=8.7 Hz), 7.22 (1H, dd, J=2.7, 4.2 Hz), 7.29-7.40 (4H, m), 7.45 (1H, d, J=8.7 Hz), 11.28 (1H, s).

(ix) Production of N-{5-[{4-fluoro-3-[(trifluoroacetyl)amino]phenyl}(methyl)amino][1,3]thiazolo[5,4-b]pyridin-2-yl}cyclopropanecarboxamide To a solution of N-{5-[(2-amino[1,3]thiazolo[5,4-b]pyridin-5-yl)(methyl)amino]-2-fluorophenyl}-2,2,2-trifluoroacetamide (385 mg, 1.00 mmol) in pyridine (10 mL) was added cyclopropanecarbonyl chloride (144 μL, 1.60 mmol) at 4° C., and the mixture was stirred at room temperature for 1 hr. The reaction mixture was concentrated under reduced pressure, and the residue was suspended in ethyl acetate (10 mL). The obtained suspension was washed with saturated aqueous sodium hydrogen carbonate solution (10 mL) and saturated brine (10 mL), and dried over anhydrous magnesium sulfate. The insoluble material was filtered off, and the filtrate was concentrated under reduced pressure. The obtained residue was purified by basic silica gel column chromatography (hexane/ethyl acetate=80/20→0/100), and the obtained solution was concentrated under reduced pressure to give the title compound (250 mg, 59%) as a colorless powder.

$^1$H-NMR (DMSO-$d_6$, 300 MHz) δ0.85-1.04 (4H, m), 1.86-2.10 (1H, m), 3.41 (3H, s), 6.65 (1H, d, J=9.0 Hz), 7.28-7.59 (3H, m), 7.80 (1H, d, J=9.0 Hz), 11.35 (1H, s), 12.47 (1H, s).

(x) Production of N-{5-[(3-amino-4-fluorophenyl)(methyl)amino][1,3]thiazolo[5,4-b]pyridin-2-yl}cyclopropanecarboxamide To a suspension of sodium borohydride (3.34 g, 88.2 mmol) in ethanol (40 mL) were added methanol (1 mL) and N-{5-[{4-fluoro-3-[(trifluoroacetyl)amino]phenyl}(methyl)amino][1,3]thiazolo[5,4-b]pyridin-2-yl}cyclopropanecarboxamide (1.71 g, 3.77 mmol) at 4° C., and the mixture was stirred for 30 min. The reaction mixture was poured into a two-layer solvent of ethyl acetate (200 mL) and 5% aqueous ammonium chloride solution (200 mL), and the mixture was vigorously stirred at room temperature for 5 min. The aqueous layer was separated, and extracted with ethyl acetate (200 mL). The combined organic layer was washed with saturated aqueous sodium hydrogen carbonate (xi) Production of 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide To a solution of 2-chloro-3-(1-cyano-1-methylethoxy)benzoic acid (4.8 g, 20 mmol) produced in Example C70(iii) in pyridine (100 mL) was added O-(7-azabenzotriazol-1-yl)-N,N,N',N'-tetramethyluronium hexafluorophosphate (7.6 g, 20 mmol), and the mixture was stirred at room temperature for 2 hr. To the obtained solution was added N-{5-[(3-amino-4-fluorophenyl)(methyl)amino][1,3]thiazolo[5,4-b]pyridin-2-yl}cyclopropanecarboxamide (3.57 g, 9.99 mmol), and the mixture was stirred at 90° C. for 3 hr. The reaction mixture was cooled to room temperature, and concentrated under reduced pressure. The obtained residue was diluted with ethyl acetate (350 mL), and washed with water (350 mL). The aqueous layer was extracted with ethyl acetate (150 mL). The combined organic layer was washed with saturated aqueous sodium hydrogen carbonate solution (250 mL×2) and saturated brine (250 mL), and dried over anhydrous magnesium sulfate. The insoluble material was filtered off, and the filtrate was concentrated under reduced pressure. The residue was purified by basic silica gel column chromatography (hexane/ethyl acetate=60/40→20/80), the obtained solution was concentrated under reduced pressure, and the residue was crystallized from ethyl acetate to give the title compound (5.02 g, 87%) as a colorless powder.

$^1$H-NMR (DMSO-$d_6$, 300 MHz) δ0.86-1.04 (4H, m), 1.79 (6H, s), 1.90-2.05 (1H, m), 3.43 (3H, s), 6.64 (1H, d, J=9.0 Hz), 7.13-7.27 (1H, m), 7.32-7.44 (2H, m), 7.50 (1H, t, J=7.7 Hz), 7.54-7.62 (1H, m), 7.79 (1H, d, J=9.0 Hz), 7.85 (1H, dd, J=2.6, 6.8 Hz), 10.50 (1H, s), 12.46 (1H, s).

Example C123

Production of 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide ethanedioate (2:1)

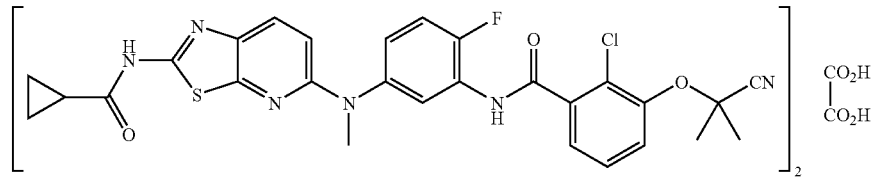

solution (200 mL) and saturated brine (200 mL), and dried over anhydrous magnesium sulfate. The insoluble material was filtered off, and the filtrate was concentrated under reduced pressure. The residue was purified by silica gel column chromatography (hexane/ethyl acetate=80/20→60/40), and the obtained solution was concentrated under reduced pressure to give the title compound (1.19 g, 88%) as a colorless powder.

$^1$H-NMR (DMSO-$d_6$, 300 MHz) δ0.71-1.08 (4H, m), 1.83-2.06 (1H, m), 3.33 (3H, s), 5.27 (2H, s), 6.34-6.47 (1H, m), 6.50 (1H, d, J=9.1 Hz), 6.67 (1H, dd, J=2.6, 8.4 Hz), 7.05 (1H, dd, J=8.4, 11.3 Hz), 7.72 (1H, d, J=9.1 Hz), 12.41 (1H, s).

2-Chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide (300 mg, 0.518 mmol) produced in Example C122(xi) was dissolved in ethyl acetate (9 mL), oxalic acid dihydrate (68.6 mg, 0.544 mmol) was added, and the mixture was stood at 55° C. To the obtained solution was added heptane, and the mixture was cooled to room temperature. The crystallized crystals were collected by filtration, and dried to give the title compound (339 mg, 98%) as colorless crystals.

$^1$H-NMR (DMSO-$d_6$, 300 MHz) δ0.82-1.01 (4H, m), 1.79 (6H, s), 1.92-2.11 (1H, m), 3.43 (3H, s), 6.64 (1H, d, J=9.0

Hz), 7.07-7.26 (1H, m), 7.31-7.65 (4H, m), 7.79 (1H, d, J=9.0 Hz), 7.85 (1H, dd, J=2.6, 7.0 Hz), 10.50 (1H, s), 12.46 (1H, s).

Example C124

Production of 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide benzenesulfonate

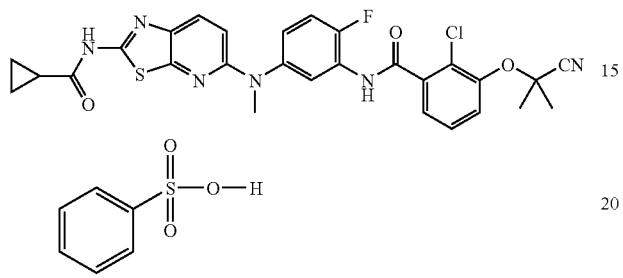

2-Chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl)benzamide (150 mg, 0.259 mmol) produced in Example C122(xi) was dissolved in ethyl acetate (4 mL), and benzenesulfonic acid (185 mg, 1.05 mmol) was added. Tetrahydrofuran was added while stirring the obtained mixture at 50° C. to give a yellow solution, and the solution was stirred at 50° C. for 15 min. The solution was concentrated under reduced pressure, and tetrahydrofuran (4 mL) was added to the obtained oily residue to give a solution. Heptane was added at 50° C. to give a saturated solution, and the solution was cooled to room temperature. The crystallized crystals were collected by filtration, and dried to give the title compound (152 mg, 80%) as colorless crystals.
$^1$H-NMR (DMSO-$d_6$, 300 MHz) δ0.73-1.08 (4H, m), 1.79 (6H, s), 1.90-2.08 (1H, m), 3.43 (3H, s), 6.64 (1H, d, J=9.0 Hz), 7.13-7.25 (1H, m), 7.25-7.45 (5H, m), 7.50 (1H, t, J=7.8 Hz), 7.54-7.64 (3H, m), 7.79 (1H, d, J=9.0 Hz), 7.85 (1H, dd, J=2.6, 7.0 Hz), 10.50 (1H, s), 12.47 (1H, s).

Example C125

Production of 2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide sulfate

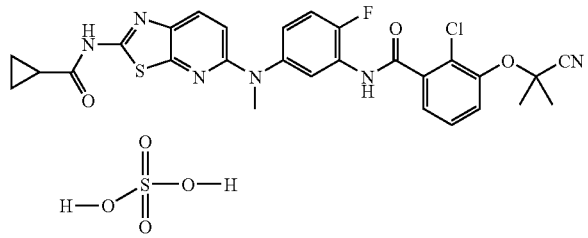

2-Chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide (150 mg, 0.259 mmol) produced in Example C122(xi) was dissolved in ethyl acetate (6 mL), and the solution was added dropwise to a suspension of sulfuric acid (51 mg, 0.52 mmol) in heptane at room temperature. Ethyl acetate (12 mL) was added, and the mixture was stirred at 50° C. for 15 min. The solution was concentrated under reduced pressure, tetrahydrofuran and heptane were added to the obtained residue at 50° C., and the mixture was cooled to room temperature. The crystallized crystals were collected by filtration, and dried to give the title compound (140 mg, 80%) as colorless crystals.
$^1$H-NMR (DMSO-$d_6$, 300 MHz) δ0.74-1.06 (4H, m), 1.79 (6H, s), 1.92-2.11 (1H, m), 3.43 (3H, s), 6.64 (1H, d, J=8.9 Hz), 7.16-7.24 (1H, m), 7.33-7.65 (4H, m), 7.79 (1H, d, J=8.9 Hz), 7.85 (1H, dd, J=2.5, 6.9 Hz), 10.51 (1H, s), 12.47 (1H, s).

Example C126

Production of 2-chloro-3-(1-cyano-1-methylethoxy)-N-[5-({2-[(cyclopropylcarbonyl)amino][1,3]thiazolo[5,4-b]pyridin-5-yl}amino)-2-fluorophenyl]benzamide

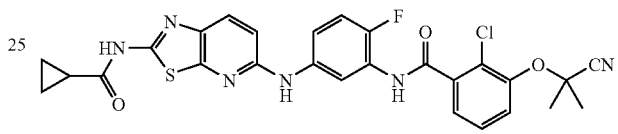

(i) Production of di-tert-butyl(2-fluoro-5-nitrophenyl)imidodicarbonate

To a solution of 2-fluoro-5-nitroaniline (15.6 g, 100 mmol) in dichloromethane (200 mL) were added di-tert-butyl bicarbonate (87.2 g, 400 mmol) and triethylamine (20.4 g, 200 mmol), and the mixture was stirred at 55° C. overnight. The reaction mixture was concentrated under reduced pressure, and the residue was purified by silica gel column chromatography (petroleum ether/ethyl acetate=10/1) to give the title compound (19.3 g, 54%) as a yellow powder.
$^1$H-NMR (CDCl$_3$, 300 MHz) δ 1.44 (18H, s), 8.12-8.16 (1H, m), 8.21-8.25 (2H, m).

(ii) Production of di-tert-butyl(5-amino-2-fluorophenyl)imidodicarbonate

To a solution of di-tert-butyl(2-fluoro-5-nitrophenyl)imidodicarbonate (256 mg, 0.718 mmol) in methanol (10 mL) was added 10% palladium-carbon (50 mg), and the mixture was stirred under a hydrogen atmosphere at room temperature overnight. 10% Palladium-carbon powder was filtered off by celite filtration, and the filtrate was concentrated under reduced pressure to give the title compound (150 mg, 64%).
$^1$H-NMR (CDCl$_3$, 300 MHz) δ1.42 (18H, s), 3.55 (2H, br s), 6.46-6.54 (1H, m), 6.55-6.59 (1H, m), 6.85-6.92 (1H, m).

(iii) Production of 5-chloro[1,3]thiazolo[5,4-b]pyridine-2-amine

Potassium thiocyanate (16.0 g, 165 mmol) and 6-chloropyridine-3-amine (2.6 g, 20.2 mmol) were dissolved in acetic acid (52 mL). To the solution was added dropwise a solution of bromine (3.2 mL, 62.5 mmol) in acetic acid (12 mL) under cooling in a water bath, and the mixture was stirred for 2 hr. The mixture was allowed to warm to room temperature and stirred for 10 hr, and water (30 mL) was added. The reaction mixture was filtered at 85° C., and the insoluble material was suspended in acetic acid (50 mL) and filtered. The obtained filtrate was neutralized with aqueous ammonia solution, and the precipitated solid was collected by filtration and recrystallized from methanol to give the title compound (2.0 g, 54%) as white crystals.

$^1$H-NMR (DMSO-d$_6$, 300 MHz) δ 7.31 (1H, d, J=8.4 Hz), 7.65 (1H, d, J=8.4 Hz), 7.93 (2H, br s).

(iv) Production of tert-butyl[5-({2-[(cyclopropylcarbonyl)amino][1,3]thiazolo[5,4-b]pyridin-5-yl}amino)-2-fluorophenyl]carbamate To a solution of cyclopropanecarboxylic acid (129 mg, 1.50 mmol) in dichloromethane (5 mL) were added oxalyl chloride (190 mg, 1.50 mmol) and N,N-dimethylformamide (40 μL), and the mixture was stirred at room temperature for 1 hr. The reaction mixture was added to a solution (10 mL) of 5-chloro[1,3]thiazolo[5,4-b]pyridine-2-amine (185 mg, 1.00 mmol) in tetrahydrofuran at 0° C., and the mixture was stirred for 2 hr. To the reaction mixture was added water (10 mL), and the mixture was extracted with ethyl acetate (30 mL×3). The organic layer was concentrated under reduced pressure to give N-(5-chloro[1,3]thiazolo[5,4-b]pyridin-2-yl)cyclopropanecarboxamide.

$^1$H-NMR (CDCl$_3$, 300 MHz) δ1.02-1.06 (2H, m), 1.23-1.30 (2H, m), 1.51-1.69 (1H, m), 7.38 (1H, d, J=8.7 Hz), 7.92 (1H, d, J=8.7 Hz), 9.93 (1H, br s).

To a mixture of N-(5-chloro[1,3]thiazolo[5,4-b]pyridin-2-yl)cyclopropanecarboxamide (76 mg, 0.300 mmol) produced above, di-tert-butyl(5-amino-2-fluorophenyl)imidodicarbonate (98 mg, 0.300 mmol), tris(dibenzylideneacetone)dipalladium (57 mg, 60.0 μmol), dicyclohexyl(2',4',6'-triisopropylbiphenyl-2-yl)phosphine (X-phos) (15 mg, 30.0 μmol) and potassium tert-butoxide (145 mg, 1.40 mmol) was added tert-butanol (20 mL) under nitrogen atmosphere, and the mixture was stirred under a microwave irradiation at 90° C. for 35 min. To the reaction mixture was added water (5 mL), and the mixture was extracted with ethyl acetate (50 mL×3). The organic layer was dried over anhydrous sodium sulfate, and concentrated under reduced pressure. The residue was purified by silica gel column chromatography (petroleum ether/ethyl acetate=1/1) to give the title compound (84 mg, 63%) as a brown powder.

$^1$H-NMR (CDCl$_3$, 300 MHz) δ0.93-1.00 (2H, m), 1.25-1.28 (2H, m), 1.50 (9H, s), 1.54-1.69 (1H, m), 6.80-6.85 (3H, m), 6.97-7.05 (1H, m), 7.16-7.22 (1H, m), 7.77 (1H, d, J=8.7 Hz), 8.02 (1H, dd, J=2.4, 7.2 Hz), 11.56 (1H, br s).

(v) Production of N-{5-[(3-amino-4-fluorophenyl)amino][1,3]thiazolo[5,4-b]pyridin-2-yl}cyclopropanecarboxamide To tert-butyl[5-({2-[(cyclopropylcarbonyl)amino][1,3]thiazolo[5,4-b]pyridin-5-yl}amino)-2-fluorophenyl]carbamate (3.40 g, 7.67 mmol) was added 4N hydrochloric acid/ethyl acetate (50 mL), and the mixture was stirred at 0° C. overnight. The reaction mixture was neutralized with saturated aqueous sodium hydrogen carbonate solution, and extracted with ethyl acetate (50 mL×3). The organic layer was concentrated under reduced pressure to give the title compound (1.70 g, 65%) as a purple powder.

$^1$H-NMR (DMSO-d$_6$, 300 MHz) δ0.92-0.97 (4H, m), 1.96-2.00 (1H, m), 5.08 (2H, br s), 6.73-6.78 (1H, m), 6.85-6.92 (2H, m), 7.16 (1H, dd, J=2.4, 8.4 Hz), 7.84 (1H, d, J=9.0 Hz), 8.97 (1H, s), 12.41 (1H, s).

(vi) Production of 2-chloro-3-(1-cyano-1-methylethoxy)-N-[5-({2-[(cyclopropylcarbonyl)amino][1,3]thiazolo[5,4-b]pyridin-5-yl}amino)-2-fluorophenyl]benzamide To a solution of 2-chloro-3-(1-cyano-1-methylethoxy)benzoic acid (278 mg, 1.16 mmol) produced in Example C70(iii) in tetrahydrofuran (2.5 mL) were added N,N-dimethylformamide (25 μL) and oxalyl chloride (125 μL, 1.46 mmol), and the mixture was stirred at room temperature for 1 hr. The reaction mixture was concentrated under reduced pressure to give 2-chloro-3-(1-cyano-1-methylethoxy)benzoyl chloride as a pale-yellow oil.

To a solution of 2-chloro-3-(1-cyano-1-methylethoxy)benzoyl chloride synthesized above in N,N-dimethylacetamide (4.0 mL) was added N-{5-[(3-amino-4-fluorophenyl)amino][1,3]thiazolo[5,4-b]pyridin-2-yl)cyclopropanecarboxamide (200 mg, 0.582 mmol), and the mixture was stirred at room temperature for 2 hr. To the reaction mixture was added saturated aqueous sodium hydrogen carbonate solution (20 mL), and the mixture was extracted with ethyl acetate (50 mL). The organic layer was washed with water (20 mL) and saturated brine (20 mL), and dried over anhydrous sodium sulfate, and concentrated under reduced pressure. The residue was purified by silica gel column chromatography (hexane/ethyl acetate=80/20→0/100) and crystallized from hexane/ethyl acetate to give the title compound (216 mg, 66%) as pale-purple crystals.

$^1$H-NMR (DMSO-d$_6$, 300 MHz) δ 0.86-1.00 (4H, m), 1.80 (6H, s), 1.91-2.04 (1H, m), 6.92 (1H, d, J=8.9 Hz), 7.20 (1H, t, J=9.3, 10.2 Hz), 7.39 (1H, dd, J=1.5, 7.0 Hz), 7.46-7.63 (2H, m), 7.63-7.73 (1H, m), 7.90 (1H, d, J=8.9 Hz), 8.16 (1H, dd, J=2.7, 7.0 Hz), 9.40 (1H, s), 10.35 (1H, s), 12.47 (1H, br s).

Example C127

Production of N-acetyl-2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide

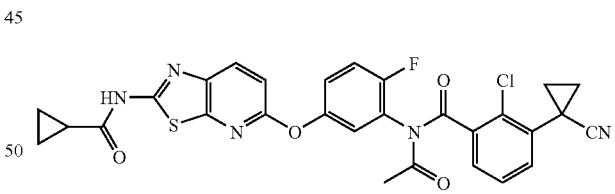

(i) Production of methyl 2-chloro-3-methylbenzoate

A mixture of 2-chloro-3-methylbenzoic acid (25.0 g, 146 mmol), conc. sulfuric acid (2 mL) and methanol (160 mL) was stirred at 80° C. for 3 hr. The reaction mixture was concentrated, was diluted with ethyl acetate and neutralized with 8N aqueous sodium hydroxide solution. The organic layer was separated, washed with saturated brine, dried over anhydrous magnesium sulfate, and filtered through a basic silica gel pad. The filtrate was concentrated under reduced pressure to give the title compound (18.0 g, 66%) as a pale-orange oil. The obtained compound was used for the next reaction without further purification.

¹H-NMR (CDCl₃, 300 MHz) δ 2.42 (3H, s), 3.93 (3H, s), 7.19 (1H, t, J=7.6 Hz), 7.32-7.38 (1H, m), 7.56 (1H, dd, J=1.2, 7.6 Hz).

(ii) Production of methyl 3-(bromomethyl)-2-chlorobenzoate

To a solution of methyl 2-chloro-3-methylbenzoate (3.60 g, 19.4 mmol) in acetonitrile (60 mL) were added 1-bromopyrrolidine-2,5-dione (11.46 g, 64.3 mmol) and 2,2'-(E)-diazen-1,2-diylbis(2-methylpropanenitrile) (960 mg, 5.84 mmol), and the mixture was stirred at 90° C. for 26 hr. The insoluble material was filtered off from the reaction mixture, and the filtrate was concentrated under reduced pressure. The obtained residue was purified by silica gel column chromatography (hexane/ethyl acetate=100/0→95/5), and the fractions containing the object product were concentrated under reduced pressure to give the title compound (3.42 g, 66%) as a colorless oil.

¹H-NMR (CDCl₃, 300 MHz) δ 3.94 (3H, s), 4.64 (2H, s), 7.31 (1H, t, J=7.7 Hz), 7.58 (1H, dd, J=1.7, 7.7 Hz), 7.71 (1H, dd, J=1.7, 7.7 Hz).

(iii) Production of methyl 2-chloro-3-(cyanomethyl)benzoate

To a solution of methyl 3-(bromomethyl)-2-chlorobenzoate (748 mg, 2.84 mmol) in N,N-dimethylformamide (7 mL) was added sodium cyanate (412 mg, 8.41 mmol), and the mixture was stirred at 80° C. for 1 hr. The reaction mixture was diluted with a mixed solvent of ethyl acetate/hexane (1:1). The solution was washed with water and saturated brine, and dried over anhydrous magnesium sulfate. The insoluble material was filtered off, and the filtrate was concentrated under reduced pressure. The obtained residue was purified by silica gel column chromatography (ethyl acetate/hexane=2/98→20/80), and the fractions containing the object product were concentrated under reduced pressure. The obtained residue was recrystallized from ethyl acetate and hexane to give the title compound (470 mg, 79%) as white crystals.

¹H-NMR (CDCl₃, 300 MHz) δ 3.91 (2H, s), 3.95 (3H, s), 7.39 (1H, t, J=7.8 Hz), 7.66-7.72 (1H, m), 7.76-7.81 (1H, m).

(iv) Production of methyl 2-chloro-3-(1-cyanocyclopropyl)benzoate

A solution of methyl 2-chloro-3-(cyanomethyl)benzoate (20.0 g, 95.3 mmol) in dimethylsulfoxide (200 mL) was cooled to 15° C., 60% sodium hydride (11.6 g, 289 mmol) was added by small portions, and the mixture was stirred at room temperature for 30 min. To the suspension was dropwise added 1,2-dibromoethane (16.5 mL, 191 mmol) at 15° C. over 10 min, and the mixture was stirred at room temperature for 4 hr. To the reaction mixture was added aqueous ammonium chloride solution (200 mL), and the mixture was extracted with diethyl ether/ethyl acetate (1:1, 3×200 mL). The combined organic layer was washed successively with water (200 mL) and saturated brine (100 mL), and dried over anhydrous magnesium sulfate. The insoluble material was filtered off, and the filtrate was concentrated under reduced pressure. The obtained residue was purified by silica gel column chromatography (hexane/ethyl acetate=95/5→65/35) to give the title compound (13.5 g, 60%) as a white powder.

¹H-NMR (CDCl₃, 300 MHz) δ 1.31-1.41 (2H, m), 1.75-1.85 (2H, m), 3.96 (3H, s), 7.32 (1H, t, J=7.7 Hz), 7.49 (1H, dd, J=1.7, 7.7 Hz), 7.74 (1H, dd, J=1.7, 7.7 Hz).

(v) Production of 2-chloro-3-(1-cyanocyclopropyl)benzoic acid

To a solution of methyl 2-chloro-3-(1-cyanocyclopropyl)benzoate (13.5 g, 57.3 mmol) in tetrahydrofuran (180 mL)/methanol (60 mL)/water (60 mL) was added lithium hydroxide monohydrate (3.62 g, 86.3 mmol), and the mixture was stirred at room temperature for 2 hr. The reaction mixture was concentrated under reduced pressure, and 6N hydrochloric acid (20 mL) was added dropwise to the obtained residue. The precipitate was collected by filtration, and washed with water to give the title compound (11.4 g, 90%) as white crystals.

¹H-NMR (DMSO-d₆, 300 MHz) δ 1.40-1.50 (2H, m), 1.72-1.85 (2H, m), 7.45 (1H, t, J=7.7 Hz), 7.68 (1H, dd, J=1.7, 7.7 Hz), 7.73 (1H, dd, J=1.7, 7.7 Hz), 13.60 (1H, br s).

(vi) Production of 2-chloro-3-(1-cyanocyclopropyl)-N-(2-fluoro-5-hydroxyphenyl)benzamide To a solution of 2-chloro-3-(1-cyanocyclopropyl)benzoic acid (16.0 g, 72.2 mmol) in tetrahydrofuran (150 mL) was added N,N-dimethylformamide (0.1 mL), and oxalyl chloride (7.2 mL, 84.0 mmol) was further added dropwise at 0° C., and the mixture was stirred at room temperature for 2.5 hr. The reaction mixture was concentrated under reduced pressure to dryness to give 2-chloro-3-(1-cyanocyclopropyl)benzoyl chloride as a pale-yellow oil.

A two-layer mixture of a solution of 3-amino-4-fluorophenol (9.00 g, 70.8 mmol) in tetrahydrofuran (50 mL) and aqueous sodium hydrogen carbonate (13.9 g, 166 mmol) solution (100 mL) was vigorously stirred, while adding dropwise a solution of 2-chloro-3-(1-cyanocyclopropyl)benzoyl chloride synthesized above in tetrahydrofuran (60 mL). The reaction mixture was stirred at room temperature for 1 hr. The organic layer was separated, and the aqueous layer was extracted with ethyl acetate (50 mL). The combined organic layer was washed with saturated brine (20 mL), dried over anhydrous magnesium sulfate, and the solvent was evaporated under reduced pressure. The residue was crystallized from hexane/ethyl acetate (120 mL/40 mL) to give the title compound (23.4 g, 100%) as a brown powder.

¹H-NMR (DMSO-d₆, 300 MHz) δ 1.40-1.49 (2H, m), 1.76-1.85 (2H, m), 6.52-6.63 (1H, m), 7.07 (1H, dd, J=9.0, 10.5 Hz), 7.39 (1H, dd, J=2.9, 6.5 Hz), 7.47 (1H, d, J=7.6 Hz), 7.53-7.60 (1H, m), 7.64 (1H, dd, J=1.7, 7.6 Hz), 9.48 (1H, s), 10.30 (1H, s).

(vii) Production of 2-chloro-3-(1-cyanocyclopropyl)-N-{2-fluoro-5-[(5-nitropyridin-2-yl)oxy]phenyl}benzamide A mixture of 2-chloro-3-(1-cyanocyclopropyl)-N-(2-fluoro-5-hydroxyphenyl)benzamide (23.0 g, 69.6 mmol), 2-chloro-5-nitropyridine (12.2 g, 77.1 mmol), potassium carbonate (11.5 g, 83.1 mmol) and N,N-dimethylformamide (70 mL) was stirred at room temperature for 4 hr. To the reaction mixture were added N,N-dimethylformamide (130 mL) and water (250 mL), and the mixture was stirred at room temperature for 1 hr. The precipitate was collected by filtration, washed with water (200 mL), and dried under reduced pressure to give the title compound (29.3 g, 93%) as a gray powder.

¹H-NMR (DMSO-d$_6$, 300 MHz) δ 1.38-1.51 (2H, m), 1.74-1.86 (2H, m), 7.08-7.19 (1H, m), 7.32 (1H, d, J=9.1 Hz), 7.42 (1H, dd, J=9.0, 10.3 Hz), 7.47 (1H, t, J=7.6 Hz), 7.56-7.62 (1H, m), 7.65 (1H, dd, J=1.7, 7.6 Hz), 7.85 (1H, dd, J=2.8, 6.4 Hz), 8.65 (1H, dd, J=2.6, 9.1 Hz), 9.06 (1H, d, J=2.6 Hz), 10.62 (1H, s).

(viii) Production of N-{5-[(5-aminopyridin-2-yl)oxy]-2-fluorophenyl}-2-chloro-3-(1-cyanocyclopropyl)benzamide A mixture of 2-chloro-3-(1-cyanocyclopropyl)-N-{2-fluoro-5-[(5-nitropyridin-2-yl)oxy]phenyl}benzamide (6.60 g, 14.6 mmol), reduced iron (1.68 g, 30.0 mmol), calcium chloride (3.33 g, 30.0 mmol), water (80 mL) and ethanol (20 mL) was stirred at 80° C. for 18 hr. The mixture was cooled to room temperature, water (250 mL), 1N aqueous sodium hydroxide solution (250 mL), ethyl acetate (300 mL) and celite (50 g) were added, and the mixture was stirred. The mixture was filtered through celite, and the insoluble material was washed with ethyl acetate (100 mL). The organic layer was separated, dried over anhydrous magnesium sulfate, and the solvent was evaporated under reduced pressure. The obtained residue was crystallized from diethyl ether to give the title compound (4.23 g, 69%) as a pale-yellow powder.

¹H-NMR (CDCl$_3$, 300 MHz) δ1.35-1.42 (2H, m), 1.80-1.85 (2H, m), 3.45-3.57 (2H, br s), 6.82 (1H, d, J=8.4 Hz), 6.82-6.88 (1H, m), 7.02 (1H, d, J=8.4 Hz), 7.12 (1H, dd, J=7.5, 8.4 Hz), 7.38 (1H, t, J=7.8 Hz), 7.50 (1H, dd, J=1.5, 7.5 Hz), 7.66 (1H, dd, J=1.8, 7.8 Hz), 7.70 (1H, d, J=3.0 Hz), 7.97-8.03 (1H, br s), 8.28 (1H, dd, J=3.0, 6.6 Hz).

(ix) Production of N-{5-[(2-amino[1,3]thiazolo[5,4-b]pyridin-5-yl)oxy]-2-fluorophenyl}-2-chloro-3-(1-cyanocyclopropyl)benzamide To a solution (50 mL) of N-{5-[(5-aminopyridin-2-yl)oxy]-2-fluorophenyl}-2-chloro-3-(1-cyanocyclopropyl)benzamide (4.23 g, 10 mmol) and potassium thiocyanate (3.89 g, 40 mmol) in acetic acid was added dropwise bromine (2.40 g, 15 mmol) at 15° C., and the mixture was stirred at room temperature for 6 hr. The yellow suspension was filtered through celite, and the yellow insoluble material was thoroughly washed with acetic acid (50 mL). The filtrate and washing solution were combined, and the mixture was concentrated under reduced pressure. The residue was suspended in 0.1N aqueous sodium hydroxide solution (100 mL), and the suspension was extracted with ethyl acetate (100 mL). The organic layer was dried over anhydrous magnesium sulfate, and the solvent was evaporated under reduced pressure. The residue was purified by silica gel chromatography (hexane/ethyl acetate=100/0→0/100). The obtained residue was crystallized from diethyl ether to give the title compound (3.32 g, 69%) as a pale-yellow powder.

¹H-NMR (DMSO-d$_6$, 300 MHz) δ 1.41-1.49 (2H, m), 1.75-1.85 (2H, m), 6.95 (1H, d, J=8.5 Hz), 6.97-7.03 (1H, m), 7.33 (1H, dd, J=9.3, 10.2 Hz), 7.46 (1H, t, J=7.6 Hz), 7.56-7.67 (4H, m), 7.69 (1H, dd, J=2.9, 6.5 Hz), 7.73 (1H, d, J=8.5 Hz), 10.53 (1H, s).

(x) Production of 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide To a solution of N-{5-[(2-amino[1,3]thiazolo[5,4-b]pyridin-5-yl)oxy]-2-fluorophenyl}-2-chloro-3-(1-cyanocyclopropyl)benzamide (9.0 g, 18.8 mmol) and pyridine (2.3 mL, 28.1 mmol) in tetrahydrofuran (90 mL) was added dropwise cyclopropanecarbonyl chloride (1.89 mL, 20.8 mmol) under ice-cooling, and the mixture was stirred at room temperature for 3 hr. Cyclopropanecarbonyl chloride (63 μL, 0.69 mmol) was further added and the mixture was stirred at room temperature for 12 hr. Water (100 mL) and saturated aqueous sodium hydrogen carbonate solution (100 mL) were added to the reaction mixture to give a suspension, and the mixture was stirred at room temperature for 30 min. The precipitate was collected by filtration, repeatedly washed with water, and dried under reduced pressure to give the title compound (9.85 g, 96%) as a white powder.

¹H-NMR (DMSO-d$_6$, 300 MHz) δ 1.01-1.09 (2H, m), 1.21-1.29 (2H, m), 1.39 (2H, dd, J=5.4, 7.5 Hz), 1.62-1.70 (1H, m), 1.81 (2H, dd, J=5.4, 7.5 Hz), 6.94-6.99 (1H, m), 7.03 (1H, d, J=8.7 Hz), 7.19 (1H, dd, J=9.0, 10.2 Hz), 7.39 (1H, t, J=7.8 Hz), 7.50 (1H, dd, J=1.5, 7.5 Hz), 7.68 (1H, dd, J=1.5, 7.5 Hz), 7.98 (1H, d, J=8.7 Hz), 8.06 (1H, d, J=3.0 Hz), 8.39 (1H, dd, J=2.7, 6.6 Hz), 9.99 (1H, br s).

(xi) Production of N-acetyl-2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide To a solution of 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide (180 mg, 0.328 mmol) in pyridine (2 mL) were added N,N-dimethylpyridine-4-amine (18.0 mg, 0.147 mmol) and acetic anhydride (138 μL, 1.46 mmol), and the mixture was stirred at room temperature for 30 min. To the reaction mixture was added water (5 mL), and the mixture was extracted with ethyl acetate (5mL×4). The organic layers were combined, washed successively with water (5 mL) and saturated brine (5 mL), dried over anhydrous magnesium sulfate, and concentrated under reduced pressure. The residue was purified by silica gel column chromatography (hexane/ethyl acetate=95/5→20/80) and, preparative liquid chromatography (0.1% trifluoroacetic acid-containing acetonitrile/0.1% trifluoroacetic acid-containing water=45/55→60/40). The obtained residue was triturated with diisopropyl ether/acetone to give the title compound (68.5 mg, 35%) as a white powder.

¹H-NMR (DMSO-d$_6$, 300 MHz) δ 0.87-1.01 (4H, m), 1.26-1.44 (2H, m), 1.64-1.87 (2H, m), 1.91-2.07 (1H, m), 2.35 (3H, s), 7.07 (1H, d, J=8.7 Hz), 7.22-7.32 (1H, m), 7.33-7.45 (2H, m), 7.50 (1H, dd, J=2.5, 6.3 Hz), 7.52-7.61 (2H, m), 8.18 (1H, d, J=8.7 Hz), 12.72 (1H, br s).

Example C128

Production of tert-butyl([2-chloro-3-(1-cyanocyclopropyl)phenyl]carbonyl}[5-({2-[(cyclopropylcarbonyl)amino][1,3]thiazolo[5,4-b]pyridin-5-yl}oxy)-2-fluorophenyl]carbamate

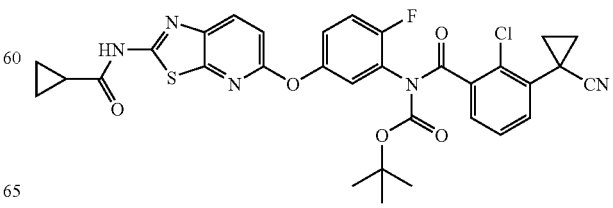

To a solution of 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide (3.0 g, 5.47 mmol) produced in Example C127(x) in pyridine (55 mL) was added dropwise a solution of di-tert-butyl bicarbonate (3.58 g, 16.4 mmol) in tetrahydrofuran (17 mL) over 5 min. The reaction mixture was stirred for 1 hr, diluted with water (120 mL), and extracted with ethyl acetate (240 mL). The organic layer was washed with saturated brine (120 mL), and dried over anhydrous sodium sulfate. The insoluble material was filtered off, and the solvent was evaporated under reduced pressure to give a colorless oil. This colorless oil was purified by silica gel column chromatography (hexane/ethyl acetate=95/5→20/80) to give the object fractions, and the solvent was evaporated under reduced pressure to give the title compound (2.25 g, 63%) as a white powder.

$^1$H-NMR (DMSO-d$_6$, 300 MHz) δ0.86-0.99 (4H, m), 1.14 (9H, s), 1.39-1.50 (2H, m), 1.72-1.85 (2H, m), 1.99 (1H, t, J=5.5 Hz), 7.16 (1H, d, J=8.7 Hz), 7.33 (1H, dd, J=2.9, 4.1 Hz), 7.42-7.57 (3H, m), 7.61-7.72 (2H, m), 8.19 (1H, d, J=8.7 Hz), 12.70 (1H, s).

Example C129

Production of 2-chloro-3-(1-cyanocyclopropyl)-N-(cyclopropylcarbonyl)-N-[5-({2-[(cyclopropylcarbonyl)amino][1,3]thiazolo[5,4-b]pyridin-5-yl}oxy)-2-fluorophenyl]benzamide To a solution of 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide (3.5 g, 6.39 mmol) produced in Example C127(x) in pyridine (35 mL) were added N,N-dimethylpyridine-4-amine (3.87 g, 31.7 mmol) and cyclopropanecarbonyl chloride (3.0 mL, 33.1 mmol) at 10° C., and the mixture was stirred at room temperature for 1.5 hr. The reaction mixture was poured into ice water (70 mL), and the mixture was extracted with ethyl acetate (80 mL×3). The organic layers were combined, washed successively with water (50 mL) and saturated brine (30 mL), dried over anhydrous magnesium sulfate, and concentrated under reduced pressure. The residue was purified by silica gel column chromatography (hexane/ethyl acetate=95/5→20/80). The obtained residue was recrystallized from ethyl acetate to give the title compound (2.47 g, 63%) as white crystals.

$^1$H-NMR (DMSO-d$_6$, 300 MHz) δ0.84-1.03 (8H, m), 1.33-1.44 (2H, m), 1.72-1.80 (2H, m), 1.81-1.93 (1H, m), 1.93-2.06 (1H, m), 7.13 (1H, d, J=8.7 Hz), 7.29-7.64 (6H, m), 8.19 (1H, d, J.=8.7 Hz), 12.71 (1H, br s).

Example C130

Production of ethyl{[2-chloro-3-(1-cyanocyclopropyl)phenyl]carbonyl}[5-({2-[(cyclopropylcarbonyl)amino][1,3]thiazolo[5,4-b]pyridin-5-yl}oxy)-2-fluorophenyl]carbamate

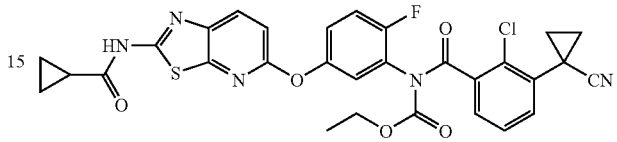

To a solution of 2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide (151 mg, 0.278 mmol) produced is in Example C127(x) in pyridine (1.5 mL) was added diethyl dicarbonate (197 μL, 1.36 mmol), and the mixture was stirred at room temperature for 1 hr. To the reaction mixture was added water (5 mL), and the mixture was extracted with ethyl acetate (5 mL×3). The organic layers were combined and washed successively with water (5 mL) and saturated brine (2 mL), dried over anhydrous magnesium sulfate, and concentrated under reduced pressure. The residue was purified by silica gel column chromatography (hexane/ethyl acetate=95/5→20/80) and crystallized from ethyl acetate to give the title compound (77.6 mg, 45%) as white crystals.

$^1$H-NMR (DMSO-d$_6$, 300 MHz) δ 0.90 (3H, t, J=7.1 Hz), 0.93-1.00 (4H, m), 1.39-1.49 (2H, m), 1.75-1.85 (2H, m), 1.93-2.06 (1H, m), 4.03 (2H, q, J=7.1 Hz), 7.16 (1H, d, J=8.7 Hz), 7.32-7.40 (1H, m), 7.43-7.51 (2H, m), 7.51-7.58 (1H, m), 7.59-7.70 (2H, m), 8.19 (1H, d, J=8.7 Hz), 12.70 (1H, br s).

Preparation Example C1

A pharmaceutical agent containing the compound of the present invention as an active ingredient can be produced, for example, according to the following formulation.

1. Capsule

| | |
|---|---|
| (1) compound of Example C1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added and the total amount is sealed in a gelatin capsule.

2. Tablet

| | |
|---|---|
| (1) compound of Example C1 | 40 mg |
| (2) lactose | 58 mg |
| (3) cornstarch | 18 mg |

| | |
|---|---|
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The rest of (4) and (5) is added to the granules and the mixture is compression formed into a tablet.

Preparation Example C2

The compound (50 mg) obtained in Example C1 is dissolved in the Japanese Pharmacopoeia distilled water for injection (50 mL), and the Japanese Pharmacopoeia distilled water for injection is added to make the total amount 100 mL. This solution is aseptically filtered. The solution (1 mL) is aseptically filled in a vial for injection, sealed and freeze-dried.

Example D1

Production of N-{3-[[2-(acetylamino)[1,3]thiazolo[5,4-d]pyrimidin-5-yl](methyl)amino]phenyl}-3-(trifluoromethyl)benzamide

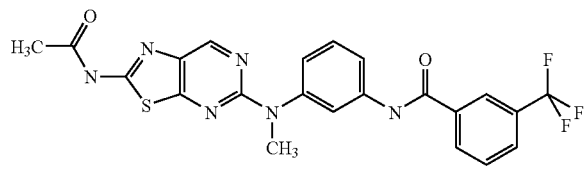 [SMILES: CC(=O)Nc1nc2cnc(N(C)c3cccc(NC(=O)c4cccc(C(F)(F)F)c4)c3)nc2s1]

Example D2

Production of N-{3-[{2-[(cyclopropylcarbonyl)amino][1,3]thiazolo[5,4-d]pyrimidin-5-yl}(methyl)amino]phenyl}-3-(trifluoromethyl)benzamide

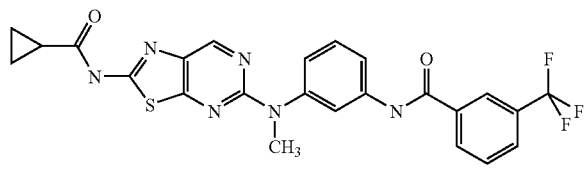 [SMILES: CN(c1cccc(NC(=O)c2cccc(C(F)(F)F)c2)c1)c1ncc2nc(NC(=O)C3CC3)sc2n1]

(i) Production of N-(3-nitrophenyl)-3-(trifluoromethyl)benzamide

To a solution of 3-nitroaniline (13.8 g, 99.9 mmol) in pyridine (200 mL) were added 3-(trifluoromethyl)benzoylchloride (21.4 g, 103 mmol) and N,N-dimethylaminopyridine (69.1 mg, 566 μmol), and the mixture was stirred at room temperature for 1.5 hr. The reaction was quenched with methanol (50 mL), and the solvent was evaporated under reduced pressure. The residue was suspended in ethyl acetate (300 mL), washed with water (200 mL×2), diluted hydrochloric acid (200 mL×2), saturated aqueous sodium hydrogen carbonate solution (200 mL) and saturated brine (100 mL), and dried over anhydrous magnesium sulfate. The insoluble material was filtered off, and the filtrate was concentrated under reduced pressure to give the title compound (31.0 g, 100%) as a colorless solid.

$^1$H-NMR (DMSO-$d_6$, 300 MHz) δ 7.69 (1H, t, J=8.4 Hz), 7.82 (1H, t, J=7.8 Hz), 7.98-8.03 (2H, m), 8.21 (1H, ddd, J=0.9, 1.8, 8.1 Hz), 8.29-8.34 (2H, m), 8.78 (1H, t, J=2.1 Hz), 10.90 (1H, br s).

(ii) Production of N-(3-aminophenyl)-3-(trifluoromethyl)benzamide

To a solution of N-(3-nitrophenyl)-3-(trifluoromethyl)benzamide (30.0 g, 96.7 mmol) in tetrahydrofuran (300 mL) was slowly added with heating under reflux aqueous sodium hydrosulfite (97.8 g, 562 mmol) solution (500 mL), and the obtained two-layer solution was vigorously stirred with heating under reflux for 2 days. After cooling the reaction solution to room temperature, the aqueous layer was separated and extracted with ethyl acetate (150 mL×2). The organic layer separated earlier was diluted with ethyl acetate (350 mL), and washed with saturated aqueous sodium hydrogen carbonate solution (150 mL×2) and saturated brine (100 mL). The collected organic layer was washed with saturated aqueous sodium hydrogen carbonate solution (150 mL×2) and saturated brine (150 mL), and dried over anhydrous magnesium sulfate. The insoluble material was filtered off, and the filtrate was concentrated under reduced pressure to give the title compound (17.8 g, 66%) as a pale-brown solid.

$^1$H-NMR (DMSO-$d_6$, 300 MHz) δ 5.14 (2H, br s), 6.34 (1H, ddd, J=1.2, 2.1, 8.1 Hz), 6.85-6.88 (1H, m), 6.99 (1H, t, J=8.1 Hz), 7.09 (1H, t, J=1.8 Hz), 7.77 (1H, t, J=7.8 Hz), 7.94 (1H, d, J=7.8 Hz), 8.22-8.26 (2H, m), 10.19 (1H, br s).

(iii) Production of N-[3-(methylamino)phenyl]-3-(trifluoromethyl)benzamide

Formic acid (2.5 mL, 66.3 mmol) and acetic anhydride (5 mL, 52.9 mmol) were mixed, and the mixture was stirred with heating at 50° C. for 3 hr. The reaction mixture was cooled to room temperature, diluted with tetrahydrofuran (50 mL), and cooled to 0° C. To the reaction mixture was added a solution of N-(3-aminophenyl)-3-(trifluoromethyl)benzamide (5.65 g, 20.2 mmol) in tetrahydrofuran (50 mL) and the mixture was stirred at the same temperature for 16 hr, during which the reaction temperature was allowed to gradually warm to room temperature. The reaction solution was concentrated under reduced pressure, and the residue was dissolved in tetrahydrofuran (50 mL) and ethyl acetate (250 mL). The solution was washed with saturated aqueous sodium hydrogen carbonate solution (150 mL×2) and saturated aqueous ammonium chloride solution (150 mL), and dried over anhydrous magnesium sulfate. The insoluble material was filtered off, and the filtrate was concentrated under reduced pressure to give N-[3-(formylamino)phenyl]-3-(trifluoromethyl)benzamide as a yellow amorphous substance. To a solution of N-[3-(formylamino)phenyl]-3-(trifluoromethyl)benzamide produced above in tetrahydrofuran (100 mL) was added a 1.9M solution (21 mL, 39.9 mmol) of borane-dimethylsulfide complex in tetrahydrofuran, and the mixture was stirred at room temperature for 1.5 hr. Since the starting materials were not completely consumed, a 1.9M solution (2 mL, 3.8 mmol) of borane-dimethylsulfide complex in tetrahydrofuran was added, and the mixture was further stirred at room temperature for 1 hr. Methanol (30 mL) and acetic acid (10 mL) were added to the reaction solution and the mixture was stirred at room temperature for 14 hr, and concentrated under reduced pressure. The residue was dissolved in ethyl acetate (250 mL), washed with saturated aqueous sodium hydrogen carbonate solution (100 mL×2) and saturated brine (100 mL), and dried over anhydrous magnesium sulfate. The insoluble material was filtered off, and the filtrate was concentrated under reduced pressure. The residue was recrystallized from ethyl acetate and hexane to give the title compound (5.54 g, total yield of 2 steps 93%) as yellow crystals.

$^1$H-NMR (DMSO-$d_6$, 300 MHz) δ 2.68 (3H, s), 5.71 (1H, br s), 6.32 (1H, ddd, J=1.2, 2.1, 8.4 Hz), 6.95-7.08 (3H, m), 7.77 (1H, t, J=7.8 Hz), 7.95 (1H, dd, J=0.6, 7.8 Hz), 8.23-8.27 (2H, m), 10.22 (1H, br s).

(iv) Production of 2-chloro-5-nitropyrimidin-4-yl thiocyanate

To a solution of 2,4-dichloro-5-nitropyrimidine (16.7 g, 85.8 mmol) in acetic acid (100 mL) was added at room temperature potassium thiocyanate (8.82 g, 90.8 mmol) over 1.5 hr or longer, and the mixture was stirred for 3 hr. The reaction mixture was poured into vigorously stirred water (500 mL), and the mixture was stirred for 30 min. The resulting solid was collected by filtration, and dried to give the title compound (16.5 g, 89%) as pale-yellow crystals.

$^1$H-NMR (CDCl$_3$, 300 MHz) δ 9.40 (1H, s).

(v) Production of 2-[methyl(3-{[3-(trifluoromethyl)benzoyl]amino}phenyl)amino]-5-nitropyrimidin-4-yl thiocyanate To a solution of N-[3-(methylamino)phenyl]-3-(trifluoromethyl)benzamide (1.11 g, 3.77 mmol) produced in the above-mentioned (iii) in tetrahydrofuran (50 mL) were added at room temperature 2-chloro-5-nitropyrimidin-4-yl thiocyanate (827 mg, 3.82 mmol) produced in the above-mentioned (iv) and N-ethyl-N-isopropylpropane-2-amine (1.5 mL, 8.61 mmol), and the mixture was stirred at room temperature for 30 min. The reaction solution was diluted with ethyl acetate, and washed with water (100 mL). The aqueous layer was extracted with ethyl acetate, and the combined organic layer was washed with saturated aqueous ammonium chloride solution, and dried over anhydrous magnesium sulfate. The insoluble material was filtered off, and the filtrate was concentrated under reduced pressure to give the title compound (1.79 g, 99%) as an orange amorphous substance.

$^1$H-NMR (DMSO-$d_6$, 300 MHz) δ 3.70 (3H, s), 7.22 (1H, d, J=8.1 Hz), 7.47-7.49 (1H, m), 7.74 (1H, d, J=9.0 Hz), 7.80 (1H, t, J=7.8 Hz), 7.90 (1H, br s), 7.99 (1H, d, J=7.8 Hz), 8.25-8.30 (2H, m), 9.08 (1H, s), 10.65 (1H, br s).

(vi) Production of N-{3-[(2-amino[1,3]thiazolo[5,4-d]pyrimidin-5-yl)(methyl)amino]phenyl}-3-(trifluoromethyl)benzamide and N-{3-[[2-(acetylamino)[1,3]thiazolo[5,4-d]pyrimidin-5-yl](methyl)amino]phenyl}-3-(trifluoromethyl)benzamide To a solution of 2-[methyl(3-{[3-(trifluoromethyl)benzoyl]amino}phenyl)amino]-5-nitropyrimidin-4-yl thiocyanate (1.79 g, 3.76 mmol) in acetic acid (100 mL) was added reduced iron (5.50 g, 98.5 mmol), and the mixture was stirred with heating at 100° C. for 1.5 hr. The reaction solution was allowed to cool to room temperature, and the insoluble material was filtered off and the residue was washed with acetic acid. The combined filtrate and washing solution were concentrated under reduced pressure, and the residue was diluted with tetrahydrofuran (50 mL) and ethyl acetate (250 mL). This liquid was washed with saturated aqueous sodium hydrogen carbonate solution (150 mL), saturated aqueous ammonium chloride solution (150 mL) and saturated brine (150 mL), and dried over anhydrous magnesium sulfate. The insoluble material was filtered off, and the filtrate was concentrated under reduced pressure. The residue was purified by basic silica gel column chromatography (ethyl acetate/methanol=100/0→90/10) and recrystallized from ethyl acetate and tetrahydrofuran to give N-{3-[(2-amino[1,3]thiazolo[5,4-d]pyrimidin-5-yl)(methyl)amino]phenyl}-3-(trifluoromethyl)benzamide (compound of Example D1) (424 mg, 26%) as colorless crystals.

$^1$H-NMR (DMSO-$d_6$, 300 MHz) δ 3.46 (3H, s), 7.11 (1H, dt, J=6.9, 1.2 Hz), 7.38 (1H, t, J=8.1 Hz), 7.60-7.66 (3H, m), 7.74-7.82 (2H, m), 7.97 (1H, d, J=7.8 Hz), 8.25-8.30 (3H, m), 10.49 (1H, br s).

In addition, N-{3-[[2-(acetylamino)[1,3]thiazolo[5,4-d]pyrimidin-5-yl](methyl)amino]phenyl}-3-(trifluoromethyl)benzamide (396 mg, 22%) was isolated by purification by the above-mentioned chromatography. The compound was recrystallized from ethyl acetate and hexane.

$^1$H-NMR (DMSO-$d_6$, 300 MHz) δ 2.19 (3H, s), 3.53 (3H, s), 7.14-7.17 (1H, m), 7.41 (1H, t, J=7.8 Hz), 7.66-7.69 (1H, m), 7.77-7.82 (2H, m), 7.98 (1H, d, J=8.1 Hz), 8.25-8.30 (2H, m), 8.74 (1H, s), 10.52 (1H, s), 12.35 (1H, s).

(vii) Production of N-(3-[{2-[(cyclopropylcarbonyl)amino][1,3]thiazolo[5,4-d]pyrimidin-5-yl}(methyl)amino]phenyl}-3-(trifluoromethyl)benzamide To a solution of N-{3-[(2-amino[1,3]thiazolo[5,4-d]pyrimidin-5-yl)(methyl)amino]phenyl}-3-(trifluoromethyl)benzamide (268 mg, 604 μmol) in pyridine (5 mL) were added N,N-dimethylpyridine-4-amine (23.9 mg, 196 μmol) and cyclopropanecarbonyl chloride (200 μL, 2.20 μmol), and the mixture was stirred at room temperature for 1 hr. To the reaction solution were added methanol (10 mL) and 2N aqueous sodium hydroxide solution (1 mL), and the mixture was stirred at room temperature for 1 more hr. The reaction solution was concentrated under reduced pressure, and diluted with ethyl acetate (100 mL) and tetrahydrofuran (10 mL). The diluted solution was washed with water (50 mL), 0.1N hydrochloric acid (50 mL) and saturated aqueous sodium hydrogen carbonate solution (50 mL), dried over anhydrous magnesium sulfate, and the insoluble material was filtered off. The filtrate was concentrated under reduced pressure, and the residue was purified by basic silica gel column chromatography (ethyl acetate/methanol=100/0→80/20), and recrystallized from ethyl acetate and tetrahydrofuran to give the title compound (compound of Example D2) (301 mg, 97%) as colorless crystals.

$^1$H-NMR (DMSO-$d_6$, 300 MHz) δ 0.94-0.98 (4H, m), 1.97-2.01 (1H, m), 3.52 (3H, s), 7.15 (1H, dt, J=6.9, 1.2 Hz), 7.41 (1H, t, J=8.1 Hz), 7.67 (1H, dd, J=0.9, 8.1 Hz), 7.77-7.82

(2H, m), 7.98 (1H, d, J=7.8 Hz), 7.25-7.30 (2H, m), 8.74 (1H, s), 10.52 (1H, br s), 12.65 (1H, br s).

Example D3

Production of 3-(1-cyano-1-methylethyl)-N-[3-({2-[(cyclopropylcarbonyl)amino][1,3]thiazolo[5,4-d]pyrimidin-5-yl}amino)phenyl]benzamide

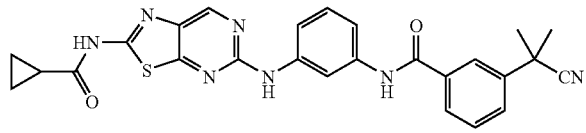

(i) Production of 3-(1-cyano-1-methylethyl)-N-(3-nitrophenyl)benzamide

To a solution of 3-(1-cyano-1-methylethyl)benzoic acid (7.85 g, 41.5 mmol) in tetrahydrofuran (80 mL) were added N,N-dimethylformamide (50 µL) and oxalyl chloride (4.33 mL, 49.8 mmol), and the mixture was stirred at room temperature for 1.5 hr. The reaction mixture was concentrated under reduced pressure to give 3-(cyano-1-methylethyl)benzoyl chloride as a pale-brown oil. To a solution of 3-nitroaniline (5.73 g, 41.5 mmol) and N,N-dimethylpyridine-4-amine (253 mg, 2.07 mmol) in pyridine (50 mL) was added dropwise a suspension of 3-(cyano-1-methylethyl)benzoyl chloride in pyridine (30 mL), and the mixture was stirred at room temperature for 2 hr. The reaction mixture was concentrated under reduced pressure, and to the residue was added saturated aqueous sodium hydrogen carbonate solution (150 mL), and the mixture was extracted with ethyl acetate (200 mL, 50 mL). The combined organic layer was washed with saturated brine (30 mL), and dried over anhydrous magnesium sulfate. The insoluble material was filtered off, and the filtrate was concentrated under reduced pressure. The obtained residue was washed with ethyl acetate/hexane mixture to give the title compound (11.46 g, 89%) as a pale-yellow solid.
$^1$H-NMR (DMSO-$d_6$, 300 MHz) δ 1.76 (6H, s), 7.58-7.73 (2H, m), 7.80 (1H, ddd, J=1.0, 2.0, 8.0 Hz), 7.94-8.02 (2H, m), 8.08 (1H, t, J=2.0 Hz), 8.21 (1H, ddd, J=1.0, 2.0, 8.0 Hz), 8.78 (1H, t, J=2.0 Hz), 10.76 (1H, br s).

(ii) Production of 3-(1-cyano-1-methylethyl)-N-[3-(formylamino)phenyl]benzamide

To a solution of 3-(1-cyano-1-methylethyl)-N-(3-nitrophenyl)benzamide (495 mg, 1.60 mmol) in ethanol (12 mL)/tetrahydrofuran (4 mL) was added 10% palladium-carbon (85 mg), and the mixture was stirred at room temperature under a hydrogen atmosphere (1 atm) for 14 hr. The insoluble material was filtered off, and the filtrate was concentrated under reduced pressure to give N-(3-aminophenyl)-3-(1-cyano-1-methylethyl)benzamide as a pale-brown oil. The obtained compound was used for the next reaction without further purification.
$^1$H-NMR (DMSO-$d_6$, 300 MHz) δ 1.75 (6H, s), 5.09 (2H, br s), 6.33 (1H, ddd, J=1.5, 2.1, 7.9 Hz), 6.82-6.89 (1H, m), 6.97 (1H, t, J=7.9 Hz), 7.06 (1H, t, J=2.1 Hz), 7.57 (1H, t, J=7.9 Hz), 7.73 (1H, ddd, J=1.5, 2.1, 7.9 Hz), 7.90 (1H, ddd, J=1.5, 2.1, 7.9 Hz), 8.00 (1H, t, J=1.5 Hz), 10.01 (1H, br s).

To a solution of the above-mentioned crude product of N-(3-aminophenyl)-3-(1-cyano-1-methylethyl)benzamide in tetrahydrofuran (15 mL) was added a mixture of formic acid (1 mL) and acetic anhydride (2 mL), and the mixture was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=40/60→20/80), and the fractions containing the object product were concentrated under reduced pressure to give the title compound (407 mg, 83%) as a colorless amorphous solid.
$^1$H-NMR (DMSO-$d_6$, 300 MHz) δ 1.75 (6H, s), 7.26-7.37 (2H, m), 7.49 (1H, dt, J=7.9, 2.0 Hz), 7.55-7.64 (1H, m), 7.75 (1H, ddd, J=0.9, 2.0, 7.9 Hz), 7.94 (1H, ddd, J=0.9, 2.0, 7.9 Hz), 7.99-8.11 (2H, m), 8.27 (1H, d, J=2.0 Hz), 10.23 (1H, br s), 10.36 (1H, br s).

(iii) Production of 2-{[3-({[3-(1-cyano-1-methylethyl)phenyl]carbonyl}amino)phenyl]amino}-5-nitropyrimidin-4-yl thiocyanate To a solution of 3-(1-cyano-1-methylethyl)-N-[3-(formylamino)phenyl]benzamide (676 mg, 2.42 mmol) in tetrahydrofuran (10 mL) were added N-ethyl-N-isopropylpropane-2-amine (643 µL, 3.63 mmol) and 2-chloro-5-nitropyrimidin-4-yl thiocyanate (576 mg, 2.66 mmol), and the mixture was stirred at room temperature for 30 min. To the reaction mixture was added saturated aqueous sodium hydrogen carbonate solution (30 mL), and the mixture was extracted with ethyl acetate (30 mL, 10 mL). The combined organic layer was washed with saturated brine (5 mL), and dried over anhydrous sodium sulfate. The insoluble material was filtered off, and the filtrate was concentrated under reduced pressure. The obtained residue was washed with ethyl acetate to give the title compound (933 mg, 84%) as a yellow solid.
$^1$H-NMR (CDCl$_3$, 300 MHz) δ 1.80 (6H, s), 6.82-6.87 (1H, m), 7.39-7.46 (1H, m), 7.53 (1H, t, J=7.6 Hz), 7.72-7.76 (1H, m), 7.90-7.95 (1H, m), 8.00 (1H, t, J=1.9 Hz), 8.02-8.07 (1H, m), 8.33-8.38 (1H, m), 8.73-8.77 (1H, m), 8.85 (1H, t, J=1.9 Hz), 9.18 (1H, s).

(iv) Production of N-{3-[(2-amino[1,3]thiazolo[5,4-d]pyrimidin-5-yl)amino]phenyl}-3-(1-cyano-1-methylethyl)benzamide To a suspension of 2-{[3-({[3-(1-cyano-1-methylethyl)phenyl]carbonyl}amino)phenyl]amino}-5-nitropyrimidin-4-yl thiocyanate (844 mg, 1.84 mmol) and reduced iron (513 mg, 9.20 mmol) in ethanol (16 mL)/1-methylpyrrolidin-2-one (8 mL) was added 1N hydrochloric acid (4 mL), and the mixture was stirred at 100° C. for 1.5 hr. The reaction mixture was neutralized with 2N aqueous sodium hydroxide solution (3 mL), and the insoluble material was filtered off. The filtrate was concentrated under reduced pressure. To the obtained residue was added saturated aqueous sodium hydrogen carbonate solution (50 mL), and the mixture was extracted with ethyl acetate (50 mL, 2×20 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=40/60→20/80), and the fractions containing the object product were concentrated under reduced pressure. The obtained residue was recrystallized from ethyl acetate and hexane to give the title compound (477 mg, 60%) as pale-purple crystals.

$^1$H-NMR (DMSO-d$_6$, 300 MHz) δ 1.76 (6H, s), 7.24 (1H, t, J=7.9 Hz), 7.29-7.36 (1H, m), 7.43-7.50 (1H, m), 7.60 (1H, t, J=7.9 Hz), 7.65 (2H, br s), 7.75 (1H, ddd, J=1.0, 2.0, 7.9 Hz), 7.91-7.97 (1H, m), 8.05 (1H, t, J=2.0 Hz), 8.10 (1H, t, J=2.0 Hz), 8.38 (1H, s), 9.51 (1H, br s), 10.28 (1H, br s).

(v) Production of 3-(1-cyano-1-methylethyl)-N-[3-({2-[(cyclopropylcarbonyl)amino][1,3]thiazolo[5,4-d]pyrimidin-5-yl}amino)phenyl]benzamide To a solution of N-{3-[(2-amino[1,3]thiazolo[5,4-d]pyrimidin-5-yl)amino]phenyl}-3-(1-cyano-1-methylethyl)benzamide (139 mg, 324 μmol) in pyridine (4 mL) was added cyclopropanecarbonyl chloride (59 μL, 648 μmol), and the mixture was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=50/50→30/70), and the fractions containing the object product were concentrated under reduced pressure. The obtained residue was recrystallized from ethyl acetate and hexane to give the title compound (96 mg, 59%) as colorless crystals.

$^1$H-NMR (DMSO-d$_6$, 300 MHz) δ 0.81-1.03 (4H, m), 1.76 (6H, s), 1.94-2.03 (1H, m), 7.27 (1H, t, J=7.9 Hz), 7.38 (1H, dd, J=1.8, 7.9 Hz), 7.51 (1H, dd, J=1.8, 7.9 Hz), 7.60 (1H, t, J=7.9 Hz), 7.75 (1H, m), 7.95 (1H, dt, J=7.9, 1.2 Hz), 8.05 (1H, t, J=1.2 Hz), 8.18 (1H, t, J=1.8 Hz), 8.84 (1H, s), 9.84 (1H, br s), 10.31 (1H, br s), 12.70 (1H, br s).

Example D4

Production of N-(3-{[2-(acetylamino)[1,3]thiazolo[5,4-d]pyrimidin-5-yl]amino)phenyl)-3-(1-cyano-1-methylethyl)benzamide

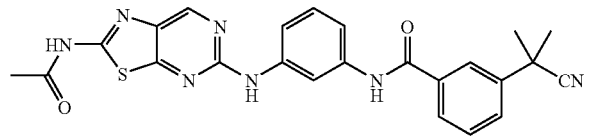

To a solution of N-{3-[(2-amino[1,3]thiazolo[5,4-d]pyrimidin-5-yl)amino]phenyl}-3-(1-cyano-1-methylethyl)benzamide (135 mg, 314 μmol) produced in Example D3(iv) in pyridine (4 mL) was added acetyl chloride (45 μL, 628 μmol), and the mixture was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=50/50→30/70), and the fractions containing the object product were concentrated under reduced pressure. The obtained residue was recrystallized from ethyl acetate and hexane to give the title compound (121 mg, 82%) as colorless crystals.

$^1$H-NMR (DMSO-d$_6$, 300 MHz) δ 1.76 (6H, s), 2.20 (3H, s), 7.27 (1H, t, J=8.0 Hz), 7.35-7.42 (1H, m), 7.50 (1H, ddd, J=1.0, 2.0, 8.0 Hz), 7.60 (1H, t, J=7.8 Hz), 7.72-7.78 (1H, m), 7.95 (1H, dt, J=7.8, 1.5 Hz), 8.05 (1H, t, J=1.5 Hz), 8.20 (1H, t, J=2.0 Hz), 8.85 (1H, s), 9.86 (1H, br s), 10.32 (1H, br s), 12.41 (1H, br s).

Example D5

Production of 3-(1-cyano-1-methylethyl)-N-{3-[{2-[(cyclopropylcarbonyl)amino][1,3]thiazolo[5,4-d]pyrimidin-5-yl}(methyl)amino]phenyl}benzamide

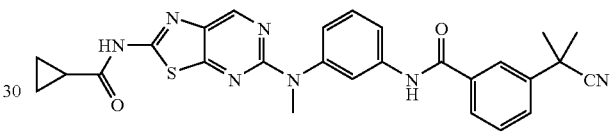

(i) Production of N-{3-[(2-amino[1,3]thiazolo[5,4-d]pyrimidin-5-yl)(methyl)amino]phenyl}-3-(1-cyano-1-methylethyl)benzamide To a solution of 3-(1-cyano-1-methylethyl)-N-[3-(formylamino)phenyl]benzamide (405 mg, 1.32 mmol) produced in Example D3(ii) in tetrahydrofuran (15 mL) was added borane dimethylsulfide complex (361 μL, 3.42 mmol), and the mixture was stirred at room temperature for 2.5 hr. To the reaction mixture was added saturated aqueous sodium hydrogen carbonate solution (20 mL), and the mixture was extracted with ethyl acetate (20 mL, 10 mL). The combined organic layer was washed with saturated brine (5 mL), and dried over anhydrous sodium sulfate. The insoluble material was filtered off, and the filtrate was concentrated under reduced pressure to give 3-(1-cyano-1-methylethyl)-N-[3-(methylamino)phenyl]benzamide as a brown oil. The obtained compound was used for the next reaction without further purification.

To a solution of the above-mentioned crude product of 3-(1-cyano-1-methylethyl)-N-[3-(methylamino)phenyl]benzamide in tetrahydrofuran (15 mL) were added N-ethyl-N-isopropylpropane-2-amine (345 μL, 1.98 mmol) and 2-chloro-5-nitropyrimidin-4-yl thiocyanate (314 mg, 1.50 mmol), and the mixture was stirred at room temperature for 1.5 hr. To the reaction mixture was added saturated aqueous sodium hydrogen carbonate solution (30 mL), and the mixture was extracted with ethyl acetate (30 mL, 10 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=85/15→70/30), and the fractions containing the object product were concentrated under reduced pressure to give 2-{[3-({[3-(1-cyano-1-methylethyl)phenyl]carbonyl}amino)phenyl](methyl)amino}-5-nitropyrimidin-4-yl thiocyanate as a yellow oil. The obtained compound was used for the next reaction without further purification.

To a suspension of the above-mentioned crude product of 2-{[3-({[3-(1-cyano-1-methylethyl)phenyl]carbonyl}amino)phenyl](methyl)amino}-5-nitropyrimidin-4-yl thiocyanate and reduced iron (368 mg, 6.59 mmol) in ethanol (8 mL)/1-methylpyrrolidin-2-one (2 mL) was added 1N hydrochloric acid (2 mL), and the mixture was stirred at 100° C. for 30 min. The reaction mixture was neutralized with 2N aqueous sodium hydroxide solution (1.5 mL), the insoluble material was filtered off, and the filtrate was concentrated under reduced pressure. To the obtained residue was added saturated aqueous sodium hydrogen carbonate solution (50 mL), and the mixture was extracted with ethyl acetate (50 mL, 2×20 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=30/70→10/90), and the fractions containing the object product were concentrated under reduced pressure. The obtained residue was recrystallized from ethyl acetate to give the title compound (211 mg, 36%) as pale-purple crystals.

$^1$H-NMR (DMSO-d$_6$, 300 MHz) δ 1.75 (6H, s), 3.46 (3H, s), 7.10 (1H, ddd, J=0.9, 2.1, 8.0 Hz), 7.37 (1H, t, J=8.0 Hz), 7.52-7.67 (4H, m), 7.71-7.79 (2H, m), 7.94 (1H, dt, J=7.6, 1.5 Hz), 8.04 (1H, t, J=1.5 Hz), 8.29 (1H, s), 10.33 (1H, br s).

(ii) Production of 3-(1-cyano-1-methylethyl)-N-{3-[{2-[(cyclopropylcarbonyl)amino][1,3]thiazolo[5,4-d]pyrimidin-5-yl}(methyl)amino]phenyl}benzamide To a solution of N-{3-[(2-amino[1,3]thiazolo[5,4-d]pyrimidin-5-yl)(methyl)amino]phenyl}-3-(1-cyano-1-methylethyl)benzamide (151 mg, 340 μmol) in N,N-dimethylacetamide (4 mL) was added cyclopropanecarbonyl chloride (389 μL, 4.32 mmol), and the mixture was stirred at room temperature for 3 hr. To the reaction mixture was added saturated aqueous sodium hydrogen carbonate solution (20 mL), and the mixture was extracted with ethyl acetate (20 mL, 5 mL). The solid which crystallized in the extract was collected by filtration to give the title compound (119 mg, 68%) as colorless crystals.

$^1$H-NMR (DMSO-d$_6$, 300 MHz) δ 0.87-1.04 (4H, m), 1.75 (6H, s), 1.92-2.04 (1H, m), 3.52 (3H, s), 7.13 (1H, ddd, J=0.8, 1.9, 8.1 Hz), 7.40 (1H, t, J=8.1 Hz), 7.60 (1H, t, J=7.7 Hz), 7.66 (1H, ddd, J=0.8, 1.9, 8.1 Hz), 7.72-7.80 (2H, m), 7.94 (1H, dt, J=7.7, 1.5 Hz), 8.04 (1H, t, J=1.5 Hz), 8.73 (1H, s), 10.36 (1H, s), 12.63 (1H, br s).

Example D6

Production of N-(3-{[2-(acetylamino)[1,3]thiazolo[5,4-d]pyrimidin-5-yl](methyl)amino}phenyl)-3-(1-cyano-1-methylethyl)benzamide

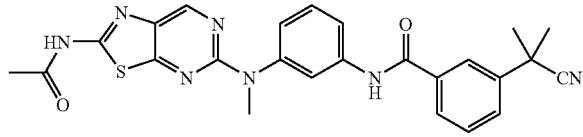

To a solution of N-{3-[(2-amino[1,3]thiazolo[5,4-d]pyrimidin-5-yl)(methyl)amino]phenyl}-3-(1-cyano-1-methylethyl)benzamide (152 mg, 343 μmol) produced in Example D5(i) in pyridine (4 mL) was added acetyl chloride (74 μL, 1.03 mmol), and the mixture was stirred at room temperature for 2 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=50/50→20/80), and the fractions containing the object product were concentrated under reduced pressure. The obtained residue was washed with ethyl acetate to give the title compound (102 mg, 61%) as a pale-purple solid.

$^1$H-NMR (DMSO-d$_6$, 300 MHz) δ 1.75 (6H, s), 2.19 (3H, s), 3.52 (3H, s), 7.13 (1H, ddd, J=0.9, 2.0, 7.9 Hz), 7.40 (1H, t, J=7.9 Hz), 7.60 (1H, t, J=7.9 Hz), 7.66 (1H, ddd, J=0.9, 2.0, 7.9 Hz), 7.72-7.77 (1H, m), 7.78 (1H, t, J=2.0 Hz), 7.94 (1H, dt, J=7.9, 1.5 Hz), 8.04 (1H, t, J=1.5 Hz), 8.73 (1H, s), 10.36 (1H, br s), 12.33 (1H, br s).

Example D7

Production of N-(5-{[3-({[3-(1-cyano-1-methylethyl)phenyl]carbonyl}amino)phenyl](methyl)amino}[1,3]thiazolo[5,4-d]pyrimidin-2-yl)pyridine-3-carboxamide

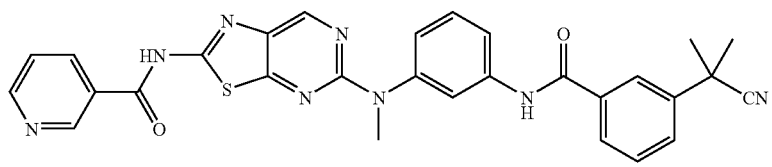 [SMILES: CN(c1cccc(NC(=O)c2cccc(C(C)(C)C#N)c2)c1)c1ncc2nc(NC(=O)c3cccnc3)sc2n1]

To a solution of N-{3-[(2-amino[1,3]thiazolo[5,4-d]pyrimidin-5-yl)(methyl)amino]phenyl}-3-(1-cyano-1-methylethyl)benzamide (150 mg, 338 μmol) produced in Example D5(i) in pyridine (4 mL) was added pyridine-3-carbonyl chloride hydrochloride (362 mg, 2.03 mmol), and the mixture was stirred at room temperature for 3 hr. To the reaction mixture was added saturated aqueous sodium hydrogen carbonate solution (30 mL), and the mixture was extracted with ethyl acetate (30 mL, 10 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=35/65→15/85), and the fractions containing the object product were concentrated under reduced pressure. The obtained residue was recrystallized from methanol, ethyl acetate and hexane to give the title compound (78 mg, 42%) as a orange crystal.

$^1$H-NMR (DMSO-$d_6$, 300 MHz) δ 1.75 (6H, s), 3.55 (3H, s), 7.16 (1H, ddd, J=1.0, 2.0, 8.1 Hz), 7.42 (1H, t, J=8.1 Hz), 7.56-7.64 (2H, m), 7.65-7.69 (1H, m), 7.76 (1H, ddd, J=1.2, 2.0, 8.1 Hz), 7.81 (1H, t, J=2.0 Hz), 7.95 (1H, ddd, J=1.2, 2.0, 8.1 Hz), 8.05 (1H, t, J=1.2 Hz), 8.43 (1H, dt, J=8.1, 2.0 Hz), 8.77-8.86 (2H, m), 9.22 (1H, d, J=1.5 Hz), 10.37 (1H, br s), 13.09 (1H, br s).

Example D8

Production of 3-(1-cyano-1-methylethyl)-N-{3-[methyl(2-{[(2E)-3-phenylprop-2-enoyl]amino}[1,3]thiazolo[5,4-d]pyrimidin-5-yl)amino]phenyl}benzamide

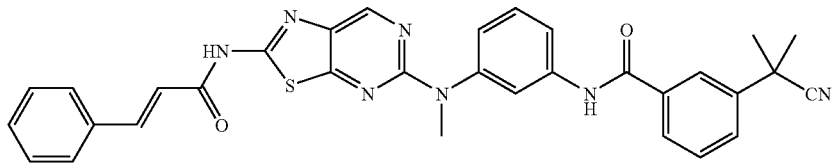 [SMILES: CN(c1cccc(NC(=O)c2cccc(C(C)(C)C#N)c2)c1)c1ncc2nc(NC(=O)/C=C/c3ccccc3)sc2n1]

To a solution of N-{3-[(2-amino[1,3]thiazolo[5,4-d]pyrimidin-5-yl)(methyl)amino]phenyl}-3-(1-cyano-1-methylethyl)benzamide (150 mg, 338 μmol) produced in Example D5(i) in pyridine (4 mL) was added cinnamoyl chloride (141 mg, 845 μmol), and the mixture was stirred at room temperature for 1 hr. To the reaction mixture was added saturated aqueous sodium hydrogen carbonate solution (15 mL), and the mixture was extracted with ethyl acetate (20L, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=30/70→10/90), and the fractions containing the object product were concentrated under reduced pressure. The obtained residue was recrystallized from ethyl acetate to give the title compound (150 mg, 77%) as yellow crystals.

$^1$H-NMR (DMSO-$d_6$, 300 MHz) δ 1.75 (6H, s), 3.54 (3H, s), 6.94 (1H, d, J=15.9 Hz), 7.15 (1H, ddd, J=0.9, 2.0, 8.0 Hz), 7.41 (1H, t, J=8.0 Hz), 7.45-7.51 (3H, m), 7.60 (1H, t, J=7.7 Hz), 7.64-7.70 (3H, m), 7.72-7.82 (3H, m), 7.95 (1H, dt, J=7.7, 1.5 Hz), 8.04 (1H, t, J=1.5 Hz), 8.76 (1H, s), 10.37 (1H, br s), 12.62 (1H, br s).

Example D9

Production of N-(5-{[3-({[3-(1-cyano-1-methylethyl)phenyl]carbonyl}amino)phenyl](methyl)amino}[1,3]thiazolo[5,4-d]pyrimidin-2-yl)-2-methyl-1H-imidazole-5-carboxamide

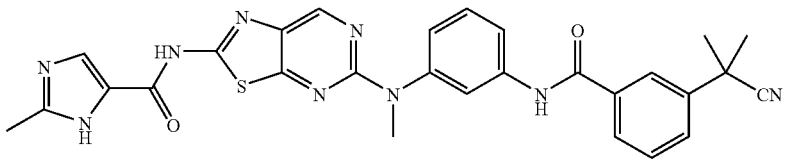 [SMILES: Cc1ncc(C(=O)Nc2nc3cnc(N(C)c4cccc(NC(=O)c5cccc(C(C)(C)C#N)c5)c4)nc3s2)[nH]1]

To a solution of N-{3-[(2-amino[1,3]thiazolo[5,4-d]pyrimidin-5-yl)(methyl)amino]phenyl}-3-(1-cyano-1-methylethyl)benzamide (150 mg, 338 μmol) produced in Example D5(i) in pyridine (4 mL) were added 2-methyl-1H-imidazole-5-carboxylic acid (146 mg, 1.01 mmol) and O-(7-azabenzotriazol-1-yl)-N,N,N',N'-tetramethyluronium hexafluorophosphate (770 mg, 2.03 mmol), and the mixture was stirred at 90° C. for 20 hr. To the reaction mixture was added saturated aqueous sodium hydrogen carbonate solution (15 mL), and the mixture was extracted with ethyl acetate (20 mL, 10 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→90/10), and the fractions containing the object product were concentrated under reduced pressure. The obtained residue was recrystallized from tetrahydrofuran and methanol to give the title compound (122 mg, 65%) as colorless crystals.

$^1$H-NMR (DMSO-$d_6$, 300 MHz) δ 1.75 (6H, s), 2.35 (3H, s), 3.53 (3H, s), 7.15 (1H, ddd, J=0.8, 2.0, 8.1 Hz), 7.41 (1H, t, J=8.1 Hz), 7.60 (1H, t, J=7.9 Hz), 7.64-7.70 (1H, m), 7.76 (1H, ddd, J=1.0, 2.0, 7.9 Hz), 7.79 (1H, t, J=2.0 Hz), 7.95 (1H, ddd, J=1.0, 2.0, 7.9 Hz), 7.97 (1H, s), 8.04 (1H, t, J=2.0 Hz), 8.75 (1H, br s), 10.37 (1H, br s), 11.73 (1H, br s), 12.54 (1H, br s).

Example D10

Production of N-{3-[{2-[(chloroacetyl)amino][1,3]thiazolo[5,4-d]pyrimidin-5-yl}(methyl)amino]phenyl}-3-(1-cyano-1-methylethyl)benzamide

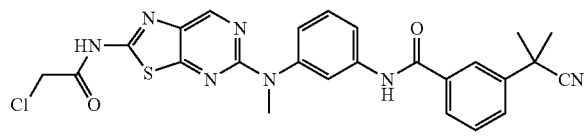 [SMILES: CN(c1cccc(NC(=O)c2cccc(C(C)(C)C#N)c2)c1)c1ncc2nc(NC(=O)CCl)sc2n1]

To a solution of N-{3-[(2-amino[1,3]thiazolo[5,4-d]pyrimidin-5-yl)(methyl)amino]phenyl}-3-(1-cyano-1-methylethyl)benzamide (800 mg, 1.80 mmol) produced in Example D5(i) in N,N-dimethylacetamide (15 mL) was added chloroacetyl chloride (356 μL, 4.50 mmol), and the mixture was stirred at room temperature for 1 hr. To the reaction mixture was added saturated aqueous sodium hydrogen carbonate solution (60 mL), and the mixture was extracted with ethyl acetate (60 mL, 10 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=60/40→30/70), and the fractions containing the object product were concentrated under reduced pressure. The obtained residue was recrystallized from ethyl acetate to give the title compound (823 mg, 88%) as white crystals.

$^1$H-NMR (DMSO-$d_6$, 300 MHz) δ 1.75 (6H, s), 3.53 (3H, s), 4.45 (2H, s), 7.09-7.18 (1H, m), 7.41 (1H, t, J=7.9 Hz), 7.60 (1H, t, J=7.9 Hz), 7.64-7.69 (1H, m), 7.75 (1H, ddd, J=0.9, 1.9, 7.9 Hz), 7.79 (1H, t, J=1.9 Hz), 7.89-7.98 (1H, m), 8.04 (1H, t, J=1.9 Hz), 8.78 (1H, s), 10.36 (1H, br s), 12.72 (1H, br s).

Example D11

Production of 3-(1-cyano-1-methylethyl)-N-{3-[methyl(2-{[(4-methylpiperazin-1-yl)acetyl]amino}[1,3]thiazolo[5,4-d]pyrimidin-5-yl)amino]phenyl}benzamide To a solution of N-{3-[(2-amino[1,3]thiazolo[5,4-d]pyrimidin-5-yl)(methyl)amino]phenyl}-3-(1-cyano-1-methylethyl)benzamide (152 mg, 343 μmol) produced in Example D5(i) in N,N-dimethylacetamide (4 mL) was added chloroacetyl chloride (68 μL, 858 μmol), and the mixture was stirred at room temperature for 1 hr. To the reaction mixture was added saturated aqueous sodium hydrogen carbonate solution (20 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was dissolved in tetrahydrofuran (4 mL), triethylamine (143 μL, 1.03 mmol) and 1-methylpiperazine (115 μL, 1.03 mmol) were added, and the mixture was stirred at 60° C. for 3 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→96/4), and the fractions containing the object product were concentrated under reduced pressure. To the obtained residue were added diisopropyl ether and ethyl acetate and the precipitate was collected by filtration to give the title compound (101 mg, 50%) as a colorless amorphous solid.

$^1$H-NMR (DMSO-$d_6$, 300 MHz) δ 1.75 (6H, s), 2.16 (3H, s), 2.29-2.41 (4H, m), 2.48-2.58 (4H, m), 3.31 (2H, s), 3.52 (3H, s), 7.14 (1H, ddd, J=1.0, 2.0, 7.9 Hz), 7.40 (1H, t, J=7.9 Hz), 7.60 (1H, t, J=7.8 Hz), 7.66 (1H, ddd, J=1.0, 2.0, 7.9 Hz), 7.75 (1H, m), 7.79 (1H, t, J=2.0 Hz), 7.94 (1H, dt, J=7.8, 1.5 Hz), 8.04 (1H, t, J=1.5 Hz), 8.74 (1H, s), 10.36 (1H, br s), 12.06 (1H, br s).

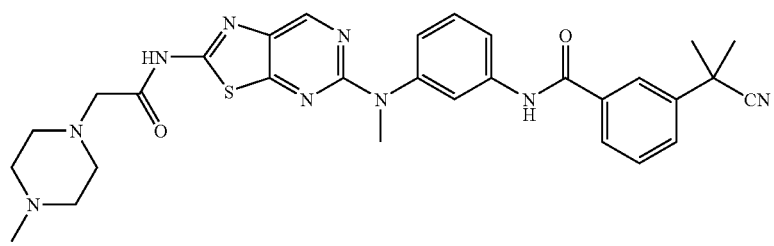 [SMILES: CN1CCN(CC(=O)Nc2nc3cnc(N(C)c4cccc(NC(=O)c5cccc(C(C)(C)C#N)c5)c4)nc3s2)CC1]

Example D12

Production of 3-(1-cyano-1-methylethyl)-N-[3-(methyl{2-[(morpholin-4-ylacetyl)amino][1,3]thiazolo[5,4-d]pyrimidin-5-yl}amino)phenyl]benzamide To a solution of N-{3-[{2-[(chloroacetyl)amino][1,3]thiazolo[5,4-d]pyrimidin-5-yl}(methyl)amino]phenyl}-3-(1-cyano-1-methylethyl)benzamide (141 mg, 271 μmol) produced in Example D10 in tetrahydrofuran (4 mL) were added triethylamine (113 μL, 813 μmol) and thiomorpholine (77 μL, 813 μmol), and the mixture was stirred at 60° C. for 3 hr. To

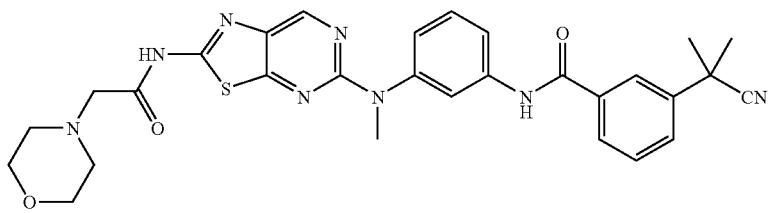

To a solution of N-{3-[{2-[(chloroacetyl)amino][1,3]thiazolo[5,4-d]pyrimidin-5-yl}(methyl)amino]phenyl}-3-(1-cyano-1-methylethyl)benzamide (141 mg, 271 μmol) produced in Example D10 in tetrahydrofuran (4 mL) were added triethylamine (113 μL, 813 μmol) and morpholine (71 μL, 813 μmol), and the mixture was stirred at 60° C. for 4 hr. To the reaction mixture was added saturated aqueous sodium hydrogen carbonate solution (15 mL), and the mixture was extracted with ethyl acetate (15 mL, 10 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0=98/2), and the fractions containing the object product were concentrated under reduced pressure. To the obtained residue were added diisopropyl ether and ethyl acetate, and the precipitate was collected by filtration to give the title compound (101 mg, 50%) as a pale-red amorphous solid.

$^1$H-NMR (DMSO-d$_6$, 300 MHz) δ 1.75 (6H, s), 2.51-2.56 (4H, m), 3.34 (2H, s), 3.53 (3H, s), 3.57-3.65 (4H, m), 7.14 (1H, ddd, J=0.9, 2.0, 8.0 Hz), 7.40 (1H, t, J=8.0 Hz), 7.60 (1H, t, J=7.8 Hz), 7.63-7.69 (1H, m), 7.73-7.78 (1H, m), 7.79 (1H, t, J=2.0 Hz), 7.94 (1H, dt, J=7.8, 1.5 Hz), 8.04 (1H, t, J=1.5 Hz), 8.74 (1H, s), 10.36 (1H, br s), 12.16 (1H, br s).

Example D13

Production of 3-(1-cyano-1-methylethyl)-N-[3-(methyl{2-[(thiomorpholin-4-ylacetyl)amino][1,3]thiazolo[5,4-d]pyrimidin-5-yl}amino)phenyl]benzamide the reaction mixture was added saturated aqueous sodium hydrogen carbonate solution (15 mL), and the mixture was extracted with ethyl acetate (15 mL, 10 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. To the obtained residue were added diisopropyl ether and ethyl acetate, and the obtained precipitate was collected by filtration to give the title compound (117 mg, 73%) as a colorless amorphous solid.

$^1$H-NMR (DMSO-d$_6$, 300 MHz) δ 1.75 (6H, s), 2.59-2.68 (4H, m), 2.75-2.84 (4H, m), 3.38 (2H, s), 3.53 (3H, s), 7.14 (1H, ddd, J=0.9, 2.0, 8.0 Hz), 7.40 (1H, t, J=8.0 Hz), 7.60 (1H, t, J=7.8 Hz), 7.66 (1H, ddd, J=0.9, 2.0, 8.0 Hz), 7.73-7.77 (1H, m), 7.79 (1H, t, J=2.0 Hz), 7.94 (1H, dt, J=7.8, 1.5 Hz), 8.04 (1H, t, J=1.5 Hz), 8.74 (1H, s), 10.36 (1H, br s), 12.08 (1H, br s).

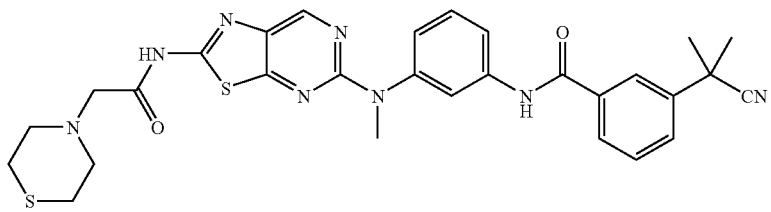 [SMILES: CN(c1cccc(NC(=O)c2cccc(C(C)(C)C#N)c2)c1)c1ncc2nc(NC(=O)CN3CCOCC3)sc2n1]

Example D14

Production of 3-(1-cyano-1-methylethyl)-N-{3-[(2-{[(4-fluoropiperidin-1-yl)acetyl]amino}[1,3]thiazolo[5,4-d]pyrimidin-5-yl)(methyl)amino]phenyl}benzamide

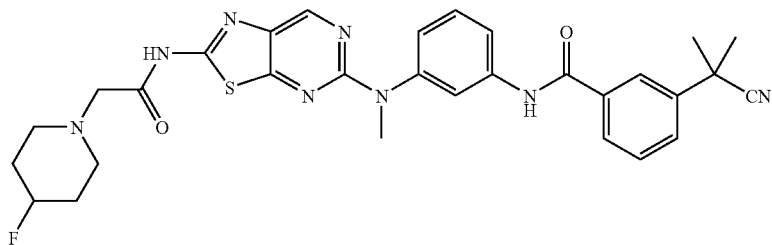 [SMILES: CN(c1cccc(NC(=O)c2cccc(C(C)(C)C#N)c2)c1)c1ncc2nc(NC(=O)CN3CCC(F)CC3)sc2n1]

To a solution of N-{3-[{2-[(chloroacetyl)amino][1,3]thiazolo[5,4-d]pyrimidin-5-yl}(methyl)amino]phenyl}-3-(1-cyano-1-methylethyl)benzamide (140 mg, 269 μmol) produced in Example D10 in tetrahydrofuran (4 mL) were added triethylamine (112 μL, 807 μmol) and 4-fluoropiperidine hydrochloride (113 mg, 807 μmol), and the mixture was stirred at 60° C. for 20 hr. To the reaction mixture was added saturated aqueous sodium hydrogen carbonate solution (10 mL), and the mixture was extracted with ethyl acetate (15 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=40/60→20/80), and the fractions containing the object product were concentrated under reduced pressure. The obtained residue was recrystallized from ethyl acetate and hexane to give the title compound (79 mg, 50%) as colorless crystals.

$^1$H-NMR (DMSO-d$_6$, 300 MHz) δ 1.75 (6H, s), 1.77-1.97 (4H, m), 2.41-2.74 (4H, m), 3.35 (2H, s), 3.52 (3H, s), 4.53-4.83 (1H, m), 7.14 (1H, ddd, J=0.9, 2.0, 8.0 Hz), 7.40 (1H, t, J=8.0 Hz), 7.60 (1H, t, J=7.9 Hz), 7.66 (1H, ddd, J=0.9, 2.0, 8.0 Hz), 7.76 (1H, ddd, J=1.0, 1.7, 7.9 Hz), 7.79 (1H, t, J=2.0 Hz), 7.94 (1H, ddd, J=1.0, 1.7, 7.9 Hz), 8.04 (1H, t, J=1.7 Hz), 8.74 (1H, s), 10.36 (1H, br s), 12.10 (1H, br s).

Example D15

Production of 3-(1-cyano-1-methylethyl)-N-{3-[(2-{[(1,1-dioxidothiomorpholin-4-yl)acetyl]amino}[1,3]thiazolo[5,4-d]pyrimidin-5-yl)(methyl)amino]phenyl}benzamide

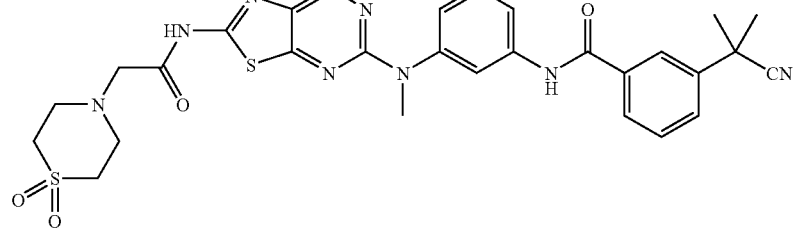

To a solution of N-{3-[{2-[(chloroacetyl)amino][1,3]thiazolo[5,4-d]pyrimidin-5-yl}(methyl)amino]phenyl}-3-(1-cyano-1-methylethyl)benzamide (140 mg, 269 μmol) produced in Example D10 in tetrahydrofuran (4 mL) were added triethylamine (112 μL, 807 μmol) and thiomorpholine 1,1-dioxide (109 mg, 807 μmol), and the mixture was stirred at 60° C. for 16 hr. To the reaction mixture was added saturated aqueous sodium hydrogen carbonate solution (10 mL), and the mixture was extracted with ethyl acetate (15 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=40/60→20/80), and the fractions containing the object product were concentrated under reduced pressure. The obtained residue was recrystallized from ethanol to give the title compound (94 mg, 56%) as a colorless solid.

$^1$H-NMR (DMSO-d$_6$, 300 MHz) δ 1.75 (6H, s), 3.02-3.22 (8H, m), 3.52 (3H, s), 3.57 (2H, s), 7.10-7.16 (1H, m), 7.40 (1H, t, J=8.0 Hz), 7.60 (1H, t, J=7.8 Hz), 7.63-7.68 (1H, m), 7.76 (1H, ddd, J=0.9, 1.7, 7.8 Hz), 7.79 (1H, t, J=1.9 Hz), 7.91-7.97 (1H, m), 8.04 (1H, t, J=1.7 Hz), 8.73 (1H, s), 10.36 (1H, br s), 12.23 (1H, br s).

Example D16

Production of 3-(1-cyano-1-methylethyl)-N-{3-[(2-{[(4,4-difluoropiperidin-1-yl)acetyl]amino}[1,3]thiazolo[5,4-d]pyrimidin-5-yl)(methyl)amino]phenyl}benzamide

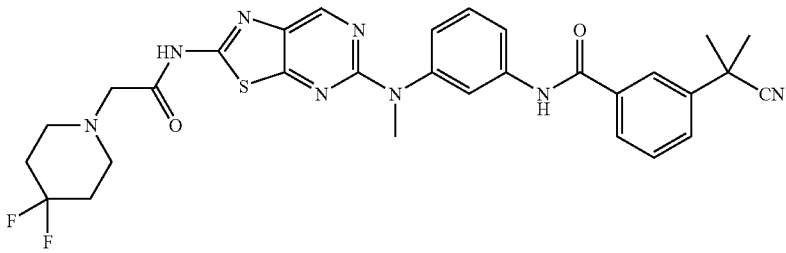 [SMILES: CN(c1cccc(NC(=O)c2cccc(C(C)(C)C#N)c2)c1)c1ncc2nc(NC(=O)CN3CCC(F)(F)CC3)sc2n1]

To a solution of N-{3-[(2-amino[1,3]thiazolo[5,4-d]pyrimidin-5-yl)(methyl)amino]phenyl}-3-(1-cyano-1-methylethyl)benzamide (152 mg, 343 μmol) produced in Example D5(i) in N,N-dimethylacetamide (4 mL) was added chloroacetyl chloride (68 μL, 858 μmol), and the mixture was stirred at room temperature for 2 hr. To the reaction mixture was added saturated aqueous sodium hydrogen carbonate solution (10 mL), and the mixture was extracted with ethyl acetate (15 mL, 5 mL). The combined organic layer was washed with saturated brine (5 mL), and dried over anhydrous sodium sulfate. The insoluble material was filtered off, and the filtrate was concentrated under reduced pressure. The obtained residue was dissolved in tetrahydrofuran (4 mL), triethylamine (143 μL, 1.03 mmol) and 4,4-difluoropiperidine hydrochloride (162 mg, 1.03 mmol) were added, and the mixture was stirred at 60° C. for 15 hr. To the reaction mixture was added saturated aqueous sodium hydrogen carbonate solution (10 mL), and the mixture was extracted with ethyl acetate (15 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=40/60→20/80), and the fractions containing the object product were concentrated under reduced pressure. The obtained residue was recrystallized from ethyl acetate and hexane to give the title compound (127 mg, 61%) as pale-red crystals.

$^1$H-NMR (DMSO-d$_6$, 300 MHz) δ 1.75 (6H, s), 1.92-2.07 (4H, m), 2.62-2.72 (4H, m), 3.44 (2H, s), 3.52 (3H, s), 7.14 (1H, ddd, J=0.8, 2.0, 8.0 Hz), 7.40 (1H, t, J=8.0 Hz), 7.60 (1H, t, J=7.8 Hz), 7.65 (1H, ddd, J=0.8, 2.0, 8.0 Hz), 7.74-7.78 (1H, m), 7.79 (1H, t, J=2.0 Hz), 7.94 (1H, dt, J=7.8, 1.5 Hz), 8.04 (1H, t, J=1.5 Hz), 8.74 (1H, s), 10.36 (1H, br s), 12.19 (1H, br s).

Example D17

Production of N-(5-{[2-(acetylamino)[1,3]thiazolo[5,4-d]pyrimidin-5-yl](methyl)amino}-2-fluorophenyl)-3-(1-cyano-1-methylethyl)benzamide

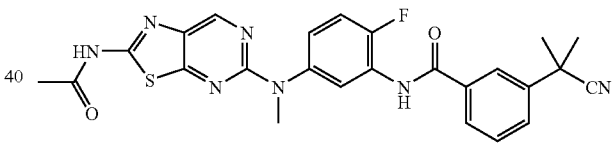

(i) Production of tert-butyl(5-amino-2-fluorophenyl)carbamate

A mixture of 2-fluoro-5-nitroaniline (28.7 g, 184 mmol) and di-tert-butyl bicarbonate (100 g, 461 mmol) was stirred at 80° C. for 24 hr. The reaction mixture was directly purified by basic silica gel column chromatography (hexane/ethyl acetate=100/0→90/10), and the fractions containing the object product were concentrated under reduced pressure to give a mixture of tert-butyl(2-fluoro-5-nitrophenyl)carbamate and di-tert-butyl(2-fluoro-5-nitrophenyl)imidodicarbonate as a yellow oil. The obtained compound was used for the next reaction without further purification.

To a solution of the above-mentioned crude product of a mixture of tert-butyl(2-fluoro-5-nitrophenyl)carbamate and di-tert-butyl(2-fluoro-5-nitrophenyl)imidodicarbonate in ethanol (600 mL)/tetrahydrofuran (60 mL) was added 10% palladium-carbon (12.0 g), and the mixture was stirred at room temperature under a hydrogen atmosphere (1 atm) for 24 hr. The insoluble material was filtered off, and the filtrate was concentrated under reduced pressure. To a solution of the obtained residue in methanol (200 mL)/tetrahydrofuran (50 mL) was added potassium carbonate (25.4 g, 184 mmol), and the mixture was stirred at 60° C. for 4 hr. The insoluble material was filtered off, and the filtrate was concentrated under reduced pressure. To the obtained residue was added water (200 mL), and the mixture was extracted with ethyl acetate (300 mL, 100 mL). The combined organic layer was washed with saturated brine (100 mL), and dried over anhydrous sodium sulfate. The insoluble material was filtered off, and the filtrate was concentrated under reduced pressure. The obtained residue was recrystallized from ethyl acetate and hexane to give the title compound (26.4 g, 63%) as pale-brown crystals.

$^1$H-NMR (DMSO-d$_6$, 300 MHz) δ 1.44 (9H, s), 4.90 (2H, br s), 6.23 (1H, ddd, J=2.7, 4.0, 8.8 Hz), 6.80 (1H, dd, J=8.8, 10.9 Hz), 6.84 (1H, dd, J=2.7, 6.9 Hz), 8.57 (1H, br s).

(ii) Production of tert-butyl
[2-fluoro-5-(methylamino)phenyl]carbamate

To a solution of tert-butyl(5-amino-2-fluorophenyl)carbamate (10.0 g, 44.2 mmol) in tetrahydrofuran (60 mL) was added a mixture of formic acid (8.34 mL, 221 mmol) and acetic anhydride (5.01 mL, 53.0 mmol), and the mixture was stirred at room temperature for 16 hr. To the reaction mixture was added saturated aqueous sodium hydrogen carbonate solution (100 mL), and the mixture was extracted with ethyl acetate (100 mL, 30 mL). The combined organic layer was washed with saturated brine (10 mL), filtered through a silica gel pad, and the filtrate was concentrated under reduced pressure to give tert-butyl [2-fluoro-5-(formylamino)phenyl]carbamate as a brown oil. The obtained compound was used for the next reaction without further purification.

To a solution of the above-mentioned crude product of tert-butyl [2-fluoro-5-(formylamino)phenyl]carbamate in tetrahydrofuran (100 mL) was added borane dimethylsulfide complex (11.7 mL, 111 mmol), and the mixture was stirred at room temperature for 1.5 hr. To the reaction mixture were successively added methanol (20 mL) and acetic acid (10 mL), and the mixture was stirred at room temperature for 30 min. The reaction mixture was concentrated under reduced pressure. To the obtained residue was added saturated aqueous sodium hydrogen carbonate solution (100 mL), and the mixture was extracted with ethyl acetate (100 mL, 30 mL). The combined organic layer was washed with saturated brine (20 mL), and dried over anhydrous sodium sulfate. The insoluble material was filtered off, and the filtrate was concentrated under reduced pressure. The obtained residue was purified by silica gel column chromatography (hexane/ethyl acetate=100/0→90/10), and the fractions containing the object product were concentrated under reduced pressure to give the title compound (7.80 g, 73%) as a yellow oil.

$^1$H-NMR (DMSO-d$_6$, 300 MHz) δ 1.45 (9 H, s), 2.61 (3H, d, J=4.8 Hz), 5.52 (1H, q, J=4.8 Hz), 6.20 (1H, ddd, J=2.6, 3.2, 9.0 Hz), 6.81 (1H, dd, J=2.6, 6.6 Hz), 6.89 (1H, dd, J=9.0, 10.4 Hz), 8.63 (1H, br s).

(iii) Production of tert-butyl {5-[(2-amino[1,3]thiazolo[5,4-d]pyrimidin-5-yl)(methyl)amino]-2-fluorophenyl}carbamate To a suspension of 2-chloro-5-nitropyrimidin-4-yl thiocyanate (2.73 g, 12.6 mmol) and sodium hydrogen carbonate (2.76 g, 32.9 mmol) in tetrahydrofuran (80 mL) was added a solution of tert-butyl [2-fluoro-5-(methylamino)phenyl]carbamate (2.63 g, 11.0 mmol) produced above in tetrahydrofuran (20 mL), and the mixture was stirred for 1.5 hr. To the reaction mixture was added water (100 mL), and the mixture was extracted with ethyl acetate (100 mL, 30 mL). The combined organic layer was washed with saturated brine (20 mL), and dried over anhydrous sodium sulfate. The insoluble material was filtered off, and the filtrate was concentrated under reduced pressure to give tert-butyl {2-fluoro-5-[methyl(5-nitro-4-thiocyanatopyrimidin-2-yl)amino] phenyl}carbamate as a yellow amorphous solid. The obtained compound was used for the next reaction without further purification.

To a solution of the above-mentioned crude product of tert-butyl {2-fluoro-5-[methyl(5-nitro-4-thiocyanatopyrimidin-2-yl)amino]phenyl}carbamate in acetic acid (70 mL) was added reduced iron (4.28 g, 76.7 mmol), and the mixture was stirred at 80° C. for 3 hr. The insoluble material was filtered off, and the filtrate was concentrated under reduced pressure. To the obtained residue was added 0.5N aqueous sodium hydroxide solution (100 mL), and the mixture was extracted with ethyl acetate (200 mL, 30 mL). The combined organic layer was washed with saturated brine (30 mL), and dried over anhydrous sodium sulfate. The insoluble material was filtered off, and the filtrate was concentrated under reduced pressure. The obtained residue was washed with tetrahydrofuran to give the title compound (1.95 g, 46%) as a pale-purple solid.

$^1$H-NMR (DMSO-d$_6$, 300 MHz) δ 1.45 (9H, s), 3.39 (3H, s), 7.04 (1H, ddd, J=2.6, 4.3, 8.8 Hz), 7.19 (1H, dd, J=8.8, 10.5 Hz), 7.54 (1H, dd, J=2.6, 7.2 Hz), 7.58 (2 H, br s), 8.26 (1H, s), 9.00 (1H, br s).

(iv) Production of N-{5-[(3-amino-4-fluorophenyl)(methyl)amino][1,3]thiazolo[5,4-d]pyrimidin-2-yl}acetamide To a solution of tert-butyl {5-[(2-amino[1,3]thiazolo[5,4-d]pyrimidin-5-yl)(methyl)amino]-2-fluorophenyl}carbamate (833 mg, 2.13 mmol) in pyridine (20 mL) was added acetyl chloride (533 μL, 7.46 mmol), and the mixture was stirred at room temperature for 1.5 hr. To the reaction mixture was added saturated aqueous sodium hydrogen carbonate solution (50 mL), and the mixture was extracted with ethyl acetate (50 mL, 15 mL). The combined organic layer was washed with saturated brine (30 mL), and dried over anhydrous sodium sulfate. The insoluble material was filtered off, and the filtrate was concentrated under reduced pressure to give tert-butyl(5-{[2-(acetylamino)[1,3]thiazolo[5,4-d]pyrimidin-5-yl]methyl)amino}-2-fluorophenyl)carbamate as a red amorphous solid. The obtained compound was used for the next reaction without further purification.

A solution of the above-mentioned crude product of tert-butyl(5-{[2-(acetylamino)[1,3]thiazolo[5,4-d]pyrimidin-5-yl](methyl)amino}-2-fluorophenyl)carbamate and anisole (1.5 mL) in trifluoroacetic acid (15 mL) was stirred at 0° C. for 2 hr. The reaction mixture was concentrated under reduced pressure, to the obtained residue was added saturated aqueous sodium hydrogen carbonate solution (50 mL), and the mixture was extracted with ethyl acetate/tetrahydrofuran mixture (1:1, 50 mL, 20 mL). The combined organic layer was washed with saturated brine (10 mL), and dried over anhydrous sodium sulfate. The insoluble material was filtered off, and the filtrate was concentrated under reduced pressure. The obtained residue was washed with ethyl acetate to give the title compound (638 mg, 90%) as a gray solid.

$^1$H-NMR (DMSO-$d_6$, 300 MHz) δ 2.18 (3H, s), 3.41 (3H, s), 5.17 (2H, br s), 6.45 (1H, ddd, J=2.6, 4.0, 8.5 Hz), 6.70 (1H, dd, J=2.6, 8.3 Hz), 6.99 (1H, dd, J=8.5, 11.3 Hz), 8.69 (1H, s), 12.31 (1H, br s).

(v) Production of N-(5-{[2-(acetylamino)[1,3]thiazolo[5,4-d]pyrimidin-5-yl](methyl)amino}-2-fluorophenyl)-3-(1-cyano-1-methylethyl)benzamide A solution of N-{5-[(3-amino-4-fluorophenyl)(methyl)amino][1,3]thiazolo[5,4-d]pyrimidin-2-yl}acetamide (100 mg, 301 μmol), 3-(1-cyano-1-methylethyl)benzoic acid (172 mg, 902 μmol) and O-(7-azabenzotriazol-1-yl)-N,N,N',N'-tetramethyluronium hexafluorophosphate (342 mg, 902 μmol) in pyridine (4 mL) was stirred at 90° C. for 5 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→97/3), and the fractions containing the object product were concentrated under reduced pressure. The obtained residue was recrystallized from ethyl acetate to give the title compound (67 mg, 44%) as colorless crystals.

$^1$H-NMR (DMSO-$d_6$, 300 MHz) δ 1.75 (6H, s), 2.19 (3H, s), 3.51 (3H, s), 7.25-7.36 (2H, m), 7.56-7.65 (2H, m), 7.77 (1H, ddd, J=7.9, 2.0, 1.0 Hz), 7.96 (1H, dt, J=7.8, 1.5 Hz), 8.09 (1H, t, J=1.5 Hz), 8.73 (1H, s), 10.28 (1H, br s), 12.34 (1H, br s).

Example D18

Production of N-(5-{[2-(acetylamino)[1,3]thiazolo[5,4-d]pyrimidin-5-yl](methyl)amino}-2-fluorophenyl)-2-chloro-3-(1-cyano-1-methylethyl)benzamide

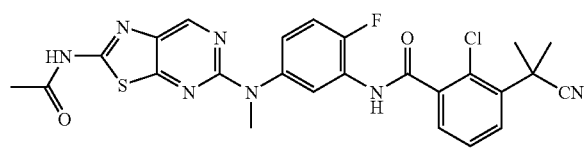 [SMILES: CC(=O)Nc1nc2cnc(N(C)c3ccc(F)c(NC(=O)c4cccc(C(C)(C)C#N)c4Cl)c3)nc2s1]

(i) Production of methyl 2-chloro-3-methylbenzoate

A mixture of 2-chloro-3-methylbenzoic acid (25.0 g, 146 mmol), conc. sulfuric acid (2 mL), and methanol (160 mL) was stirred at 80° C. for 3 hr. The reaction mixture was concentrated, and diluted with ethyl acetate and neutralized with 8N aqueous sodium hydroxide solution. The organic layer was separated, washed with saturated brine, dried over anhydrous magnesium sulfate, and filtered through a basic silica gel pad. The filtrate was concentrated under reduced pressure to give the title compound (18.0 g, 66%) as a pale-orange oil. The obtained compound was used for the next reaction without further purification.

$^1$H-NMR (CDCl$_3$, 300 MHz) δ 2.42 (3H, s), 3.93 (3H, s), 7.19 (1H, t, J=7.6 Hz), 7.32-7.38 (1H, m), 7.56 (1H, dd, J=1.2, 7.6 Hz).

(ii) Production of methyl 3-(bromomethyl)-2-chlorobenzoate

To a solution of methyl 2-chloro-3-methylbenzoate (3.60 g, 19.4 mmol) in acetonitrile (60 mL) were added 1-bromopyrrolidine-2,5-dione (11.46 g, 64.3 mmol) and 2,2'-(E)-diazen-1,2-diylbis(2-methylpropanenitrile) (960 mg, 5.84 mmol), and the mixture was stirred at 90° C. for 26 hr. The insoluble material was filtered off from the reaction mixture, and the filtrate was concentrated under reduced pressure. The obtained residue was purified by silica gel column chromatography (hexane/ethyl acetate=100/0→95/5), and the fractions containing the object product were concentrated under reduced pressure to give the title compound (3.42 g, 66%) as a colorless oil.

$^1$H-NMR (CDCl$_3$, 300 MHz) δ 3.94 (3H, s), 4.64 (2H, s), 7.31 (1H, t, J=7.7 Hz), 7.58 (1H, dd, J=1.7, 7.7 Hz), 7.71 (1H, dd, J=1.7, 7.7 Hz).

(iii) Production of methyl 2-chloro-3-(cyanomethyl)benzoate

To a solution of methyl 3-(bromomethyl)-2-chlorobenzoate (748 mg, 2.84 mmol) in N,N-dimethylformamide (7 mL) was added sodium cyanate (412 mg, 8.41 mmol), and the mixture was stirred at 80° C. for 1 hr. The reaction mixture was diluted with a mixed solvent of ethyl acetate/hexane (1:1). The solution was washed with water and saturated brine, and dried over anhydrous magnesium sulfate. The insoluble material was filtered off, and the filtrate was concentrated under reduced pressure. The obtained residue was purified by silica gel column chromatography (ethyl acetate/hexane=2/98→20/80), and the fractions containing the object product were concentrated under reduced pressure. The obtained residue was recrystallized from ethyl acetate and hexane to give the title compound (470 mg, 79%) as white crystals.

$^1$H-NMR (CDCl$_3$, 300 MHz) δ 3.91 (2H, s), 3.95 (3H, s), 7.39 (1H, t, J=7.8 Hz), 7.66-7.72 (1H, m), 7.76-7.81 (1H, m).

(iv) Production of methyl 2-chloro-3-(1-cyano-1-methylethyl)benzoate

A solution of methyl 2-chloro-3-(cyanomethyl)benzoate (30.0 g, 143 mmol) in dimethylsulfoxide (300 mL) was cooled to 15° C., 60% sodium hydride (17.3 g, 432 mmol) was added by small portions, and the mixture was stirred at room temperature for 30 min. To the suspension was dropwise added methyl iodide (27 mL, 434 mmol) at 15° C. over 15 min, and the mixture was stirred at room temperature for 15 hr. To the reaction mixture was added saturated aqueous ammonium chloride solution (300 mL), and the mixture was extracted with diethyl ether/ethyl acetate mixture (1:1, 3×300 mL). The combined organic layer was washed m successively with water (200 mL) and saturated brine (100 mL), and dried over anhydrous magnesium sulfate. The insoluble material was filtered off, and the filtrate was concentrated under reduced pressure. The obtained residue was purified by silica gel column chromatography (hexane/ethyl acetate=95/5→50/50), and the fractions containing the object product were concentrated under reduced pressure to give the title compound (27.1 g, 80%) as a pale-yellow oil.

$^1$H-NMR (CDCl$_3$, 300 MHz) δ 1.90 (6H, s), 3.95 (3H, s), 7.36 (1H, dd, J=7.6, 8.1 Hz), 7.56-7.67 (2H, m).

(v) Production of 2-chloro-3-(1-cyano-1-methylethyl)benzoic acid

To a solution of methyl 2-chloro-3-(1-cyano-1-methylethyl)benzoate (1.67 g, 7.02 mmol) in tetrahydrofuran (24 mL)/methanol (8 mL)/water (8 mL) was added lithium hydroxide-monohydrate (501 mg, 11.9 mmol), and the mixture was stirred at room temperature for 2 hr. The reaction mixture was concentrated under reduced pressure, and 6N hydrochloric acid (2.8 mL) was added dropwise to the residue. The precipitate was collected by filtration, and washed with water to give the title compound (1.43 g, 91%) as a white powder.

$^1$H-NMR (CDCl$_3$, 300 MHz) δ 1.92 (6H, s), 7.41 (1H, t, J=7.8 Hz), 7.67 (1H, dd, J=1.6, 7.8 Hz), 7.85 (1H, dd, J=1.6, 7.8 Hz).

(vi) Production of N-(5-{[2-(acetylamino)[1,3]thiazolo[5,4-d]pyrimidin-5-yl](methyl)amino}-2-fluorophenyl)-2-chloro-3-(1-cyano-1-methylethyl)benzamide A solution of N-{5-[(3-amino-4-fluorophenyl)(methyl)amino][1,3]thiazolo[5,4-d]pyrimidin-2-yl}acetamide (100 mg, 301 μmol) produced in Example D17(iv), 2-chloro-3-(1-cyano-1-methylethyl)benzoic acid (202 mg, 902 μmol) and O-(7-azabenzotriazol-1-yl)-N,N,N',N'-tetramethyluronium hexafluorophosphate (342 mg, 902 μmol) in pyridine (4 mL) was stirred at 90° C. for 5 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=10/90→0/100) and silica gel column chromatography (hexane/ethyl acetate=40/60→10/90), and the fractions containing the object product were concentrated under reduced pressure. The obtained residue was recrystallized from ethyl acetate to give the title compound (84 mg, 52%) as colorless crystals.

$^1$H-NMR (DMSO-d$_6$, 300 MHz) δ 1.85 (6H, s), 2.19 (3H, s), 3.51 (3H, s), 7.25 (1H, ddd, J=2.5, 4.6, 8.9 Hz), 7.34 (1H, dd, J=8.9, 10.2 Hz), 7.52 (1H, t, J=7.7 Hz), 7.59 (1H, dd, J=1.8, 7.7 Hz), 7.66 (1H, dd, J=1.8, 7.7 Hz), 7.86 (1H, dd, J=2.5, 7.0 Hz), 8.73 (1H, s), 10.52 (1H, br s), 12.35 (1H, br s).

Example D19

Production of N-(5-{[2-(acetylamino)[1,3]thiazolo[5,4-d]pyrimidin-5-yl](methyl)amino}-2-fluorophenyl)-2-chloro-3-(1-cyanocyclopropyl)benzamide

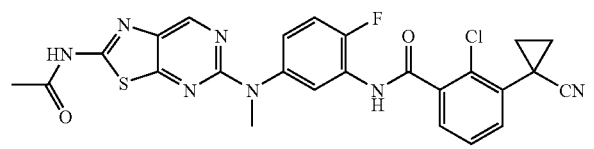 [SMILES: CC(=O)Nc1nc2cnc(N(C)c3ccc(F)c(NC(=O)c4cccc(C5(C#N)CC5)c4Cl)c3)nc2s1]

(i) Production of methyl 2-chloro-3-(1-cyanocyclopropyl)benzoate

A solution of methyl 2-chloro-3-(cyanomethyl)benzoate (20.0 g, 95.3 mmol) produced in Example D18(iii) in dimethylsulfoxide (200 mL) was cooled to 15° C., 60% sodium hydride (11.6 g, 289 mmol) was added by small portions, and the mixture was stirred at room temperature for 30 min. To the suspension was added dropwise 1,2-dibromoethane (16.5 mL, 191 mmol) at 15° C. over 10 min, and the mixture was stirred at room temperature for 4 hr. To the reaction mixture was added saturated aqueous ammonium chloride solution (200 mL), and the mixture was extracted with diethyl ether/ethyl acetate (1:1, 3×200 mL). The combined organic layer was washed successively with water (200 mL) and saturated brine (100 mL), and dried over anhydrous magnesium sulfate. The insoluble material was filtered off, and the filtrate was concentrated under reduced pressure. The obtained residue was purified by silica gel column chromatography (hexane/ethyl acetate=95/5→65/35) to give the title compound (13.5 g, 60%) as a white powder.

$^1$H-NMR (CDCl$_3$, 300 MHz) δ 1.31-1.41 (2H, m), 1.75-1.85 (2H, m), 3.96 (3H, s), 7.32 (1H, t, J=7.7 Hz), 7.49 (1H, dd, J=1.7, 7.7 Hz), 7.74 (1H, dd, J=1.7, 7.7 Hz).

(ii) Production of 2-chloro-3-(1-cyanocyclopropyl)benzoic acid

To a solution of methyl 2-chloro-3-(1-cyanocyclopropyl)benzoate (13.5 g, 57.3 mmol) in tetrahydrofuran (180 mL)/methanol (60 mL)/water (60 mL) was added lithium hydroxide monohydrate (3.62 g, 86.3 mmol), and the mixture was stirred at room temperature for 2 hr. The reaction mixture was concentrated under reduced pressure, and to the obtained residue was dropwise added 6N hydrochloric acid (20 mL). The precipitate was collected by filtration, and washed with water to give the title compound (11.4 g, 90%) as white crystals.

$^1$H-NMR (DMSO-d$_6$, 300 MHz) δ 1.40-1.50 (2H, m), 1.72-1.85 (2H, m), 7.45 (1H, t, J=7.7 Hz), 7.68 (1H, dd, J=1.7, 7.7 Hz), 7.73 (1H, dd, J=1.7, 7.7 Hz), 13.60 (1H, br s).

(iii) Production of N-(5-{[2-(acetylamino)[1,3]thiazolo[5,4-d]pyrimidin-5-yl](methyl)amino}-2-fluorophenyl)-2-chloro-3-(1-cyanocyclopropyl)benzamide A solution of N-{5-[(3-amino-4-fluorophenyl)(methyl)amino][1,3]thiazolo[5,4-d]pyrimidin-2-yl}acetamide (100 mg, 301 μmol) produced in Example D17(iv), 2-chloro-3-(1-cyanocyclopropyl)benzoic acid (167 mg, 753 μmol) and O-(7-azabenzotriazol-1-yl)-N,N,N',N'-tetramethyluronium hexafluorophosphate (286 mg, 753 μmol) in pyridine (4 mL) was stirred at 90° C. for 3 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100) and silica gel column chromatography (hexane/ethyl acetate=40/60→20/80), and the fractions containing the object product were concentrated under reduced pressure. The obtained residue was recrystallized from ethyl acetate to give the title compound (79 mg, 49%) as colorless crystals.

$^1$H-NMR (DMSO-d$_6$, 300 MHz) δ 1.38-1.53 (2H, m), 1.76-1.80 (2H, m), 2.19 (3H, s), 3.51 (3H, s), 7.25 (1H, ddd, J=2.5, 4.5, 8.9 Hz), 7.34 (1H, dd, J=8.9, 9.9 Hz), 7.48 (1H, t, J=7.5 Hz), 7.60 (1H, dd, J=1.5, 7.5 Hz), 7.65 (1H, dd, J=1.5, 7.5 Hz), 7.87 (1H, dd, J=2.5, 6.9 Hz), 8.74 (1H, s), 10.49 (1H, br s), 12.35 (1H, br s).

Example D20

Production of N-(5-{[2-(acetylamino)[1,3]thiazolo[5,4-d]pyrimidin-5-yl](methyl)amino}-2-fluorophenyl)-3-(1,1-dimethylprop-2-yn-1-yl)benzamide

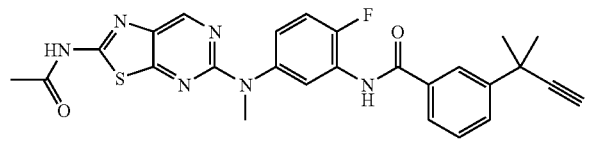 [SMILES: C#CC(C)(C)c1cccc(C(=O)Nc2cc(N(C)c3ncc4nc(NC(C)=O)sc4n3)ccc2F)c1]

(i) Production of 3-(1,1-dimethyl-2-oxoethyl)benzoic acid

To a solution of 3-(1-cyano-1-methylethyl)benzoic acid (8.60 g, 45.5 mmol) in toluene (60 mL)/tetrahydrofuran (40 mL) was added dropwise a 1.0M solution of diisobutylaluminum hydride in hexane (100 mL, 100 mmol) at −78° C. over 1 hr. After the completion of the dropwise addition, the mixture was stirred at −78° C. for 1 hr and at 0° C. for 1 hr. The reaction mixture was poured into a mixture of ethyl acetate (200 mL) and 3N hydrochloric acid (300 mL), and the organic layer and the aqueous layer were separated and the aqueous layer was extracted with ethyl acetate (2×100 mL). The combined organic layer was washed with saturated brine (50 mL), and dried over anhydrous magnesium sulfate. The insoluble material was filtered off, and the filtrate was concentrated under reduced pressure. The obtained residue was recrystallized from ethyl acetate and hexane to give the title compound (6.39 g, 73%) as colorless crystals.

$^1$H-NMR (DMSO-d$_6$, 300 MHz) δ 1.43 (6H, s), 7.53 (1H, dt, J=0.6, 7.5 Hz), 7.58 (1H, dt, J=7.5, 1.6 Hz), 7.83-7.85 (1H, m), 7.88 (1H, dt, J=7.5, 1.6 Hz), 9.54 (1H, s), 13.06 (1H, br s).

(ii) Production of methyl 3-(1,1-dimethylprop-2-yn-1-yl)benzoate

To a solution of 3-(1,1-dimethyl-2-oxoethyl)benzoic acid (3.50 g, 18.2 mmol) in acetone (60 mL) were added potassium carbonate (3.78 g, 27.3 mmol) and methyl iodide (3.40 mL, 54.6 mmol), and the mixture was stirred at 60° C. for 5 hr. The insoluble material was filtered off, and the filtrate was concentrated under reduced pressure. To the obtained residue was added saturated aqueous sodium hydrogen carbonate solution (50 mL), and the mixture was extracted with ethyl acetate (100 mL, 30 mL). The combined organic layer was washed with saturated brine (20 mL), and dried over anhydrous magnesium sulfate. The insoluble material was filtered off, and the filtrate was concentrated under reduced pressure to give methyl 3-(1,1-dimethyl-2-oxoethyl)benzoate as a yellow oil.

To a suspension of p-acetamidobenzenesulfonyl azide (5.25 g, 21.9 mmol) and potassium carbonate (7.55 g, 54.6 mmol) in acetonitrile (100 mL) was added dimethyl (2-oxopropyl)phosphonate (3.00 mL, 21.9 mmol), and the mixture was stirred at room temperature for 2 hr. Then, to the reaction mixture was added a solution of methyl 3-(1,1-dimethyl-2-oxoethyl)benzoate in methanol (20 mL), and the mixture was stirred at room temperature for 16 hr. The insoluble material was filtered off, and the filtrate was concentrated under reduced pressure. To the obtained residue was added saturated aqueous sodium hydrogen carbonate solution (70 mL), and the mixture was extracted with ethyl acetate (100 mL). The combined organic layer was washed with saturated brine (20 mL), and dried over anhydrous magnesium sulfate. The insoluble material was filtered off, and the filtrate was concentrated under reduced pressure. The obtained residue was purified by basic silica gel column chromatography (hexane/ethyl acetate=100/0→90/10), and the fractions containing the object product were concentrated under reduced pressure to give the title compound (2.26 g, 61%) as a colorless oil.

$^1$H-NMR (DMSO-d$_6$, 300 MHz) δ 1.56 (6H, s), 3.34 (1H, s), 3.86 (3H, s), 7.51 (1H, dt, J=0.6, 7.8 Hz), 7.80-7.88 (2H, m), 8.17 (1H, dt, J=0.6, 1.8 Hz).

(iii) Production of 3-(1,1-dimethylprop-2-yn-1-yl)benzoic acid

To a solution of methyl 3-(1,1-dimethylprop-2-yn-1-yl)benzoate (2.26 g, 11.2 mmol) in methanol (15 mL)/tetrahydrofuran (10 mL) was added 2N aqueous sodium hydroxide solution (11.2 mL, 22.4 mmol), and the mixture was stirred at 60° C. for 3 hr. The reaction mixture was neutralized with 6N hydrochloric acid (5 mL), 1N hydrochloric acid (50 mL) was added, and the mixture was extracted with ethyl acetate (100 mL, 20 mL). The combined organic layer was washed with saturated brine (10 mL), and dried over anhydrous magnesium sulfate. The insoluble material was filtered off, and the filtrate was concentrated under reduced pressure. The obtained residue was recrystallized from ethyl acetate and hexane to give the title compound (1.94 g, 92%) as colorless crystals.

$^1$H-NMR (DMSO-d$_6$, 300 MHz) δ 1.56 (6H, s), 3.33 (1H, s), 7.48 (1H, t, J=7.6 Hz), 7.72-7.88 (2H, m), 8.16 (1H, t, J=1.6 Hz), 13.01 (1H, br s).

(iv) Production of N-(5-{[2-(acetylamino)[1,3]thiazolo[5,4-d]pyrimidin-5-yl](methyl)amino}-2-fluorophenyl)-3-(1,1-dimethylprop-2-yn-1-yl)benzamide A solution of N-{5-[(3-amino-4-fluorophenyl)(methyl)amino][1,3]thiazolo[5,4-d]pyrimidin-2-yl}acetamide (100 mg, 301 μmol) produced in Example D17(iv), 3-(1,1-dimethylprop-2-yn-1-yl)benzoic acid (141 mg, 753 μmol) and O-(7-azabenzotriazol-1-yl)-N,N,N',N'-tetramethyluronium hexafluorophosphate (286 mg, 753 μmol) in pyridine (4 mL) was stirred at 90° C. for 3 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=40/60→10/90), and the fractions containing the object product were concentrated under reduced pressure. The obtained residue was recrystallized from tetrahydrofuran and hexane to give the title compound (94 mg, 62%) as colorless crystals.

$^1$H-NMR (DMSO-d$_6$, 300 MHz) δ 1.59 (6H, s), 2.19 (3H, s), 3.32 (1H, s), 3.51 (3H, s), 7.28 (1H, ddd, J=2.5, 4.8, 9.3 Hz), 7.34 (1H, t, J=9.3 Hz), 7.51 (1H, t, J=7.8 Hz), 7.60 (1H, dd, J=2.5, 6.9 Hz), 7.79 (1H, ddd, J=1.2, 1.7, 7.8 Hz), 7.86

(1H, ddd, J=1.2, 1.7, 7.8 Hz), 8.17 (1H, t, J=1.7 Hz), 8.73 (1H, s), 10.20 (1H, br s), 12.34 (1H, br s).

Example D21

Production of N-(3-{[2-(acetylamino)[1,3]thiazolo[5,4-d]pyrimidin-5-yl](cyclopropyl)amino}phenyl)-3-(1-cyano-1-methylethyl)benzamide

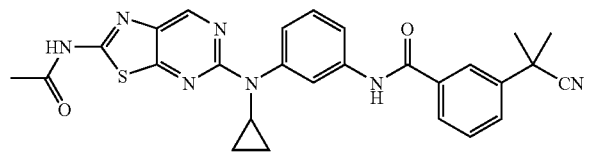 [SMILES: CC(=O)Nc1nc2cnc(N(c3cccc(NC(=O)c4cccc(C(C)(C)C#N)c4)c3)C3CC3)nc2s1]

(i) Production of tert-butyl(3-nitrophenyl)carbamate

To a solution of 3-nitroaniline (15.4 g, 112 mmol) in acetonitrile (220 ml) were added di-tert-butyl bicarbonate (62.2 g, 285 mmol), triethylamine (23.2 mL, 168 mmol) and N,N-dimethylpyridine-4-amine (1.36 g, 11.2 mmol), and the mixture was stirred at room temperature for 42 hr. The reaction mixture was concentrated under reduced pressure. To a solution of the obtained residue in methanol (100 mL)/tetrahydrofuran (100 mL) was added potassium carbonate (30.8 g, 223 mmol), and the mixture was stirred at 60° C. for 1 hr. To the reaction mixture was added water (200 mL), and the mixture was extracted with ethyl acetate (300 mL, 100 mL). The combined organic layer was washed with saturated brine (50 mL), and dried over anhydrous magnesium sulfate. The insoluble material was filtered off, and the filtrate was concentrated under reduced pressure. The obtained residue was purified by silica gel column chromatography (hexane/ethyl acetate=100/0→90/10), and the fractions containing the object product were concentrated under reduced pressure. The obtained residue was recrystallized from ethyl acetate and hexane to give the title compound (18.6 g, 70%) as pale-yellow needle crystals.

$^1$H-NMR (DMSO-$d_6$, 300 MHz) δ 1.50 (9H, s), 7.54 (1H, t, J=8.2 Hz), 7.77 (1H, ddd, J=1.0, 2.2, 8.2 Hz), 7.82 (1H, ddd, J=1.0, 2.2, 8.2 Hz), 8.48 (1H, t, J=2.2 Hz), 9.92 (1H, br s).

(ii) Production of tert-butyl(3-aminophenyl)carbamate

To a solution of tert-butyl(3-nitrophenyl)carbamate (17.1 g, 71.7 mmol) in ethanol (90 mL)/tetrahydrofuran (30 mL) was added 10% palladium-carbon (1.53 g), and the mixture was stirred at room temperature under a hydrogen atmosphere (3 atm) for 9 hr. The insoluble material was filtered off, and the filtrate was concentrated under reduced pressure. The obtained residue was washed with diethyl ether/hexane mixture to give the title compound (14.7 g, 98%) as a colorless solid.

$^1$H-NMR (DMSO-$d_6$, 300 MHz) δ 1.45 (9H, s), 4.96 (2H, br s), 6.16 (1H, ddd, J=0.8, 2.0, 7.8 Hz), 6.52 (1H, ddd, J=0.8, 2.0, 7.8 Hz), 6.76-6.88 (2H, m), 8.99 (1H, br s).

(iii) Production of tert-butyl [3-(cyclopropylamino)phenyl]carbamate

To a solution of tert-butyl(3-aminophenyl)carbamate (6.91 g, 33.2 mmol) in methanol (30 mL) were added acetic acid (5.69 mL, 99.5 mmol) and [(1-ethoxycyclopropyl)oxy](trimethyl)silane (7.98 mL, 39.8 mmol), and the mixture was stirred at 60° C. for 4 hr. The reaction mixture was concentrated under reduced pressure. A solution of the obtained residue in tetrahydrofuran (20 mL) was added dropwise to a suspension of sodium tetrahydroborate (2.51 g, 66.4 mmol) and boron trifluoride diethyl ether complex (8.33 mL, 66.4 mmol) in tetrahydrofuran (30 mL) (the suspension was stirred in advance at room temperature for 1 hr) at 0° C. over 30 min, and the mixture was stirred at room temperature for 2.5 hr. To the reaction mixture was added saturated aqueous sodium hydrogen carbonate solution (100 mL), and the mixture was extracted with ethyl acetate (2×50 mL). The combined organic layer was washed with saturated brine (20 mL), and dried over anhydrous sodium sulfate. The insoluble material was filtered off, and the filtrate was concentrated under reduced pressure. The obtained residue was purified by silica gel column chromatography (hexane/ethyl acetate=95/5→90/10), and the fractions containing the object product were concentrated under reduced pressure to give the title compound (4.87 g, 59%) as a colorless solid.

$^1$H-NMR (DMSO-$d_6$, 300 MHz) δ 0.29-0.38 (2H, m), 0.58-0.68 (2H, m), 1.45 (9H, s), 2.19-2.31 (1H, m), 5.96 (1H, d, J=1.1 Hz), 6.31 (1H, ddd, J=1.0, 2.1, 8.1 Hz), 6.63 (1H, ddd, J=1.0, 2.1, 8.1 Hz), 6.85-6.98 (2H, m), 9.02 (1H, br s).

(iv) Production of tert-butyl {3-[(2-amino[1,3]thiazolo[5,4-d]pyrimidin-5-yl)(cyclopropyl)amino]phenyl)carbamate To a solution of tert-butyl [3-(cyclopropylamino)phenyl]carbamate (5.51 g, 15.4 mmol) in tetrahydrofuran (100 mL) were added N-ethyl-N-isopropylpropane-2-amine (8.06 mL, 46.2 mmol) and 2-chloro-5-nitropyrimidin-4-yl thiocyanate (6.66 g, 30.7 mmol), and the mixture was stirred at room temperature for 1 hr. To the reaction mixture was added water (100 mL), and the mixture was extracted with ethyl acetate (2×50 mL). The combined organic layer was washed with saturated brine (30 mL), and filtered through a silica gel pad. The obtained filtrate was concentrated under reduced pressure to give tert-butyl {3-[cyclopropyl(5-nitro-4-thiocyanatopyrimidin-2-yl)amino]phenyl}carbamate as a brown amorphous solid. The obtained compound was used for the next reaction without further purification.

To a solution of the above-mentioned crude product of tert-butyl {3-[cyclopropyl(5-nitro-4-thiocyanatopyrimidin-2-yl)amino]phenyl}carbamate in ethanol (60 mL)/1-methylpyrrolidin-2-one (15 mL)/water (10 mL) were added reduced iron (4.29 g, 76.9 mmol) and calcium chloride (8.53 g, 76.9 mmol), and the mixture was stirred at 100° C. for 5 hr, and at room temperature for 2 days. The insoluble material was filtered off, and the filtrate was concentrated under reduced pressure. To the obtained residue was added water (200 mL), and the mixture was extracted with ethyl acetate (200 mL, 50 mL). The combined organic layer was filtered through a silica gel pad, and the filtrate was concentrated under reduced pressure. The obtained residue was purified by silica gel column chromatography (hexane/ethyl acetate=40/60→10/90), and the fractions containing the object product were concentrated under reduced pressure. The obtained residue was washed with ethyl acetate and hexane to give the title compound (2.37 g, 39%) as a gray solid.

$^1$H-NMR (CDCl$_3$, 300 MHz) δ 0.36-0.52 (2H, m), 0.77-0.89 (2H, m), 1.46 (9H, s), 2.98-3.11 (1H, m), 6.81 (1H, d, J=8.1 Hz), 7.14-7.31 (2 H, m), 7.35 (1H, s), 7.60 (2H, br s), 8.28 (1H, s), 9.35 (1H, br s).

(v) Production of N-{5-[(3-aminophenyl)(cyclopropyl)amino][1,3]thiazolo[5,4-d]pyrimidin-2-yl}acetamide To a solution of tert-butyl {3-[(2-amino[1,3]thiazolo[5,4-d]pyrimidin-5-yl)(cyclopropyl)amino]phenyl}carbamate (1.20 g, 3.01 mmol) in pyridine (20 mL) was added acetyl chloride (859 μL, 12.1 mmol), and the mixture was stirred at room temperature for 1 hr. To the reaction mixture was added water (60 mL), and the mixture was extracted with ethyl acetate (60 mL, 20 mL). The combined organic layer was washed with saturated brine (10 mL), and filtered through a basic silica gel pad. The filtrate was concentrated under reduced pressure to give tert-butyl(3-{[2-(acetylamino)[1,3]thiazolo[5,4-d]pyrimidin-5-yl](cyclopropyl)amino}phenyl)carbamate as a dark-purple solid. The obtained compound was used for the next reaction without further purification.

A solution of the above-mentioned crude product of tert-butyl(3-{[2-(acetylamino)[1,3]thiazolo[5,4-d]pyrimidin-5-yl](cyclopropyl)amino}phenyl)carbamate and anisole (1.5 mL) in trifluoroacetic acid (15 mL) was stirred at 0° C. for 1 hr. The reaction mixture was concentrated under reduced pressure, to the obtained residue was added saturated aqueous sodium hydrogen carbonate solution (60 mL), and the mixture was extracted with ethyl acetate/tetrahydrofuran mixture (9:1, 60 mL, 20 mL). The combined organic layer was washed with saturated brine (10 mL), and dried over anhydrous sodium sulfate. The insoluble material was filtered off, and the filtrate was concentrated under reduced pressure. The obtained residue was washed with ethyl acetate to give the title compound (820 mg, 80%) as a purple solid.

$^1$H-NMR (DMSO-$d_6$, 300 MHz) δ 0.42-0.51 (2H, m), 0.79-0.88 (2H, m), 2.17 (3H, s), 3.06-3.16 (1H, m), 5.08 (2H, br s), 6.34 (1H, ddd, J=0.9, 2.0, 7.9 Hz), 6.40 (1H, t, J=2.0 Hz), 6.45 (1H, ddd, J=0.9, 2.0, 7.9 Hz), 7.02 (1H, t, J=7.9 Hz), 8.69 (1H, s), 12.29 (1H, br s).

(vi) Production of N-(3-{[2-(acetylamino)[1,3]thiazolo[5,4-d]pyrimidin-5-yl](cyclopropyl)amino}phenyl)-3-(1-cyano-1-methylethyl)benzamide A solution of N-{5-[(3-aminophenyl)(cyclopropyl)amino][1,3]thiazolo[5,4-d]pyrimidin-2-yl}acetamide (120 mg, 353 μmol), 3-(1-cyano-1-methylethyl)benzoic acid (80 mg, 424 μmol) and O-(7-azabenzotriazol-1-yl)-N,N,N',N'-tetramethyluronium hexafluorophosphate (201 mg, 530 μmol) in pyridine (3 mL) was stirred at 60° C. for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→95/5), and the fractions containing the object product were concentrated under reduced pressure. The obtained residue was recrystallized from ethyl acetate to give the title compound (106 mg, 59%) as colorless crystals.

$^1$H-NMR (DMSO-$d_6$, 300 MHz) δ 0.45-0.58 (2H, m), 0.85-0.95 (2H, m), 1.75 (6H, s), 2.19 (3H, s), 3.14-3.26 (1H, m), 6.97-7.08 (1H, m), 7.35-7.43 (1H, m), 7.60 (1H, t, J=7.8 Hz), 7.65-7.72 (2H, m), 7.75 (1H, ddd, J=0.9, 1.8, 7.8 Hz), 7.91-7.97 (1H, m), 8.04 (1H, t, J=1.8 Hz), 8.75 (1H, s), 10.36 (1H, br s), 12.34 (1H, br s).

Example D22

Production of N-(3-{[2-(acetylamino)[1,3]thiazolo[5,4-d]pyrimidin-5-yl](cyclopropyl)amino}phenyl)-2-chloro-3-(1-cyano-1-methylethyl)benzamide

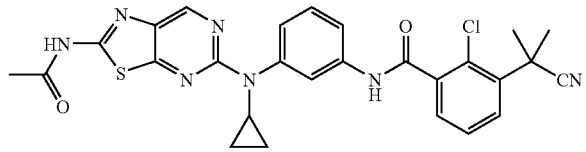 [SMILES: CC(=O)Nc1nc2cnc(N(c3cccc(NC(=O)c4cccc(C(C)(C)C#N)c4Cl)c3)C3CC3)nc2s1]

A solution of N-{5-[(3-aminophenyl)(cyclopropyl)amino][1,3]thiazolo[5,4-d]pyrimidin-2-yl}acetamide (120 mg, 353 μmol) produced in Example D21(v), 2-chloro-3-(1-cyano-1-methylethyl)benzoic acid (95 mg, 424 μmol) produced in Example D18(v) and O-(7-azabenzotriazol-1-yl)-N,N,N',N'-tetramethyluronium hexafluorophosphate (201 mg, 530 μmol) in pyridine (3 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→97/3), and the fractions containing the object product were concentrated under reduced pressure. The obtained residue was recrystallized from ethyl acetate to give the title compound (137 mg, 71%) as colorless crystals.

$^1$H-NMR (DMSO-$d_6$, 300 MHz) δ 0.47-0.56 (2H, m), 0.86-0.96 (2H, m), 1.85 (6H, s), 2.19 (3H, s), 3.14-3.23 (1H, m), 7.02 (1H, ddd, J=0.8, 2.0, 7.9 Hz), 7.38 (1H, t, J=7.9 Hz), 7.53 (1H, t, J=7.6 Hz), 7.57-7.63 (2H, m), 7.63-7.69 (2H, m), 8.75 (1H, s), 10.64 (1H, br s), 12.34 (1H, br s).

Example D23

Production of N-(3-{[2-(acetylamino)[1,3]thiazolo[5,4-d]pyrimidin-5-yl](cyclopropyl)amino}phenyl)-3-(trifluoromethoxy)benzamide

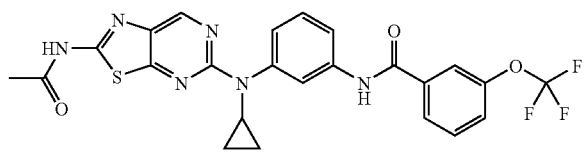 [SMILES: CC(=O)Nc1nc2cnc(N(c3cccc(NC(=O)c4cccc(OC(F)(F)F)c4)c3)C3CC3)nc2s1]

A solution of N-{5-[(3-aminophenyl)(cyclopropyl)amino][1,3]thiazolo[5,4-d]pyrimidin-2-yl}acetamide (120 mg, 353

μmol) produced in Example D21(v), 3-(trifluoromethoxy) benzoic acid (77 mg, 371 μmol) and O-(7-azabenzotriazol-1-yl)-N,N,N',N'-tetramethyluronium hexafluorophosphate (161 mg, 424 μmol) in pyridine (3 mL) was stirred at room temperature for 30 min. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→98/2), and the fractions containing the object product were concentrated under reduced pressure. The obtained residue was recrystallized from ethyl acetate to give the title compound (134 mg, 71%) as colorless crystals.

¹H-NMR (DMSO-d₆, 300 MHz) δ 0.46-0.57 (2H, m), 0.85-0.97 (2H, m), 2.19 (3H, s), 3.13-3.25 (1H, m), 7.04 (1H, ddd, J=1.0, 1.8, 8.0 Hz), 7.40 (1H, t, J=8.0 Hz), 7.57-7.64 (1H, m), 7.65-7.74 (3H, m), 7.88-7.95 (1H, m), 8.02 (1H, dt, J=7.7, 1.3 Hz), 8.75 (1H, s), 10.42 (1H, br s), 12.34 (1H, br s).

Example D24

Production of N-(3-{[2-(acetylamino)[1,3]thiazolo[5,4-d]pyrimidin-5-yl](cyclopropyl)amino}phenyl)-2-chloro-3-(trifluoromethyl)benzamide

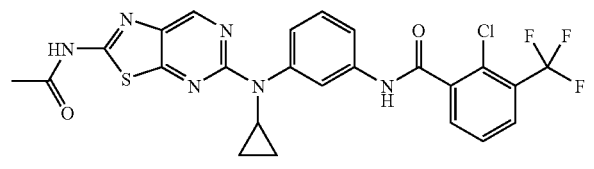 [SMILES: CC(=O)Nc1nc2cnc(N(c3cccc(NC(=O)c4cccc(C(F)(F)F)c4Cl)c3)C3CC3)nc2s1]

A solution of N-{5-[(3-aminophenyl)(cyclopropyl)amino][1,3]thiazolo[5,4-d]pyrimidin-2-yl}acetamide (120 mg, 353 μmol) produced in Example D21(v), 2-chloro-3-(trifluoromethyl)benzoic acid (84 mg, 371 μmol) and O-(7-azabenzotriazol-1-yl)-N,N,N',N'-tetramethyluronium hexafluorophosphate (161 mg, 424 μmol) in pyridine (3 mL) was stirred at room temperature for 30 min. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=10/90→0/100), and the fractions containing the object product were concentrated under reduced pressure. The obtained residue was recrystallized from ethyl acetate to give the title compound (124 mg, 64%) as colorless crystals.

¹H-NMR (DMSO-d₆, 300 MHz) δ 0.48-0.56 (2H, m), 0.84-0.96 (2H, m), 2.19 (3H, s), 3.14-3.24 (1H, m), 7.04 (1H, ddd, J=1.0, 1.9, 8.0 Hz), 7.39 (1H, t, J=8.0 Hz), 7.58 (1H, ddd, J=1.0, 1.9, 8.0 Hz), 7.63-7.72 (2H, m), 7.90-7.95 (1H, m), 7.98 (1H, dd, J=7.9, 1.3 Hz), 8.75 (1H, s), 10.72 (1H, br s), 12.35 (1H, br s).

Example D25

Production of 3-(1-cyano-1-methylethyl)-N-[3-({2-[(cyclopropylcarbonyl)amino][1,3]thiazolo[5,4-d]pyrimidin-5-yl}amino)-4-methylphenyl]benzamide

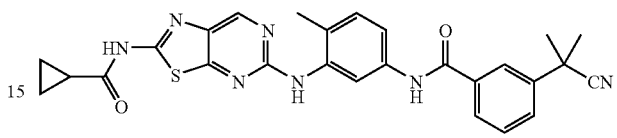

(i) Production of N-(3-amino-4-methylphenyl)-3-(1-cyano-1-methylethyl)benzamide

To a suspension of 3-(1-cyano-1-methylethyl)benzoic acid (9.87 g, 52.2 mmol) in toluene (150 mL) was added thionyl chloride (25.3 g, 213 mmol), and the mixture was stirred at 120° C. for 2 hr. The reaction mixture was concentrated under reduced pressure to give 3-(1-cyano-1-methylethyl)benzoyl chloride as a colorless oil. To a solution of 4-methyl-3-nitroaniline (7.63 g, 50.2 mmol) in pyridine (150 mL) were added N,N-dimethylpyridine-4-amine (122 mg, 1.00 mmol) and 3-(1-cyano-1-methylethyl)benzoyl chloride, and the mixture was stirred at room temperature for 14 hr. To the reaction mixture was added 1N hydrochloric acid (200 mL), and the mixture was extracted with ethyl acetate (150 mL, 100 mL). The combined organic layer was washed with saturated aqueous sodium hydrogen carbonate solution (150 mL), and dried over anhydrous magnesium sulfate. After filtration through a silica gel pad, the filtrate was concentrated under reduced pressure to give 3-(1-cyano-1-methylethyl)-N-(4-methyl-3-nitrophenyl)benzamide as a yellow oil. The obtained compound was used for the next reaction without further purification.

To a solution of the above-mentioned crude product of 3-(1-cyano-1-methylethyl)-N-(4-methyl-3-nitrophenyl)benzamide in tetrahydrofuran (300 mL) was added an aqueous solution (500 mL) of sodium dithionite (78.1 g, 629 mmol), and the mixture was stirred at 100° C. for 2 hr. The organic layer of the reaction mixture was separated, and the aqueous layer was extracted with ethyl acetate (2×150 mL). The combined organic layer was washed with saturated brine (150 mL), and dried over anhydrous magnesium sulfate. The insoluble material was filtered off, and the filtrate was concentrated under reduced pressure. The obtained residue was purified by silica gel column chromatography (hexane/ethyl acetate=98/2→0/100), and the fractions containing the object product were concentrated under reduced pressure to give the title compound (5.60 g, 38%) as a yellow solid.

¹H-NMR (DMSO-d₆, 300 MHz) δ 1.77 (6H, s), 2.03 (3H, s), 4.90 (2H, br s), 6.82 (1H, dd, J=1.8, 8.1 Hz), 6.88 (1H, d, J=8.1 Hz), 7.09 (1H, d, J=1.8 Hz), 7.57 (1H, t, J=7.8 Hz), 7.72 (1H, ddd, J=1.2, 1.9, 7.8 Hz), 7.90 (1H, dt, J=1.2, 1.9, 7.8 Hz), 8.01 (1H, t, J=1.9 Hz), 9.99 (1H, br s).

(ii) Production of 2-{[5-({[3-(1-cyano-1-methylethyl)phenyl]carbonyl}amino)-2-methylphenyl]amino}-5-nitropyrimidin-4-yl thiocyanate To a solution of N-(3-amino-4-methylphenyl)-3-(1-cyano-1-methylethyl)benzamide (1.00 g, 3.41 mmol) in tetrahydrofuran (15 mL) were added N-ethyl-N-isopropylpropane-2-amine (893 μL, 5.11 mmol) and 2-chloro-5-nitropyrimidin-4-yl thiocyanate (812 mg, 3.75 mmol), and the mixture was stirred at room temperature for 1.5 hr. To the reaction mixture was added saturated aqueous sodium hydrogen carbonate solution (30 mL), and the mixture was extracted with ethyl acetate (30 mL, 10 mL). The combined organic layer was washed with saturated brine (10 mL), and dried over anhydrous sodium sulfate. The insoluble material was filtered off, and the filtrate was concentrated under reduced pressure. The obtained residue was washed with ethyl acetate to give the title compound (1.41 g, 88%) as a yellow solid.

$^1$H-NMR (CDCl$_3$, 300 MHz) δ1.80 (6H, s), 2.42 (3H, s), 7.20-7.33 (1H, m), 7.52 (1H, t, J=7.8 Hz), 7.73 (1H, ddd, J=1.1, 1.8, 7.8 Hz), 7.87-7.94 (2H, m), 7.99 (1H, t, J=1.8 Hz), 8.23 (1H, dd, J=1.8, 8.3 Hz), 8.70-8.76 (2H, m), 9.17 (1H, br s).

(iii) Production of N-{3-[(2-amino[1,3]thiazolo[5,4-d]pyrimidin-5-yl)amino]-4-methylphenyl}-3-(1-cyano-1-methylethyl)benzamide To a solution of 2-{[5-({[3-(1-cyano-1-methylethyl)phenyl]carbonyl}amino)-2-methylphenyl]amino}-5-nitropyrimidin-4-yl thiocyanate (1.09 mmol, 515 mg) in 1-methylpyrrolidin-2-one (9 mL)/ethanol (6 mL) were added 10% palladium-carbon (120 mg) and acetic acid (0.5 mL), and the mixture was stirred at room temperature under a hydrogen atmosphere (3.0 atm) for 19 hr. The insoluble material was filtered off, saturated aqueous sodium hydrogen carbonate solution (30 mL) was added, and the mixture was extracted with ethyl acetate (30 mL, 20 ml). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=40/60→10/90), and the fractions containing the object product were concentrated under reduced pressure. The obtained residue was recrystallized from ethyl acetate and hexane to give the title compound (281 mg, 58%) as purple crystals.

$^1$H-NMR (DMSO-$_6$, 300 MHz) δ 1.75 (6H, s), 2.69 (3H, s), 7.17 (1H, d, J=8.4 Hz), 7.47 (1H, dd, J=2.2, 8.4 Hz), 7.54-7.63 (3H, m), 7.74 (1H, ddd, J=1.5, 2.0, 8.0 Hz), 7.90 (1H, d, J=2.2 Hz), 7.93 (1H, ddd, J=1.5, 2.0, 8.0 Hz), 8.03 (1H, t, J=1.5 Hz), 8.29 (1H, s), 8.56 (1H, br s), 10.23 (1H, br s).

(iv) Production of 3-(1-cyano-1-methylethyl)-N-[3-({2-[(cyclopropylcarbonyl)amino][1,3]thiazolo[5,4-d]pyrimidin-5-yl}amino)-4-methylphenyl]benzamide To a solution of N-{3-[(2-amino[1,3]thiazolo[5,4-d]pyrimidin-5-yl)amino]-4-methylphenyl}-3-(1-cyano-1-methylethyl)benzamide (137 mg, 309 μmol) in pyridine (3 mL) was added cyclopropanecarbonyl chloride (68 μL, 742 μmol), and the mixture was stirred at room temperature for 2 hr. To the reaction mixture was added saturated aqueous sodium hydrogen carbonate solution (20 mL), and the mixture was extracted with ethyl acetate/tetrahydrofuran mixture (9:1, 20 mL, 5 mL). The combined organic layer was washed with saturated brine (5 mL), and dried over anhydrous sodium sulfate. The insoluble material was filtered off, and the filtrate was concentrated under reduced pressure. The obtained residue was recrystallized from methanol and ethyl acetate to give the title compound (56 mg, 35%) as pale-red crystals.

$^1$H-NMR (DMSO-d$_6$, 300 MHz) δ 0.86-1.02 (4H, m), 1.75 (6H, s), 1.92-2.02 (1H, m), 2.20 (3H, s), 7.21 (1H, d, J=8.2 Hz), 7.51 (1H, dd, J=2.2, 8.2 Hz), 7.59 (1H, t, J=7.8 Hz), 7.72-7.76 (1H, m), 7.90 (1H, d, J=2.2 Hz), 7.93 (1H, dt, J=7.8, 1.5 Hz), 8.03 (1H, t, J=1.5 Hz), 8.73 (1H, s), 8.97 (1H, br s), 10.25 (1H, br s), 12.64 (1H, br s).

Example D26

Production of N-(3-{[2-(acetylamino)[1,3]thiazolo[5,4-d]pyrimidin-5-yl]amino}-4-methylphenyl)-3-(1-cyano-1-methylethyl)benzamide

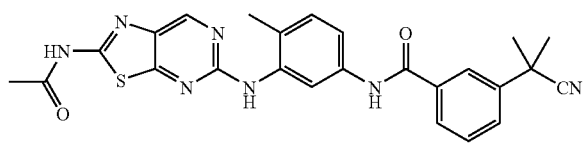 [SMILES: CC(=O)Nc1nc2cnc(Nc3cc(NC(=O)c4cccc(C(C)(C)C#N)c4)ccc3C)nc2s1]

To a solution of N-{3-[(2-amino[1,3]thiazolo[5,4-d]pyrimidin-5-yl)amino]-4-methylphenyl}-3-(1-cyano-1-methylethyl)benzamide (161 mg, 363 μmol) produced in Example D25(iii) in pyridine (4 mL) was added acetyl chloride (65 μL, 908 μmol), and the mixture was stirred at room temperature for 1 hr. To the reaction mixture was added saturated aqueous sodium hydrogen carbonate solution (20 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was recrystallized from ethyl acetate to give the title compound (129 mg, 73%) as colorless crystals.

$^1$H-NMR (DMSO-d$_6$, 300 MHz) δ 1.75 (6H, s), 2.18 (3H, s), 2.20 (3H, s), 7.21 (1H, d, J=8.5 Hz), 7.51 (1H, dd, J=2.2, 8.5 Hz), 7.59 (1H, t, J=7.7 Hz), 7.72-7.76 (1H, m), 7.87-7.97 (2H, m), 8.03 (1H, t, J=1.7 Hz), 8.74 (1H, s), 8.99 (1H, s), 10.26 (1H, br s), 12.35 (1H, br s).

Example D27

Production of 3-(1-cyano-1-methylethyl)-N-{4-methyl-3-[(2-{[(2E)-3-phenylprop-2-enoyl]amino}[1,3]thiazolo[5,4-d]pyrimidin-5-yl)amino]phenyl}benzamide

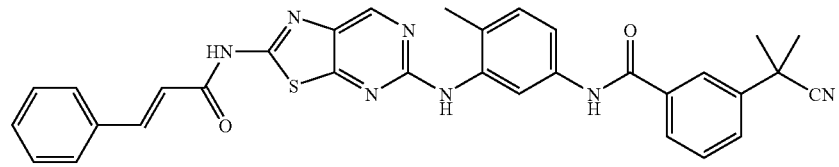 [SMILES: Cc1ccc(NC(=O)c2cccc(C(C)(C)C#N)c2)cc1Nc1ncc2nc(NC(=O)/C=C/c3ccccc3)sc2n1]

To a solution of N-{3-[(2-amino[1,3]thiazolo[5,4-d]pyrimidin-5-yl)amino]-4-methylphenyl}-3-(1-cyano-1-methylethyl)benzamide (150 mg, 338 μmol) produced in Example D25(iii) in pyridine (4 mL) was added cinnamoyl chloride (141 mg, 845 μmol), and the mixture was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=30/70→10/90), and the fractions containing the object product were concentrated under reduced pressure. The obtained residue was recrystallized from ethyl acetate to give the title compound (108 mg, 56%) as pale-yellow crystals.

¹H-NMR (DMSO-d₆, 300 MHz) δ 1.75 (6H, s), 2.21 (3H, s), 6.94 (1H, d, J=15.9 Hz), 7.22 (1H, d, J=8.5 Hz), 7.43-7.55 (4H, m), 7.59 (1H, t, J=7.8 Hz), 7.63-7.69 (2H, m), 7.71-7.82 (2H, m), 7.87-7.97 (2H, m), 8.04 (1H, t, J=1.8 Hz), 8.78 (1H, s), 9.03 (1H, br s), 10.27 (1H, br s), 12.62 (1H, br s).

Example D28

Production of N-(5-{[5-({[3-(1-cyano-1-methylethyl)phenyl]carbonyl}amino)-2-methylphenyl]amino}[1,3]thiazolo[5,4-d]pyrimidin-2-yl)-2-methyl-1H-imidazole-5-carboxamide

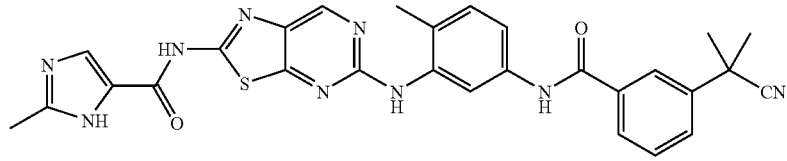 [SMILES: Cc1ncc(C(=O)Nc2nc3cnc(Nc4cc(NC(=O)c5cccc(C(C)(C)C#N)c5)ccc4C)nc3s2)[nH]1]

To a solution of N-{3-[(2-amino[1,3]thiazolo[5,4-d]pyrimidin-5-yl)amino]-4-methylphenyl}-3-(1-cyano-1-methylethyl)benzamide (150 mg, 338 μmol) produced in Example D25(iii) in pyridine (4 mL) were added 2-methyl-1H-imidazole-5-carboxylic acid (194 mg, 1.35 mmol) and O-(7-azabenzotriazol-1-yl)-N,N,N',N'-tetramethyluronium hexafluorophosphate (899 mg, 2.36 mmol), and the mixture was stirred at 90° C. for 28 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→92/8), and the fractions containing the object product were concentrated under reduced pressure. The obtained residue was recrystallized from tetrahydrofuran and ethyl acetate to give the title compound (80 mg, 43%) as colorless crystals.

¹H-NMR (DMSO-d₆, 300 MHz) δ 1.75 (6H, s), 2.21 (3H, s), 2.36 (3H, s), 7.22 (1H, d, J=8.4 Hz), 7.53 (1H, dd, J=2.1, 8.4 Hz), 7.59 (1H, t, J=7.8 Hz), 7.74 (1H, ddd, J=1.0, 1.9, 7.8 Hz), 7.88-7.96 (2H, m), 7.97 (1H, s), 8.03 (1H, t, J=1.9 Hz), 8.76 (1H, s), 9.00 (1H, br s), 10.27 (1H, br s), 11.70 (1H, br s), 12.53 (1H, br s).

Example D29

Production of N-(5-{[5-({[3-(1-cyano-1-methylethyl)phenyl]carbonyl}amino)-2-methylphenyl]amino}[1,3]thiazolo[5,4-d]pyrimidin-2-yl)-5-(1-methylethyl)-1H-pyrazole-3-carboxamide

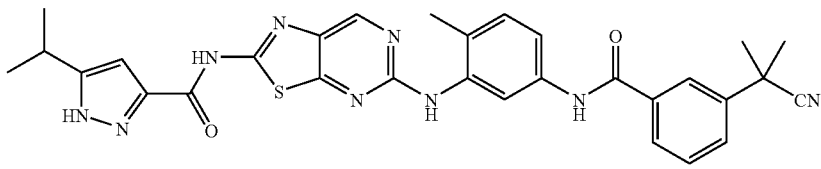 [SMILES: Cc1ccc(NC(=O)c2cccc(C(C)(C)C#N)c2)cc1Nc1ncc2nc(NC(=O)c3cc(C(C)C)[nH]n3)sc2n1]

To a solution of N-{3-[(2-amino[1,3]thiazolo[5,4-d]pyrimidin-5-yl)amino]-4-methylphenyl}-3-(1-cyano-1-methylethyl)benzamide (82 mg, 185 μmol) produced in Example D25(iii) in pyridine (3 mL) were added 5-(1-methylethyl)-1H-pyrazole-3-carboxylic acid (57 mg, 370 μmol) and O-(7-azabenzotriazol-1-yl)-N,N,N',N'-tetramethyluronium hexafluorophosphate (211 mg, 555 μmol), and the mixture was stirred at 90° C. for 21 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→92/8), and the fractions containing the object product were concentrated under reduced pressure. The obtained residue was recrystallized from N,N-dimethylformamide and diethyl ether to give the title compound (34 mg, 32%) as pale-yellow crystals.

¹H-NMR (DMSO-d₆, 300 MHz) δ 1.25 (6H, d, J=7.0 Hz), 1.75 (6H, s), 2.21 (3H, s), 2.92-3.11 (1H, m), 6.74 (1H, br s), 7.22 (1H, d, J=8.4 Hz), 7.53 (1H, dd, J=2.2, 8.4 Hz), 7.59 (1H, t, J=7.9 Hz), 7.74 (1H, ddd, J=1.0, 1.9, 7.9 Hz), 7.90-7.97 (2H, m), 8.03 (1H, t, J=1.9 Hz), 8.78 (1H, br s), 9.03 (1H, br s), 10.27 (1H, br s), 12.28 (1H, br s), 13.41 (1H, br s).

Example D30

Production of N-(5-{[5-({[3-(1-cyano-1-methyl-ethyl)phenyl]carbonyl}amino)-2-methylphenyl]amino}[1,3]thiazolo[5,4-d]pyrimidin-2-yl)-1-methyl-1H-pyrazole-3-carboxamide

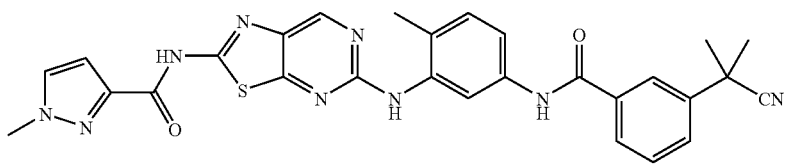 [SMILES: Cc1ccc(NC(=O)c2cccc(C(C)(C)C#N)c2)cc1Nc1ncc2nc(NC(=O)c3ccn(C)n3)sc2n1]

To a solution of N-{3-[(2-amino[1,3]thiazolo[5,4-d]pyrimidin-5-yl)amino]-4-methylphenyl}-3-(1-cyano-1-methylethyl)benzamide (80 mg, 180 µmol) produced in Example D25(iii) in pyridine (3 mL) were added 1-methyl-1H-pyrazole-3-carboxylic acid (45 mg, 360 µmol) and O-(7-azabenzotriazol-1-yl)-N,N,N',N'-tetramethyluronium hexafluorophosphate (205 mg, 540 µmol), and the mixture was stirred at 90° C. for 17 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→92/8), and the fractions containing the object product were concentrated under reduced pressure. The obtained residue was recrystallized from ethyl acetate to give the title compound (40 mg, 40%) as pale-yellow crystals.

$^1$H-NMR (DMSO-$d_6$, 300 MHz) δ 1.75 (6H, s), 2.21 (3H, s), 3.97 (3H, s), 6.99 (1H, d, J=2.3 Hz), 7.22 (1H, d, J=8.4 Hz), 7.53 (1H, dd, J=2.3, 8.4 Hz), 7.59 (1H, t, J=7.8 Hz), 7.74 (1H, ddd, J=1.0, 1.9, 7.8 Hz), 7.87-7.97 (3H, m), 8.03 (1H, t, J=1.9 Hz), 8.76 (1H, s), 8.99 (1H, br s), 10.27 (1H, br s), 12.43 (1H, br s).

Example D31

Production of N-(5-{[5-({[3-(1-cyano-1-methyl-ethyl)phenyl]carbonyl}amino)-2-methylphenyl]amino}[1,3]thiazolo[5,4-d]pyrimidin-2-yl)-5-methyl-1H-pyrazole-3-carboxamide

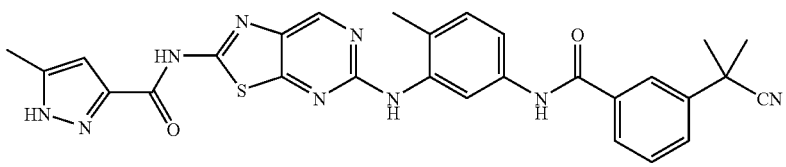 [SMILES: Cc1cc(C(=O)Nc2nc3cnc(Nc4cc(NC(=O)c5cccc(C(C)(C)C#N)c5)ccc4C)nc3s2)n[nH]1]

To a solution of N-{3-[(2-amino[1,3]thiazolo[5,4-d]pyrimidin-5-yl)amino]-4-methylphenyl}-3-(1-cyano-1-methylethyl)benzamide (80 mg, 180 µmol) produced in Example D25(iii) in pyridine (3 mL) were added 5-methyl-1H-pyrazole-3-carboxylic acid (45 mg, 360 µmol) and O-(7-azabenzotriazol-1-yl)-N,N,N',N'-tetramethyluronium hexafluorophosphate (205 mg, 540 µmol), and the mixture was stirred at 90° C. for 16 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→90/10), and the fractions containing the object product were concentrated under reduced pressure. The obtained residue was recrystallized from N,N-dimethylformamide and diethyl ether to give the title compound (41 mg, 41%) as a white solid.

$^1$H-NMR (DMSO-$d_6$, 300 MHz) δ 1.75 (6H, s), 2.21 (3H, s), 2.29 (3H, br s), 6.70 (1H, br s), 7.21 (1H, d, J=8.4 Hz), 7.53 (1H, dd, J=2.1, 8.4 Hz), 7.59 (1H, t, J=7.8 Hz), 7.74 (1H, ddd, J=1.0, 1.9, 7.8 Hz), 7.90-7.96 (2H, m), 8.03 (1H, t, J=1.9 Hz), 8.77 (1H, br s), 9.01 (1H, br s), 10.27 (1H, br s), 12.30 (1H, br s), 13.35 (1H, br s).

Example D32

Production of 3-(1-cyano-1-methylethyl)-N-[4-methyl-3-({2-[(morpholin-4-ylacetyl)amino][1,3]thiazolo[5,4-d]pyrimidin-5-yl}amino)phenyl]benzamide

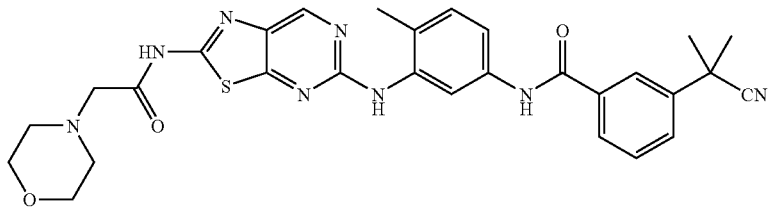 [SMILES: Cc1ccc(NC(=O)c2cccc(C(C)(C)C#N)c2)cc1Nc1ncc2nc(NC(=O)CN3CCOCC3)sc2n1]

(i) Production of N-[3-({2-[(chloroacetyl)amino][1,3]thiazolo[5,4-d]pyrimidin-5-yl}amino)-4-methylphenyl]-3-(1-cyano-1-methylethyl)benzamide To a solution of N-{3-[(2-amino[1,3]thiazolo[5,4-d]pyrimidin-5-yl)amino]-4-methylphenyl}-3-(1-cyano-1-methylethyl)benzamide (948 mg, 2.14 mmol) produced in Example D25(iii) in N,N-dimethylacetamide (20 mL) was added chloroacetyl chloride (425 μL, 5.34 mmol), and the mixture was stirred at room temperature for 30 min. To the reaction mixture was added water (60 mL), and the mixture was extracted with ethyl acetate (30 mL, 15 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=60/40→30/70), and the fractions containing the object product were concentrated under reduced pressure. The obtained residue was washed with ethyl acetate to give the title compound (778 mg, 71%) as a white solid.

$^1$H-NMR (DMSO-$d_6$, 300 MHz) δ 1.75 (6H, s), 2.20 (3H, s), 4.45 (2H, s), 7.22 (1H, d, J=8.4 Hz), 7.52 (1H, dd, J=2.1, 8.4 Hz), 7.59 (1H, t, J=7.9 Hz), 7.74 (1H, ddd, J=1.1, 1.9, 7.9 Hz), 7.90 (1H, d, J=2.1 Hz), 7.93 (1H, ddd, J=1.1, 1.9, 7.9 Hz), 8.03 (1H, t, J=1.9 Hz), 8.80 (1H, s), 9.08 (1H, br s), 10.27 (1H, br s), 12.74 (1H, br s).

(ii) Production of 3-(1-cyano-1-methylethyl)-N-[4-methyl-3-({2-[(morpholin-4-ylacetyl)amino][1,3]thiazolo[5,4-d]pyrimidin-5-yl}amino)phenyl]benzamide To a solution of N-[3-({2-[(chloroacetyl)amino][1,3]thiazolo[5,4-d]pyrimidin-5-yl}amino)-4-methylphenyl]-3-(1-cyano-1-methylethyl)benzamide (152 mg, 292 μmol) in tetrahydrofuran (4 mL)/N,N-dimethylformamide (0.5 mL) were added triethylamine (121 μL, 876 μmol) and morpholine (76 μL, 876 μmol), and the mixture was stirred at 60° C. for 15 hr. To the reaction mixture was added water (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→97/3), and the fractions containing the object product were concentrated under reduced pressure. The obtained residue was recrystallized from tetrahydrofuran and hexane to give the title compound (131 mg, 78%) as colorless crystals.

$^1$H-NMR (DMSO-$d_6$, 300 MHz) δ 1.75 (6H, s), 2.20 (3H, s), 2.47-2.55 (4H, m), 3.33 (2H, s), 3.56-3.65 (4H, m), 7.21 (1H, d, J=8.4 Hz), 7.51 (1H, dd, J=2.2, 8.4 Hz), 7.59 (1H, t, J=7.8 Hz), 7.74 (1H, ddd, J=1.0, 1.9, 7.8 Hz), 7.89-7.97 (2H, m), 8.03 (1H, t, J=1.9 Hz), 8.76 (1H, s), 9.01 (1H, br s), 10.26 (1H, br s), 12.16 (1H, br s).

Example D33

Production of 3-(1-cyano-1-methylethyl)-N-{4-methyl-3-[(2-{[(4-methylpiperazin-1-yl)acetyl]amino}[1,3]thiazolo[5,4-d]pyrimidin-5-yl)amino]phenyl}benzamide

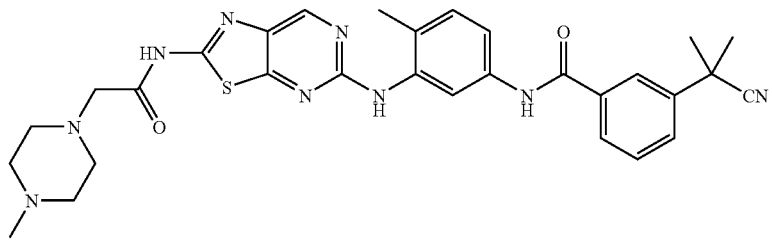 [SMILES: Cc1ccc(NC(=O)c2cccc(C(C)(C)C#N)c2)cc1Nc1ncc2nc(NC(=O)CN3CCN(C)CC3)sc2n1]

To a solution of N-[3-({2-[(chloroacetyl)amino][1,3]thiazolo[5,4-d]pyrimidin-5-yl}amino)-4-methylphenyl]-3-(1-cyano-1-methylethyl)benzamide (150 mg, 288 μmol) produced in Example D32(i) in tetrahydrofuran (4 mL)/N,N-dimethylformamide (0.5 mL) were added triethylamine (120 μL, 864 μmol) and 1-methylpiperazine (96 μL, 864 μmol), and the mixture was stirred at 60° C. for 3 hr. To the reaction mixture was added water (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=97/3→92/8), and the fractions containing the object product were concentrated under reduced pressure. The obtained residue was recrystallized from tetrahydrofuran, ethyl acetate and hexane to give the title compound (137 mg, 82%) as colorless crystals.

$^1$H-NMR (DMSO-d$_6$, 300 MHz) δ 1.75 (6H, s), 2.15 (3H, s), 2.20 (3H, s), 2.29-2.38 (4H, m), 2.47-2.52 (4H, m), 3.30 (2H, s), 7.21 (1H, d, J=8.4 Hz), 7.51 (1H, dd, J=2.2, 8.4 Hz), 7.59 (1H, t, J=7.9 Hz), 7.74 (1H, ddd, J=1.0, 1.9, 7.9 Hz), 7.88-7.96 (2H, m), 8.03 (1H, t, J=1.9 Hz), 8.74 (1H, s), 8.99 (1H, br s), 10.25 (1H, br s), 12.09 (1H, br s).

Example D34

Production of 3-(1-cyano-1-methylethyl)-N-{3-[(2-{[(4,4-difluoropiperidin-1-yl)acetyl]amino}[1,3]thiazolo[5,4-d]pyrimidin-5-yl)amino]-4-methylphenyl}benzamide

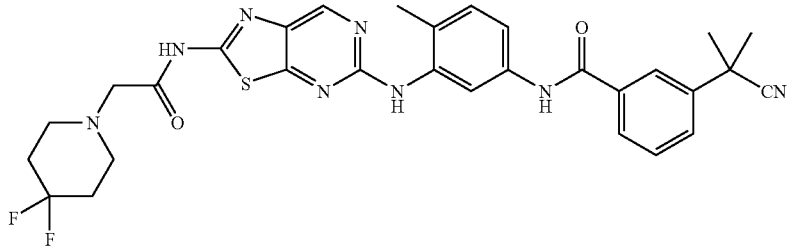 [SMILES: Cc1ccc(NC(=O)c2cccc(C(C)(C)C#N)c2)cc1Nc1ncc2nc(NC(=O)CN3CCC(F)(F)CC3)sc2n1]

To a solution of N-[3-({2-[(chloroacetyl)amino][1,3]thiazolo[5,4-d]pyrimidin-5-yl}amino)-4-methylphenyl]-3-(1-cyano-1-methylethyl)benzamide (150 mg, 288 μmol) produced in Example D32(i) in tetrahydrofuran (4 mL)/N,N-dimethylformamide (0.5 mL) were added triethylamine (180 μL, 1.30 mmol) and 4,4-difluoropiperidine hydrochloride (68 mg, 432 μmol), and the mixture was stirred at 60° C. for 7 hr. To the reaction mixture was added water (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. The obtained residue was recrystallized from ethyl acetate to give the title compound (82 mg, 47%) as colorless crystals.

$^1$H-NMR (DMSO-d$_6$, 300 MHz) δ 1.75 (6H, s), 1.91-2.08 (4H, m), 2.20 (3H, s), 2.65-2.72 (4H, m), 3.44 (2H, s), 7.21 (1H, d, J=8.3 Hz), 7.51 (1H, dd, J=2.2, 8.3 Hz), 7.59 (1H, t, J=7.8 Hz), 7.74 (1H, ddd, J=1.0, 1.9, 7.8 Hz), 7.88-7.97 (2H, m), 8.03 (1H, t, J=1.9 Hz), 8.76 (1H, s), 9.01 (1H, br s), 10.26 (1H, br s), 12.19 (1H, br s).

Example D35

Production of N-(3-{[2-(acetylamino)[1,3]thiazolo[5,4-d]pyrimidin-5-yl]amino}-4-methylphenyl)-2-chloro-3-(1-cyano-1-methylethyl)benzamide

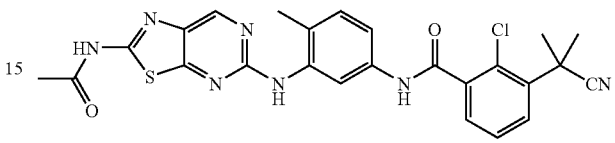

(i) Production of tert-butyl(4-methyl-3-nitrophenyl)carbamate

To a solution of 4-methyl-3-nitroaniline (15.0 g, 98.6 mmol) in tetrahydrofuran (40 mL) was added di-tert-butyl bicarbonate (25.8 g, 118 mmol), and the mixture was stirred at 70° C. for 15 hr and concentrated under reduced pressure. The obtained residue was recrystallized from ethyl acetate and hexane to give the title compound (22.2 g, 89%) as pale-yellow crystals.

$^1$H-NMR (DMSO-d$_6$, 300 MHz) δ 1.48 (9H, s), 2.43 (3H, s), 7.38 (1H, d, J=8.6 Hz), 7.58 (1H, dd, J=2.3, 8.6 Hz), 8.22 (1H, d, J=2.3 Hz), 9.76 (1H, br s).

(ii) Production of tert-butyl(3-amino-4-methylphenyl)carbamate

To a solution of tert-butyl(4-methyl-3-nitrophenyl)carbamate (10.1 g, 39.8 mmol) in ethanol (60 mL)/tetrahydrofuran (20 mL) was added 10% palladium-carbon (2.12 g), and the mixture was stirred at room temperature under a hydrogen atmosphere (3 atm) for 22 hr. The insoluble material was filtered off, and the filtrate was concentrated under reduced pressure to give the title compound (8.82 g, 99%) as a colorless solid.

$^1$H-NMR (DMSO-d$_6$, 300 MHz) δ 1.44 (9H, s), 1.95 (3H, s), 4.72 (2H, br s), 6.48 (1H, d, J=7.8 Hz), 6.73 (1H, d, J=7.8 Hz), 6.82 (1H, s), 8.90 (1H, br s).

(iii) Production of tert-butyl {3-[(2-amino[1,3]thiazolo[5,4-d]pyrimidin-5-yl)amino]-4-methylphenyl}carbamate To a solution of tert-butyl(3-amino-4-methylphenyl)carbamate (8.82 g, 39.7 mmol) in tetrahydrofuran (200 mL) were added N-ethyl-N-isopropylpropane-2-amine (10.4 mL, 59.8 mmol) and 2-chloro-5-nitropyrimidin-4-yl thiocyanate (9.49 g, 43.8 mmol), and the mixture was stirred at room temperature for 30 min. To the reaction mixture was added saturated aqueous sodium hydrogen carbonate solution (200 mL), and the mixture was extracted with ethyl acetate (150 mL, 2×30 mL). The combined organic layer was washed with saturated brine (20 mL), and dried over anhydrous sodium sulfate. The insoluble material was filtered off, and the filtrate was concentrated under reduced pressure to give tert-butyl {3-[(5-nitro-4-thiocyanatopyrimidin-2-yl)amino]-4-methylphenyl}carbamate as a yellow amorphous solid. The obtained compound was used for the next reaction without further purification.

To a solution of the above-mentioned crude product of tert-butyl {3-[(5-nitro-4-thiocyanatopyrimidin-2-yl)amino]-4-methylphenyl}carbamate in ethanol (120 mL)/1-methylpyrrolidin-2-one (80 mL) were added reduced iron (6.68 g, 120 mmol) and aqueous solution (20 mL) of calcium chloride (13.3 g, 120 mmol), and the mixture was stirred at 100° C. for 16 hr. The insoluble material was filtered off, and the filtrate was concentrated under reduced pressure. To the obtained residue was added water (350 mL), and the mixture was extracted with ethyl acetate (200 mL, 2×80 mL). The combined organic layer was washed with saturated brine (50 mL), filtered through a silica gel pad, and the filtrate was concentrated under reduced pressure. The obtained residue was washed with ethyl acetate to give the title compound (5.24 g, 35%) as a gray solid.

$^1$H-NMR (CDCl$_3$, 300 MHz) δ 1.46 (9H, s), 2.11 (3H, s), 7.04 (1H, d, J=8.4 Hz), 7.14 (1H, dd, J=2.1, 8.4 Hz), 7.56 (2H, br s), 7.59 (1H, d, J=2.1 Hz), 8.26 (1H, s), 8.48 (1H, br s), 9.20 (1H, br s).

(iv) Production of tert-butyl(3-{[2-(acetylamino)[1,3]thiazolo[5,4-d]pyrimidin-5-yl]amino}-4-methylphenyl)carbamate To a solution of tert-butyl {3-[(2-amino[1,3]thiazolo[5,4-d]pyrimidin-5-yl)amino]-4-methylphenyl)carbamate (1.20 g, 3.22 mmol) in pyridine (20 mL) was added acetyl chloride (575 μL, 8.06 mmol), and the mixture was stirred at room temperature for 1 hr. To the reaction mixture was added saturated aqueous sodium hydrogen carbonate solution (50 mL), and the mixture was extracted with ethyl acetate (50 mL, 10 mL). The combined organic layer was washed with saturated brine (10 mL), filtered through a basic silica gel pad, and the filtrate was concentrated under reduced pressure. The obtained residue was recrystallized from ethyl acetate to give the title compound (1.31 g, 98%) as a pale-purple solid.

$^1$H-NMR (CDCl$_3$, 300 MHz) δ 1.46 (9H, s), 2.12 (3H, s), 2.18 (3H, s), 7.07 (1H, d, J=8.4 Hz), 7.18 (1H, dd, J=2.1, 8.4 Hz), 7.60 (1H, d, J=2.1 Hz), 8.71 (1H, s), 8.88 (1H, br s), 9.23 (1H, br s), 12.33 (1H, br s).

(v) Production of N-{5-[(5-amino-2-methylphenyl)amino][1,3]thiazolo[5,4-d]pyrimidin-2-yl}acetamide A solution of tert-butyl(3-{[2-(acetylamino)[1,3]thiazolo[5,4-d]pyrimidin-5-yl]amino}-4-methylphenyl)carbamate (1.27 g, 3.06 mmol) and anisole (2 mL) in trifluoroacetic acid (20 mL) was stirred at 0° C. for 1 hr. The reaction mixture was concentrated under reduced pressure, saturated aqueous sodium hydrogen carbonate solution (50 mL) was added to the obtained residue, and the mixture was extracted with ethyl acetate/tetrahydrofuran mixture (1:1, 50 mL, 2×10 mL). The combined organic layer was washed with saturated brine (5 mL), and dried over anhydrous sodium sulfate. The insoluble material was filtered off, and the filtrate was concentrated under reduced pressure. The obtained residue was washed with ethyl acetate to give the title compound (795 mg, 83%) as a pale-green solid.

$^1$H-NMR (DMSO-d$_6$, 300 MHz) δ 2.03 (3H, s), 2.18 (3H, s), 4.83 (2H, br s), 6.31 (1H, dd, J=2.4, 8.1 Hz), 6.76 (1H, d, J=2.4 Hz), 6.84 (1H, d, J=8.1 Hz), 8.67 (1H, br s), 8.70 (1H, s), 12.31 (1H, br s).

(vi) Production of N-(3-{[2-(acetylamino)[1,3]thiazolo[5,4-d]pyrimidin-5-yl]amino}-4-methylphenyl)-2-chloro-3-(1-cyano-1-methylethyl)benzamide A solution of N-{5-[(5-amino-2-methylphenyl)amino][1,3]thiazolo[5,4-d]pyrimidin-2-yl}acetamide (120 mg, 382 μmol), 2-chloro-3-(1-cyano-1-methylethyl)benzoic acid (111 mg, 500 μmol) produced in Example D18(v) and O-(7-azabenzotriazol-1-yl)-N,N,N',N'-tetramethyluronium hexafluorophosphate (189 mg, 500 μmol) in pyridine (4 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→95/5), and the fractions containing the object product were concentrated under reduced pressure. The obtained residue was recrystallized from ethyl acetate to give the title compound (133 mg, 67%) as colorless crystals.

$^1$H-NMR (DMSO-d$_6$, 300 MHz) δ 1.84 (6H, s), 2.18 (3H, s), 2.19 (3H, s), 7.19 (1H, d, J=8.4 Hz), 7.47 (1H, dd, J=2.1, 8.4 Hz), 7.51-7.61 (2H, m), 7.65 (1H, dd, J=2.1, 7.5 Hz), 7.89 (1H, d, J=2.1 Hz), 8.73 (1H, s), 8.97 (1H, br s), 10.52 (1H, s), 12.35 (1H, br s).

Example D36

Production of N-(3-{[2-(acetylamino)[1,3]thiazolo[5,4-d]pyrimidin-5-yl]amino}-4-methylphenyl)-2-chloro-3-(1-cyanocyclopropyl)benzamide

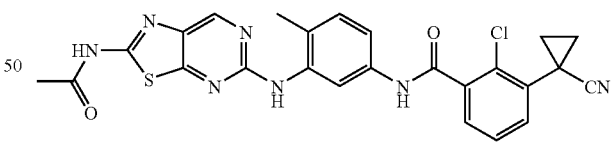

A solution of N-{5-[(5-amino-2-methylphenyl)amino][1,3]thiazolo[5,4-d]pyrimidin-2-yl}acetamide (120 mg, 382 μmol) produced in Example D35(v), 2-chloro-3-(1-cyanocyclopropyl)benzoic acid (110 mg, 500 μmol) produced in Example D19(ii) and O-(7-azabenzotriazol-1-yl)-N,N,N',N'-tetramethyluronium hexafluorophosphate (189 mg, 500 μmol) in pyridine (4 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→95/5), and the fractions containing the object product were concentrated under reduced pressure. The obtained residue was recrystallized from ethyl acetate to give the title compound (133 mg, 67%) as colorless crystals.

$^1$H-NMR (DMSO-d$_6$, 300 MHz) δ 1.40-1.51 (2H, m), 1.74-1.86 (2H, m), 2.18 (3H, s), 2.19 (3H, s), 7.20 (1H, d, J=8.3 Hz), 7.41-7.53 (2H, m), 7.59 (1H, dd, J=1.8, 7.7 Hz), 7.64 (1H, dd, J=1.8, 7.7 Hz), 7.90 (1H, d, J=2.1 Hz), 8.73 (1H, s), 8.98 (1H, br s), 10.50 (1H, br s), 12.35 (1H, br s).

Example D37

Production of N-(3-{[2-(acetylamino)[1,3]thiazolo[5,4-d]pyrimidin-5-yl]amino}-4-methylphenyl)-3-(trifluoromethoxy)benzamide

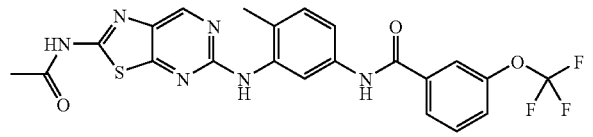 [SMILES: CC(=O)Nc1nc2cnc(Nc3cc(NC(=O)c4cccc(OC(F)(F)F)c4)ccc3C)nc2s1]

A solution of N-{5-[(5-amino-2-methylphenyl)amino][1,3]thiazolo[5,4-d]pyrimidin-2-yl}acetamide (120 mg, 382 µmol) produced in Example D35(v), 3-(trifluoromethoxy)benzoic acid (102 mg, 500 µmol) and O-(7-azabenzotriazol-1-yl)-N,N,N',N'-tetramethyluronium hexafluorophosphate (189 mg, 500 µmol) in pyridine (4 mL) was stirred at room temperature for 2 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→95/5), and the fractions containing the object product were concentrated under reduced pressure. The obtained residue was recrystallized from tetrahydrofuran to give the title compound (78 mg, 40%) as colorless crystals.

$^1$H-NMR (DMSO-d$_6$, 300 MHz) δ 2.18 (3H, s), 2.20 (3H, s), 7.21 (1H, d, J=8.4 Hz), 7.51 (1H, dd, J=2.2, 8.4 Hz), 7.57-7.63 (1H, m), 7.68 (1H, t, J=7.8 Hz), 7.87-7.95 (2H, m), 8.01 (1H, dt, J=7.8, 1.3 Hz), 8.73 (1H, s), 8.98 (1H, br s), 10.33 (1H, br s), 12.34 (1H, br s).

Example D38

Production of N-(3-{[2-(acetylamino)[1,3]thiazolo[5,4-d]pyrimidin-5-yl]amino}-4-methylphenyl)-2-chloro-3-(trifluoromethyl)benzamide

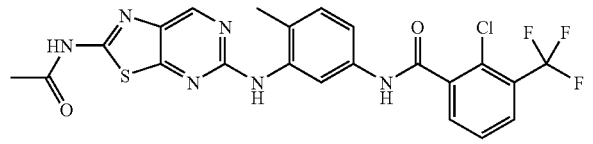 [SMILES: CC(=O)Nc1nc2cnc(Nc3cc(NC(=O)c4cccc(C(F)(F)F)c4Cl)ccc3C)nc2s1]

A solution of N-{5-[(5-amino-2-methylphenyl)amino][1,3]thiazolo[5,4-d]pyrimidin-2-yl}acetamide (120 mg, 382 µmol) produced in Example D35(v), 2-chloro-3-(trifluoromethyl)benzoic acid (112 mg, 500 µmol) and O-(7-azabenzotriazol-1-yl)-N,N,N',N'-tetramethyluronium hexafluorophosphate (189 mg, 500 µmol) in pyridine (4 mL) was stirred at room temperature for 2 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→97/3), and the fractions containing the object product were concentrated under reduced pressure. The obtained residue was recrystallized from ethyl acetate to give the title compound (154 mg, 77%) as colorless crystals.

$^1$H-NMR (DMSO-d$_6$, 300 MHz) δ 2.18 (3H, s), 2.19 (3H, s), 7.21 (1H, d, J=8.4 Hz), 7.46 (1H, dd, J=2.2, 8.4 Hz), 7.67 (1H, t, J=7.8 Hz), 7.86-7.93 (2H, m), 7.97 (1H, dd, J=1.2, 7.8 Hz), 8.73 (1H, s), 8.98 (1H, br s), 10.59 (1H, br s), 12.35 (1H, br s).

Example D39

Production of N-(3-{[2-(acetylamino)[1,3]thiazolo[5,4-d]pyrimidin-5-yl]amino}-4-methylphenyl)-3-(1,1-dimethylprop-2-yn-1-yl)benzamide

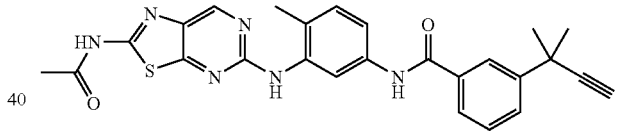

A solution of N-{5-[(5-amino-2-methylphenyl)amino][1,3]thiazolo[5,4-d]pyrimidin-2-yl}acetamide (120 mg, 382 µmol) produced in Example D35(v), 3-(1,1-dimethylprop-2-yn-1-yl)benzoic acid (458 mg, 458 µmol) produced in Example D20(iii) and O-(7-azabenzotriazol-1-yl)-N,N,N',N'-tetramethyluronium hexafluorophosphate (174 mg, 458 µmol) in pyridine (4 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. The obtained residue was recrystallized from tetrahydrofuran to give the title compound (145 mg, 78%) as colorless crystals.

$^1$H-NMR (DMSO-d$_6$, 300 MHz) δ 1.59 (6H, s), 2.18 (3H, s), 2.19 (3H, s), 3.31 (1H, s), 7.20 (1H, d, J=8.3 Hz), 7.46-7.54 (2H, m), 7.74-7.78 (1H, m), 7.83 (1H, dt, J=7.6, 1.5 Hz), 7.90

(1H, d, J=2.1 Hz), 8.07 (1H, t, J=1.5 Hz), 8.75 (1H, s), 9.00 (1H, br s), 10.20 (1H, br s), 12.35 (1H, br s).

Example D40

Production of N-(3-{[2-(acetylamino)[1,3]thiazolo[5,4-d]pyrimidin-5-yl]amino}-4-methylphenyl)-3-(difluoromethoxy)benzamide

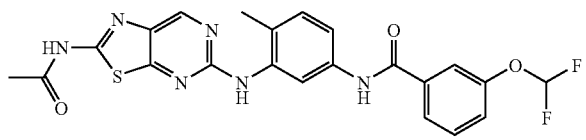 [SMILES: CC(=O)Nc1nc2cnc(Nc3cc(NC(=O)c4cccc(OC(F)F)c4)ccc3C)nc2s1]

A solution of N-{5-[(5-amino-2-methylphenyl)amino][1,3]thiazolo[5,4-d]pyrimidin-2-yl}acetamide (120 mg, 382 µmol) produced in Example D35(v), 3-(difluoromethoxy)benzoic acid (86 mg, 458 µmol) and O-(7-azabenzotriazol-1-yl)-N,N,N',N'-tetramethyluronium hexafluorophosphate (174 mg, 458 µmol) in pyridine (3 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. The obtained residue was recrystallized from tetrahydrofuran and ethyl acetate to give the title compound (113 mg, 61%) as colorless crystals.
$^1$H-NMR (DMSO-$d_6$, 300 MHz) δ 2.19 (3H, s), 2.20 (3H, s), 7.21 (1H, d, J=8.4 Hz), 7.33 (1H, t, J=73.8 Hz), 7.40 (1H, dt, J=7.9, 1.6 Hz), 7.52 (1H, dd, J=2.3, 8.4 Hz), 7.59 (1H, t, J=7.9 Hz), 7.73 (1H, t, J=1.6 Hz), 7.84 (1H, dt, J=7.9, 1.6 Hz), 7.93 (1H, d, J=2.3 Hz), 8.75 (1H, s), 9.00 (1H, br s), 10.26 (1H, br s), 12.35 (1H, br s).

Example D41

Production of N-(3-{[2-(acetylamino)[1,3]thiazolo[5,4-d]pyrimidin-5-yl]amino}-4-methylphenyl)-3-(1,1,2,2-tetrafluoromethoxy)benzamide

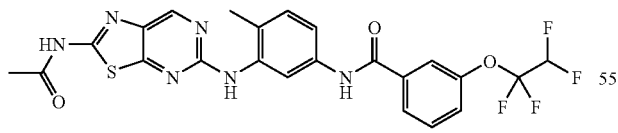

A solution of N-{5-[(5-amino-2-methylphenyl)amino][1,3]thiazolo[5,4-d]pyrimidin-2-yl}acetamide (120 mg, 382 µmol) produced in Example D35(v), 3-(1,1,2,2-tetrafluoromethoxy)benzoic acid (109 mg, 458 µmol) and O-(7-azabenzotriazol-1-yl)-N,N,N',N'-tetramethyluronium hexafluorophosphate (174 mg, 458 µmol) in pyridine (3 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. The obtained residue was recrystallized from methanol and ethyl acetate to give the title compound (89 mg, 44%) as colorless crystals.
$^1$H-NMR (DMSO-$d_6$, 300 MHz) δ 2.19 (3H, s), 2.20 (3H, s), 6.85 (1H, tt, J=3.0, 51.8 Hz), 7.21 (1H, d, J=8.7 Hz), 7.48-7.54 (2H, m), 7.65 (1H, t, J=7.9 Hz), 7.83 (1H, t, J=1.7 Hz), 7.92 (1H, d, J=2.3 Hz), 7.97 (1H, dt, J=7.9, 1.2 Hz), 8.75 (1H, s), 8.99 (1H, br s), 10.32 (1H, br s), 12.34 (1H, br s).

Example D42

Production of N-(3-{[2-(acetylamino)[1,3]thiazolo[5,4-d]pyrimidin-5-yl]amino}-4-methylphenyl)-3-(2-cyanopropyl)benzamide

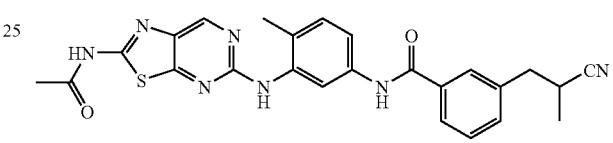

(i) Production of methyl 3-[(1E)-2-cyanoethenyl]benzoate

To a solution of methyl 3-formylbenzoate (1.00 g, 6.09 mmol) in tetrahydrofuran (10 mL) were added potassium carbonate (1.02 g, 7.31 mmol), diethyl (cyanomethyl)phosphonate (1.29 g, 7.31 mmol) and water (0.2 mL), and the mixture was stirred at 70° C. for 1 hr. To the reaction mixture was added water (30 mL), and the mixture was extracted with ethyl acetate (30 mL, 10 mL). The combined organic layer was washed with saturated brine (5 mL), and dried over anhydrous sodium sulfate. The insoluble material was filtered off, and the filtrate was concentrated under reduced pressure. The obtained residue was recrystallized from ethyl acetate and hexane to give the title compound (730 mg, 64%) as colorless needle crystals.
$^1$H-NMR (DMSO-$d_6$, 300 MHz) δ 3.88 (3H, s), 6.61 (1H, d, J=16.8 Hz), 7.61 (1H, t, J=7.8 Hz), 7.77 (1H, d, J=16.8 Hz), 7.96 (1H, dt, J=7.8, 1.5 Hz), 8.02 (1H, dt, J=7.8, 1.5 Hz), 8.20 (1H, t, J=1.5 Hz).

(ii) Production of methyl 3-[(1E)-2-cyanoprop-1-en-1-yl]benzoate

To a suspension of trimethylsulfoxonium iodide (2.88 g, 13.1 mmol) in dimethyl sulfoxide (10 mL) was added 60% sodium hydride (150 mg, 11.2 mmol), and the mixture was stirred at room temperature for 2.5 hr. To the reaction mixture was added methyl 3-[(1E)-2-cyanoethenyl]benzoate (700 mg, 3.74 mmol), and the mixture was stirred at room temperature for 16 hr. To the reaction mixture was added saturated aqueous ammonium chloride solution (30 mL), and the mixture was extracted with ethyl acetate (30 mL, 10 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (hexane/ethyl acetate=95/5→85/15), and the fractions containing the object product were concentrated under reduced pressure to give the title compound (205 mg, 27%) as a colorless solid.

$^1$H-NMR (DMSO-d$_6$, 300 MHz) δ 2.45 (3H, d, J=1.0 Hz), 3.88 (3H, s), 6.23 (1H, d, J=1.0 Hz), 7.61 (1H, t, J=7.7 Hz), 7.91-7.96 (1H, m), 8.03 (1H, dt, J=7.7, 1.2 Hz), 8.14 (1H, t, J=1.6 Hz).

(iii) Production of 3-(2-cyanopropyl)benzoic acid

To a solution of methyl 3-[(1E)-2-cyanoprop-1-en-1-yl]benzoate (108 mg, 537 μmol) in ethanol (4 mL)/tetrahydrofuran (1 mL) was added 10% palladium-carbon (20 mg), and the mixture was stirred at room temperature under a hydrogen atmosphere (1 atm) for 4 hr. The insoluble material was filtered off, and the filtrate was concentrated under reduced pressure to give methyl 3-(2-cyanopropyl)benzoate as a colorless oil.

To a solution of methyl 3-(2-cyanopropyl)benzoate produced above in methanol (2 mL)/tetrahydrofuran (1 mL) was added 2N aqueous sodium hydroxide solution (537 μL, 1.07 mmol), and the mixture was stirred at 50° C. for 1 hr. The reaction mixture was neutralized with 6N hydrochloric acid (300 μL), 1N hydrochloric acid (5 mL) was added, and the mixture was extracted with ethyl acetate (5 mL, 2 mL). The combined organic layer was washed with saturated brine (2 mL), and dried over anhydrous magnesium sulfate. The insoluble material was filtered off, and the filtrate was concentrated under reduced pressure to give the title compound (105 mg, quantitatively) as a white solid.

$^1$H-NMR (DMSO-d$_6$, 300 MHz) δ 1.32 (3H, dd, J=0.8, 7.0 Hz), 2.86 (2H, d, J=7.0 Hz), 3.17-3.29 (1H, m), 7.48 (1H, t, J=7.6 Hz), 7.60 (1H, dt, J=7.6, 1.1 Hz), 7.84 (1H, dt, J=7.6, 1.1 Hz), 7.90 (1H, t, J=1.1 Hz), 12.86 (1H, br s).

(iv) Production of N-(3-{[2-(acetylamino)[1,3]thiazolo[5,4-d]pyrimidin-5-yl]amino}-4-methylphenyl)-3-(2-cyanopropyl)benzamide A solution of N-{5-[(5-amino-2-methylphenyl)amino][1,3]thiazolo[5,4-d]pyrimidin-2-yl}acetamide (130 mg, 413 μmol) produced in Example D35(v), 3-(2-cyanopropyl)benzoic acid (102 mg, 537 μmol) produced above and O-(7-azabenzotriazol-1-yl)-N,N,N',N'-tetramethyluronium hexafluorophosphate (188 mg, 500 μmol) in pyridine (4 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. The obtained residue was recrystallized from ethyl acetate and hexane to give the title compound (130 mg, 65%) as colorless crystals.

$^1$H-NMR (DMSO-d$_6$, 300 MHz) δ 1.36 (3H, d, J=7.1 Hz), 2.19 (3H, s), 2.20 (3H, s), 2.88 (2H, d, J=7.1 Hz), 3.18-3.28 (1H, m), 7.20 (1H, d, J=8.7 Hz), 7.45-7.58 (3H, m), 7.83 (1H, dt, J=7.4, 1.6 Hz), 7.87 (1H, br s), 7.91 (1H, d, J=2.1 Hz), 8.75 (1H, s), 8.99 (1H, br s), 10.16 (1H, br s), 12.34 (1H, br s).

Example D43

Production of N-(3-{[2-(acetylamino)[1,3]thiazolo[5,4-d]pyrimidin-5-yl]amino}-4-methylphenyl)-3-(2-cyanoethyl)benzamide

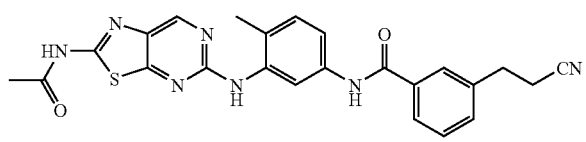 [SMILES: CC(=O)Nc1nc2cnc(Nc3cc(NC(=O)c4cccc(CCC#N)c4)ccc3C)nc2s1]

(i) Production of methyl 3-(2-cyanoethyl)benzoate

To a solution of methyl 3-formylbenzoate (2.00 g, 12.2 mmol) in tetrahydrofuran (20 mL) were added potassium carbonate (2.02 g, 14.6 mmol), diethyl(cyanomethyl)phosphonate (2.29 mL, 14.6 mmol) and water (0.4 mL), and the mixture was stirred at 60° C. for 1 hr. To the reaction mixture was added water (50 mL), and the mixture was extracted with ethyl acetate (50 mL, 20 mL). The combined organic layer was washed with saturated brine (10 mL), and dried over anhydrous sodium sulfate. The insoluble material was filtered off, and the filtrate was concentrated under reduced pressure to give methyl 3-(2-cyanoethenyl)benzoate as a white solid. The obtained compound was used for the next reaction without further purification.

To a solution of the above-mentioned crude product of methyl 3-(2-cyanoethenyl)benzoate in ethanol (45 mL)/tetrahydrofuran (15 mL) was added 10% palladium-carbon (648 mg), and the mixture was stirred at room temperature under a hydrogen atmosphere (1 atm) for 2 hr. The insoluble material was filtered off, and the filtrate was concentrated under reduced pressure. The obtained residue was purified by silica gel column chromatography (hexane/ethyl acetate=90/10→75/25), and the fractions containing the object product were concentrated under reduced pressure to give the title compound (2.03 g, 88%) as a colorless oil.

$^1$H-NMR (DMSO-d$_6$, 300 MHz) δ 2.85 (2H, dt, J=6.9, 1.2 Hz), 2.93-3.00 (2H, m), 3.86 (3H, s), 7.49 (1H, dt, J=0.5, 7.6 Hz), 7.60 (1H, ddd, J=1.5, 1.8, 7.6 Hz), 7.86 (1H, ddd, J=1.5, 1.8, 7.6 Hz), 7.91 (1H, dt, J=0.5, 1.8 Hz).

(ii) Production of 3-(2-cyanoethyl)benzoic acid

To a solution of methyl 3-(2-cyanoethyl)benzoate (169 mg, 893 μmol) in methanol (3 mL)/tetrahydrofuran (1 mL) was added 2N aqueous sodium hydroxide solution (893 μL, 1.79 mmol), and the mixture was stirred at 60° C. for 4 hr. The reaction mixture was neutralized with 6N hydrochloric acid (500 μL), 1N hydrochloric acid (15 mL) was added, and the mixture was extracted with ethyl acetate (20 mL, 5 mL). The combined organic layer was washed with saturated brine (5 mL), and dried over anhydrous magnesium sulfate. The insoluble material was filtered off, and the filtrate was concentrated under reduced pressure to give the title compound (151 mg, 96%) as a white solid.

$^1$H-NMR (DMSO-d$_6$, 300 MHz) δ 2.80-2.89 (2H, m), 2.91-3.00 (2H, m), 7.46 (1H, t, J=7.6 Hz), 7.56 (1H, dt, J=7.6, 1.5 Hz), 7.83 (1H, dt, J=7.6, 1.5 Hz), 7.89 (1H, t, J=1.5 Hz), 12.94 (1H, br s).

(iii) Production of N-(3-{[2-(acetylamino)[1,3]thiazolo[5,4-d]pyrimidin-5-yl]amino}-4-methylphenyl)-3-(2-cyanoethyl)benzamide A solution of N-{5-[(5-amino-2-methylphenyl)amino][1,3]thiazolo[5,4-d]pyrimidin-2-yl}acetamide (120 mg, 382 μmol) produced in Example D35(v), 3-(2-cyanoethyl)benzoic acid (74 mg, 420 μmol) and O-(7-azabenzotriazol-1-yl)-N,N,N',N'-tetramethyluronium hexafluorophosphate (160 mg, 420 μmol) in pyridine (4 mL) was stirred at room temperature for 1 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=30/70→0/100), and the fractions containing the object product were concentrated under reduced pressure. The obtained residue was recrystallized from tetrahydrofuran and ethyl acetate to give the title compound (117 mg, 65%) as pale-yellow crystals.

$^1$H-NMR (DMSO-$d_6$, 300 MHz) δ 2.19 (6H, s), 2.83-2.92 (2H, m), 2.94-3.04 (2H, m), 7.20 (1H, d, J=8.7 Hz), 7.44-7.56 (3H, m), 7.79-7.88 (2H, m), 7.92 (1H, d, J=2.1 Hz), 8.75 (1H, s), 9.00 (1H, br s), 10.17 (1H, br s), 12.35 (1H, br s).

Example D44

Production of N-(3-{[2-(acetylamino)[1,3]thiazolo[5,4-d]pyrimidin-5-yl]amino}-4-methylphenyl)-3-(2-cyano-2-methylpropyl)benzamide

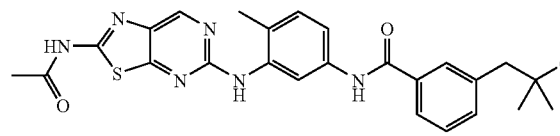

(i) Production of methyl 3-(2-cyano-2-methylpropyl)benzoate

To a solution of methyl 3-(2-cyanoethyl)benzoate (510 mg, 2.70 mmol) produced in Example D43(i) in tetrahydrofuran (15 mL) was added methyl iodide (671 μL, 10.8 mmol), and a 1.1M solution (7.35 mL, 8.09 mmol) of lithium hexamethyldisilazide in tetrahydrofuran was added dropwise at −78° C. over 30 min. After the completion of the dropwise addition, the mixture was stirred at −78° C. for 1 hr. The reaction mixture was poured into a mixture of ethyl acetate (50 mL) and saturated aqueous ammonium chloride solution (50 mL), and the organic layer and the aqueous layer were separated. The aqueous layer was extracted with ethyl acetate (50 mL). The combined organic layer was washed with saturated brine (10 mL), and dried over anhydrous magnesium sulfate. The insoluble material was filtered off, and the filtrate was concentrated under reduced pressure. The obtained residue was purified by silica gel column chromatography (hexane/ethyl acetate=95/5→85/15), and the fractions containing the object product were concentrated under reduced pressure to give the title compound (260 mg, 44%) as a yellow oil.

$^1$H-NMR (DMSO-$d_6$, 300 MHz) δ 1.30 (6H, s), 2.94 (2H, s), 3.86 (3H, s), 7.52 (1H, t, J=7.8 Hz), 7.58 (1H, dt, J=7.8, 1.6 Hz), 7.87-7.93 (2H, m).

(ii) Production of 3-(2-cyano-2-methylpropyl)benzoic acid

To a solution of methyl 3-(2-cyano-2-methylpropyl)benzoate (260 mg, 1.20 mmol) in methanol (6 mL)/tetrahydrofuran (2 mL) was added 2N aqueous sodium hydroxide solution (1.20 mL, 2.39 mmol), and the mixture was stirred at 60° C. for 2 hr. The reaction mixture was neutralized with 6N hydrochloric acid (600 μL), 1N hydrochloric acid (30 mL) was added, and the mixture was extracted with ethyl acetate (30 mL, 10 mL). The combined organic layer was washed with saturated brine (5 mL), and dried over anhydrous magnesium sulfate. The insoluble material was filtered off, and the filtrate was concentrated under reduced pressure to give the title compound (230 mg, 95%) as a white solid.

$^1$H-NMR (DMSO-$d_6$, 300 MHz) δ 1.31 (6H, s), 2.93 (2H, s), 7.43-7.58 (2H, m), 7.81-7.92 (2H, m), 12.98 (1H, br s).

(iii) Production of N-(3-{[2-(acetylamino)[1,3]thiazolo[5,4-d]pyrimidin-5-yl]amino}-4-methylphenyl)-3-(2-cyano-2-methylpropyl)benzamide A solution of N-{5-[(5-amino-2-methylphenyl)amino][1,3]thiazolo[5,4-d]pyrimidin-2-yl}acetamide (120 mg, 382 μmol) produced in Example D35(v), 3-(2-cyano-2-methylpropyl)benzoic acid (86 mg, 420 μmol) and O-(7-azabenzotriazol-1-yl)-N,N,N',N'-tetramethyluronium hexafluorophosphate (160 mg, 420 μmol) in pyridine (4 mL) was stirred at room temperature for 2 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=30/70→0/100), and the fractions containing the object product were concentrated under reduced pressure. The obtained residue was washed with methanol to give the title compound (108 mg, 56%) as a colorless solid.

$^1$H-NMR (DMSO-$d_6$, 300 MHz) δ 1.33 (6H, s), 2.19 (3H, s), 2.19 (3H, s), 2.94 (2H, s), 7.20 (1H, d, J=8.5 Hz), 7.46-7.57 (3H, m), 7.83 (1H, br s), 7.85-7.91 (1H, m), 7.92 (1H, d, J=2.3 Hz), 8.74 (1H, s), 8.99 (1H, br s), 10.19 (1H, br s), 12.35 (1H, br s).

Example D45

Production of N-(3-{[2-(acetylamino)[1,3]thiazolo[5,4-d]pyrimidin-5-yl]amino}-4-methylphenyl)-3-(1-cyano-1-methylethoxy)benzamide

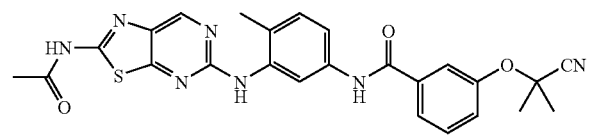 [SMILES: CC(=O)Nc1nc2cnc(Nc3cc(NC(=O)c4cccc(OC(C)(C)C#N)c4)ccc3C)nc2s1]

(i) Production of methyl 3-(cyanomethoxy)benzoate

To a solution of 3-methyl hydroxybenzoate (5.00 g, 32.9 mmol) in acetone (60 mL) were added bromoacetonitrile (2.63 mL, 39.4 mmol) and potassium carbonate (6.81 g, 49.3 mmol), and the mixture was stirred at 60° C. for 4 hr. To the reaction mixture was added saturated aqueous sodium hydrogen carbonate solution (100 mL), and the mixture was extracted with ethyl acetate (100 mL, 30 mL). The combined organic layer was washed with saturated brine (10 mL), and dried over anhydrous magnesium sulfate. The insoluble material was filtered off, and the filtrate was concentrated under reduced pressure. The obtained residue was purified by basic silica gel column chromatography (hexane/ethyl acetate=90/10→80/20), and the fractions containing the object product were concentrated under reduced pressure to give the title compound (5.43 g, 86%) as a colorless oil.

$^1$H-NMR (DMSO-$d_6$, 300 MHz) δ 3.87 (3H, s), 5.27 (2H, s), 7.37 (1H, ddd, J=1.3, 2.6, 7.8 Hz), 7.54 (1H, t, J=7.8 Hz), 7.59 (1H, dd, J=1.3, 2.6 Hz), 7.68 (1H, dt, J=7.8, 1.3 Hz).

(ii) Production of methyl 3-(1-cyano-1-methylethoxy)benzoate

To a solution of methyl 3-(cyanomethoxy)benzoate (6.00 g, 31.4 mmol) in tetrahydrofuran (200 mL) was added methyl iodide (15.6 mL, 251 mmol), and a 1.1M solution (62.8 mL, 69.0 mmol) of lithium hexamethyl disilazide in tetrahydrofuran was added dropwise at −78° C. over 1.5 hr. After the completion of the dropwise addition, the mixture was stirred at −78° C. for 2 hr. The reaction mixture was poured into a mixture of ethyl acetate (150 mL) and saturated aqueous ammonium chloride solution (150 mL), and the organic layer and the aqueous layer were separated. The aqueous layer was extracted with ethyl acetate (50 mL). The combined organic layer was washed with saturated brine (50 mL), and dried over anhydrous magnesium sulfate. The insoluble material was filtered off, and the filtrate was concentrated under reduced pressure. The obtained residue was purified by silica gel column chromatography (hexane/ethyl acetate=100/0→90/10), and the fractions containing the object product were concentrated under reduced pressure to give the title compound (2.07 g, 30%) as a yellow oil.

$^1$H-NMR (DMSO-$d_6$, 300 MHz) δ 1.71 (6H, s), 3.86 (3H, s), 7.46 (1H, ddd, J=1.2, 2.4, 7.8 Hz), 7.56 (1H, dt, J=0.3, 7.8 Hz), 7.69-7.72 (1H, m), 7.79 (1H, ddd, J=1.2, 2.4, 7.8 Hz).

(iii) Production of 3-(1-cyano-1-methylethoxy)benzoic acid

To a solution of methyl 3-(1-cyano-1-methylethoxy)benzoate (2.07 g, 9.44 mmol) in methanol (12 mL)/tetrahydrofuran (4 mL) was added 2N aqueous sodium hydroxide solution (9.44 mL, 18.9 mmol), and the mixture was stirred at room temperature for 30 min. The reaction mixture was neutralized with 6N hydrochloric acid (5 mL), 1N hydrochloric acid (50 mL) was added, and the mixture was extracted with ethyl acetate (50 mL, 20 mL). The combined organic layer was washed with saturated brine (10 mL), and dried over anhydrous magnesium sulfate. The insoluble material was filtered off, and the filtrate was concentrated under reduced pressure. The obtained residue was purified by silica gel column chromatography (hexane/ethyl acetate=90/10→50/50), and the fractions containing the object product were concentrated under reduced pressure. The obtained residue was recrystallized from ethyl acetate and hexane to give the title compound (1.01 g, 51%) as colorless crystals.

(iv) Production of N-(3-{[2-(acetylamino)[1,3]thiazolo[5,4-d]pyrimidin-5-yl]amino}-4-methylphenyl)-3-(1-cyano-1-methylethoxy)benzamide A solution of N-{5-[(5-amino-2-methylphenyl)amino][1,3]thiazolo[5,4-d]pyrimidin-2-yl}acetamide (83 mg, 265 µmol) produced in Example D35(v), 3-(1-cyano-1-methylethoxy)benzoic acid (71 mg, 345 µmol) and O-(7-azabenzotriazol-1-yl)-N,N,N',N'-tetramethyluronium hexafluorophosphate (120 mg, 318 µmol) in pyridine (3 mL) was stirred at room temperature for 1.5 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=30/70→0/100), and the fractions containing the object product were concentrated under reduced pressure. The obtained residue was recrystallized from tetrahydrofuran and hexane to give the title compound (61 mg, 46%) as a colorless solid.

$^1$H-NMR (DMSO-$d_6$, 300 MHz) δ 1.74 (6H, s), 2.19 (3H, s), 2.19 (3H, s), 7.20 (1H, d, J=8.4 Hz), 7.40 (1H, ddd, J=1.0, 2.0, 8.1 Hz), 7.51 (1H, dd, J=2.1, 8.4 Hz), 7.56 (1H, t, J=8.1 Hz), 7.70 (1H, t, J=2.0 Hz), 7.79 (1H, ddd, J=1.0, 2.0, 8.1 Hz), 7.92 (1H, d, J=2.1 Hz), 8.74 (1H, s), 9.00 (1H, br s), 10.24 (1H, br s), 12.35 (1H, br s).

Example D46

Production of N-(5-{[2-(acetylamino)[1,3]thiazolo[5,4-d]pyrimidin-5-yl]amino}-4-chloro-2-fluorophenyl)-3-(1-cyano-1-methylethyl)benzamide

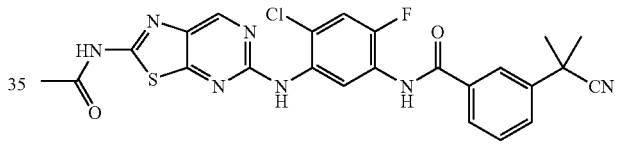

(i) Production of tert-butyl(5-amino-4-chloro-2-fluorophenyl)carbamate

To a solution of tert-butyl(5-amino-2-fluorophenyl)carbamate (795 mg, 3.51 mmol) produced in Example D17(i) in N,N-dimethylformamide (15 mL) was added 1-chloropyrrolidine-2,5-dione (493 mg, 3.69 mmol), and the mixture was stirred at room temperature for 3 hr. To the reaction mixture was added saturated aqueous sodium hydrogen carbonate solution (50 mL), and the mixture was extracted with ethyl acetate (50 mL, 15 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=100/0→90/10), and the fractions containing the object product were concentrated under reduced pressure to give the title compound (727 mg, 79%) as a yellow solid.

$^1$H-NMR (DMSO-$d_6$, 300 MHz) δ 1.45 (9H, s), 5.19 (2H, br s), 7.10 (1H, s), 7.13 (1H, s), 8.80 (1H, br s).

(ii) Production of tert-butyl {5-[(2-amino[1,3]thiazolo[5,4-d]pyrimidin-5-yl)amino]-4-chloro-2-fluorophenyl}carbamate To a solution of tert-butyl(5-amino-4-chloro-2-fluorophenyl)carbamate (5.17 g, 19.8 mmol) in tetrahydrofuran (10 mL) were added N-ethyl-N-isopropylpropane-2-amine (6.93 mL, 39.6 mmol) and 2-chloro-5-nitropyrimidin-4-yl thiocyanate (6.44 g, 29.7 mmol), and the mixture was stirred at room temperature for 1 hr. To the reaction mixture was added water (200 mL), and the mixture was extracted with ethyl acetate (300 mL, 50 mL). The combined organic layer was washed with saturated brine (30 mL), and dried over anhydrous sodium sulfate. The insoluble material was filtered off, and the filtrate was concentrated under reduced pressure to give tert-butyl {4-chloro-2-fluoro-5-[(5-nitro-4-thiocyanatopyrimidin-2-yl)amino]phenyl}carbamate as a yellow amorphous solid. The obtained compound was used for the next reaction without further purification.

To a solution of the above-mentioned crude product of tert-butyl {4-chloro-2-fluoro-5-[(5-nitro-4-thiocyanatopyrimidin-2-yl)amino]phenyl}carbamate in acetic acid (20 mL) was added reduced iron (697 mg, 12.5 mmol), and the mixture was stirred at 80° C. for 30 min. The insoluble material was filtered off, and the filtrate was concentrated under reduced pressure. To the obtained residue was added saturated aqueous sodium hydrogen carbonate solution (50 mL), and the mixture was extracted with ethyl acetate/tetrahydrofuran mixture (1:1, 50 mL, 20 mL). The combined organic layer was washed with saturated brine (10 mL), and dried over anhydrous sodium sulfate. The insoluble material was filtered off, and the filtrate was concentrated under reduced pressure. The obtained residue was washed with ethyl acetate to give the title compound (487 mg, 6%) as a pale-yellow solid.

$^1$H-NMR (DMSO-$d_6$, 300 MHz) δ 1.45 (9H, s), 7.46 (1H, d, J=10.2 Hz), 7.65 (2H, br s), 8.00 (1H, d, J=7.9 Hz), 8.30 (1H, s), 8.60 (1H, br s), 9.09 (1H, br s).

(iii) Production of N-{5-[(5-amino-2-chloro-4-fluorophenyl)amino][1,3]thiazolo[5,4-d]pyrimidin-2-yl}acetamide To a solution of tert-butyl {5-[(2-amino[1,3]thiazolo[5,4-d]pyrimidin-5-yl)amino]-4-chloro-2-fluorophenyl}carbamate (470 mg, 1.14 mmol) in pyridine (10 mL) was added acetyl chloride (204 μL, 2.86 mmol), and the mixture was stirred at room temperature for 1 hr. To the reaction mixture was added saturated aqueous sodium hydrogen carbonate solution (50 mL), and the mixture was extracted with ethyl acetate/tetrahydrofuran mixture (1:1, 50 mL, 20 mL). The combined organic layer was washed with saturated brine (10 mL), and dried over anhydrous sodium sulfate. The insoluble material was filtered off, and the filtrate was concentrated under reduced pressure to give tert-butyl(5-{[2-(acetylamino)[1,3]thiazolo[5,4-d]pyrimidin-5-yl]amino}-4-chloro-2-fluorophenyl)carbamate as a brown amorphous solid. The obtained compound was used for the next reaction without further purification.

A solution of the above-mentioned crude product of tert-butyl(5-{[2-(acetylamino)[1,3]thiazolo[5,4-d]pyrimidin-5-yl]amino}-4-chloro-2-fluorophenyl)carbamate and anisole (1 mL) in trifluoroacetic acid (15 mL) was stirred at 0° C. for 1 hr. The reaction mixture was concentrated under reduced pressure, saturated aqueous sodium hydrogen carbonate solution (30 mL) was added to the obtained residue, and the mixture was extracted with ethyl acetate/tetrahydrofuran mixture (1:1, 50 mL, 10 mL). The combined organic layer was washed with saturated brine (10 mL), and dried over anhydrous sodium sulfate. The insoluble material was filtered off, and the filtrate was concentrated under reduced pressure. The obtained residue was washed with ethyl acetate to give the title compound (297 mg, 74%) as a yellow solid.

$^1$H-NMR (DMSO-$d_6$, 300 MHz) δ 2.19 (3H, s), 5.34 (2H, br s), 7.15 (1H, d, J=9.1 Hz), 7.20 (1H, d, J=11.0 Hz), 8.75 (1H, s), 8.75 (1H, br s), 12.38 (1H, br s).

(iv) Production of N-(5-{[2-(acetylamino)[1,3]thiazolo[5,4-d]pyrimidin-5-yl]amino}-4-chloro-2-fluorophenyl)-3-(1-cyano-1-methylethyl)benzamide A solution of N-{5-[(5-amino-2-chloro-4-fluorophenyl)amino][1,3]thiazolo[5,4-d]pyrimidin-2-yl}acetamide (100 mg, 283 μmol), 3-(1-cyano-1-methylethyl)benzoic acid (128 mg, 680 μmol) and O-(7-azabenzotriazol-1-yl)-N,N,N',N'-tetramethyluronium hexafluorophosphate (258 mg, 680 μmol) in pyridine (3 mL) was stirred at 90° C. for 9 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=10/90→0/100), and the fractions containing the object product were concentrated under reduced pressure. The obtained residue was recrystallized from ethyl acetate to give the title compound (99 mg, 67%) as colorless crystals.

$^1$H-NMR (DMSO-$d_6$, 300 MHz) δ 1.75 (6H, s), 2.19 (3H, s), 7.61 (1H, t, J=7.9 Hz), 7.63 (1H, d, J=9.9 Hz), 7.78 (1H, ddd, J=1.0, 1.9, 7.9 Hz), 7.96 (2H, m), 8.09 (1H, t, J=1.9 Hz), 8.78 (1H, s), 9.13 (1H, br s), 10.34 (1H, br s), 12.40 (1H, br s).

Example D47

Production of N-(5-{[2-(acetylamino)[1,3]thiazolo[5,4-d]pyrimidin-5-yl]amino}-4-chloro-2-fluorophenyl)-2-chloro-3-(1-cyano-1-methylethyl)benzamide

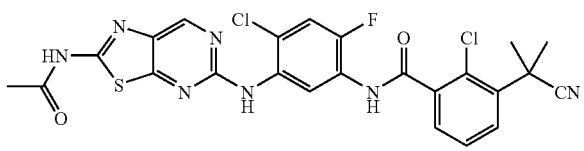 [SMILES: CC(=O)Nc1nc2cnc(Nc3cc(NC(=O)c4cccc(C(C)(C)C#N)c4Cl)c(F)cc3Cl)nc2s1]

A solution of N-{5-[(5-amino-2-chloro-4-fluorophenyl)amino][1,3]thiazolo[5,4-d]pyrimidin-2-yl}acetamide (100 mg, 283 μmol) produced in Example D46(iii), 3-(1-cyano-1-methylethyl)benzoic acid (128 mg, 680 μmol) produced in Example D18(v) and O-(7-azabenzotriazol-1-yl)-N,N,N',N'-tetramethyluronium hexafluorophosphate (258 mg, 680 μmol) in pyridine (3 mL) was stirred at 90° C. for 23 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/80→0/100), and the fractions containing the object product were concentrated under reduced pressure. The obtained residue was recrystallized from ethyl acetate to give the title compound (113 mg, 59%) as colorless crystals.

$^1$H-NMR (DMSO-$d_6$, 300 MHz) δ 1.85 (6H, s), 2.19 (3H, s), 7.53 (1H, t, J=7.9 Hz), 7.60 (1H, dd, J=1.9, 7.9 Hz), 7.62

(1H, d, J=10.0 Hz), 7.67 (1H, dd, J=1.9, 7.9 Hz), 8.22 (1H, d, J=7.7 Hz), 8.78 (1H, s), 9.17 (1H, br s), 10.59 (1H, br s), 12.40 (1H, br s).

Example D48

Production of N-(5-{[2-(acetylamino)[1,3]thiazolo [5,4-d]pyrimidin-5-yl]amino}-4-chloro-2-fluorophenyl)-3-(1,1-dimethylprop-2-yn-1-yl)benzamide

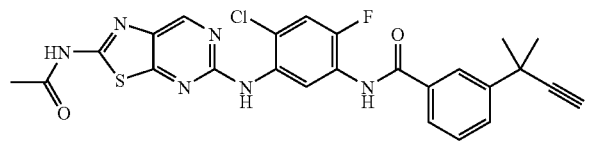 [SMILES: C#CC(C)(C)c1cccc(C(=O)Nc2cc(Nc3ncc4nc(NC(C)=O)sc4n3)c(Cl)cc2F)c1]

A solution of N-{5-[(5-amino-2-chloro-4-fluorophenyl) amino][1,3]thiazolo[5,4-d]pyrimidin-2-yl}acetamide (78 mg, 221 μmol) produced in Example D46(iii), 3-(1,1-dimethylprop-2-yn-1-yl)benzoic acid (79 mg, 442 μmol) produced in Example D20(iii) and O-(7-azabenzotriazol-1-yl)-N,N,N', N'-tetramethyluronium hexafluorophosphate (168 mg, 442 μmol) in pyridine (3 mL) was stirred at 90° C. for 5 hr. To the reaction mixture was added saturated aqueous sodium hydrogen carbonate solution (15 mL), and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by basic silica gel column chromatography (hexane/ethyl acetate=20/ 80→0/100), and the fractions containing the object product were concentrated under reduced pressure. The obtained residue was recrystallized from ethyl acetate and hexane to give the title compound (89 mg, 77%) as colorless crystals.

$^1$H-NMR (DMSO-$d_6$, 300 MHz) δ 1.59 (6H, s), 2.19 (3H, s), 3.32 (1H, s), 7.52 (1H, t, J=7.8 Hz), 7.62 (1H, d, J=10.0 Hz), 7.80 (1H, ddd, J=1.1, 1.8, 7.8 Hz), 7.85-7.90 (1H, m), 7.96 (1H, d, J=7.7 Hz), 8.13 (1H, t, J=1.8 Hz), 8.77 (1H, s), 9.10 (1H, br s), 10.27 (1H, br s), 12.39 (1H, br s).

Preparation Example D1

A pharmaceutical agent containing the compound of the present invention as an active ingredient can be produced, for example, according to the following formulation.

1. Capsule

| (1) compound of Example D1 | 40 mg |
|---|---|
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added and the total amount is sealed in a gelatin capsule.

2. Tablet

| (1) compound of Example D1 | 40 mg |
|---|---|
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The rest of (4) and (5) is added to the granules and the mixture is compression formed into a tablet.

Preparation Example D2

The compound (50 mg) obtained in Example D1 is dissolved in the Japanese Pharmacopoeia distilled water for injection (50 mL), and the Japanese Pharmacopoeia distilled water for injection is added to make the total amount 100 mL. This solution is aseptically filtered. The solution (1 mL) is aseptically filled in a vial for injection, sealed and freeze-dried.

Experimental Example 1

Cloning of Human BRAF Gene and Preparation of Recombinant Baculovirus

Human BRAF gene was cloned by PCR using human Testis cDNA library (Clontech) as a template. The primer used for PCR was prepared from base sequence (Genbank Accession No.: NM_004333) information of BRAF gene by adding a base sequence encoding flag peptide and a recognition sequence of the restriction enzyme to area encoding the BRAF kinase domain region, so that the protein contains an N-terminal Flag. The primer base sequence is shown below.
BRAF-U:

5'-AAAGAATTCACCATGGACTACAAGGACGACGATGACAAGACCCCCC

CTGCCTCATTACCTGG

CT-3' (SEQ ID NO:1) and
BRAF-L:

(SEQ ID NO: 2)
5'-AAAAGTCGACTCAGTGGACAGGAAACGCACCATAT-3'

The PCR reaction was conducted using Pyrobest (Takara Shuzo Co., Ltd). The obtained PCR product was electrophoresed on agarose gel (1%), the DNA fragment amplified by PCR was recovered from the gel, and then digested with restriction enzymes EcoRI and SalI. The DNA treated with the restriction enzymes was electrophoresed on agarose gel (1%), and the obtained DNA fragment was recovered. The recovered DNA fragment was ligated to plasmid pFAST-BAC1 (Invitrogen) digested with restriction enzymes EcoRI and SalI to give expression plasmid pFB-BRAF, and the base sequence of the insert fragment was confirmed. In addition, mutation was introduced into V600E using a Quick change Site Directed Mutagenesis kit (Stratagene). The base sequences of the primers used are shown in the following.

V600E-U:

```
5'-GGTCTAGCTACAGAGAAATCTCGATGGAG-3'  (SEQ ID NO: 3)
``` and
V600E-L:

```
5'-CTCCATCGAGATTTCTCTGTAGCTAGACC-3'  (SEQ ID NO: 4)
```

The obtained plasmid was sequenced to confirm the introduction of mutation into V600E. The DNA was digested with restriction enzymes EcoRI and SalI, DNA treated with the restriction enzymes was electrophoresed on agarose gel (1%), and the obtained DNA fragment was recovered. The recovered DNA fragment was ligated to plasmid pFASTBAC1 (Invitrogen) digested with restriction enzymes EcoRI and SalI to give expression plasmid pFB-V600E.

Using BAC-TO-BAC Baculovirus Expression System (Invitrogen), virus stock BAC-V600E of recombinant baculovirus was prepared.

Experimental Example 2

Preparation of BRAF (V600E) Protein

SF-21 cells were sown at $1\times10^6$ cells/mL to Sf-900II SFM medium (1 L, Invitrogen) containing 10% fetal bovine serum (Trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hr, recombinant baculovirus BAC-V600E (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at -80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 µm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 µg/mL of FLAG peptide. The buffer of this concentrate was exchanged using NAP25 column (Amersham Bioscience) equilibrated with buffer A and the fractions were cryopreserved at -80° C.

Test Example 1

Determination of BRAF (V600E) Kinase Inhibitory Activity

A test compound (2.5 µL) dissolved in dimethyl sulfoxide (DMSO) was added to 37.5 µL of a reaction solution (25 mM HEPES (pH 7.5), 10 mM magnesium acetate, 1 mM dithiothreitol) containing BRAF (V600E) enzyme (30 ng) and recombinant type protein GST-MEK1 (K96R) 250 ng, and the mixture was incubated at room temperature for 10 min. ATP solution (10 µL, 2.5 µM ATP, 0.1 µCi [γ-$^{32}$P]ATP) was added to the obtained mixture, and the mixture was reacted at room temperature for 20 min. The reaction was quenched by adding 50 µL of ice-cooled 20% trichloroacetic acid (Wako Pure Chemical Industries, Ltd.). The reaction solution was allowed to stand at 4° C. for 30 min, and the acid-precipitable fraction was transferred to GF/C filter plate (Millipore Corporation) using cell harvester (PerkinElmer). The plate was dried at 45° C. for 60 min, and 40 µL of MicroScinti 0 (PerkinElmer) was added thereto. The radioactivity was measured using TopCount (PerkinElmer). The kinase inhibitory rate (%) of the test compound was calculated by the following formula:

Inhibitory rate (%)=(1-(count of test compound-blank)÷(control-blank))×100

The count of the solution reacted without addition of the compound was used as a "control", and the count of the solution without the compound and enzyme was used as a "blank".

The obtained results are shown in Table 1. The results show that the compound of the present invention strongly inhibits an activity of BRAF (V600E) kinase.

TABLE 1

| Ex. No. (Compound No.) | Inhibitory rate (%) at 1.0 µM |
|---|---|
| A2 | 100 |
| B2 | 100 |
| B6 | 100 |
| C1 | 100 |
| C8 | 99 |
| C17 | 99 |
| C20 | 100 |
| C22 | 100 |
| C25 | 100 |
| C30 | 100 |
| C36 | 100 |
| C41 | 100 |
| C60 | 100 |
| C63 | 101 |
| C75 | 100 |
| D1 | 98 |

Test Example 2

Colon Cancer Cell HT-29 Intracellular MEK Phosphorylation Inhibitory Action in vitro A cell suspension (500 µL) of human colon cancer cell HT-29 was plated in a 48-well plate (100,000 cells/well), and the cells were cultured overnight at 37° C. in the presence of 5% $CO_2$, treated with a test compound (250 µL/well) diluted in 3-fold dilution series and cultured for two more hours. After 2 hr, the culture medium containing the test compound was removed, and the cells were lysed with SDS sample buffer (100 µL/well) and heated at 95° C. for 5 min. Thereafter, the cells were applied to SDS-PAGE, and the protein was transferred onto Sequi-Blot™ PVDF Membrane (Bio-Rad) by the Western blot method. The cells were blocked with a block-Ace solution (Snow Brand Milk Products Co., Ltd) dissolved in phosphate buffer to 5% W/V, and reacted overnight with anti-phosphorylated MEK1/2 (Ser217/221) (Cell signaling #9121) diluted 1000-fold with phosphate buffer containing 0.4% block-Ace. The membrane was washed with phosphate buffer containing 0.1% Tween 20 (Wako Pure Chemical Industries, Ltd.), and reacted at room temperature for 1 hr with HRP labeled rabbit IgG polyclonal antibody (Cell signaling #7074) diluted 1000-fold with phosphate buffer containing 0.4% block-Ace. The membrane was washed in the same manner as above, chemical luminescence of a phosphorylated MEK1/2 protein labeled with the antibody, which was caused by ECL-plus Detection Reagent (Amersham bioscience), was detected by Luminescent Image Analyzer LAS-1000 (FUJIFILM Corporation). Taking the luminescence of the control group free of the test compound as 100%, the concentration ($IC_{50}$ value) of the compound necessary for inhibiting the residual luminescence to 50% of the control group was calculated. The results are shown in Table 2.

TABLE 2

| Ex. No. (Compound No.) | $IC_{50}$ (nM) |
|---|---|
| A4 | <500 |
| B3 | <500 |
| C2 | <500 |
| C9 | <500 |
| C11 | <500 |
| C13 | <500 |
| C16 | <500 |
| C26 | <500 |
| C35 | <500 |
| C40 | <500 |
| C51 | <500 |
| C65 | <500 |
| C99 | <500 |
| D2 | <500 |

Test Example 3

Colon Cancer Cell HT-29 Growth Suppressive Action in vitro

A cell suspension (100 μL, 3,000 cells/well) of human colon cancer cell HT-29 (purchased from ATCC) was plated in a 96-well plate, and the cells were cultured at 37° C. in a 5% carbon dioxide gas incubator. The next day, 2-fold serial dilution of each test compound solution (diluted from maximum concentration 20 μM) (100 μL) was added, and the cells were cultured for 3 days. The culture medium containing the test compound was removed, and the cells were washed with phosphate buffer (PBS). A 50% trichloroacetic acid solution was added to the final concentration of 10% (v/v), and the mixture was stood overnight at 4° C., whereby the cells were fixed to the plate. Then, a dye SRB 0.4% (w/v) solution (dissolved in 1% acetic acid) was added at 50 μl/well, whereby the cell protein was fixed and stained (Skehan et al., Journal Of National Cancer Institute, vol. 82, pp. 1107-1112, 1990). The cells were washed 3 times with 1% acetic acid solution (200 μL/well), and 100 μL of an extract (10 mM Tris buffer) was added to extract the dye. The absorbance at an absorption wavelength 550 nM was measured, and cell amount was measured as a protein amount. Taking the protein amount of the control group free of the test compound as 100%, the proportion of the residual protein amount of each treatment group was determined and the concentration of the compound necessary for suppressing the residual cell amount to 50% of the control ($IC_{50}$ value) was calculated. The results are shown in Table 3.

TABLE 3

| Ex. No. (Compound No.) | $IC_{50}$ (nM) |
|---|---|
| A4 | <500 |
| B4 | <500 |
| C6 | <500 |
| C12 | <500 |
| C15 | <500 |
| C19 | <500 |
| C23 | <500 |
| C24 | <500 |
| C28 | <500 |
| C66 | <500 |
| C88 | <500 |
| C122 | <500 |
| C126 | <500 |
| D11 | <500 |
| D25 | <500 |
| D33 | <500 |
| D35 | <500 |

INDUSTRIAL APPLICABILITY

The compounds, a salt thereof and a prodrug thereof of the present invention show superior inhibitory activity on Raf. Therefore, a clinically useful agent for the prophylaxis or treatment of diseases related to Raf (e.g., cancer etc.) can be provided. Moreover, since compounds, a salt thereof and a prodrug thereof of the present invention are also superior in efficacy expression, pharmacokinetics, solubility, interaction with other pharmaceutical products, safety and stability, they are useful as pharmaceutical agents.

This application is based on Japanese patent application Nos. 2007-223284 and 2008-187953, the contents of which are incorporated in full herein by this reference.

The invention claimed is:

1. A compound represented by the formula

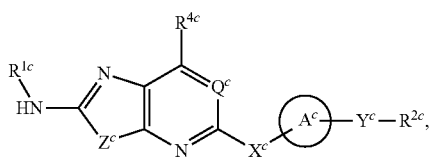

(III)

wherein $R^{1c}$ is (1) $C_{1-6}$ alkyl-carbonyl optionally having 1 to 3 substituents selected from the group consisting of
  (i) hydroxy,
  (ii) $C_{1-6}$ alkyl-oxy,
  (iii) di-$C_{1-6}$ alkylamino, and
  (iv) a 5- or 6-membered nonaromatic heterocyclic group optionally having 1 or 2 substituents selected from
    (a) hydroxy,
    (b) halogen,
    (c) $C_{1-6}$ alkyl optionally substituted by hydroxy, and
    (d) $C_{3-8}$ cycloalkyl, (2) $C_{2-6}$ alkenyl-carbonyl having substituent(s) selected from the group consisting of
  (i) $C_{6-10}$ aryl optionally having 1 to 3 halogen atoms, and
  (ii) a 5- or 6-membered monocyclic aromatic heterocyclic group, (3) $C_{3-8}$ cycloalkyl-carbonyl optionally having 1 to 3 $C_{1-6}$ alkyl, or (4) 5- or 6-membered monocyclic aromatic heterocyclyl-carbonyl $R^{2c}$ is $C_{6-10}$ aryl optionally having 1 or 2 substituents selected from the group consisting of
  (1) halogen,
  (2) $C_{3-8}$ cycloalkyl optionally having cyano,
  (3) $C_{1-6}$ alkyl-oxy optionally having 1 to 3 substituents selected from the group consisting of halogen and cyano, and
  (4) $C_{1-6}$ alkyl optionally having 1 to 3 substituents selected from the group consisting of halogen, $C_{2-6}$ alkynyl, and cyano;

$R^{4c}$ is hydrogen;

$X^c$ is —O—, —NH—, or —N(CH$_3$)

$Y^c$ is —NHCO— or —CONH—

$Z^c$ is —S—;

$Q^c$ is =CH—; and ring $A^c$ is a benzene ring optionally having 1 or 2 substituents selected from the group consisting of
  (1) $C_{1-6}$ alkyl optionally having 1 to 3 halogen atoms,
  (2) cyano,
  (3) halogen, and
  (4) $C_{1-6}$ alkyl-oxy;

or a salt thereof.

2. The compound of claim 1, wherein $X^c$ is —O—.

3. The compound of claim 1, wherein $Y^c$ is —NHCO—.

4. 2-Chloro-3-(1-cyano-1-methylethyl)-N-[5-({2-[(cyclopropylcarbonyl)amino][1,3]thiazolo[5,4-b]pyridin-5-yl}oxy)-2-fluorophenyl]benzamide;

N-(5-{[2-(acetylamino)[1,3]thiazolo[5,4-b]pyridin-5-yl]oxy}-2-fluorophenyl)-2-chloro-3-(1-cyanocyclopropyl)benzamide;

2-chloro-3-(1-cyanocyclopropyl)-N-[5-({2-[(cyclopropylcarbonyl)amino][1,3]thiazolo[5,4-b]pyridin-5-yl}oxy)-2-fluorophenyl]benzamide;

2-chloro-3-(1-cyanocyclopropyl)-N-[5-({2-[(cyclopropylcarbonyl)amino][1,3]thiazolo[5,4-b]pyridin-5-yl}oxy)-2,4-difluorophenyl]benzamide;

2-chloro-3-(1-cyano-1-methylethoxy)-N-{5-[{2-[(cyclopropylcarbonyl)amino][1,3]thiazolo[5,4-b]pyridin-5-yl}(methy)amino]-2-fluorophenyl}benzamide;

2-chloro-3-(1-cyano-1-methylethoxy)-N-{5-[{2-[(cyclopropylcarbonyl)amino][1,3]thiazolo[5,4-b]pyridin-5-yl}(methyl)amino]-2-fluorophenyl}benzamide benzenesulfonate; or 2-chloro-3-(1-cyano-1-methylethoxy)-N-[5-({2-[(cyclopropylcarbonyl)amino][1,3]thiazolo[5,4-b]pyridin-5-yl}amino)-2-fluorophenyl]benzamide;

or a salt thereof.

5. A pharmaceutical agent comprising the compound of claim 1 or a salt thereof.

6. The compound of claim 1, wherein $Y^c$ is —CONH—.

* * * * *

UNITED STATES PATENT AND TRADEMARK OFFICE
CERTIFICATE OF CORRECTION

PATENT NO. : 8,344,135 B2  
APPLICATION NO. : 12/675663  
DATED : January 1, 2013  
INVENTOR(S) : Hirose et al.

Page 1 of 1

It is certified that error appears in the above-identified patent and that said Letters Patent is hereby corrected as shown below:

In the Claims:

Column 348, line 43 (Claim 1): Delete "–N(CH$_3$)" and insert -- –N(CH$_3$)– --.

Column 348, line 45 (Claim 1): Delete "–S" and insert -- –S– --.

Column 349, line 3 (Claim 4): Delete "methy" and insert -- methyl --.

Signed and Sealed this  
Fourteenth Day of May, 2013

Teresa Stanek Rea  
*Acting Director of the United States Patent and Trademark Office*